United States Patent
Crews et al.

(10) Patent No.: US 10,730,862 B2
(45) Date of Patent: *Aug. 4, 2020

(54) COMPOUNDS AND METHODS FOR THE ENHANCED DEGRADATION OF TARGETED PROTEINS AND OTHER POLYPEPTIDES BY AN E3 UBIQUITIN LIGASE

(71) Applicants: YALE UNIVERSITY, New Haven, CT (US); GLAXOSMITHKLINE INTELLECTUAL PROPERTY DEVELOPMENT LIMITED, Brentford, Middlesex (GB); CAMBRIDGE ENTERPRISE LIMITED UNIVERSITY OF CAMBRIDGE, Cambridge (GB)

(72) Inventors: Craig M. Crews, New Haven, CT (US); Dennis Buckley, New Haven, CT (US); Alessio Ciulli, Cambridge (GB); William Jorgensen, Deep River, CT (US); Peter C. Gareiss, Milford, CT (US); Inge Van Molle, Cambridge (GB); Jeffrey Gustafson, New Haven, CT (US); Hyun-Seop Tae, New Haven, CT (US); Julien Michel, Edinburgh (GB); Denton Wade Hoyer, Niantic, CT (US); Anke G. Roth, Levenhagen (DE); John David Harling, Stevenage (GB); Ian Edward David Smith, Stevenage (GB); Afjal Hussain Miah, Stevenage (GB); Sebastien Andre Campos, Stevenage (GB); Joelle Le, Stevenage (GB)

(73) Assignees: Yale University, New Haven, CT (US); Glaxosmithkline Intellectual Property Development, Brenford, Middlesex (GB); Cambridge Enterprise Limited University of Cambridge, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/371,956

(22) PCT Filed: Jan. 11, 2013

(86) PCT No.: PCT/US2013/021136
§ 371 (c)(1),
(2) Date: Jul. 11, 2014

(87) PCT Pub. No.: WO2013/106643
PCT Pub. Date: Jul. 18, 2013

(65) Prior Publication Data
US 2014/0356322 A1   Dec. 4, 2014

Related U.S. Application Data

(60) Provisional application No. 61/585,769, filed on Jan. 12, 2011.

(51) Int. Cl.
C07D 413/14 (2006.01)
C07D 417/12 (2006.01)
(Continued)

(52) U.S. Cl.
CPC .......... *C07D 413/14* (2013.01); *A61K 31/422* (2013.01); *A61K 31/427* (2013.01);
(Continued)

(58) Field of Classification Search
CPC ... C07D 413/14; C07D 417/12; C07D 417/14
See application file for complete search history.

(56) References Cited

U.S. PATENT DOCUMENTS

| 4,522,811 A | 6/1985 | Eppstein et al. |
| 5,681,858 A | 10/1997 | Stevens et al. |

(Continued)

FOREIGN PATENT DOCUMENTS

| CN | 101768155 A | 7/2010 |
| EP | 805147 A1 | 11/1997 |

(Continued)

OTHER PUBLICATIONS

Buckley et al. Angew. Chem. Int. Ed. 2012, 51, 11463-11467.*
National Center for Biotechnology Information. PubChem Compound Database; CID=21042819, https://pubchem.ncbi.nlm.nih.gov/compound/21042819 (accessed Feb. 7, 2016).*
CAS Registry No. 1004933-70-3, which entered STN on Feb. 21, 2008.*
PCT International Search Report and Written Opinion for PCT/US2013/021136 dated Jun. 27, 2013.
Supplementary Search Report for European Patent Application No. 13736209.1 dated Jun. 19, 2015.
Aghajanyy, et al., "Chemical genetics screen for enhancers of rapamycin identifies a specific inhibitor of an SCF family E3 ubiquitin ligase", Nature Biotechnology 28(7), Jun. 27, 2010, 738-742.

(Continued)

*Primary Examiner* — Matthew P Coughlin
(74) *Attorney, Agent, or Firm* — Saul Ewing Arnstein & Lehr LLP; Kathryn Doyle; Domingos J. Silva

(57) ABSTRACT

The present invention relates to bifunctional compounds, which find utility as modulators of targeted ubiquitination, especially inhibitors of a variety of polypeptides and other proteins that are degraded and/or otherwise inhibited by bifunctional compounds of the present invention. In particular, the present invention is directed to compounds, which contain on one end a VHL ligand that binds to the ubiquitin ligase and on the other end a moiety that binds a target protein, such that the target protein is placed in proximity to the ubiquitin ligase to effect degradation (and inhibition) of that protein. The present invention exhibits a broad range of pharmacological activities associated with compounds of the present invention, consistent with the degradation/inhibition of targeted polypeptides.

14 Claims, 106 Drawing Sheets

(51) Int. Cl.

| | | |
|---|---|---|
| *C07D 417/14* | (2006.01) | |
| *C07D 401/06* | (2006.01) | |
| *C07D 401/10* | (2006.01) | |
| *C07D 403/06* | (2006.01) | |
| *C07D 405/06* | (2006.01) | |
| *C07D 405/12* | (2006.01) | |
| *C07D 207/16* | (2006.01) | |
| *C07D 413/12* | (2006.01) | |
| *C07D 207/26* | (2006.01) | |
| *C12N 9/00* | (2006.01) | |
| *A61K 47/54* | (2017.01) | |
| *A61K 47/64* | (2017.01) | |
| *A61K 47/55* | (2017.01) | |
| *A61K 31/422* | (2006.01) | |
| *A61K 31/427* | (2006.01) | |
| *A61K 31/437* | (2006.01) | |
| *A61K 31/4439* | (2006.01) | |
| *A61K 31/454* | (2006.01) | |
| *A61K 31/5377* | (2006.01) | |
| *A61K 38/05* | (2006.01) | |
| *A61K 38/06* | (2006.01) | |
| *A61K 45/06* | (2006.01) | |
| *C07D 413/06* | (2006.01) | |
| *C07D 471/04* | (2006.01) | |
| *C07J 43/00* | (2006.01) | |

(52) U.S. Cl.
CPC ........ *A61K 31/437* (2013.01); *A61K 31/4439* (2013.01); *A61K 31/454* (2013.01); *A61K 31/5377* (2013.01); *A61K 38/05* (2013.01); *A61K 38/06* (2013.01); *A61K 45/06* (2013.01); *A61K 47/545* (2017.08); *A61K 47/55* (2017.08); *A61K 47/64* (2017.08); *C07D 207/16* (2013.01); *C07D 207/26* (2013.01); *C07D 401/06* (2013.01); *C07D 401/10* (2013.01); *C07D 403/06* (2013.01); *C07D 405/06* (2013.01); *C07D 405/12* (2013.01); *C07D 413/06* (2013.01); *C07D 413/12* (2013.01); *C07D 417/12* (2013.01); *C07D 417/14* (2013.01); *C07D 471/04* (2013.01); *C07J 43/003* (2013.01); *C12N 9/93* (2013.01)

(56) References Cited

U.S. PATENT DOCUMENTS

| | | | |
|---|---|---|---|
| 6,306,663 | B1 | 10/2001 | Kenten et al. |
| 6,559,280 | B2 | 5/2003 | Kenten et al. |
| 6,670,348 | B1 | 12/2003 | Rosen et al. |
| 7,041,298 | B2 | 5/2006 | Deshaies et al. |
| 7,074,620 | B2 | 7/2006 | Kenten et al. |
| 7,208,157 | B2 | 4/2007 | Sakamoto et al. |
| 7,273,920 | B2 | 9/2007 | Kenten et al. |
| 7,683,160 | B2 | 3/2010 | Eckhardt et al. |
| 7,915,293 | B2 * | 3/2011 | Ramesh ............... C07C 233/75 514/316 |
| 9,500,653 | B2 | 11/2016 | Crews et al. |
| 9,632,089 | B2 | 4/2017 | Crews et al. |
| 9,938,264 | B2 * | 4/2018 | Crews ................. C07D 417/14 |
| 9,988,376 | B2 * | 6/2018 | Campos ............... C07D 413/14 |
| 9,993,514 | B2 * | 6/2018 | Campos ............... A61K 38/06 |
| 10,071,164 | B2 * | 9/2018 | Crew ................... A61K 45/06 |
| 2003/0133927 | A1 | 7/2003 | DeFeo-Jones et al. |
| 2003/0143590 | A1 | 7/2003 | Ramakrishnan |
| 2003/0162787 | A1 * | 8/2003 | Bigge ................. C07D 207/16 514/252.03 |
| 2005/0215550 | A1 * | 9/2005 | Tang ................... C07D 401/14 514/235.5 |
| 2006/0128632 | A1 | 6/2006 | Sharma et al. |
| 2006/0259992 | A1 | 11/2006 | Koren et al. |
| 2008/0214501 | A1 | 9/2008 | Pan et al. |
| 2009/0269420 | A1 | 10/2009 | Jeske et al. |
| 2010/0048517 | A1 | 2/2010 | Hu et al. |
| 2010/0286127 | A1 | 11/2010 | Miyoshi et al. |
| 2012/0270800 | A1 | 10/2012 | Verdine et al. |
| 2014/0088143 | A1 | 3/2014 | Jain |
| 2014/0256700 | A1 | 9/2014 | Poss et al. |
| 2014/0302523 | A1 | 10/2014 | Crews et al. |
| 2014/0371206 | A1 | 12/2014 | Albrecht et al. |
| 2015/0119435 | A1 | 4/2015 | Crews et al. |
| 2015/0141470 | A1 | 5/2015 | Garraway et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0214972 | A1 | 7/2016 | Jin et al. |
| 2016/0272639 | A1 | 9/2016 | Crew et al. |

FOREIGN PATENT DOCUMENTS

| | | |
|---|---|---|
| EP | 2985285 A1 | 2/2016 |
| RU | 2509080 C9 | 8/2014 |
| WO | 3742216 A1 | 11/1997 |
| WO | 9818493 A2 | 5/1998 |
| WO | 9902175 A1 | 1/1999 |
| WO | 0022110 A2 | 4/2000 |
| WO | 0050445 A1 | 8/2000 |
| WO | 0066119 A1 | 11/2000 |
| WO | 0128593 A2 | 4/2001 |
| WO | 0175145 A2 | 10/2001 |
| WO | 0222577 A2 | 3/2002 |
| WO | 02066512 A1 | 8/2002 |
| WO | 02100845 A1 | 12/2002 |
| WO | 03057820 A2 | 7/2003 |
| WO | 2006069063 A1 | 6/2006 |
| WO | 2006113942 A2 | 10/2006 |
| WO | 2007022638 A1 | 3/2007 |
| WO | 2007106670 A2 | 9/2007 |
| WO | 2008011392 A2 | 1/2008 |
| WO | 2008067495 A2 | 6/2008 |
| WO | 2008115663 A1 | 9/2008 |
| WO | 2008134679 A1 | 11/2008 |
| WO | 2009015254 A1 | 1/2009 |
| WO | 2010027564 A2 | 3/2010 |
| WO | 2010107485 A1 | 9/2010 |
| WO | 2010141805 A1 | 12/2010 |
| WO | 2011005510 A2 | 1/2011 |
| WO | 2011008260 A1 | 1/2011 |
| WO | 2011082007 A2 | 7/2011 |
| WO | 2011082077 A1 | 7/2011 |
| WO | 2011143660 A2 | 11/2011 |
| WO | 2011143669 A2 | 11/2011 |
| WO | 2011160016 A2 | 12/2011 |
| WO | 2012003281 A2 | 1/2012 |
| WO | 2012009649 A1 | 1/2012 |
| WO | 2012040527 A2 | 3/2012 |
| WO | 2012054110 A2 | 4/2012 |
| WO | 2012078559 A2 | 6/2012 |
| WO | 2012090104 A1 | 7/2012 |
| WO | 2012142498 A2 | 10/2012 |
| WO | 2013106643 A2 | 7/2013 |
| WO | 2013106646 A2 | 7/2013 |
| WO | 2013170147 A1 | 11/2013 |
| WO | 2014001356 A1 | 1/2014 |
| WO | 2014108452 A1 | 7/2014 |
| WO | 2014123418 A1 | 8/2014 |
| WO | 2014128111 A1 | 8/2014 |
| WO | 2015000867 A1 | 1/2015 |
| WO | 2015000868 A1 | 1/2015 |
| WO | 2015074064 A2 | 5/2015 |
| WO | 2015160845 A2 | 10/2015 |
| WO | 2016050821 A1 | 4/2016 |
| WO | 2016069578 A1 | 5/2016 |
| WO | 2016118666 A1 | 7/2016 |
| WO | 2016146985 A1 | 9/2016 |
| WO | 2016169989 A1 | 10/2016 |

(56) References Cited

FOREIGN PATENT DOCUMENTS

| WO | 2016172134 A2 | 10/2016 |
|---|---|---|
| WO | 2016197114 A1 | 12/2016 |

OTHER PUBLICATIONS

Boitano, et al., "Aryl Hydrocarbon Receptor Antagonists Promote the Expansion of Human Hematopoietic Stem Cells", Science 329, Sep. 10, 2010, 1345-1348.
Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.
Buckley, et al., "Small-molecule inhibitors of the interaction between the E3 ligase VHL and HIF1α", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Jounral of the American Chemical Society 134(10), Feb. 27, 2012, 4465-4468.
Chang, et al., "Structural basis for G9a-like protein lysine methyltransferase inhibition by BIX-01294", Nat Struct Mol Biol. 16(3), Mar. 2009, 312-317.
Chung, et al., "Discovery and Characterization of Small Molecule Inhibitors of the BET Family Bromodomains", J Med Chem. 54(11), Jun. 9, 2011, 3827-3838.
Cyrus, et al., "Jostling for position: optimizing linker location in the design of estrogen receptor-targeting PROTACs", ChemMedChem. 5(7), Jul. 5, 2010, 979-985.
Dawson, et al., "Inhibition of BET recruitment to chromatin as an effective treatment for MLL-fusion leukaemia", Nature 478, Oct. 2, 2011, 529-533.
Filippakopoulos, et al., "Selective inhibition of BET bromodomains", Nature 468, Dec. 23, 2010, 1067-1073.
Finnin, et al., "Structures of a histone deacetylase homologue bound to the TSA and SAHA inhibitors", Nature 401, Sep. 9, 1999, 188-193.
Hewings, et al., "3,5-Dimethylisoxazoles Act as Acetyllysine-mimetic Bromodomain", J Med Chem. 54(19), Oct. 13, 2011, 6761-6770.
Hon, et al., "Structureal basis for the recognition of hydroxyproline in Hlf-1a by pVHL", Nature 417, Jun. 27, 2002, 975-978 (Abstract).
Jiang, et al., "Synthesis of 7alpha-substituted derivatives of 17beta-estradiol", Steroids 71(5), May 2006, 334-342 (Abstract).
Lee, et al., "Targeted Degradation of the Aryl Hydrocarbon Receptor by the PROTAC Approach: A Useful Chemical Genetic Tool", ChemBioChem. 8(17), Nov. 23, 2007, 2058-2062.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Llinàs-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lountos, et al., "Structural Characterization of Inhibitor Complexes with Checkpoint Kinase 2 (Chk2), a Drug Target for Cancer Therapy", J Struct Biol.176(3), Dec. 2011, 292-301.
Mehellou, et al., "Twenty-six years of anti-HIV drug discovery: where do we stand and where do we go?", J Med Chem. 53(2), Jan. 28, 2010, 521-538.
Millan, et al. "Design and Synthesis of Inhaled p38 Inhibitors for the Treatment of Chronic Obstructive Pulmonary Disease", J Med Chem.54(22), Nov. 24, 2011, 7797-7814.
Min, et al., "Structue of an HIV-1-alpha—pVHL complex: hydroxyproline recognition in signaling", Science 296, Jun. 27, 2002, 1886-1889.
Nicodeme, et al., "Suppression of inflammation by a synthetic histone mimic", Nature 468, Dec. 23, 2010, 1119-1123.
Prakash, et al., "Stereoselective Nucleophilic Trifluoromethylation of N-(tert-Butylsulfinyl)imines by Using Trimethyl (trifluoromethyl)silane", Angew Chem Int Ed Engl. 40(3), Feb. 2, 2001, 589-590 (Abstract).

Rodriguez-Gonzalez, et al., "Targeting steroid hormone receptors for ubiquitination and degradation in breast and prostate cancer", Oncogene. 27(57), Dec. 4, 2008, 7201-7211.
Rusch, et al., "Identification of acyl protein thioesterases 1 and 2 as the cellular targets of the Ras-signaling modulators palmostatin B and M", Angew Chem Int Ed Engl.50(42), Oct. 10, 2011, 9838-9842.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).
Schenkel, et al., "Discovery of Potent and Highly Selective Thienopyridine Janus Kinase 2 Inhibitors", J Med Chem.54(24), Dec. 22, 2011, 8440-8450.
Schneekloth, et al., "Chemical Genetic Control of Protein Levels: Selective in Vivo Targeted Degradation", J Am Chem Soc. 126(12), Mar. 31, 2004, 3748-3754.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Valle, et al., "Tricyclic Series of Heat Shock Protein 90 (HSP90) Inhibitors Part I: Discovery of Tricyclic Imidazo[4,5- c]Pyridines as Potent Inhibitors of the HSP90 Molecular Chaperone", J Med Chem. 54(20), Oct. 27, 2011, 7206-7219.
Van Eis, et al., "2,6-Naphthyridines as potent and selective inhibitors of the novel protein kinase C isozymes", Bioorg Med Chem Lett.21(24), Dec. 15, 2011, 7367-7372.
Van Molle, et al., "Dissecting fragment-based lead discovery at the von Hippel-Lindau protein:hypoxia inducible factor 1α protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Wright, et al., "Structure-Activity Relationships in Purine-Based Inhibitor Binding to HSP90 Isoforms", Chem Biol. 11(6), Jun. 2004, 775-785.
Carmony, K.C. et al., "PROTAC-Induced Proteolytic Targeting," Methods Mol. Biol., 2012, vol. 832, pp. 627-638.
Cyrus, K. et al., "Impact of Linker Length on the Activity of PROTACs," Mol. Biosyst., 2011, vol. 7, No. 2, pp. 359-364.
Cyrus, K. et al., "Two-Headed PROTAC: An Effective New Tool for Targeted Protein Degradation," Chembiochem., 2010, vol. 11, No. 11, pp. 1531-1534.
Jang, E.R. et al., "Targeted Degradation of Proteins by PROTACs," Curr. Protoc. Chem. Biol., 2010, vol. 2, No. 2, pp. 71-87.
Puppala, D. et al., "Development of an Aryl Hydrocarbon Receptor Antagonist Using the Proteolysis-Targeting Chimeric Molecules Approach: A Potential Tool for Chemoprevention," Mol. Pharmacol., 2008, vol. 73, No. 4, pp. 1064-1071.
Zhang, D. et al., "Targted Degradation of Proteins by Small Molecules: A Novel Tool for Functional Proteomics," Comb. Chem. High Throughput Screen., 2004, vol. 7, No. 7, pp. 689-697.
Carlson, et al., "Selection of small-molecule mediators of the RNA regulation of PKR, the RNA-dependent protein kinase", Chembiochem. 3(9), 2002, 859-865.
Aghajan, et al., "Chemical genetics screen for enhancers of rapamycin identifies a specific inhibitor of an SCF family E3 ubiquitin ligase", Nat Biotechnol. 28(7), 2010, 738-742.
Ahn, et al., "HIF-1alpha peptide derivatives with modifications at the hydroxyproline residue as activators of HIF-1alpha", Bioorg Med Chem Lett. 19(15), 2009, 4403-4405.
Bargagna-Mohan, et al., "Use of PROTACS as molecular probes of angiogenesis", Bioorg Med Chem Lett. 15(11), 2005, 2724-2727.
Rotili, et al., "Photoactivable peptides for identifying enzyme-substrate and protein-protein interactions", Chem Commun (Camb). 47(5), 2011, 1488-1490.
CAS Registry No. 155180-53-3 ,1994.
CAS Registry No. 871986-52-6 ,2006.

(56) References Cited

OTHER PUBLICATIONS

Corson, et al.,"Design and applications of bifunctional small molecules: why two heads are better than one," ACS Chemical Biology 3(11) ,2008 ,677-692.
Crews, et al.,"Targeting the undruggable proteome: the small molecules of my dreams," Chem Biol. 17 (6) ,2010 ,551-555.
Gosink, et al.,"Redirecting the specificity of ubiquitination by modifying ubiquitin-conjugating enzymes," Proc Natl Acad Sci U S A. 92(20) ,1995 ,9117-9121.
Hines, et al.,"Posttranslational protein knockdown coupled to receptor tyrosine kinase activation with phosphoPROTACs," Proc Natl Acad Sci U S A. 110(22) ,2013 ,8942-8947.
Ivan, et al.,"HIFa Targeted for VHL-Mediated Destruction by Proline Hydroxylation: Implications for O2 Sensing," Science 292 (5516) ,2001 ,464-468.
Schneekloth, et al.,"Targeted intracellular protein degradation induced by a small molecule: En route to chemical proteomics," Bioorg Med Chem Lett. 18(22) ,2008 ,5904-5908.
CAS 155255-73-5 ,May 1994.
Allan, et al., Therapeutic androgen receptor ligands, Nucl Recept Signal. 1 ,2003 ,e009.
Asangani, et al., Therapeutic targeting of BET bromodomain proteins in castration-resistant prostate cancer, Nature. 510(7504) ,Jun. 2014 ,278-282.
Belkina, et al., BET domain co-regulators in obesity, inflammation and cancer, Nat Rev Cancer. 12(7) ,Jun. 2012 ,465-477.
Bradbury, et al., Small-molecule androgen receptor downregulators as an approach to treatment of advanced prostate cancer, Bioorg Med Chem Lett. 21(18) ,Sep. 2011 ,5442-5445.
Ceribelli, et al., Blockade of oncogenic IkB kinase activity in diffuse large B-cell lymphoma by bromodomain and extraterminal domain protein inhibitors, Proc Natl Acad Sci U S A. 111(31) ,Aug. 2014 , 11365-11370.
Chapuy, et al., Discovery and characterization of super-enhancer-associated dependencies in diffuse large B cell lymphoma., Cancer Cell. 24(6) ,Dec. 2013 ,777-790.
Delmore, et al., BET bromodomain inhibition as a therapeutic strategy to target c-Myc, Cell. 146(6) ,Sep. 2011 ,904-917.
Di, et al., Reactivation of p53 by inhibiting Mdm2 E3 ligase: a novel antitumor approach, Curr Cancer Drug Targets. 11(8) ,Oct. 2011 , 987-994.
Dixon, et al., Identifying druggable disease-modifying gene products, Curr Opin Chem Biol. 13(5-6) ,Dec. 2009 ,549-555.
Galdeano, et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities, J Med Chem. 57(20) ,2014 ,8657-8663.
Gangjee, et al., The contribution of a 2-amino group on receptor tyrosine kinase inhibition and antiangiogenic activity in 4-anilinosubstituted pyrrolo[2,3-d]pyrimidines, Bioorg Med Chem Lett. 20(10) ,May 2010 ,3177-3181.
Golub, et al., Molecular classification of cancer: class discovery and class prediction by gene expression monitoring, Science. 286 (5439) ,Oct. 1999 ,531-537.
Hoffmann, et al., Characterization of new estrogen receptor destabilizing compounds: effects on estrogen-sensitive and tamoxifen-resistant breast cancer, J Natl Cancer Inst. 96(3) ,Feb. 2004 ,210-218.
Ishikawa, et al., Design and synthesis of novel human epidermal growth factor receptor 2 (HER2)/epidermal growth factor receptor (EGFR) dual inhibitors bearing a pyrrolo[3,2-d]pyrimidine scaffold, J Med Chem. 54(23) ,Dec. 2011 ,8030-8050.
Jung, et al., Structure-activity relationship for thiohydantoin androgen receptor antagonists for castration-resistant prostate cancer (CRPC), J Med Chem. 53(7) ,Apr. 2010 ,2779-2796.
Kim, et al., Heat shock protein as molecular targets for breast cancer therapeutics, J Breast Cancer. 14(3) ,Sep. 2011 ,167-174.
Konecny, et al., Activity of the dual kinase inhibitor lapatinib (GW572016) against HER-2-overexpressing and trastuzumab-treated breast cancer cells, Cancer Res. 66(3) ,Feb. 2006 ,1630-1639.
Levine, et al., Targeting the androgen receptor with steroid conjugates, J Med Chem. 57(20) ,Oct. 2014 ,8224-8237.
Lovén, et al., Selective inhibition of tumor oncogenes by disruption of super-enhancers, Cell. 153(2) ,Apr. 2013 ,320-334.
Martin-Kohler, et al., Furo[2,3-d]pyrimidines and Oxazolo[5,4-d]pyrimidines as Inhibitors of Receptor Tyrosine Kinases (RTK), Helvetica Chimica Acta 87 ,2004 ,956-975.
Mohler, et al., Androgen receptor antagonists: a patent review (2008-2011), Expert Opin Ther Pat. 22(5) ,May 2012 ,541-565.
Noel, et al., Abstract C244: Development of the BET bromodomain inhibitor OTX015, Mol Cancer Ther; 12(11 Suppl): Abstract C244. ,2013 ,Abstract Only.
Puissant, et al., Targeting MYCN in neuroblastoma by BET bromodomain inhibition, Cancer Discov. 3(3) ,Mar. 2013 ,308-323.
Robertson, et al., Fulvestrant (Faslodex)—How to Make a Good Drug Better, The Oncologist 12 ,2007 ,774-784.
Sequist, et al., Randomized phase II study of erlotinib plus tivantinib versus erlotinib plus placebo in previously treated non-small-cell lung cancer, J Clin Oncol. 29(24) ,Aug. 2011 ,3307-3315.
Zillhardt, et al., Foretinib (GSK1363089), an orally available multikinase inhibitor of c-Met and VEGFR-2, blocks proliferation, induces anoikis, and impairs ovarian cancer metastasis, Clin Cancer Res. 17(12) ,Jun. 2011 ,4042-4051.
Seiler , et al., "Ethanol inhibits insulin receptor tyrosine kinase", Alcohol Clin Exp Res. 24(12), Dec. 2000, 1869-1872.
Extended European Search Report for European Patent Application No. 19181352.6 dated Jan. 13, 2020.
Lohse , et al., "Synthesis and Deconvolution of the First Combinatorial Library of Glycosidase Inhibitors", Bioorg Med Chem. 7(9), Sep. 1999, 1965-1971.

\* cited by examiner

A

B

A

B

A

B

A

5

B

6

A

7

B

8

A

9

B

10

A

B

A

B

A

15

B

DEALA-Hyp-YIPD

| Compound Number | Chemical Structure |
|---|---|
| 1 | 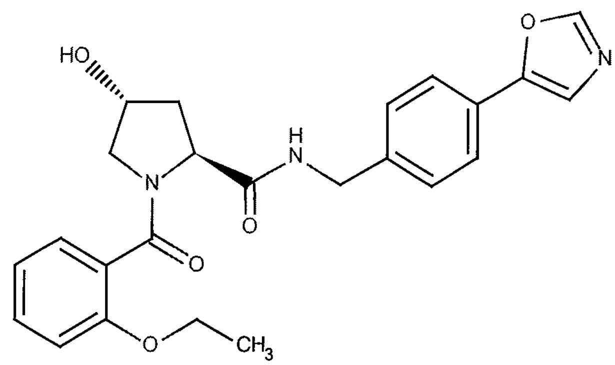 |
| 2 | 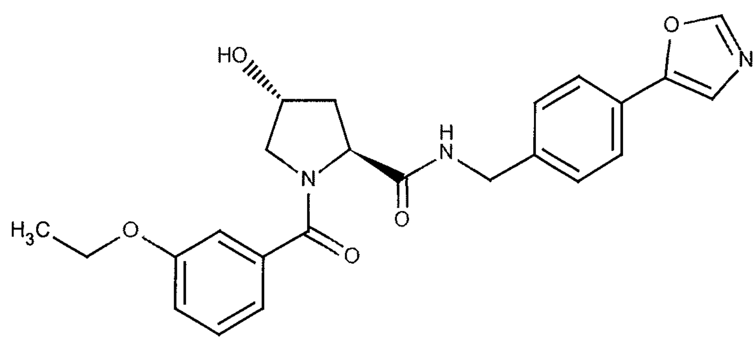 |
| 3 | 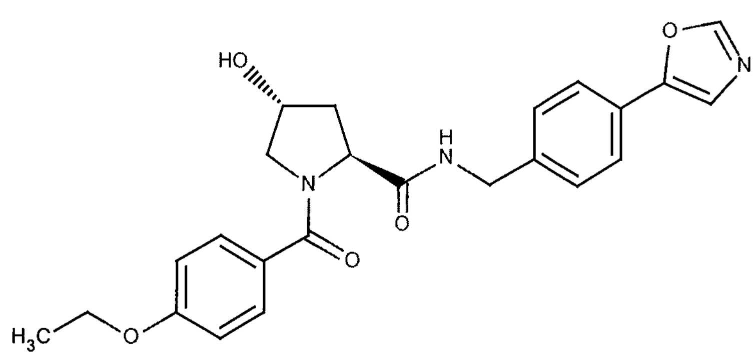 |

| Compound Number | Chemical Structure |
|---|---|
| 4 |  |
| 5 |  |
| 6 |  |

| Compound Number | Chemical Structure |
|---|---|
| 7 | 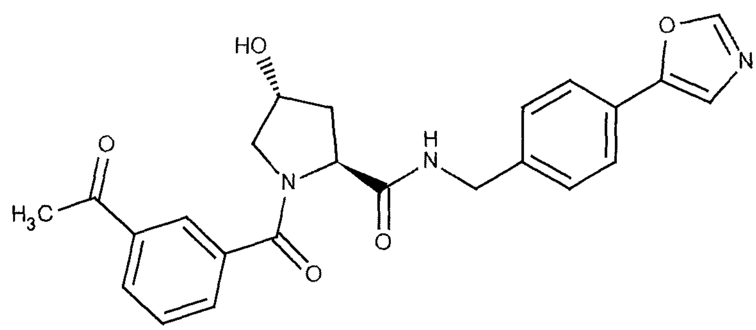 |
| 8 | 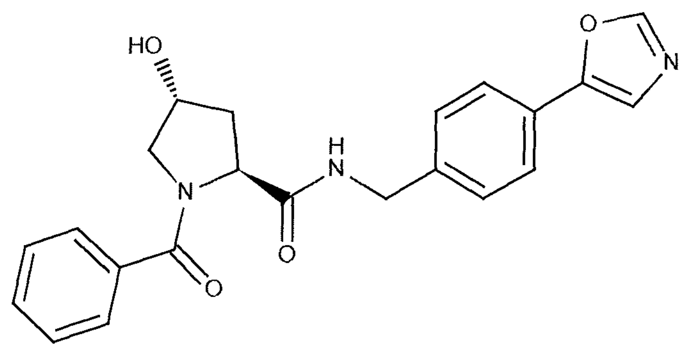 |
| 9 | 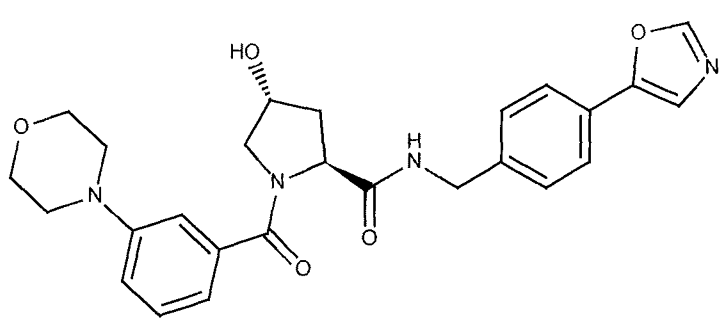 |

| Compound Number | Chemical Structure |
|---|---|
| 10 |  |
| 11 |  |
| 12 |  |

| Compound Number | Chemical Structure |
|---|---|
| 13 | 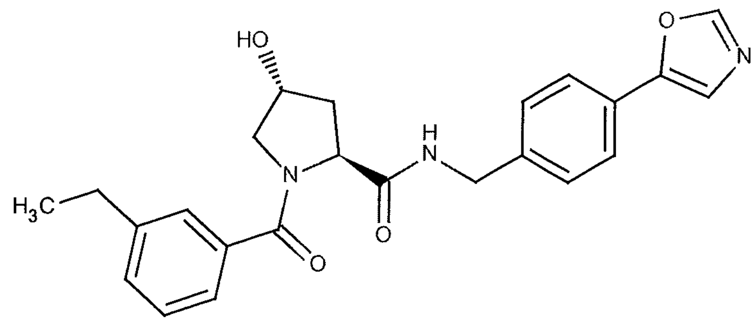 |
| 14 | 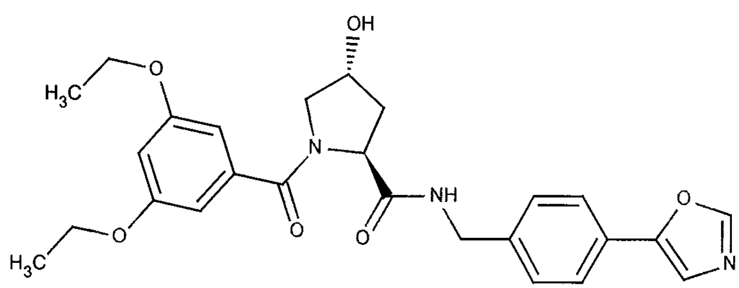 |
| 15 | 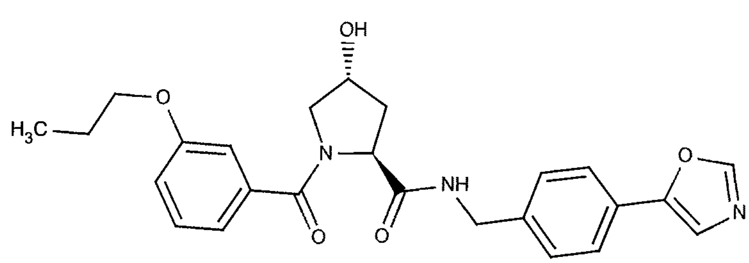 |

| Compound Number | Chemical Structure |
|---|---|
| 16 | 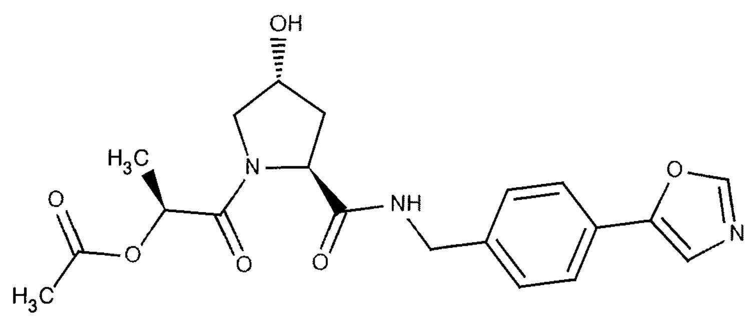 |
| 17 | 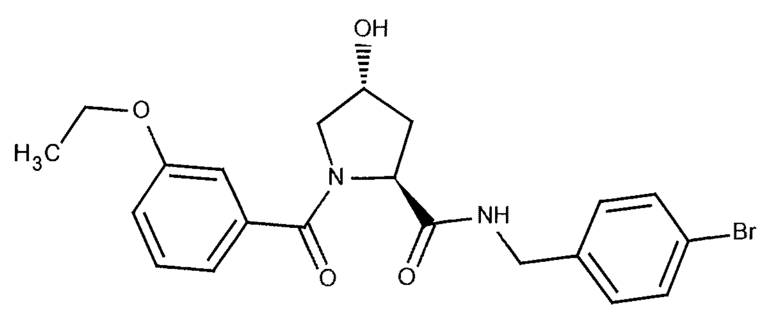 |
| 18 | 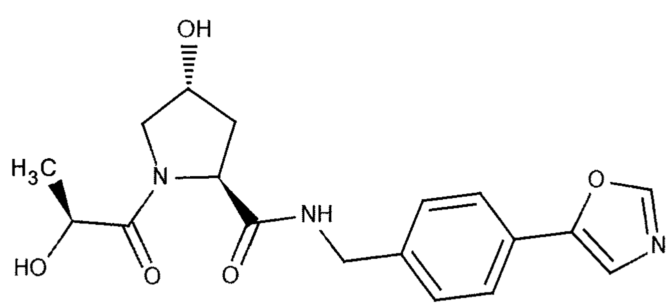 |

| Compound Number | Chemical Structure |
|---|---|
| 19 | 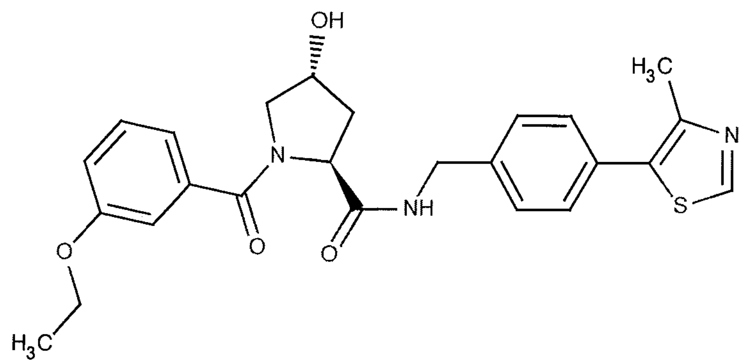 |
| 20 | 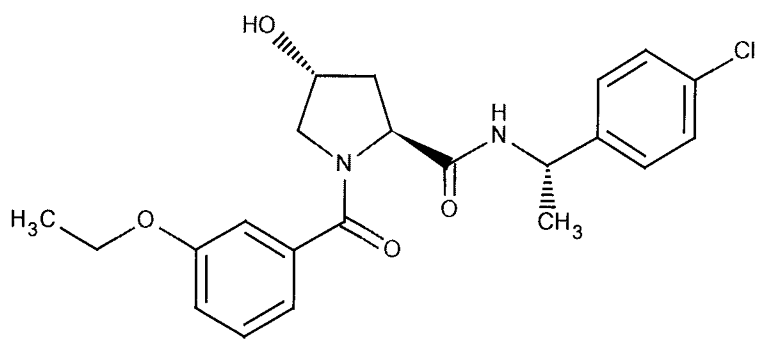 |
| 21 | 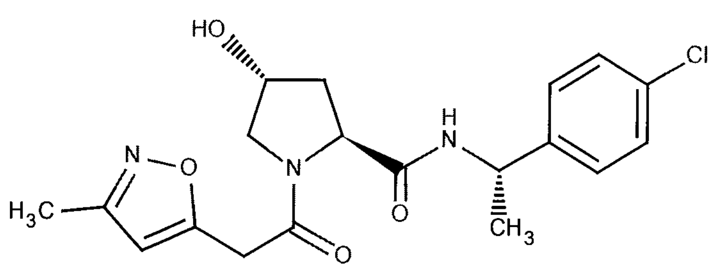 |

| Compound Number | Chemical Structure |
|---|---|
| 22 | 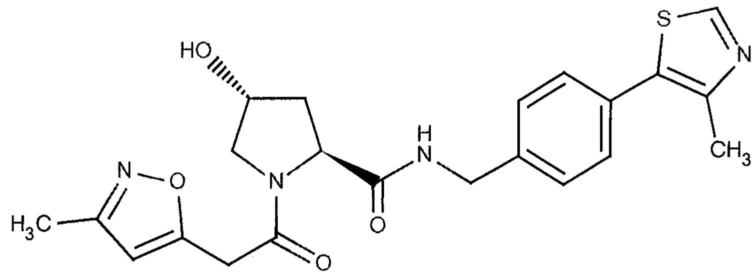 |
| 23 | 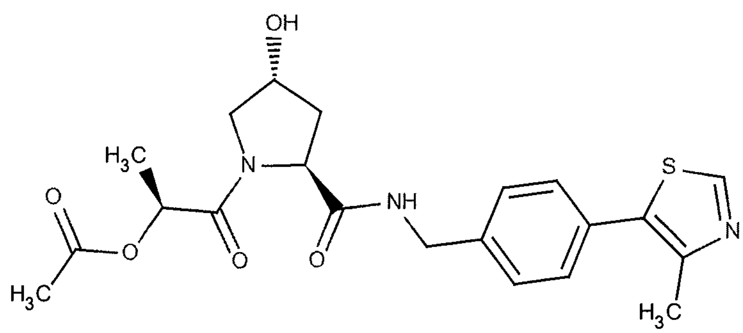 |
| 24 | 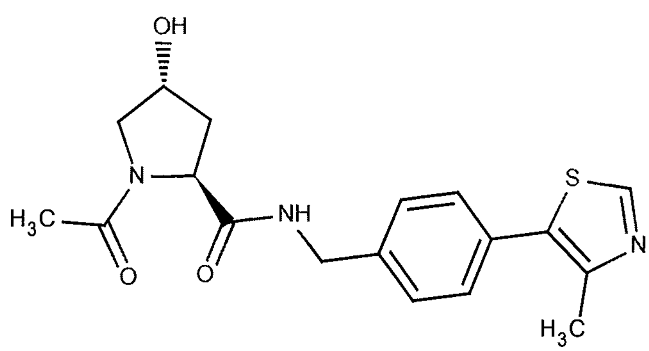 |

| Compound Number | Chemical Structure |
|---|---|
| 25 | 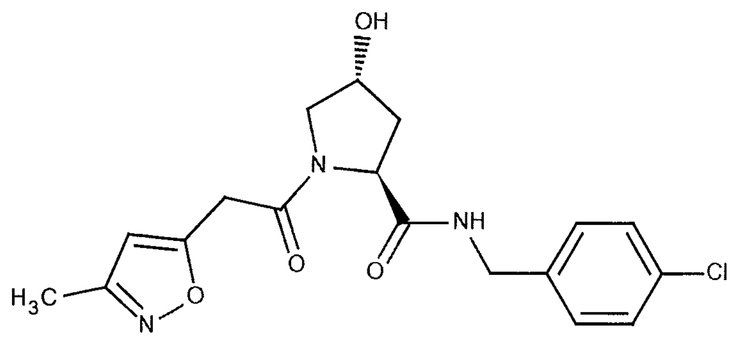 |
| 26 | 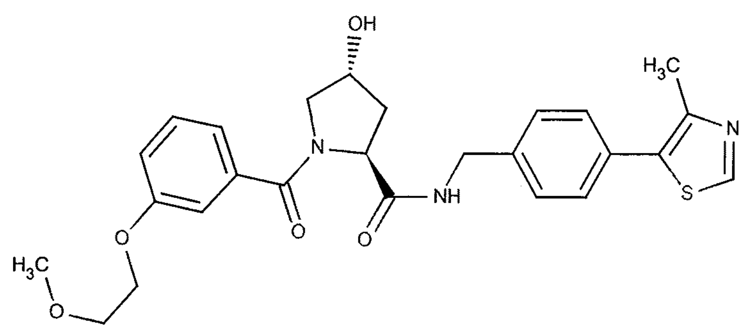 |
| 27 | 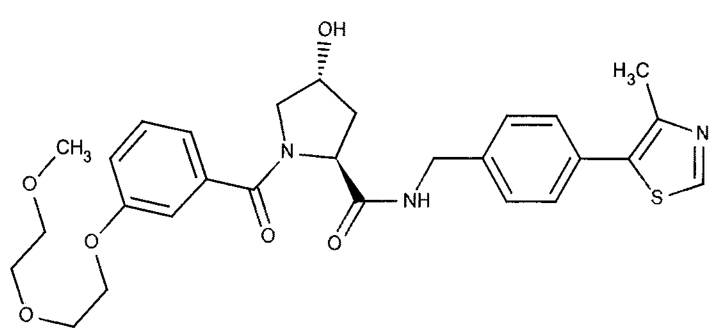 |

| Compound Number | Chemical Structure |
|---|---|
| 28 | 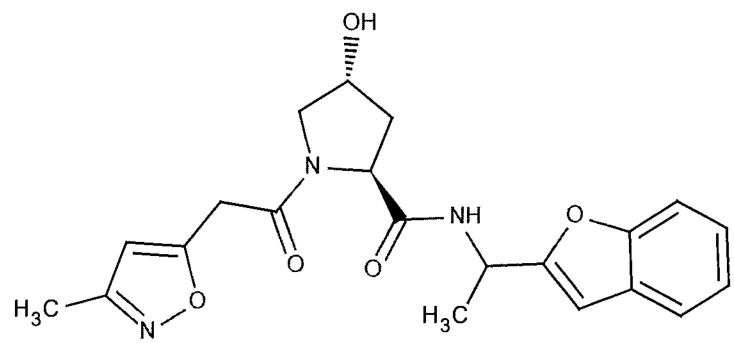 |
| 29 | 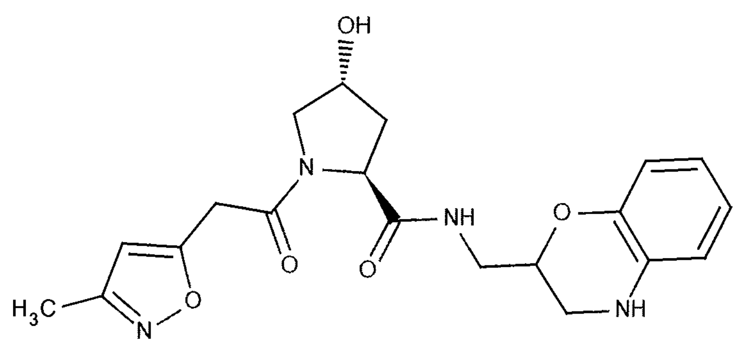 |
| 30 | 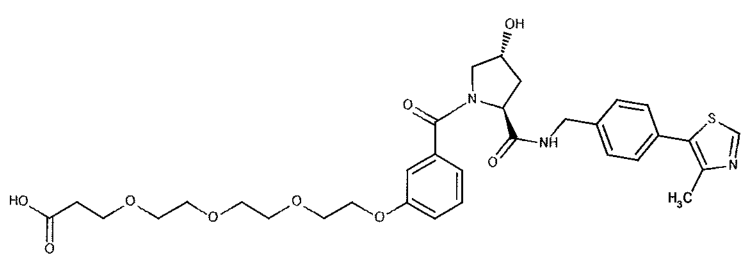 |

| Compound Number | Chemical Structure |
|---|---|
| 31 |  |
| 32 |  |
| 33 |  |

| Compound Number | Chemical Structure |
|---|---|
| 34 | 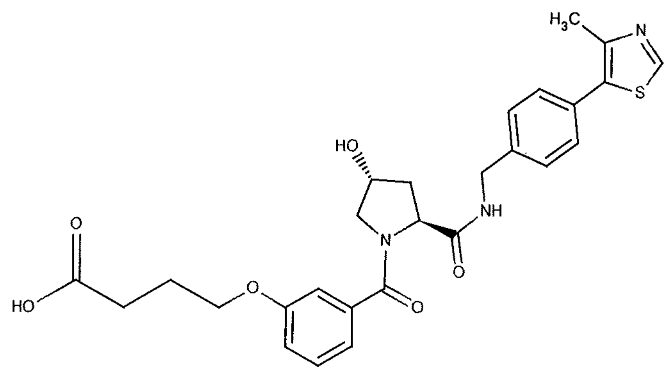 |
| 35 | 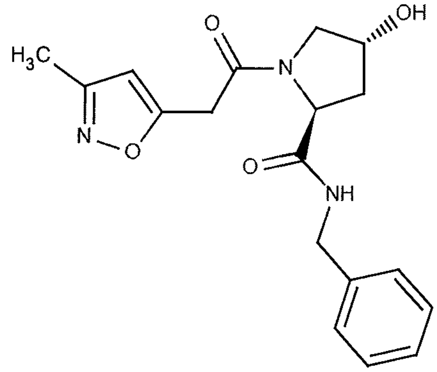 |
| 36 | 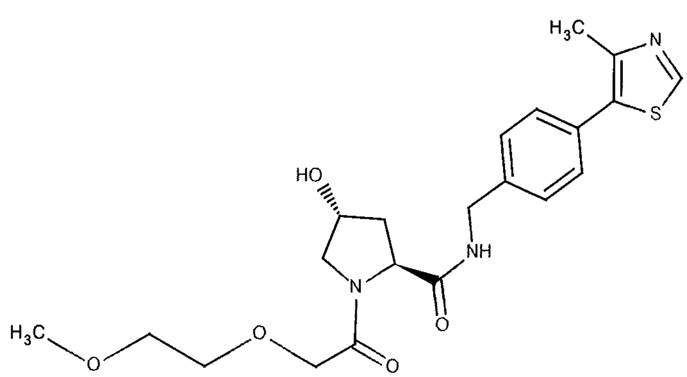 |

| Compound Number | Chemical Structure |
|---|---|
| 37 | 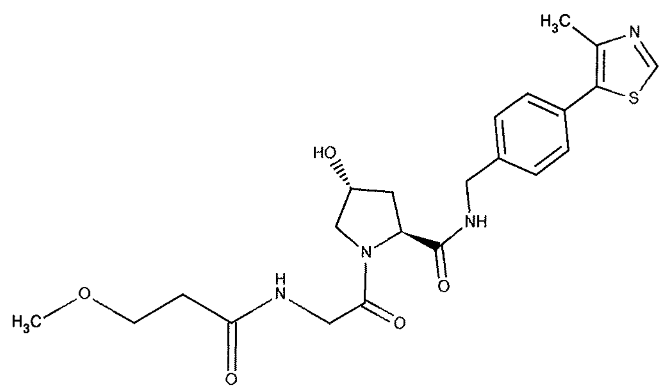 |
| 38 | 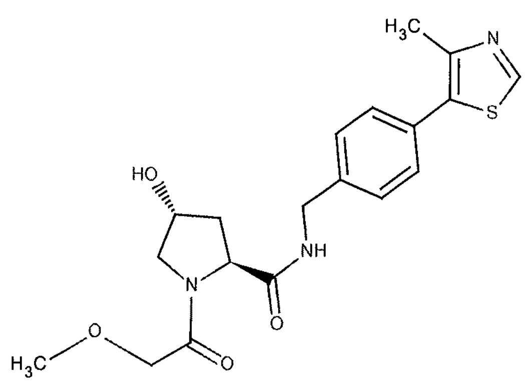 |
| 39 | 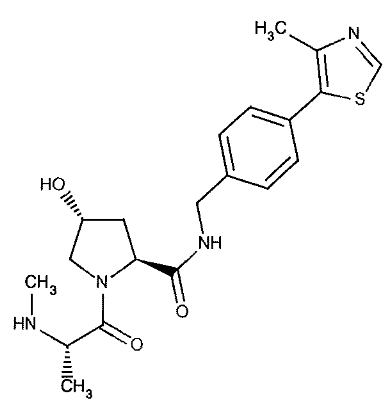 |

| Compound Number | Chemical Structure |
|---|---|
| 40 | 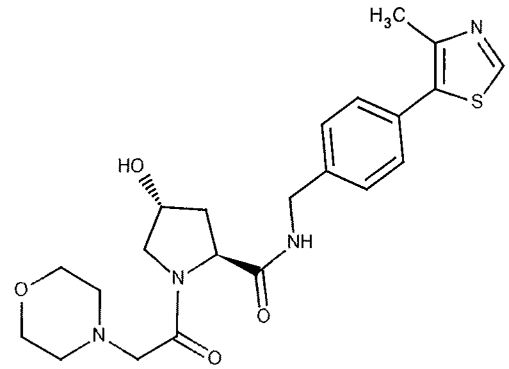 |
| 41 | 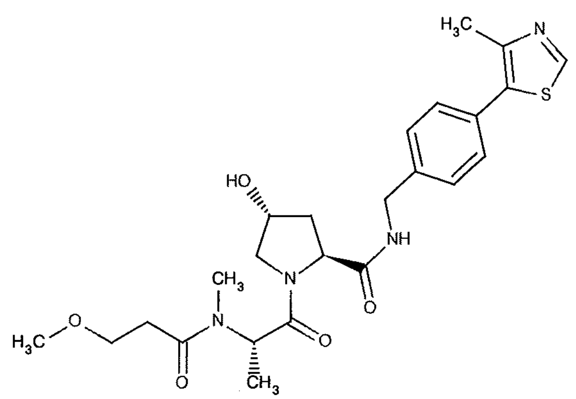 |
| 42 | 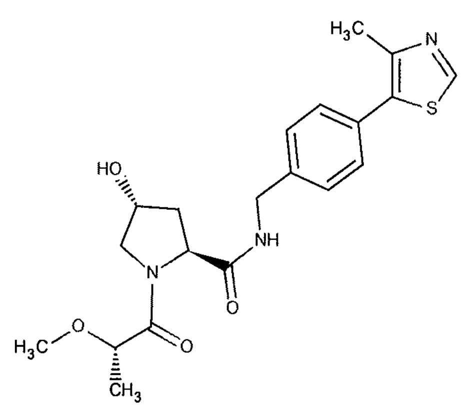 |

| Compound Number | Chemical Structure |
|---|---|
| 43 | 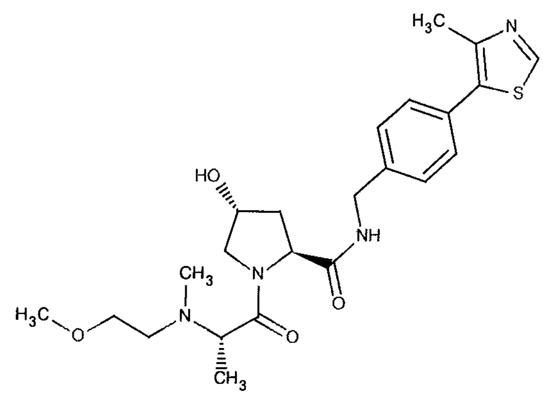 |
| 44 | 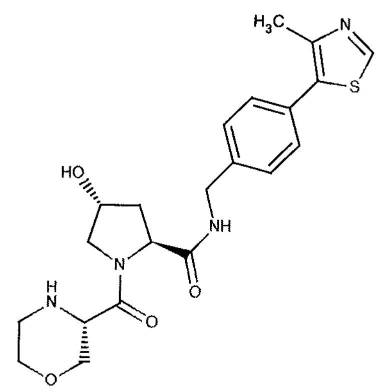 |
| 45 | 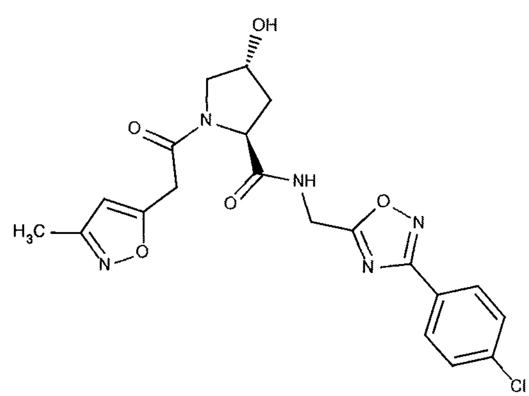 |

| Compound Number | Chemical Structure |
|---|---|
| 46 | 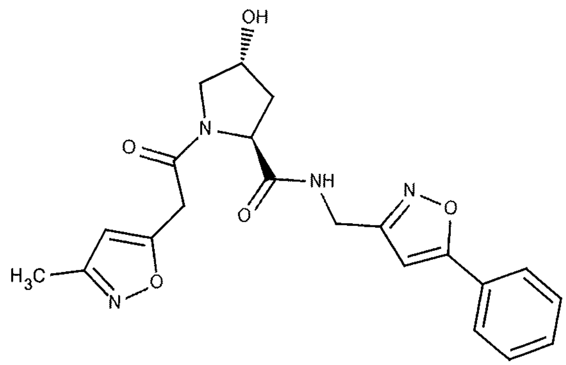 |
| 47 | 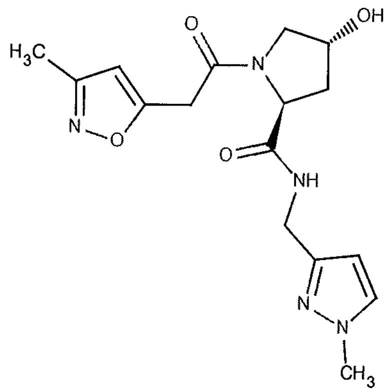 |
| 48 | 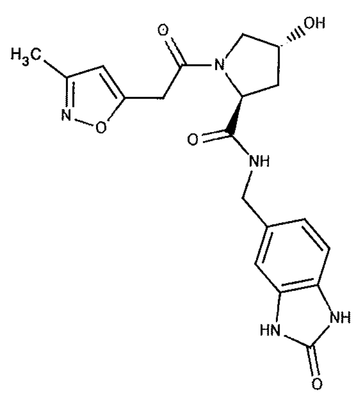 |

| Compound Number | Chemical Structure |
| --- | --- |
| 49 | 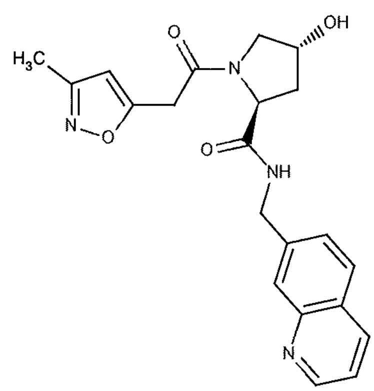 |
| 50 | 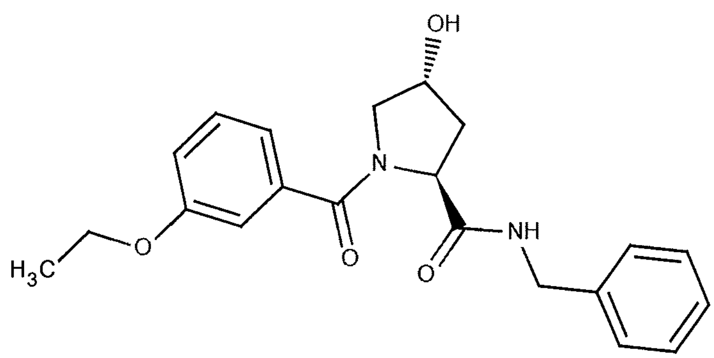 |
| 51 | 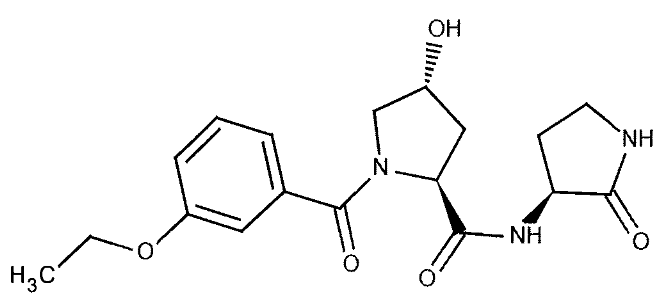 |

| Compound Number | Chemical Structure |
|---|---|
| 52 |  |
| 53 |  |
| 54 |  |

| Compound Number | Chemical Structure |
|---|---|
| 55 | 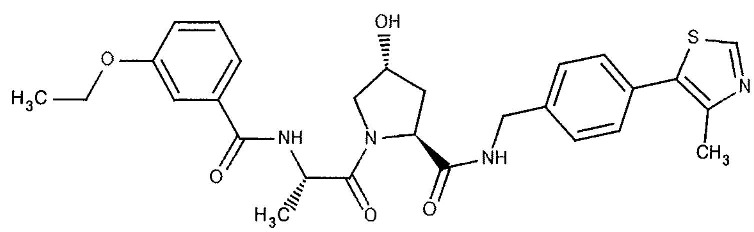 |
| 56 | 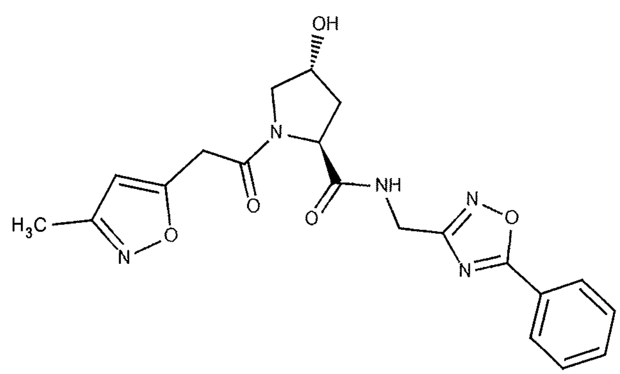 |
| 57 | 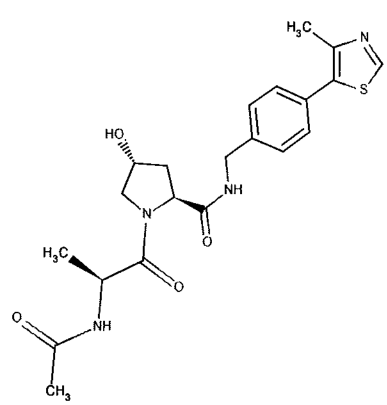 |

| Compound Number | Chemical Structure |
|---|---|
| 58 | 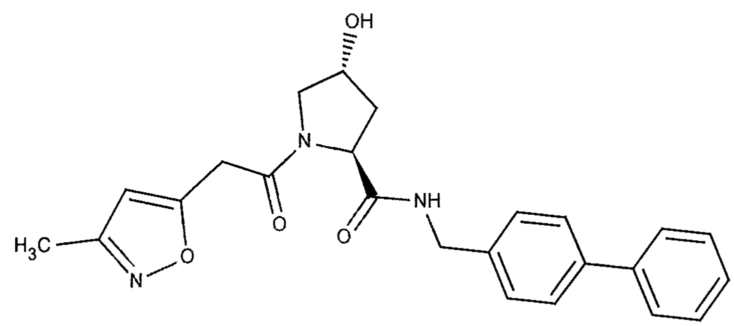 |
| 59 | 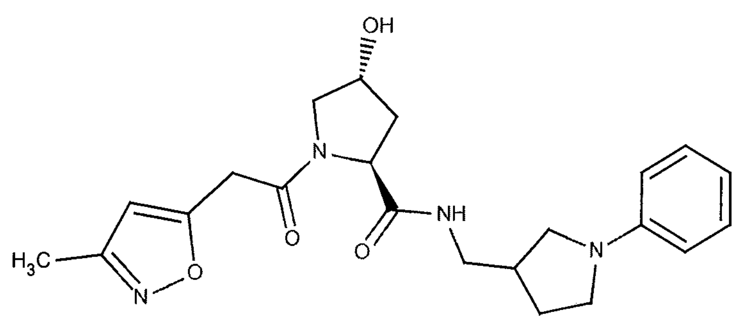 |
| 60 | 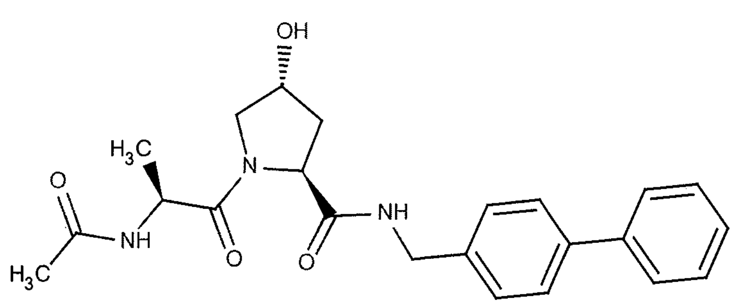 |

| Compound Number | Chemical Structure |
|---|---|
| 61 | 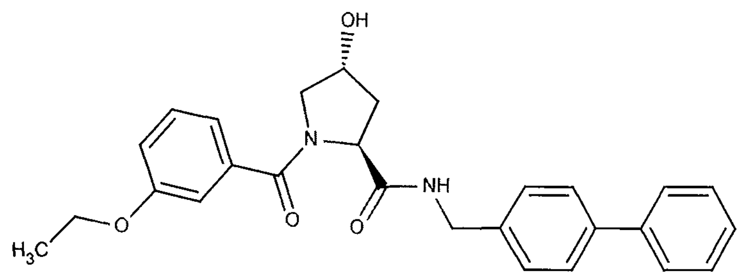 |
| 62 | 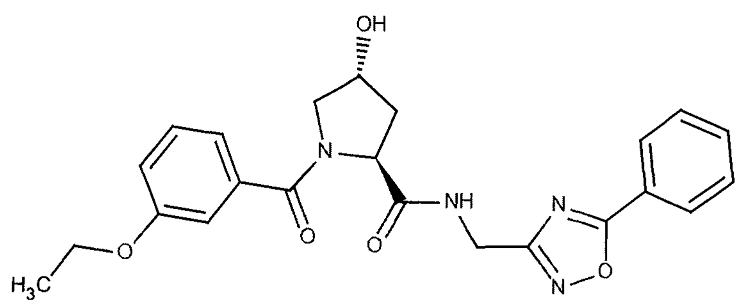 |
| 63 | 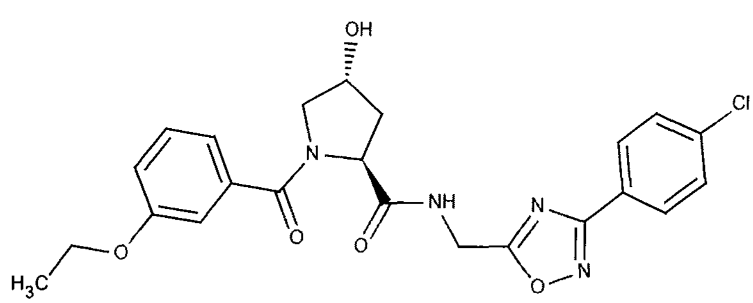 |

| Compound Number | Chemical Structure |
|---|---|
| 64 |  |
| 65 |  |
| 66 |  |

| Compound Number | Chemical Structure |
|---|---|
| 67 | 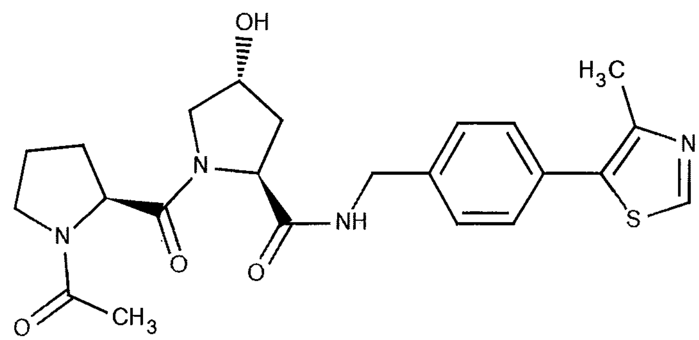 |
| 68 | 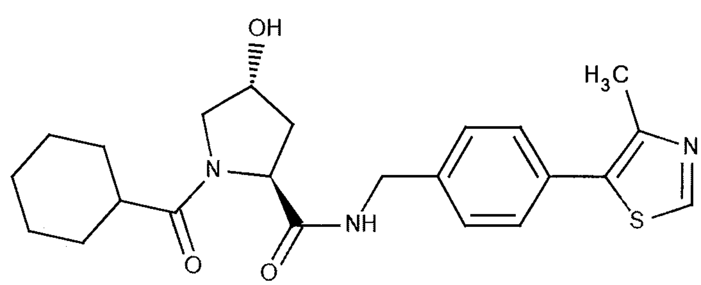 |
| 69 | 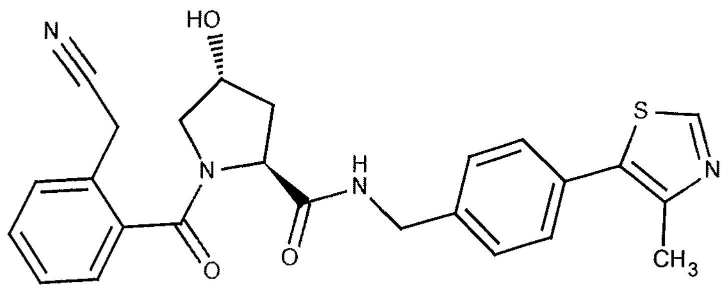 |

| Compound Number | Chemical Structure |
|---|---|
| 70 | 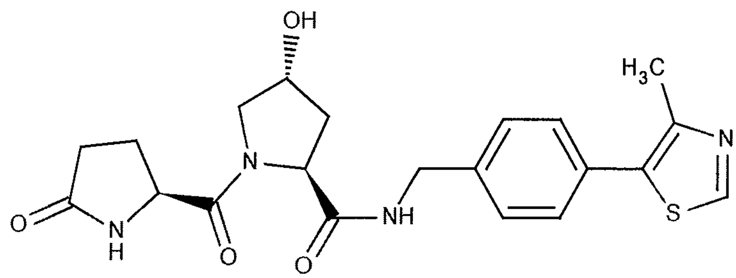 |
| 71 | 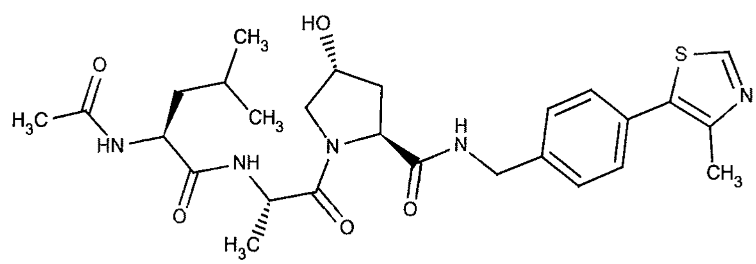 |
| 72 | 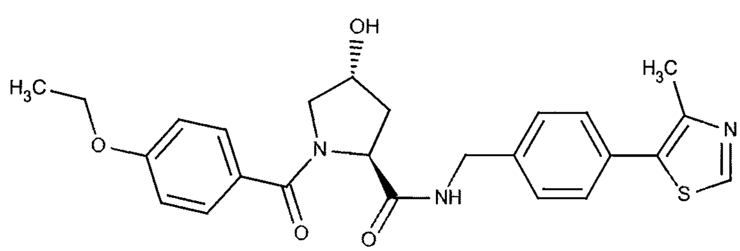 |

| Compound Number | Chemical Structure |
|---|---|
| 73 | 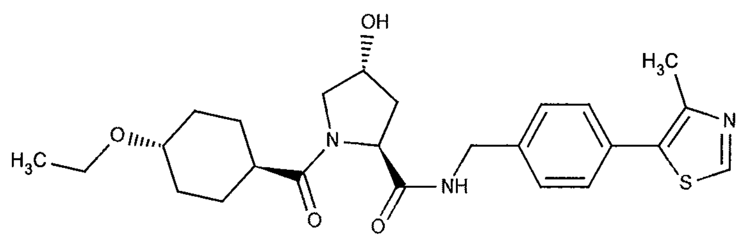 |
| 74 | 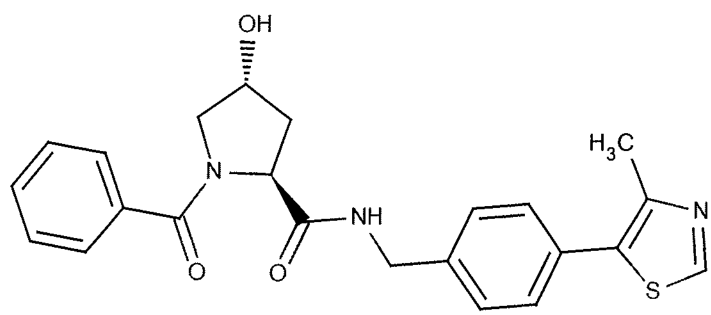 |
| 75 | 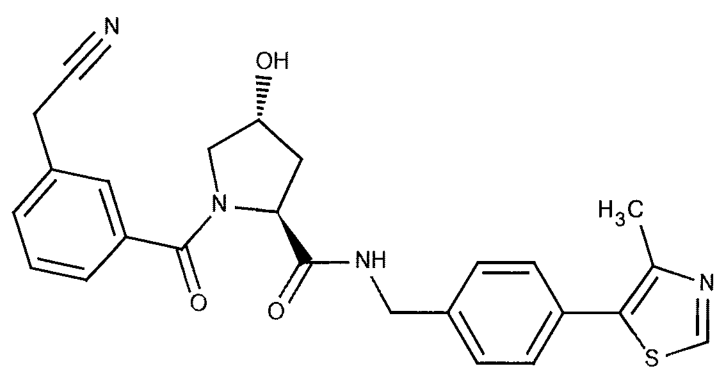 |

| Compound Number | Chemical Structure |
|---|---|
| 76 | 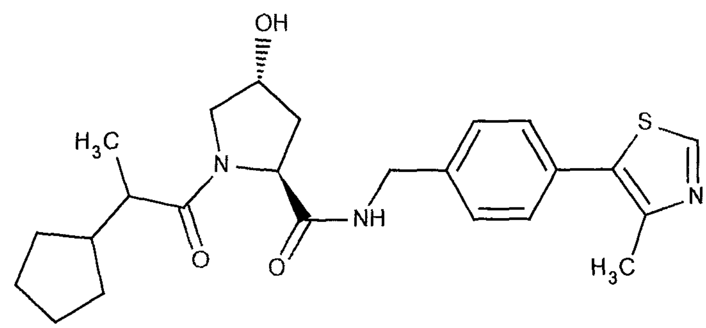 |
| 77 | 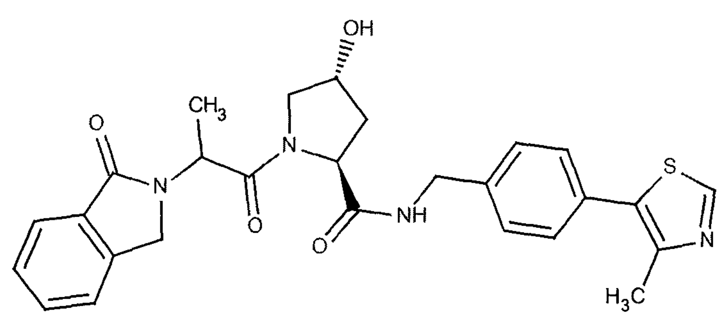 |
| 78 | 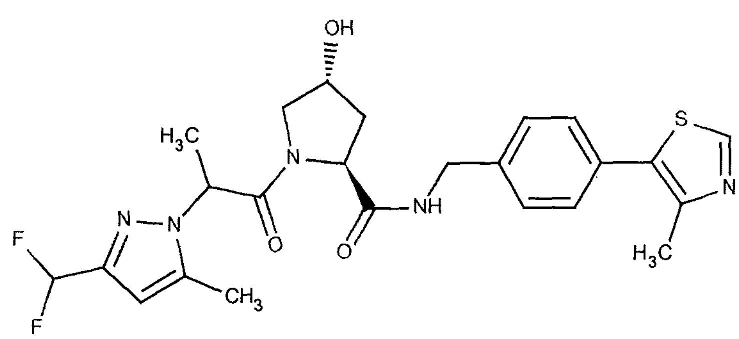 |

| Compound Number | Chemical Structure |
|---|---|
| 79 | 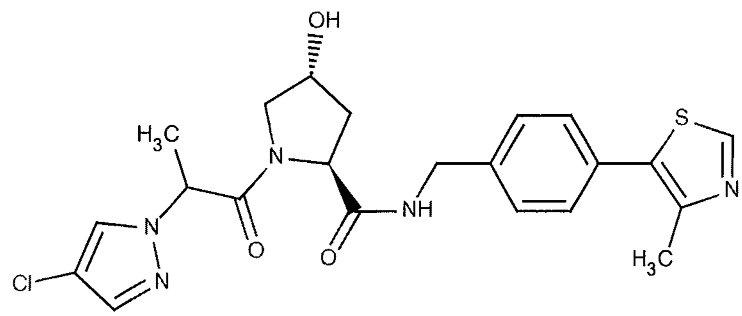 |
| 80 | 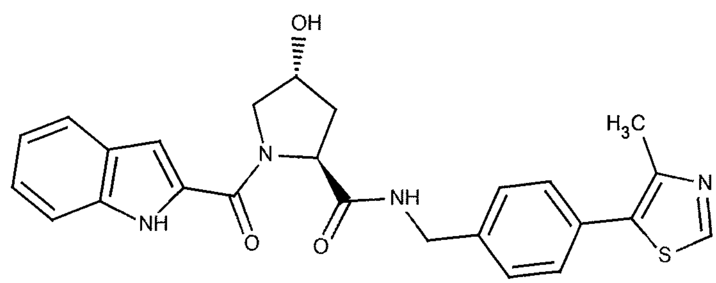 |
| 81 | 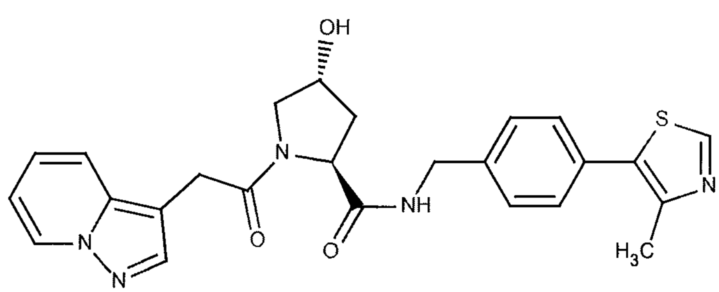 |

| Compound Number | Chemical Structure |
|---|---|
| 82 |  |
| 83 |  |
| 84 |  |

| Compound Number | Chemical Structure |
|---|---|
| 85 | 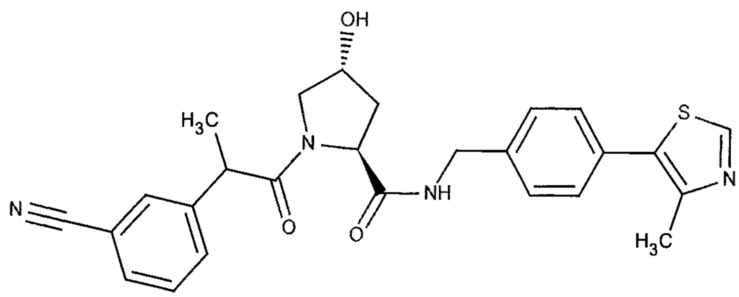 |
| 86 | 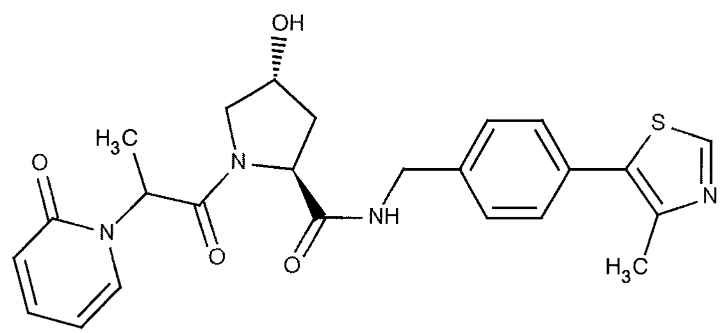 |
| 87 | 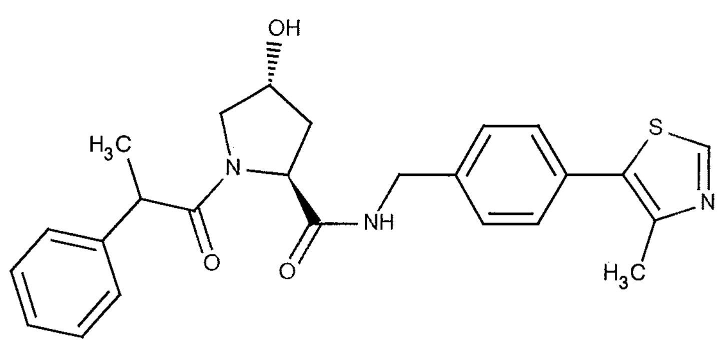 |

| Compound Number | Chemical Structure |
|---|---|
| 88 | 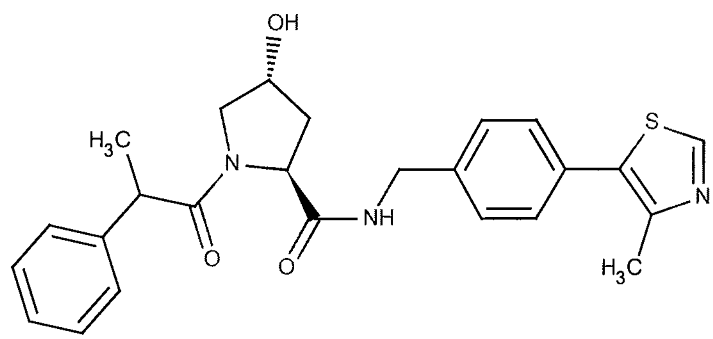 |
| 89 | 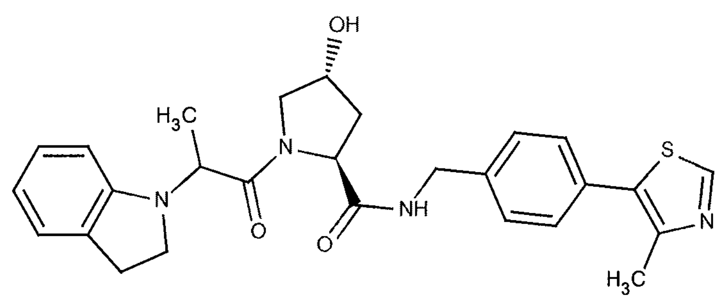 |
| 90 | 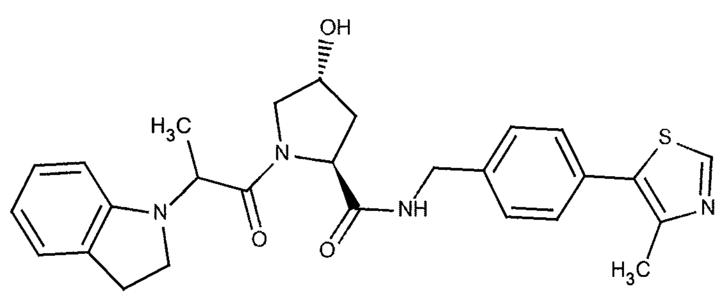 |

| Compound Number | Chemical Structure |
| --- | --- |
| 91 |  |
| 92 |  |
| 93 |  |

| Compound Number | Chemical Structure |
|---|---|
| 94 | 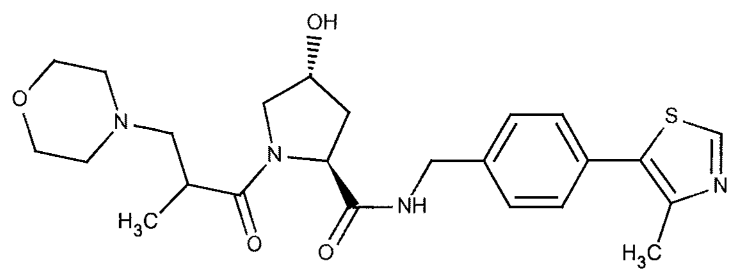 |
| 95 | 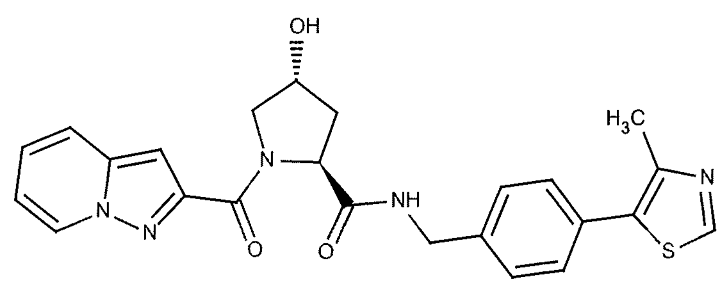 |
| 96 | 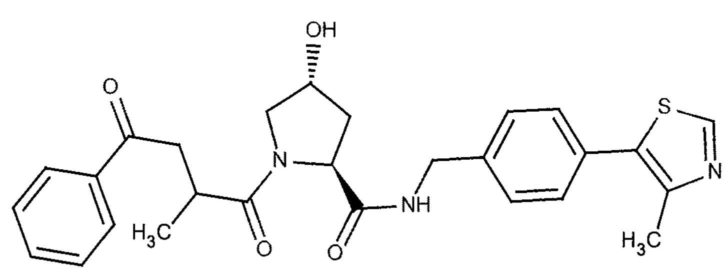 |

| Compound Number | Chemical Structure |
|---|---|
| 97 | 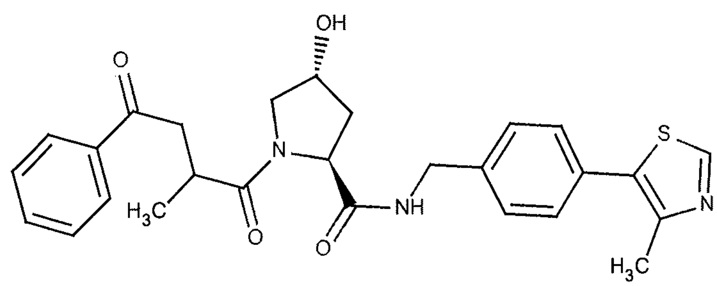 |
| 98 | 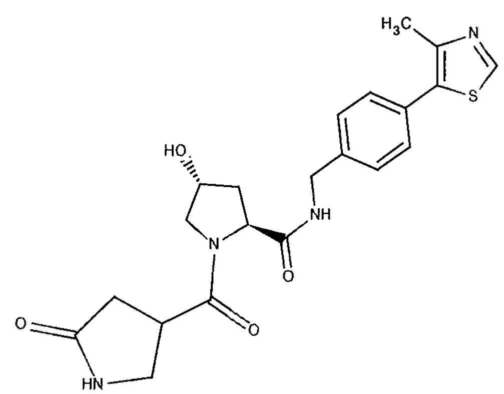 |
| 99 | 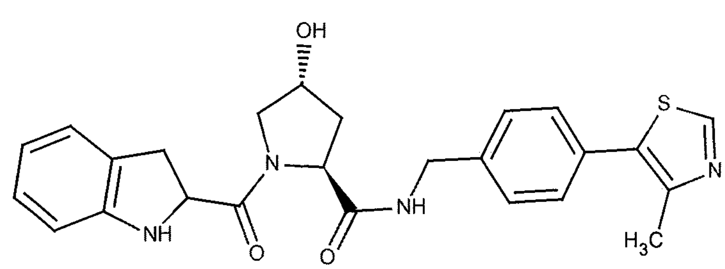 |

| Compound Number | Chemical Structure |
|---|---|
| 100 | 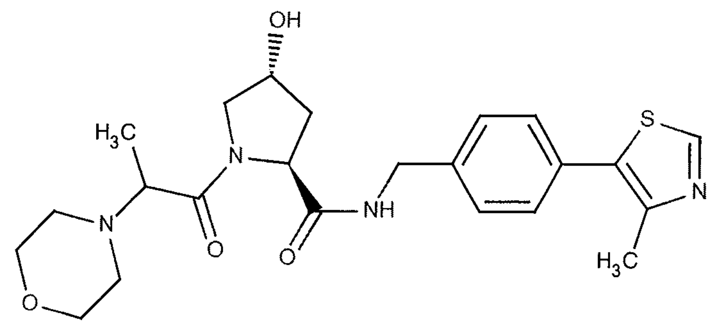 |
| 101 | 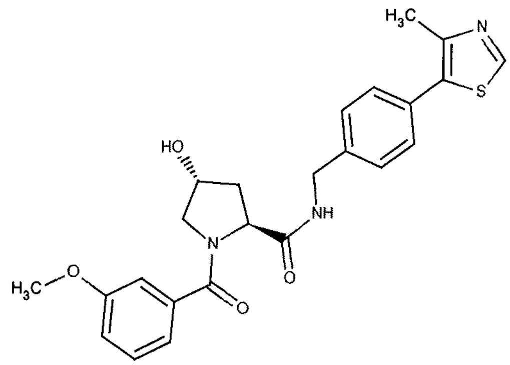 |
| 102 | 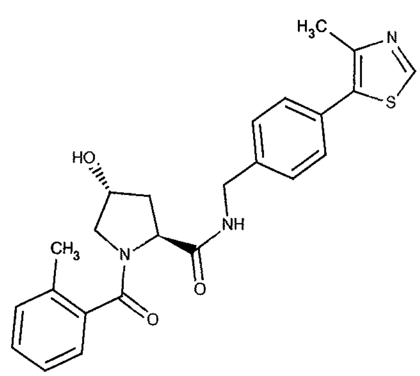 |

| Compound Number | Chemical Structure |
|---|---|
| 103 |  |
| 104 |  |
| 105 |  |

| Compound Number | Chemical Structure |
|---|---|
| 106 | 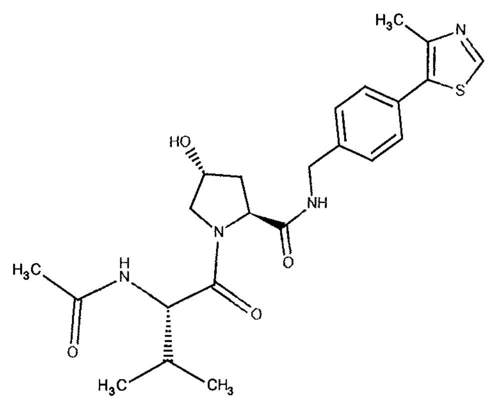 |
| 107 | 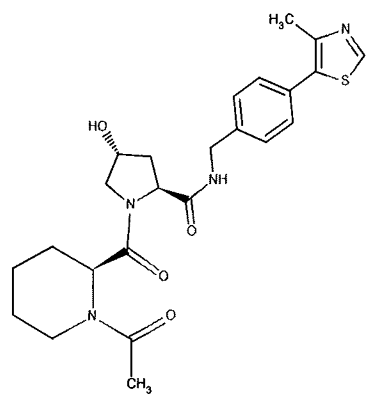 |
| 108 | 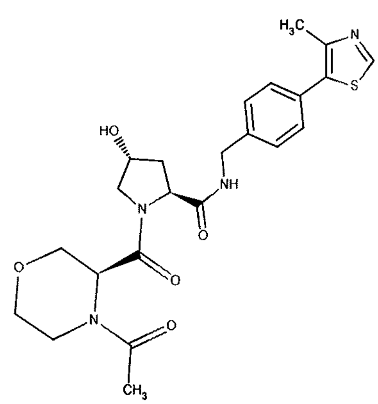 |
| |  |

| Compound Number | Chemical Structure |
|---|---|
| 109 |  |
| 110 |  |
| 111 |  |

| Compound Number | Chemical Structure |
|---|---|
| 112 | 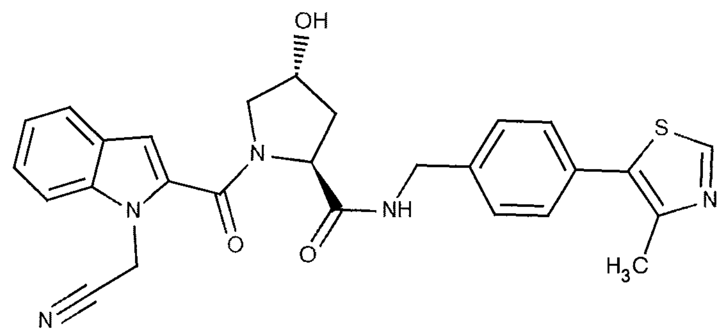 |
| 113 | 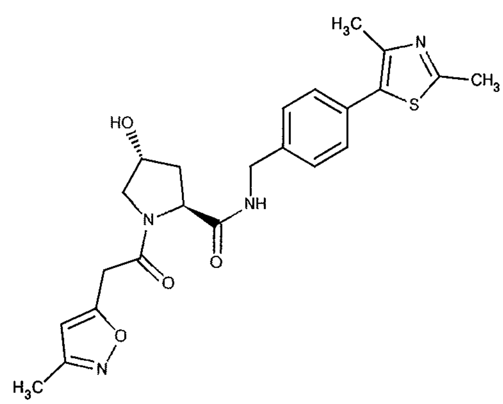 |
| 114 | 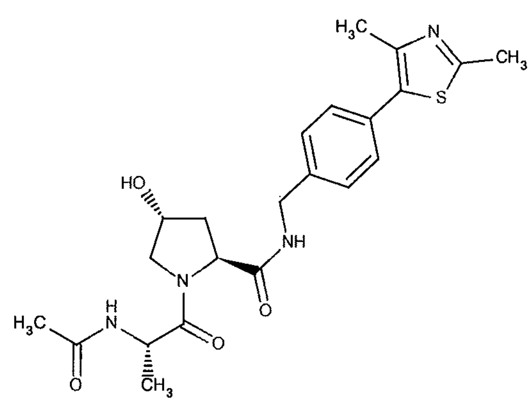 |

| Compound Number | Chemical Structure |
|---|---|
| 115 | 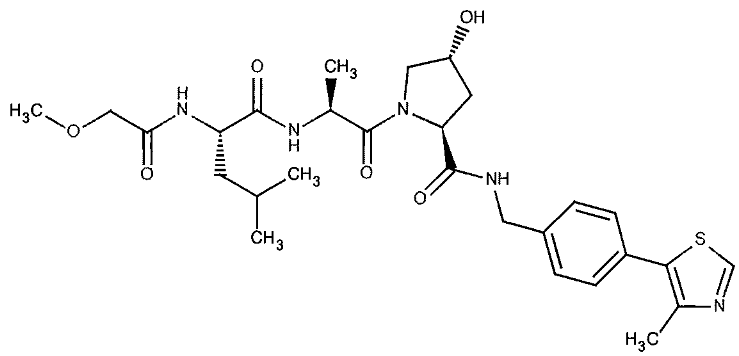 |
| 116 | 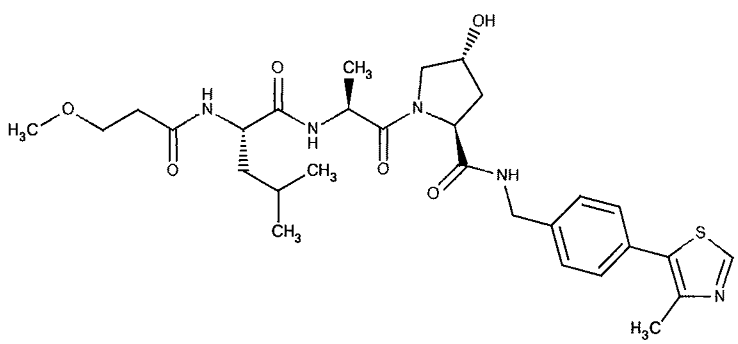 |
| 117 | 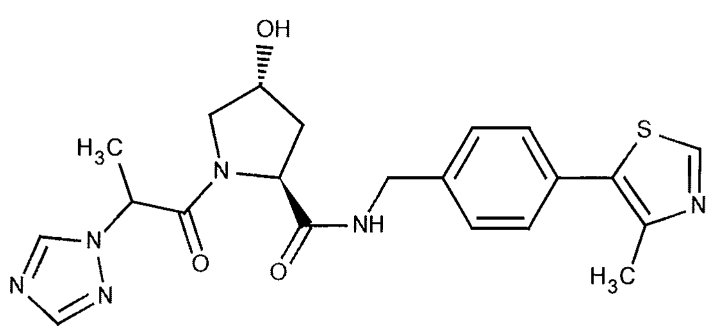 |

| Compound Number | Chemical Structure |
|---|---|
| 118 | 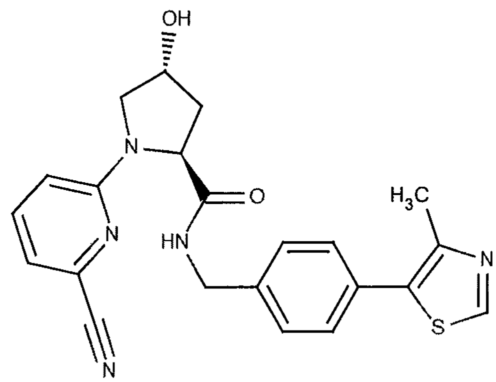 |
| 119 | 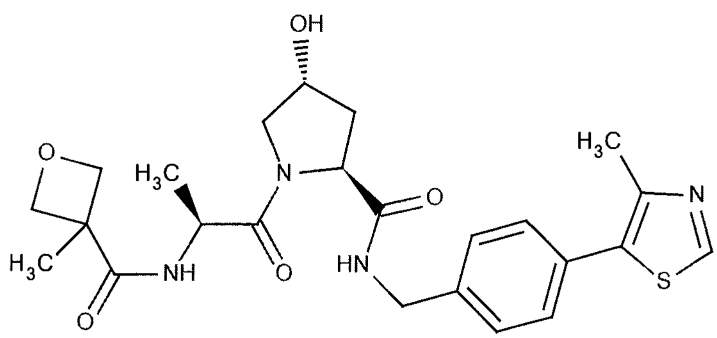 |
| 120 | 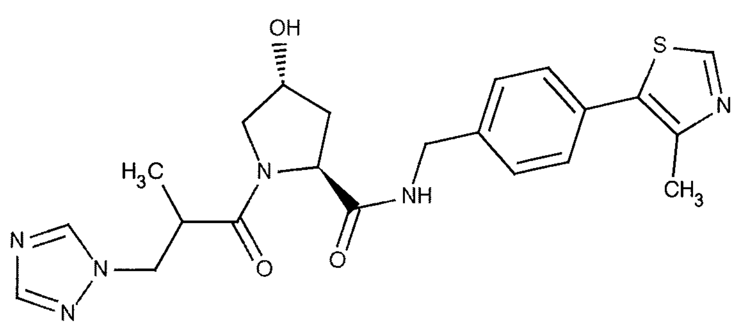 |

| Compound Number | Chemical Structure |
|---|---|
| 121 | 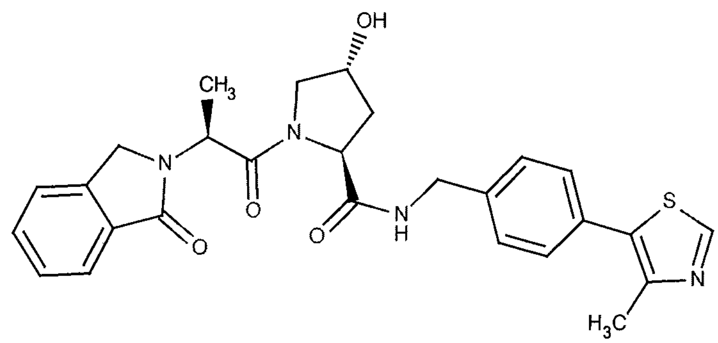 |
| 122 | 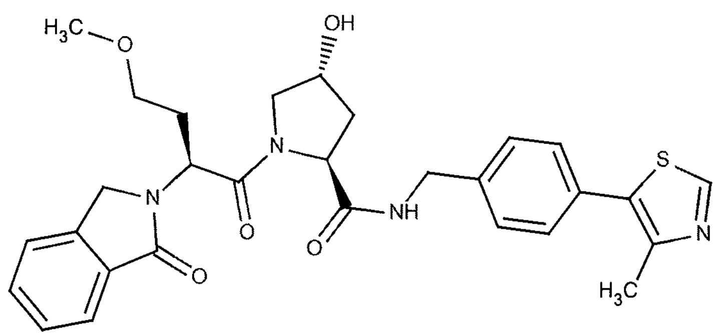 |
| 123 | 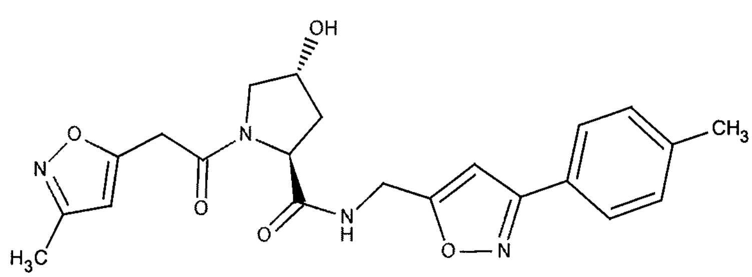 |

| Compound Number | Chemical Structure |
|---|---|
| 124 | 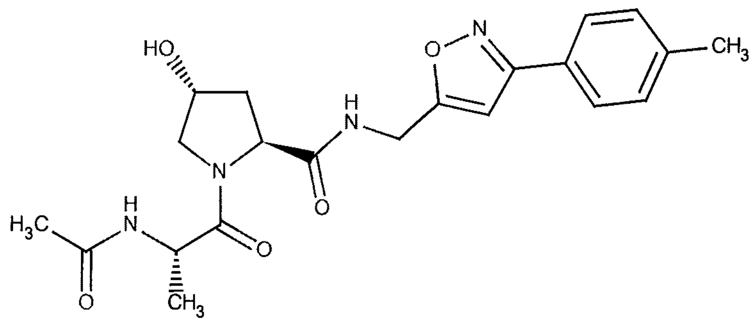 |
| 125 | 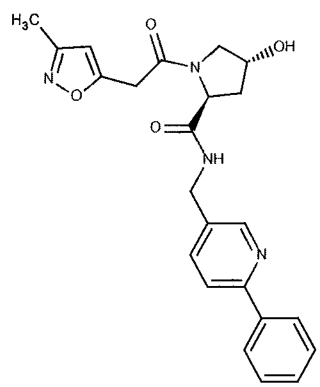 |
| 126 | 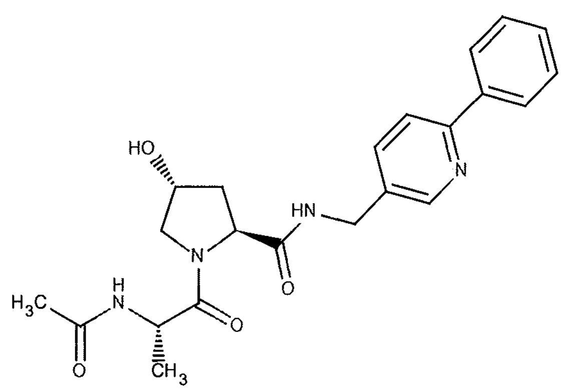 |

| Compound Number | Chemical Structure |
|---|---|
| 127 | 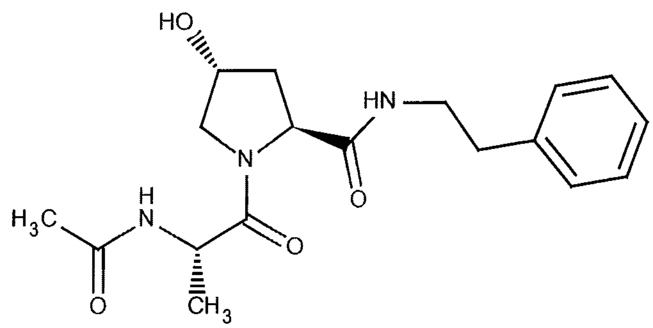 |
| 128 | 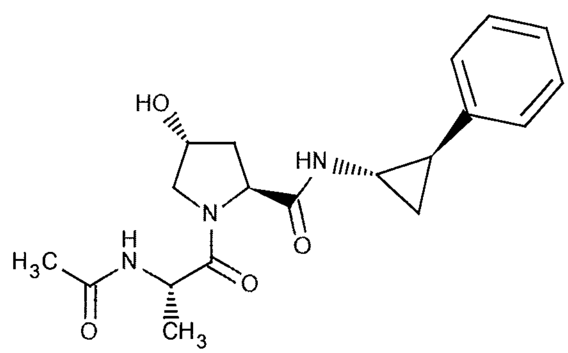 |
| 129 | 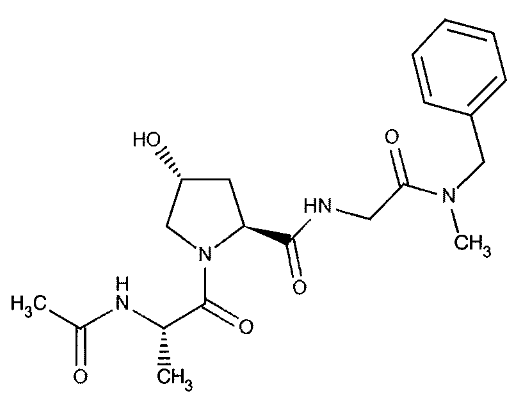 |

| Compound Number | Chemical Structure |
|---|---|
| 130 | 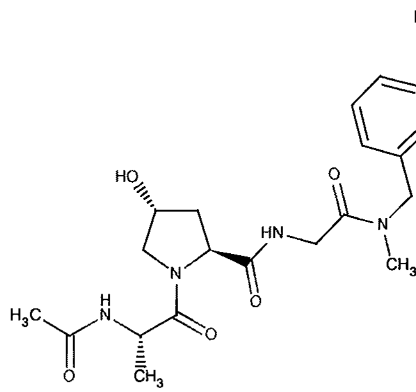 |
| 131 | 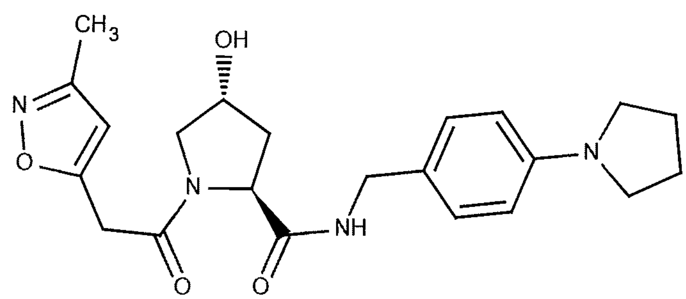 |
| 132 | 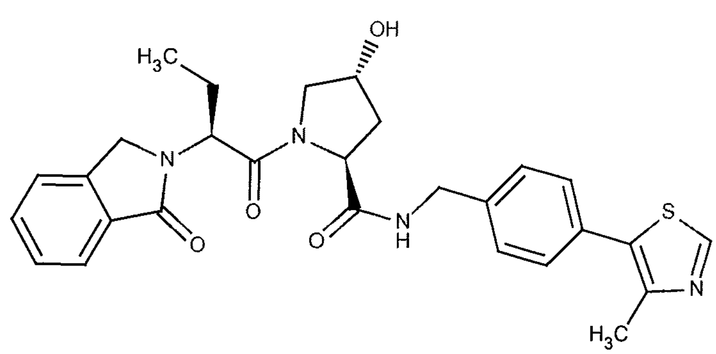 |

| Compound Number | Chemical Structure |
|---|---|
| 133 |  |
| 134 |  |
| 135 |  |

| Compound Number | Chemical Structure |
|---|---|
| 136 | 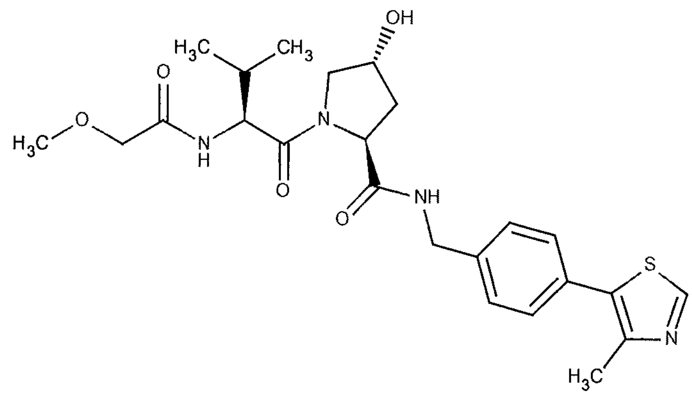 |
| 137 | 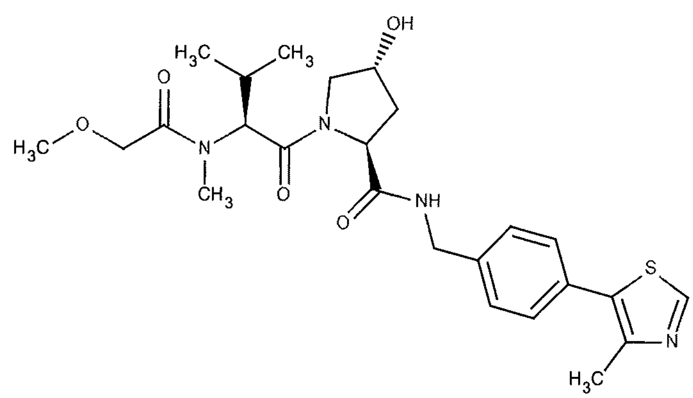 |
| 138 | 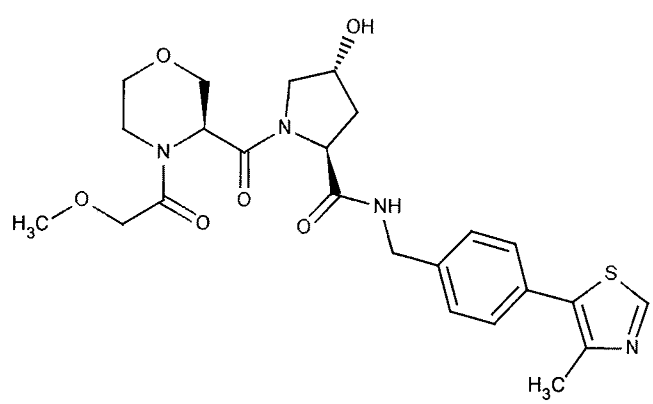 |

FIGURE 15 (Cont'd)

| Compound Number | Chemical Structure |
| --- | --- |
| 139 | 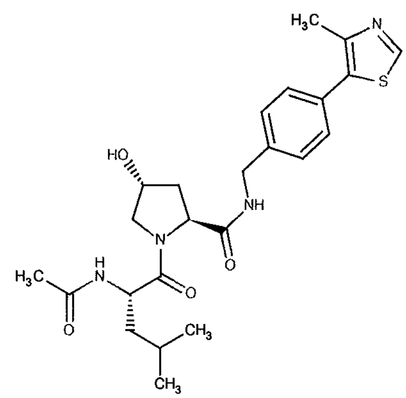 |
| 140 | 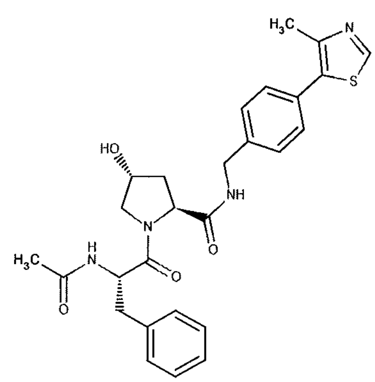 |
| 141 | 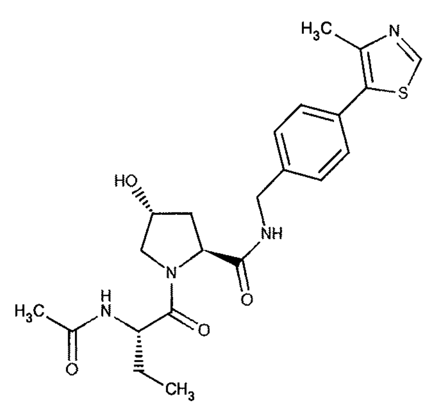 |

| Compound Number | Chemical Structure |
|---|---|
| 142 | 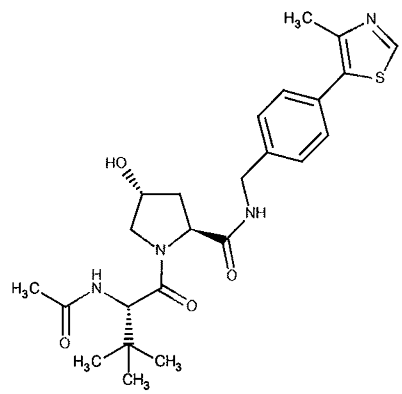 |
| 143 | 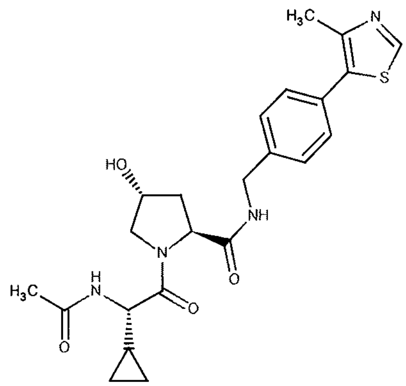 |
| 144 | 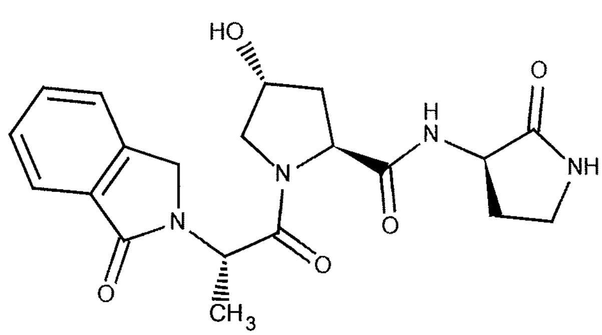 |

| Compound Number | Chemical Structure |
|---|---|
| 145 | 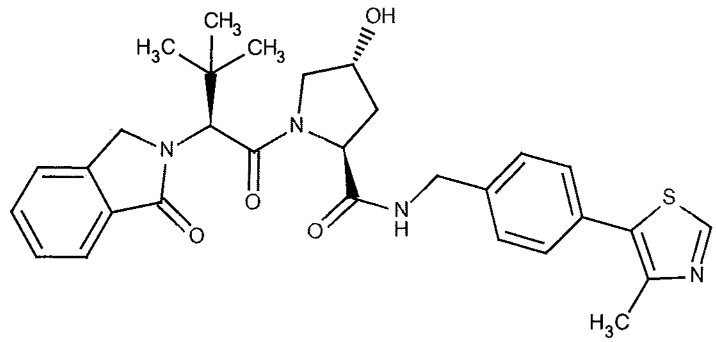 |
| 146 | 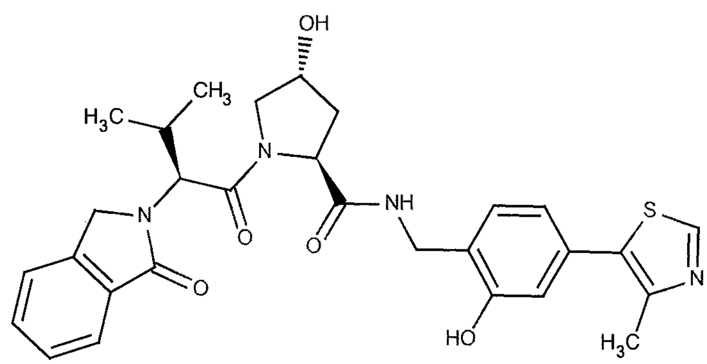 |
| 147 | 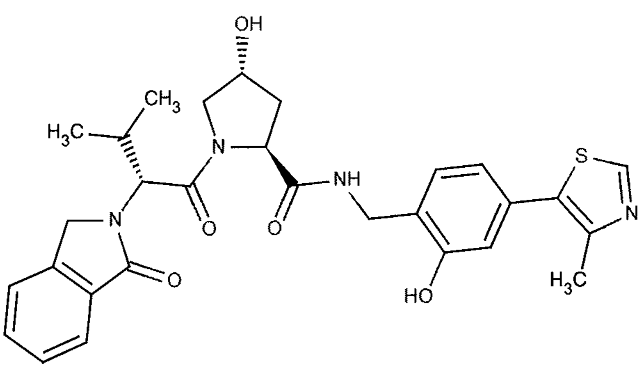 |

| Compound Number | Chemical Structure |
|---|---|
| 148 | 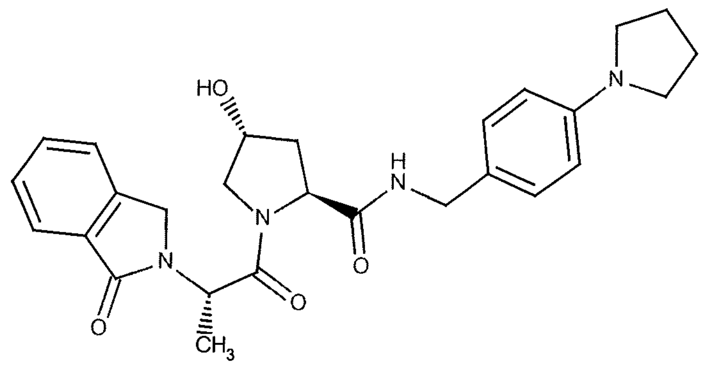 |
| 149 | 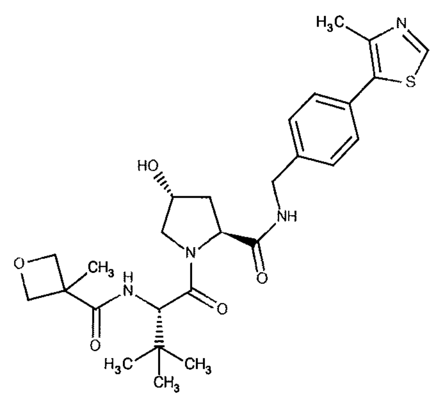 |
| 150 | 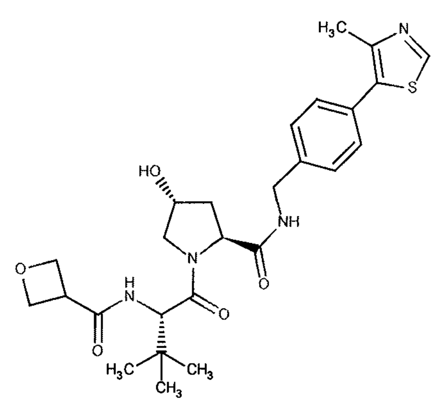 |

| Compound Number | Chemical Structure |
|---|---|
| 151 | 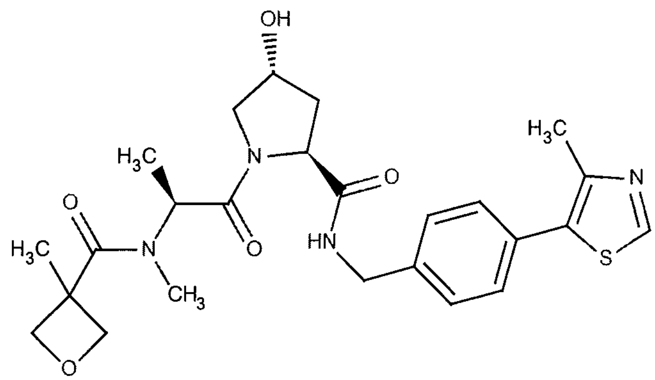 |
| 152 | 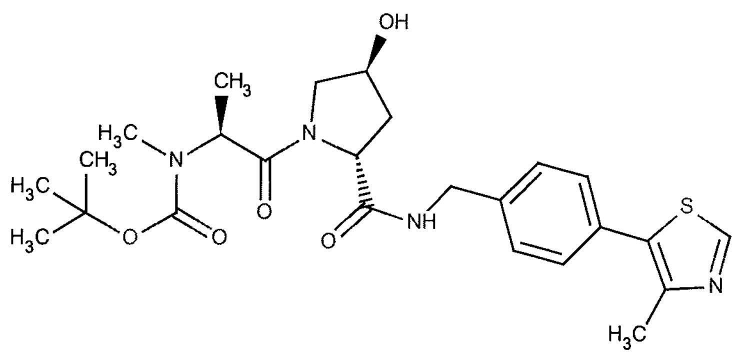 |
| 153 | 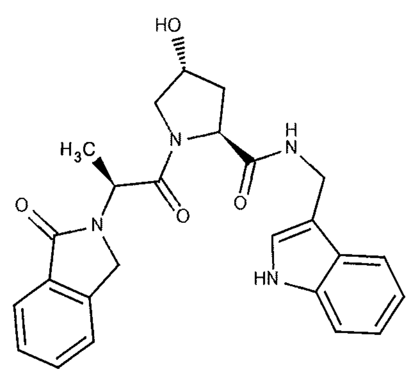 |

| Compound Number | Chemical Structure |
|---|---|
| 154 | 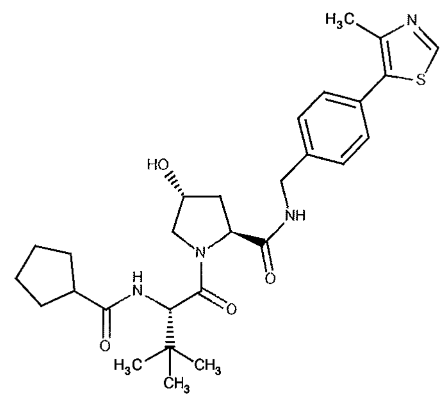 |
| 155 | 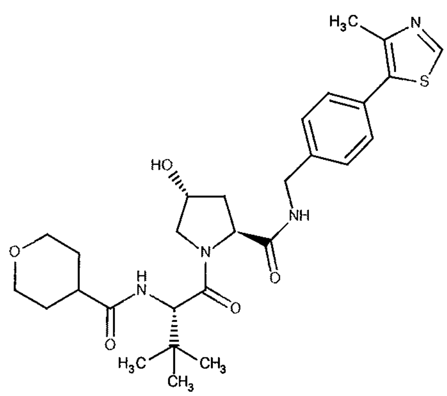 |
| 156 | 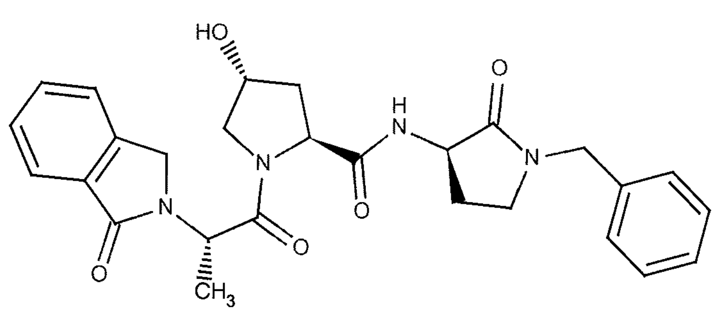 |

| Compound Number | Chemical Structure |
|---|---|
| 157 | 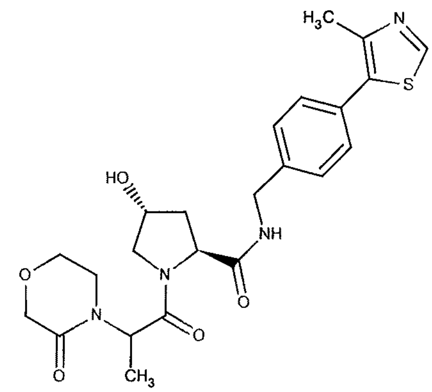 |
| 158 | 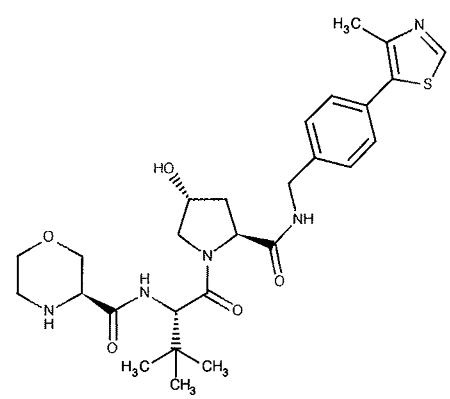 |
| 159 | 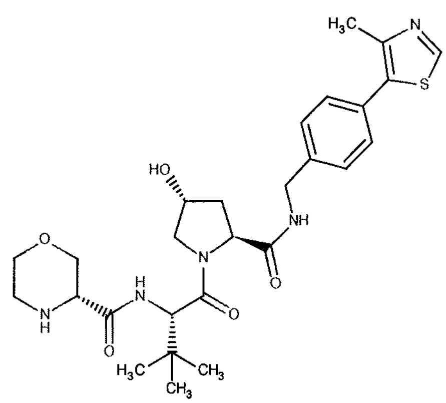 |

| Compound Number | Chemical Structure |
|---|---|
| 160 | 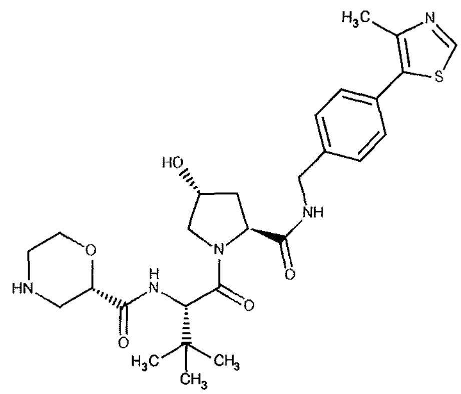 |
| 161 | 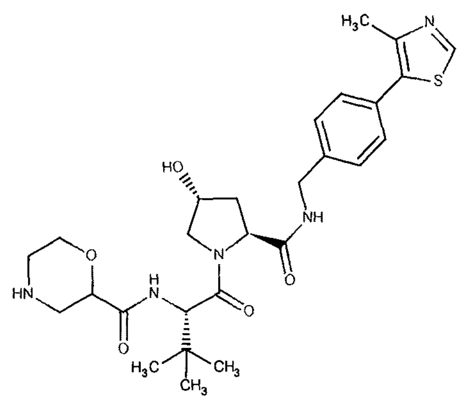 |
| 162 | 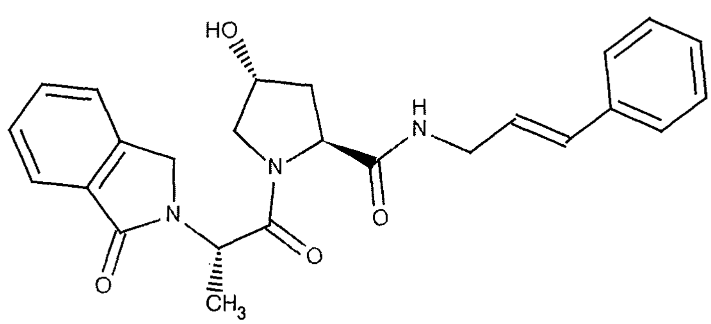 |

| Compound Number | Chemical Structure |
|---|---|
| 163 | 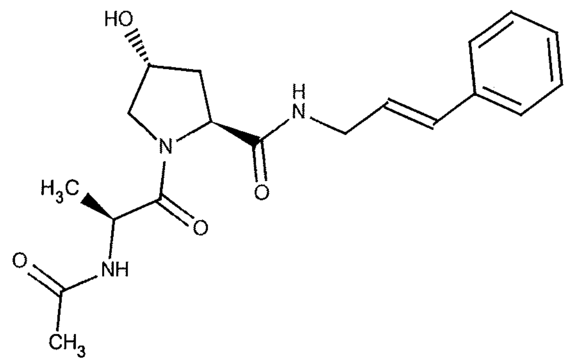 |
| 164 | <br>Isomer 1 |
| 165 | <br>Isomer 2 |

| Compound Number | Chemical Structure |
|---|---|
| 166 | {.center} Isomer 1 |
| 167 | {.center} Isomer 2 |
| 168 | 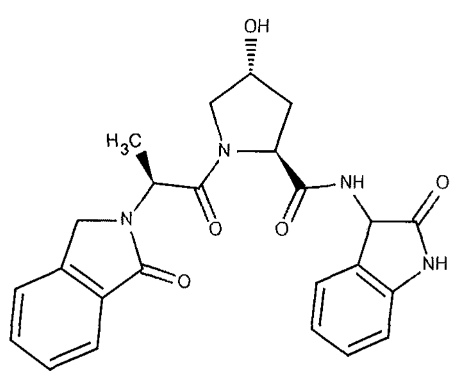 |

| Compound Number | Chemical Structure |
|---|---|
| 169 | 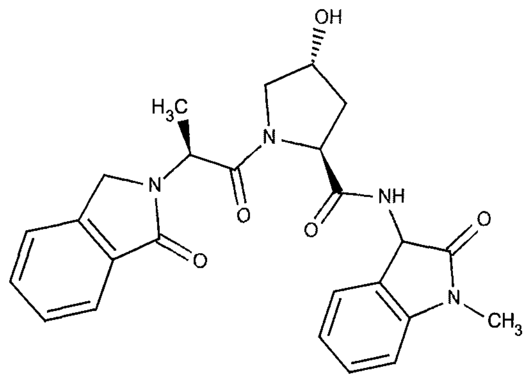 |
| 170 | <br>Isomer 1 |
| 171 | <br>Isomer 2 |

| Compound Number | Chemical Structure |
|---|---|
| 172 | 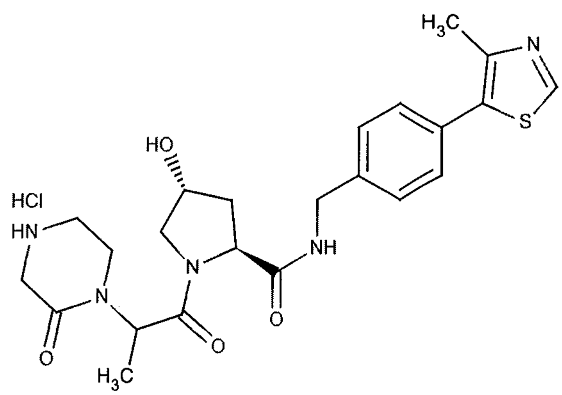 |
| 173 | 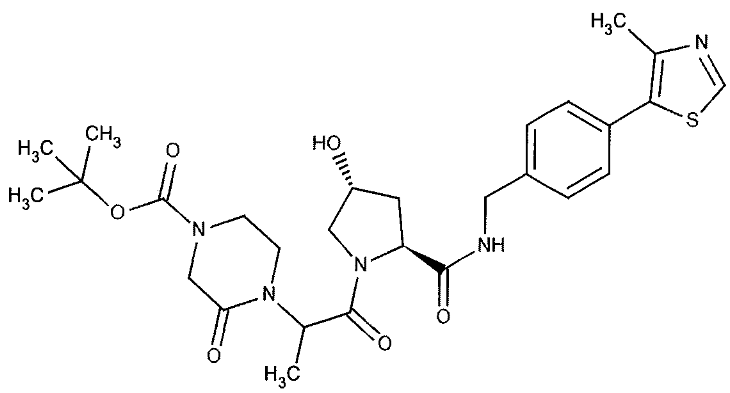 |
| 174 | 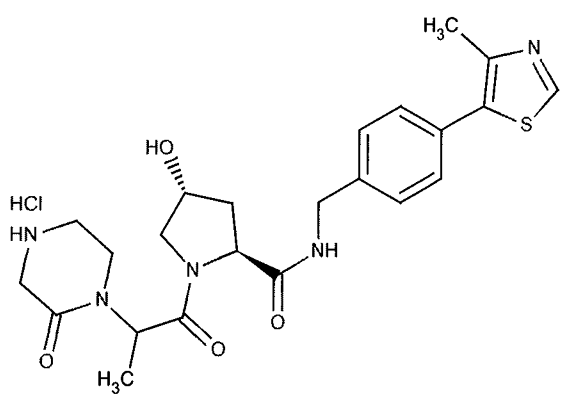 |

| Compound Number | Chemical Structure |
|---|---|
| 175 | 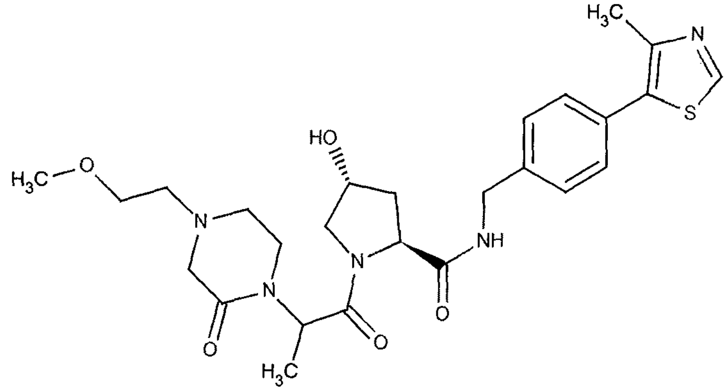 |
| 176 | 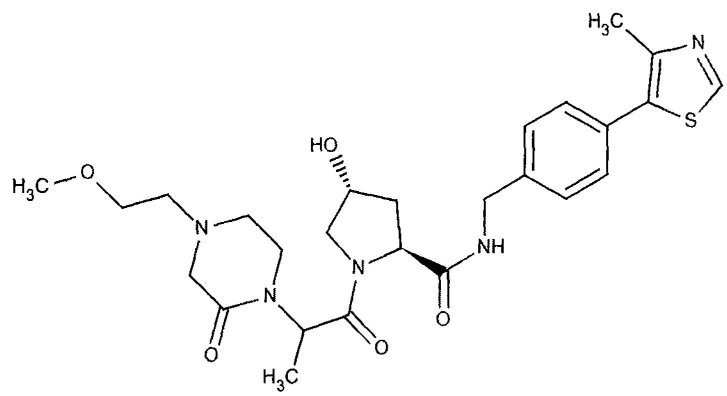 |
| 177 | 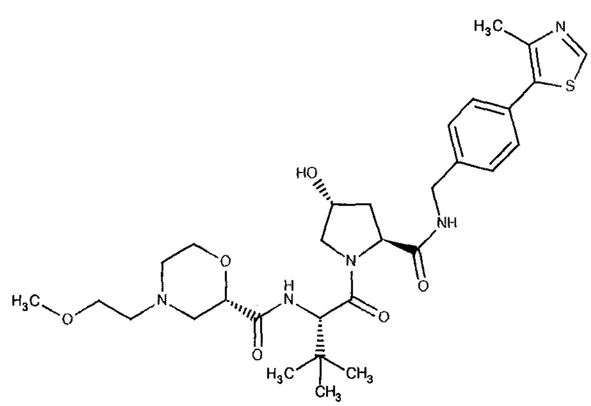 |

| Compound Number | Chemical Structure |
|---|---|
| 178 | 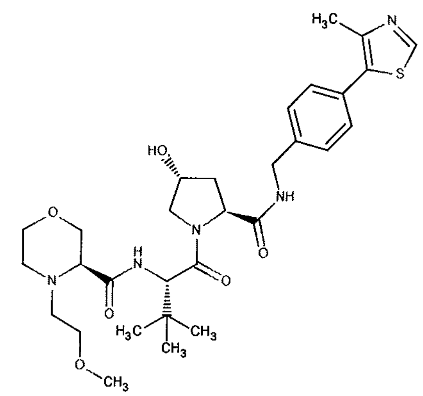 |
| 179 | 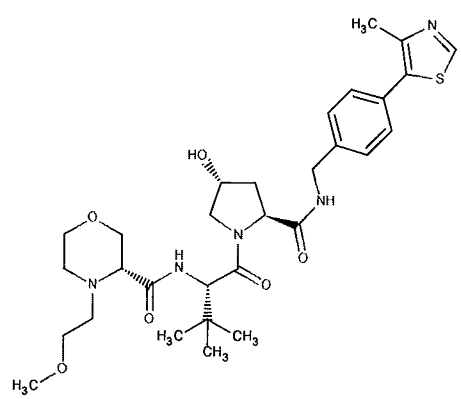 |
| 180 | 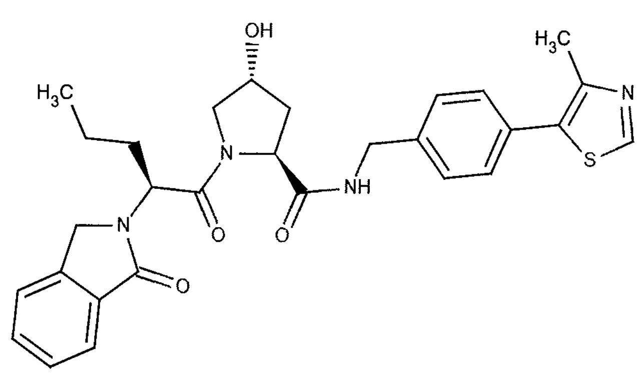 |

| Compound Number | Chemical Structure |
|---|---|
| 181 | 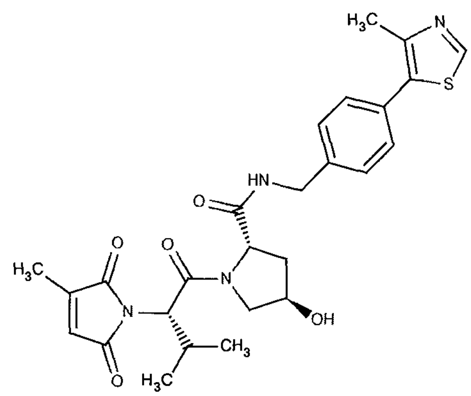 |
| 182 | 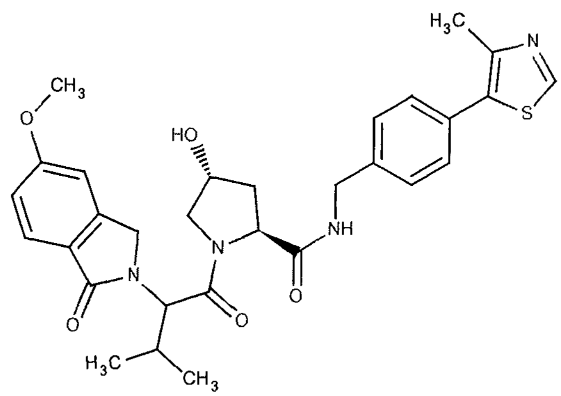 |
| 183 | 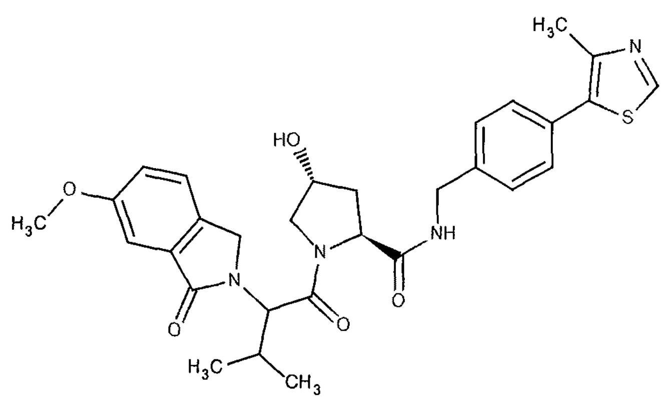 |

| Compound Number | Chemical Structure |
|---|---|
| 184 | 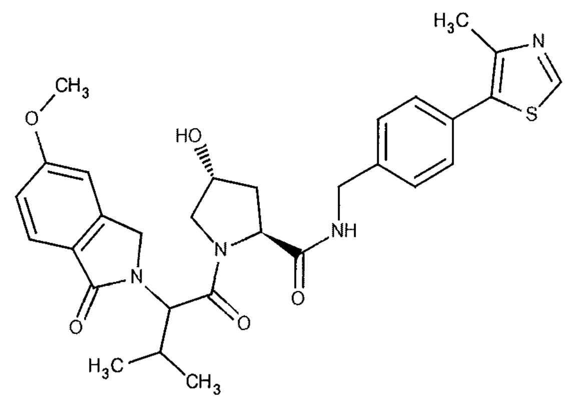 |
| 185 | 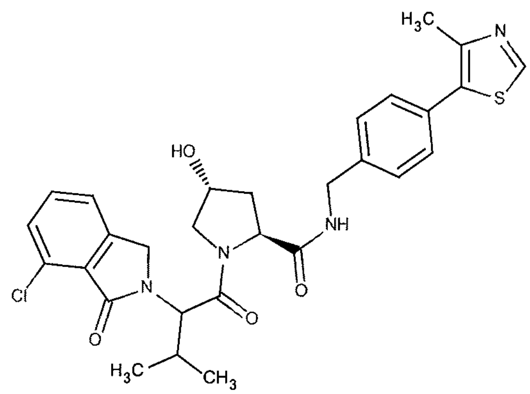 |

COMPOUNDS AND METHODS FOR THE ENHANCED DEGRADATION OF TARGETED PROTEINS AND OTHER POLYPEPTIDES BY AN E3 UBIQUITIN LIGASE

CROSS-REFERENCE TO RELATED APPLICATIONS

The present application is a 35 U.S.C. § 371 national phase application of, and claims priority to, PCT Application No. PCT/US2013/021136, filed Jan. 11, 2013, which claims priority under 35 U.S.C. § 119(e) to U.S. Provisional Patent Application No. 61/585,769, filed Jan. 12, 2012, all of which applications are incorporated herein by reference in their entireties.

RELATED APPLICATIONS AND GRANT SUPPORT

Statement Regarding Federally Sponsored Research or Development

This invention was made with government support under AI084140 awarded by National Institutes of Health. The government has certain rights in the invention.

FIELD OF THE INVENTION

The present invention relates to bifunctional compounds, which find utility as modulators of targeted ubiquitination, especially inhibitors of a variety of polypeptides and other proteins, which are degraded and/or otherwise inhibited by bifunctional compounds according to the present invention. In particular, the present invention is directed to compounds, which contain on one end a VHL ligand, which binds to the VHL E3 ubiquitin ligase (defined as a ubiquitin ligand binding moiety or ULM group) and on the other end a moiety, which binds a target protein (defined as a protein/polypeptide targeting moiety or PTM group) such that the target protein/polypeptide is placed in proximity to the ubiquitin ligase to effect degradation (and inhibition) of that protein. The present invention exhibits a broad range of pharmacological activities associated with compounds according to the present invention, consistent with the degradation/inhibition of targeted polypeptides.

PARTIES TO A JOINT RESEARCH AGREEMENT

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are YALE UNIVERSITY, GLAXOSMITHKLINE INTELLECTUAL PROPERTY DEVELOPMENT LIMITED, and CAMBRIDGE ENTERPRISE LIMITED UNIVERSITY OF CAMBRIDGE.

BACKGROUND OF THE INVENTION

E3 ubiquitin ligases (of which over 600 are known in humans)[1] confer substrate specificity for ubiquitination and are more attractive therapeutic targets than general proteasome inhibitors[3,4] due to their specificity for certain protein substrates. Although the development of ligands of E3 ligase has proven challenging, in part due to the fact that they must disrupt protein-protein interactions[5] recent developments have provided specific ligands which bind to these ligases. Protein-protein interaction interactions are notoriously difficult to target using small molecules due to their large contact surfaces and the shallow grooves or flat interfaces involved. Conversely, most small molecule drugs bind enzymes or receptors in tight and well-defined pockets.[6] Since the discovery of nutlins, the first small molecule E3 ligase inhibitors,[7] additional compounds have been reported that target Inhibitors of Apoptosis Proteins (IAPs),[8,9] $SCF^{Met30}$,[10] and $SCF^{Cdc4}$;[11] however, the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1.[12] The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. While HIF-1α is constitutively expressed, its intracellular levels are kept very low under normoxic conditions via its hydroxylation by prolyl hydroxylase domain (PHD) proteins and subsequent VHL-mediated ubiquitination (FIG. 1).

Using rational design, we have generated the first small molecule ligands of Von Hippel Lindau (VHL), the substrate recognition subunit of the E3 ligase VCB, an important target in cancer, chronic anemia and ischemia.[2] We have also obtained crystal structures of VHL with our most potent ligand, 15, confirming that the compound mimics the binding mode of the transcription factor HIF-1α, the major substrate of VHL.

From earlier biochemical and structural studies of a hydroxylated HIF peptide bound to VHL, it became clear that hydroxyproline played an important role in mediating this protein:protein interaction. As a consequence of that work, the present inventors developed a hydroxylated HIF peptide:VHL fluorescence polarization (FP) binding assay with which they assayed >120 compounds possessing the central hydroxyproline residue flanked by non-peptidic moieties. Further to that research, the inventors now have developed co-crystal structures of VHL complexed with seven of the top compounds. Analysis of these ligand bound structures is driving the design/synthesis of the next generation of VHL ligands, which are linked with protein binding moieties to produce bifunctional compounds according to the present invention.

A principal rationale for the present invention is the need for a small molecule E3 ligase ligand for our PROTAC (Proteolysis Targeting Chimera) technology. This technology brings targeted proteins/polypeptides to E3 ligases for ubiquitination and subsequent proteasomal degradation. In several proof-of-concept experiments, the present inventors demonstrated the utility of this approach using the short peptide sequence from HIF that binds VHL. In order to make a more 'drug-like' PROTAC, the inventors have replaced the HIF peptide with a 'small molecule' VHL ligand, thus providing a means to recruit proteins to E3 ligases for ubiquitination and degradation, to the endpoint of providing therapies based upon this protein degradation.

OBJECTS OF THE INVENTION

It is an object of the invention to provide compounds which function to recruit endogenous proteins to E3 Ubiquitin Ligase for degradation.

It is an additional object of the invention to provide compounds which modulate protein degradation in a patient or subject and can be used for treating disease states or conditions which are modulated through the degraded protein.

It is another object of the invention to provide pharmaceutical compositions based upon the above-described modulators, especially including inhibitors for therapeutic treatment of a patient or subject, preferably including a human patient or subject.

It is also an object of the invention to provide methods for determining protein binding moieties which bind to proteins of interest.

It is yet another object of the invention to provide methods for identifying endogenous proteins in a biological system, especially including a human system, which bind to protein binding moieties in compounds according to the present invention.

It is still another object of the invention to provide methods for identifying the effects of the degradation of proteins of interest in a biological system using compounds according to the present invention.

It is still another aspect of the invention to provide methods for treating patients where the degradation of a targeted protein will produce an intended therapeutic effect.

It is another object of the invention to provide compounds and compositions which may be used in a first medical application.

It is yet another aspect of the invention to provide compounds and/or compositons which are used for treating patients where the degradation of a targeted protein will produce an intended therapeutic effect.

Any one or more of these and/or other objects of the invention may be readily gleaned from a routine scrutiny of the description of the invention which follows.

BRIEF DESCRIPTION OF THE FIGURES

FIGS. 6-12A and B show the activity of individual compounds according to the present invention in the described VHL polarization/displacement assay. Compounds according to the present invention are indicated with numerals at the top of each graph. Control compound is presented in FIG. 15 B and served as minimum polarization (maximum displacement) for comparison purposes. The percent inhibition as presented was determined by normalizing to maximum and minimum polarization, and graphed against the log [VL]. $IC_{50}$ values were determined using Prism 5 for each replicate (n=9), where were then averaged to determine the average $IC_{50}$ and the standard of error of the mean (SEM).

BRIEF DESCRIPTION OF THE INVENTION

Figure 1:
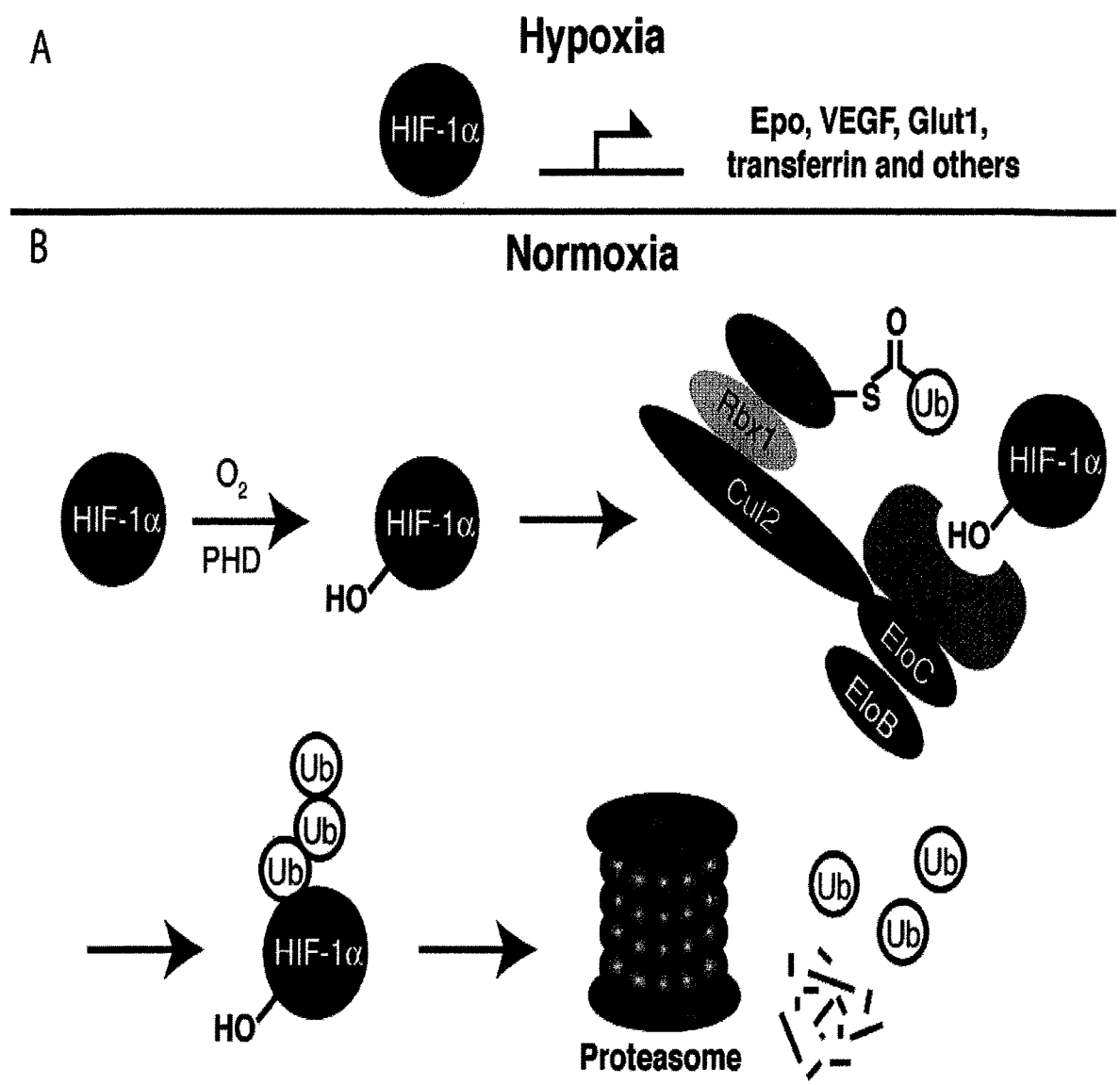
FIG. 1 shows (A) HIF-1α accumulation leads to the transcriptional upregulation of genes involved in the hypoxic response, such as erythropoietin and VEGF. (B) Under normoxic conditions, HIF-1α is hydroxylated, recognized by VHL, ubiquitinated and degraded by the proteasome, preventing transcriptional upregulation.

The present invention is based on the discovery that an ubiquitin pathway protein ubiquitinates any target protein once the ubiquitin pathway protein and the target protein are placed in proximity by a chimeric construct that binds the ubiquitin pathway protein and the target protein. Accordingly the present invention provides a composition that results in the ubiquitination of a chosen target protein. The present invention also provides a library of compositions and the use thereof.

In one embodiment, the present invention provides a composition useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked together, preferably through a linker, wherein the ubiquitin pathway protein binding moiety recognizes an ubiquitin pathway protein and the targeting moiety recognizes a target protein and wherein the ubiquitin pathway protein binding moiety is coupled to the targeting moiety.

In another embodiment, the present invention provides a library of compounds. The library comprises more than one compound wherein each composition has a formula of A-B, wherein A is a ubiquitin pathway protein binding moiety (preferably, an E3 ubiquitin ligase moiety as otherwise disclosed herein) and B is a protein binding member of a molecular library, wherein A is coupled (preferably, through a linker moiety) to B, and wherein the ubiquitin pathway protein binding moiety recognizes an ubiquitin pathway protein, in particular, an E3 ubiquitin ligase. In a particular embodiment, the library contains a specific ubiquitination recognition peptide of VHL for an E3 ubiquitin ligase (ubiquitin pathway protein binding moiety as otherwise disclosed herein) with random target protein binding elements (e.g., a chemical compound library). As such, the target protein is not determined in advance and the method can be used to determine the activity of a putative protein binding element and its pharmacological value as a target upon degradation by ubiquitin ligase.

In still another embodiment, the present invention provides a method of screening a library of the present invention to identify a compound containing a targeting moiety, which recognizes a target protein associated with a predetermined function of a cell. The method comprises incubating a cell with a pool of entities from the library; monitoring the predetermined function of the cell; identifying a pool of entities that change the predetermined function of the cell; incubating the cell with a composition from the identified pool of entities; monitoring the predetermined function of the cell; and identifying a composition that changes the predetermined function of the cell, wherein the identified composition contains a targeting moiety which recognizes a target protein associated with the predetermined function.

In another embodiment, the present invention provides a method of screening a library of the present invention to identify a composition containing a targeting moiety, which recognizes a target protein associated with a predetermined function of a cell. The method comprises incubating a cell with each composition from the library; monitoring the predetermined function of the cell; identifying a composition that changes the predetermined function of the cell; wherein the identified composition contains a targeting moiety, which recognizes a target protein associated with the predetermined function.

In still another embodiment, the present invention provides a method of identifying a target protein associated with a predetermined function of a cell. The method comprises incubating a cell with a composition from the library of the present invention; monitoring the predetermined function of the cell; identifying a composition that changes the predetermined function of the cell; identifying a target protein that binds to the identified composition, wherein the target protein is associated with the predetermined function of the cell.

In yet another embodiment, the present invention provides a method of identifying a target protein associated with a predetermined function of a cell. The method comprises incubating a cell with a pool of entities from the library of the present invention; monitoring the predetermined function of the cell; identifying a pool of entities that change the predetermined function of the cell; incubating the cell with a composition from the identified pool of entities; monitoring the predetermined function of the cell; identifying a composition that changes the predetermined function of the cell; and identifying a target protein that binds to the identified composition, wherein the target protein is associated with the predetermined function of the cell.

In yet another embodiment, the present invention provides a method of ubiquitinating/degrading a target protein in a cell. The method comprises administering a bifunctional composition comprising an ubiquitin pathway protein binding moiety and a targeting moiety, preferably linked through a linker moiety, as otherwise described herein, wherein the ubiquitin pathway protein binding moiety is coupled to the targeting moiety and wherein the ubiquitin pathway protein binding moiety recognizes a ubiquitin pathway protein (e.g., an ubiquitin ligase, preferably an E3 ubiquitin ligase) and the targeting moiety recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In another embodiment, the present invention is directed to a method of treating a patient in need for a disease state or condition modulated through a protein where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In one embodiment, the present invention is directed to a compound according to the structure:

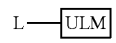

Where L is a linker group and ULM is a ubiquitin ligase binding moiety, wherein said linker group is optionally further linked to a PTM group.

In another embodiment, the present invention is directed to a compound which comprises a PTM group according to the general structure:

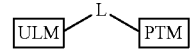

Where ULM is an ubiquitin ligase binding moiety, preferably a ligand, which binds an ubiquitin ligase, preferably an E3 ubiquitin ligase;

PTM is a chemical moiety (protein targeting moiety), which binds to a target protein or polypeptide, which is ubiquitinated by an ubiquitin ligase and is chemically linked directly to the ULM group or through a linker moiety L, or PTM is alternatively a ULM' group which also an ubiquitin ligase binding moiety, which may be the same or different than the ULM group and is linked directly to the ULM group directly or through the linker moiety; and L is a linker moiety which may be present or absent and which chemically (covalently) links ULM to PTM, Or a pharmaceutically acceptable salt, enantiomer, stereoisomer, solvate or polymorph thereof.

In certain aspects of the invention, where PTM is a ULM' group, the compound resembles a dimeric compound where both ends of the compound comprise an ubiquitin ligase binding moiety as otherwise described herein.

In preferred aspects of the invention, ULM and where present, ULM', are each independently a group according to the chemical structure:

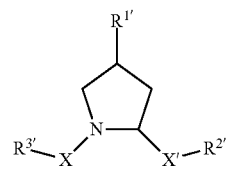

Where $R^{1'}$ is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—$(C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—$(C_1$-$C_6$ alkyl), an optionally substituted —$(CH_2)_n$C(O)—O—$(C_1$-$C_6$ alkyl), an optionally substituted —$(CH_2O)_n$COOH, an optionally substituted —$(OCH_2)_n$O—$(C_1$-$C_6$ alkyl), an optionally substituted —$(CH_2O)_n$C(O)—$(C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—$(C_1$-$C_6$ alkyl), an optionally substituted —$(CH_2CH_2O)_n$C(O)—$(C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ are each independently H or a $C_1$-$C_6$ alkyl group which may be optionally substituted with one or two hydroxyl groups or up to three halogen groups (preferably fluorine);

$R_S$ is a $C_1$-$C_6$ alkyl group, an optionally substituted aryl, heteroaryl or heterocycle group or a —$(CH_2)_m NR_1R_2$ group, X and X' are each independently C=O, C=S, —S(O), $S(O)_2$, (preferably X and X' are both C=O);

$R^{2'}$ is an optionally substituted —$(CH_2)_n$—(C=O)$_u$(NR$_1$)$_v$(SO$_2$)$_w$alkyl group, an optionally substituted —$(CH_2)_n$—(C=O)$_u$(NR$_1$)$_v$(SO$_2$)$_w$NR$_{1N}$R$_{2N}$ group, an optionally substituted —$(CH_2)_n$—(C=O)$_u$(NR$_1$)$_v$(SO$_2$)$_w$-Aryl, an optionally substituted —$(CH_2)_n$—(C=O)$_u$(NR$_1$)$_v$(SO$_2$)$_w$-Heteroaryl, an optionally substituted —$(CH_2)_n$—(C=O)$_v$NR$_1$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—(C=O)$_u$(NR$_1$)$_v$(SO$_2$)$_w$-Aryl, an optionally substituted —NR$^1$—(CH$_2$)$_n$—(C=O)$_u$(NR$_1$)$_v$(SO$_2$)$_w$-Heteroaryl or an optionally substituted —NR$^1$—(CH$_2$)$_n$—(C=O)$_v$NR$_1$(SO$_2$)$_w$-Heterocycle, an optionally substituted
—$X^{R2'}$-alkyl group; an optionally substituted
—$X^{R2'}$-Aryl group; an optionally substituted
—$X^{R2'}$-Heteroaryl group; an optionally substituted
—$X^{R2'}$-Heterocycle group; an optionally substituted;

$R^{3'}$ is an optionally substituted alkyl, an optionally substituted —(CH$_2$)$_n$—C(O)$_u$(NR$_1$)$_v$(SO$_2$)$_w$-alkyl, an optionally substituted —(CH$_2$)$_n$—C(O)$_u$(NR$_1$)$_v$(SO$_2$)$_w$—NR$_{1N}$R$_{2N}$, an optionally substituted —(CH$_2$)$_n$—C(O)$_u$(NR$_1$)$_v$(SO$_2$)$_w$—NR$_1$C(O)R$_{1N}$, an optionally substituted —(CH$_2$)$_n$—C(O)$_u$(NR$_1$)$_v$(SO$_2$)$_w$—C(O)NR$_1$R$_2$, an optionally substituted —(CH$_2$)$_n$—C(O)$_u$(NR$_1$)$_v$(SO$_2$)$_w$-Aryl, an optionally substituted —(CH$_2$)$_n$—C(O)$_u$(NR$_1$)$_v$(SO$_2$)$_w$-Heteroaryl, an optionally substituted —(CH$_2$)$_n$—C(O)$_u$(NR$_1$)$_v$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—C(O)$_u$(NR$_1$)$_v$(SO$_2$)$_w$-Aryl, an optionally substituted —NR$^1$—(CH$_2$)$_n$—C(O)$_u$(NR$_1$)$_v$(SO$_2$)$_w$-Heteroaryl, an optionally substituted —NR$^1$—(CH$_2$)$_n$—C(O)$_u$(NR$_1$)$_v$(SO$_2$)$_w$-Heterocycle, an optionally substituted —O—(CH$_2$)$_n$—(C=O)$_u$(NR$_1$)$_v$(SO$_2$)$_w$-alkyl, an optionally substituted —O—(CH$_2$)$_n$—(C=O)$_u$(NR$_1$)$_v$(SO$_2$)$_w$—NR$_{1N}$R$_{2N}$, an optionally substituted —O—(CH$_2$)$_n$—(C=O)$_u$(NR$_1$)$_v$(SO$_2$)$_w$—NR$_1$C(O)R$_{1N}$, an optionally substituted —O—(CH$_2$)$_n$—(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle;
—(CH$_2$)$_n$—(V)$_{n'}$—(CH$_2$)$_n$—(V)$_{n'}$-alkyl group, an optionally substituted
—(CH$_2$)$_n$—(V)$_{n'}$—(CH$_2$)$_n$—(V)$_{n'}$-Aryl group, an optionally substituted
—(CH$_2$)$_n$—(V)$_{n'}$—(CH$_2$)$_n$—(V)$_{n'}$-Heteroaryl group, an optionally substituted
—(CH$_2$)$_n$—(V)$_{n'}$—(CH$_2$)$_n$—(V)$_{n'}$-Heterocycle group, an optionally substituted
—(CH$_2$)$_n$—N(R$_{1'}$)(C=O)$_{m'}$—(V)$_{n'}$-alkyl group, an optionally substituted
—(CH$_2$)$_n$—N(R$_{1'}$)(C=O)$_{m'}$—(V)$_{n'}$-Aryl group, an optionally substituted
—(CH$_2$)$_n$—N(R$_{1'}$)(C=O)$_{m'}$—(V)$_{n'}$-Heteroaryl group, an optionally substituted
—(CH$_2$)$_n$—N(R$_{1'}$)(C=O)$_{m'}$—(V)$_{n'}$-Heterocycle group, an optionally substituted
—$X^{R3'}$-alkyl group; an optionally substituted
—$X^{R3'}$-Aryl group; an optionally substituted
—$X^{R3'}$-Heteroaryl group; an optionally substituted
—$X^{R3'}$-Heterocycle group; an optionally substituted;

Where R$_{1N}$ and R$_{2N}$ are each independently H, $C_1$-$C_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V is O, S or NR$_1$;
$R_1$ is the same as above;
$R^1$ and $R_{1'}$ are each independently H or a $C_1$-$C_3$ alkyl group;
$X^{R2'}$ and $X^{R3'}$ are each independently an optionally substituted —CH$_2$)$_n$—, —CH$_2$)$_n$—CH(X$_v$)=CH(X$_v$)— (cis or trans), —CH$_2$)$_n$—CH≡CH—, —(CH$_2$CH$_2$O)$_n$— or a $C_3$-$C_6$ cycloalkyl group, where X$_v$ is H, a halo or a $C_1$-$C_3$ alkyl group which is optionally substituted;

Each m is independently 0, 1, 2, 3, 4, 5, 6;
Each m' is independently 0 or 1;
Each n is independently 0, 1, 2, 3, 4, 5, 6;

Each n' is independently 0 or 1;
Each u is independently 0 or 1;
Each v is independently 0 or 1;
Each w is independently 0 or 1; and wherein any one or more of $R^{1'}$, $R^{2'}$, $R^{3'}$, X and X' of ULM is modified to be covalently bonded to the PTM group through a linker group when PTM is not ULM', or when PTM is ULM', any one or more of $R^{1'}$, $R^{2'}$, $R^{3'}$, X and X' of each of ULM and ULM' are modified to be covalently bonded to each other directly or through a linker group, or a pharmaceutically acceptable salt, stereoisomer, solvate or polymorph thereof.

In alternative aspects of the present invention ULM and when present, ULM', are each independently a group according to the chemical structure:

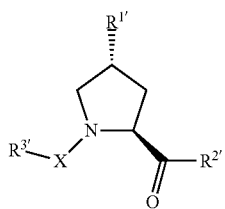

Wherein each of $R^{1'}$, $R^{2'}$ and $R^3$ are the same as above and X is C=O, C=S, —S(O) group or a S(O)$_2$ group, more preferably a C=O group, and
wherein any one or more of $R^{1'}$, $R^{2'}$ and $R^{3'}$ are modified to bind a linker group to which is further covalently bonded to the PTM group when PTM is not ULM', or when PTM is ULM', any one or more of $R^{1'}$, $R^{2'}$, $R^{3'}$ of each of ULM and ULM' are modified to be covalently bonded to each other directly or through a linker group, or a pharmaceutically acceptable salt, enantiomer, diastereomer, solvate or polymorph thereof.

In still further preferred aspects of the invention, ULM, and when present, ULM', are each independently according to the chemical structure:

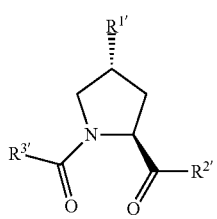

wherein any one or more of $R^{1'}$, $R^{2'}$ and $R^{3'}$ are modified to bind a linker group to which is further covalently bonded to the PTM group when PTM is not ULM', or when PTM is ULM', any one or more of $R^{1'}$, $R^{2'}$, $R^{3'}$ of each of ULM and ULM' are modified to be covalently bonded to each other directly or through a linker group, or a pharmaceutically acceptable salt, enantiomer, diastereomer, solvate or polymorph thereof.

In further preferred aspects of the invention, $R^{1'}$ is preferably a hydroxyl group or a group which may be metabolized to a hydroxyl or carboxylic group, such that the compound represents a prodrug form of an active compound. Exemplary preferred $R^{1'}$ groups include, for example, —(CH$_2$)$_n$OH, (CH$_2$)$_n$—O—(C$_1$-C$_6$)alkyl group, —(CH$_2$)$_n$COOH, —(CH$_2$O)$_n$H, an optionally substituted —(CH$_2$)$_n$OC(O)—(C$_1$-C$_6$ alkyl), or an optionally substituted —(CH$_2$)$_n$C(O)—O—(C$_1$-C$_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded.

X and X', where present, are preferably a C=O, C=S, —S(O) group or a S(O)$_2$ group, more preferably a C=O group.

$R^{2'}$ is preferably an optionally substituted —NR$^1$-T-Aryl, an optionally substituted —NR$^1$-T-Heteroaryl group or an optionally substituted —NR$^1$-T-Heterocycle, where R$^1$ is H or CH$_3$, preferably H and T is an optionally substituted —(CH$_2$)$_n$— group, wherein each one of the methylene groups may be optionally substituted with one or two substituents, preferably selected from halogen, an amino acid sidechain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for $R^{2'}$ include optionally substituted phenyl or naphthyl groups, preferably phenyl groups, wherein the phenyl group is optionally substituted with a linker group to which is attached a PTM group (including a ULM' group), a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM' group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

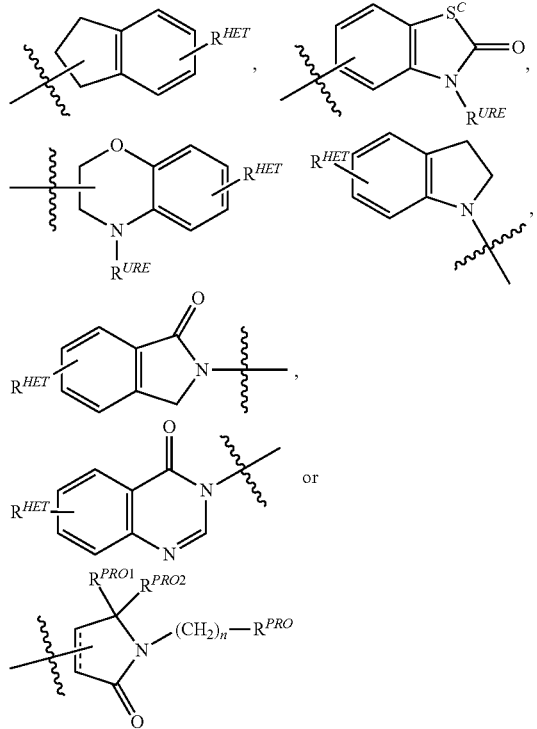

Where $S^c$ is $CHR^{SS}$, $NR^{URE}$, or O;

$R^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ is H, a C$_1$-C$_6$ alkyl (preferably H or C$_1$-C$_3$ alkyl) or a —C(O)(C$_1$-C$_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

$R^{PRO1}$ and $R^{PRO2}$ are each independently H, an optionally substituted C$_1$-C$_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally substituted with a linker group to which is attached a PTM group (including a ULM group).

In certain preferred aspects,

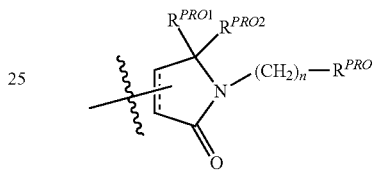

is a

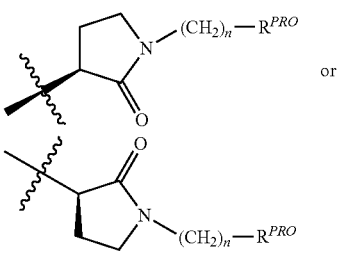

group,

Where $R^{PRO}$ and n are the same as above.

Preferred heteroaryl groups for $R^{2'}$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

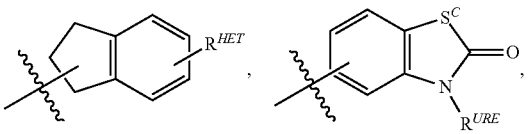

-continued

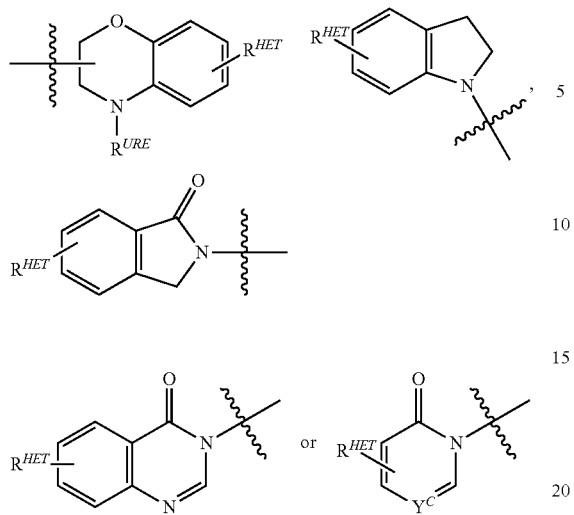

Where $S^c$ is $CHR^{SS}$, $NR^{URE}$, or O;

$R^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$, where R$_a$ is H or a C$_1$-C$_6$ alkyl group (preferably C$_1$-C$_3$ alkyl), each of which groups may be optionally substituted with a linker group to which is attached a PTM group (including a ULM group);

Preferred heterocycle groups for R$^{2'}$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

Preferably, a group,

Where $R^{PRO}$ is H, optionally substituted C$_1$-C$_6$ alkyl or an optionally substituted aryl, heteroaryl or heterocyclic group; $R^{PRO1}$ and $R^{PRO2}$ are each independently H, an optionally substituted C$_1$-C$_3$ alkyl group or together form a keto group and Each n is independently 0, 1, 2, 3, 4, 5, or 6 (often 0 or 1), each of which groups may be optionally substituted with a linker group to which is attached a PTM group (including a ULM group).

Preferred R$^{2'}$ substituents for use in the present invention also include specifically (and without limitation to the specific compound disclosed) the R$^{2'}$ substituents which are found in the identified compounds disclosed herein (which includes the specific compounds which are disclosed in the present specification, and the figures which are attached hereto). Each of these R$^{2'}$ substituents may be used in conjunction with any number of R$^{3'}$ substituents which are also disclosed herein.

R$^{3'}$ is preferably an optionally substituted-T-Aryl, an optionally substituted-T-Heteroaryl, an optionally substituted-T-Heterocycle, an optionally substituted —NR$^1$-T-Aryl, an optionally substituted —NR$^1$-T-Heteroaryl or an optionally substituted —NR$^1$-T-Heterocycle, where R$^1$ is H or a C$_1$-C$_3$ alkyl group, preferably H or CH$_3$, T is an optionally substituted —(CH$_2$)$_n$— group, wherein each one of the methylene groups may be optionally substituted with one or two substituents, preferably selected from halogen, a C$_1$-C$_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, each of which groups is optionally substituted.

Preferred aryl groups for R$^{3'}$ include optionally substituted phenyl or naphthyl groups, preferably phenyl groups, wherein the phenyl or naphthyl group is optionally substituted with a linker group to which is attached a [PTM] group (including a [ULM] group) and/or a halogen (preferably F or Cl), an amine, monoalkyl- or dialkyl amine (preferably, dimethylamine), an amido group (preferably a —(CH$_2$)$_m$—NR$_1$C(O)R$_2$ group where m, R$_1$ and R$_2$ are the same as above), a halo (often F or Cl), OH, CH$_3$, CF$_3$, OMe, OCF$_3$, NO$_2$, CN or a S(O)$_2$R$_S$ group (R$_S$ is a C$_1$-C$_6$ alkyl group, an optionally substituted aryl, heteroaryl or heterocycle group or a —(CH$_2$)$_m$NR$_1$R$_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, CH$_3$, CF$_3$, OMe, OCF$_3$, NO$_2$, CN or a linker group to which is attached a [PTM] group (including a [ULM] group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a [PTM] group (including a [ULM] group).

Preferred Heteroaryl groups for R$^{3'}$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

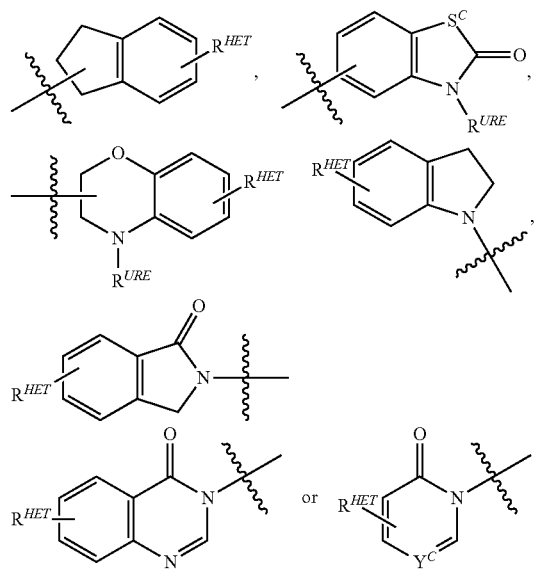

Where S$^C$ is CHR$^{SS}$, NR$^{URE}$, or O;

R$^{HET}$ H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl). Each of said heteroaryl groups may be optionally substituted with a linker group to which is attached a [PTM] group (including a [ULM] group).

Preferred heterocycle groups for R$^{3'}$ include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

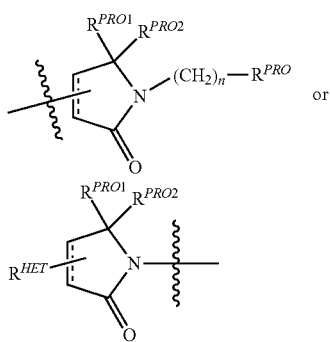

Preferably, a

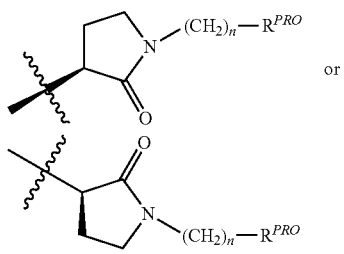

group,

Where $R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and Each n is 0, 1, 2, 3, 4, 5, or 6 (preferably 0 or 1), wherein each of said Heterocycle groups may be optionally substituted with a linker group to which is attached a PTM group (including a ULM' group).

Preferred $R^{3'}$ substituents for use in the present invention also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents which are also disclosed herein.

In certain alternative preferred embodiments, $R^{2'}$ is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, Where $R_1$ is H or a $C_1$-$C_3$ alkyl group (preferably H);
$X^{R2'}$ is an optionally substituted —$(CH_2)_n$—, —$(CH_2)_n$—CH$(X_v)$=CH$(X_v)$— (cis or trans), —$(CH_2)_n$—CH≡CH—, —$(CH_2CH_2O)_n$— or a $C_3$-$C_6$ cycloalkyl group;

where $X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or naphthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

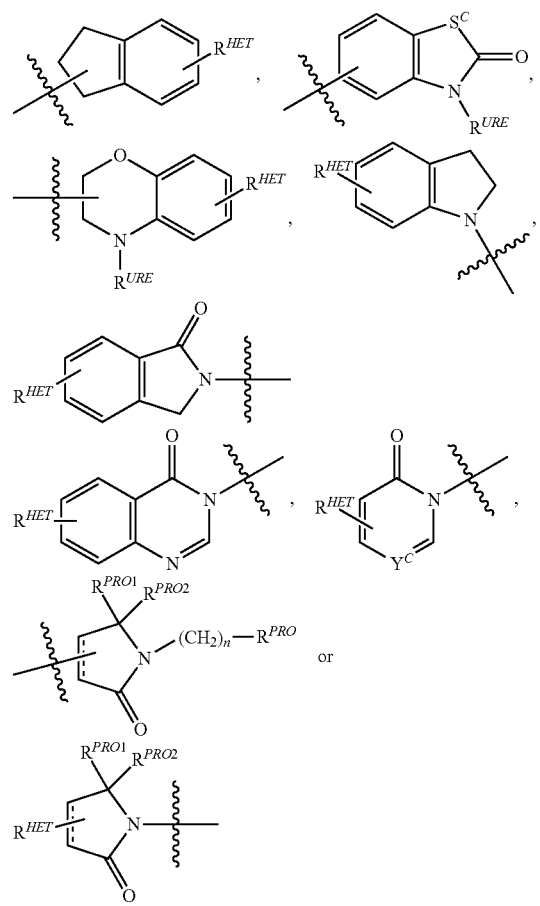

Where $S^c$ is $CHR^{SS}$, $NR^{URE}$, or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group where —C≡C—R$_a$ where R$_a$ is H or a C$_1$-C$_6$ alkyl group (preferably C$_1$-C$_3$ alkyl);

R$^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ are each independently H, an optionally substituted C$_1$-C$_3$ alkyl group or together form a keto group, and Each n is independently 0, 1, 2, 3, 4, 5, or 6 (preferably 0 or 1). Each of said groups may be optionally substituted with a linker group to which is attached a PTM group (including a ULM group).

In certain alternative preferred embodiments of the present invention, R$^{3'}$ is an optionally substituted —(CH$_2$)$_n$—(V)$_{n'}$—(CH$_2$)$_n$—(V)$_{n'}$—R$^{S3'}$ group, an optionally substituted —(CH$_2$)$_n$—N(R$_{1'}$)(C=O)$_m$—(V)$_{n'}$—R$^{S3'}$ group, an optionally substituted —X$^{R3'}$-alkyl group, an optionally substituted —X$^{R3'}$-Aryl group; an optionally substituted —X$^{R3'}$-HET group, an optionally substituted —X$^{R3'}$-Aryl-HET group or an optionally substituted —X$^{R3'}$-HET-Aryl group, Where R$^{S3'}$ is an optionally substituted alkyl group (C$_1$-C$_{10}$, preferably C$_1$-C$_6$ alkyl), an optionally substituted Aryl group or a HET group;

R$_{1'}$ is H or a C$_1$-C$_3$ alkyl group (preferably H);

V is O, S or NR$_{1'}$;

X$^{R3'}$ is —(CH$_2$)$_n$—, —(CH$_2$CH$_2$O)$_n$—, —(CH$_2$)$_n$—CH(X$_v$)=CH(X$_v$)— (cis or trans), —(CH$_2$)$_n$—CH≡CH—, or a C$_3$-C$_6$ cycloalkyl group, all optionally substituted;

where X$_v$ is H, a halo or a C$_1$-C$_3$ alkyl group which is optionally substituted with one or two hydroxyl groups or up to three halogen groups;

Alkyl is an optionally substituted C$_1$-C$_{10}$ alkyl (preferably a C$_1$-C$_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a C$_1$-C$_3$ alkyl group, preferably methyl or a halo group, preferably F or Cl), or a group according to the chemical structure:

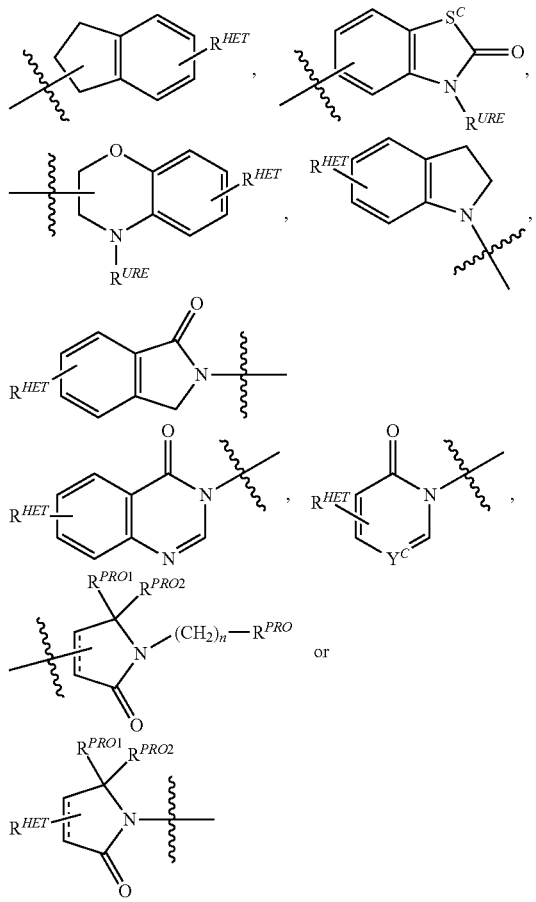

Where S$^c$ is CHR$^{SS}$, NR$^{URE}$, or O;

R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$, where R$_a$ is H or a C$_1$-C$_6$ alkyl group (preferably C$_1$-C$_3$ alkyl);

R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or $C-R^{YC}$, where $R^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{PRO}$ is H, H optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

$R^{PRO1}$ and $R^{PRO2}$ are each independently H, an optionally substituted C$_1$-C$_3$ alkyl group or together form a keto group, and Each n is independently 0, 1, 2, 3, 4, 5, or 6 (preferably 0 or 1);

Each m' is 0 or 1; and

Each n' is 0 or 1,

Wherein each of said compounds, preferably on the alkyl, Aryl or Het groups, is substituted with a linker group to which is attached a PTM group (including a ULM group).

In alternative embodiments, $R^{3'}$ is —(CH$_2$)$_n$-Aryl, —(CH$_2$CH$_2$O)$_n$-Aryl, —(CH$_2$)$_n$—HET or —(CH$_2$CH$_2$O)$_n$—HET;

Where Aryl is phenyl which is optionally substituted with one or two substitutents, wherein said substituent(s) is preferably selected from —(CH$_2$)$_n$OH, C$_1$-C$_6$ alkyl which itself is further optionally substituted with CN, halo (up to three halo groups), OH, —(CH$_2$)$_n$O(C$_1$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, or said Aryl group is substituted with —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(O)(C$_0$-C$_6$) alkyl, —(CH$_2$)$_n$—C(O)O(C$_0$-C$_6$) alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, groups, CN, NO$_2$, an optionally substituted —(CH$_2$)$_n$—(V)$_{m'}$—(CH$_2$)$_n$—(V)$_{m'}$—(C$_1$-C$_6$) alkyl group, a —(V)$_{m'}$—(CH$_2$CH$_2$O)$_n$—R$^{PEG}$ group where V is O, S or NR$_1$, R$_1$, is H or a C$_1$-C$_3$ alkyl group (preferably H) and $R^{PEG}$ is H or a C$_1$-C$_6$ alkyl group which is optionally substituted (including being optionally substituted with a carboxyl group), or said Aryl group is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a C$_1$-C$_3$ alkyl group, preferably methyl or a halo group, preferably F or Cl), or a group according to the chemical structure:

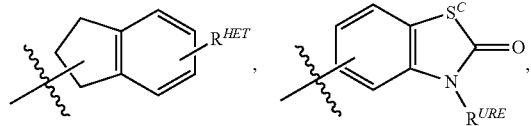

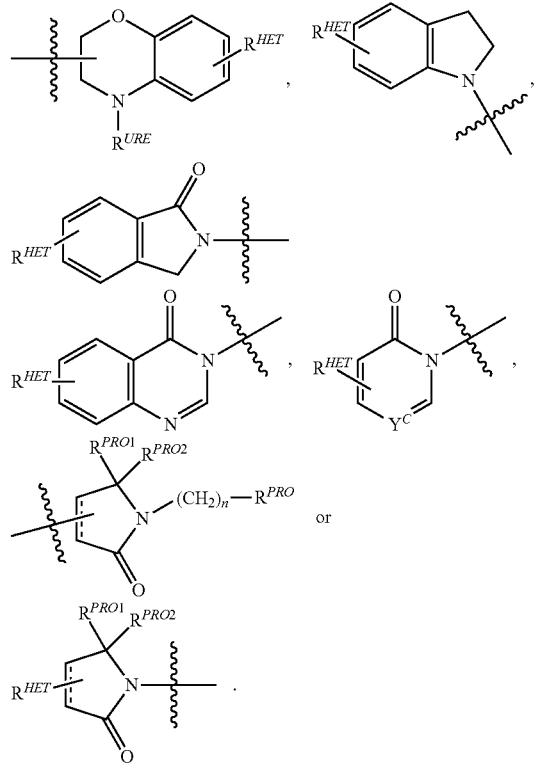

Where $S^c$ is $CHR^{SS}$, $NR^{URE}$, or O;

$R^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or $C—R^{YC}$, where $R^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{PRO}$ is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group;

HET is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

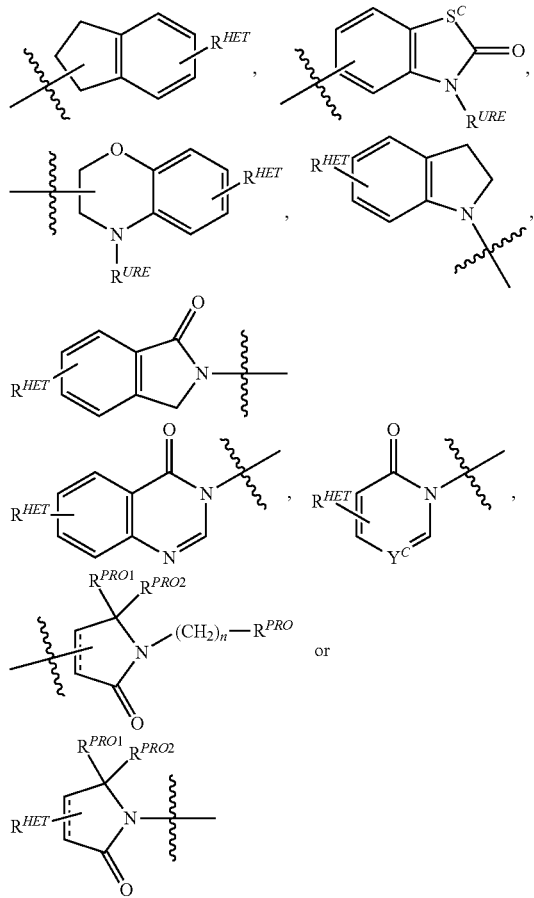

Where $S^c$ is $CHR^{SS}$, $NR^{URE}$, or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{PRO}$ is H, optionally substituted $C_1$-$C_6$ alkyl or an optionally substituted aryl, heteroaryl or heterocyclic group;
$R^{PRO}$ and $R^{PRO2}$ are each independently H, an optionally substituted $C_1$-$C_3$ alkyl group or together form a keto group,
Each m' is independently 0 or 1, and
Each n is independently 0, 1, 2, 3, 4, 5, or 6 (preferably 0 or 1),
Wherein each of said compounds, preferably on said Aryl or HET groups is substituted with a linker group to which is attached a 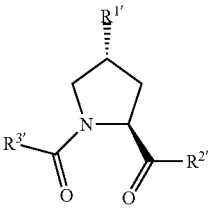 group (including a ULM group).

In still additional embodiments, preferred compounds include those according to the chemical structure:

[Structure of pyrrolidine with R$^{1'}$, R$^{2'}$, R$^{3'}$ substituents]

Where $R^{1'}$ is OH or a group which is metabolized in a patient or subject to OH;
$R^{2'}$ is a —NH—$CH_2$-Aryl-HET (preferably, a phenyl linked directly to a methyl substituted thiazole);
$R^{3'}$ is a —CHR$^{CR3'}$—NH—C(O)—R$^{3P1}$ group or a —CHR$^{CR3'}$—R$^{3P2}$ group;
Where R$^{CR3'}$ is a $C_1$-$C_4$ alkyl group, preferably methyl, isopropyl or tert-butyl;
R$^{3P1}$ is $C_1$-$C_3$ alkyl (preferably methyl), an optionally substituted oxetane group (preferably methyl substituted, a —(CH$_2$)$_n$OCH$_3$ group where n is 1 or 2 (preferably 2), or a

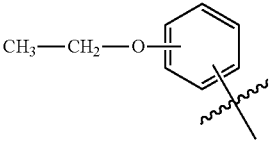

group (the ethyl ether group is preferably meta-substituted on the phenyl moiety), a morpholino grop (linked to the carbonyl at the 2- or 3-position;

$R^{3P2}$ is a

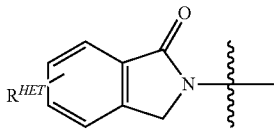

group,

Where Aryl is phenyl;

HET is an optionally substituted thiazole or isothiazole; and $R^{HET}$ is H or a halo group (preferably H), Or a pharmaceutically acceptable salt, stereoisomer, solvate or polymorph thereof, wherein each of said compounds is substituted with a linker group to which is attached a PTM group (including a ULM group)

In an alternative embodiment, ULM groups for inclusion in compounds according to the present invention include:

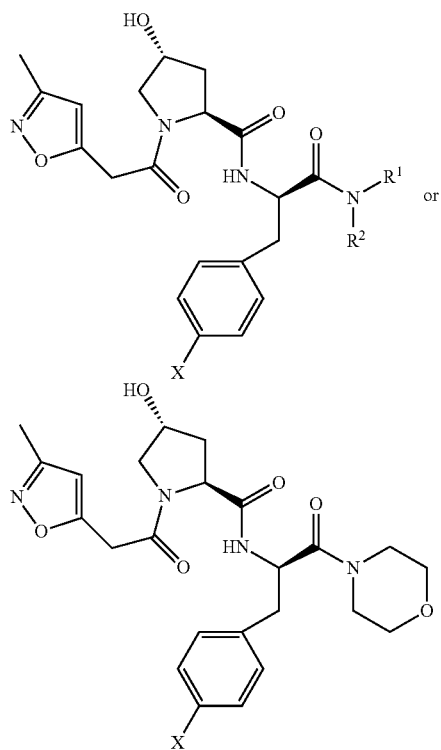

Where X is Cl, F, $C_1$-$C_3$ alkyl (preferably methyl) or heterocycle (preferably an optionally substituted heterocycle, including as defined above for $R^{3'}$;

$R^1$ and $R^2$ are each independently H, $C_1$-$C_3$ alkyl (preferably methyl), or phenyl and each of said compounds is substituted with a linker group or a linker group to which is attached a PTM group, or a pharmaceutically acceptable salt, enantiomer, diastereomer, solvate or polymorph thereof.

Additional preferred ULM groups for inclusion in compounds according to the present invention include:

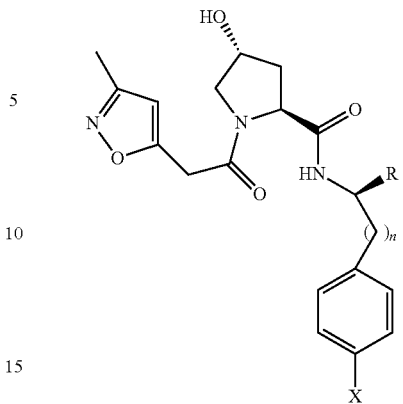

Where n is 0 or 1;

R is a linker or a linker attached to a PTM group

X is H, F, Cl, $C_1$-$C_3$ alkyl (preferably methyl) or heterocycle (preferably an optionally substituted heterocycle, especially including a water soluble heterocycle such as a morpholino group, including as defined above for $R^{3'}$), or a pharmaceutically acceptable salt, enantiomer, diastereomer, solvate or polymorph thereof.

Additional preferred ULM groups for inclusion in compounds according to the present invention include for example:

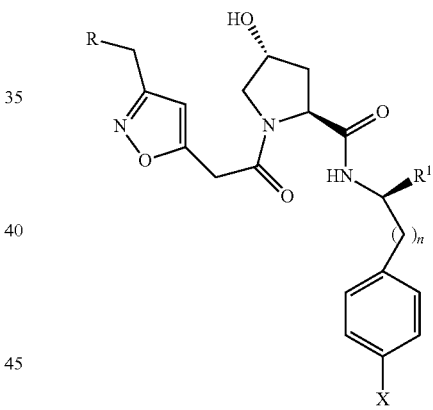

Where n is 0 or 1;

R is a linker or a linker attached to a PTM group a linker or a linker attached to a PTM group linked to the ULM group through an amide, ester, ether or carbamate group;

$R^1$ is $C_1$-$C_3$ alkyl (optionally substituted with one or two hydroxyl groups) or —C(O)N$R^3R^4$ where $R^3$ and $R^4$ are each independently H, $C_1$-$C_3$ alkyl (preferably methyl), phenyl or heterocycle (including a heterocycle such as a morpholino, piperazine or other group which increases water solubility), X is H, F, Cl, $C_1$-$C_3$ alkyl (preferably methyl) or heterocycle (preferably an optionally substituted heterocycle, including a water soluble heterocycle, including as defined above for $R^{3'}$), or a pharmaceutically acceptable salt, enantiomer, diastereomer, solvate or polymorph thereof.

Still further preferred ULM groups for inclusion in compounds according to the present invention include for example:

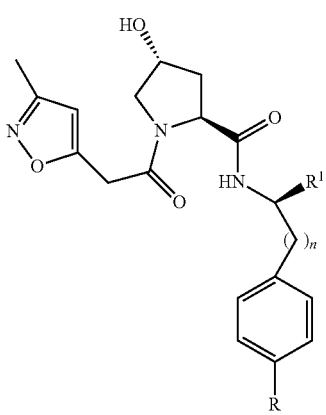

Where n is 0 or 1;

$R^1$ is a linker or a linker attached to a PTM group linked to the ULM group through an amide, ester, ether, carbamate or heterocyclic group (preferably an optionally substituted heterocycle, including as defined above for $R^{3'}$);

R is H, F, Cl, $C_1$-$C_3$ alkyl (optionally substituted with one or two hydroxyl groups, preferably methyl), —O—C(O)NR$^3$R$^4$ or —C(O)NR$^3$R$^4$ wherein each of $R^3$ and $R^4$ is independently H, $C_1$-$C_3$ alkyl (preferably methyl), phenyl or heterocycle, including a water soluble heterocycle, or A pharmaceutically acceptable salt, enantiomer, diastereomer, solvate or polymorph thereof.

Yet still further preferred ULM groups for inclusion in compounds according to the present invention include for example:

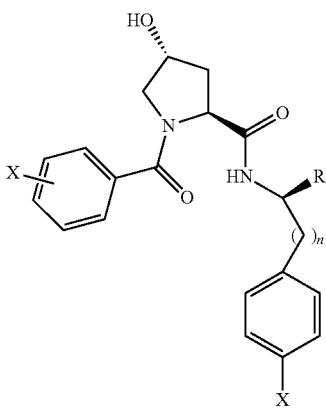

Where n is 0 or 1;

R is a linker or a linker attached to a PTM group linked to the ULM group through an amide, ester, ether, carbamate or heterocyclic group; and Each X is independently is H, F, Cl, $C_1$-$C_3$ alkyl (optionally substituted with one or two hydroxyl groups, preferably methyl), heterocycle (preferably an optionally substituted heterocycle, including a water soluble heterocycle, and/or as defined above for $R^{3'}$), —O—C(O)NR$^3$R$^4$ or —C(O)NR$^3$R$^4$ wherein each of $R^3$ and $R^4$ is independently H, $C_1$-$C_3$ alkyl (preferably methyl), or phenyl, or a pharmaceutically acceptable salt, enantiomer, diastereomer, solvate or polymorph thereof.

Yet additional further preferred ULM groups for inclusion in compounds according to the present invention include for example:

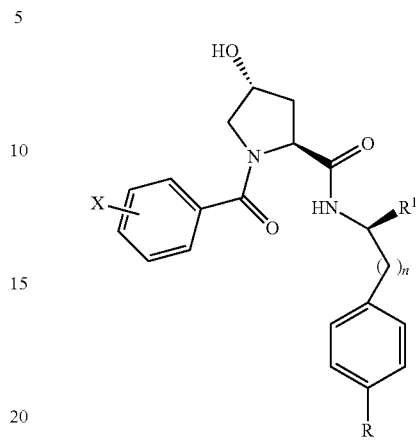

Where n is 0 or 1;

R is a linker or a linker attached to a PTM group linked to the ULM group through an amide, ester, ether, carbamate or heterocyclic group;

$R^1$ is $C_1$-$C_3$ alkyl, which is optionally substituted with one or two hydroxyl groups, —O—C(O)NR$^3$R$^4$ or —C(O)NR$^3$R$^4$ wherein each of $R^3$ and $R^4$ is independently H, $C_1$-$C_3$ alkyl (preferably methyl), or phenyl; and X is independently is H, F, Cl, $C_1$-$C_3$ alkyl (optionally substituted with one or two hydroxyl groups, preferably methyl) or heterocycle (preferably an optionally substituted heterocycle, including a water soluble heterocycle, and/or as defined above for $R^{3'}$), or a pharmaceutically acceptable salt, enantiomer, diastereomer, solvate or polymorph thereof.

Yet additional further preferred ULM groups for inclusion in compounds according to the present invention include for example:

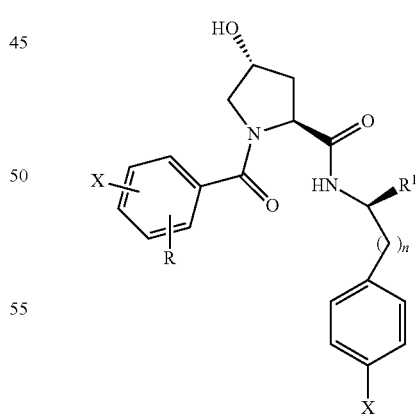

Where n is 0 or 1;

R is a linker or a linker attached to a PTM group linked to the ULM group through an amide, ester, ether, carbamate or heterocyclic group;

$R^1$ is H, $C_1$-$C_3$ alkyl, which is optionally substituted with one or two hydroxyl groups, —O—C(O)NR$^3$R$^4$ or —C(O)NR$^3$R$^4$ wherein each of R$^3$ and R$^4$ is independently H, C$_1$-C$_3$ alkyl (preferably methyl), or phenyl; and Each X is independently is H, F, Cl, C$_1$-C$_3$ alkyl (optionally substituted with one or two hydroxyl groups, preferably methyl) or heterocycle (preferably an optionally substituted heterocycle, including a water soluble heterocycle and/or including as defined above for R$^{3'}$), or a pharmaceutically acceptable salt, enantiomer, diastereomer, solvate or polymorph thereof.

Figure 19:
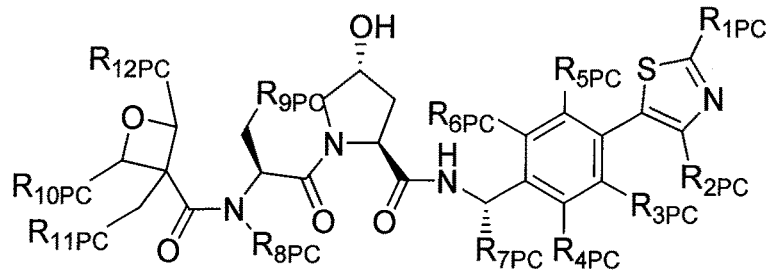
FIG. 19 shows a genus of preferred compounds according to the present invention.
Figure 19:
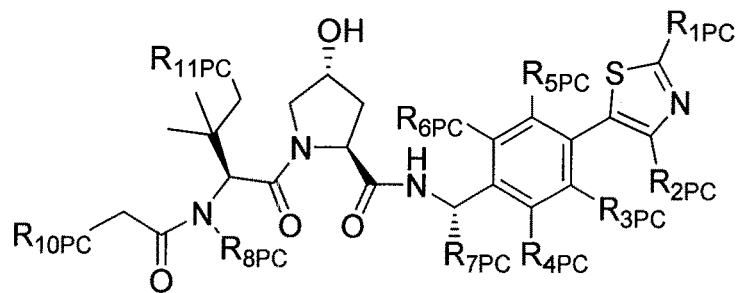
Figure 19:
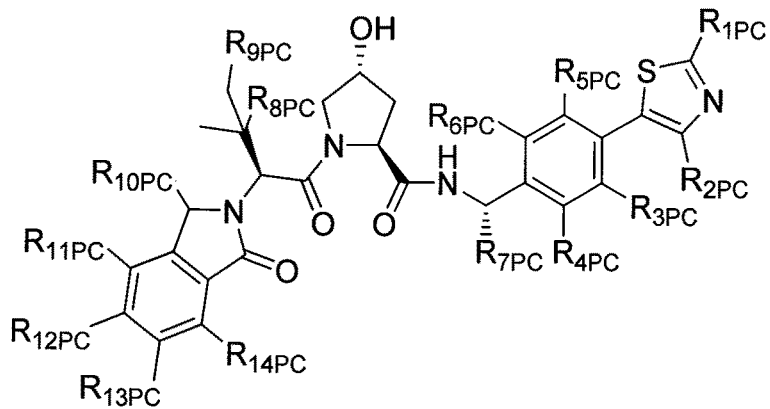
Figure 19:
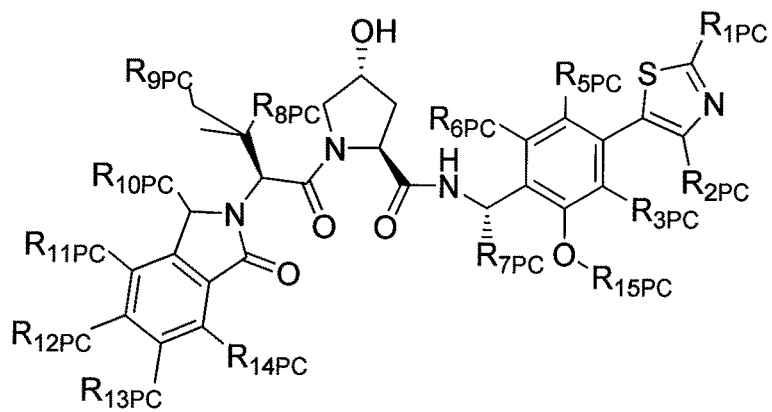
Figure 19:
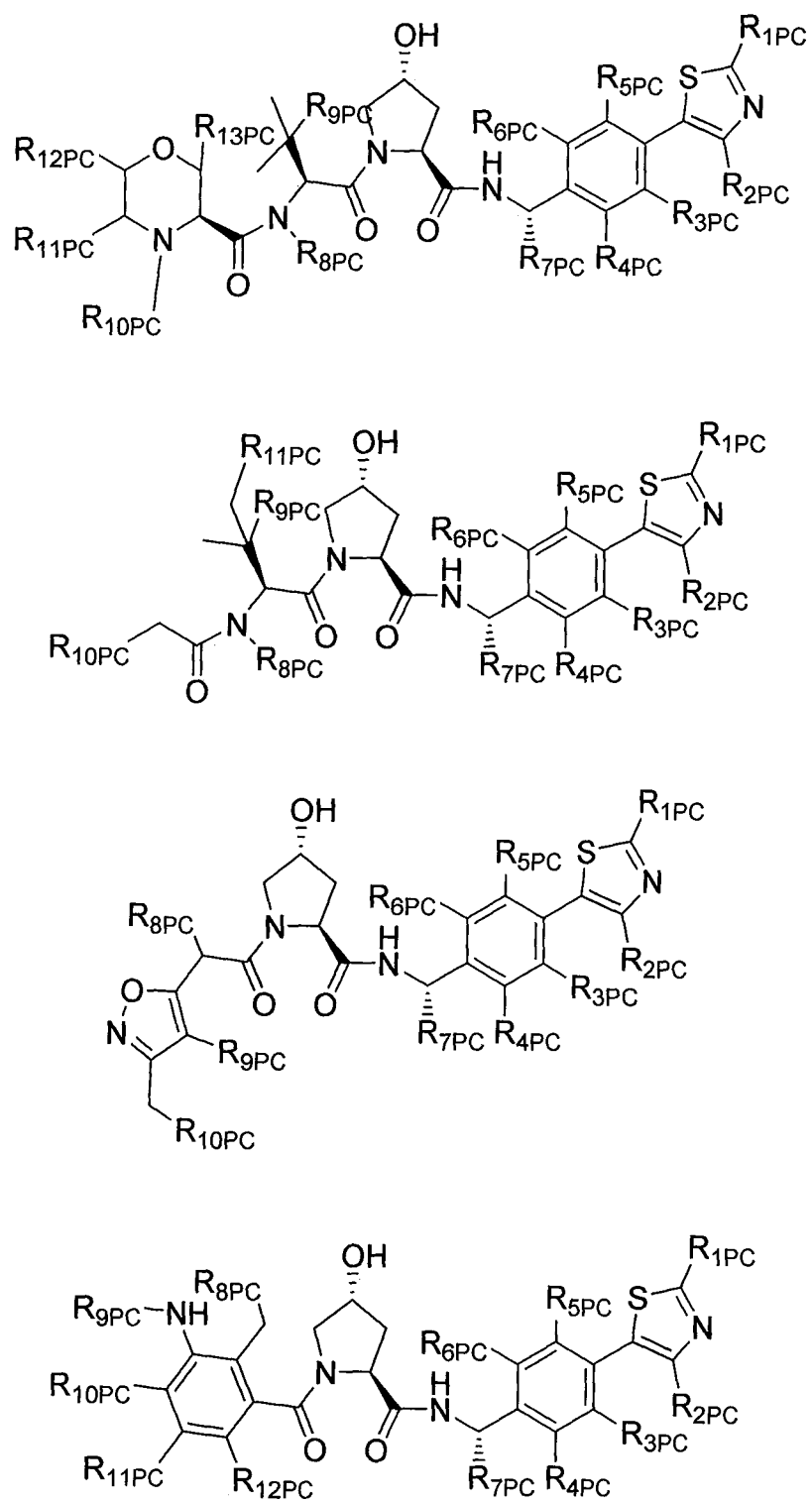
Figure 19:
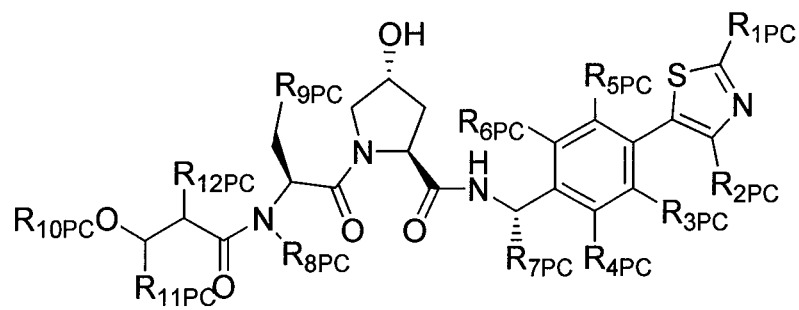
Figure 19:
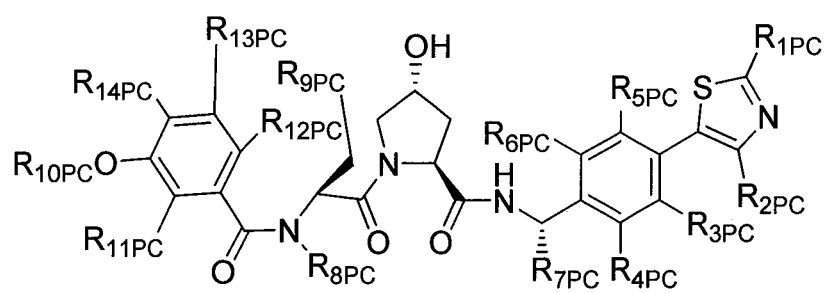
Figure 19:
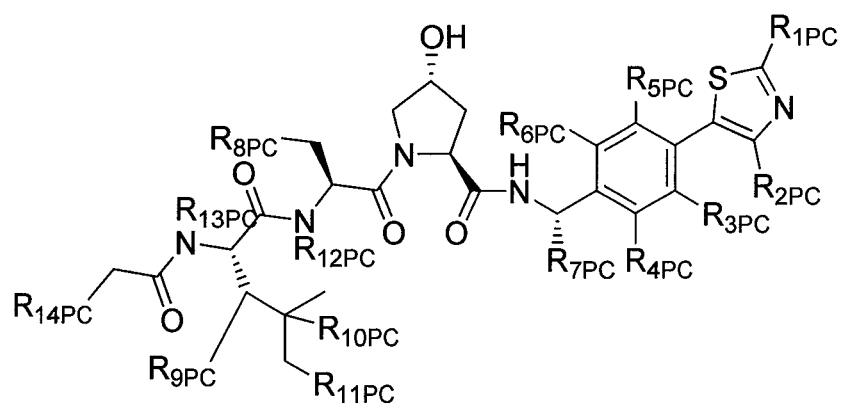
Figure 19:
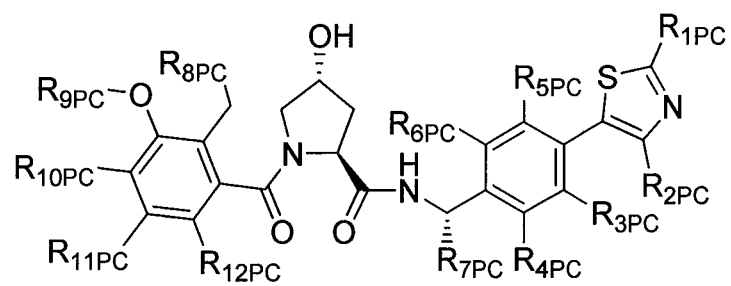
Figure 19:
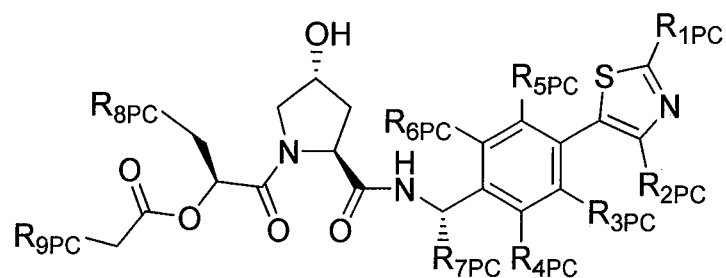
Figure 19:
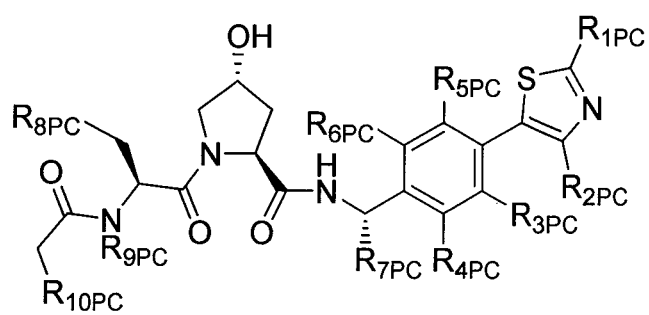
Figure 19:
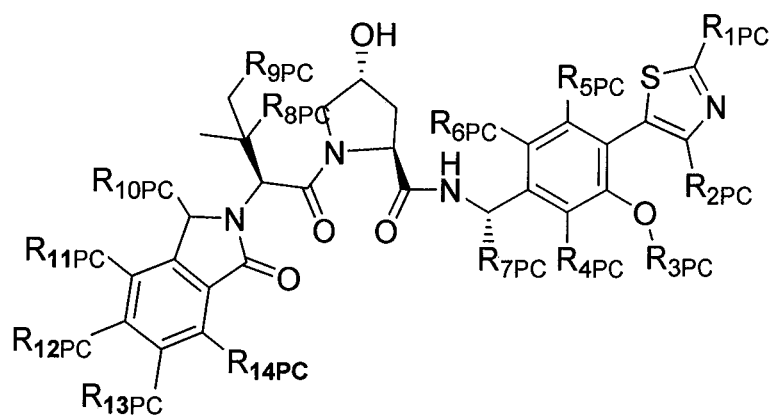

In an additional embodiment, particularly preferred compounds according to the present invention may be identified according to any one or more of the chemical structures as set forth in FIG. 19 hereof:

Wherein any one or more of R$_{1PC}$, R$_{2PC}$, R$_{3PC}$, R$_{4PC}$, R$_{5PC}$, R$_{6PC}$, R$_{7PC}$, R$_{8PC}$, R$_{9PC}$, R$_{10PC}$, R$_{11PC}$, R$_{12PC}$, R$_{13PC}$ and R$_{14PC}$ is a

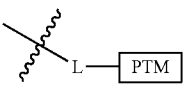

group,

Where L is a linker group and PTM is a protein targeting moiety, or

A pharmaceutically acceptable salt, stereoisomer, solvate or polymorph thereof.

In preferred embodiments, no more than two of R$_{1PC}$, R$_{2PC}$, R$_{3PC}$, R$_{4PC}$, R$_{5PC}$, R$_{6PC}$, R$_{7PC}$, R$_{8PC}$, R$_{9PC}$, R$_{10PC}$, R$_{11PC}$, R$_{12PC}$, R$_{13PC}$ and R$_{14PC}$ is a

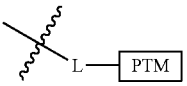

group and the other of groups R$_{1PC}$, R$_{2PC}$, R$_{3PC}$, R$_{4PC}$, R$_{5PC}$, R$_{6PC}$, R$_{7PC}$, R$_{8PC}$, R$_{9PC}$, R$_{10PC}$, R$_{11PC}$, R$_{12PC}$, R$_{13PC}$ and R$_{14PC}$ are independently H or a CH$_3$ group, often H.

Certain preferred embodiments are directed to compounds according to the chemical structure:

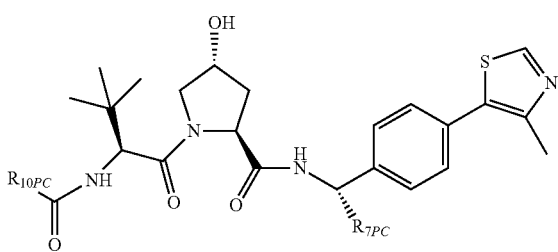

Wherein R$_{7PC}$ and R$_{10PC}$ are each independently a

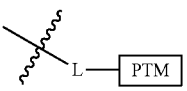

group or H, or
A pharmaceutically acceptable salt, stereoisomer, solvate or polymorph thereof. Preferably, either of R$_{7PC}$ or R$_{10PC}$ is a

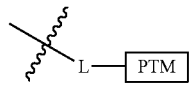

group and the other R$_{7PC}$ or R$_{10PC}$ is H.

In other preferred embodiments, the compound has the chemical structure:

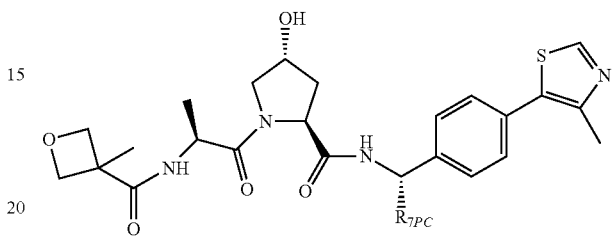

Wherein R$_{7PC}$ is a

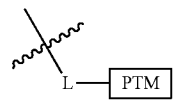

group, or

A pharmaceutically acceptable salt, stereoisomer, solvate or polymorph thereof.

In still other preferred embodiments, the compound has the chemical structure:

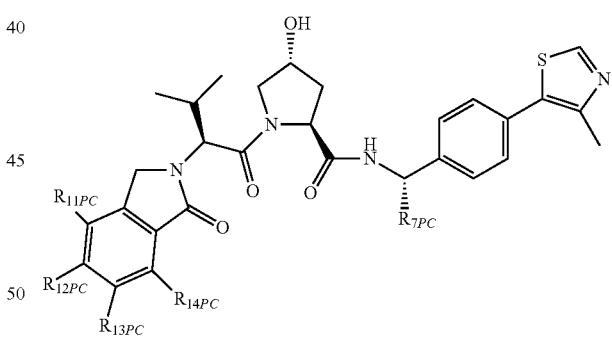

Wherein R$_{7PC}$, R$_{11PC}$, R$_{12PC}$, R$_{13PC}$ and R$_{14PC}$ are each independently a

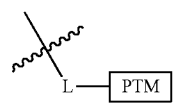

group or H, or

A pharmaceutically acceptable salt, stereoisomer, solvate or polymorph thereof. Preferably, one of R$_{7PC}$, R$_{11PC}$, R$_{12PC}$, R$_{13PC}$ and R$_{14PC}$ is a

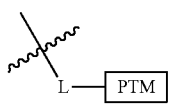

group and the other groups are H, or
A pharmaceutically acceptable salt, stereoisomer, solvate or polymorph thereof.

In still other preferred embodiments, the compound has the chemical structure:

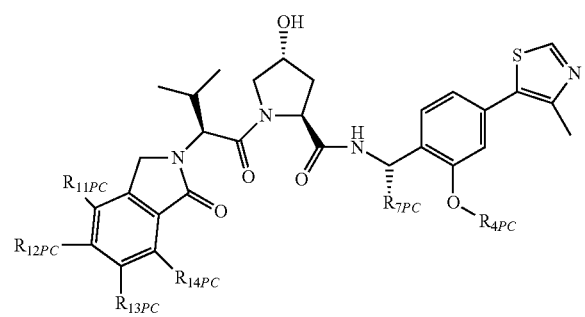

Wherein $R_{4PC}$, $R_{7PC}$, $R_{11PC}$, $R_{12PC}$, $R_{13PC}$ and $R_{14PC}$ are each independently a

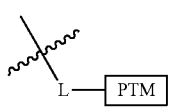

group or H, or
A pharmaceutically acceptable salt, stereoisomer, solvate or polymorph thereof. Preferably, either of $R_{4PC}$, $R_{7PC}$ or one of $R_{11PC}$, $R_{12PC}$, $R_{13PC}$ and $R_{14PC}$ is a

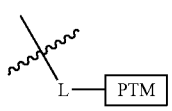

group and the other groups are H, or
A pharmaceutically acceptable salt, stereoisomer, solvate or polymorph thereof.

In still other preferred embodiments, the compound has the chemical structure:

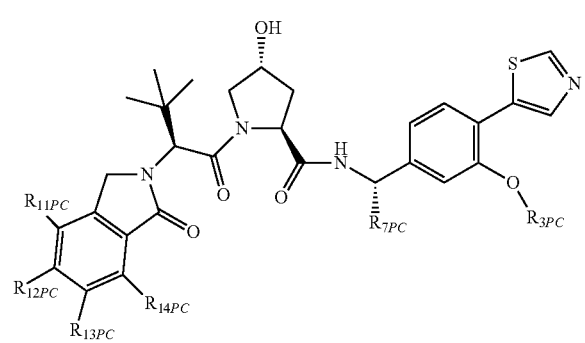

Wherein $R_{3PC}$, $R_{7PC}$, $R_{11PC}$, $R_{12PC}$, $R_{13PC}$ and $R_{14PC}$ are each independently a

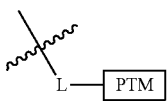

group or H, or
A pharmaceutically acceptable salt, stereoisomer, solvate or polymorph thereof. Preferably, one of $R_{3PC}$, $R_{7PC}$, $R_{11PC}$, $R_{12PC}$, $R_{13PC}$ and $R_{14PC}$ is a

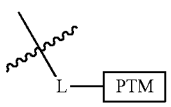

group and the other groups are H, or
A pharmaceutically acceptable salt, stereoisomer, solvate or polymorph thereof.

In still other preferred embodiments, the compound has the chemical structure:

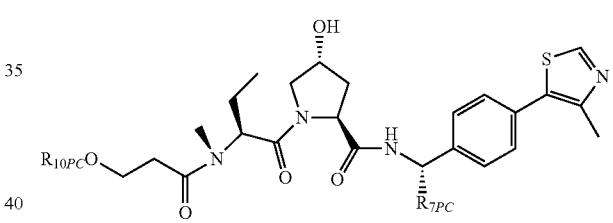

Wherein $R_{7PC}$ and $R_{10PC}$ are each independently a

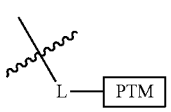

group or H, or
A pharmaceutically acceptable salt, stereoisomer, solvate or polymorph thereof. Preferably, one of $R_{7PC}$ and $R_{10PC}$ is a

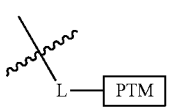

group and the other group is H, or
A pharmaceutically acceptable salt, stereoisomer, solvate or polymorph thereof.

In still other preferred embodiments, the compound has the chemical structure:

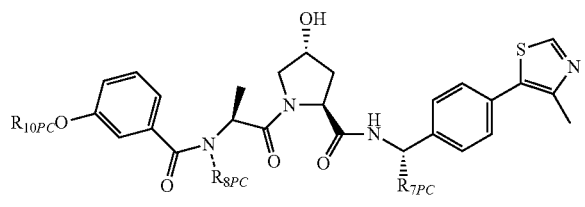

Wherein $R_{7PC}$ and $R_{10PC}$ are each independently a

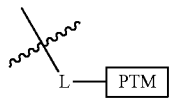

group or H and $R_{8PC}$ is H or $CH_3$, or
A pharmaceutically acceptable salt, stereoisomer, solvate or polymorph thereof. Preferably, one of $R_{7PC}$ and $R_{10PC}$ is a

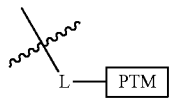

group and the other group is H and $R_{8PC}$ is H, or
A pharmaceutically acceptable salt, stereoisomer, solvate or polymorph thereof.

In still other preferred embodiments, the compound has the chemical structure:

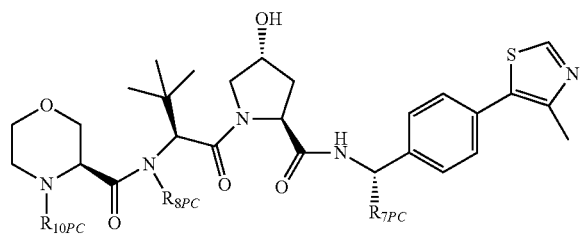

Wherein $R_{7PC}$ and $R_{10PC}$ are each independently a

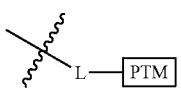

group or H and $R_{8PC}$ is H or $CH_3$, or
A pharmaceutically acceptable salt, stereoisomer, solvate or polymorph thereof. Preferably, one of $R_{7PC}$ and $R_{10PC}$ is a

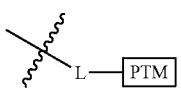

group and the other group is H and $R_{8PC}$ is H, or
A pharmaceutically acceptable salt, stereoisomer, solvate or polymorph thereof.
In still other preferred embodiments, the compound has the chemical structure:

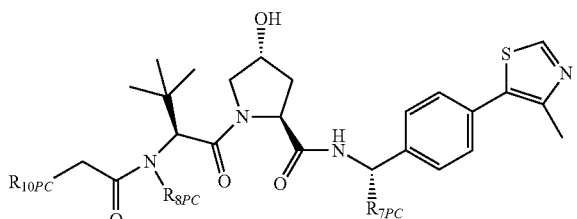

Wherein $R_{7PC}$ and $R_{10PC}$ are each independently a

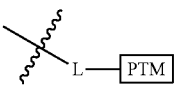

group or H and $R_{8PC}$ is H or $CH_3$ or
A pharmaceutically acceptable salt, stereoisomer, solvate or polymorph thereof. Preferably, one of $R_{7PC}$ and $R_{10PC}$ is a

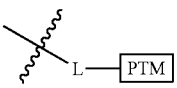

group and the other group is H and $R_{8PC}$ is H, or
A pharmaceutically acceptable salt, stereoisomer, solvate or polymorph thereof.

In still other preferred embodiments, the compound has the chemical structure:

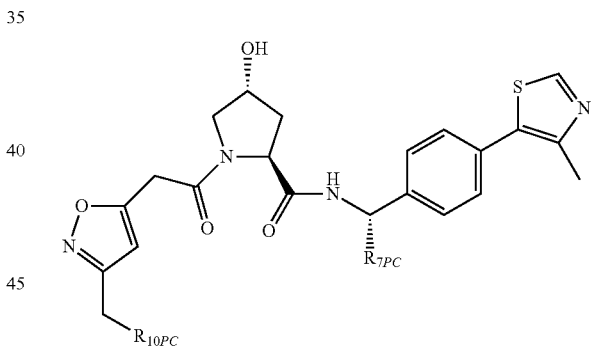

Wherein $R_{7PC}$ and $R_{10PC}$ are each independently a

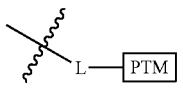

group or H, or
A pharmaceutically acceptable salt, stereoisomer, solvate or polymorph thereof. Preferably, one of $R_{7PC}$ and $R_{10PC}$ is a

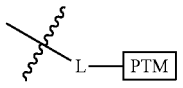

group and the other group is H, or

A pharmaceutically acceptable salt, stereoisomer, solvate or polymorph thereof.

In still other preferred embodiments, the compound has the chemical structure:

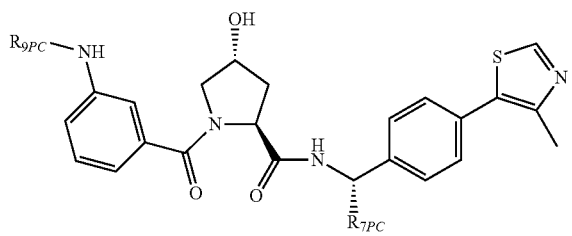

Wherein $R_{7PC}$ and $R_{9PC}$ are each independently a

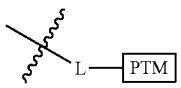

group or H, or

A pharmaceutically acceptable salt, stereoisomer, solvate or polymorph thereof. Preferably, one of $R_{7PC}$ and $R_{9PC}$ is a

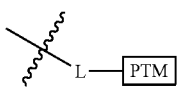

group and the other group is H, or

A pharmaceutically acceptable salt, stereoisomer, solvate or polymorph thereof.

In still other preferred embodiments, the compound has the chemical structure:

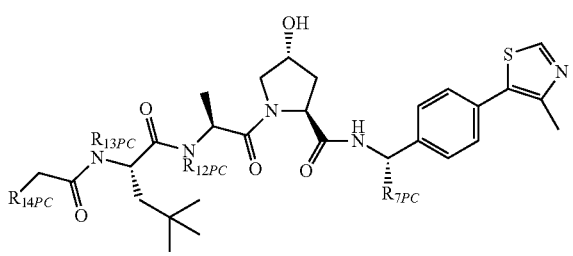

Wherein $R_{7PC}$ and $R_{14PC}$ are each independently a

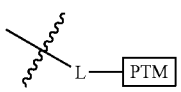

group or H and each of $R_{12PC}$ and $R_{13PC}$ is H or CH$_3$, or

A pharmaceutically acceptable salt, stereoisomer, solvate or polymorph thereof. Preferably, one of $R_{7PC}$ and $R_{14PC}$ is a

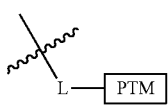

group and the other of $R_{7PC}$ and $R_{14PC}$ group is H and each of $R_{12PC}$ and $R_{13PC}$ is H, A pharmaceutically acceptable salt, stereoisomer, solvate or polymorph thereof.

In still other preferred embodiments, the compound has the chemical structure:

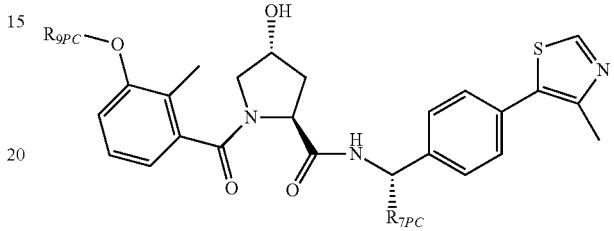

Wherein $R_{7PC}$ and $R_{9PC}$ are each independently a

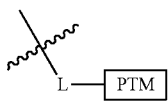

group or H, or

A pharmaceutically acceptable salt, stereoisomer, solvate or polymorph thereof. Preferably, one of $R_{7PC}$ and $R_{9PC}$ is a

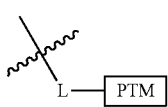

group and the other group is H, or

A pharmaceutically acceptable salt, stereoisomer, solvate or polymorph thereof.

In still other preferred embodiments, the compound has the chemical structure:

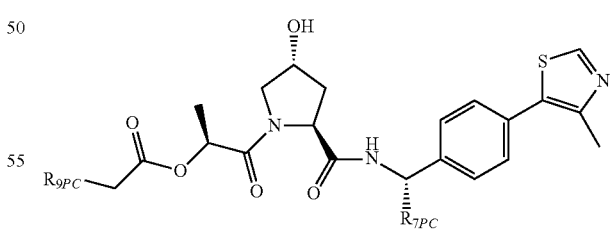

Wherein $R_{7PC}$ and $R_{9PC}$ are each independently a

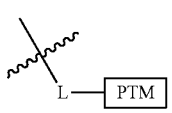

group or H, or

A pharmaceutically acceptable salt, stereoisomer, solvate or polymorph thereof. Preferably, one of $R_{7PC}$ and $R_{9PC}$ is a

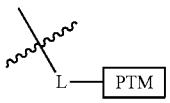

group and the other group is H, or
A pharmaceutically acceptable salt, stereoisomer, solvate or polymorph thereof.

In still other preferred embodiments, the compound has the chemical structure:

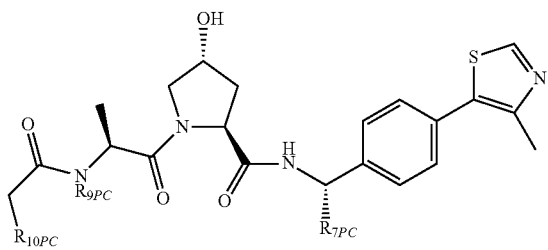

Wherein $R_{7PC}$ and $R_{10PC}$ are each independently a

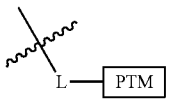

group or H and $R_{9PC}$ is H or $CH_3$, or
A pharmaceutically acceptable salt, stereoisomer, solvate or polymorph thereof. Preferably, one of $R_{7PC}$ and $R_{10PC}$ is a

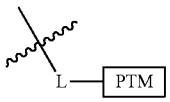

group and the other group is H and $R_{9PC}$ is H, or
A pharmaceutically acceptable salt, stereoisomer, solvate or polymorph thereof.

In the above embodiments, the linker group may be any linker group as described hereinabove, below is preferably a polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In preferred embodiments, the linker group L is a group:

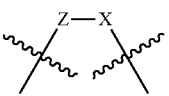

Where Z is a group which links ULM to X; and
X is a group linking Z to group PTM (including a ULM' group).

In preferred aspects, Z is absent (a bond), $-(CH_2)_i-O$, $-(CH_2)_i-S$, $-(CH_2)_i-N-R$, a

group wherein $X_1Y_1$ forms an amide group, or a urethane group, ester or thioester group, or a

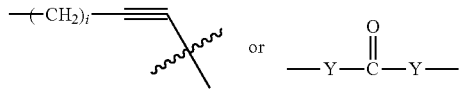

group

Each R is H, or a $C_1$-$C_3$ alkyl, an alkanol group or a heterocycle (including a water soluble heterocycle, preferably, a morpholino, piperidine or piperazine group to promote water solubility of the linker group);

Each Y is independently a bond, O, S or N—R;

and each i is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

In preferred aspects X is a

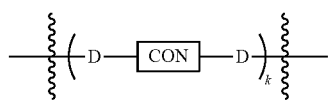

group

Where each D is independently a bond (absent),

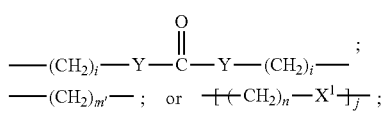

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

k is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

X' is O, S or N—R, preferably O;

Y is the same as above; and

CON is a connector group (which may be a bond) which connects Z to X, when present in the linker group.

In preferred aspects, CON is a bond (absent), a heterocycle including a water soluble heterocycle such as a piperazinyl or other group or a

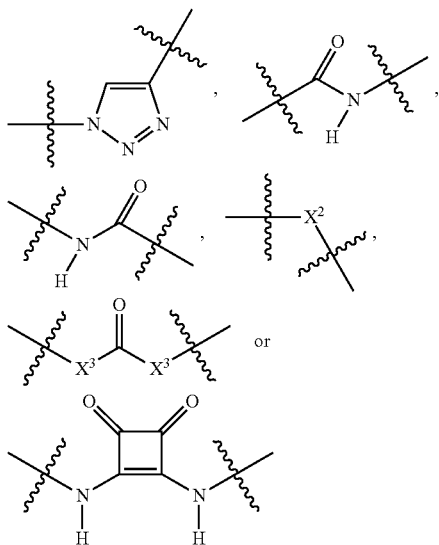

group,
Where $X^2$ is O, S, $NR^4$, S(O), $S(O)_2$, —$S(O)_2O$, —$OS(O)_2$, or $OS(O)_2O$;
$X^3$ is O, S, $CHR^4$, $NR^4$; and
$R^4$ is H or a $C_1$-$C_3$ alkyl group optionally substituted with one or two hydroxyl groups, or a pharmaceutically acceptable salt, enantiomer or stereoisomer thereof.

In alternative preferred aspects, the linker group is a (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units.

In alternative preferred aspects, CON is a

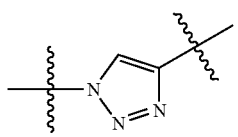 [SMILES: *c1cn(*)nn1]

group or an amide group.

Although the ULM group and PTM group (including a ULM group) may be covalently linked to the linker group through any group which is appropriate and stable to the chemistry of the linker, in preferred aspects of the present invention, the linker is independently covalently bonded to the ULM group and the PTM group (including a ULM group) preferably through an amide, ester, thioester, keto group, carbamate (urethane) or ether, each of which groups may be inserted anywhere on the ULM group and PTM group (including a ULM group) to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

In preferred aspects of the invention, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present invention. Any protein in a eukaryotic system or a microbial system, including a virus, bacteria or fungus, as otherwise described herein, are targets for ubiquitination mediated by the compounds according to the present invention. Preferably, the target protein is a eukaryotic protein. In certain aspects, the protein binding moiety is a haloalkane (preferably a C1-C10 alkyl group which is substituted with at least one halo group, preferably a halo group at the distil end of the alkyl group (i.e., away from the linker or ULM group), which may covalently bind to a dehalogenase enzyme in a patient or subject or in a diagnostic assay.

PTM groups according to the present invention include, for example, include any moiety which binds to a protein specifically (binds to a target protein) and includes the following non-limiting examples of small molecule target protein moieties: Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PTM groups for use in the present invention are preferably represented by the chemical structure —$(CH_2)_v$-Halo where v is any integer from 2 to about 12, often about 3 to about 8, more often about 4 to about 6. Halo may be any halogen, but is preferably Cl or Br, more often Cl.

In still other embodiments, the PTM group is a

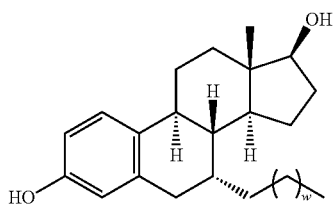

group, where w is 0 to 3, preferably 1 or 2. This group binds selectively to estrogen receptors and is useful for treating diseases which are modulated through estrogen receptors, and in particular cancers, such as breast cancer, endometrial cancer, ovarian cancer and uterine cancer, among others.

The present invention may be used to treat a number of disease states and/or conditions, including any disease state and/or condition in which proteins are dysregulated and where a patient would benefit from the degradation of proteins.

In another aspect, the present invention relates to pharmaceutical compositions comprising an effective amount of a compound as set forth hereinabove, in combination with a pharmaceutically acceptable carrier, additive or excipient, and optionally an additional bioactive agent.

In alternative aspects, the present invention relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

DETAILED DESCRIPTION OF THE INVENTION

The following terms are used to describe the present invention. In instances where a term is not specifically defined herein, that term is given an art-recognized meaning by those of ordinary skill applying that term in context to its use in describing the present invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond ⚌ is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "VCB E3 Ubiquitin Ligase", "Hippel-Lindau E3 Ubiquitin Ligase" or "Ubiquitin Ligase" is used to describe a target enzyme(s) binding site of ubiquitin ligase moieties in the bifunctional (chimeric) compounds according to the present invention. VCB E3 is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

Protein target moieties according to the present invention include, for example, Haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR). The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

I. Heat Shock Protein 90 (HSP90) Inhibitors:

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) *J. Med. Chem.* 54: 7206, including

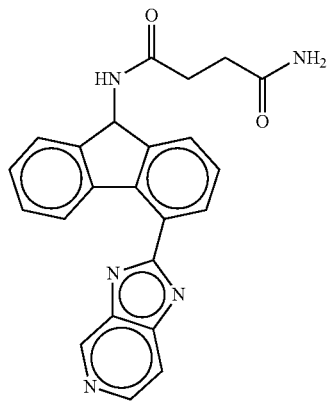

N-[4-(3H-IMIDAZO[4,5-C]PYRIDIN-2-YL)-9H-FLUOREN-9-YL]-SUCCINAMIDE

Derivatized where a linker group L or a

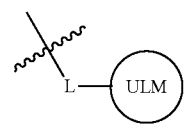

group is attached via the terminal amide group;

2. The HSP90 inhibitor p54 (modified):

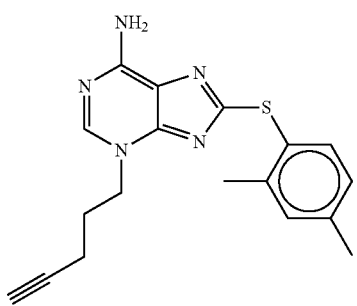

8-[(2,4-dimethylphenyl)sulfanyl]-3-pent-4-yn-1-yl-3H-purin-6-amine

Where a linker group L or a

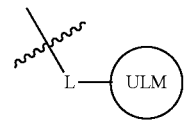

group is attached via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. MED. CHEM* vol: 51, pag:196 (2008), including the compound 2GJ (5-[2,4-DIHYDROXY-5-(1-METHYL-ETHYL)PHENYL]-N-ETHYL-4-[4-(MORPHOLIN-4-YL-METHYL)PHENYL]ISOXAZOLE-3-CARBOXAMIDE) having the structure:

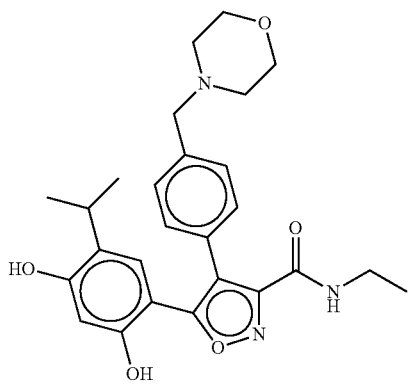

Derivatized, where a linker group L or a

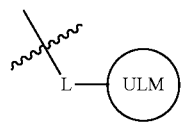

group is attached via the amide group (at the amine or at the alkyl group on the amine;

4. The HSP90 inhibitors (modified) identified in Wright, et al., Structure-Activity Relationships in Purine-Based Inhibitor Binding to HSP90 Isoforms, *Chem Biol.* 2004 June; 11(6):775-85, including the HSP90 inhibitor PU3 having the structure:

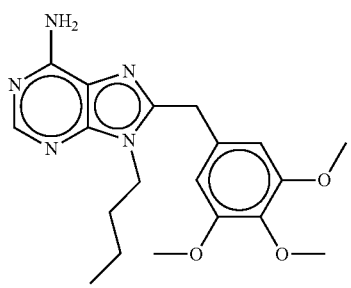

Where a linker group L or

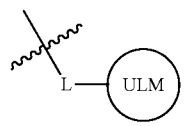

is attached via the butyl group; and

5. The HSP90 inhibitor Geldanamycin ((4E,6Z,8S,9S,10E, 12S,13R,14S,16R)-13-hydroxy-8,14,19-trimethoxy-4,10, 12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or a

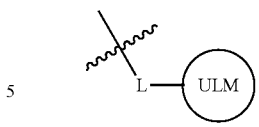

group is attached via the amide group).

II. Kinase and Phosphatase Inhibitors:

Kinase inhibitors as used herein include, but are not limited to:

1. Erlotinib Derivative Tyrosine Kinase Inhibitor

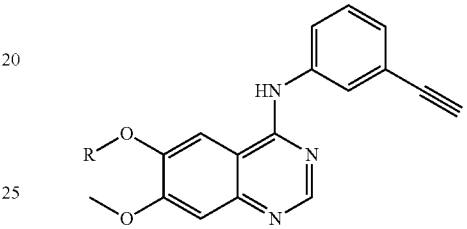

Where R is a linker group L or a

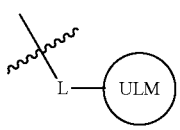

group attached via the ether group;

2. The kinase inhibitor Sunitanib (derivatized):

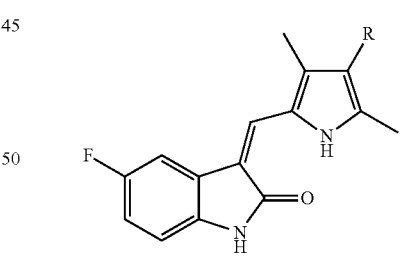

(Derivatized where R is a linker group L or a

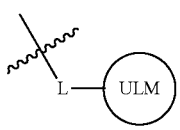

group attached to the pyrrole moiety);

3. Kinase Inhibitor Sorafenib (derivatized)

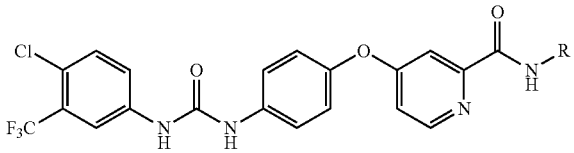

(Derivatized where R is a linker group L or a

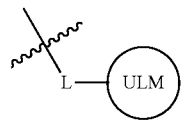

group attached to the phenyl moiety);

4. The kinase inhibitor Desatinib (derivatized)

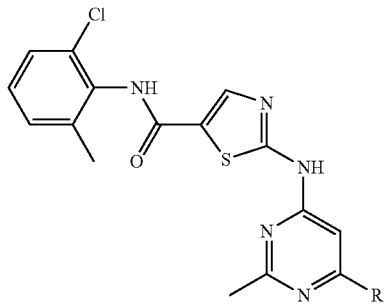

(Derivatized where R is a linker group L or a

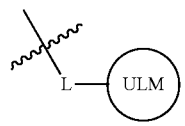

attached to the pyrimidine);

5. The kinase inhibitor Lapatinib (derivatized)

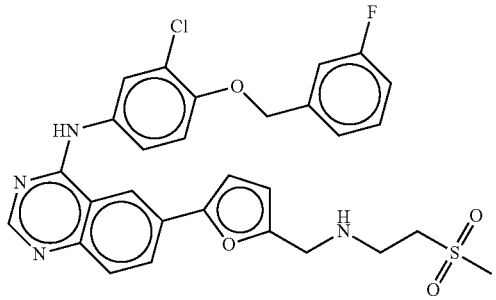

Lapatinib

Derivatized where a linker group L or a

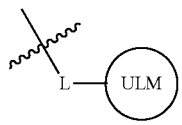

group is attached via the terminal methyl of the sulfonyl methyl group;

6. The kinase inhibitor U09-CX-5279 (derivatized)

7.

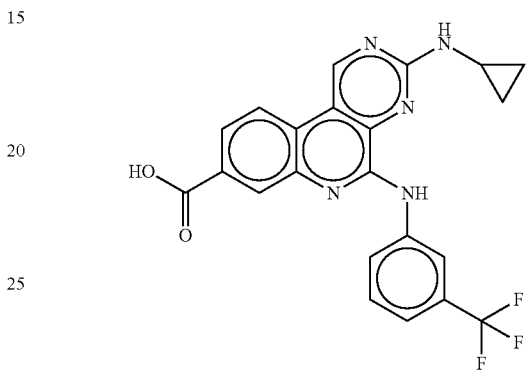

CX-5279
3-(cyclopropylamino)-5-{[3-(trifluoromethyl)phenyl]amino}pyrimido[4,5-c]quinoline-8-carboxylic acid Derivatized where a linker group L or a

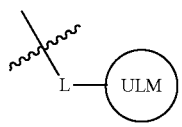

group is attached via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, *J. MED. CHEM.* vol:54, pag:7797 (2011), including the kinase inhibitors Y1W and Y1X (Derivatized) having the structures:

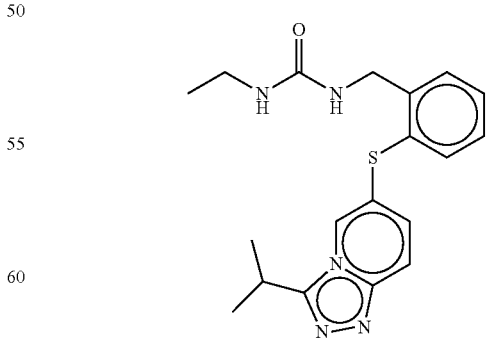

YIX
1-ethyl-3-(2-{[3-(1-methylethyl)[1,2,4]triazolo[4,3-a]pyridin-6-yl]sulfanyl}benzyl)urea Derivatized where a linker group L or a

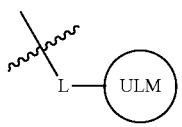

group is attached preferably via the propyl group;

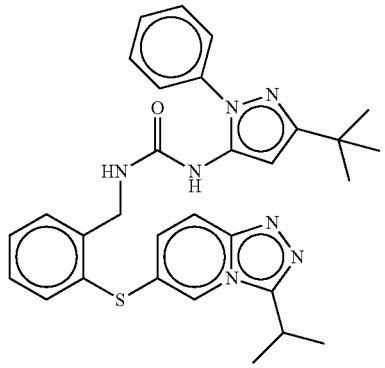

1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea

YIW

Derivatized where a linker group L or a

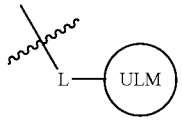

group is attached preferably via either the propyl group or the butyl group;

8. The kinase inhibitors identified in Schenkel, et al., Discovery of Potent and Highly Selective Thienopyridine Janus Kinase 2 Inhibitors *J. Med. Chem.*, 2011, 54 (24), pp 8440-8450, including the compounds 6TP and 0TP (Derivatized) having the structures:

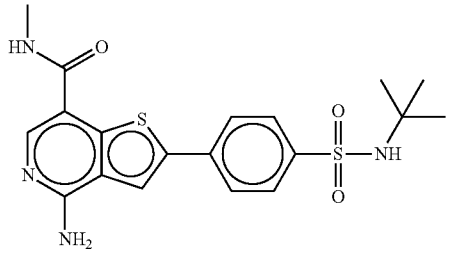

6TP 4-amino-2-[4-(tert-butylsulfamoyl)phenyl]-N-methylthieno[3,2-c]pyridine-7-carboxamide Thienopyridine 19

Derivatized where a linker group L or a

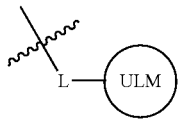

group is attached preferably via the terminal methyl group bound to amide moiety;

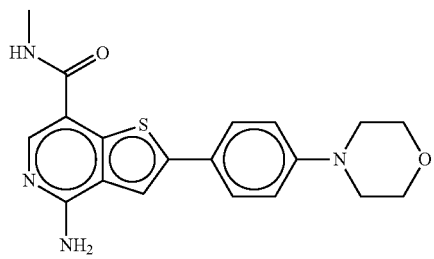

0TP 4-amino-N-methyl-2-[4-(morpholin-4-yl)phenyl]thieno[3,2-c]pyridine-7-carboxamide Thienopyridine 8

Derivatized where a linker group L or a

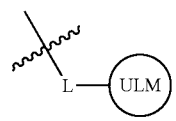

group is attached preferably via the terminal methyl group bound to the amide moiety;

9. The kinase inhibitors identified in Van E is, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

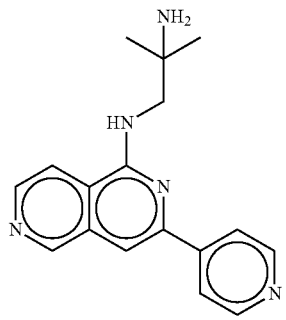

07U 2-methyl-N~1~-[3-(pyridin-4-yl)-2,6-naphthyridin-1-yl]propane-1,2-diamine

Derivatized where a linker group L or a

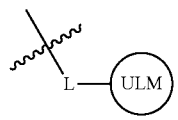

group is attached preferably via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol:176, pag:292 (2011), including the kinase inhibitor YCF having the structure:

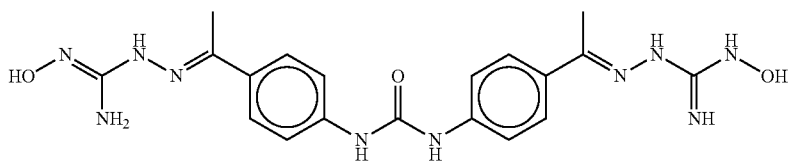

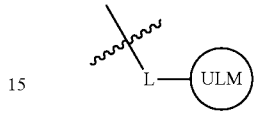

Derivatized where a linker group L or a

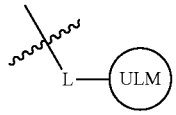

group is attached preferably via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol:176, pag:292 (2011), including the kinase inhibitors XK9 and NXP (derivatized) having the structures:

XK9

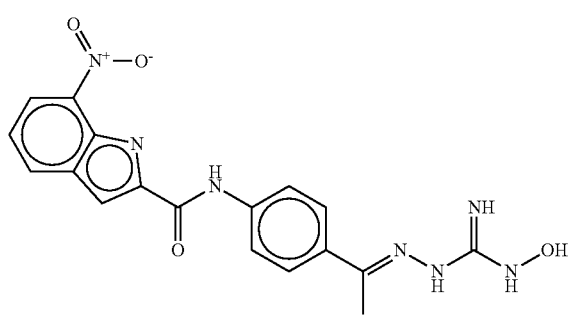

N-{4-[(1E)-N-(N-hydroxycarbamimidoyl)ethanehydrazonoyl]phenyl}-7-nitro-1H-indole-2-carboxamide

NXP

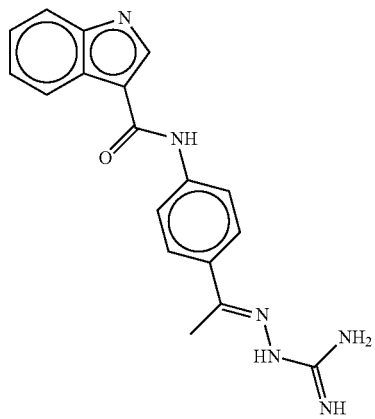

N-{4-[(1E)-N-CARBAMIMIDOYLETHANEHYDRAZONOYL]PHENYL}-1H-INDOLE-3-CARBOXAMIDE

Derivatized where a linker group L or a

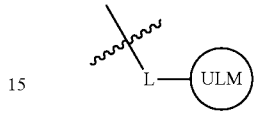

group is attached preferably via the terminal hydroxyl group (XK9) or the hydrazone group (NXP);

12. The kinase inhibitor Afatinib (derivatized) (N-[4-[(3-Chloro-4-fluorophenyl)amino]-7-[[(3S)-tetrahydro-3-furanyl]oxy]-6-quinazolinyl]-4(dimethylamino)-2-butenamide) (Derivatized where a linker group L or a

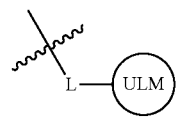

group is attached preferably via the aliphatic amine group);

13. The kinase inhibitor Fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a

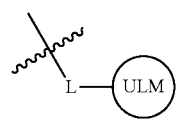

group is attached preferably via a methoxy group);

14. The kinase inhibitor Gefitinib (derivatized) (N-(3-chloro-4-fluoro-phenyl)-7-methoxy-6-(3-morpholin-4-yl-propoxy)quinazolin-4-amine) (Derivatized where a linker group L or a

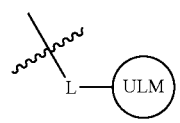

group is attached preferably via a methoxy or ether group);

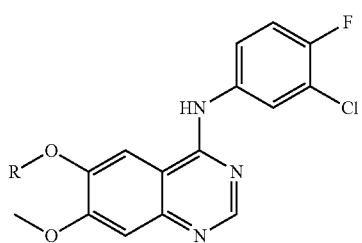

15. The kinase inhibitor Lenvatinib (derivatized) (4-[3-chloro-4-(cyclopropylcarbamoylamino)phenoxy]-7-methoxy-quinoline-6-carboxamide) (Derivatized where a linker group L or a

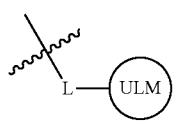

group is attached preferably via the cyclopropyl group);

16. The kinase inhibitor Vandetanib (derivatized) (N-(4-bromo-2-fluorophenyl)-6-methoxy-7-[(1-methylpiperidin-4-yl)methoxy]quinazolin-4-amine) (derivatized where a linker group L or a

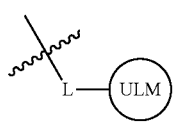

group is attached preferably via the methoxy or hydroxyl group); and

17. The kinase inhibitor Vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide) (Derivatized where a linker group L or a

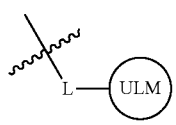

group is attached preferably via the sulfonyl propyl group);

18. The kinase inhibitor Gleevec (derivatized):

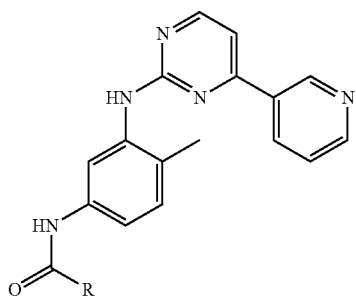

(Derivatized where R as a linker group L or a

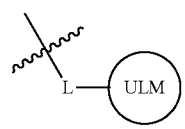

group is attached preferably via the amide group or via the aniline amine group);

19. The kinase inhibitor Pazopanib (derivatized) (VEGFR3 inhibitor):

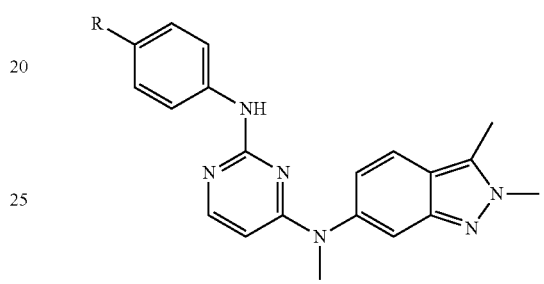

(Derivatized where R is a linker group L or a

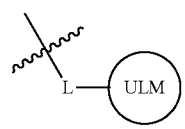

group preferably attached to the phenyl moiety or via the aniline amine group);

20. The kinase inhibitor AT-9283 (Derivatized) Aurora Kinase Inhibitor

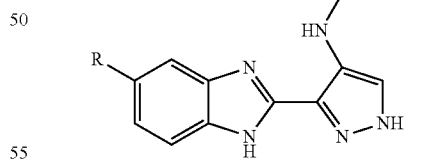

(where R is a linker group L or a

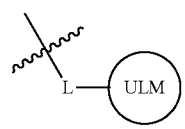

group attached preferably to the phenyl moiety);

21. The kinase inhibitor TAE684 (derivatized) ALK inhibitor

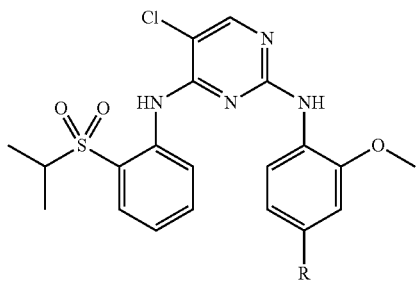

(where R is a linker group L or a

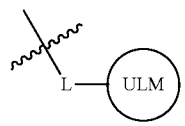

group attached preferably to the phenyl moiety);

22. The kinase inhibitor Nilotanib (derivatized) Ab1 inhibitor:

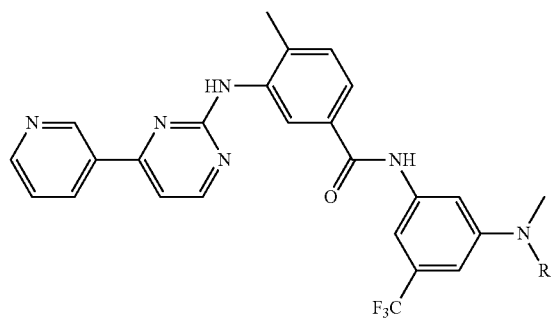

(Derivatized where R is a linker group L or a

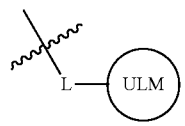

group attached preferably to the phenyl moiety or the aniline amine group);

27. Kinase Inhibitor NVP-BSK805 (derivatized) JAK2 Inhibitor

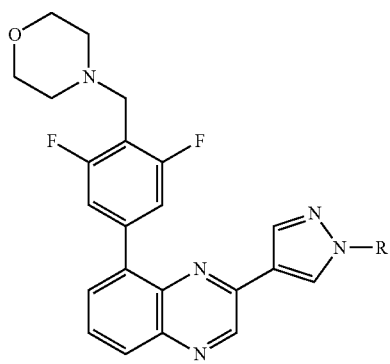

(Derivatized where R is a linker group L or a

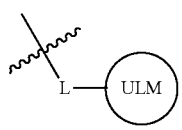

group attached to the phenyl moiety or the diazole group);

28. Kinase Inhibitor Crizotinib Derivatized Alk Inhibitor

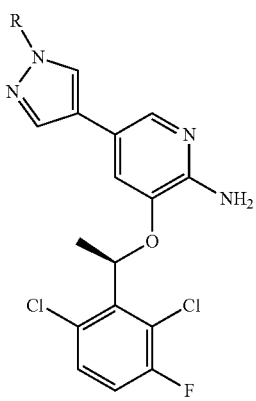

(Derivatized where R is a linker group L or a

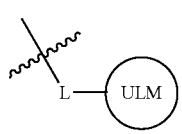

group attached to the phenyl moiety or the diazole group);

29. Kinase Inhibitor JNJ FMS (derivatized) Inhibitor

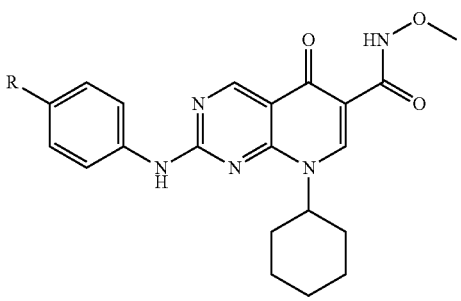

(Derivatized where R is a linker group L or a

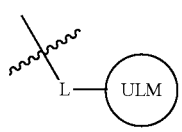

group attached preferably to the phenyl moiety);

30. The kinase inhibitor Foretinib (derivatized) Met Inhibitor

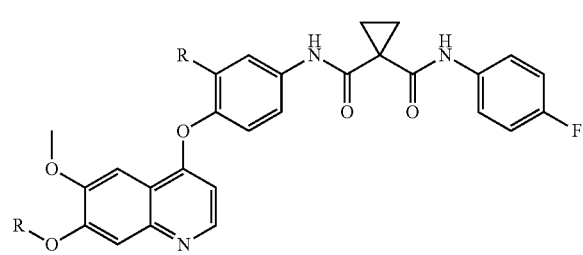

(Derivatized where R is a linker group L or a

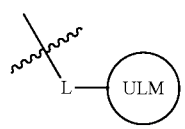

group attached to the phenyl moiety or a hydroxyl or ether group on the quinoline moiety);

31. The allosteric Protein Tyrosine Phosphatase Inhibitor PTP1B (derivatized):

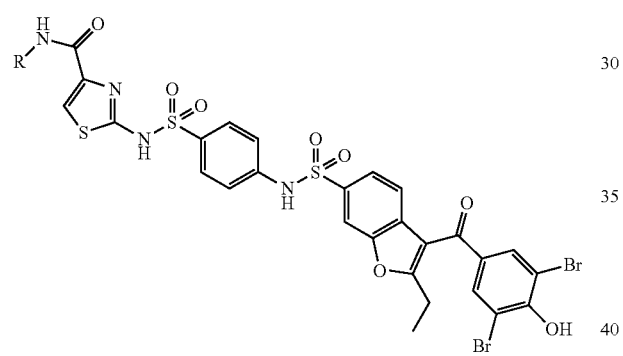

Derivatized where a linker group L or a

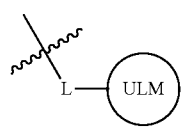

group is preferably attached at R, as indicated.

32. The inhibitor of SHP-2 Domain of Tyrosine Phosphatase (derivatized):

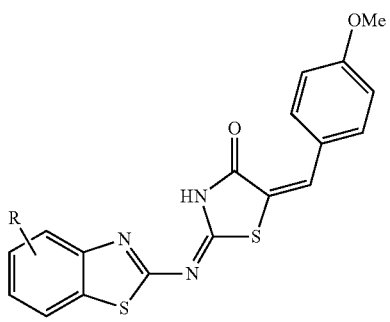

Derivatized where a linker group L or a

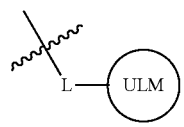

group is attached preferably at R.

33. The inhibitor (derivatized) of BRAF (BRAF$^{V600E}$)/MEK:

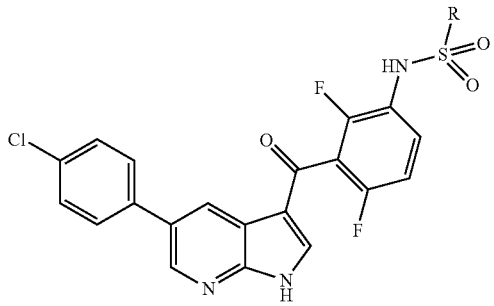

Derivatized where a linker group L or a

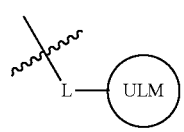

group is attached preferably at R.

34. Inhibitor (derivatized) of Tyrosine Kinase ABL

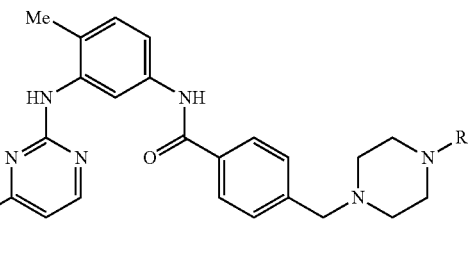

(Derivatized where "R" designates a site for attachment of a linker group L or a

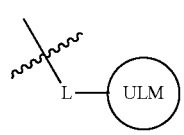

group on the piperazine moiety).

III. MDM2 Inhibitors:
MDM2 inhibitors as used herein include, but are not limited to:
1. The MDM2 inhibitors identified in Vassilev, et al., In vivo activation of the p53 pathway by small-molecule antagonists of MDM2, *SCIENCE* vol:303, pag:844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

Nutlin-3

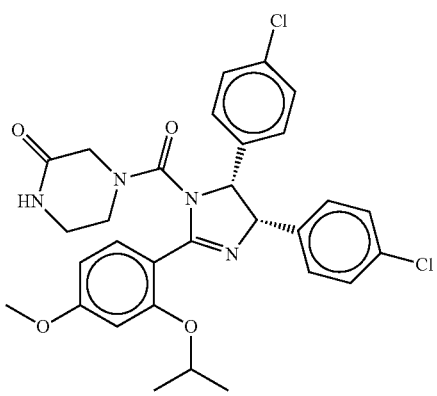

(Derivatized where a linker group L or a

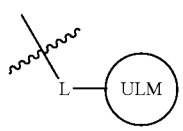

group is attached preferably at the methoxy group or as a hydroxyl group)

Nutlin-2

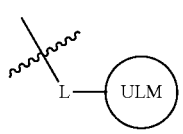

(Derivatized where a linker group L or a group is attached preferably at the methoxy group or hydroxyl group);

Nutlin-1

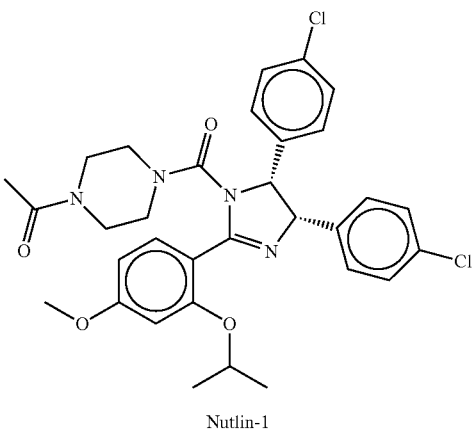

(Derivatized where a linker group L or a

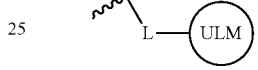

group is attached via the methoxy group or as a hydroxyl group); and

2. Trans-4-Iodo-4'-Boranyl-Chalcone

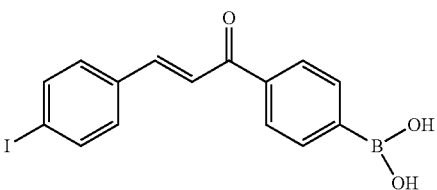 [SMILES: O=C(/C=C/c1ccc(I)cc1)c1ccc(B(O)O)cc1]

(Derivatized where a linker group L or a linker group L or a

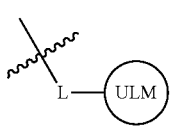

group is attached a linker group L or a

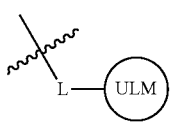

group is attached group is attached via a hydroxy group);

IV. Compounds Targeting Human BET Bromodomain-Containing Proteins:

Compounds targeting Human BET Bromodomain-containing proteins include, but are not limited to the compounds associated with the targets as described below, where "R" designates a site for linker group L or a

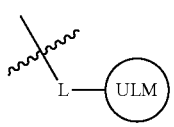

group attachment:
1.
Protein Targets: Brd2, Brd3, Brd4

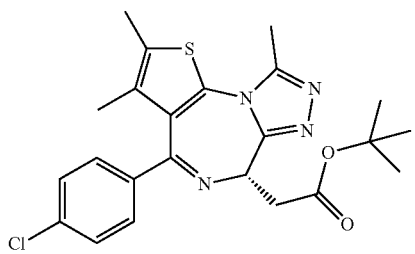

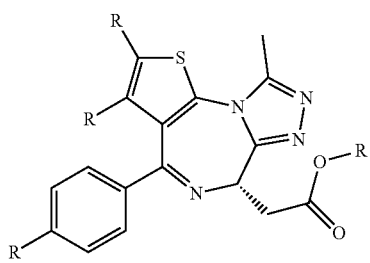

JQ1, Filippakopoulos et al. Selective inhibition of BET bromodomains. Nature (2010)
2.

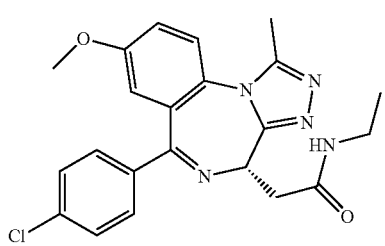

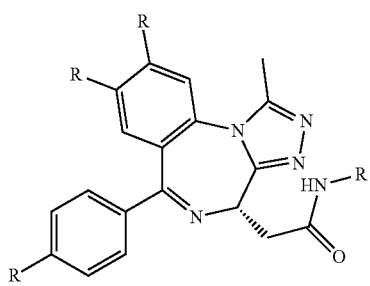

I-BET, Nicodeme et al. Suppression of inflammation by a synthetic histone mimic. Nature (2010) Chung et al. Discovery and Characterization of Small Molecule Inhibitors of the BET Family Bromodomains. Journal of medicinal chemistry (2011)

3.

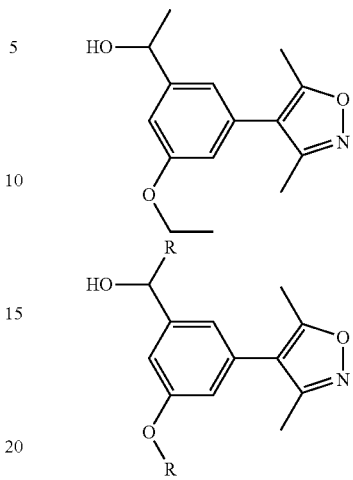

4d, Hewings et al. 3,5-Dimethylisoxazoles Act As Acetyl-lysine-mimetic Bromodomain Ligands. J. Med. Chem. (2011) vol. 54 (19) pp. 6761-70
4.

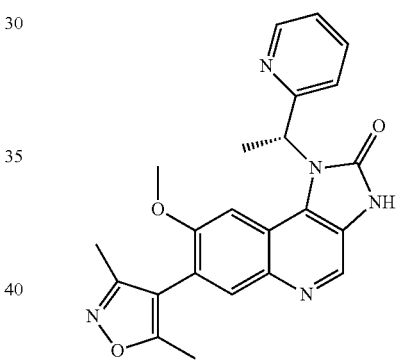

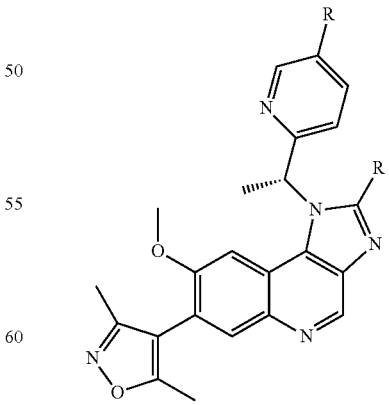

I-BET151, Dawson et al. Inhibition of BET recruitment to chromatin as an effective treatment for MLL-fusion leukaemia. Nature (2011)

(Where R, in each instance, designates a site for attachment of a linker group L or a

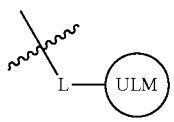

group).

V. HDAC Inhibitors:

HDAC Inhibitors (derivatized) include, but are not limited to:

1.

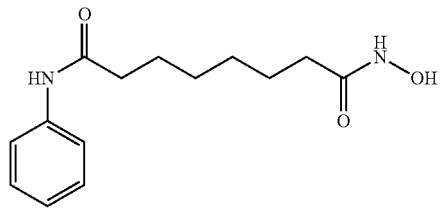

SAHA

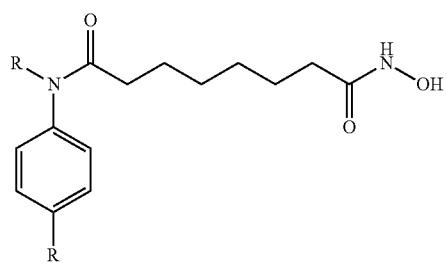

Finnin, M. S. et al. Structures of a histone deacetylase homologue bound to the TSA and SAHA inhibitors. Nature 401, 188-193 (1999).

(Derivatized where "R" designates a site for attachment of a linker group L or a

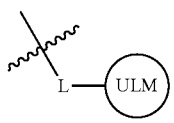

group); and

2. Compounds as defined by formula (I) of PCT WO0222577 ("DEACETYLASE INHIBITORS") (Derivatized where a linker group L or a

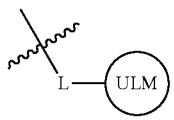

group is attached via the hydroxyl group);

VI. Human Lysine Methyltransferase Inhibitors:

Human Lysine Methyltransferase inhibitors include, but are not limited to:

1.

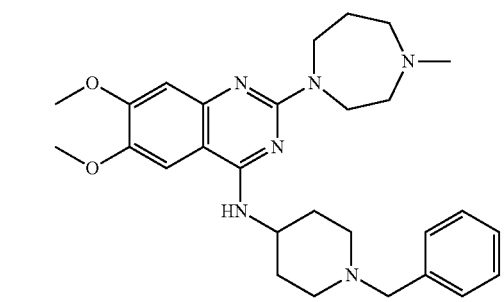

BIX-01294

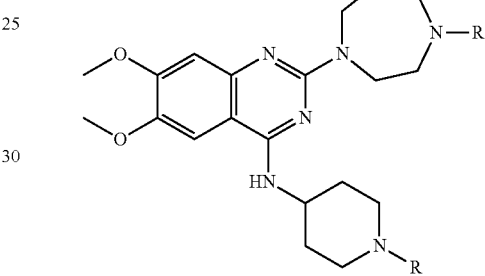

Chang et al. Structural basis for G9a-like protein lysine methyltransferase inhibition by BIX-01294. Nat Struct Mol Biol (2009) vol. 16 (3) pp. 312-7

(Derivatized where "R" designates a site for attachment of a linker group L or a

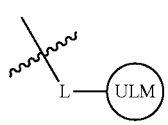

group);

2.

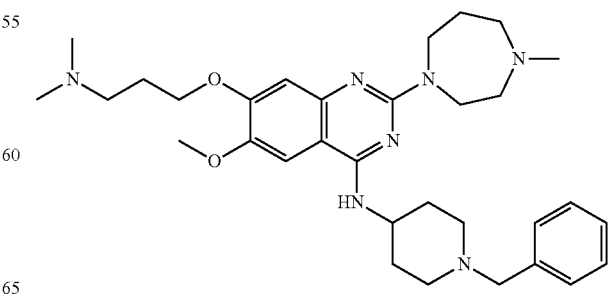

UNC0224

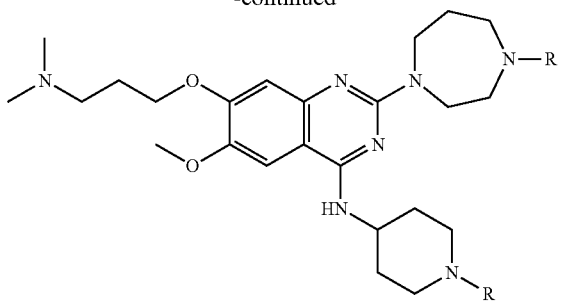

Liu F, Chen X, Allali-Hassani A, et al. Discovery of a 2,4-diamino-7-aminoalkoxyquinazoline as a potent and selective inhibitor of histone lysine methyltransferase G9a. J Med Chem 2009; 52(24):7950-3

(Derivatized where "R" designates a potential site for attachment of a linker group L or a

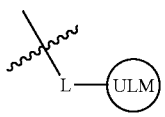

group);

3. Azacitidine (derivatized) (4-amino-1-β-D-ribofuranosyl-1,3,5-triazin-2(1H)-one) (Derivatized where a linker group L or a

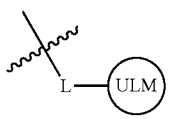

group is attached via the hydroxy or amino groups); and

4. Decitabine (derivatized) (4-amino-1-(2-deoxy-b-D-erythro-pentofuranosyl)-1,3,5-triazin-2(1H)-one) (Derivatized where a linker group L or a

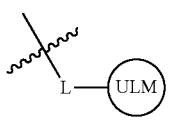

group is attached via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics* 2003 December; 2(12):1350-8;

2. Estradiol (derivatized), which may be bound to a linker group L or a

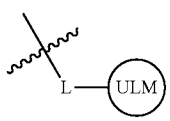

group as is generally described in Rodriguez-Gonzalez, et al., Targeting steroid hormone receptors for ubiquitination and degradation in breast and prostate cancer, *Oncogene* (2008) 27, 7201-7211;

3. Estradiol, testosterone (derivatized) and related derivatives, including but not limited to DHT and derivatives and analogs thereof, having the structure(s) and binding to a linker group L or a

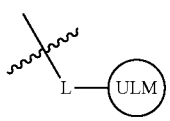

group as generally described in Sakamoto, et al., Development of Protacs to target cancer-promoting proteins for ubiquitination and degradation, *Mol Cell Proteomics* 2003 December; 2(12):1350-8; and 4. Ovalicin, fumagillin (derivatized), and derivatives and analogs thereof, having the structure(s) and binding to a linker group L or a

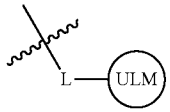

group as is generally described in Sakamoto, et al., Protacs: chimeric molecules that target proteins to the Skp1-Cullin-F box complex for ubiquitination and degradation *Proc Natl Acad Sci USA*. 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a

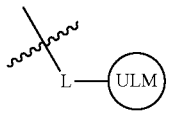

group as is generally described in Schneekloth, et al., Chemical Genetic Control of Protein Levels: Selective in Vivo Targeted Degradation, *J. AM. CHEM. SOC.* 2004, 126, 3748-3754;

2. Glucocorticoids (e.g., hydrocortisone, prednisone, prednisolone, and methylprednisolone) (Derivatized where a linker group L or a

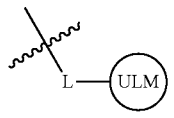

group is to bound, e.g. to any of the hydroxyls) and beclometasone dipropionate (Derivatized where a linker group or a

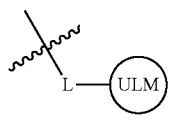

is bound, e.g. to a proprionate);

3. Methotrexate (Derivatized where a linker group or a

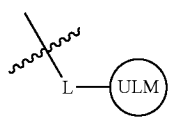

group can be bound, e.g. to either of the terminal hydroxyls);

4. Ciclosporin (Derivatized where a linker group or a

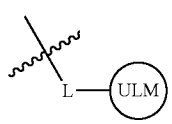

group can be bound, e.g. at any of the butyl groups);

5. Tacrolimus (FK-506) and rapamycin (Derivatized where a linker group L or a

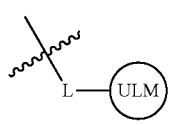

group can be bound, e.g. at one of the methoxy groups); and

6. Actinomycins (Derivatized where a linker group L or a

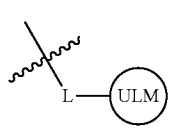

group can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker group L or a

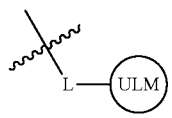

group as is generally illustrated in Lee, et al., Targeted Degradation of the Aryl Hydrocarbon Receptor by the PROTAC Approach: A Useful Chemical Genetic Tool, *ChemBioChem* Volume 8, Issue 17, pages 2058-2062, Nov. 23, 2007); and 2. SR1 and LGC006 (derivatized such that a linker group L or a

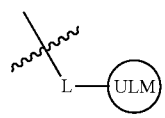

is bound), as described in Boitano, et al., Aryl Hydrocarbon Receptor Antagonists Promote the Expansion of Human Hematopoietic Stem Cells, *Science* 10 Sep. 2010: Vol. 329 no. 5997 pp. 1345-1348.

X. Compounds Targeting RAF Receptor (Kinase):

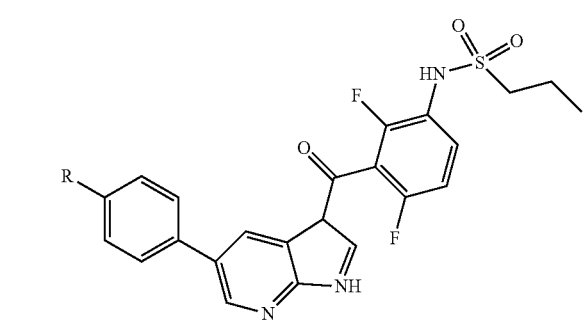

PLX4032

(Derivatized where "R" designates a site for linker group L or

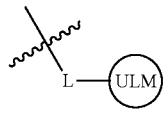

group attachment).

XI. Compounds Targeting FKBP

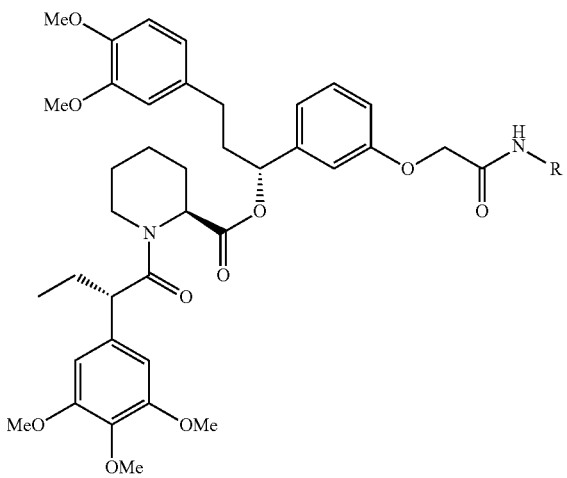

(Derivatized where "R" designates a site for a linker group L or a

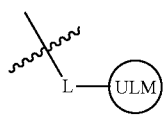

group attachment).

XII. Compounds Targeting Androgen Receptor (AR)
1. RU59063 Ligand (derivatized) of Androgen Rceptor

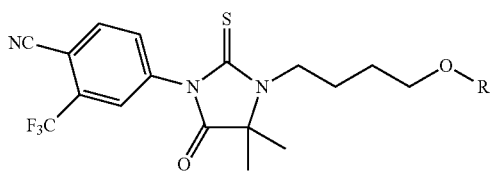

(Derivatized where "R" designates a site for a linker group L or a

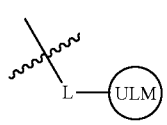

group attachment).
2. SARM Ligand (derivatized) of Androgen Receptor

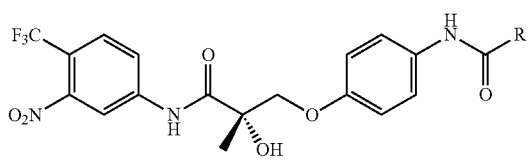

(Derivatized where "R" designates a site for a linker group L or a

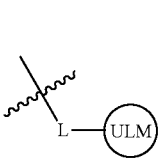

group attachment).

3. Androgen Receptor Ligand DHT (derivatized)

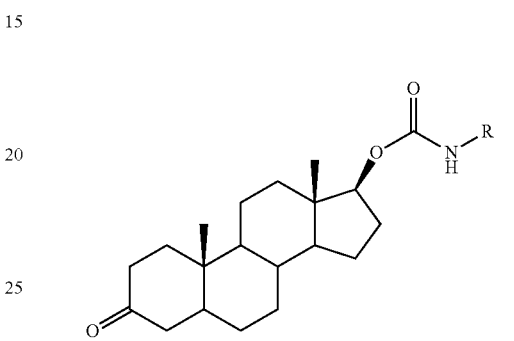

(Derivatized where "R" designates a site for a linker group L or

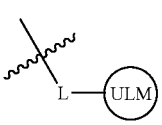

group attachment).

XIII. Compounds Targeting Estrogen Receptor (ER) ICI-182780
1. Estrogen Receptor Ligand

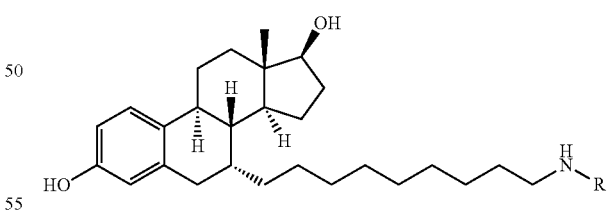

(Derivatized where "R" designates a site for linker group L or

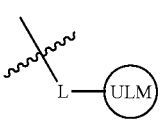

group attachment).

XIV. Compounds Targeting Thyroid Hormone Receptor (TR)
1. Thyroid Hormone Receptor Ligand (Derivatized)

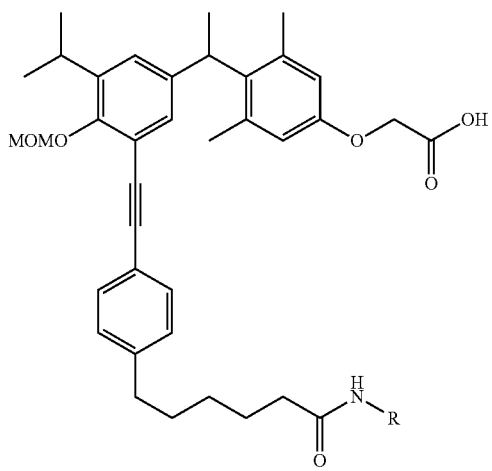

(Derivatized where "R" designates a site for linker group L or

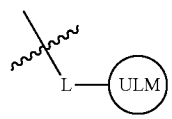

group attachment and MOMO indicates a methoxymethoxy group).

XV. Compounds Targeting HIV Protease
1. Inhibitor of HIV Protease (Derivatized)

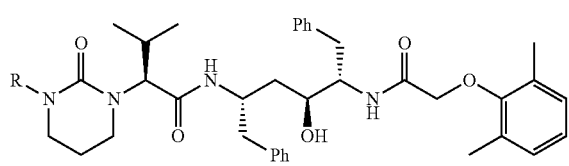

(Derivatized where "R" designates a site for linker group L or

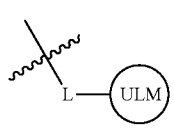

group attachment). See, *J. Med. Chem.* 2010, 53, 521-538.

2. Inhibitor of HIV Protease

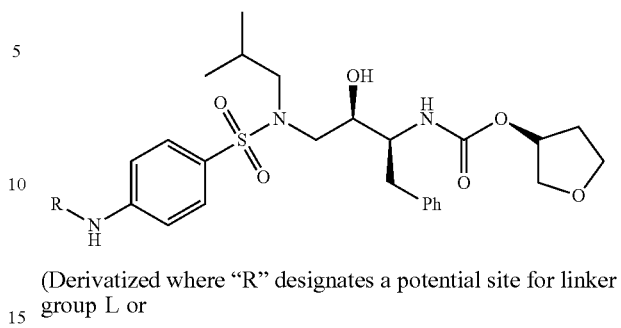

(Derivatized where "R" designates a potential site for linker group L or

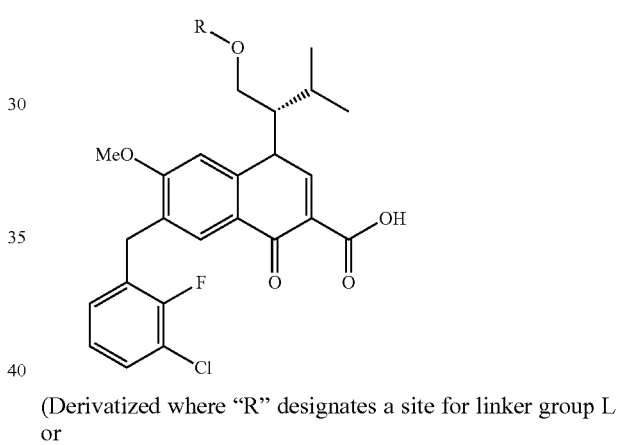

group attachment). See, *J. Med. Chem.* 2010, 53, 521-538.

XVI. Compounds targeting HIV Integrase
1. Inhibitor of HIV Integrase (Derivatized)

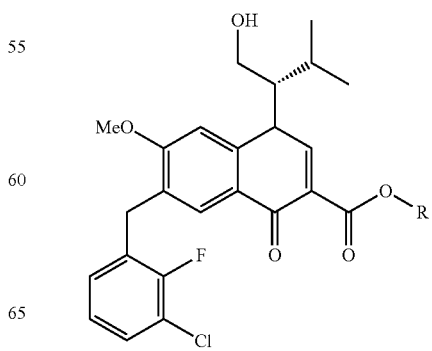

(Derivatized where "R" designates a site for linker group L or group attachment). See, *J. Med. Chem.* 2010, 53, 6466.
2. Inhibitor of HIV Integrase (Derivatized)

(Derivatized where "R" designates a site for linker group L or

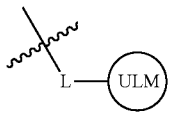

group attachment). See, gJ. Med. Chem. 2010, 53, 6466.

XVII. Compounds Targeting HCV Protease

1. Inhibitors of HCV Protease (Derivatized)

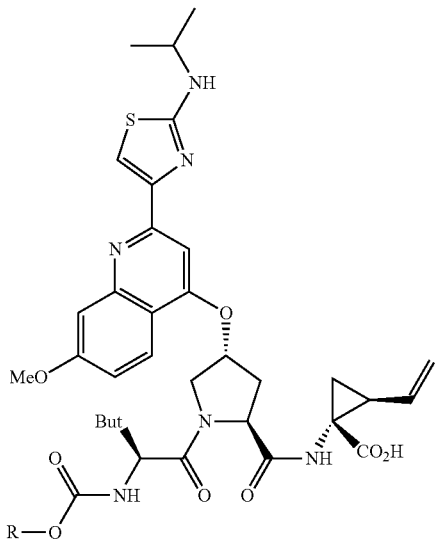

(Derivatized where "R" designates a site for linker group L or

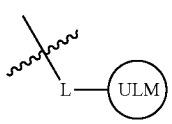

group attachment).

XVIII. Compounds Targeting Acyl-Protein Thioesterase-1 and -2 (APT1 and APT2)

1. Inhibitor of APT1 and APT2 (Derivatized)

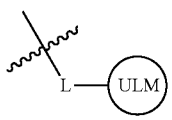

(Derivatized where "R" designates a site for linker group L or

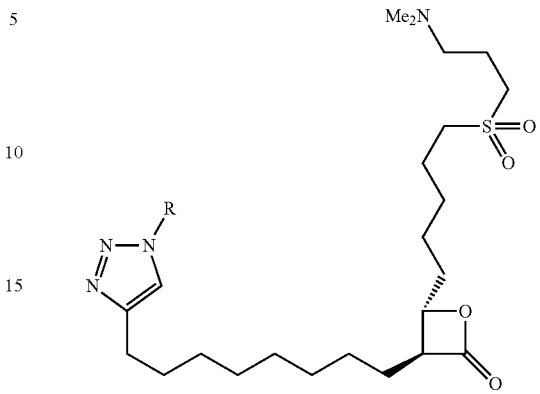

group attachment). See, Angew. Chem. Int. Ed. 2011, 50, 9838-9842, where L is a linker group as otherwise described herein and said ⊖ group is as otherwise described herein such that

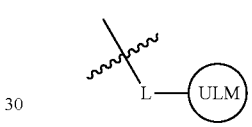

binds the ⊖ group to a ⊕ group as otherwise described herein.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to ⊖ groups through linker groups L.

Target proteins which may be bound to the protein target moiety and degraded by the ligase to which the ubiquitin ligase binding moiety is bound include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others More specifically, a number of drug targets for human therapeutics represent protein targets to which protein target moiety may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyl-transferases, geranylgeranyl transferase, TrkA a receptor for NGF, beta-amyloid, tyrosine kinase Flk-IIKDR vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase,
adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related diagnostic proteins as described in PCT/US 2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present invention, the level of activity of the protein may be altered for therapeutic end result.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyl (Marfan syndrome), Stickler syndrome, Arthrochalasis multiplex congenital (Ehlers-Danlos syndrome # arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotimidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease Tomaculous neuropathy (hereditary neuropathy with liability to pressure palsies) Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present invention to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6,Azgly 10](pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis retinoic acid, phenylalanine mustard, uracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucleoeoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present invention include, for example, other NNRTI's (i.e., other than the NNRTI's according to the present invention) may be selected from the group consisting of nevirapine (B1-R6-587), delavirdine (U-90152S/T), efavirenz (DMP-266), UC-781 (N-[4-chloro-3-(3-methyl-2-butenyloxy)phenyl]-2-methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4''-dimethoxy-5',5''-bis (methoxycarbonyl)-6,6-diphenylhexenoate), Methyl 3-Bromo-5-(1-5-bromo-4-methoxy-3-(methoxycarbonyl)phenyl) hept-1-enyl)-2-methoxybenzoate (Alkenyldiarylmethane analog, Adam analog), 5Cl3PhS-2Indo1CONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazinel pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy) methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy) methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]hiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)] thiourea, N-(2-Phenethyl)-N'-(2-thiazolyl)thiourea (LY-73497), L-697,639, L-697,593, L-697,661, 3-[2-(4,7-Difluorobenzoxazol-2-yeethyl]-5-ethyl-6-methyl(pypridin-2(1H)-thione (2-Pyridinone Derivative), 3-[[(2-Methoxy-5,6-dimethyl-3-pyridyl)methyl]amine]-5-ethyl-6-methyl (pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a] isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "independently" is used herein to indicate that the variable, which is independently applied, varies independently from application to application.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein. The term "Alkenyl" refers to linear, branch-chained or cyclic $C_2$-$C_{10}$ (preferably $C_2$-$C_6$) hydrocarbon radicals containing at least one C=C bond. The term "Alkynyl" refers to linear, branch-chained or cyclic $C_2$-$C_{10}$ (preferably $C_2$-$C_6$) hydrocarbon radicals containing at least one C≡C bond. The term "alkylene" when used, refers to a —($CH_2$)— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), more preferably a methyl group, but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example —Si$R_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary non-aromatic heterocyclic groups for use in the present invention include, for example, pyrrolidinyl, pyrrolinyl, piperidinyl, piperazinyl, N-methylpiperazinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others, as described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the present compounds described above, are coadministered in combination with at least one additional bioactive agent, especially including an anticancer agent. In particularly preferred aspects of the invention, the co-administration of compounds results in synergistic therapeutic, including anticancer therapy.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The present invention includes, where applicable, the compositions comprising the pharmaceutically acceptable salts, in particular, acid or base addition salts of compounds of the present invention. The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds of the present invention may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient. Compounds according to the present invention may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present invention can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

General Synthetic Approaches

Generic scheme for the synthesis of ULM derivatives is described here. Briefly, the compounds according to the present invention are synthesized pursuant to the general solution phase synthetic scheme (presented hereinbelow) and/or general scheme I, which is directed to phase synthesis of compounds according to the present invention. Initially a hydroxyl-protected carboxy substituted (and protected) pyrusing this approach. The solid phase synthetic method can also be used and employs similar methods used in the solution phase synthesis, the major difference being that the hydroxyl group may be bound to a solid support as the other steps of the synthesis occur. The general synthetic methods are applicable to virtually all of the compounds of the present invention with facile modifications being made consistent with the state of chemical synthetic art as used directly or adapted from the specific teachings of the examples which follow.

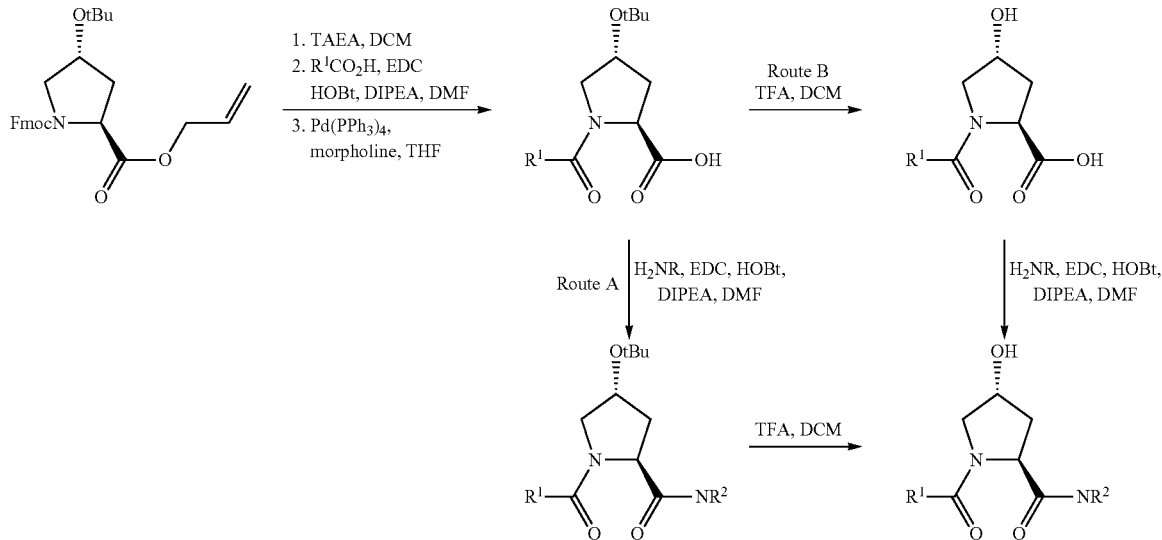

Scheme 1 Solution Phase Synthesis of UML Derivatives According to the Present Invention rolidine compound is reacted with a carboxylic acid containing reagent, which introduces a carbonyl group at the amine of the pyrollidine ring to form an amide group. Alternatively, the pyrrolidine amine may be protected and the carboxylic acid moiety may be condensed with a nucleophilic group on a right hand fragment to provide an amide on the right hand portion of the pyrrolidine moiety. The left and right hand fragments to be condensed onto, respectively, the amine and carboxylic acid group of the pyrrolidine moiety are preferably prepared prior to condensing onto the pyrrolidine group, but other approaches may be taken to introduce groups onto the pyrrolidine group. The individual components which are combined to produce a ULM group can be prepared using blocking groups at preferred functional groups on the ULM group which can be removed so as to react with and covalently link a linker group which is prepared to accommodate a PTM moiety to which is already bound a protein binding moiety. or PTM group or may be further reacted to form a covalent bound with a PTM group, which may also may comprise a ULM' group as otherwise described herein. Thus, a carboxylic acid containing left hand fragment may be condensed onto the amine group of the pyrroline, thus forming an amide group with an $R^1$ left hand fragment as depicted below. Onto the carboxyl group, any number of nucleophilic (preferably, amine containing) right hand fragments (pre-synthesized) may be condensed onto the carboxyl group to provide an amide group with an $R^2$ right hand fragment as depicted below. Formation of the pre-synthesized groups to condense onto the amine and/or the carboxyl moiety of the pyrrolidine proceeds in a facile manner. Virtually any compound can be synthesized readily Scheme 2
Solid Phase Synthesis of Compounds According to the Present Invention

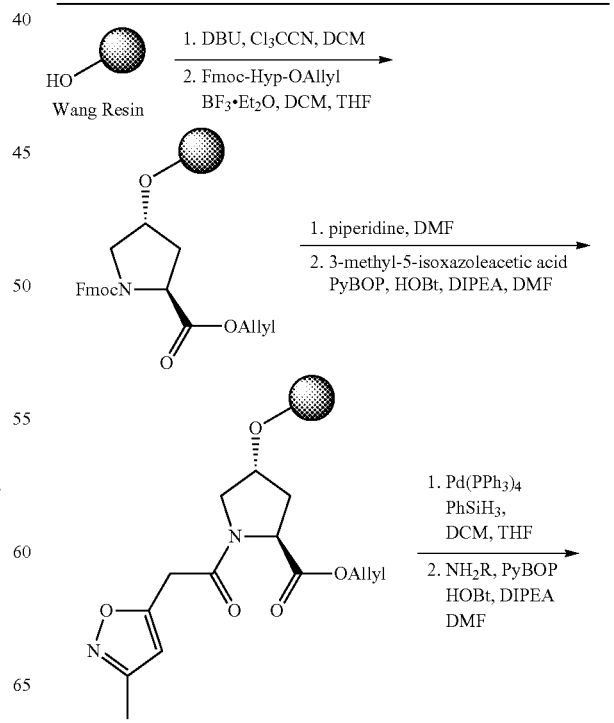

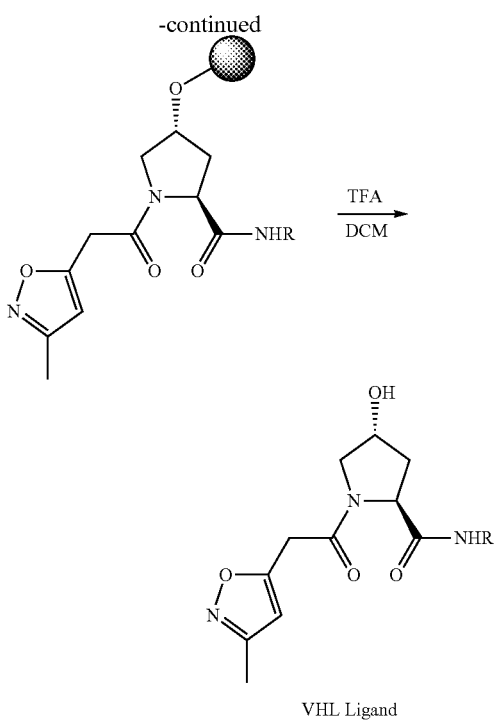

VHL Ligand

Alternative General Method for Solid Phase Synthesis of VHL Ligands according to the present invention (details for which are presented in the second set of examples), set forth herein:

Synthetic Approaches for Compound Generation to Screen for Target Protein Binding Elements (PTM) and Ubiquitination Ligand Moieties (ULM) of the Subject Invention Two basic methods which are used in combinatorial chemistry to identify PTM moieties and ULM moieties are solid-phase and solution-phase methods. Using these methods combinatorial compounds are created either by solution-phase synthesis or by producing compounds bound covalently to solid-phase particles. Once their moieties are identified they may be modified using appropriate groups (electrophilic and/or nucleophilic), and condensed onto linker groups to produce bifunctional compounds according to the present invention.

Solid Phase Methods

Solid Phase Methods rely on the teachings of Fruchtel, et al. 1996, *Angew. Chem. Int. Ed*. Engl. 35, 17-42; which is incorporated by reference in its entirety herein).

Solid-phase synthesis makes it easier to conduct multistep reactions and to drive reactions to completion, because excess reagents can be added and then easily washed away after each reaction step. Another key factor in favor of solid-phase synthesis is that it makes it possible to use split synthesis, a technique developed in 1982. Split synthesis produces large support-bound libraries in which each solid-phase particle holds a single compound, or soluble libraries produced by cleavage of compounds from the solid support. For example in a split synthesis method if you have 3 compound addition steps with 10 compounds used at each step i.e. 10 containers for those compounds. This will generate $10^3$ compounds. Also, if you consider all the reaction steps included in a synthesis 10,000 compounds made via a solid phase methods using a three-step chemistry may only require about 22 containers for the chemistry and about 66 liquid handling steps relative to the 10,000 containers and 30,000 liquid handling steps. When you combine these advantages of solid phase synthesis with split synthesis, a significant level of synergy is achieved.

Solution Phase Methods

Solution phase chemistry is favored by many for library construction due to the wider range of organic reactions available for solution-phase synthesis, the technology used traditionally by most synthetic organic chemists, and products in solution can be more easily identified in standard drug target assays and characterized. A problem for solution-phase synthesis of one molecule at a time is the final purification that can be both expensive and slow. Chromatography is commonly a first resort since it usually works. In addition, the problems associated with solution chemistry are compounded when attempting to make tens of thousands of compounds to generate a library or a 'book' for a library.

In the generation of libraries of compounds numerous methods have been devised resulting in the wide spread use of large libraries of chemicals to readily allow the discovery of potential drug candidates. The generation of chemical libraries that are free in solution is typically the goal of most of the pharmaceutical industry. This aim is due to the nature of many of the drug targets and the associated assays. Also the construction and utility of chemical libraries is typically facilitated but the generation of master plates of compounds in solution to form the basis of the chemical library. Thus the general advantages of the solid phase synthesis methods are typically not fully realized in the context of the current drug discovery efforts. The main reason for this is the interest not in binding of the compound to the drug target but to demonstrate that the activity of the drug target is altered, which typically requires compound free in solution. Further concerns with libraries of compounds on a solid phase arise from concerns of the potential influence of the linker and steric effects on the compounds bound to the solid phase.

Thus methods for the discovery of compounds, which bind to target molecules is known in the art. Also, the optimization of the initially discovered compound is well known in the art where the affinity is improved by generation of a pool of related compound via a more selective combinatorial chemistry approach.

The present invention provides a mechanism to overcome these problems in drug and small molecule discovery.

Addition of the Ubiquitin Ligase Binding Moiety (ULM)

At this point in the compound discovery path for the subject invention, the target protein-binding element of the compounds of the invention has been identified. These optimal binding molecules are then subjected to further chemistry to add the ubiquitin ligase binding moiety (ULM), pursuant to the disclosure of the present application.

An alternative approach to the discovery of the target protein-binding moiety is based on solution phase screening. In such an example compounds (available either via synthesis, natural products or from companies such as ArQule (www.arqule.com), Pharmacopeia (www.pharmacopiea), and Cerep (www.cerep.com) are obtained and added to the target protein of interest and then subjected to size exclusion to remove the unbound compounds. The protein bound fraction is then subjected to GC/MS to identify the molecules. In this way the solution phase screening is made rapid and facile for compounds in solution. There are numerous additional ways to determine ligand binding, including, for example, detecting changes in the Tm of the protein upon the ligand binding, among others.

Screening for Target Protein Binding Elements

Initially a target protein is selected, for example, an enzyme or protein involved in a particular biological process. Target protein for the subject invention come from numerous fields where small molecules are used to achieve modulation of a biological system in eukaryotic organisms. Examples of such fields are antivirals, antimicrobials, antiparasitics, or other drug targets in a human patient, which may be rather diverse, etc.

The target protein is then either purified from a natural source in order to provide sufficient material for the screen or expressed via recombinant methods to provide sufficient material for the screens.

The target protein is then either labeled directly with a detectable species such as a radioactive, electrochemiluminescent, and chemiluminescent or fluorescent label or with an indirectly detectable species such as an enzyme, or particle. Alternatively an antibody or equivalent with binding activity to the target protein is labeled.

The next step is to provide a library of compounds for screening. A library of from 1,000 to 1,000,000 is typical of the size that is screened. These are available from a series of companies, which are well known in the art. These libraries of compounds are used to screen for the binding of the target protein. Ideally compounds are bought still bound to the solid phase or are screened for binding directly to immobilized target protein using methods as described below for screening.

It is also possible to generate a chemical library of various potential binding molecules bound to a solid phase following conventional methods to give rise to differing potential compounds. The optimal methods for the construction of the chemical library is to employ the methods of split synthesis coupled to the solid phase (as outlined above). The library is generated using a series of solid phase chemistries such as to give rise to various compilations that form the basis of a library. The library is screened in the form of a library or in the form of the compilations. Typically one would take the products from the split synthesis and pool the solid phase and use this as the basis for the screen.

To the pool of beads used as the solid phase for the synthesis, a mixture of buffer, detergents, salts and blocking agents such as serum albumin or other proteins are added. This buffer addition step is used to block the beads or solid phase in such a way that any significant non-specific binding of the selected target protein does not occur. Following this blocking step the beads are washed and followed by the addition of the target protein either labeled or not. The beads or solid phase are then incubated to allow the binding of the target protein binding elements to the target protein. Following the incubation of the target molecule to the beads or solid phase the beads are washed and then the binding of the labeled target protein detected directly. In an alternative format, if the target protein is labeled with an indirectly detectable label such as an enzyme, the beads are then placed in to a substrate reaction solution to detect the presence of the enzyme label. In the case of an enzyme label, substrates for these detection methods are based on insoluble chromogenic products. In the case where the target protein is not labeled and an antibody or equivalent is available, the beads are subjected to another binding reaction where the antibody or equivalent, is labeled either directly or indirectly as suggested for the labeling of the target protein. It is also possible at this step to not use a labeled antibody or equivalent and to add a further step where the labeled antibody or equivalent is used. These additional steps can be detected using the same standard methods known in the art as suggested for the directly labeled target protein.

Following these steps a series of beads are identified and these beads are selected from the bead population and subject to analysis to determine the structure of the binding molecule that is able to bind the target protein as in this example. This is achieved by the use of GC/MS or via molecular tags used during the construction of the library as described earlier. Alternatively, a pool which was positive is re-made generating a series of sub pools for screening and further re-synthesis and dividing out of the various pooled compounds until a single compound is presented in a single well for analysis allowing the determination of the active compound.

This method can be repeated and/or adapted for identifying peptide target binding moieties (PTM) for virtually any target protein.

Screening for Binding Molecules from Chemical Libraries

The step of screening for specific molecules is made easy in the invention as only binding activity is desired and not specific modulation of the target protein as is required in traditional drug discovery.

One can buy a library of compounds for screening. A library of from 1,000 to 1,000,000 is typical of the size that might be screened. These are available from a number of companies. These libraries of compounds are used to screen for the binding of the target protein. Ideally, compounds are purchased still bound to the solid phase or are screened for binding directly to immobilized target protein using methods as described below for screening.

It is also possible to generate a library of from 1,000 to 100,000 compounds contained on a solid phase using split synthesis methods as described earlier. The library may be constructed using a series of chemical methods resulting in pools of the solid phase used during synthesis, which form the basis of the entries which make up the library. In addition at the final chemical coupling step used to construct the various entries the solid phase pools are stored in sub-pools in the libraries. These so called entries and sub-pools form the basis for screening as they contain not only pools of compounds but also a known chemical-coupling step used in synthesis.

The library can then be screened using two approaches. In both cases the solid phase from the chemical library to be screened is subjected incubation with assay buffers with blocking agents such as for example; proteins (i.e. BSA, gelatin), polyvinylpyrrolidone, ficoll, heparin, detergents (i.e. SDS, Tween, NP40, Triton X-100). This incubation step is to block the non-specific binding sites on the solid phase used in the generation of the library and allow the determination of specific binding events. This initial incubation is an art recognized step in various binding assays such as ELISA, southerns, westerns etc. Following this incubation with blocking agents the protein of interest is then added to a buffer which typically has the same composition as that during the blocking step but can also be modified using lower or no additional blocking agents with the exception of the detergents which are typically always present during a binding reaction.

In one of the screening methods the entries following the blocking step are then subjected to binding with the purified target protein. The solid phase from this incubation is then washed and subjected to a second binding step with a labeled reagent which binds to the tag sequence added to the receptor sub-unit during the recombinant engineering for the expression of the receptor sub-unit. Typically an antibody to this tag recognizes the tag sequence; examples that are in common use are the myc, flag, and his epitopes. Following the incubation with the tag specific binding species the presence of the labeled binding species is detected by the presence of the label that is typically an enzyme such as alkaline phosphatase or peroxidase. The detection step typically makes use of an insoluble chromogenic substrate that is readily detected by eye or by image analysis systems.

In an alternative method soluble substrates can also be used and screened using ELISA plate readers, eye or other spectrophotometric methods. In its simplest form the various entries from the library are screened by eye to look for beads that have developed a color due to the enzymatic action on the chromogenic substrate. These colored beads indicate that the receptor subunit is binding to one of the compounds within the group of entries the next step is to determine if these so called positive group of entries contain specific binding or if binding is just to the tag binding reagent or some non-specific activation of the chromogenic substrate. To achieve this, the positive entries are screened with out the specific binding step to the receptor sub-unit. If these positive entries now become negative or show significantly reduced signals interms of positive solid phases with in the mixture then these are considered to be real positive hits in the screen. These real positive entries are then subjected to re-synthesis. In this re-synthesis the initial chemical steps to create the specific binding molecule is unknown only the last chemical coupling step in the compound synthesis is know, as this formed the last chemical step which constructed the group of entries. During the re-synthesis of the positive chapter the chemical step prior to the last chemical coupling is carried out as in the initial synthesis but the solid phase is not pooled and split for the final chemical coupling but are maintained as separate pools then subjected to the chemical coupling step know for that chapter. This resynthesis results in the formation of a new series of solid phase compound pools which have the last two chemical coupling steps known. This new series of solid phase compound pools are screened as in the initial screen and positive pools are checked as previously for the binding specificity to identify positive pools. The positive pool(s) now allow the re-synthesis of the pool(s) with the last two steps for the generation of the compound, which specifically binds to the receptor subunit. The positive pools are then subjected to the same cycle of re-synthesis and screening as just described but with the last two chemical coupling steps know the pools are maintained individually prior to the last know step. In this way the synthesis of the specific compound able to bind to the receptor sub-unit is deconvoluted from the chemical library and identified.

In an alternative method the positive solid phase is removed from the screen and collected. These are then subjected to the cleavage reaction, which removed the specific chemistry from the solid phase followed by the analysis of the various chemical species using GC to separate the individual compounds followed by MS to determine the molecular weight. This information coupled with the synthesis methods used is used to determine the compound identity. After the determination of these various candidate specific binding molecules they are then re-synthesized and subjected to the binding assay to check if these are the specific compounds that resulted in the positive solid phases.

Screening of the Ubiquitin Ligase Binding Moiety

This screening effort following methods and protocols known in the art allows the identification of compounds according to the present invention that bind to ubiquitin ligase. These compounds, already identified here, form the basis for the development of compounds of the invention. These compounds are then subjected to further chemistry based on the use of the linker group used in the development of the solid phase chemistry. To this linker group the various ubiquitin ligase binding moieties and/or protein binding moieties are added, generally through condensation reactions or other reactions to couple a ligand to a ubiquitin ligase binding moiety or a protein binding moiety. These reactions are well known in the art. Derivatization of linker groups is well-known in the art and can consist of providing a nucleophilic group (e.g., an alcohol, amine, thiol or other nucleophilic group) or an electrophilic group (e.g., ester, carboxylic acid, acyl halide, halogen, etc.) at either or both ends of the linker group which may be used to condense an appropriately modified ULM group and/or PTM group onto the linker to produce a covalent bond. This final step of chemistry generates the compounds of the invention. The compounds of the invention are then subject to analysis to determine which of the compounds from the chemical library screen with which of the individual ubiquitin ligase binding moiety element is able to function most effectively in the targeted ubiquitination and/or degradation of the target protein. The ubiquitin ligase binding moiety may be determined by the methods as otherwise described in the examples section hereinbelow. In addition, the compounds of the invention can be tested in a mammalian tissue culture system where the target protein either intact or as an engineered fragment is expressed. In such a mammalian tissue culture system, the compounds effect on the target protein's level is determined by making use of the tag sequence which can be engineered into the recombinant expression of the target protein during the construction of the mammalian tissue culture test system. The tag sequence is used to determine the levels of the target protein during the incubation with the potential compounds screened and synthesized as described above. This assay for the tag sequence can take the form of a western blot or via an ELISA, for example. Other tags, which are valuable to use are those based on the green fluorescent protein, which allows the analysis of protein levels in living cells and/or organisms.

The compounds that show the optimal activity in the test systems will then form the basis for the next stage of drug development. In this next stage these selected compounds are subjected to the recognized drug development path. The drug development path determines the potential value of the compounds by evaluating a series of factors including bioavailability; toxicology, pharmacology and efficacy in animal models before the compounds are considered for human testing.

Protein Level Control

This invention also relates to a method for the control of protein levels with a cell. This is based on the use of compounds of the invention, which are known to interact with a specific target protein such that degradation of a target protein in vivo will result in the control of the amount of protein in a biological system, prerferably to a particular therapeutic benefit.

The following examples are used to assist in describing the present invention, but should not be seen as limiting the present invention in any way.

EXAMPLES

First Set

Figure 2:
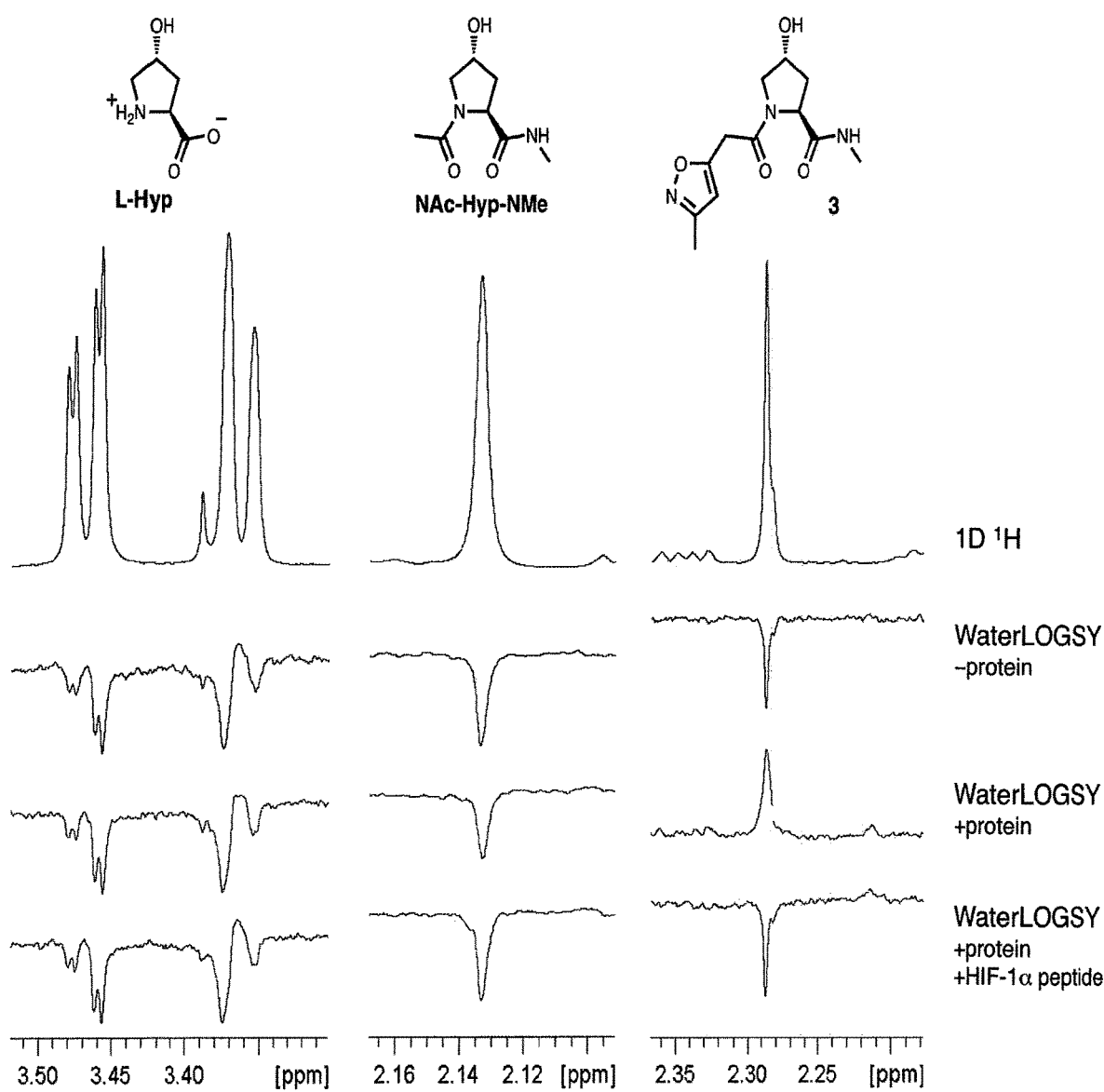
FIG. 2. WaterLOGSY NMR spectroscopy shows binding of 3, but not L-Hyp or NAc-Hyp-NMe to VHL.
Figure 3:
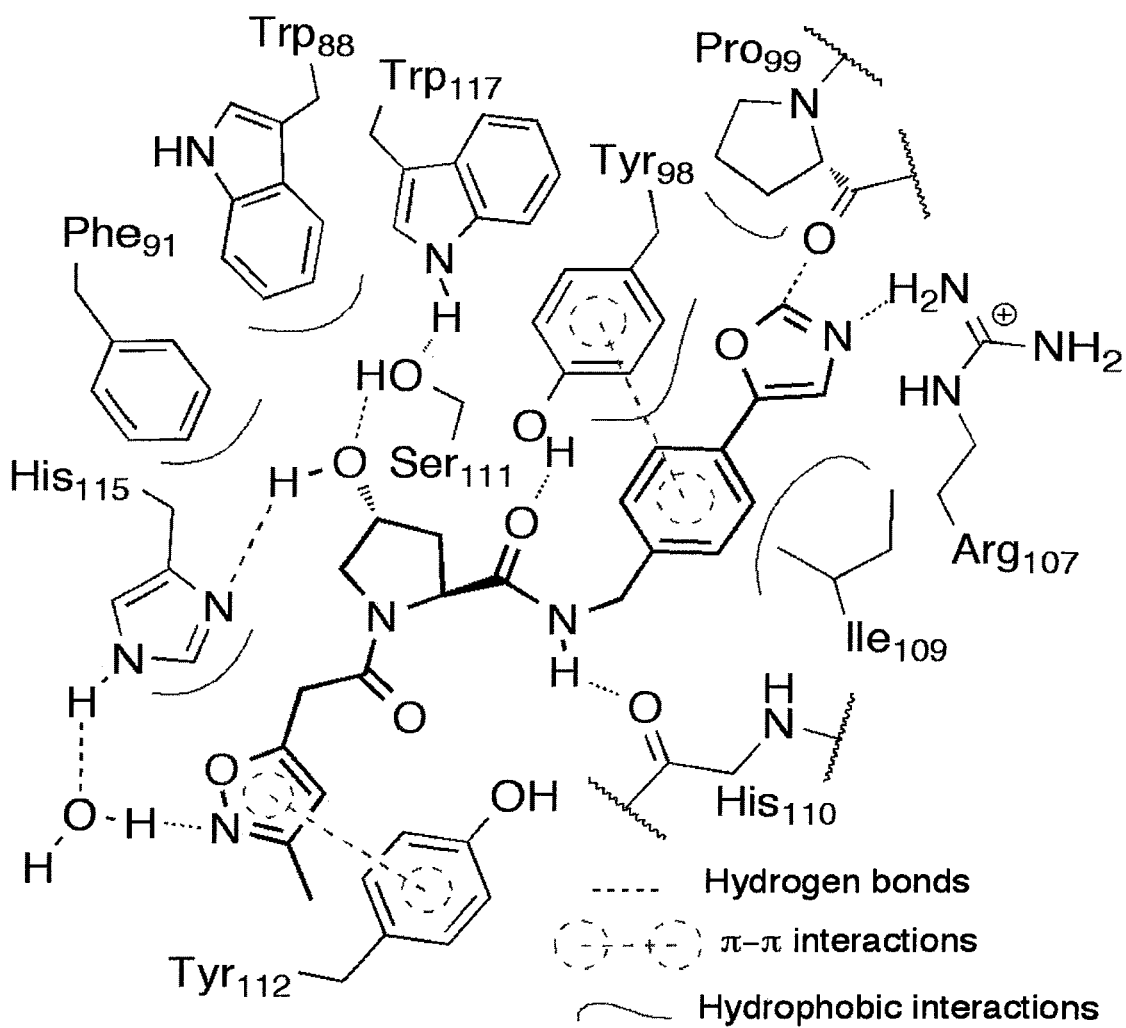
FIG. 3 shows a pictorial representation shows the key interactions between 15 and VHL.
Figure 4:
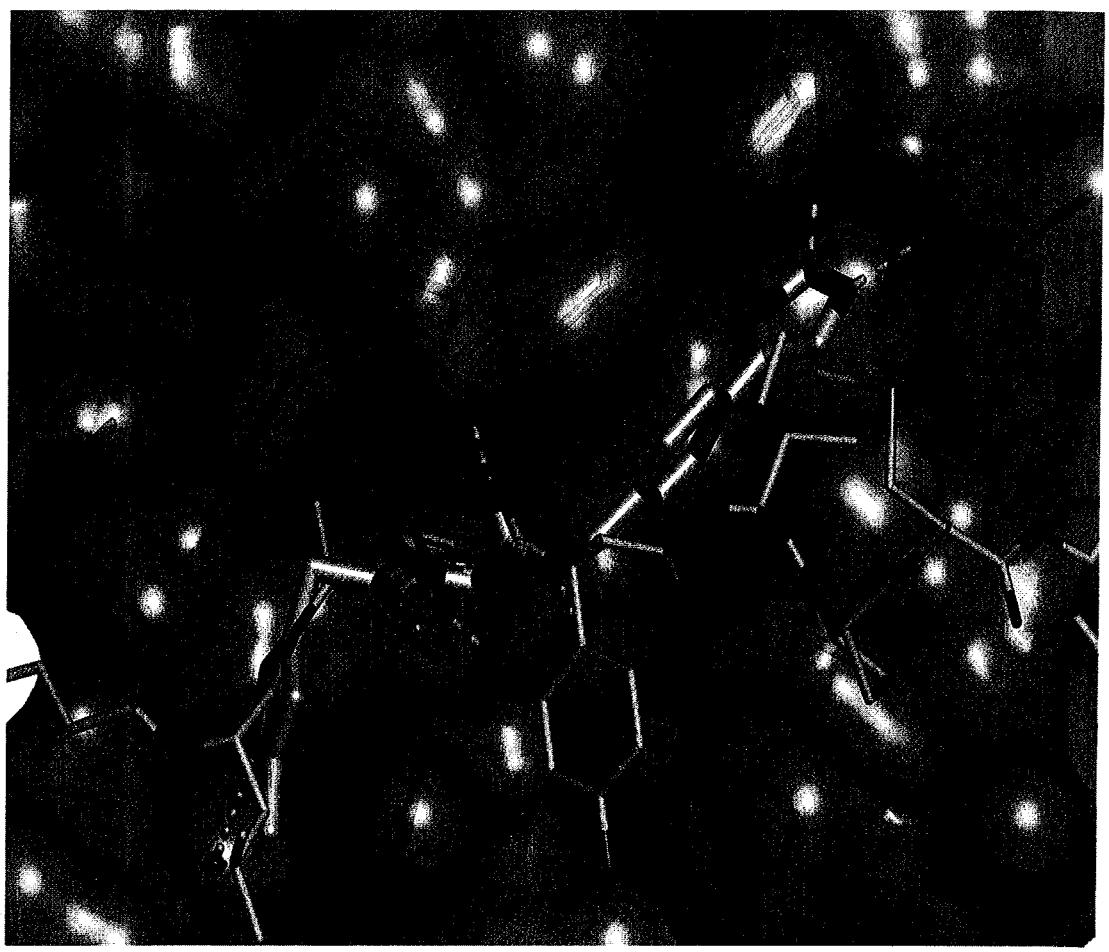
FIG. 4 shows the 2.9 Å co-crystal structure of 15 (lightest gray carbons) bound to VHL indicates that its binding mimics that of the HIF-1α peptide (light gray carbons, pdb 1LM8[17])
Figure 5:
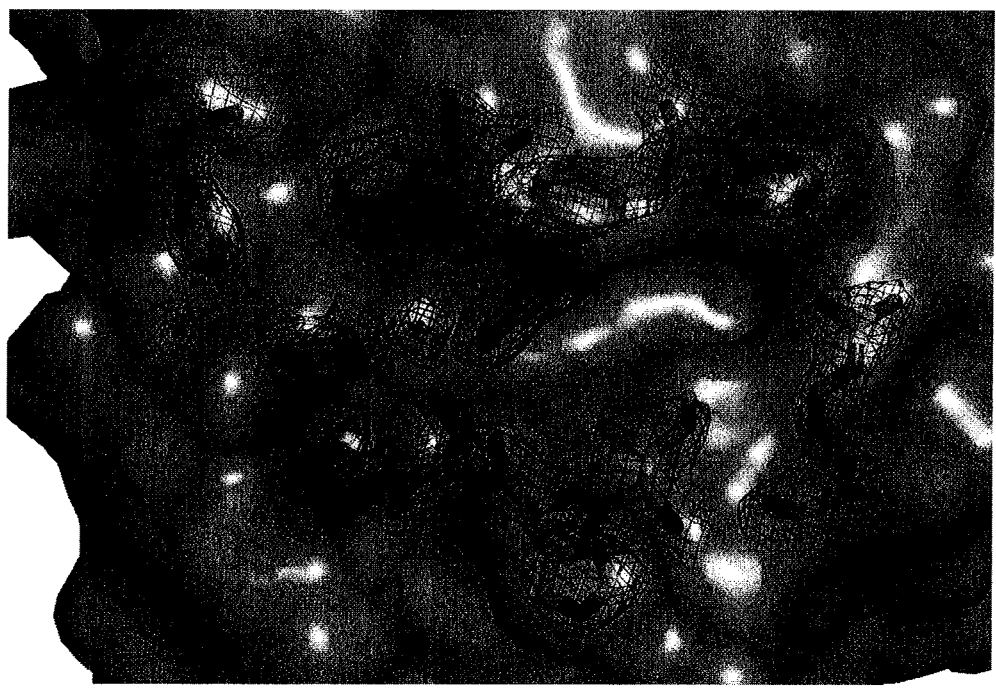
FIG. 5 shows the crystal structures of $V_{54}BC$ apo (A) and in complex with 15 (B). Electron density ($2F_o-F_c$) superimposed around Hyp binding site residues (sticks, yellow carbons) and conserved water molecules (red dots), and 15 (sticks, cyan carbons) are shown in blue and are contoured at 1.2σ. The protein surface is shown in green at 50% transparency.
Figure 5:
Figure 6:
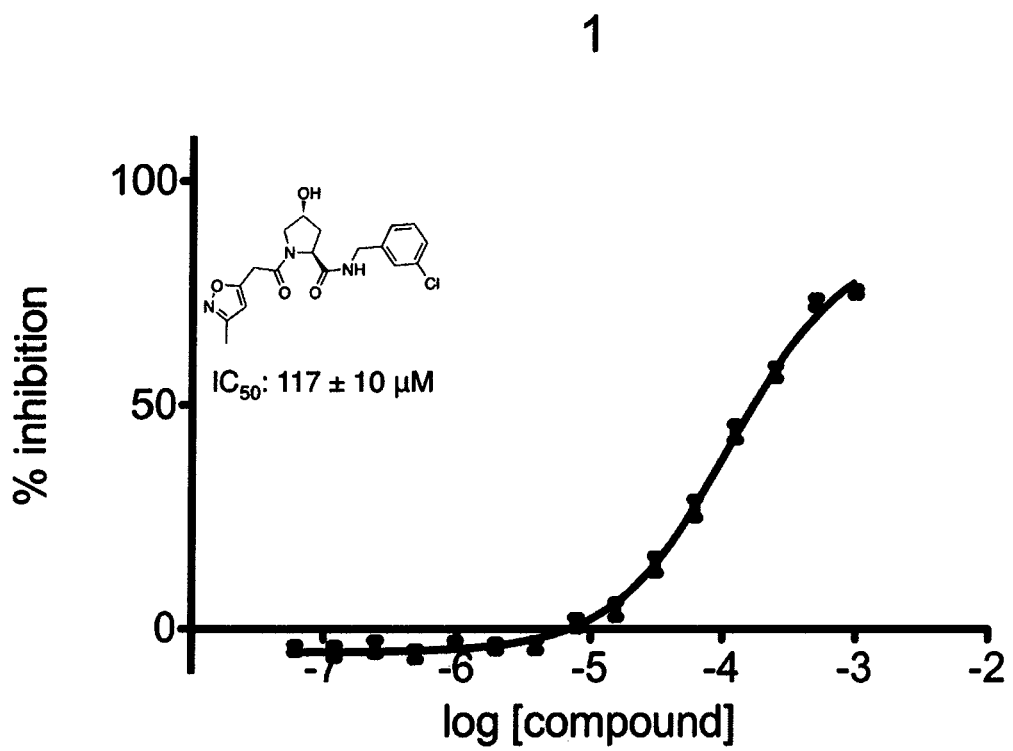
Figure 6:
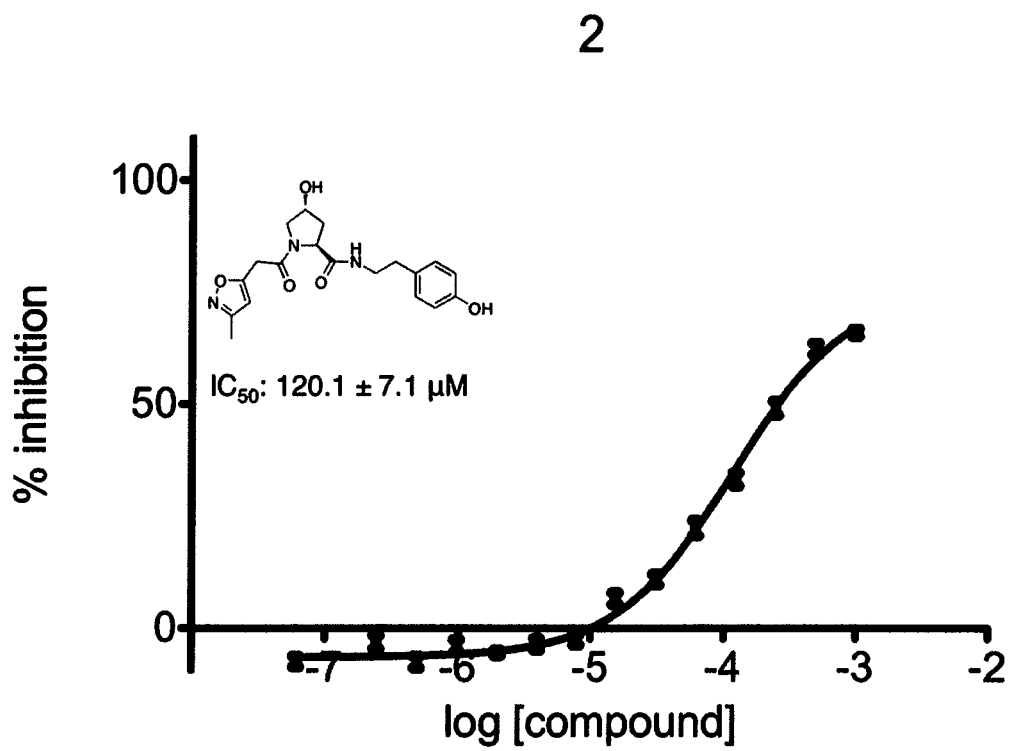
Figure 7:
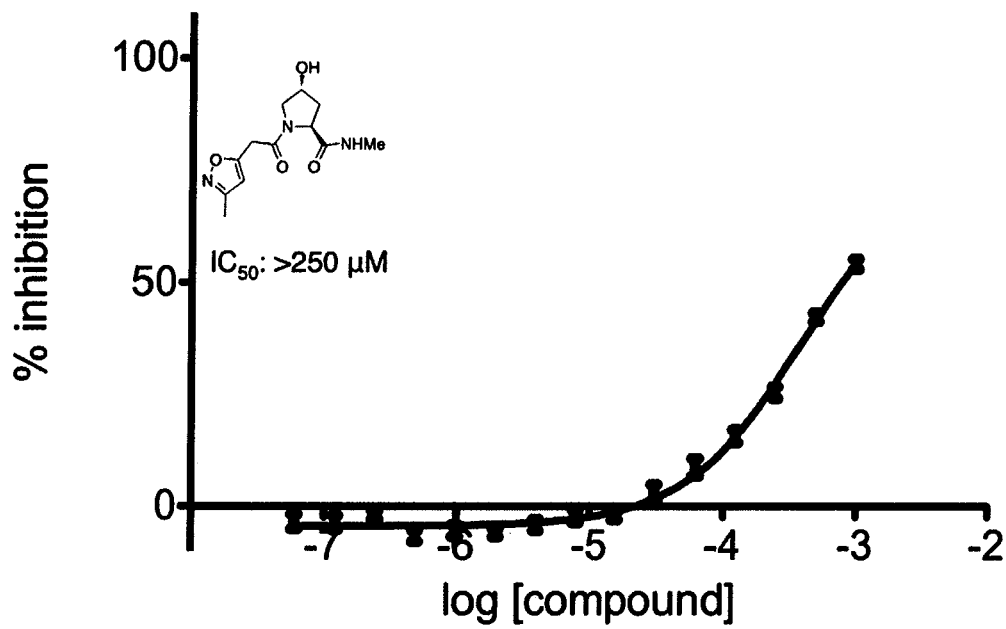
Figure 7:
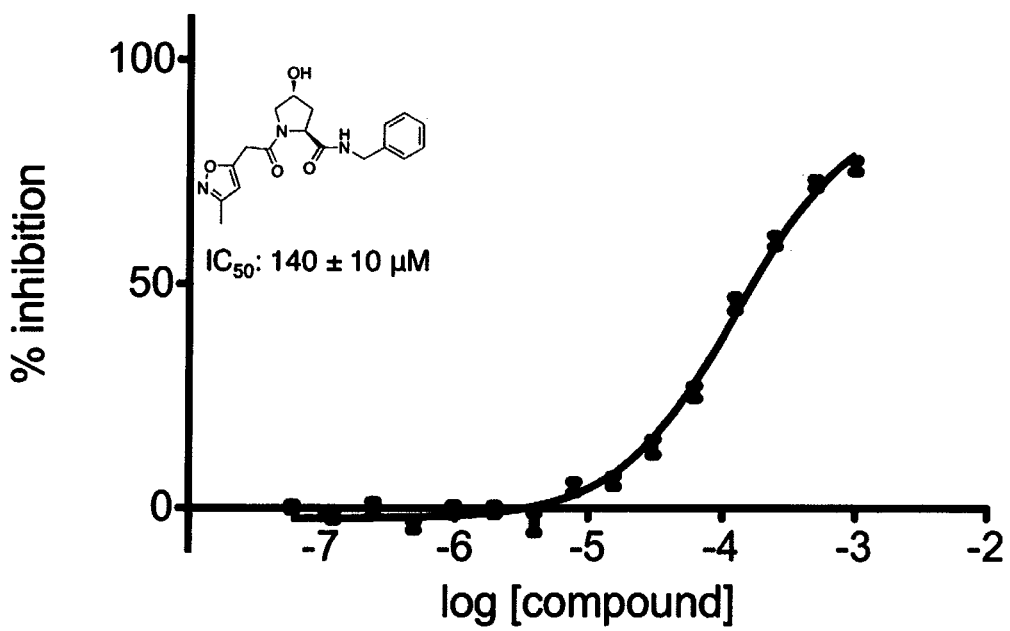
Figure 8:
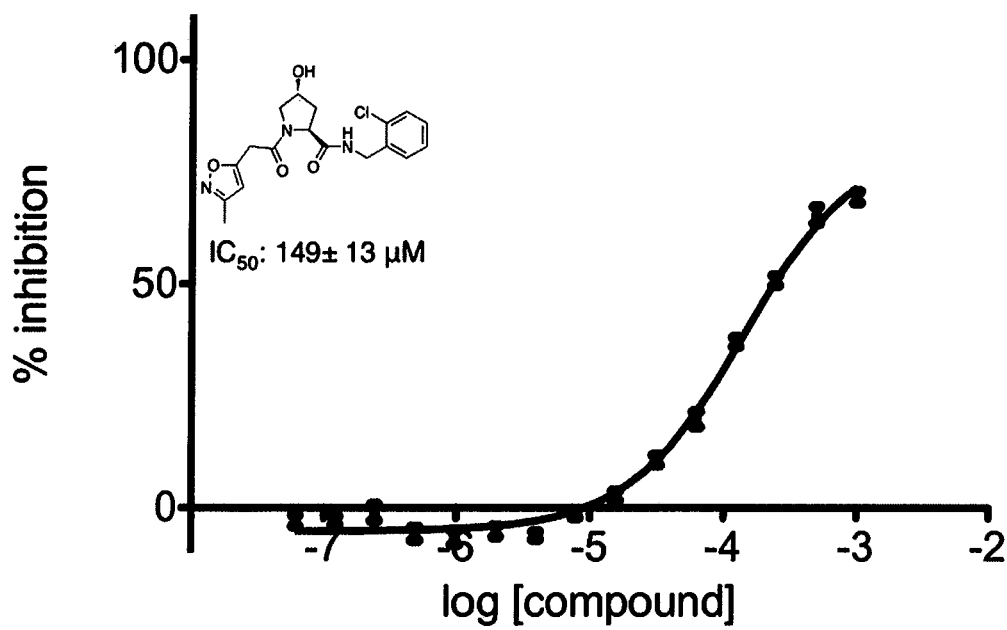
Figure 8:
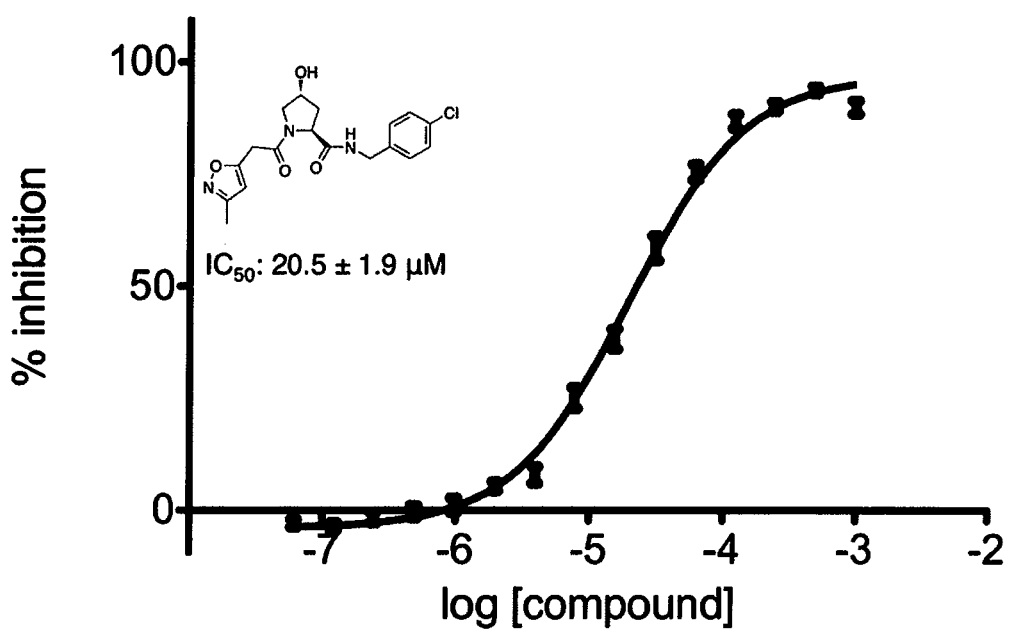
Figure 9:
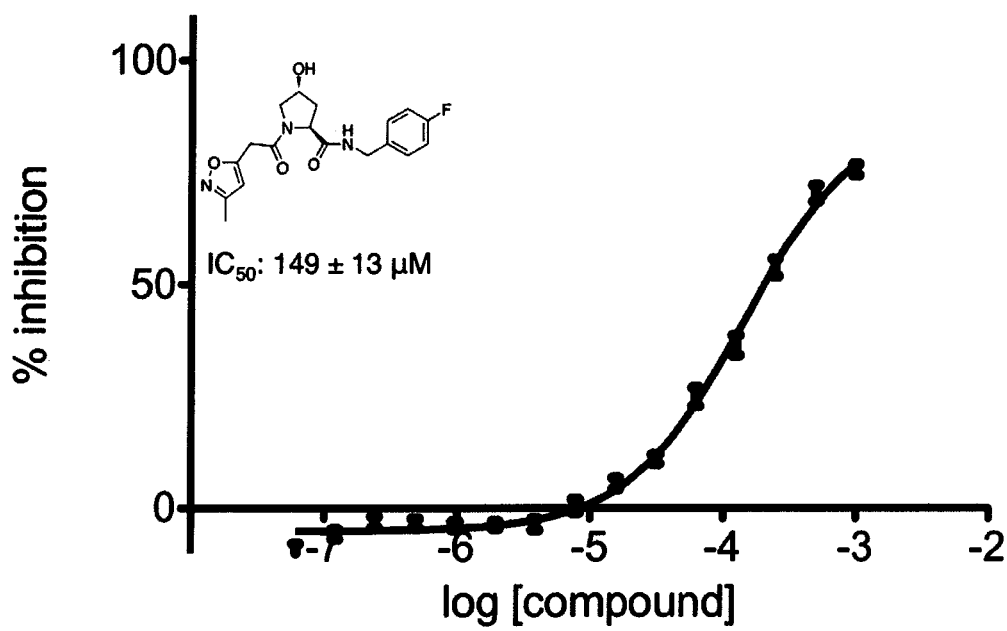
Figure 9:
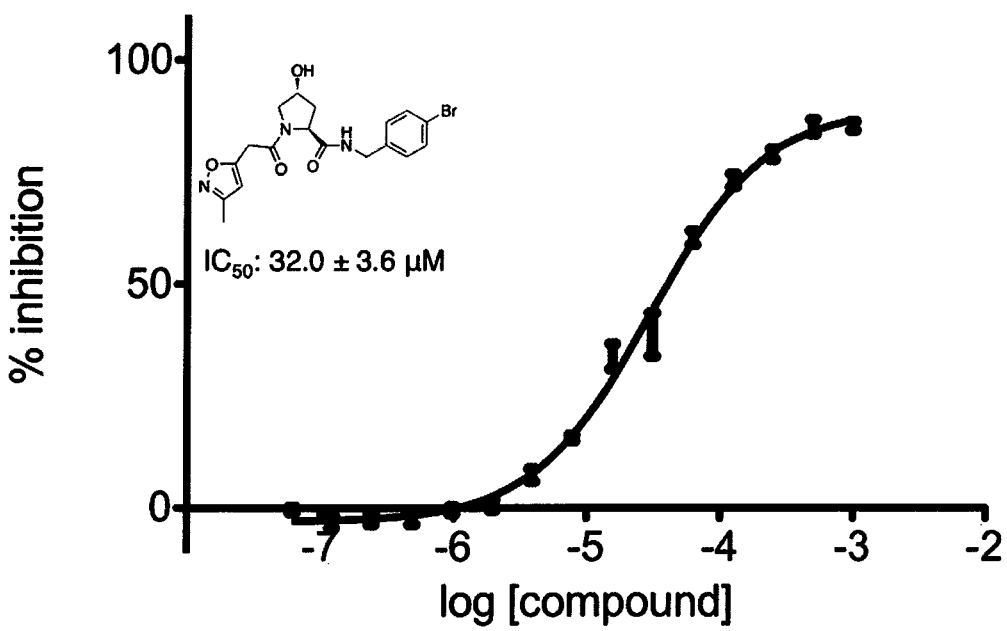
Figure 9A:
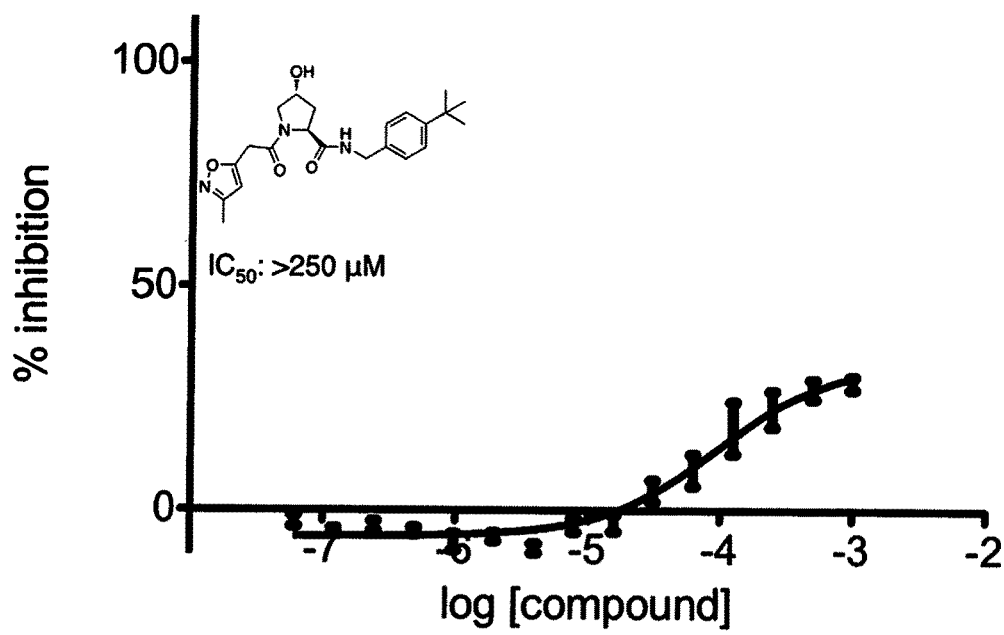
Figure 9A:
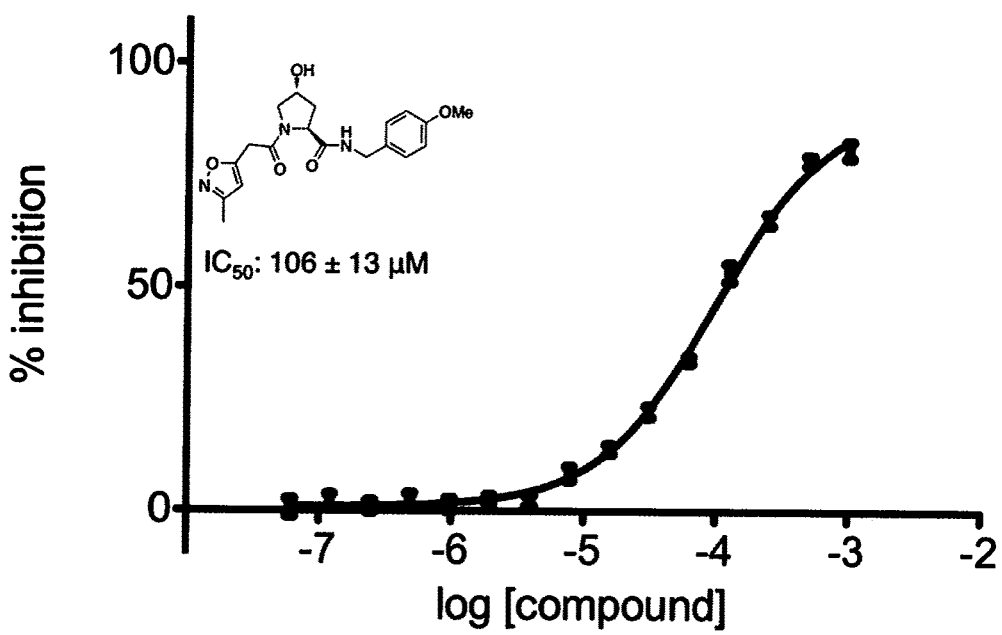
Figure 10:
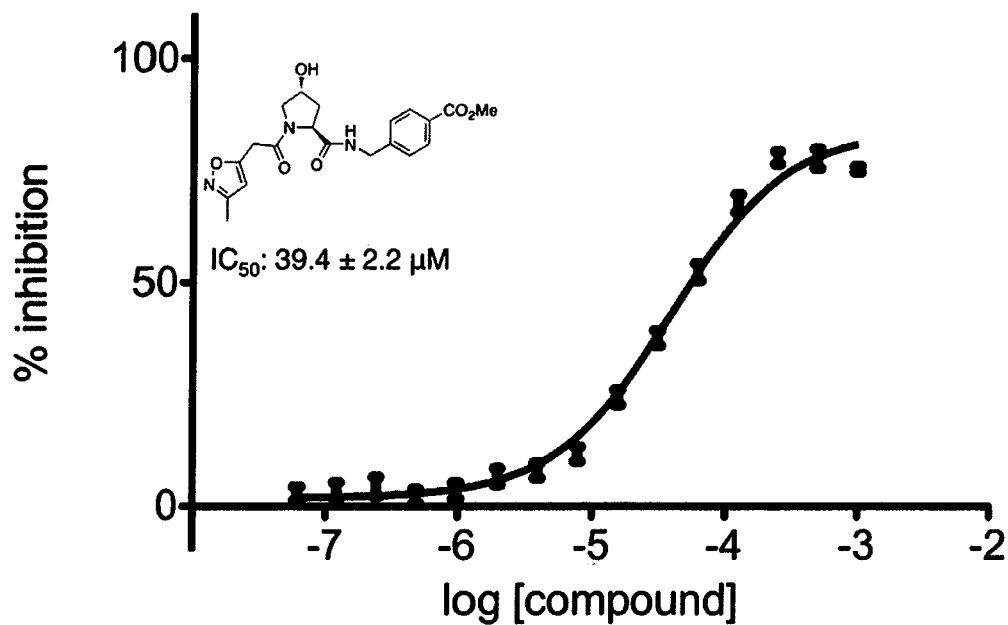
Figure 10:
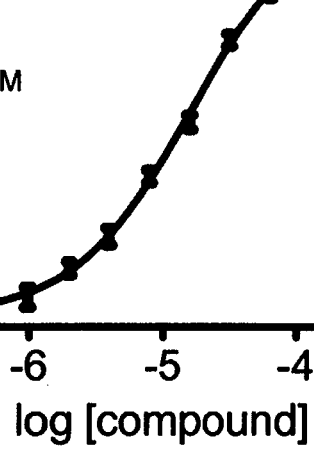
Figure 11:
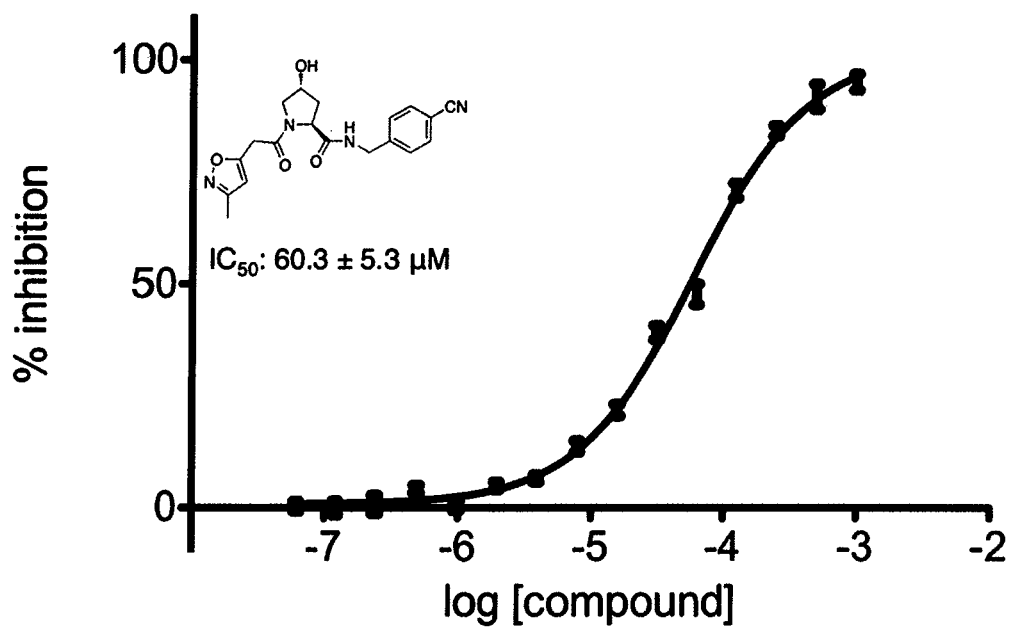
Figure 11:
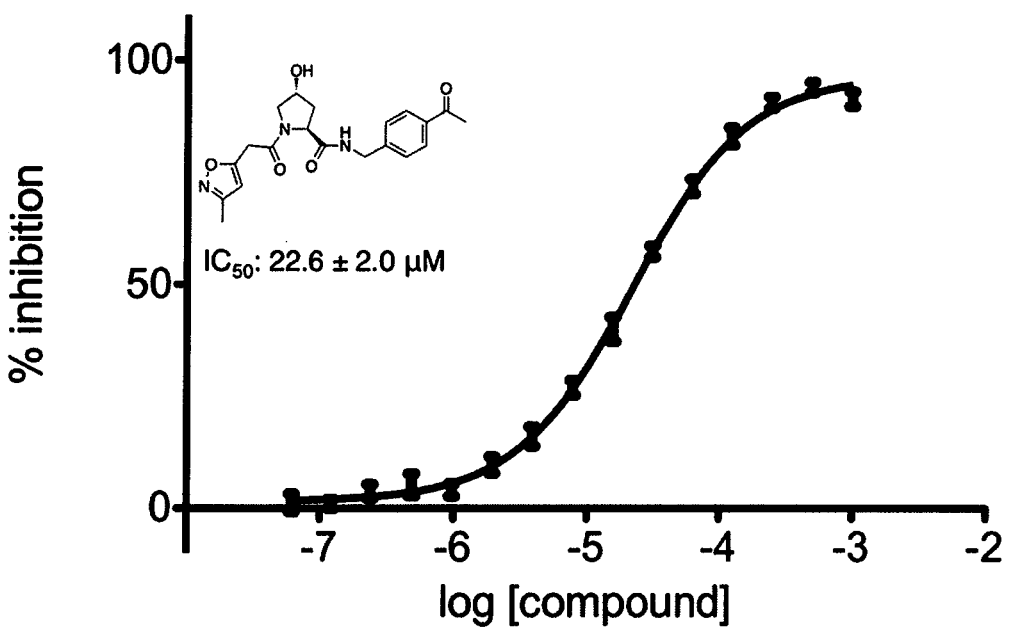
Figure 12:
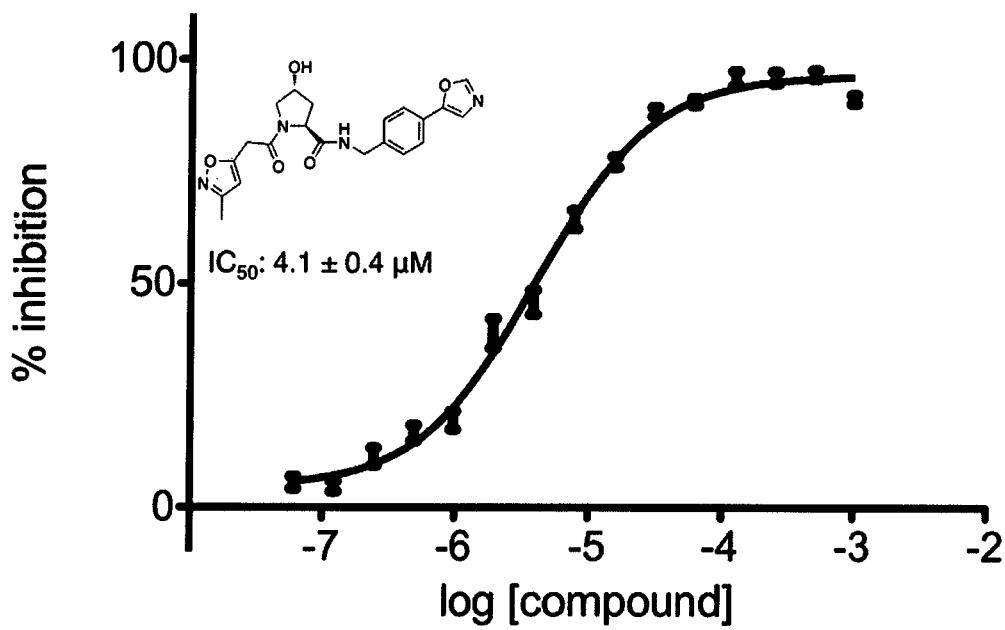
Figure 12:
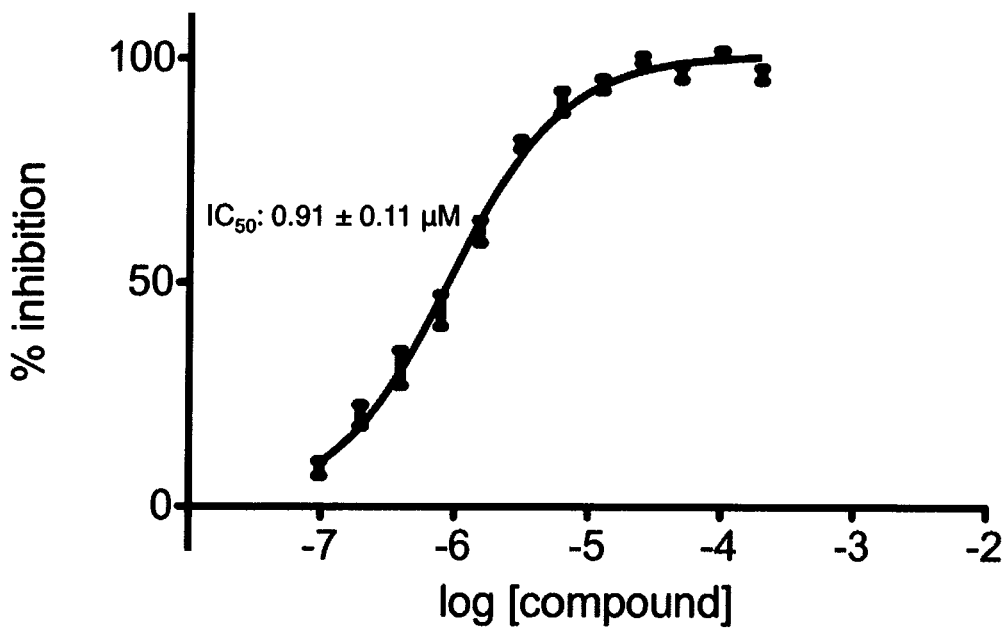
Figure 13:
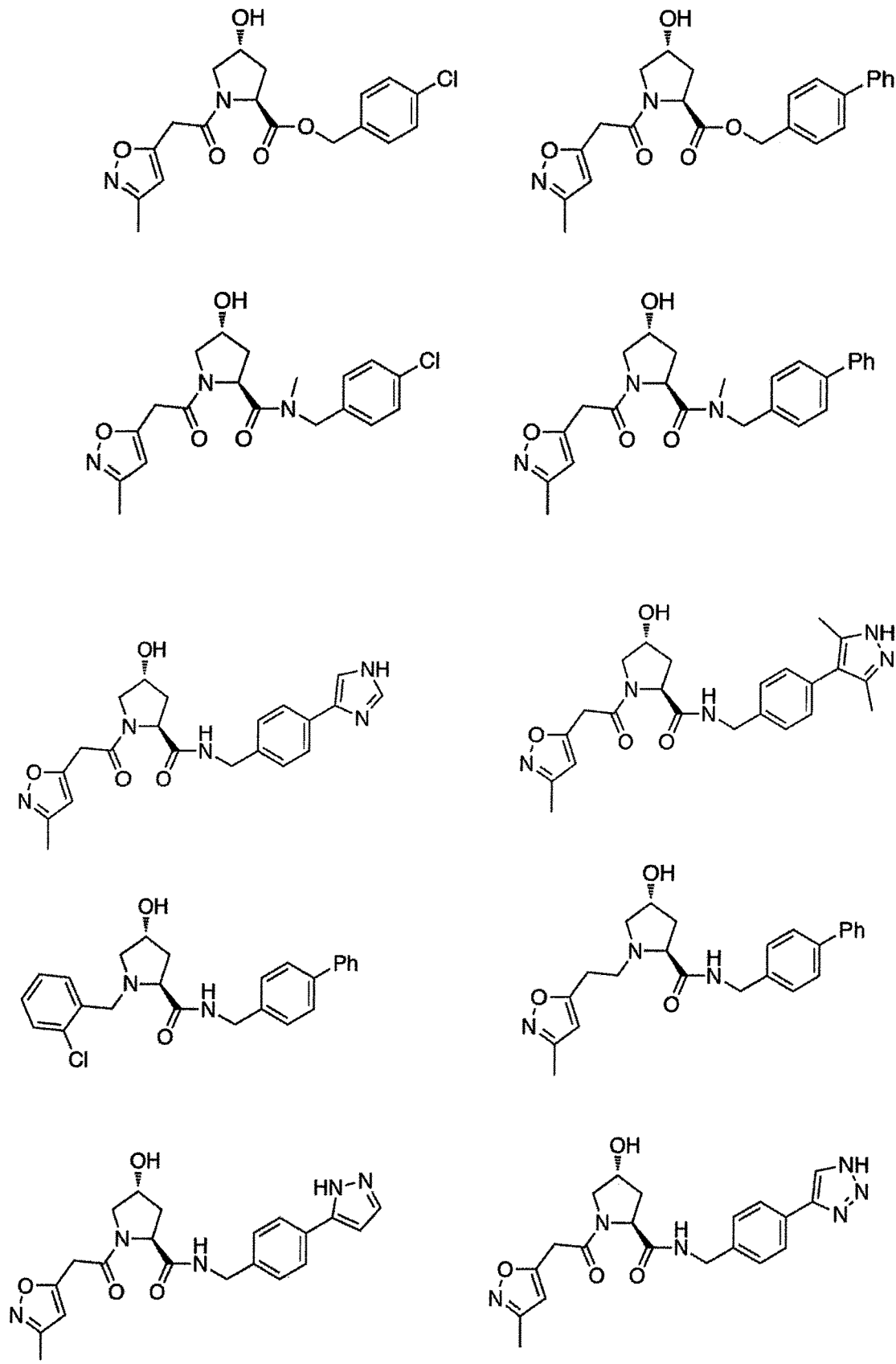
FIG. 13 (along with Table 2—Affinity Table) shows numerous exemplary compounds according to the present invention.
Figure 13:
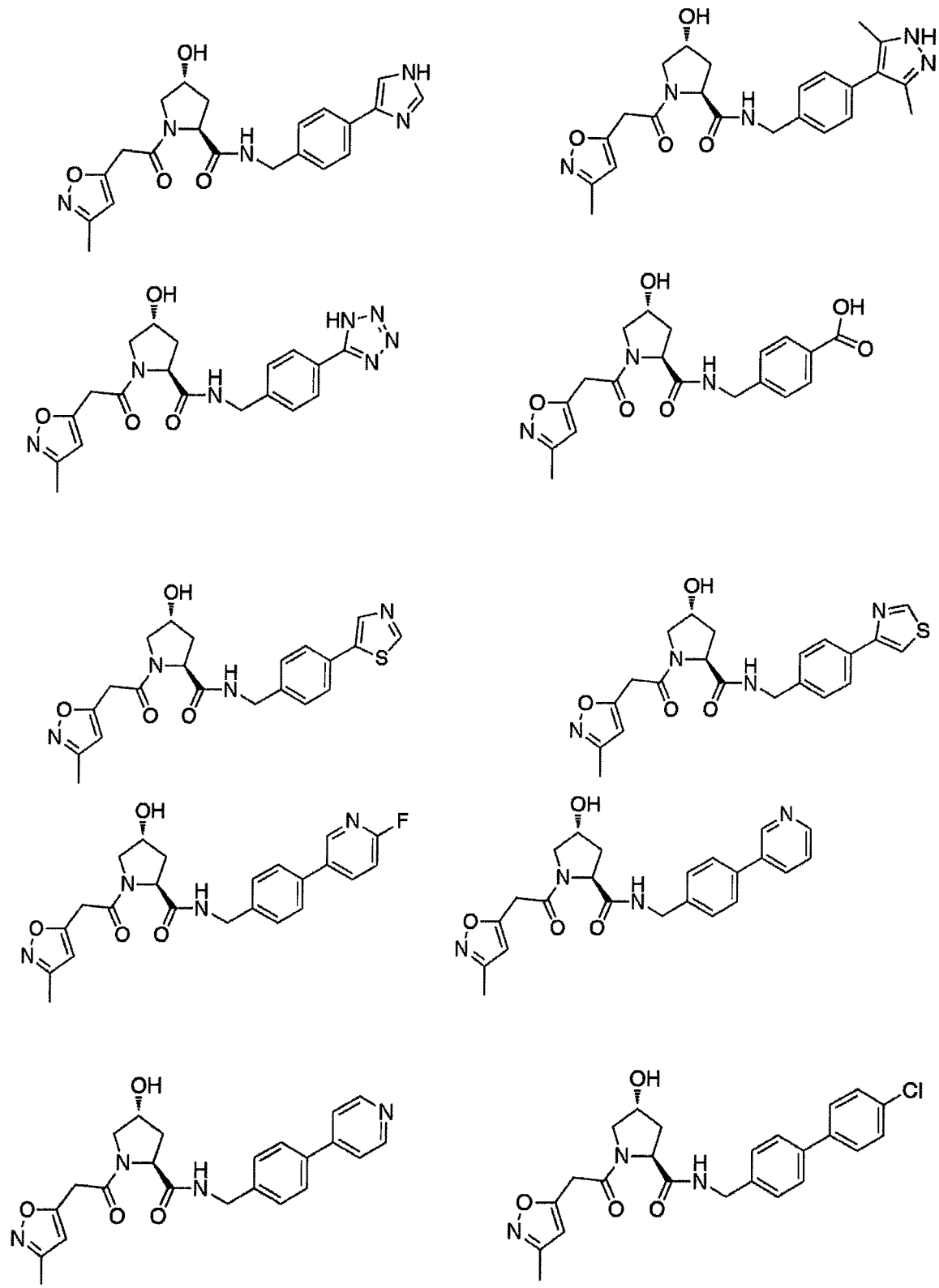
Figure 13:
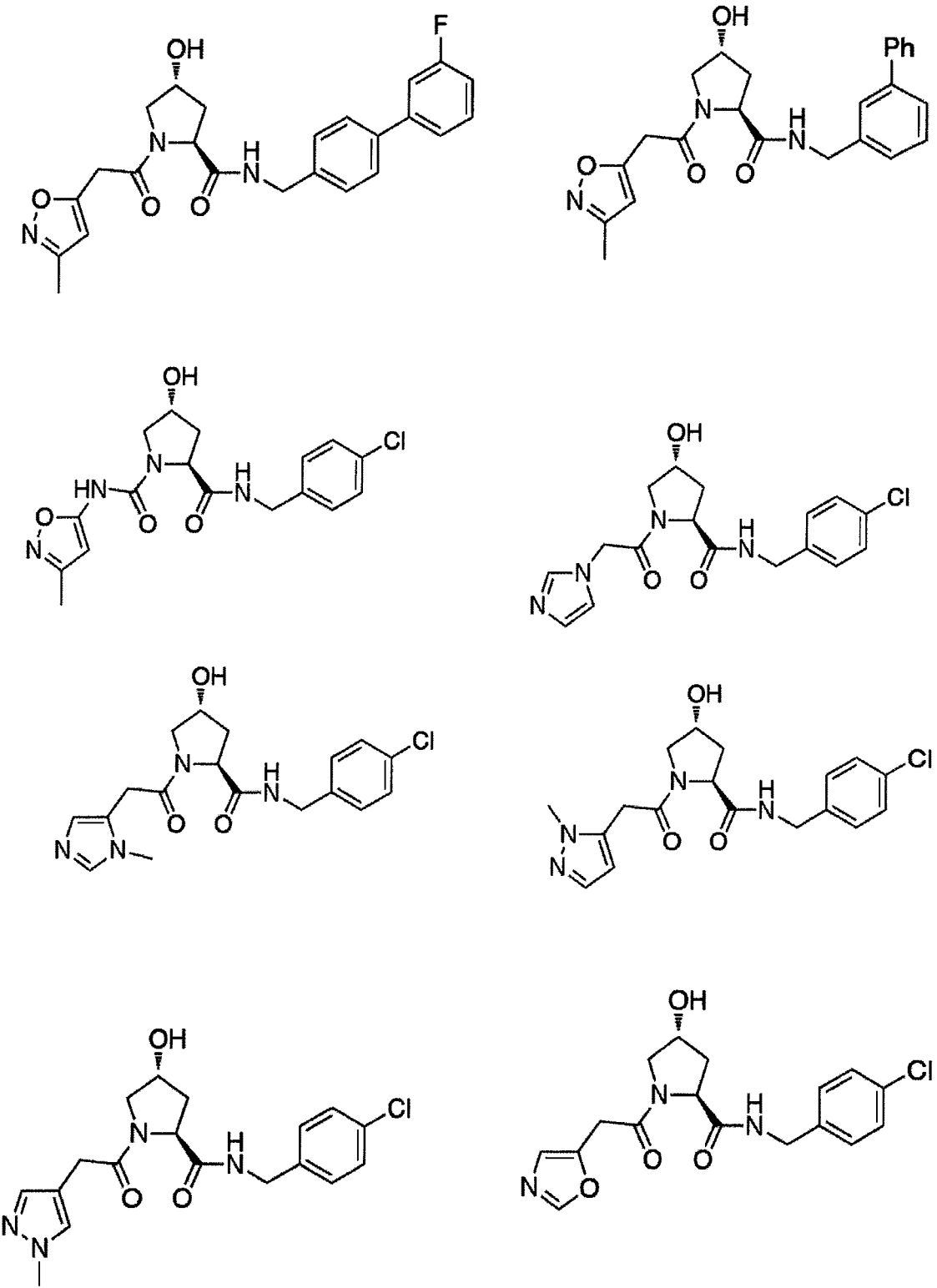
Figure 13:
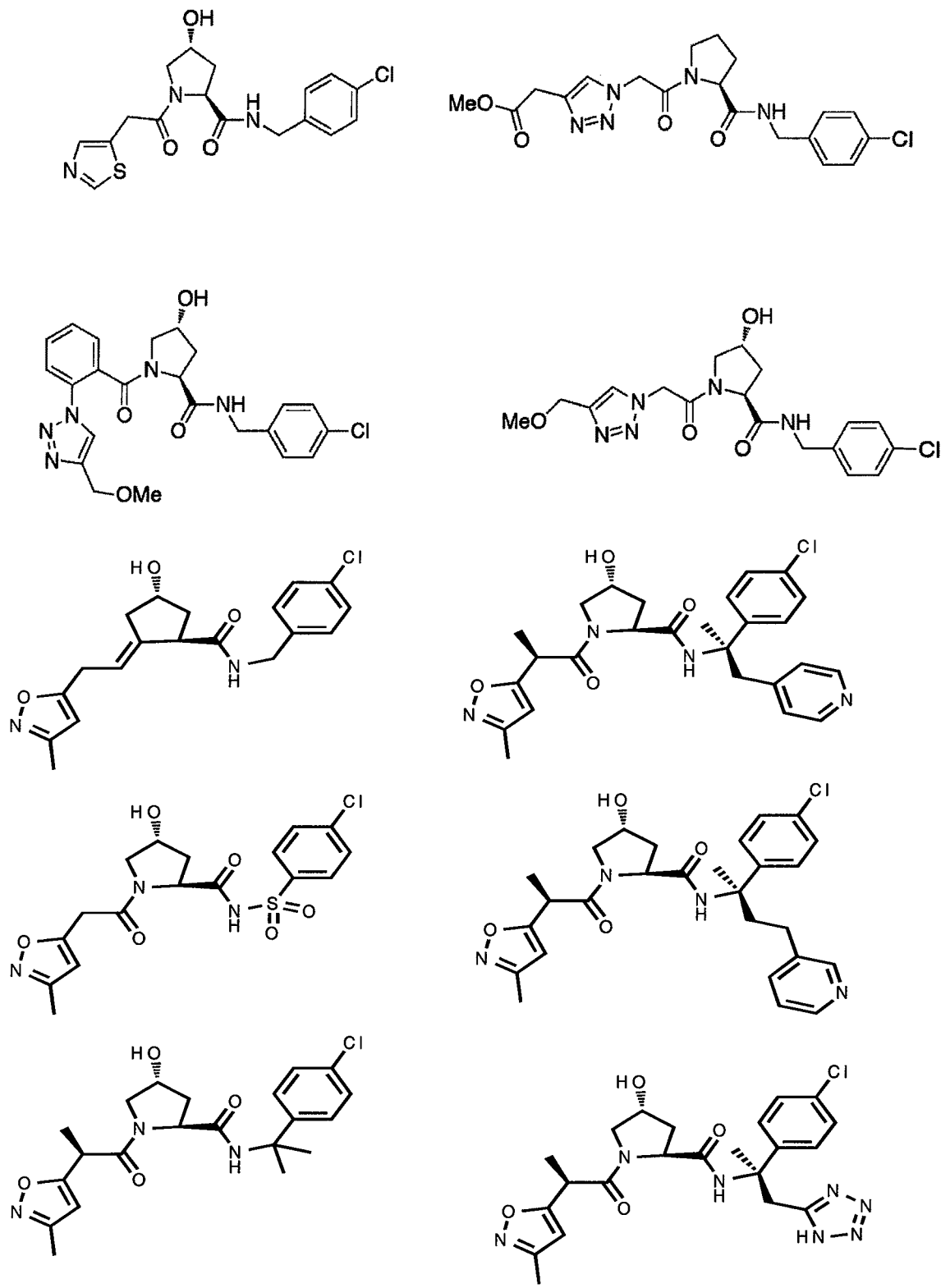
Figure 14:
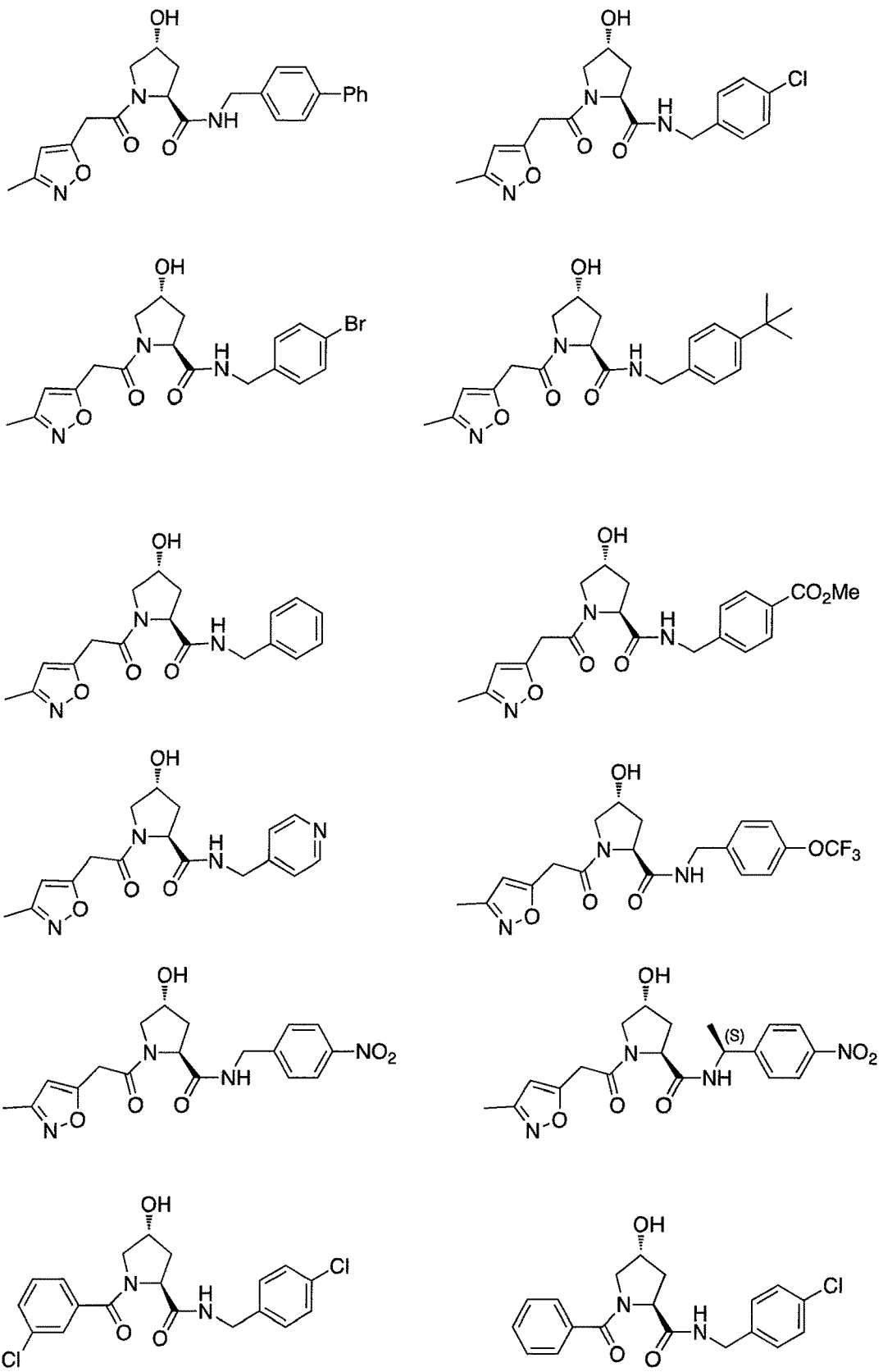
FIG. 14 shows numerous preferred compounds from Table 2 according to the present invention.
Figure 14:
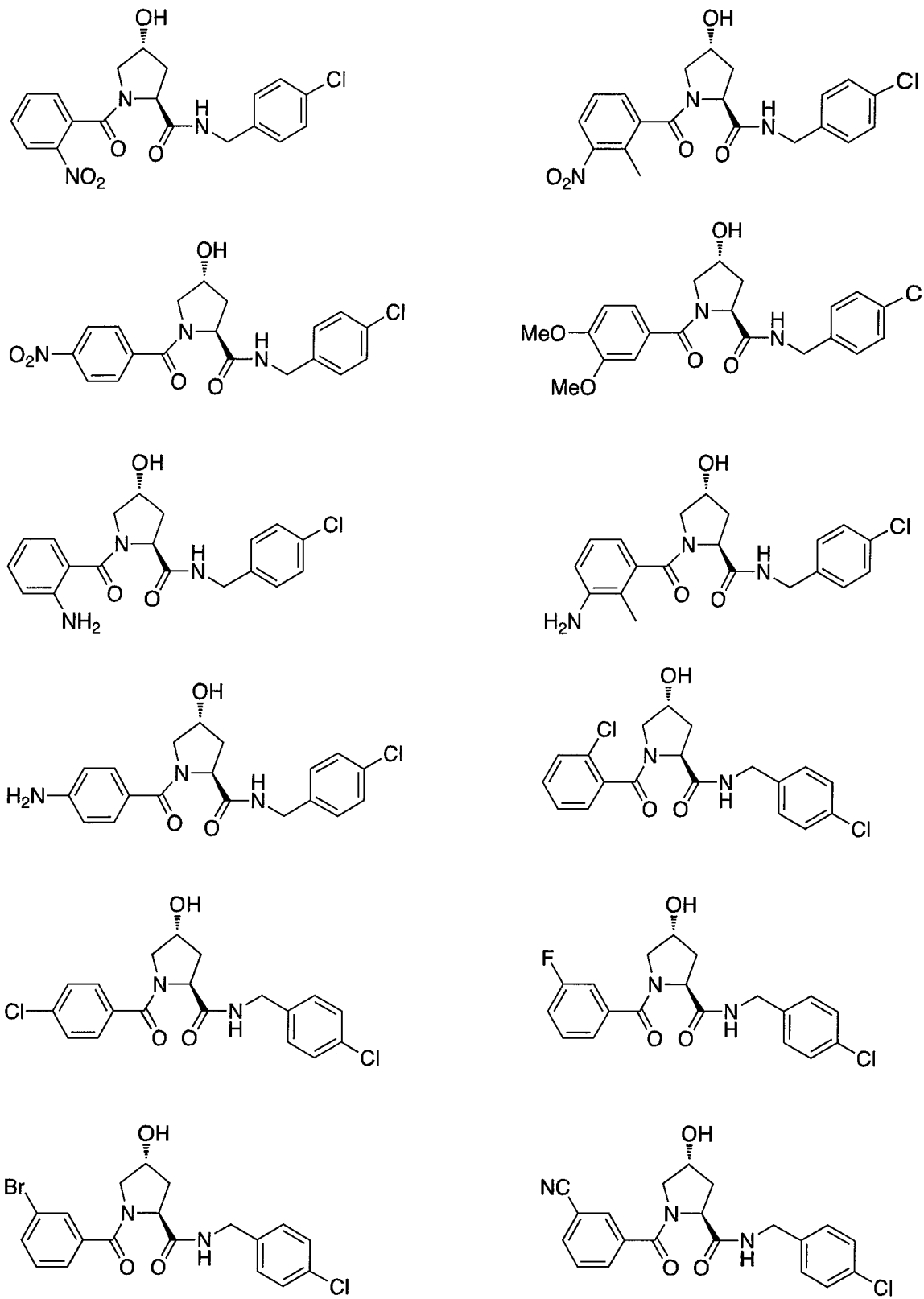
Figure 14:
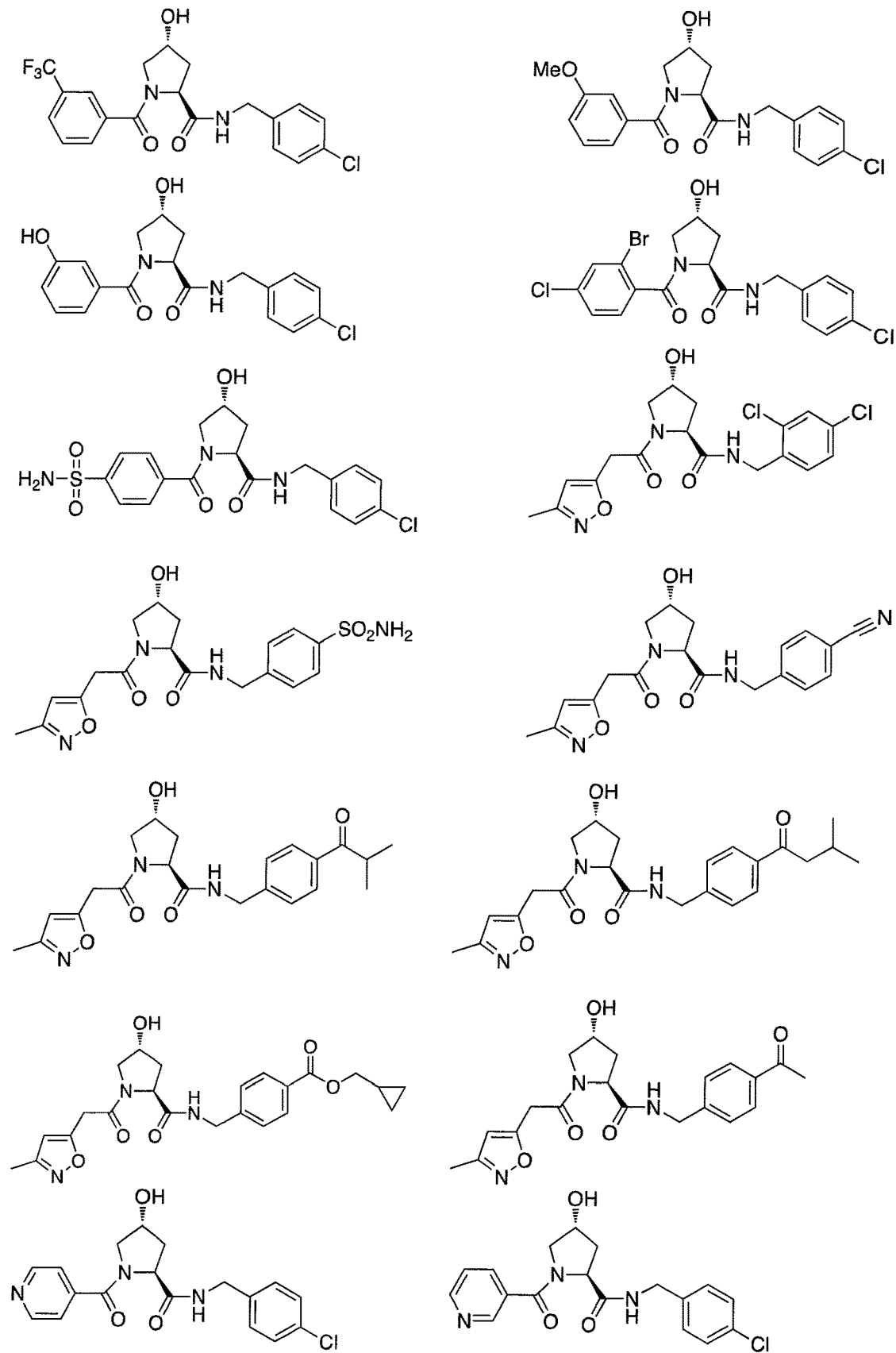
Figure 14:
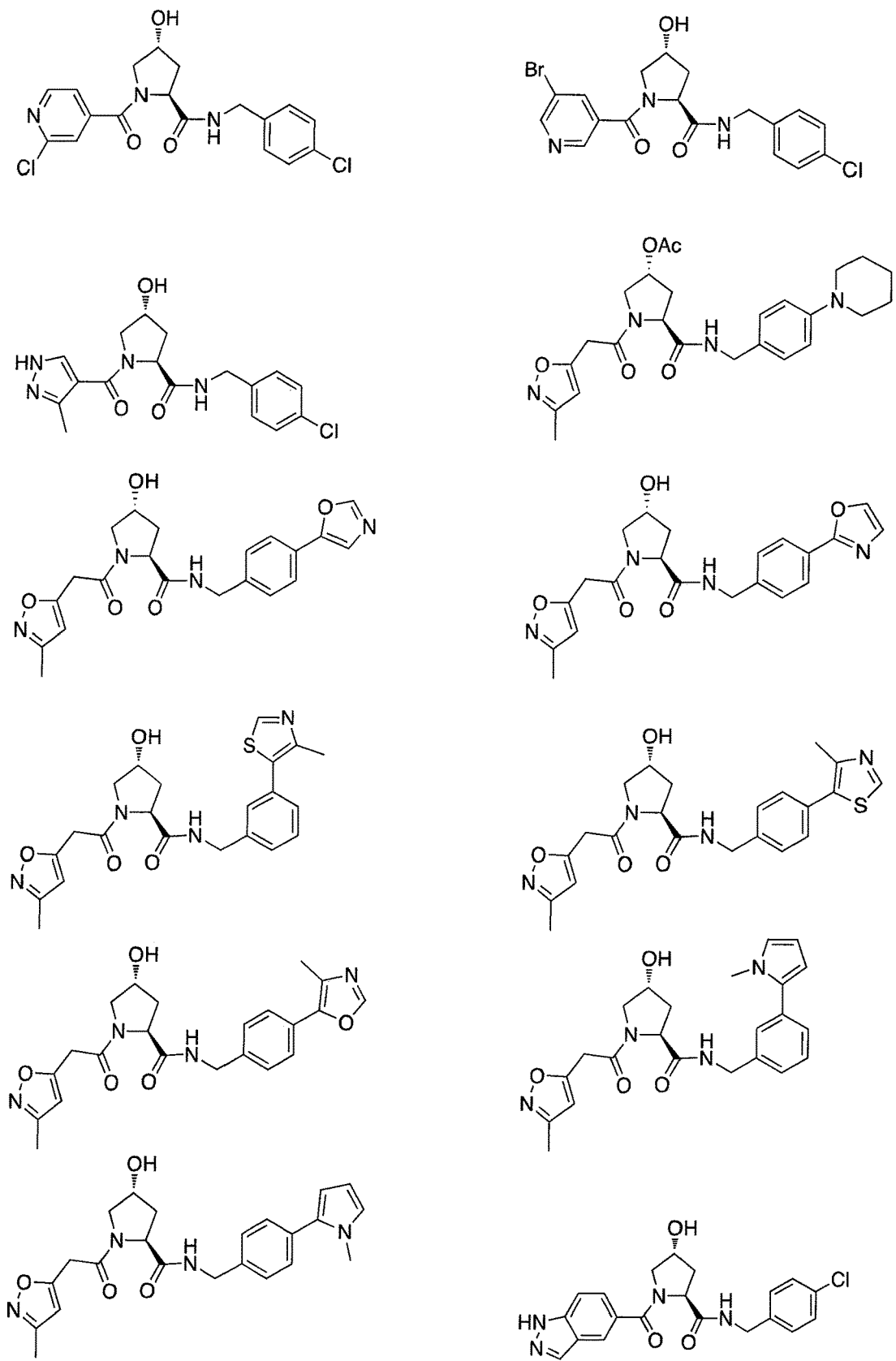
Figure 14:
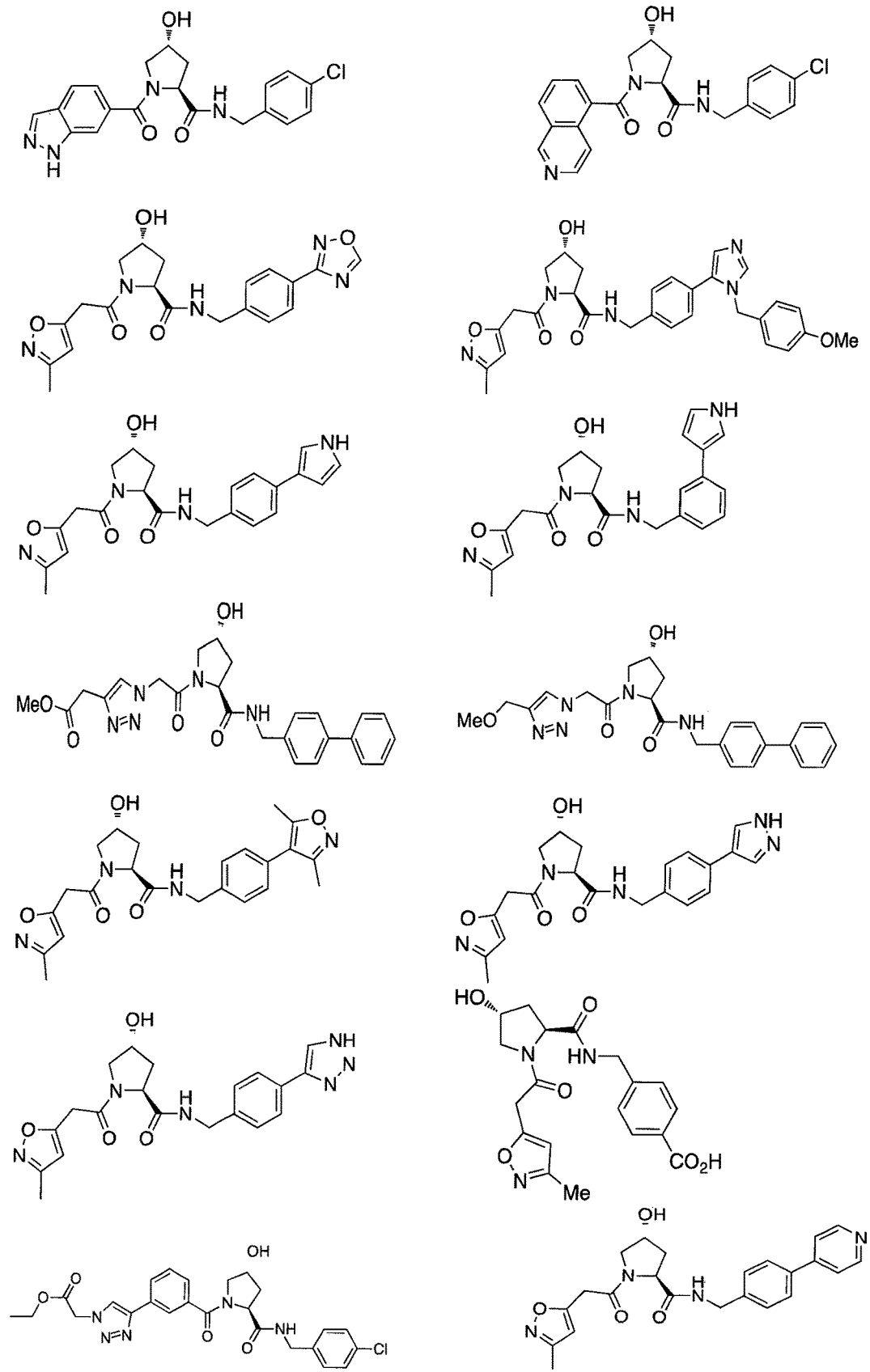
Figure 14:
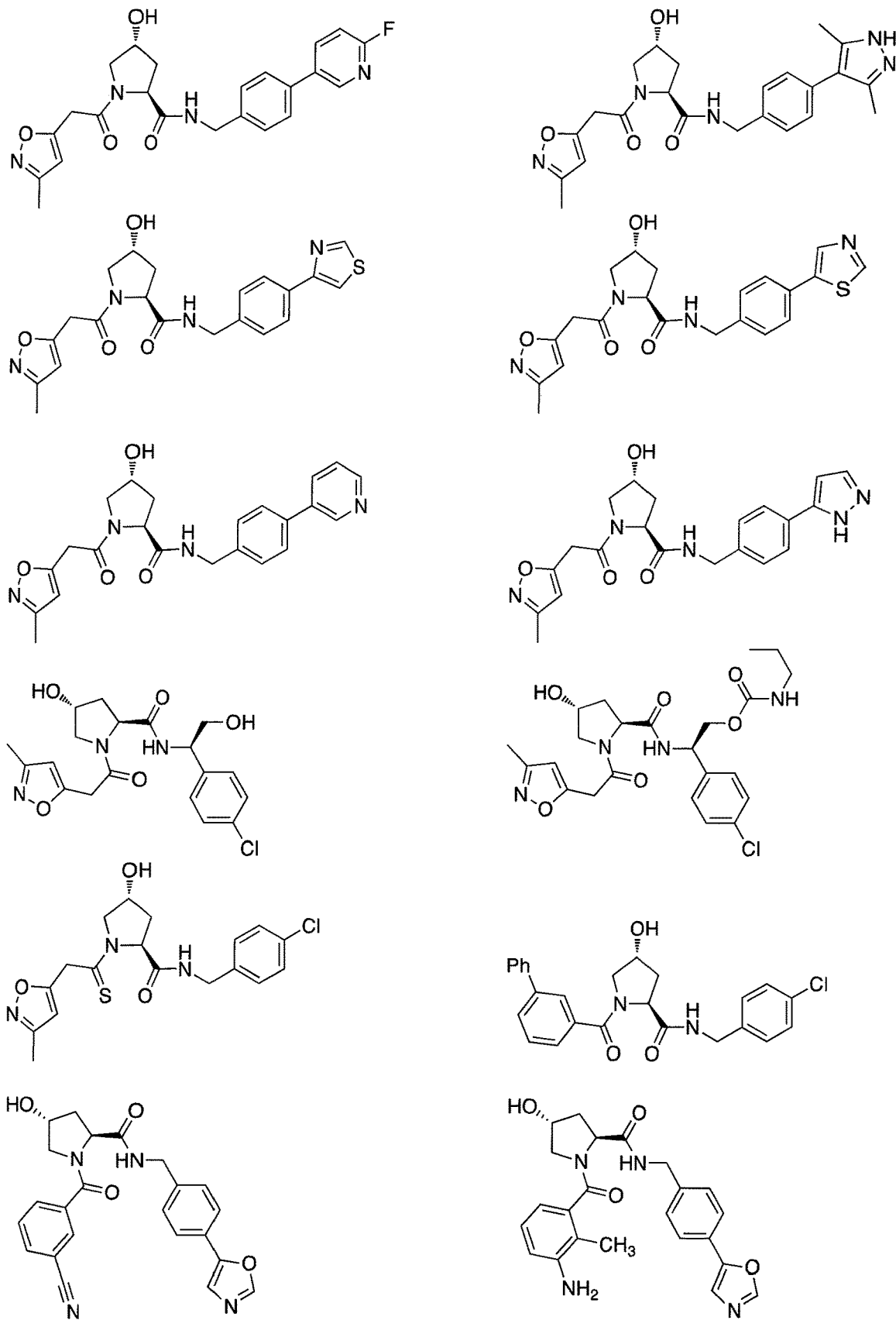
Figure 14:
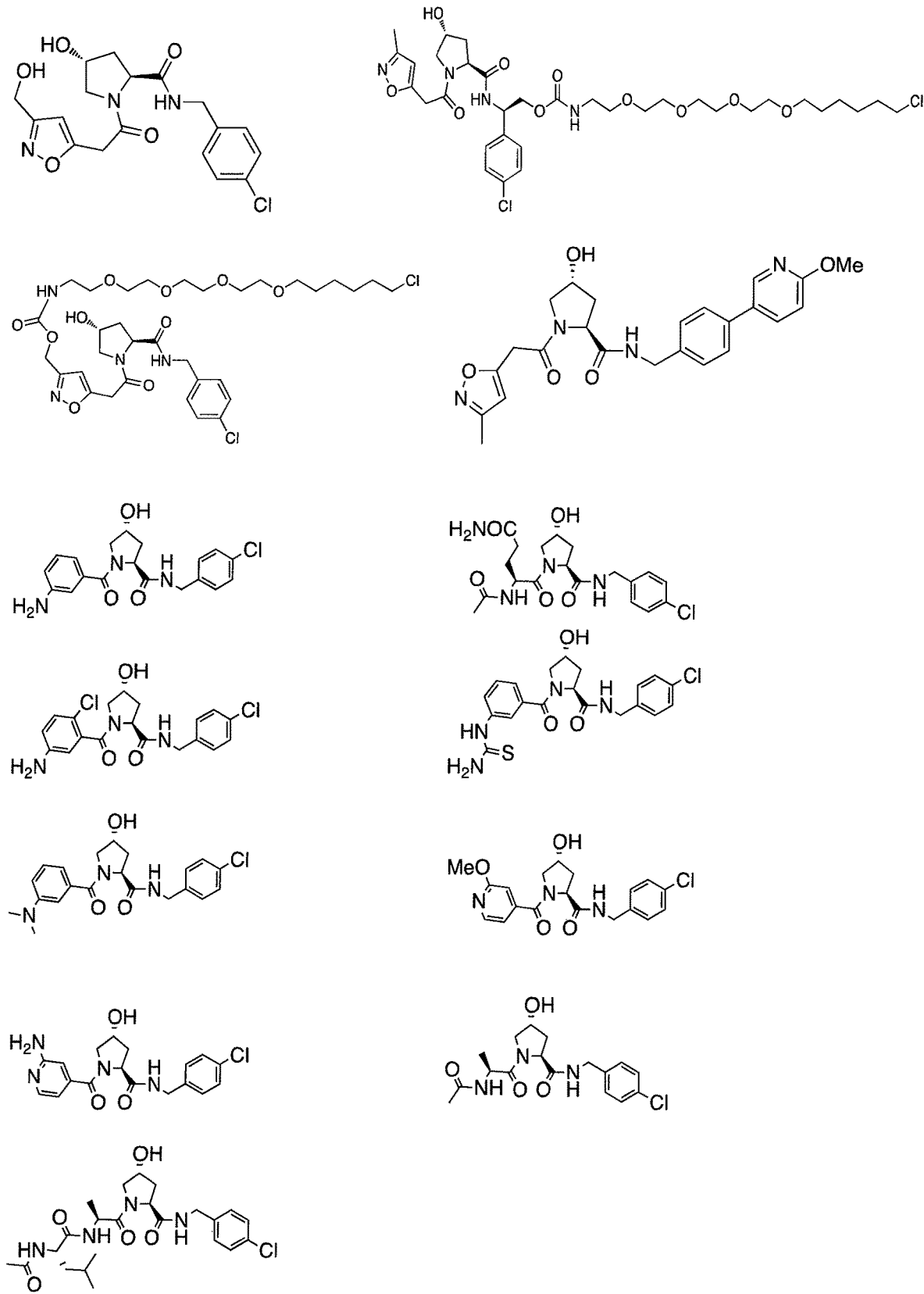
Figure 14:
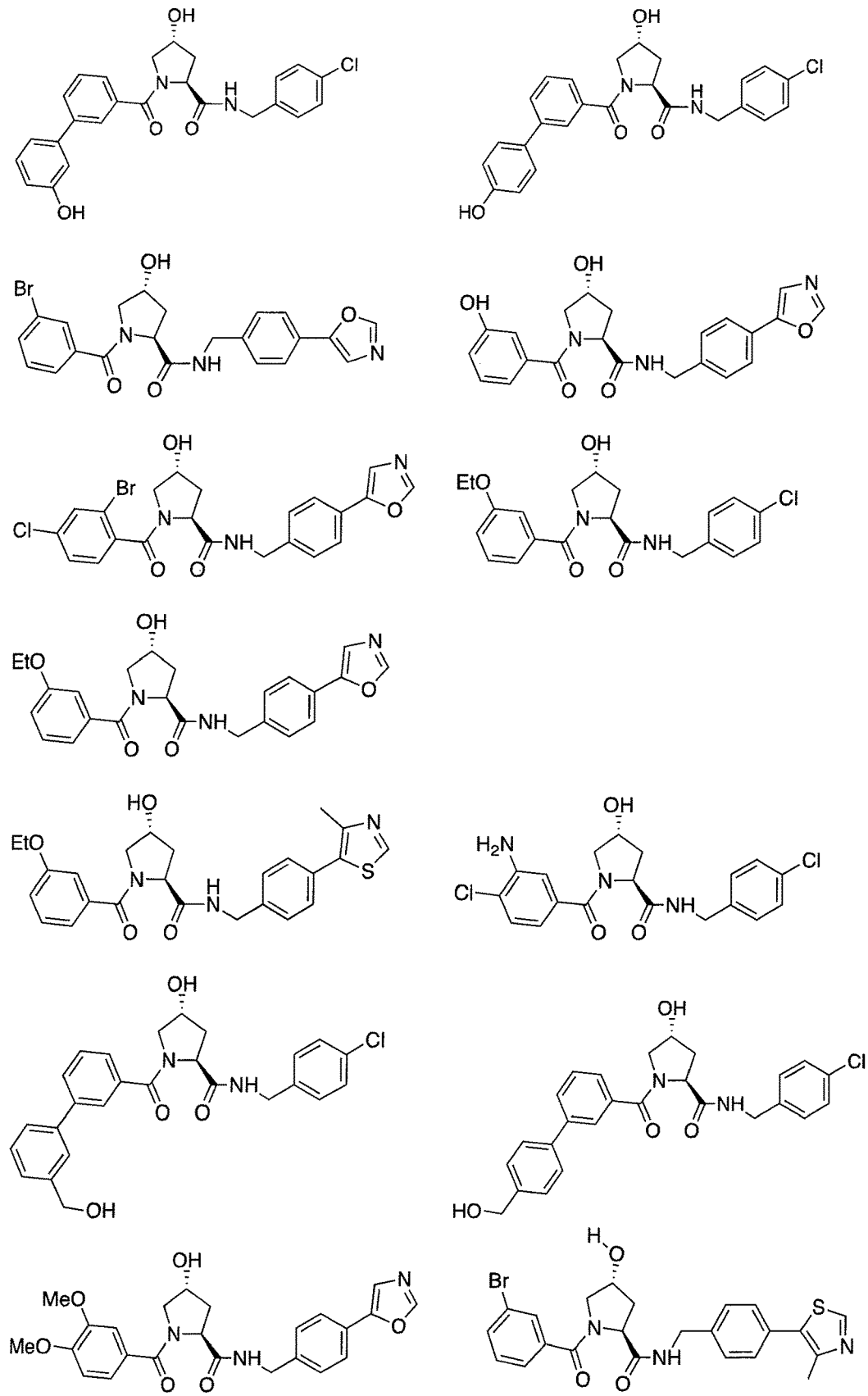
Figure 14:
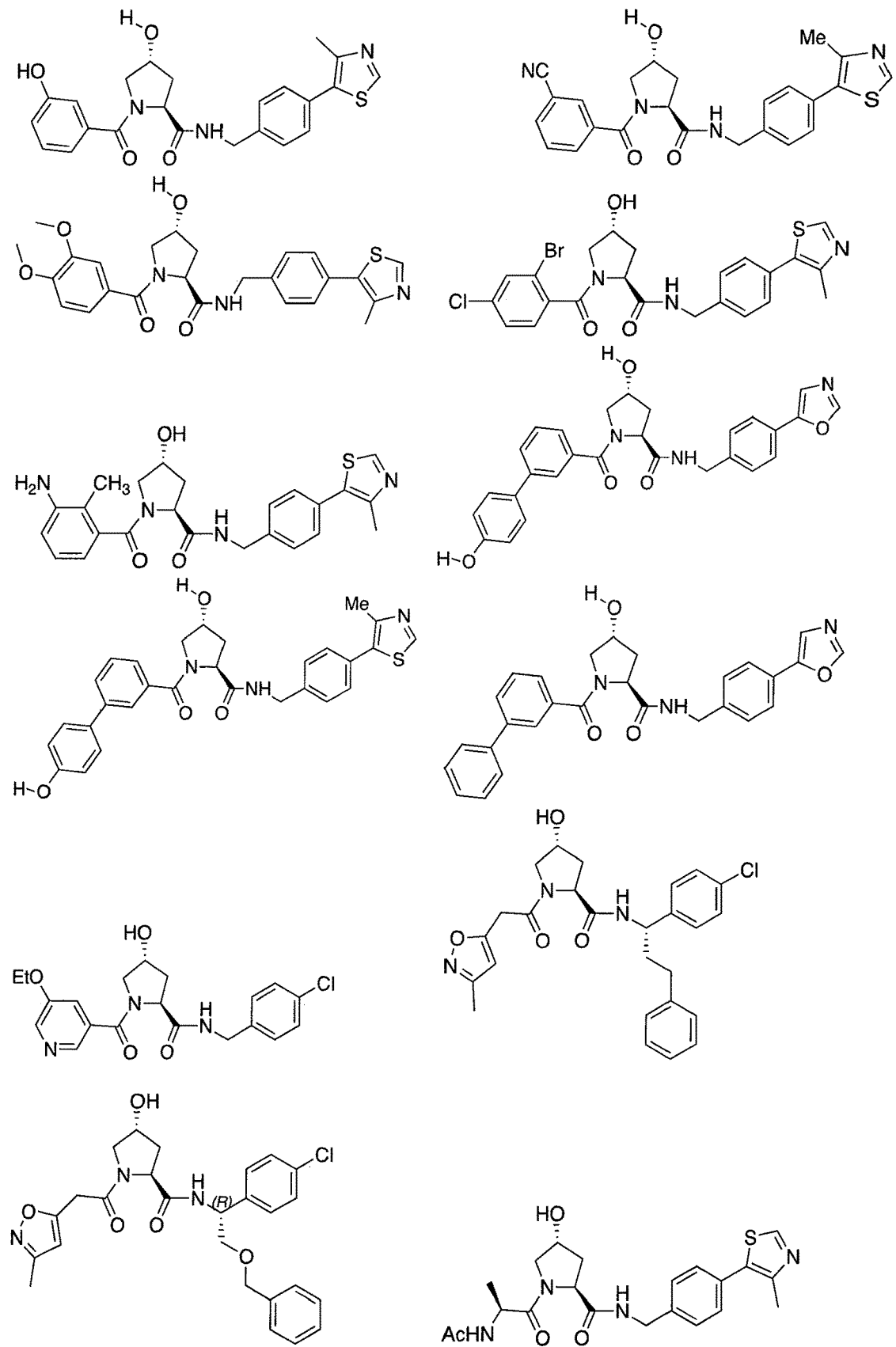
Figure 14:
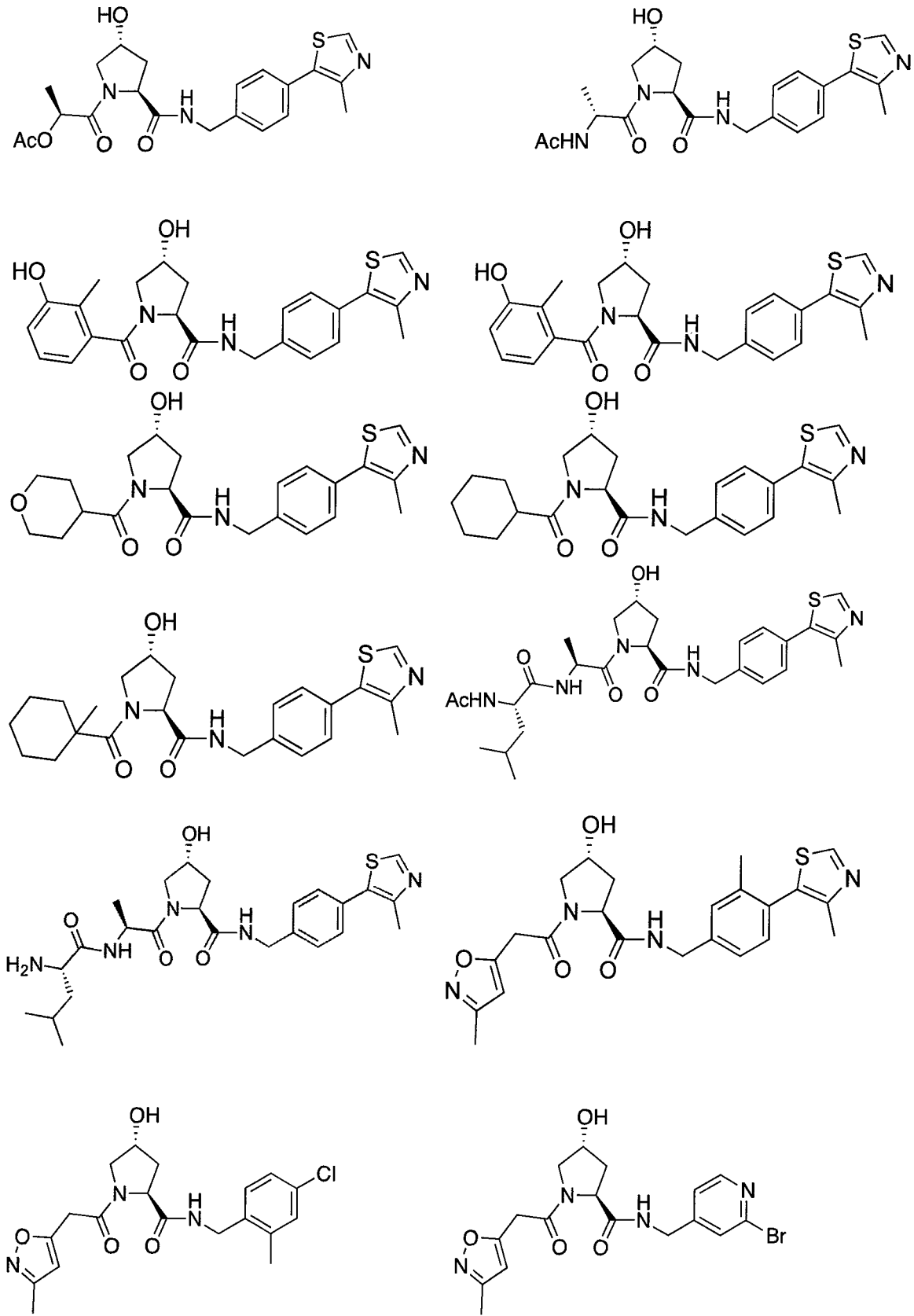
Figure 14:
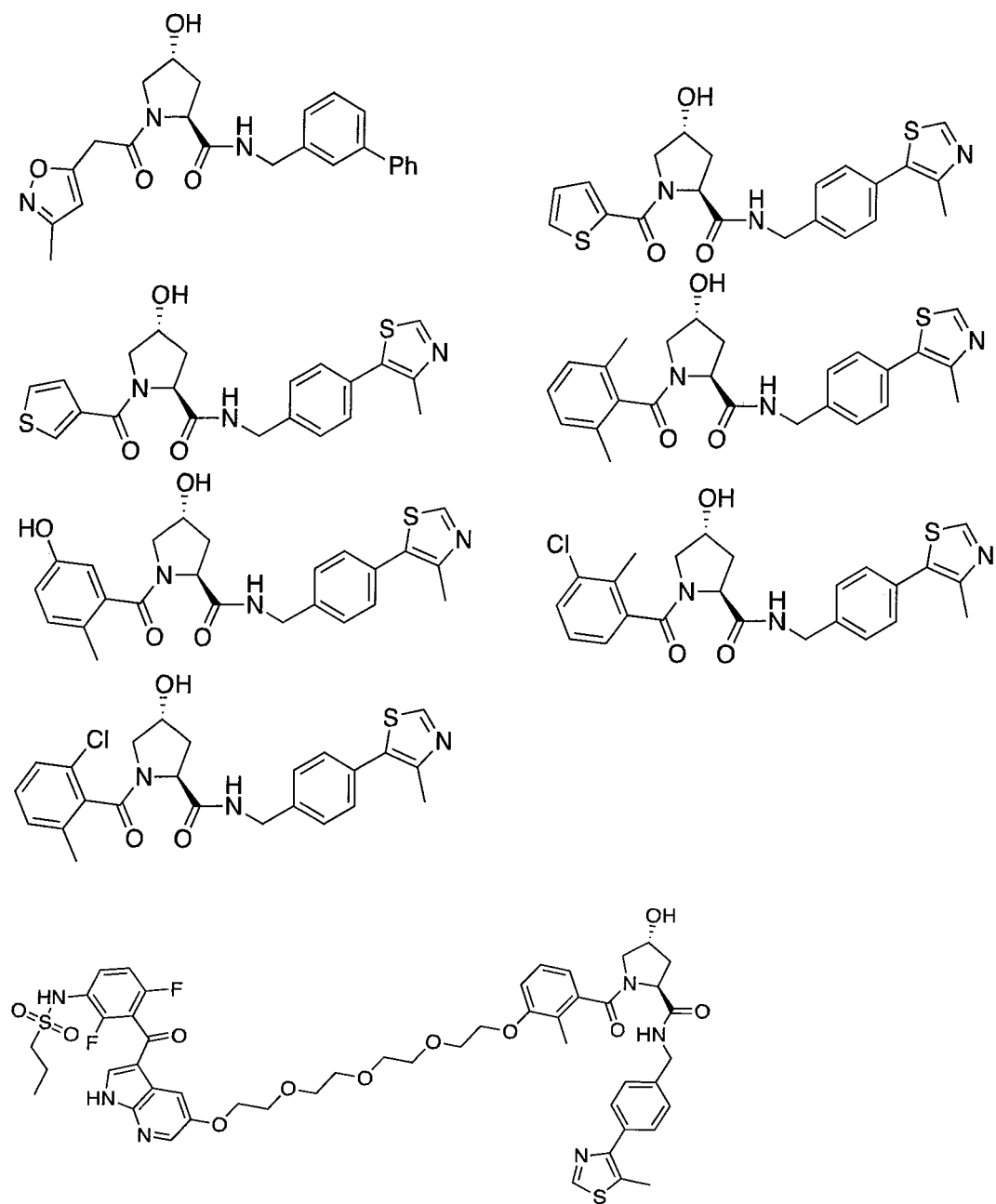

The inventors initially hypothesized that small molecule inhibitors of the VHL/HIF-1α interaction could be rationally designed using hydroxyproline (Hyp) as a starting point, since residue Hyp564 on HIF-1α makes key interactions with VHL[14] and is crucial for HIF-1α binding[15]. The inventors used the de-novo design software BOMB to guide the selection of plausible hydroxyproline analogs.[16] 1 and 2 were synthesized to test a promising design featuring an isoxazole moiety positioned to interact with a crystallographic water observed in the structure of VHL bound to the HIF peptide (549-582)[14] and a benzyl group stacked along the side chain of Tyr98. Their ability to bind to VHL was measured by the competition of a fluorescent HIF-1α peptide using fluorescence polarization (FP).[17] Both were able to displace the fluorescent peptide albeit at high concentrations (Table 1A). While the smaller 3 was unable to fully displace the fluorescent peptide, the observed binding to VHL through the use of WaterLOGSY and saturation transfer difference (STD) NMR. As no binding was observed with hydroxyproline alone, this suggested that the inventors identified a minimal pharmacophore (see FIG. 2).

TABLE 1A

Binding of Initial Ligands to VHL

| R | IC$_{50}$ (μM)$^a$ | SEM (μM) |
|---|---|---|
| 1 (3-chlorobenzyl) | 117 | 10 |
| 2 (4-hydroxyphenethyl) | 120.1 | 7.1 |
| 3 CH$_3$ | >250 | N/A |

$^a$Average IC$_{50}$ values were determined from three independent trials, each in triplicate.

Encouraged by these initial results, the inventors sought to increase the affinity of our VHL ligands by modifying the benzylamine moiety of 1 while maintaining the methylisoxazole fragment. In order to generate analogs rapidly, we developed a solid phase synthesis that involved the attachment of Fmoc-Hyp-OAllyl to Wang resin.[18] Fmoc deprotection, coupling with 3-methyl-5-isoxazoleacetic acid followed by allyl ester deprotection and coupling with various amines and subsequent cleavage with trifluoroacetic acid led to the rapid generation of VHL ligands (Scheme 1).[19,20] These ligands were then tested for their ability to bind VHL using the HIF peptide FP displacement assay.

Incorporation of various halogenated benzylamines showed that para substitution yielded the highest affinity and that there were only slight differences of affinity between chlorides and bromides, although the corresponding fluoride was less potent. We also found that substitution with electron withdrawing groups such as esters, nitro groups, nitriles, and ketones led to more potent ligands than substitution with the electron donating methoxy and t-butyl substituents. Molecular dynamics simulations suggested that Arg107 is flexible and could accommodate bulkier groups at the para position. Therefore, we considered larger heterocyclic substituents at the para position of the benzylamine moiety and synthesized 15, which was found to bind with a 4.1 μM IC$_{50}$ value (Table 2, below).

Fluorescence Polarization Assay

Ability of VHL ligands to compete for the HIF1a binding site on VCB was determined through a fluorescence polarization competition assay as described in the literature (Buckley et al. JACS, 2012, 134, 4465-4468). VHL ligands were dissolved in DMSO (100 mM), and then diluted 10 fold with VHL buffer. The compounds were then diluted 2 fold with 10% DMSO in buffer (20 uL into uL of 10% DMSO in buffer) 14 times. Aqueous DEALA-Hyp-YIPD was used as a positive control. 278 nM FAM-DEALA-Hyp-YIPD (DMSO) was diluted 1000 fold into VHL buffer. For polarization displacement assays, 9 uL of 1 uM V1-213CB (450 nM final), 2 uL of VHL Ligands (VL) compounds in 10% DMSO (1% DMSO final), and 9 uL of 278 nM FAM-DEALA-Hyp-YIPD were added to a 384 well plate (Corning 3575). The plate was then shaken for 1 minute, and centrifuged for 1 minute, before reading fluorescence polarization on a Perkin Elmer Envision 2101 Multilabel reader (excitation 486 nM, emission 535 nM). Wells containing V1-213CB, DMSO vehicle, FAM-DEALA-Hyp-YIPD served as maximum polarization (or minimum displacement). Wells containing buffer in place of V1-213CB, DMSO vehicle, FAM-DEALA-Hyp-YIPD served as minimum polarization (or maximum displacement). The percent inhibition was determined by normalization to maximum and minimum polarization, and graphed against the log [VL]. IC50 values were then determined using Prism 5 for each replicate (n=9), which were then averaged to determine the average IC50 and the standard error of the mean (SEM). The results for a number of exemplary compounds are presented in Table 2 Affinity Table herein below.

TABLE 2

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL001 | >1000 | | 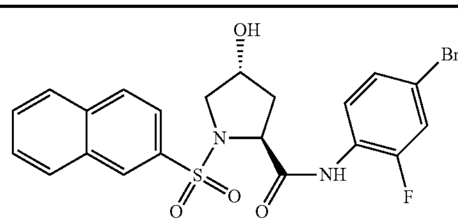 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL002 | 241.1 | 120 | 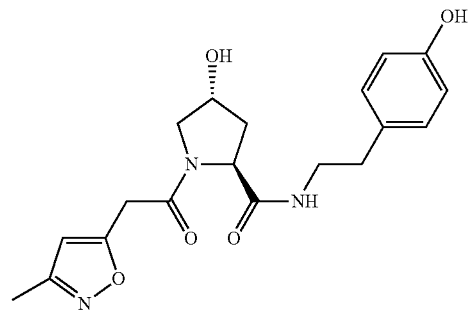 [SMILES: Cc1cc(CC(=O)N2C[C@H](O)C[C@H]2C(=O)NCCc2ccc(O)cc2)on1] |
| VL003 | >1000 | | 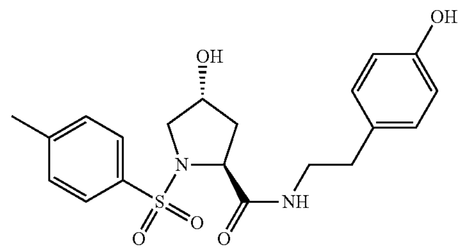 [SMILES: Cc1ccc(S(=O)(=O)N2C[C@H](O)C[C@H]2C(=O)NCCc2ccc(O)cc2)cc1] |
| VL004 | 123.1 | 117 | 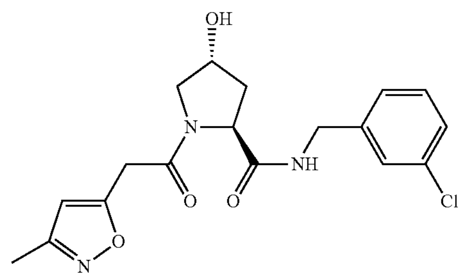 [SMILES: Cc1cc(CC(=O)N2C[C@H](O)C[C@H]2C(=O)NCc2cccc(Cl)c2)on1] |
| VL005 | >1000 | | 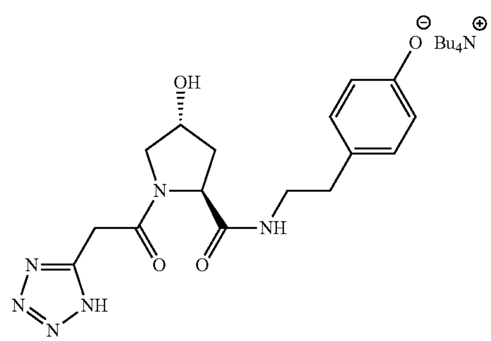 [SMILES: O=C(NCCc1ccc([O-])cc1)[C@@H]1C[C@@H](O)CN1C(=O)Cc1nnn[nH]1 ; "Bu4N"] |
| VL006 | Inactive | | 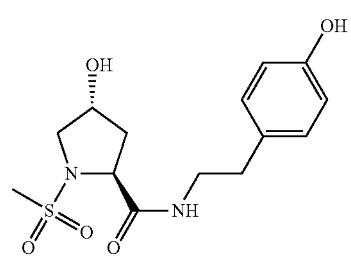 [SMILES: CS(=O)(=O)N1C[C@H](O)C[C@H]1C(=O)NCCc1ccc(O)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL007 | Inactive | | 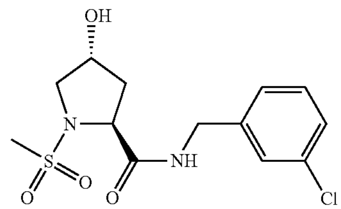 [SMILES: CS(=O)(=O)N1C[C@H](O)C[C@H]1C(=O)NCc1cccc(Cl)c1] |
| VL008 | >1000 | | 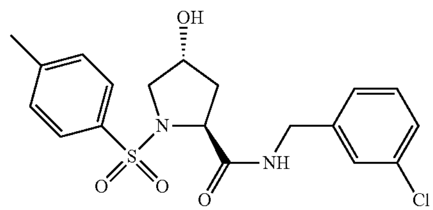 [SMILES: Cc1ccc(S(=O)(=O)N2C[C@H](O)C[C@H]2C(=O)NCc2cccc(Cl)c2)cc1] |
| VL009 | Inactive | | 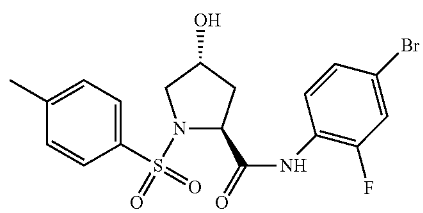 [SMILES: Cc1ccc(S(=O)(=O)N2C[C@H](O)C[C@H]2C(=O)Nc2ccc(Br)cc2F)cc1] |
| VL010 | Inactive | | 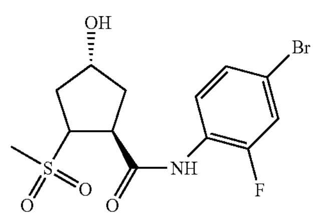 [SMILES: CS(=O)(=O)C1C[C@H](O)C[C@H]1C(=O)Nc1ccc(Br)cc1F] |
| VL011 | >1000 | | 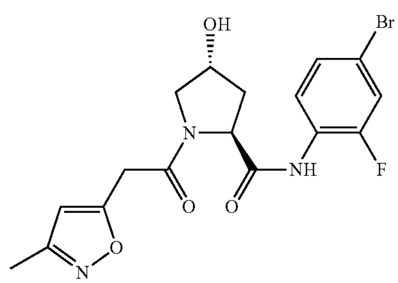 [SMILES: Cc1cc(CC(=O)N2C[C@H](O)C[C@H]2C(=O)Nc2ccc(Br)cc2F)on1] |
| VL012 | >1000 | | 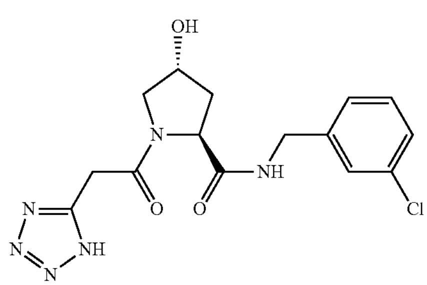 [SMILES: O=C(NCc1cccc(Cl)c1)[C@@H]1C[C@@H](O)CN1C(=O)Cc1nnn[nH]1] |

US 10,730,862 B2
105 106
TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL013 | 240 | | 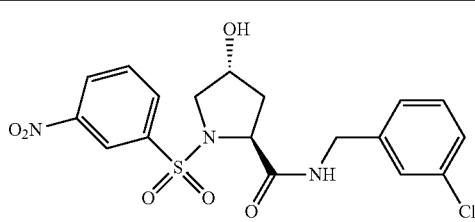 |
| VL014 | 4.7 | | 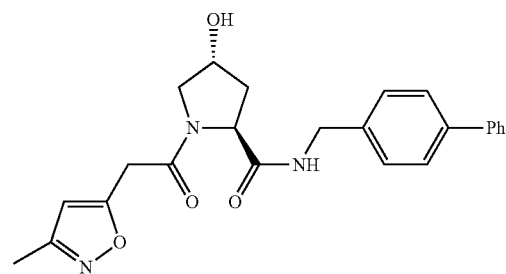 [SMILES: Cc1cc(CC(=O)N2C[C@H](O)C[C@H]2C(=O)NCc2ccc(-c3ccccc3)cc2)on1] |
| VL015 | >1000 | | 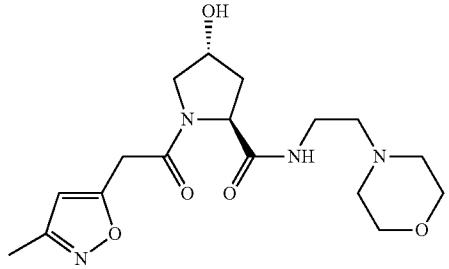 [SMILES: Cc1cc(CC(=O)N2C[C@H](O)C[C@H]2C(=O)NCCN2CCOCC2)on1] |
| VL016 | ~730 | | 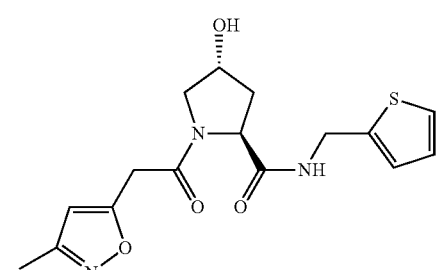 |
| VL017 | ~510 | | 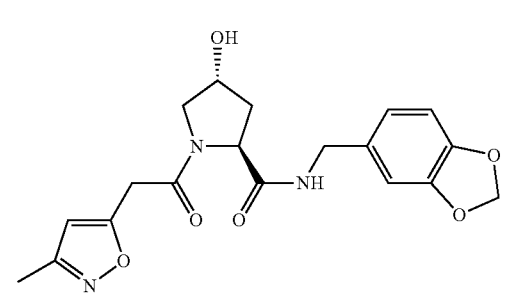 [SMILES: Cc1cc(CC(=O)N2C[C@H](O)C[C@H]2C(=O)NCc2ccc3c(c2)OCO3)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL018 | 280 | | 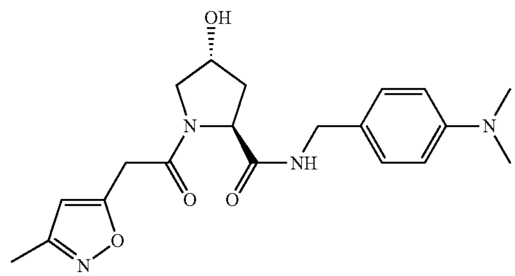 |
| VL019 | 450.5 | | 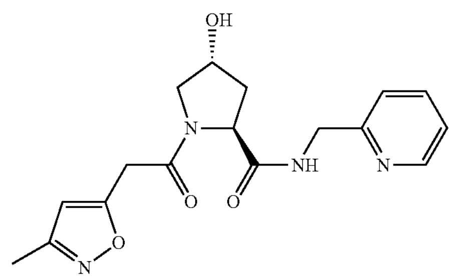 [SMILES: Cc1cc(CC(=O)N2C[C@H](O)C[C@H]2C(=O)NCc2ccccn2)on1] |
| VL020 | 295.4 | 149 | 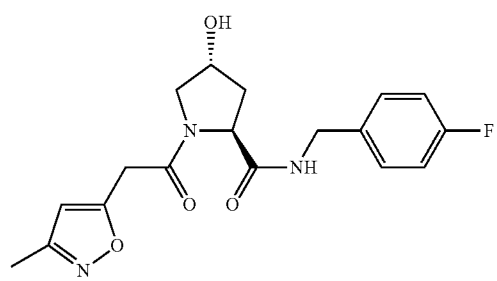 [SMILES: Cc1cc(CC(=O)N2C[C@H](O)C[C@H]2C(=O)NCc2ccc(F)cc2)on1] |
| VL021 | 36 | 20.5 | 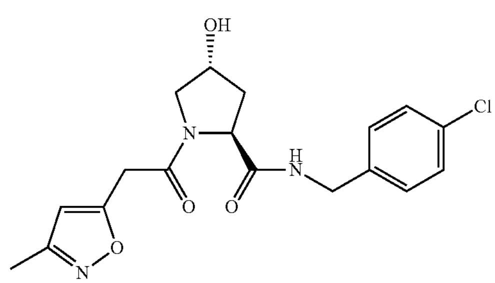 [SMILES: Cc1cc(CC(=O)N2C[C@H](O)C[C@H]2C(=O)NCc2ccc(Cl)cc2)on1] |
| VL022 | ~870 | | 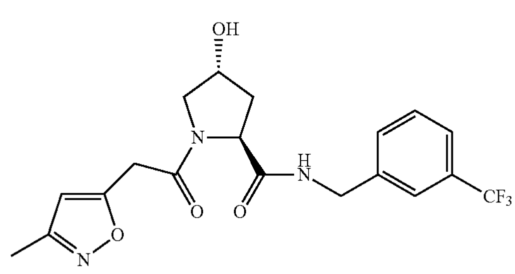 [SMILES: Cc1cc(CC(=O)N2C[C@H](O)C[C@H]2C(=O)NCc2cccc(C(F)(F)F)c2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL023 | 589 | | 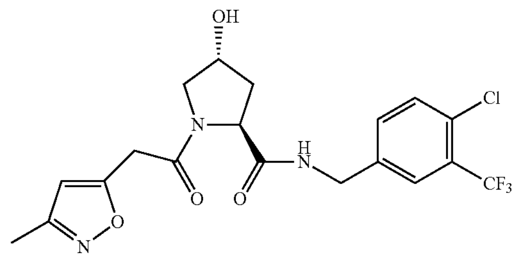 [SMILES: Cc1cc(CC(=O)N2C[C@H](O)C[C@H]2C(=O)NCc2ccc(Cl)c(C(F)(F)F)c2)on1] |
| VL024 | 511 | | 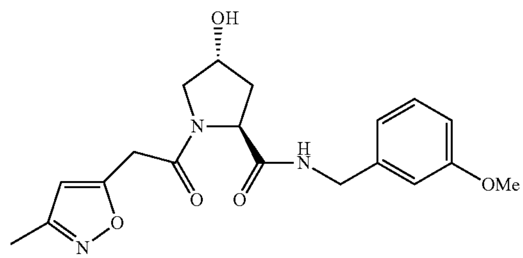 [SMILES: COc1cccc(CNC(=O)[C@@H]2C[C@@H](O)CN2C(=O)Cc2cc(C)no2)c1] |
| VL025 | 517 | | 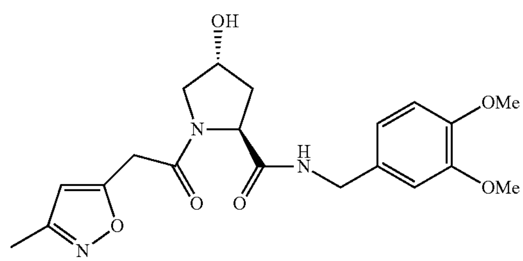 [SMILES: COc1ccc(CNC(=O)[C@@H]2C[C@@H](O)CN2C(=O)Cc2cc(C)no2)cc1OC] |
| VL026 | >1000 | >250 | 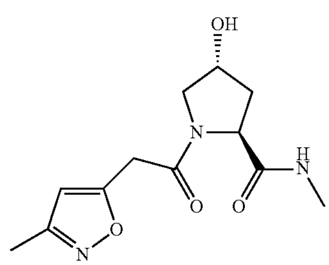 |
| VL027 | >1000 | | 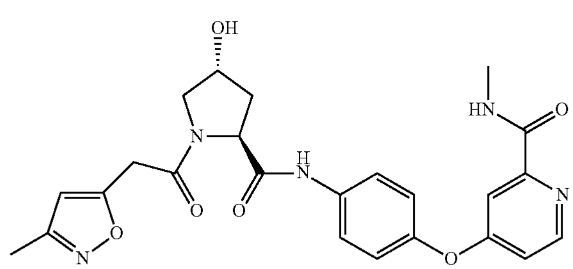 [SMILES: CNC(=O)c1cc(Oc2ccc(NC(=O)[C@@H]3C[C@@H](O)CN3C(=O)Cc3cc(C)no3)cc2)ccn1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL028 | 210.0 | 149 | 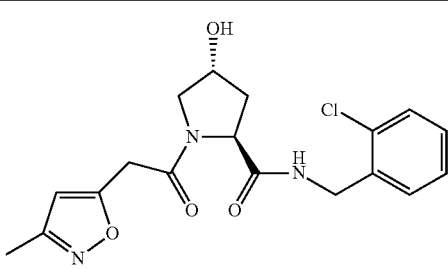 |
| VL029 | 24.9 | 32 | 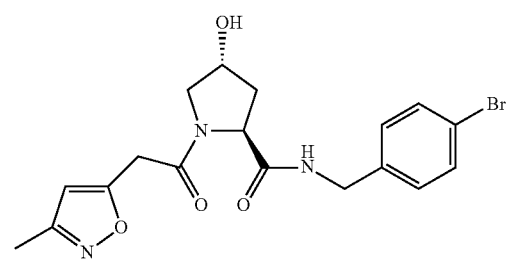 [SMILES: Cc1cc(CC(=O)N2C[C@H](O)C[C@H]2C(=O)NCc2ccc(Br)cc2)on1] |
| VL030 | 215 | | 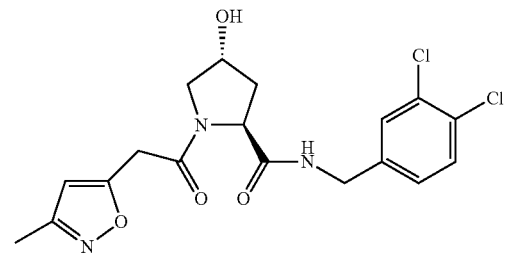 [SMILES: Cc1cc(CC(=O)N2C[C@H](O)C[C@H]2C(=O)NCc2ccc(Cl)c(Cl)c2)on1] |
| VL031 | 68.5 | >250 | 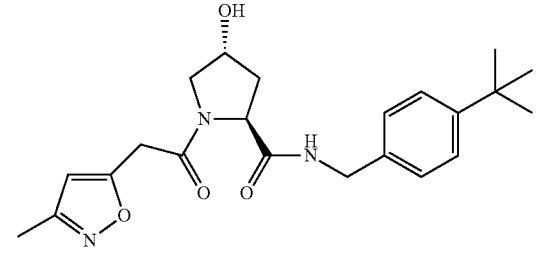 [SMILES: Cc1cc(CC(=O)N2C[C@H](O)C[C@H]2C(=O)NCc2ccc(C(C)(C)C)cc2)on1] |
| VL032 | 639 | | 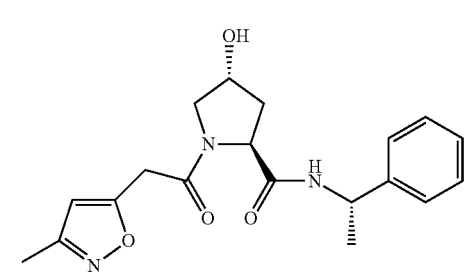 [SMILES: Cc1cc(CC(=O)N2C[C@H](O)C[C@H]2C(=O)N[C@@H](C)c2ccccc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL033 | >1000 | | 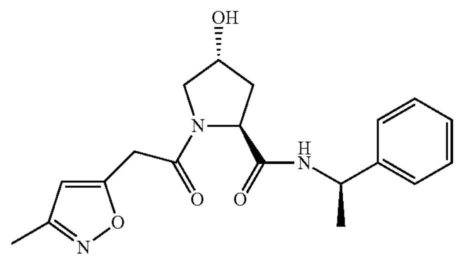 [SMILES: Cc1cc(CC(=O)N2C[C@H](O)C[C@H]2C(=O)N[C@H](C)c2ccccc2)on1] |
| VL034 | 130.7 | 130 | 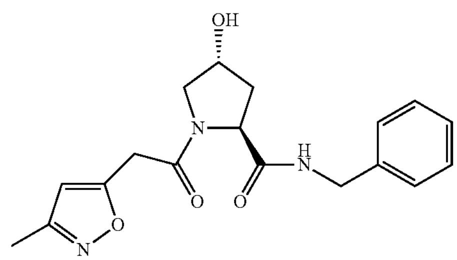 [SMILES: Cc1cc(CC(=O)N2C[C@H](O)C[C@H]2C(=O)NCc2ccccc2)on1] |
| VL035 | 34 | 39.4 | 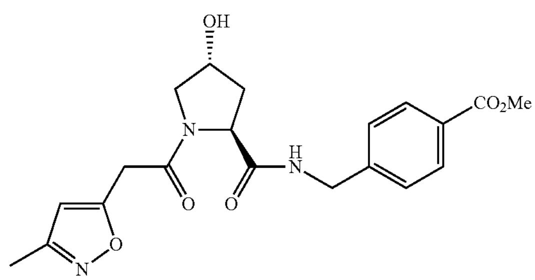 [SMILES: COC(=O)c1ccc(CNC(=O)[C@@H]2C[C@@H](O)CN2C(=O)Cc2cc(C)no2)cc1] |
| VL036 | 743.5 | | 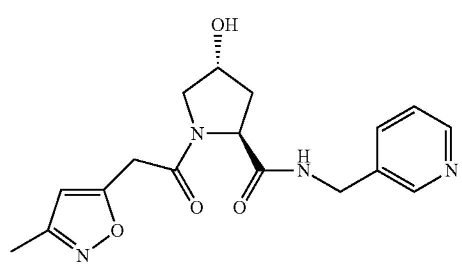 [SMILES: Cc1cc(CC(=O)N2C[C@H](O)C[C@H]2C(=O)NCc2cccnc2)on1] |
| VL037 | 88.8 | | 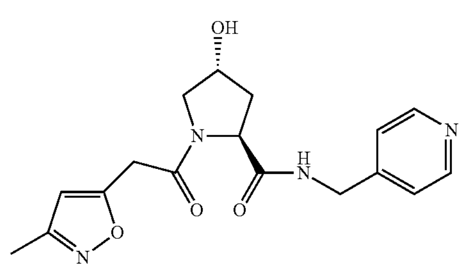 [SMILES: Cc1cc(CC(=O)N2C[C@H](O)C[C@H]2C(=O)NCc2ccncc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL039 | >1000 | | 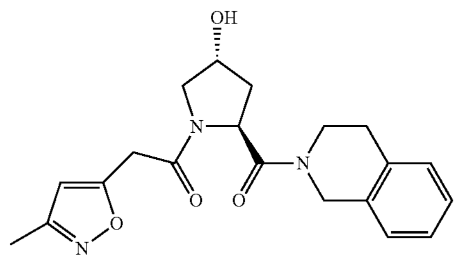 [SMILES: Cc1cc(CC(=O)N2C[C@H](O)C[C@H]2C(=O)N2CCc3ccccc3C2)on1] |
| VL043 | >1000 | | 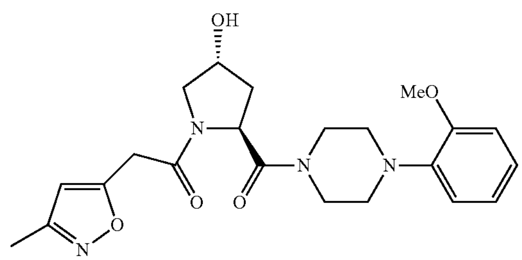 [SMILES: COc1ccccc1N1CCN(C(=O)[C@@H]2C[C@@H](O)CN2C(=O)Cc2cc(C)no2)CC1] |
| VL044 | 285.8 | | 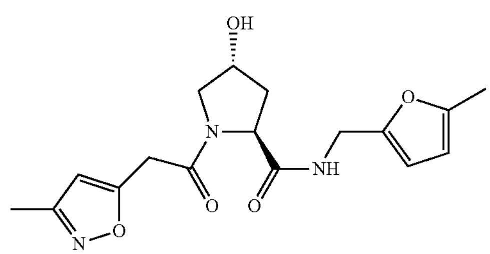 |
| VL045 | 145.6 | | 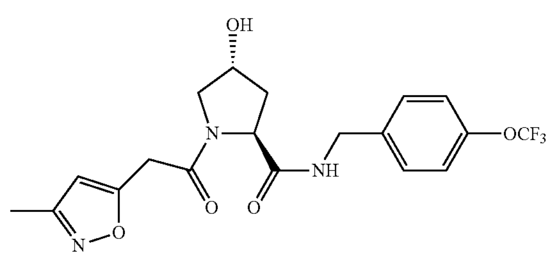 [SMILES: Cc1cc(CC(=O)N2C[C@H](O)C[C@H]2C(=O)NCc2ccc(OC(F)(F)F)cc2)on1] |
| VL046 | 215.2 | | 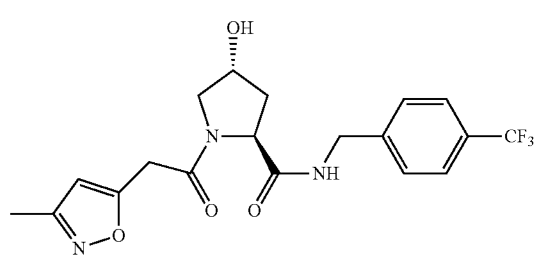 [SMILES: Cc1cc(CC(=O)N2C[C@H](O)C[C@H]2C(=O)NCc2ccc(C(F)(F)F)cc2)on1] |

TABLE 2-continued
Affinity Table.
(Most compounds showed activity within the range of about 200 μM or lower).
| VHL ligand No. | $IC_{50}(\mu M)$ 10% DMSO | $IC_{50}(\mu M)$ 1% DMSO | Chemical Structure |
|---|---|---|---|
| VL047 | 405.7 | 106 | 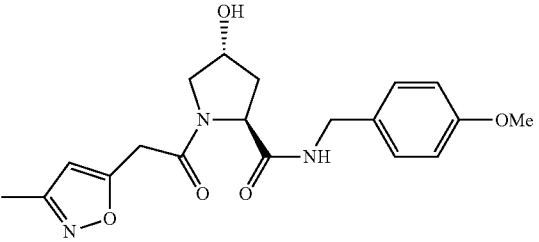 [SMILES: COc1ccc(CNC(=O)[C@@H]2C[C@@H](O)CN2C(=O)Cc2cc(C)no2)cc1] |
| VL048 | 24.8 | 16 | 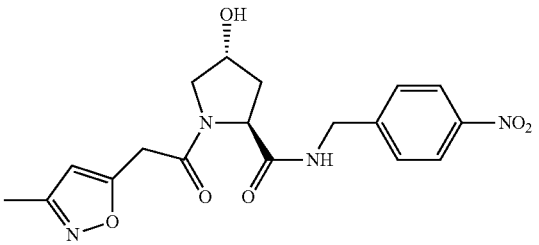 [SMILES: Cc1cc(CC(=O)N2C[C@H](O)C[C@H]2C(=O)NCc2ccc([N+](=O)[O-])cc2)on1] |
| VL049 | 15.1 | | 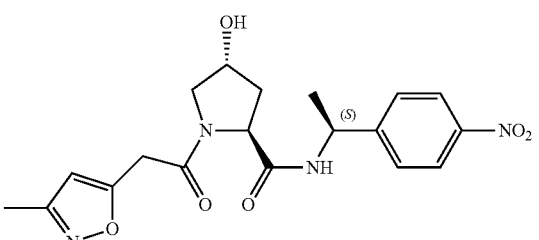 |
| VL050 | 332.1 | | 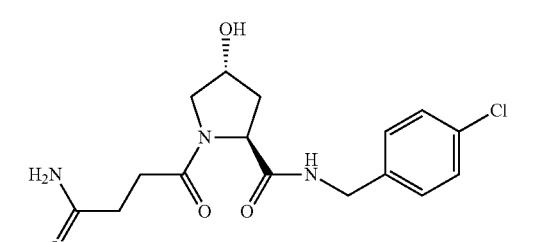 |
| VL051 | >1000 | | 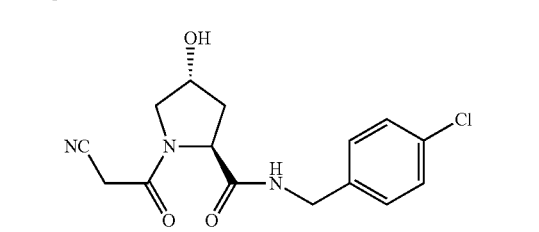 [SMILES: N#CCC(=O)N1C[C@H](O)C[C@H]1C(=O)NCc1ccc(Cl)cc1] |
| VL052 | >1000 | | 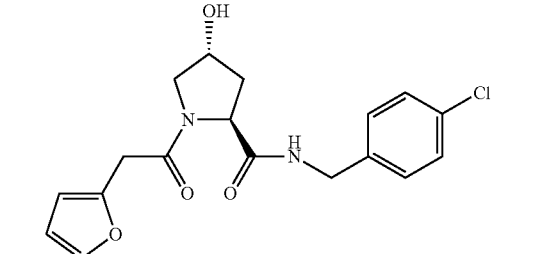 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL053 | >1000 | | 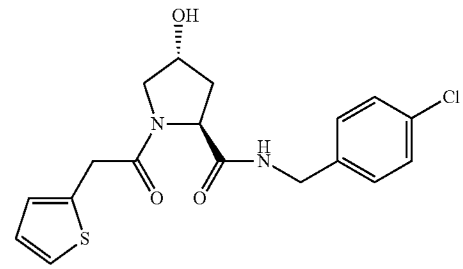 [SMILES: O=C(NCc1ccc(Cl)cc1)[C@@H]1C[C@@H](O)CN1C(=O)Cc1cccs1] |
| VL054 | 139.6 | | 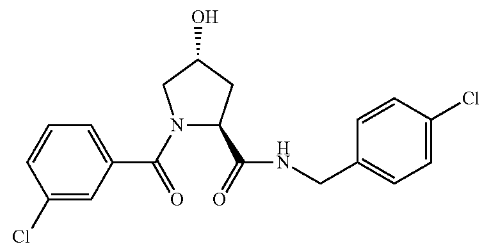 [SMILES: O=C(NCc1ccc(Cl)cc1)[C@@H]1C[C@@H](O)CN1C(=O)c1cccc(Cl)c1] |
| VL055 | 910.3 | | 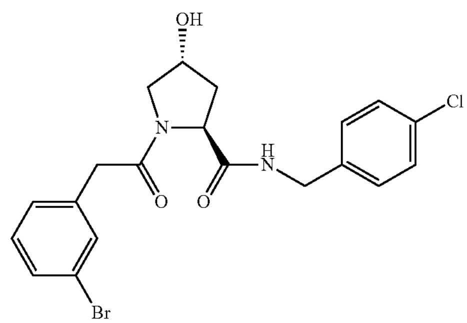 [SMILES: O=C(NCc1ccc(Cl)cc1)[C@@H]1C[C@@H](O)CN1C(=O)Cc1cccc(Br)c1] |
| VL056 | 938.5 | | 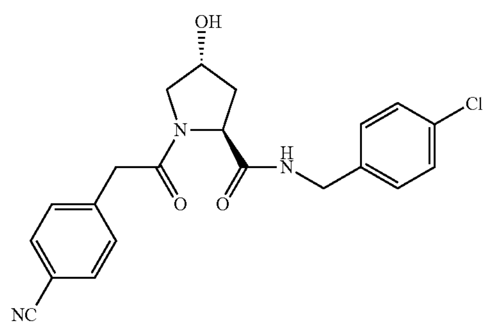 [SMILES: N#Cc1ccc(CC(=O)N2C[C@H](O)C[C@H]2C(=O)NCc2ccc(Cl)cc2)cc1] |
| VL057 | >1000 | | 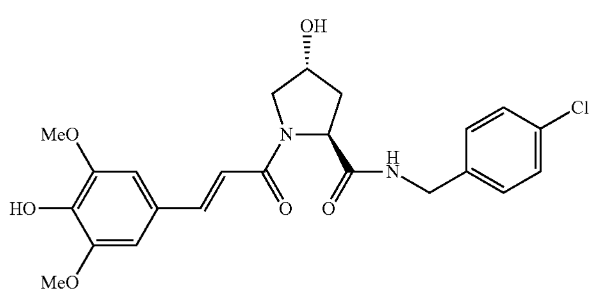 [SMILES: COc1cc(/C=C/C(=O)N2C[C@H](O)C[C@H]2C(=O)NCc2ccc(Cl)cc2)cc(OC)c1O] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL058 | >1000 | | 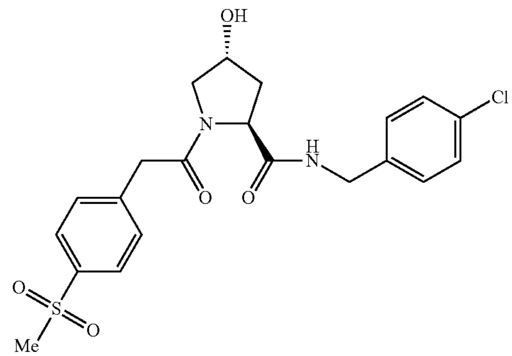 [SMILES: CS(=O)(=O)c1ccc(CC(=O)N2C[C@H](O)C[C@H]2C(=O)NCc2ccc(Cl)cc2)cc1] |
| VL059 | 205.4 | | 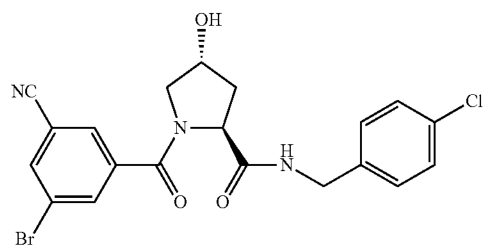 [SMILES: N#Cc1cc(Br)cc(C(=O)N2C[C@H](O)C[C@H]2C(=O)NCc2ccc(Cl)cc2)c1] |
| VL060 | >1000 | | 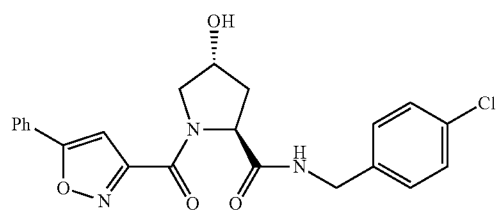 [SMILES: O=C(NCc1ccc(Cl)cc1)[C@@H]1C[C@@H](O)CN1C(=O)c1cc(-c2ccccc2)on1] |
| VL061 | 419.5 | | 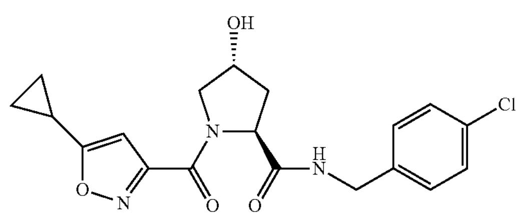 [SMILES: O=C(NCc1ccc(Cl)cc1)[C@@H]1C[C@@H](O)CN1C(=O)c1cc(C2CC2)on1] |
| VL062 | >1000 | | 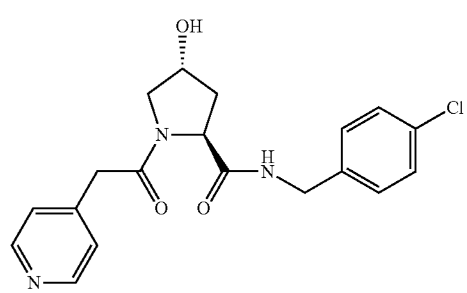 [SMILES: O=C(NCc1ccc(Cl)cc1)[C@@H]1C[C@@H](O)CN1C(=O)Cc1ccncc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL063 | >1000 | | 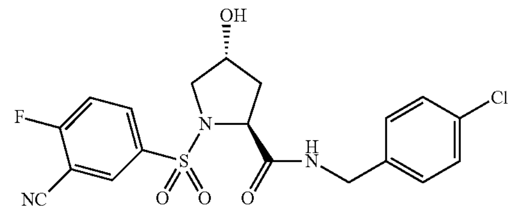 [SMILES: N#Cc1cc(S(=O)(=O)N2C[C@H](O)C[C@H]2C(=O)NCc2ccc(Cl)cc2)ccc1F] |
| VL064 | 110.0 | | 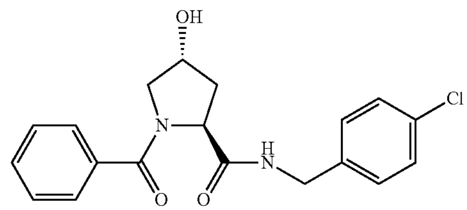 [SMILES: O=C(NCc1ccc(Cl)cc1)[C@@H]1C[C@@H](O)CN1C(=O)c1ccccc1] |
| VL065 | 74.2 | | 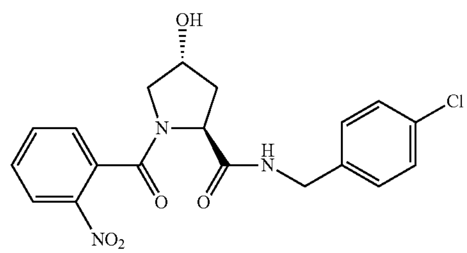 [SMILES: O=C(NCc1ccc(Cl)cc1)[C@@H]1C[C@@H](O)CN1C(=O)c1ccccc1[N+](=O)[O-]] |
| VL066 | 72.4 | | 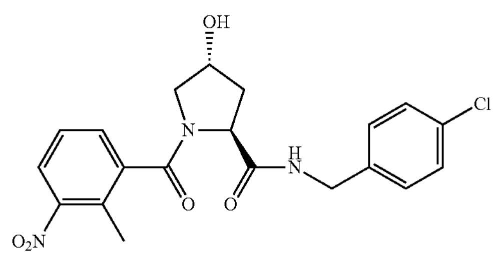 [SMILES: Cc1c(C(=O)N2C[C@H](O)C[C@H]2C(=O)NCc2ccc(Cl)cc2)cccc1[N+](=O)[O-]] |
| VL067 | 70.7 | | 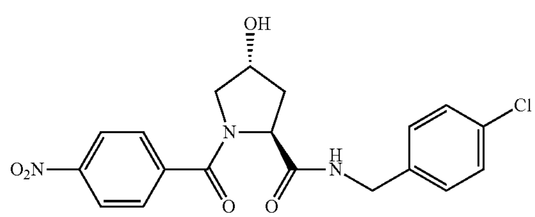 [SMILES: O=C(NCc1ccc(Cl)cc1)[C@@H]1C[C@@H](O)CN1C(=O)c1ccc([N+](=O)[O-])cc1] |
| VL068 | >1000 | | 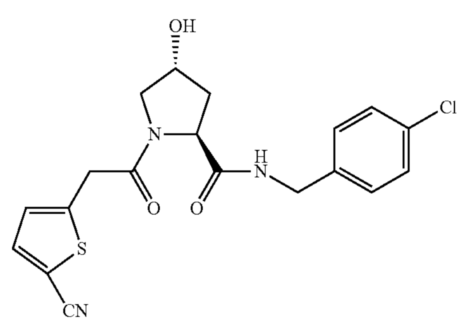 [SMILES: N#Cc1ccc(CC(=O)N2C[C@H](O)C[C@H]2C(=O)NCc2ccc(Cl)cc2)s1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL069 | 23.8 | | 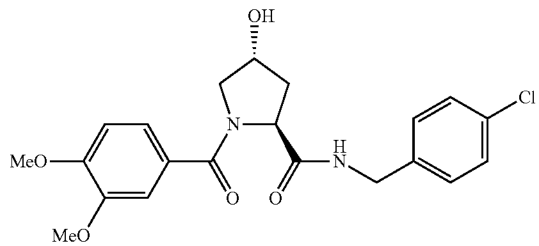 [SMILES: COc1ccc(C(=O)N2C[C@H](O)C[C@H]2C(=O)NCc2ccc(Cl)cc2)cc1OC] |
| VL070 | 38.2 | | 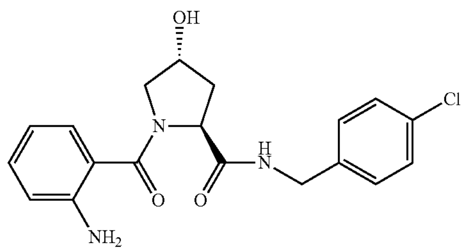 |
| VL071 | 10.4 | | 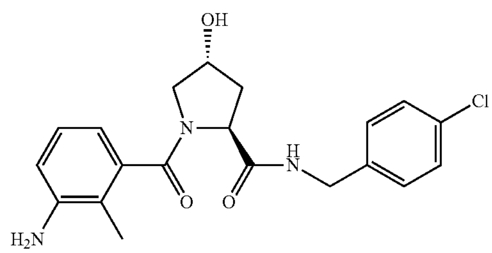 |
| VL072 | 29.5 | | 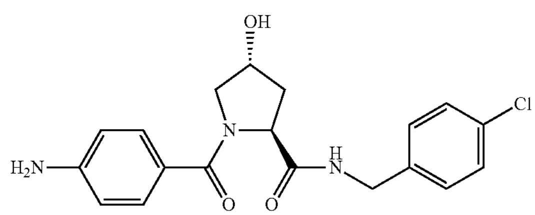 |
| VL073 | 39 | | 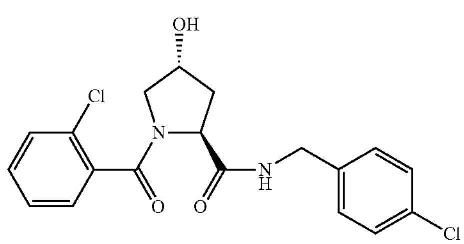 [SMILES: O=C(NCc1ccc(Cl)cc1)[C@@H]1C[C@@H](O)CN1C(=O)c1ccccc1Cl] |
| VL074 | 42.9 | | 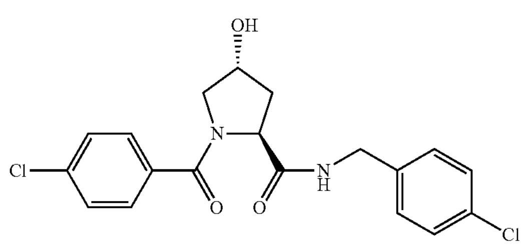 [SMILES: O=C(NCc1ccc(Cl)cc1)[C@@H]1C[C@@H](O)CN1C(=O)c1ccc(Cl)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
| --- | --- | --- | --- |
| VL075 | 35.5 | | 3-fluorobenzoyl-hydroxyproline-(4-chlorobenzyl)amide |
| VL076 | 19.6 | | 3-bromobenzoyl-hydroxyproline-(4-chlorobenzyl)amide |
| VL077 | 8.9 | | 3-cyanobenzoyl-hydroxyproline-(4-chlorobenzyl)amide |
| VL078 | 60.2 | | 3-(trifluoromethyl)benzoyl-hydroxyproline-(4-chlorobenzyl)amide |
| VL079 | 26.3 | | 3-methoxybenzoyl-hydroxyproline-(4-chlorobenzyl)amide |
| VL080 | 17.0 | | 3-hydroxybenzoyl-hydroxyproline-(4-chlorobenzyl)amide |

TABLE 2-continued

Affinity Table.
(Most compounds showed activity within the range of about 200 µM or lower).

| VHL ligand No. | IC$_{50}$(µM) 10% DMSO | IC$_{50}$(µM) 1% DMSO | Chemical Structure |
|---|---|---|---|
| VL081 | 15.5 | | 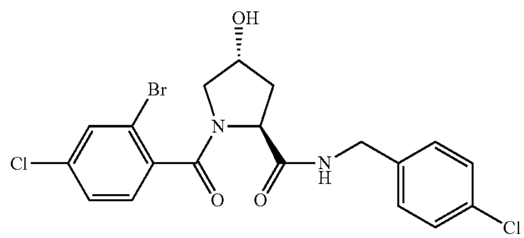 [SMILES: O=C(NCc1ccc(Cl)cc1)[C@@H]1C[C@@H](O)CN1C(=O)c1ccc(Cl)cc1Br] |
| VL082 | 29.0 | | 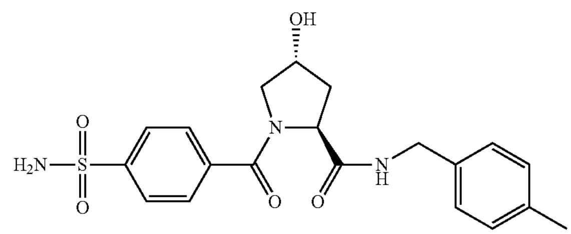 [SMILES: Cc1ccc(CNC(=O)[C@@H]2C[C@@H](O)CN2C(=O)c2ccc(S(N)(=O)=O)cc2)cc1] |
| VL083 | >1000 | | 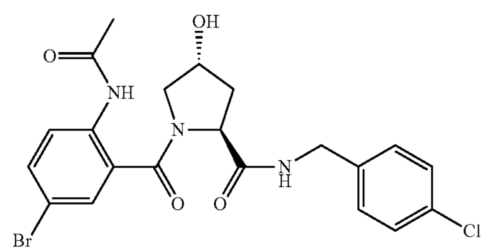 [SMILES: CC(=O)Nc1ccc(Br)cc1C(=O)N1C[C@H](O)C[C@H]1C(=O)NCc1ccc(Cl)cc1] |
| VL084 | 460.3 | | 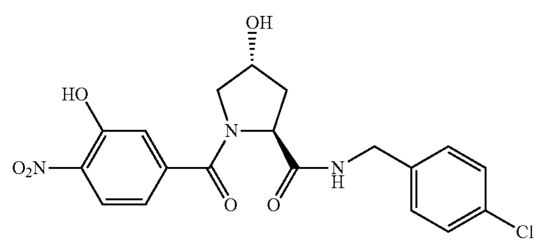 [SMILES: O=C(NCc1ccc(Cl)cc1)[C@@H]1C[C@@H](O)CN1C(=O)c1ccc([N+](=O)[O-])c(O)c1] |
| VL085 | 27.1 | | 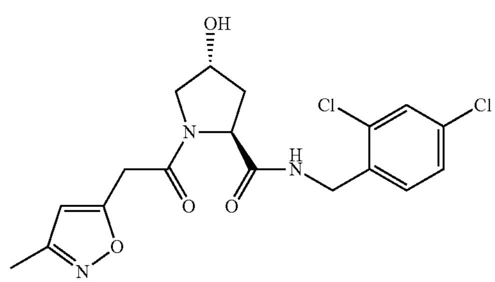 [SMILES: Cc1cc(CC(=O)N2C[C@H](O)C[C@H]2C(=O)NCc2ccc(Cl)cc2Cl)on1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL086 | 168.4 | | 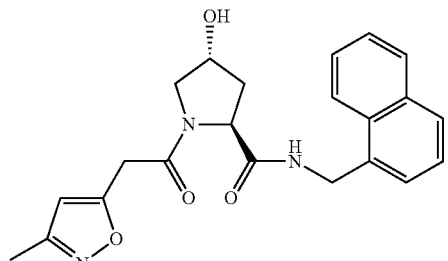 |
| VL087 | 102.6 | | 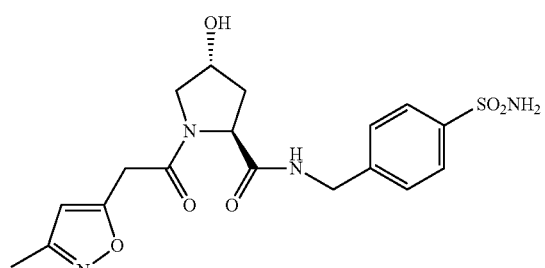 |
| VL088 | 18.2 | 60 | 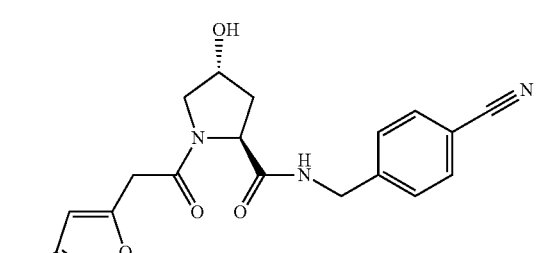 |
| VL089 | 40.8 | | 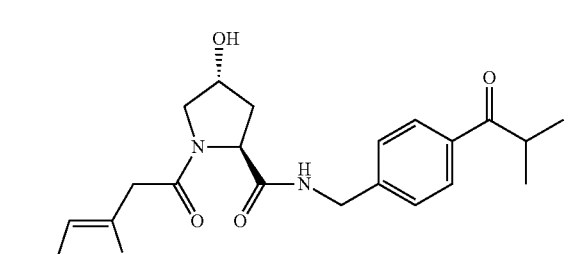 |
| VL090 | 45.2 | | 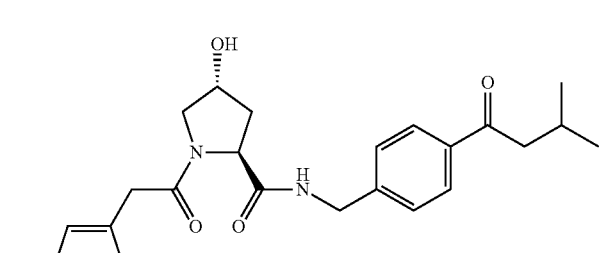 |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL091 | 23.0 | | 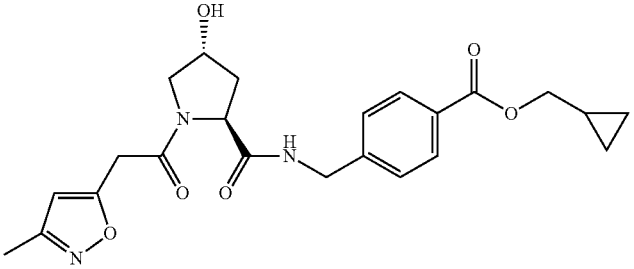 [SMILES: Cc1cc(CC(=O)N2C[C@H](O)C[C@H]2C(=O)NCc2ccc(C(=O)OCC3CC3)cc2)on1] |
| VL093 | 510 | | 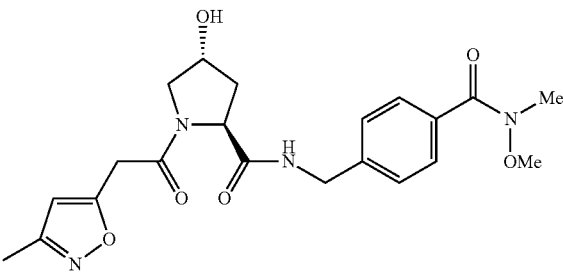 [SMILES: CON(C)C(=O)c1ccc(CNC(=O)[C@@H]2C[C@@H](O)CN2C(=O)Cc2cc(C)no2)cc1] |
| VL094 | 540 | | 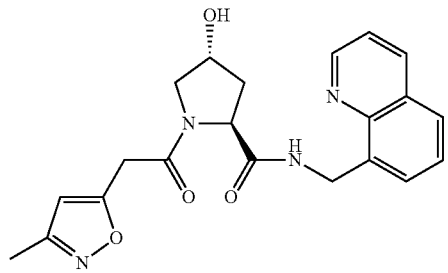 [SMILES: Cc1cc(CC(=O)N2C[C@H](O)C[C@H]2C(=O)NCc2cccc3cccnc23)on1] |
| VL095 | 14.8 | 22.6 | 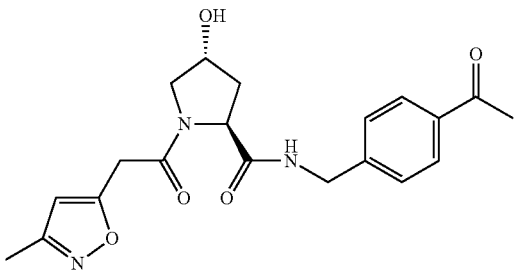 [SMILES: CC(=O)c1ccc(CNC(=O)[C@@H]2C[C@@H](O)CN2C(=O)Cc2cc(C)no2)cc1] |
| VL096 | 32.5 | | 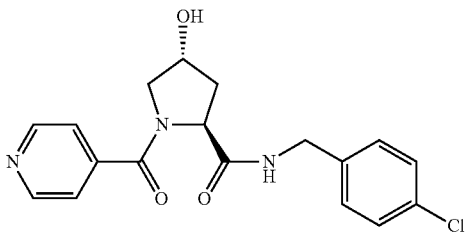 [SMILES: O=C(NCc1ccc(Cl)cc1)[C@@H]1C[C@@H](O)CN1C(=O)c1ccncc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL097 | 49.4 | | 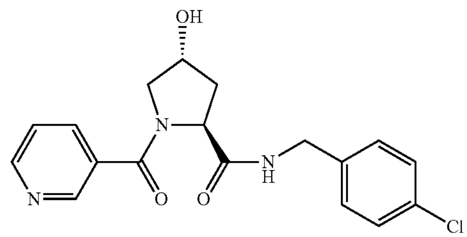 [SMILES: O=C(NCc1ccc(Cl)cc1)[C@@H]1C[C@@H](O)CN1C(=O)c1cccnc1] |
| VL098 | 244.4 | | 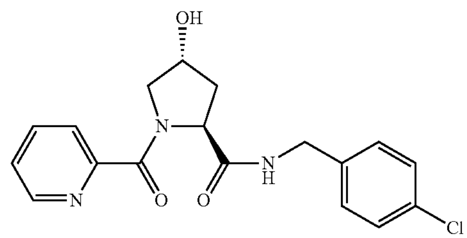 [SMILES: O=C(NCc1ccc(Cl)cc1)[C@@H]1C[C@@H](O)CN1C(=O)c1ccccn1] |
| VL099 | 39.6 | | 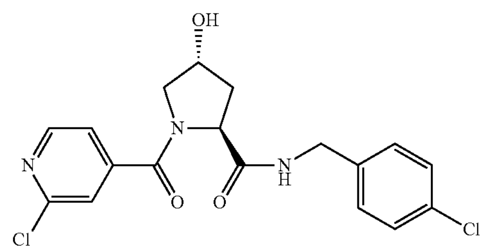 [SMILES: O=C(NCc1ccc(Cl)cc1)[C@@H]1C[C@@H](O)CN1C(=O)c1ccnc(Cl)c1] |
| VL100 | 63.6 | | 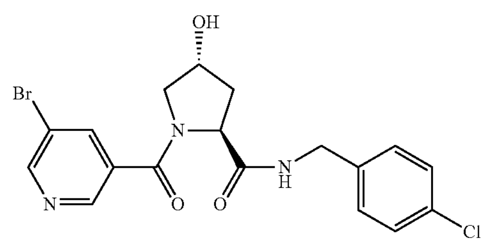 [SMILES: O=C(NCc1ccc(Cl)cc1)[C@@H]1C[C@@H](O)CN1C(=O)c1cncc(Br)c1] |
| VL101 | 940 | | 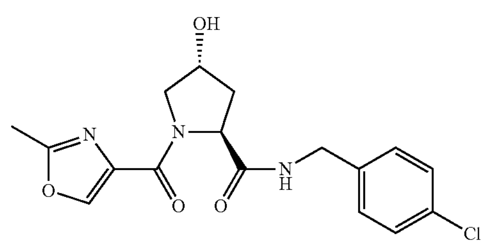 [SMILES: Cc1nc(C(=O)N2C[C@H](O)C[C@H]2C(=O)NCc2ccc(Cl)cc2)co1] |
| VL102 | 64.5 | | 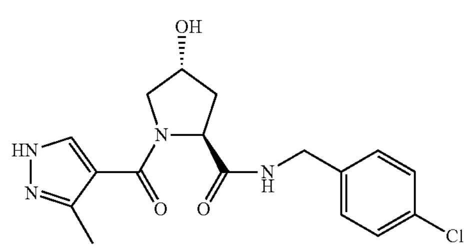 [SMILES: Cc1n[nH]cc1C(=O)N1C[C@H](O)C[C@H]1C(=O)NCc1ccc(Cl)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL104 | >1000 | | 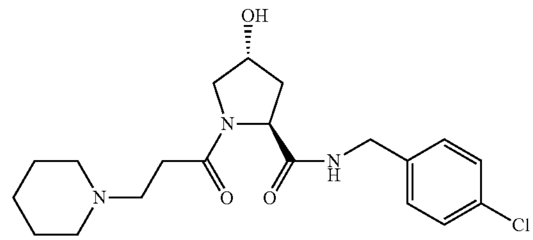 [SMILES: O=C(NCc1ccc(Cl)cc1)[C@@H]1C[C@@H](O)CN1C(=O)CCN1CCCCC1] |
| VL105 | >1000 | | 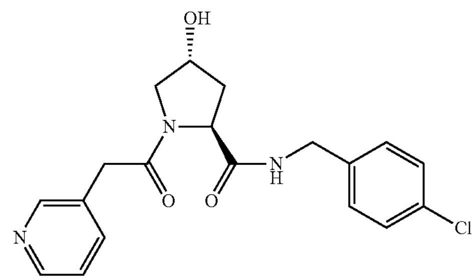 [SMILES: O=C(NCc1ccc(Cl)cc1)[C@@H]1C[C@@H](O)CN1C(=O)Cc1cccnc1] |
| VL106 | >1000 | | 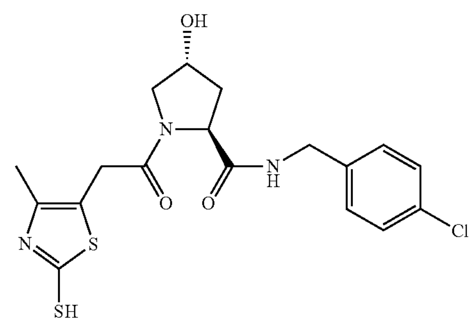 [SMILES: Cc1nc(S)sc1CC(=O)N1C[C@H](O)C[C@H]1C(=O)NCc1ccc(Cl)cc1] |
| VL108 | 347.2 | | 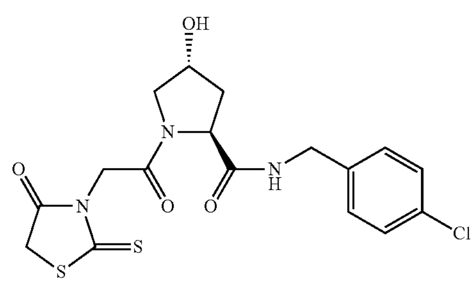 [SMILES: O=C(NCc1ccc(Cl)cc1)[C@@H]1C[C@@H](O)CN1C(=O)CN1C(=O)CSC1=S] |
| VL109 | 349.0 | | 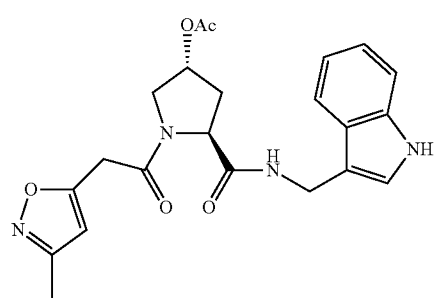 [SMILES: CC(=O)O[C@@H]1C[C@@H](C(=O)NCc2c[nH]c3ccccc23)N(C(=O)Cc2cc(C)no2)C1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
| --- | --- | --- | --- |
| VL110 | 138.0 | | 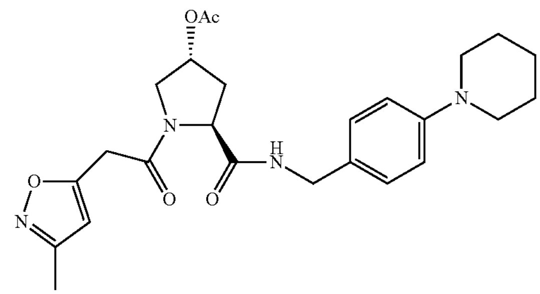 [SMILES: CC(=O)O[C@@H]1C[C@@H](C(=O)NCc2ccc(N3CCCCC3)cc2)N(C(=O)Cc2cc(C)no2)C1] |
| VL111 | 4.1 | 4.1 | 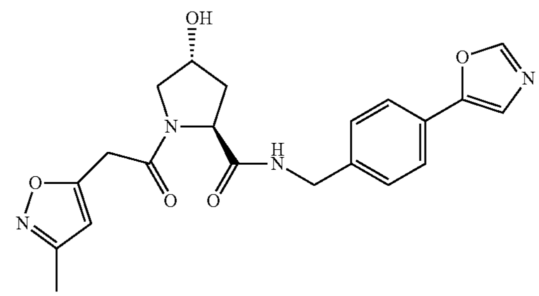 |
| VL112 | 11.3 | | 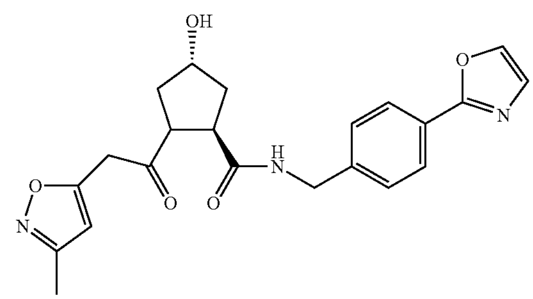 [SMILES: Cc1cc(CC(=O)C2C[C@H](O)C[C@H]2C(=O)NCc2ccc(-c3ncco3)cc2)on1] |
| VL113 | Inactive | Inactive | 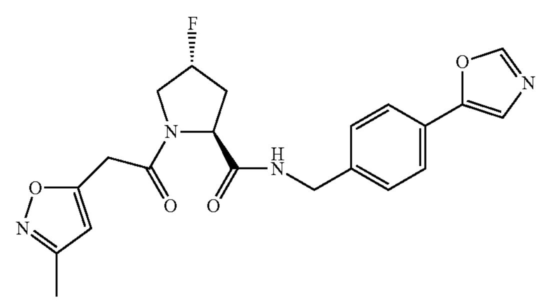 [SMILES: Cc1cc(CC(=O)N2C[C@H](F)C[C@H]2C(=O)NCc2ccc(-c3cnco3)cc2)on1] |
| VL114 | Inactive | Inactive | 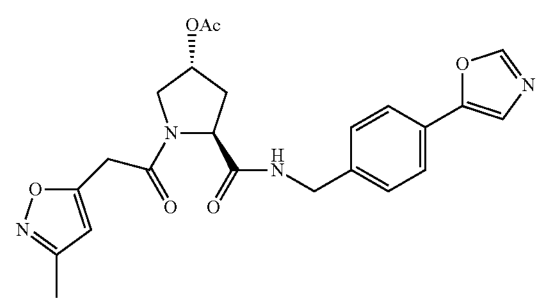 [SMILES: CC(=O)O[C@@H]1C[C@@H](C(=O)NCc2ccc(-c3cnco3)cc2)N(C(=O)Cc2cc(C)no2)C1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL115 | 17.0 | 19 | 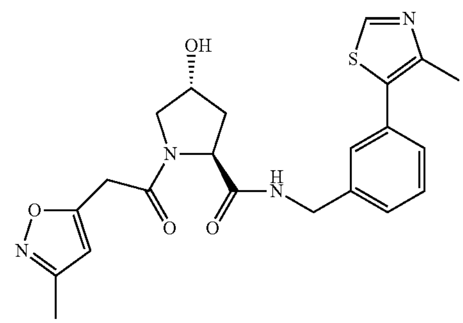 [SMILES: Cc1cc(CC(=O)N2C[C@H](O)C[C@H]2C(=O)NCc2cccc(-c3scnc3C)c2)on1] |
| VL116 | 2.9 | 2.9 | 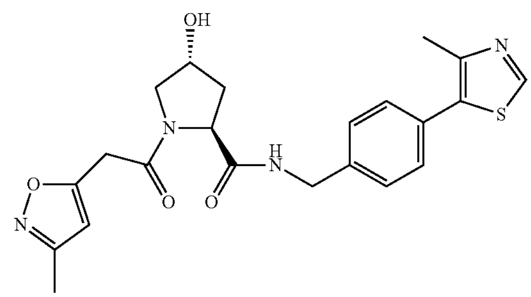 |
| VL117 | 5.0 | 13 | 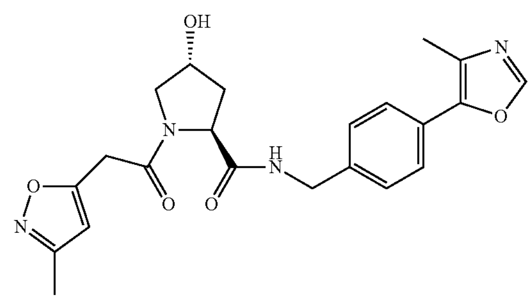 [SMILES: Cc1cc(CC(=O)N2C[C@H](O)C[C@H]2C(=O)NCc2ccc(-c3ocnc3C)cc2)on1] |
| VL118 | 16.4 | 31 | 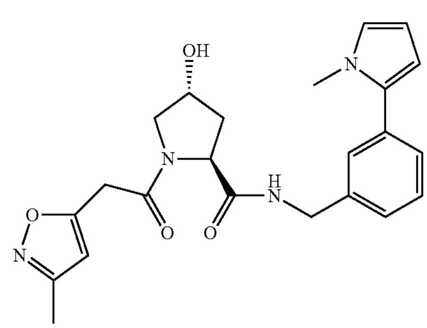 [SMILES: Cc1cc(CC(=O)N2C[C@H](O)C[C@H]2C(=O)NCc2cccc(-c3cccn3C)c2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL119 | 17.8 | 33 | 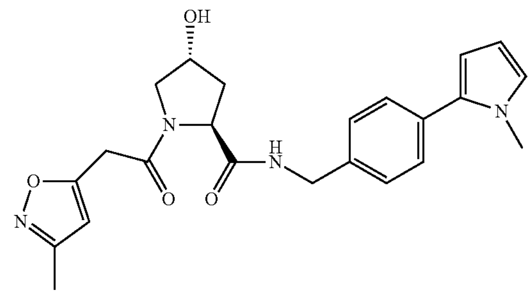 [SMILES: Cc1cc(CC(=O)N2C[C@H](O)C[C@H]2C(=O)NCc2ccc(-c3cccn3C)cc2)on1] |
| VL120 | >1000 | >1000 | 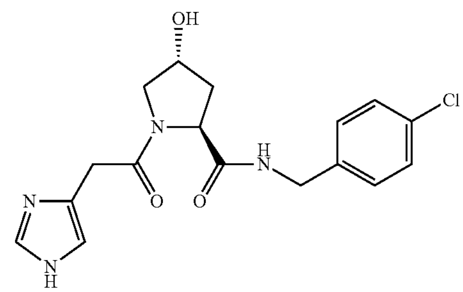 [SMILES: O=C(NCc1ccc(Cl)cc1)[C@@H]1C[C@@H](O)CN1C(=O)Cc1c[nH]cn1] |
| VL121 | >1000 | >1000 | 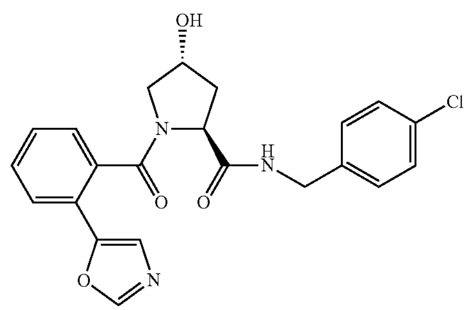 [SMILES: O=C(NCc1ccc(Cl)cc1)[C@@H]1C[C@@H](O)CN1C(=O)c1ccccc1-c1cnco1] |
| VL122 | 102.1 | 220 | 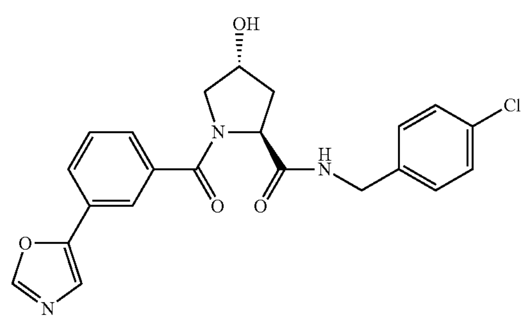 [SMILES: O=C(NCc1ccc(Cl)cc1)[C@@H]1C[C@@H](O)CN1C(=O)c1cccc(-c2cnco2)c1] |
| VL123 | 560 | 404 | 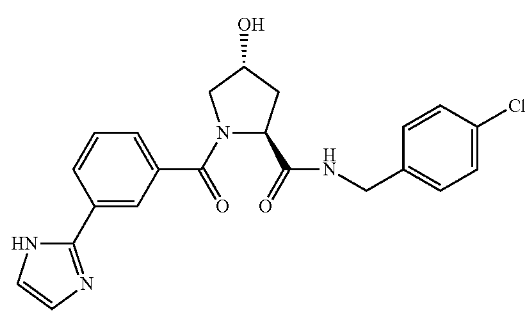 [SMILES: O=C(NCc1ccc(Cl)cc1)[C@@H]1C[C@@H](O)CN1C(=O)c1cccc(-c2ncc[nH]2)c1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL124 | 990 | 670 | 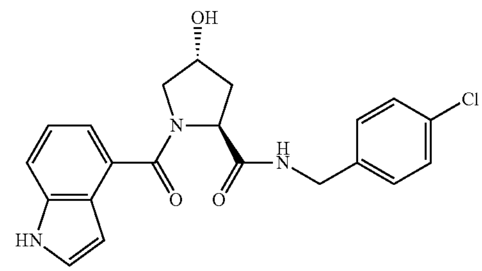 |
| VL125 | 790 | 568 | 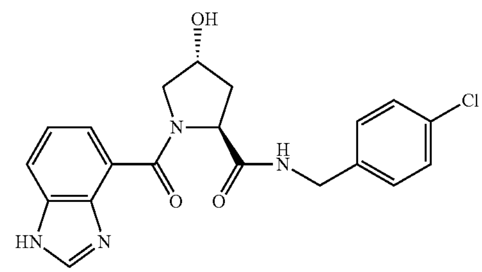 [SMILES: O=C(NCc1ccc(Cl)cc1)[C@@H]1C[C@@H](O)CN1C(=O)c1cccc2[nH]ccc12] |
| VL126 | 88.1 | 82 | 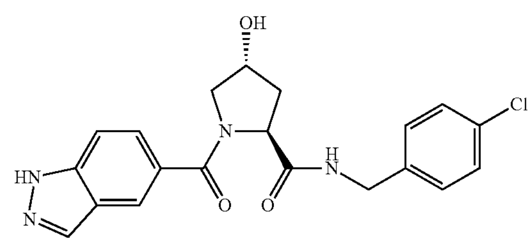 [SMILES: O=C(NCc1ccc(Cl)cc1)[C@@H]1C[C@@H](O)CN1C(=O)c1ccc2[nH]ncc2c1] |
| VL127 | 47.7 | 73 | 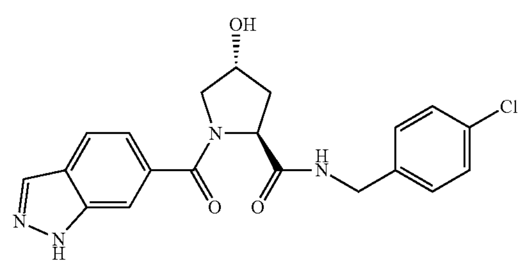 [SMILES: O=C(NCc1ccc(Cl)cc1)[C@@H]1C[C@@H](O)CN1C(=O)c1ccc2cn[nH]c2c1] |
| VL128 | 57.9 | 224 | 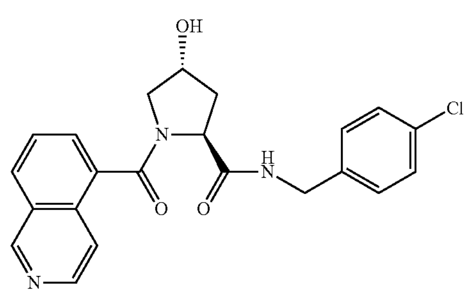 [SMILES: O=C(NCc1ccc(Cl)cc1)[C@@H]1C[C@@H](O)CN1C(=O)c1cccc2cnccc12] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL129 | 760 | 493 | 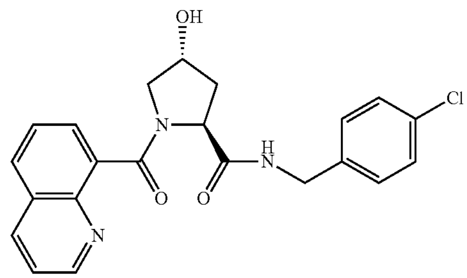 [SMILES: O=C(NCc1ccc(Cl)cc1)[C@@H]1C[C@@H](O)CN1C(=O)c1cccc2cccnc12] |
| VL130 | >1000 | >1000 | 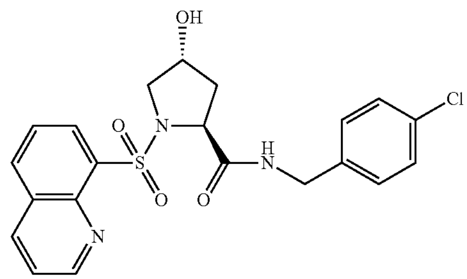 [SMILES: O=C(NCc1ccc(Cl)cc1)[C@@H]1C[C@@H](O)CN1S(=O)(=O)c1cccc2cccnc12] |
| VL131 | 8.0 | 19 | 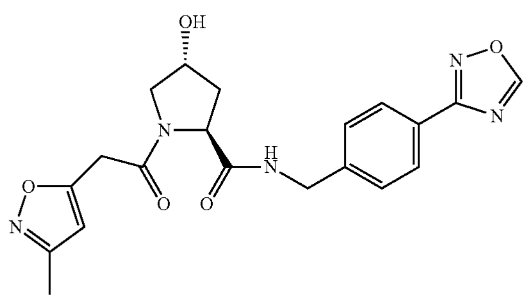 [SMILES: Cc1cc(CC(=O)N2C[C@H](O)C[C@H]2C(=O)NCc2ccc(-c3ncon3)cc2)on1] |
| VL132 | 77.7 | 85 | 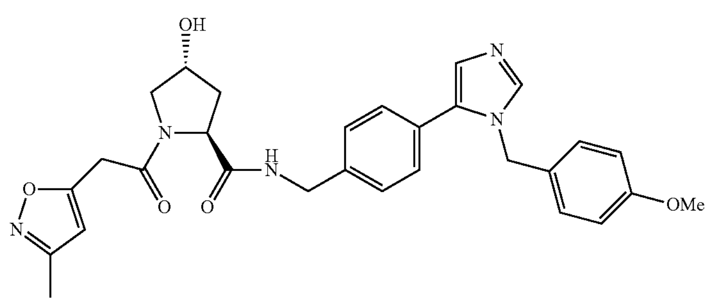 [SMILES: COc1ccc(Cn2cncc2-c2ccc(CNC(=O)[C@@H]3C[C@@H](O)CN3C(=O)Cc3cc(C)no3)cc2)cc1] |
| VL133 | 2.2 | 7.5 | 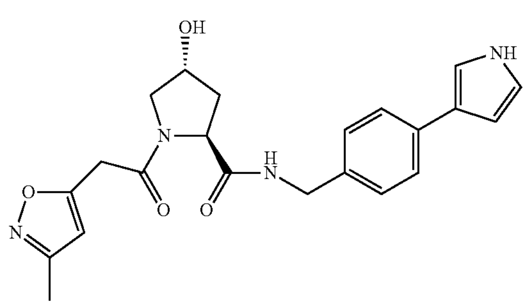 [SMILES: Cc1cc(CC(=O)N2C[C@H](O)C[C@H]2C(=O)NCc2ccc(-c3cc[nH]c3)cc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL134 | 48.1 | 54 | 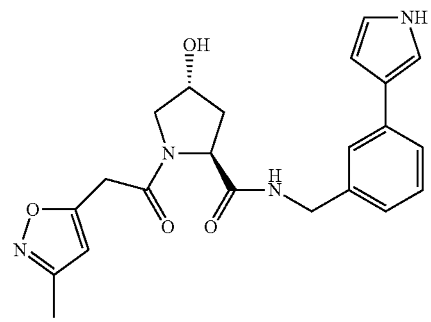 [SMILES: Cc1cc(CC(=O)N2C[C@H](O)C[C@H]2C(=O)NCc2cccc(-c3cc[nH]c3)c2)on1] |
| VL135 | Inactive | >1000 | 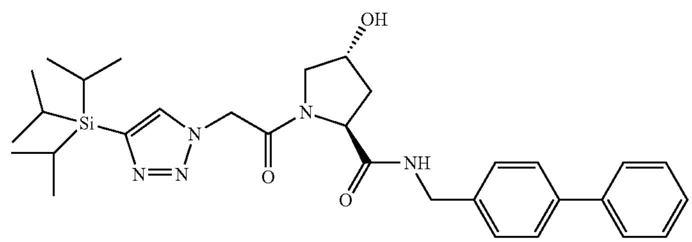 [SMILES: CC(C)[Si](c1cn(CC(=O)N2C[C@H](O)C[C@H]2C(=O)NCc2ccc(-c3ccccc3)cc2)nn1)(C(C)C)C(C)C] |
| VL136 | 28.2 | 540 | 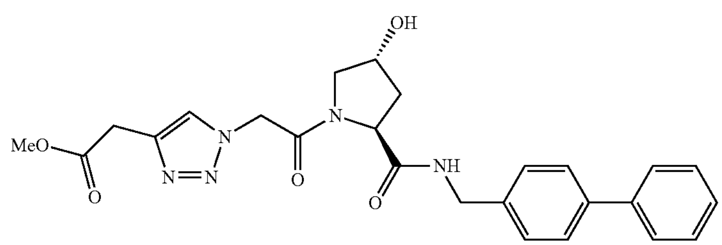 [SMILES: COC(=O)Cc1cn(CC(=O)N2C[C@H](O)C[C@H]2C(=O)NCc2ccc(-c3ccccc3)cc2)nn1] |
| VL137 | 35.6 | 128 | 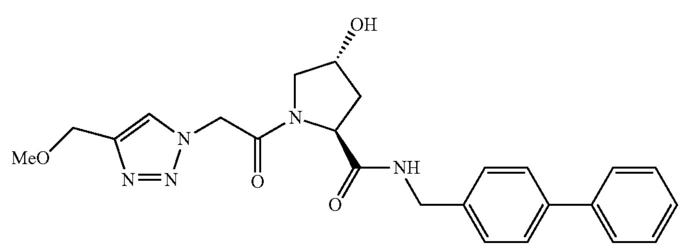 [SMILES: COCc1cn(CC(=O)N2C[C@H](O)C[C@H]2C(=O)NCc2ccc(-c3ccccc3)cc2)nn1] |
| VL138 | 52.2 | 70 | 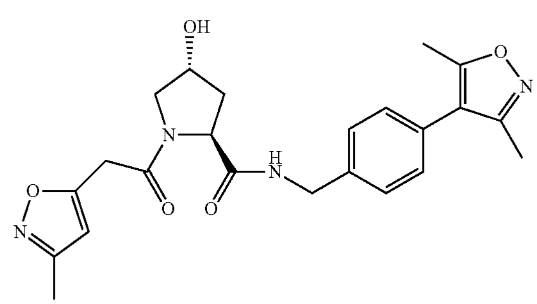 [SMILES: Cc1cc(CC(=O)N2C[C@H](O)C[C@H]2C(=O)NCc2ccc(-c3c(C)noc3C)cc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL139 | 24.7 | 44 | 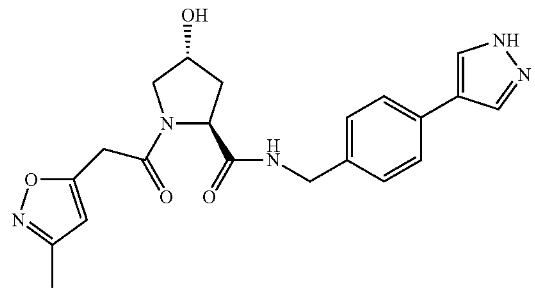 [SMILES: Cc1cc(CC(=O)N2C[C@H](O)C[C@H]2C(=O)NCc2ccc(-c3cn[nH]c3)cc2)on1] |
| VL140 | 10.3 | 17 | 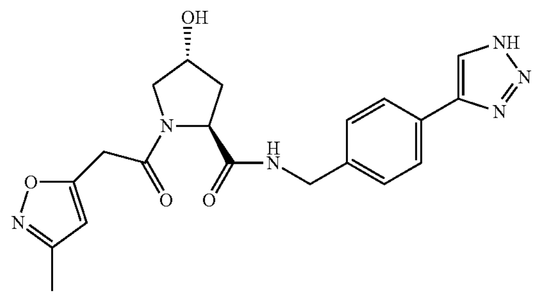 [SMILES: Cc1cc(CC(=O)N2C[C@H](O)C[C@H]2C(=O)NCc2ccc(-c3c[nH]nn3)cc2)on1] |
| VL141 | 191.8 | 220 | 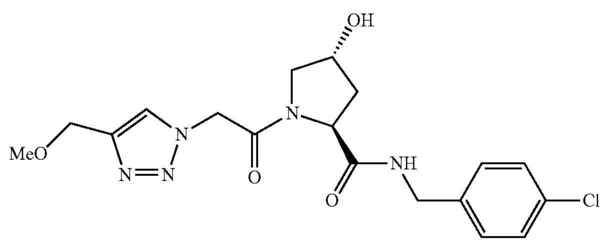 [SMILES: COCc1cn(CC(=O)N2C[C@H](O)C[C@H]2C(=O)NCc2ccc(Cl)cc2)nn1] |
| VL142 | 780 | >1000 | 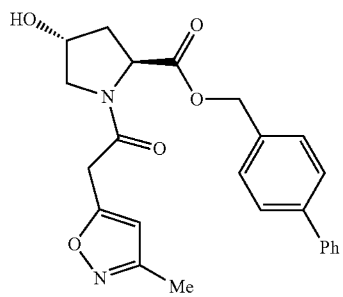 [SMILES: Cc1cc(CC(=O)N2C[C@H](O)C[C@H]2C(=O)OCc2ccc(-c3ccccc3)cc2)on1] |
| VL143 | >1000 | >1000 | 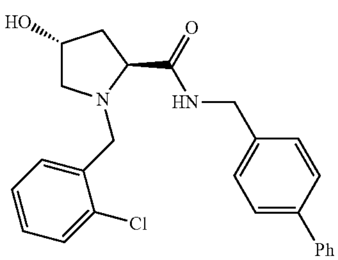 [SMILES: O=C(NCc1ccc(-c2ccccc2)cc1)[C@@H]1C[C@@H](O)CN1Cc1ccccc1Cl] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL144 | >1000 | >1000 | 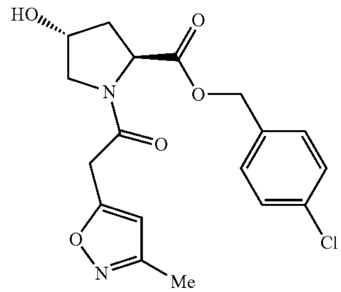 [SMILES: Cc1cc(CC(=O)N2C[C@H](O)C[C@H]2C(=O)OCc2ccc(Cl)cc2)on1] |
| VL145 | >1000 | >1000 | 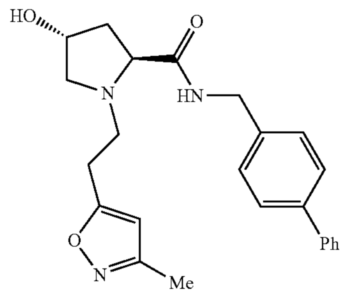 [SMILES: Cc1cc(CCN2C[C@H](O)C[C@H]2C(=O)NCc2ccc(-c3ccccc3)cc2)on1] |
| VL146 | 128.9 | 196 | 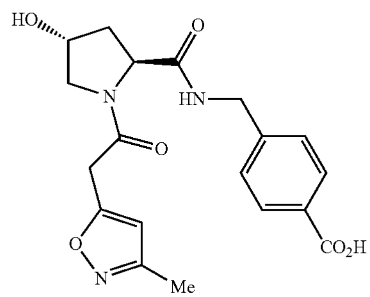 [SMILES: Cc1cc(CC(=O)N2C[C@H](O)C[C@H]2C(=O)NCc2ccc(C(=O)O)cc2)on1] |
| VL147 | >1000 | >1000 | 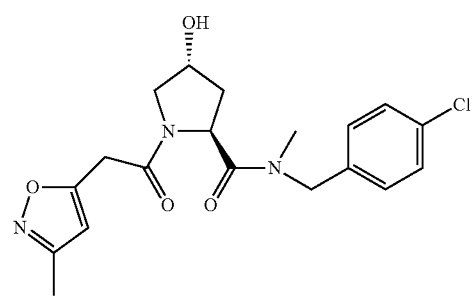 [SMILES: Cc1cc(CC(=O)N2C[C@H](O)C[C@H]2C(=O)N(C)Cc2ccc(Cl)cc2)on1] |
| VL148 | 23.8 | 113 | 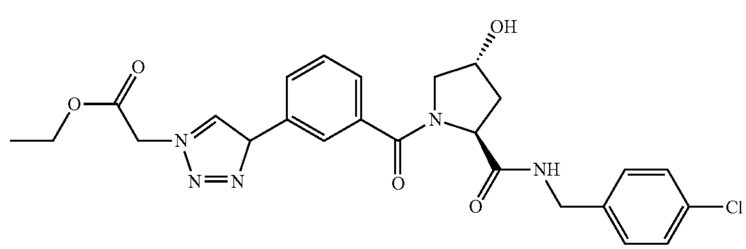 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
| --- | --- | --- | --- |
| VL149 | | | 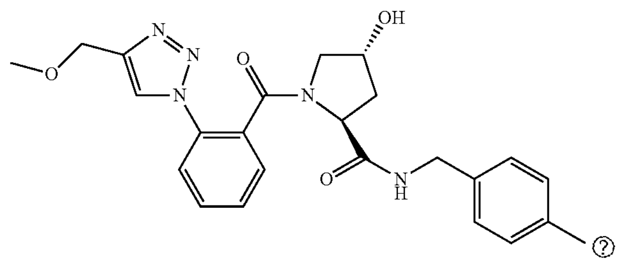 |
| VL150 | 16.0 | 41 | 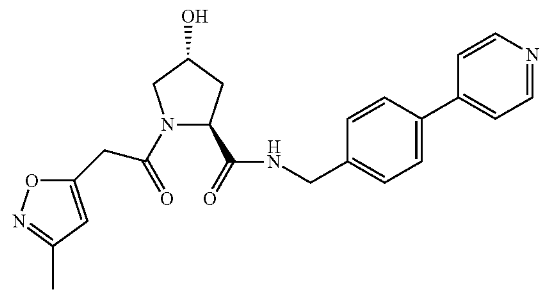 [SMILES: Cc1cc(CC(=O)N2C[C@H](O)C[C@H]2C(=O)NCc2ccc(-c3ccncc3)cc2)on1] |
| VL151 | 11 | 33 | 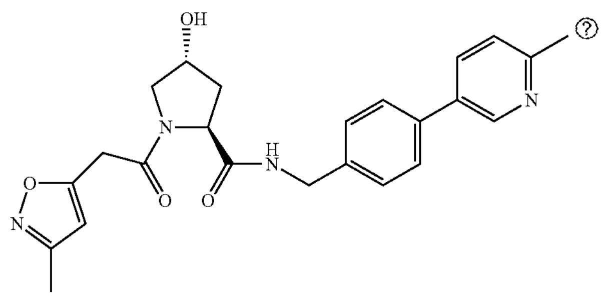 [SMILES: Cc1ccc(-c2ccc(CNC(=O)[C@@H]3C[C@@H](O)CN3C(=O)Cc3cc(C)no3)cc2)cn1] |
| VL152 | 22.8 | 32 | 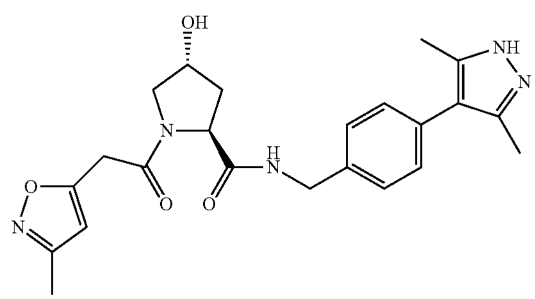 [SMILES: Cc1cc(CC(=O)N2C[C@H](O)C[C@H]2C(=O)NCc2ccc(-c3c(C)n[nH]c3C)cc2)on1] |
| VL153 | 978.3 | | 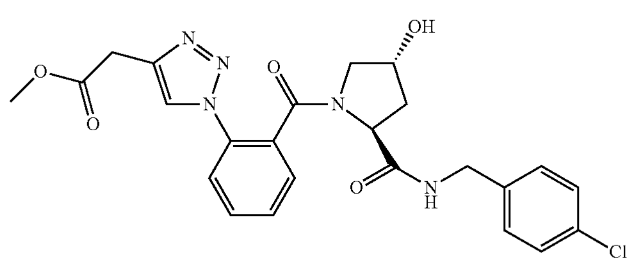 [SMILES: COC(=O)Cc1cn(-c2ccccc2C(=O)N2C[C@H](O)C[C@H]2C(=O)NCc2ccc(Cl)cc2)nn1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
| --- | --- | --- | --- |
| VL154 | 118.3 | 77 | 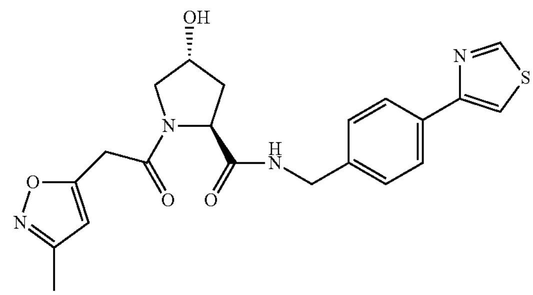 [SMILES: Cc1cc(CC(=O)N2C[C@H](O)C[C@H]2C(=O)NCc2ccc(-c3cscn3)cc2)on1] |
| VL155 | 17.4 | 14 | 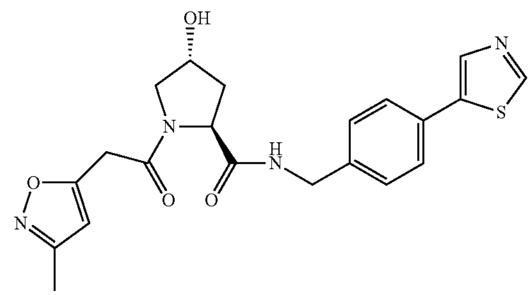 [SMILES: Cc1cc(CC(=O)N2C[C@H](O)C[C@H]2C(=O)NCc2ccc(-c3cncs3)cc2)on1] |
| VL156 | >1000 | >1000 | 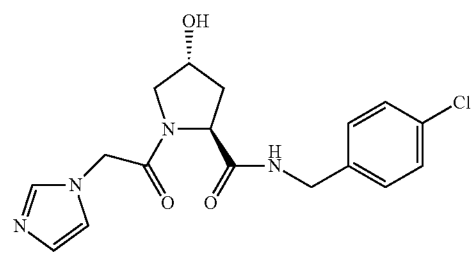 [SMILES: O=C(NCc1ccc(Cl)cc1)[C@@H]1C[C@@H](O)CN1C(=O)Cn1ccnc1] |
| VL157 | 371.7 | 360 | 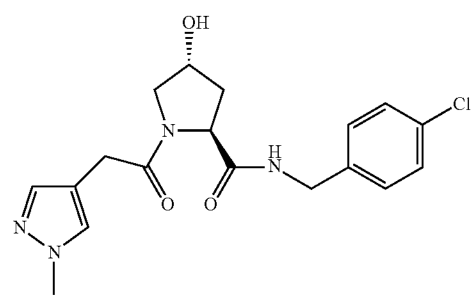 [SMILES: Cn1cc(CC(=O)N2C[C@H](O)C[C@H]2C(=O)NCc2ccc(Cl)cc2)cn1] |
| VL158 | 265.8 | 180 | 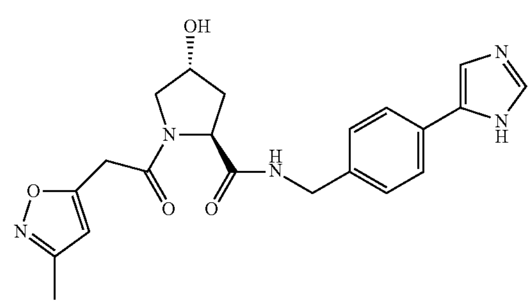 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
| --- | --- | --- | --- |
| VL159 | 66.9 | 54 | 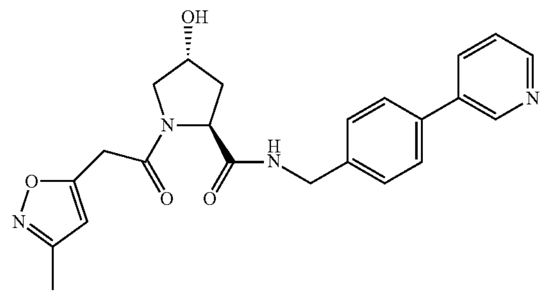 [SMILES: Cc1cc(CC(=O)N2C[C@H](O)C[C@H]2C(=O)NCc2ccc(-c3cccnc3)cc2)on1] |
| VL160 | 12.1 | 9 | 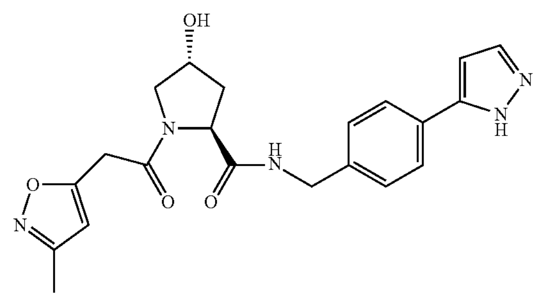 [SMILES: Cc1cc(CC(=O)N2C[C@H](O)C[C@H]2C(=O)NCc2ccc(-c3ccn[nH]3)cc2)on1] |
| VL161 | 36.4 | 35 | 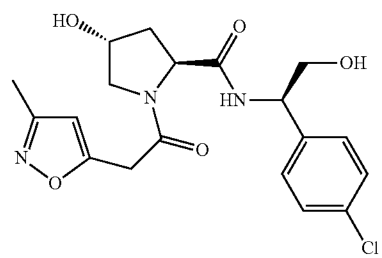 [SMILES: Cc1cc(CC(=O)N2C[C@H](O)C[C@H]2C(=O)N[C@@H](CO)c2ccc(Cl)cc2)on1] |
| VL162 | 235.4 | 250 | 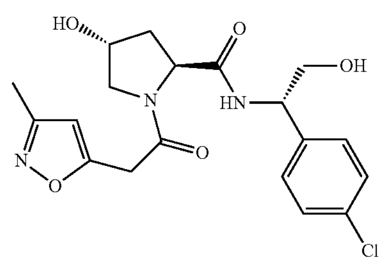 [SMILES: Cc1cc(CC(=O)N2C[C@H](O)C[C@H]2C(=O)N[C@H](CO)c2ccc(Cl)cc2)on1] |
| VL163 | 507.5 | 610 | 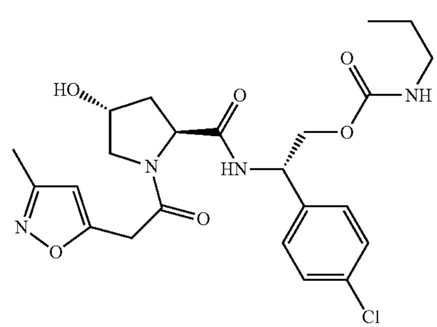 [SMILES: CCCNC(=O)OC[C@@H](NC(=O)[C@@H]1C[C@@H](O)CN1C(=O)Cc1cc(C)no1)c1ccc(Cl)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL164 | 72.9 | 40 | 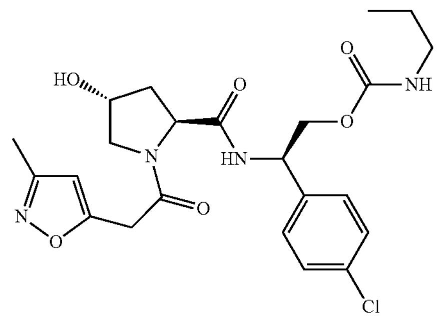 [SMILES: CCCNC(=O)OC[C@H](NC(=O)[C@@H]1C[C@@H](O)CN1C(=O)Cc1cc(C)no1)c1ccc(Cl)cc1] |
| VL165 | | | 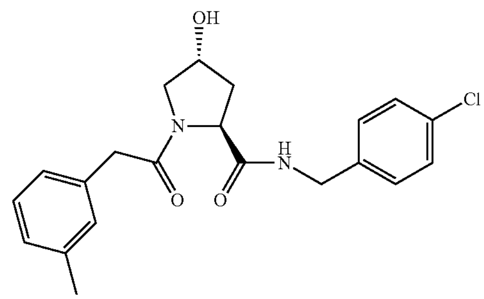 [SMILES: Cc1cccc(CC(=O)N2C[C@H](O)C[C@H]2C(=O)NCc2ccc(Cl)cc2)c1] |
| VL166 | | | 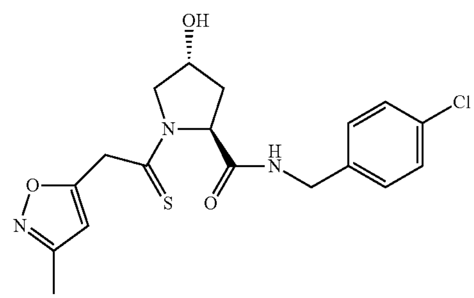 [SMILES: Cc1cc(CC(=S)N2C[C@H](O)C[C@H]2C(=O)NCc2ccc(Cl)cc2)on1] |
| VL167 | | | 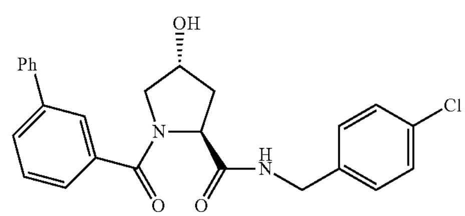 [SMILES: O=C(NCc1ccc(Cl)cc1)[C@@H]1C[C@@H](O)CN1C(=O)c1cccc(-c2ccccc2)c1] |
| VL168 | | | 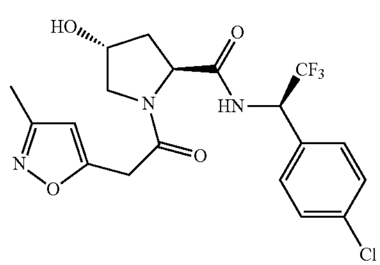 [SMILES: Cc1cc(CC(=O)N2C[C@H](O)C[C@H]2C(=O)N[C@H](c2ccc(Cl)cc2)C(F)(F)F)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL169 | | | 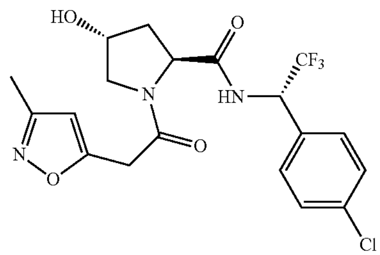 [SMILES: Cc1cc(CC(=O)N2C[C@H](O)C[C@H]2C(=O)N[C@@H](c2ccc(Cl)cc2)C(F)(F)F)on1] |
| VL170 | | | 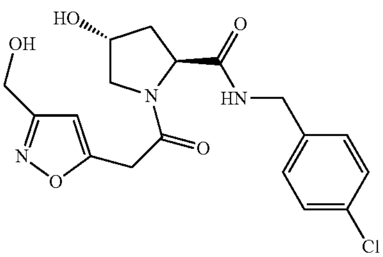 [SMILES: O=C(NCc1ccc(Cl)cc1)[C@@H]1C[C@@H](O)CN1C(=O)Cc1cc(CO)no1] |
| VL171 | | | 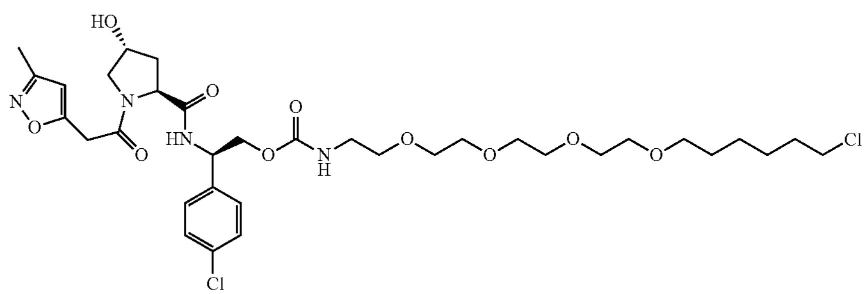 [SMILES: Cc1cc(CC(=O)N2C[C@H](O)C[C@H]2C(=O)N[C@@H](COC(=O)NCCOCCOCCOCCOCCCCCCCl)c2ccc(Cl)cc2)on1] |
| VL172 | | | 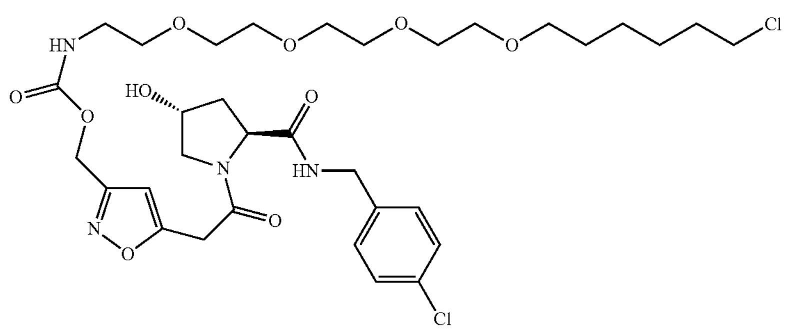 [SMILES: O=C(NCCOCCOCCOCCOCCCCCCCl)OCc1cc(CC(=O)N2C[C@H](O)C[C@H]2C(=O)NCc2ccc(Cl)cc2)on1] |
| VL173 | | | 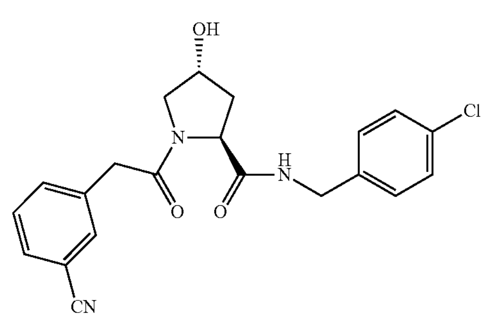 [SMILES: N#Cc1cccc(CC(=O)N2C[C@H](O)C[C@H]2C(=O)NCc2ccc(Cl)cc2)c1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL174 | | | 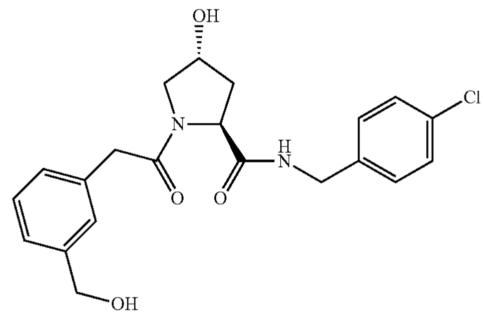 [SMILES: O=C(NCc1ccc(Cl)cc1)[C@@H]1C[C@@H](O)CN1C(=O)Cc1cccc(CO)c1] |
| VL175 | | | 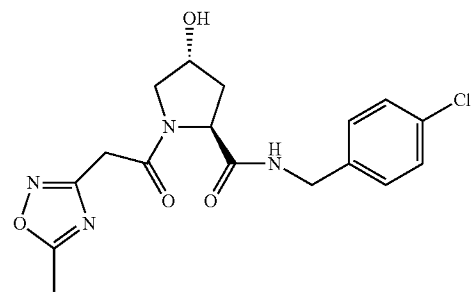 [SMILES: Cc1nc(CC(=O)N2C[C@H](O)C[C@H]2C(=O)NCc2ccc(Cl)cc2)no1] |
| VL176 | | | 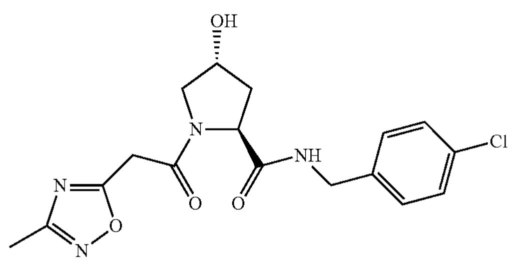 [SMILES: Cc1noc(CC(=O)N2C[C@H](O)C[C@H]2C(=O)NCc2ccc(Cl)cc2)n1] |
| VL177 | | | 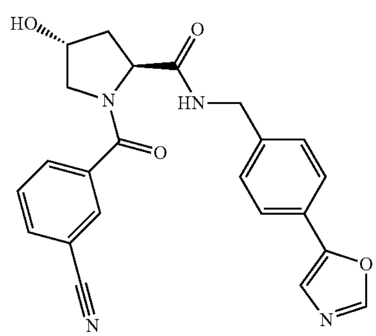 [SMILES: N#Cc1cccc(C(=O)N2C[C@H](O)C[C@H]2C(=O)NCc2ccc(-c3cnco3)cc2)c1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL178 | | | 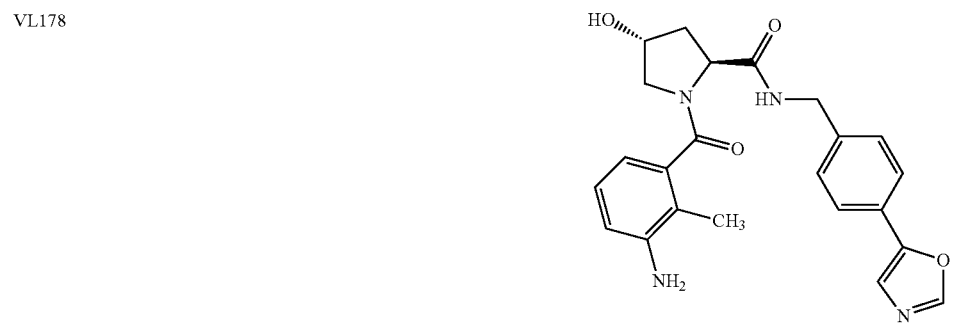 |
| VL179 | | | 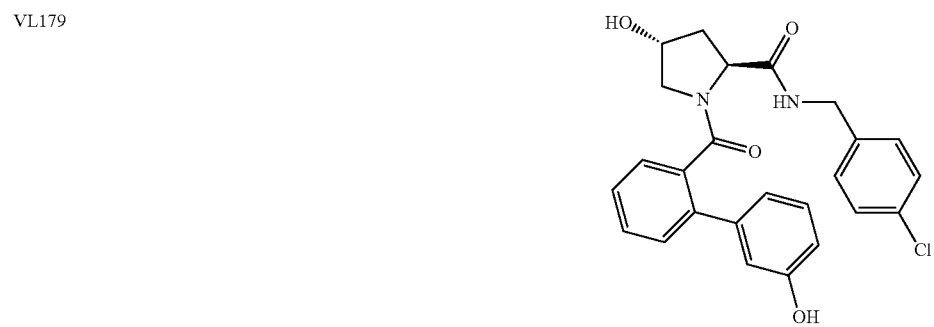 |
| VL180 | | | 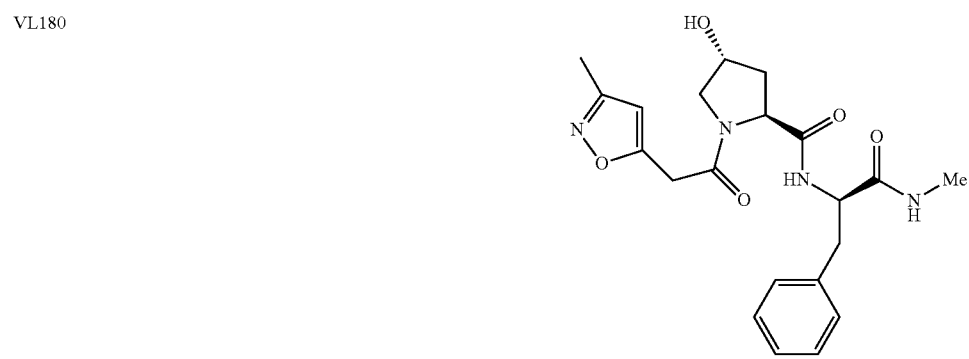 |
| VL181 | | | 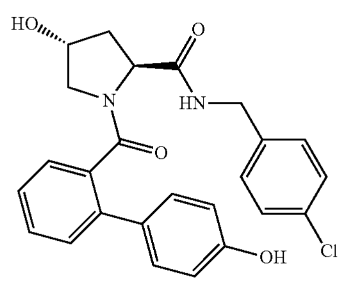 [SMILES: O=C(NCc1ccc(Cl)cc1)[C@@H]1C[C@@H](O)CN1C(=O)c1ccccc1-c1ccc(O)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL183 | | | 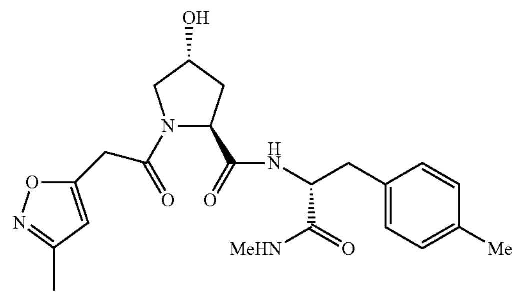 [SMILES: CNC(=O)[C@@H](Cc1ccc(C)cc1)NC(=O)[C@@H]1C[C@@H](O)CN1C(=O)Cc1cc(C)no1] |
| VL184 | | | 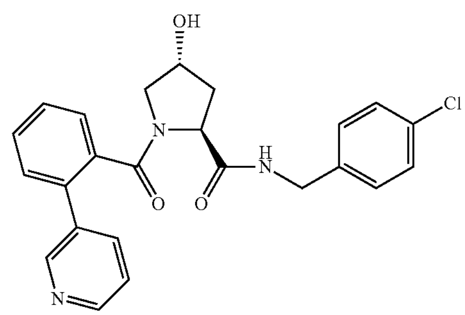 [SMILES: O=C(NCc1ccc(Cl)cc1)[C@@H]1C[C@@H](O)CN1C(=O)c1ccccc1-c1cccnc1] |
| VL185 | | | 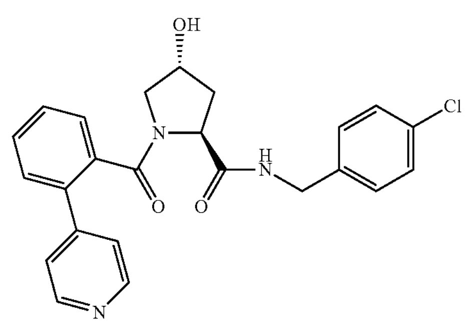 [SMILES: O=C(NCc1ccc(Cl)cc1)[C@@H]1C[C@@H](O)CN1C(=O)c1ccccc1-c1ccncc1] |
| VL186 | | | 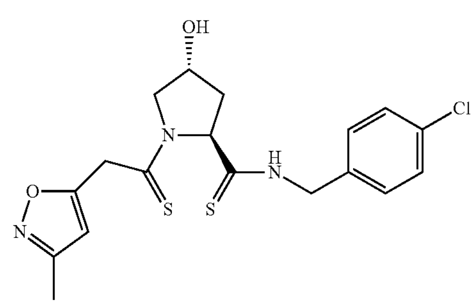 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL187 | | | 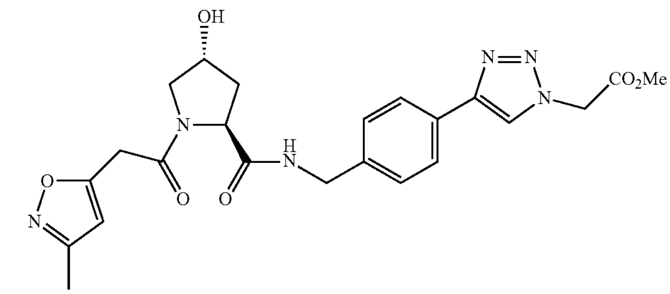 [SMILES: COC(=O)Cn1cc(-c2ccc(CNC(=O)[C@@H]3C[C@@H](O)CN3C(=O)Cc3cc(C)no3)cc2)nn1] |
| VL188 | | | 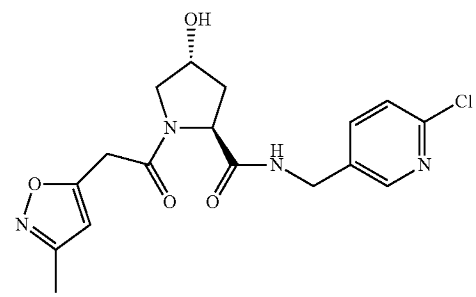 [SMILES: Cc1cc(CC(=O)N2C[C@H](O)C[C@H]2C(=O)NCc2ccc(Cl)nc2)on1] |
| VL189 | | | 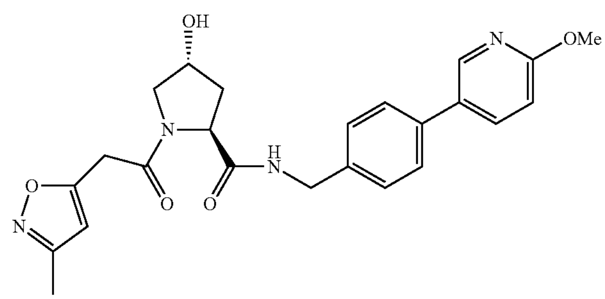 [SMILES: COc1ccc(-c2ccc(CNC(=O)[C@@H]3C[C@@H](O)CN3C(=O)Cc3cc(C)no3)cc2)cn1] |
| VL190 | | | 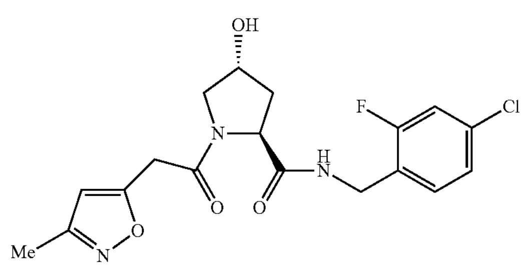 [SMILES: Cc1cc(CC(=O)N2C[C@H](O)C[C@H]2C(=O)NCc2ccc(Cl)cc2F)on1] |
| VL191 | | | 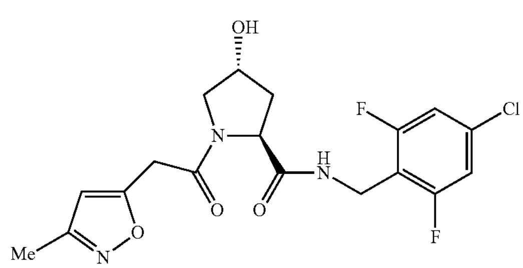 [SMILES: Cc1cc(CC(=O)N2C[C@H](O)C[C@H]2C(=O)NCc2c(F)cc(Cl)cc2F)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL192 | | | 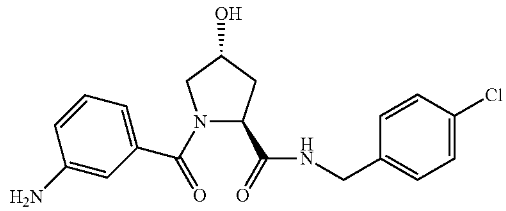 |
| VL193 | | | 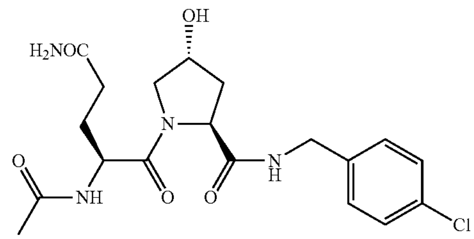 [SMILES: CC(=O)N[C@@H](CCC(N)=O)C(=O)N1C[C@H](O)C[C@H]1C(=O)NCc1ccc(Cl)cc1] |
| VL194 | | | 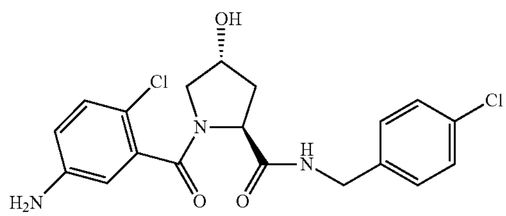 [SMILES: Nc1ccc(Cl)c(C(=O)N2C[C@H](O)C[C@H]2C(=O)NCc2ccc(Cl)cc2)c1] |
| VL195 | | | 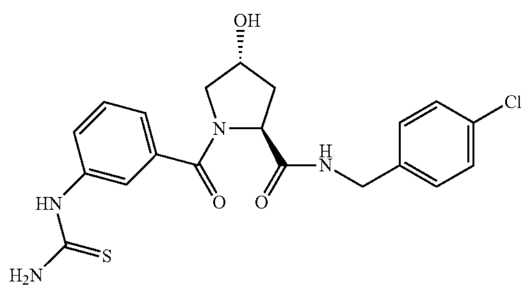 [SMILES: NC(=S)Nc1cccc(C(=O)N2C[C@H](O)C[C@H]2C(=O)NCc2ccc(Cl)cc2)c1] |
| VL196 | | | 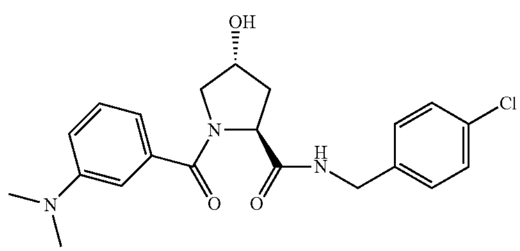 [SMILES: CN(C)c1cccc(C(=O)N2C[C@H](O)C[C@H]2C(=O)NCc2ccc(Cl)cc2)c1] |
| VL197 | | | 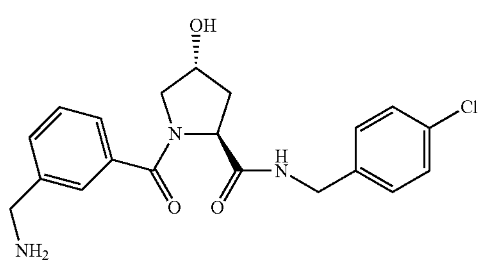 [SMILES: NCc1cccc(C(=O)N2C[C@H](O)C[C@H]2C(=O)NCc2ccc(Cl)cc2)c1] |

TABLE 2-continued
Affinity Table.
(Most compounds showed activity within the range of about 200 µM or lower).
| VHL ligand No. | IC$_{50}$(µM) 10% DMSO | IC$_{50}$(µM) 1% DMSO | Chemical Structure |
|---|---|---|---|
| VL198 | | | 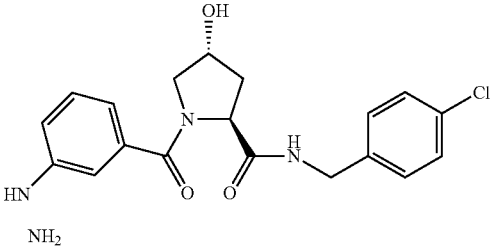 |
| VL199 | | | 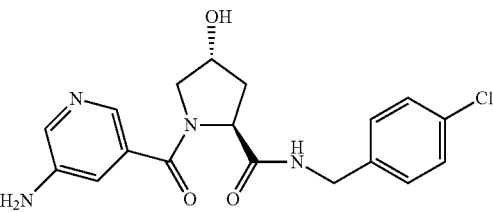 [SMILES: Nc1cncc(C(=O)N2C[C@H](O)C[C@H]2C(=O)NCc2ccc(Cl)cc2)c1] |
| VL200 | | | 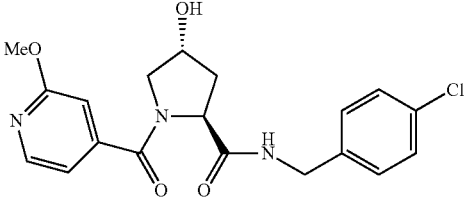 [SMILES: COc1cc(C(=O)N2C[C@H](O)C[C@H]2C(=O)NCc2ccc(Cl)cc2)ccn1] |
| VL201 | | | 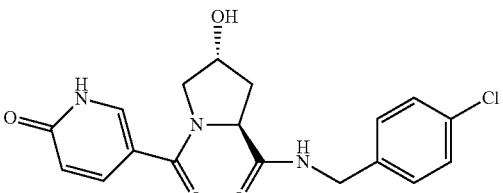 |
| VL202 | | | 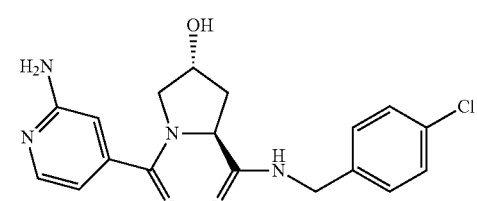 |
| VL203 | | | 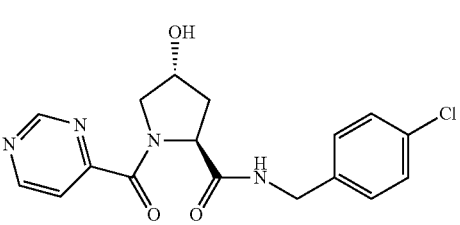 [SMILES: O=C(NCc1ccc(Cl)cc1)[C@@H]1C[C@@H](O)CN1C(=O)c1ccncn1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL204 | | | 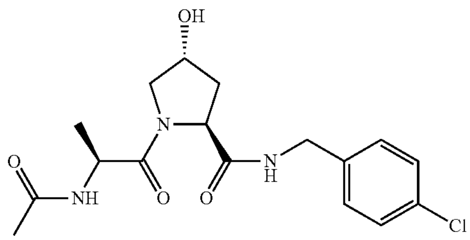 [SMILES: CC(=O)N[C@@H](C)C(=O)N1C[C@H](O)C[C@H]1C(=O)NCc1ccc(Cl)cc1] |
| VL205 | | | 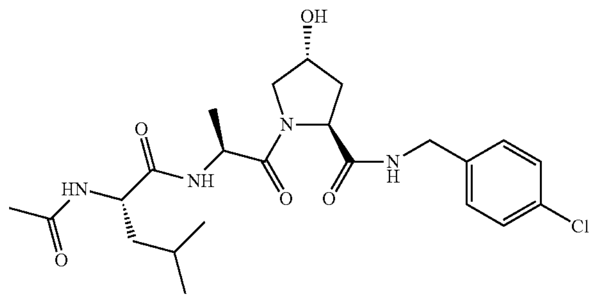 [SMILES: CC(=O)N[C@@H](CC(C)C)C(=O)N[C@@H](C)C(=O)N1C[C@H](O)C[C@H]1C(=O)NCc1ccc(Cl)cc1] |
| VL206 | | | 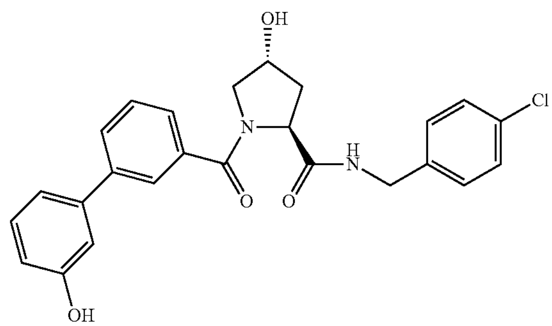 [SMILES: O=C(NCc1ccc(Cl)cc1)[C@@H]1C[C@@H](O)CN1C(=O)c1cccc(-c2cccc(O)c2)c1] |
| VL207 | | | 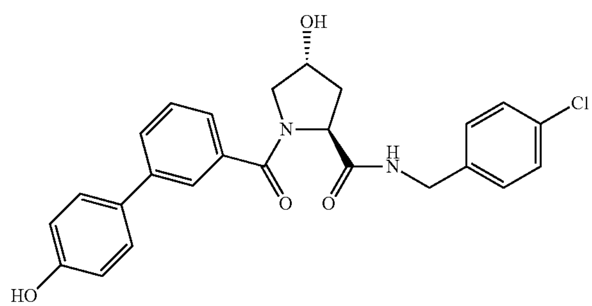 [SMILES: O=C(NCc1ccc(Cl)cc1)[C@@H]1C[C@@H](O)CN1C(=O)c1cccc(-c2ccc(O)cc2)c1] |
| VL208 | | | 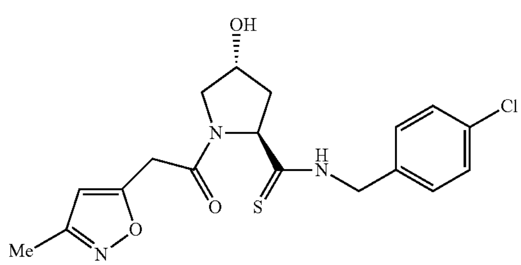 [SMILES: Cc1cc(CC(=O)N2C[C@H](O)C[C@H]2C(=S)NCc2ccc(Cl)cc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL209 | | | 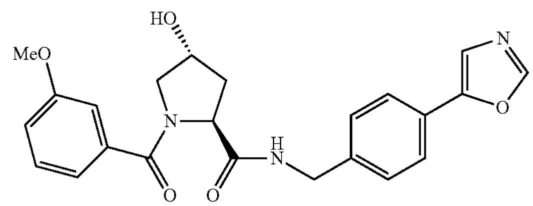 [SMILES: COc1cccc(C(=O)N2C[C@H](O)C[C@H]2C(=O)NCc2ccc(-c3cnco3)cc2)c1] |
| VL210 | | | 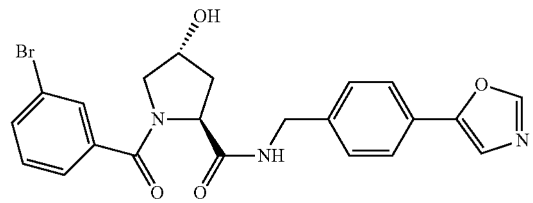 [SMILES: O=C(NCc1ccc(-c2cnco2)cc1)[C@@H]1C[C@@H](O)CN1C(=O)c1cccc(Br)c1] |
| VL211 | | | 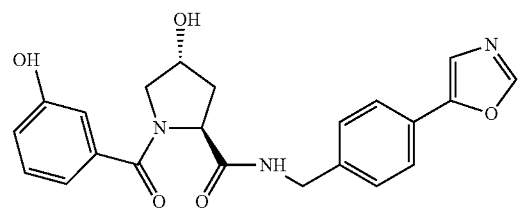 [SMILES: O=C(NCc1ccc(-c2cnco2)cc1)[C@@H]1C[C@@H](O)CN1C(=O)c1cccc(O)c1] |
| VL212 | | | 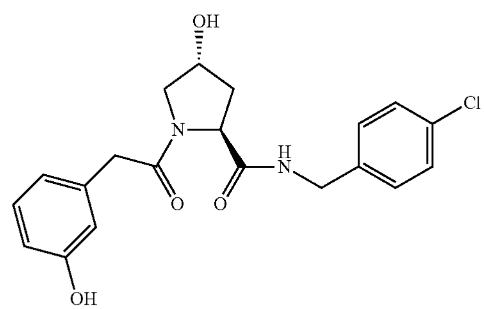 [SMILES: O=C(NCc1ccc(Cl)cc1)[C@@H]1C[C@@H](O)CN1C(=O)Cc1cccc(O)c1] |
| VL213 | | | 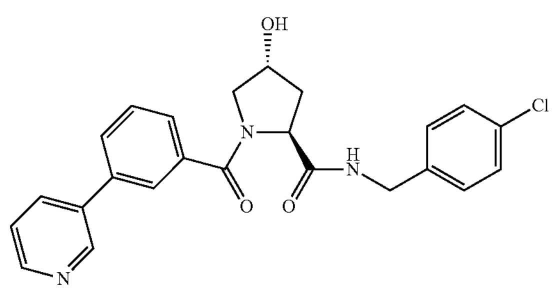 [SMILES: O=C(NCc1ccc(Cl)cc1)[C@@H]1C[C@@H](O)CN1C(=O)c1cccc(-c2cccnc2)c1] |
| VL214 | | | 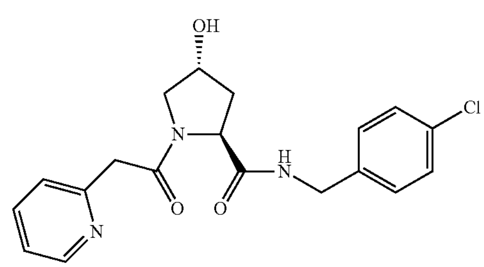 [SMILES: O=C(NCc1ccc(Cl)cc1)[C@@H]1C[C@@H](O)CN1C(=O)Cc1ccccn1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL215 | | | 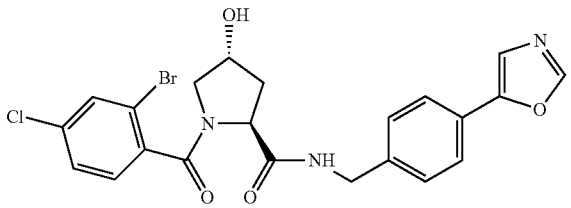 [SMILES: O=C(NCc1ccc(-c2cnco2)cc1)[C@@H]1C[C@@H](O)CN1C(=O)c1ccc(Cl)cc1Br] |
| VL216 | | | 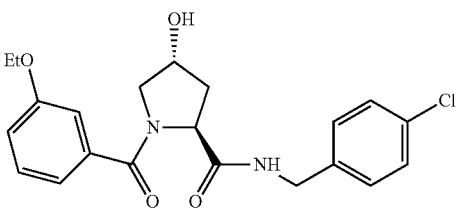 [SMILES: CCOc1cccc(C(=O)N2C[C@H](O)C[C@H]2C(=O)NCc2ccc(Cl)cc2)c1] |
| VL217 | | | 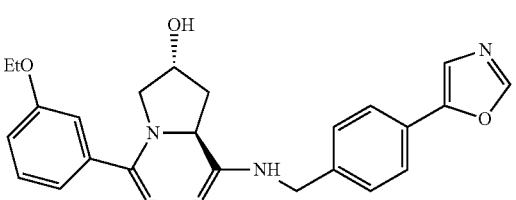 |
| VL218 | | | 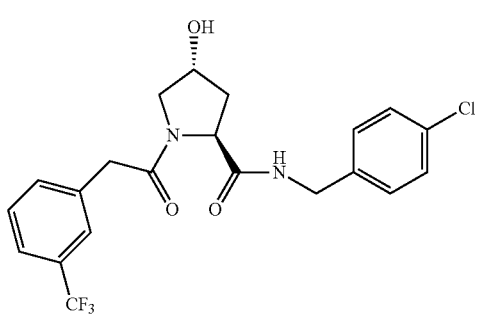 [SMILES: O=C(NCc1ccc(Cl)cc1)[C@@H]1C[C@@H](O)CN1C(=O)Cc1cccc(C(F)(F)F)c1] |
| VL219 | | | 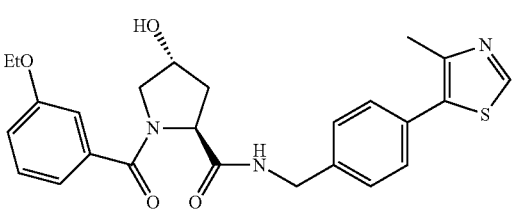 [SMILES: CCOc1cccc(C(=O)N2C[C@H](O)C[C@H]2C(=O)NCc2ccc(-c3scnc3C)cc2)c1] |
| VL220 | | | 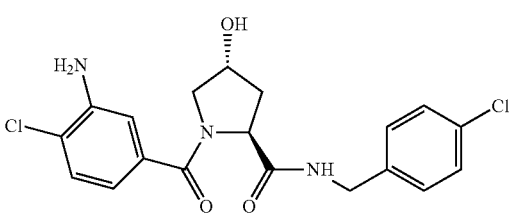 [SMILES: Nc1cc(C(=O)N2C[C@H](O)C[C@H]2C(=O)NCc2ccc(Cl)cc2)ccc1Cl] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL221 | | | 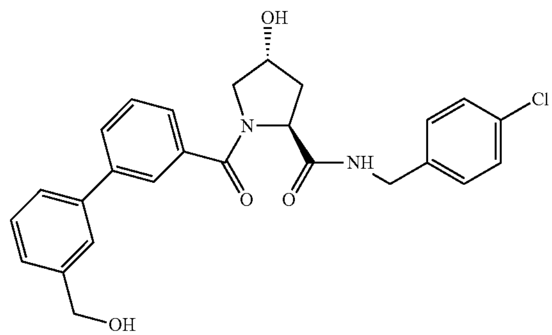 [SMILES: O=C(NCc1ccc(Cl)cc1)[C@@H]1C[C@@H](O)CN1C(=O)c1cccc(-c2cccc(CO)c2)c1] |
| VL222 | | | 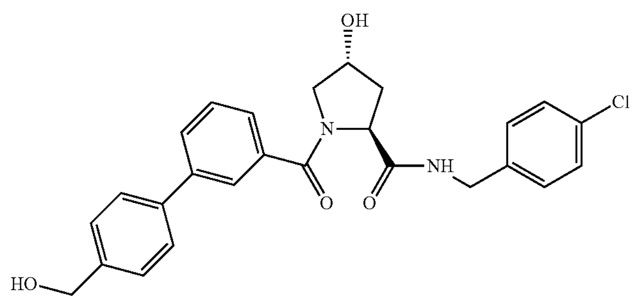 [SMILES: O=C(NCc1ccc(Cl)cc1)[C@@H]1C[C@@H](O)CN1C(=O)c1cccc(-c2ccc(CO)cc2)c1] |
| VL223 | | | 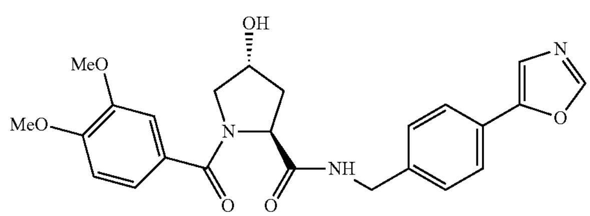 [SMILES: COc1ccc(C(=O)N2C[C@H](O)C[C@H]2C(=O)NCc2ccc(-c3cnco3)cc2)cc1OC] |
| VL224 | | | 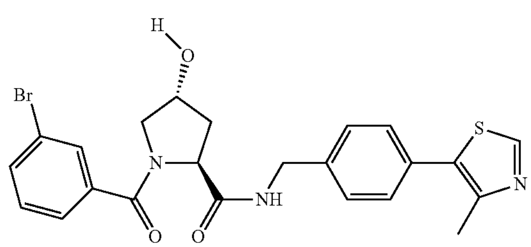 [SMILES: Cc1ncsc1-c1ccc(CNC(=O)[C@@H]2C[C@@H](O)CN2C(=O)c2cccc(Br)c2)cc1] |
| VL225 | | | 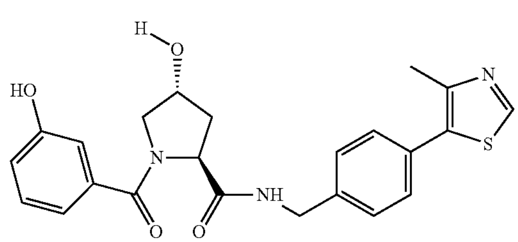 [SMILES: Cc1ncsc1-c1ccc(CNC(=O)[C@@H]2C[C@@H](O)CN2C(=O)c2cccc(O)c2)cc1] |

185 186
TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL226 | | | 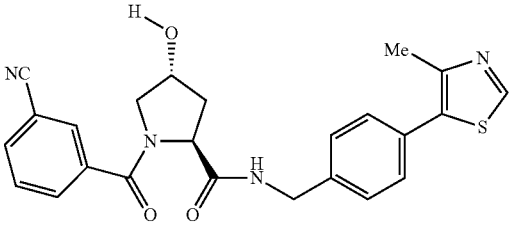 [SMILES: Cc1ncsc1-c1ccc(CNC(=O)[C@@H]2C[C@@H](O)CN2C(=O)c2cccc(C#N)c2)cc1] |
| VL227 | | | 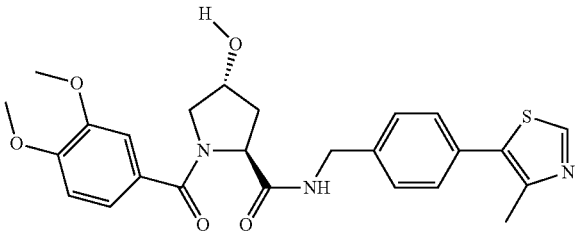 [SMILES: COc1ccc(C(=O)N2C[C@H](O)C[C@H]2C(=O)NCc2ccc(-c3scnc3C)cc2)cc1OC] |
| VL228 | | | 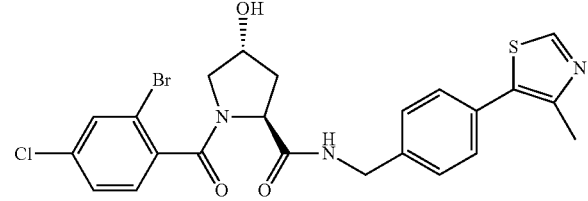 [SMILES: Cc1ncsc1-c1ccc(CNC(=O)[C@@H]2C[C@@H](O)CN2C(=O)c2ccc(Cl)cc2Br)cc1] |
| VL229 | | | 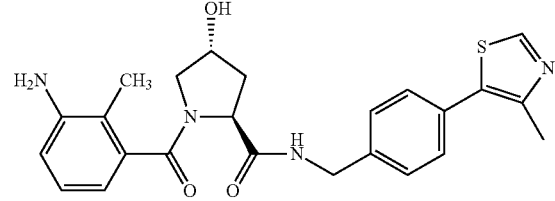 [SMILES: Cc1ncsc1-c1ccc(CNC(=O)[C@@H]2C[C@@H](O)CN2C(=O)c2cccc(N)c2C)cc1] |
| VL230 | | | 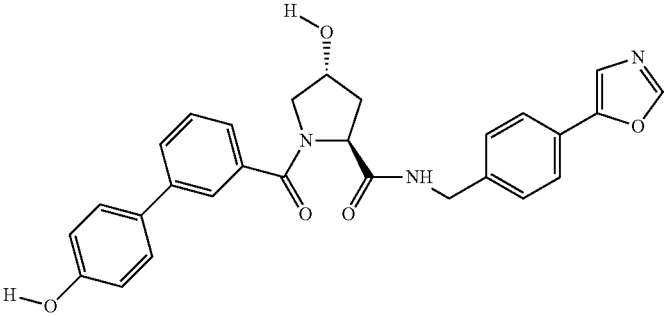 [SMILES: O=C(NCc1ccc(-c2cnco2)cc1)[C@@H]1C[C@@H](O)CN1C(=O)c1cccc(-c2ccc(O)cc2)c1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL231 | | | 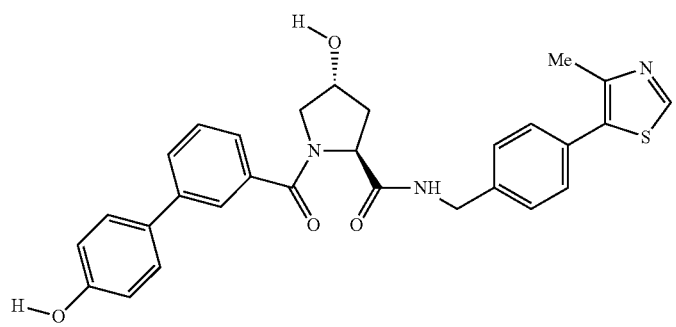 [SMILES: Cc1ncsc1-c1ccc(CNC(=O)[C@@H]2C[C@@H](O)CN2C(=O)c2cccc(-c3ccc(O)cc3)c2)cc1] |
| VL232 | | | 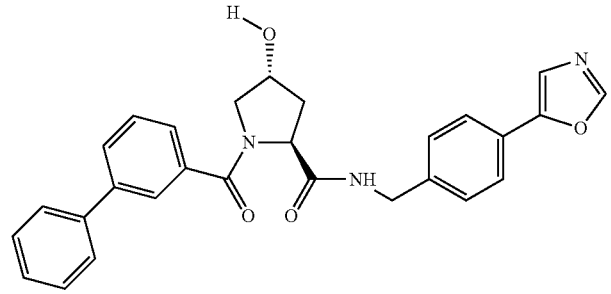 [SMILES: O=C(NCc1ccc(-c2cnco2)cc1)[C@@H]1C[C@@H](O)CN1C(=O)c1cccc(-c2ccccc2)c1] |
| VL237 | | | 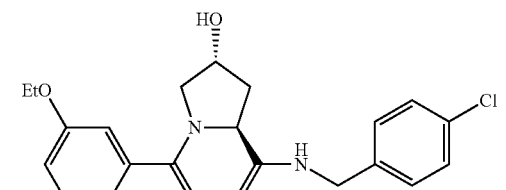 |
| VL238 | | | 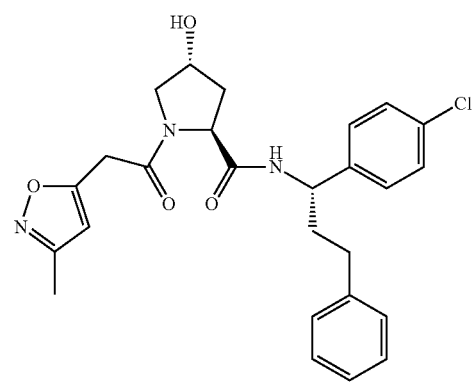 [SMILES: Cc1cc(CC(=O)N2C[C@H](O)C[C@H]2C(=O)N[C@@H](CCc2ccccc2)c2ccc(Cl)cc2)on1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL239 | | | 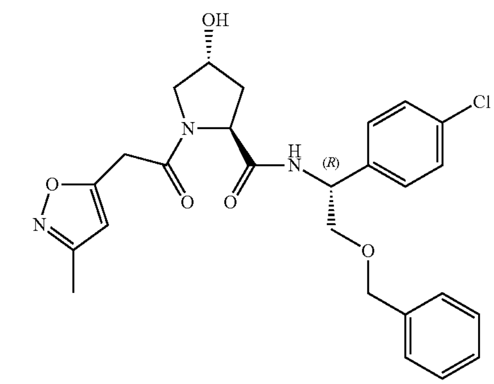 |
| VL240 | | | 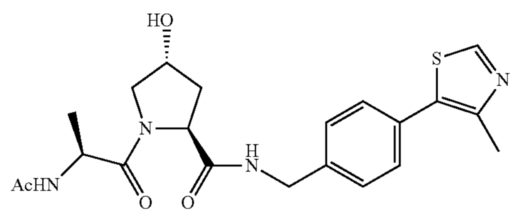 [SMILES: CC(=O)N[C@@H](C)C(=O)N1C[C@H](O)C[C@H]1C(=O)NCc1ccc(-c2scnc2C)cc1] |
| VL241 | | | 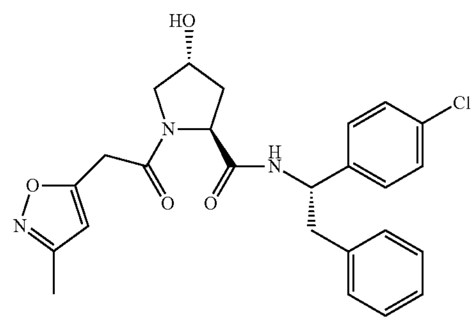 [SMILES: Cc1cc(CC(=O)N2C[C@H](O)C[C@H]2C(=O)N[C@@H](Cc2ccccc2)c2ccc(Cl)cc2)on1] |
| VL242 | | | 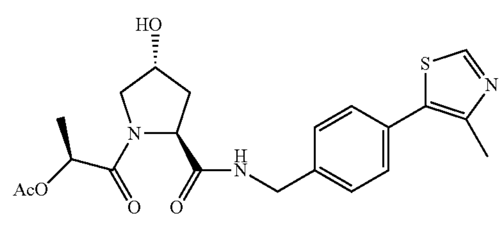 [SMILES: CC(=O)O[C@@H](C)C(=O)N1C[C@H](O)C[C@H]1C(=O)NCc1ccc(-c2scnc2C)cc1] |
| VL243 | | | 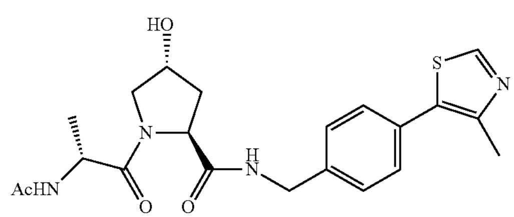 [SMILES: CC(=O)N[C@H](C)C(=O)N1C[C@H](O)C[C@H]1C(=O)NCc1ccc(-c2scnc2C)cc1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL244 | | | 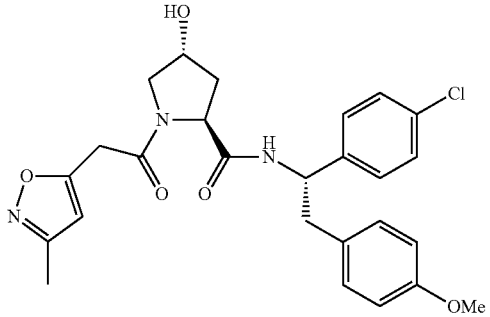 [SMILES: COc1ccc(C[C@H](NC(=O)[C@@H]2C[C@@H](O)CN2C(=O)Cc2cc(C)no2)c2ccc(Cl)cc2)cc1] |
| VL245 | | | 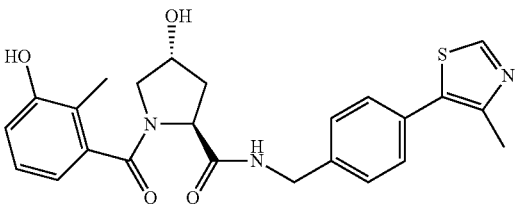 |
| VL247 | | | 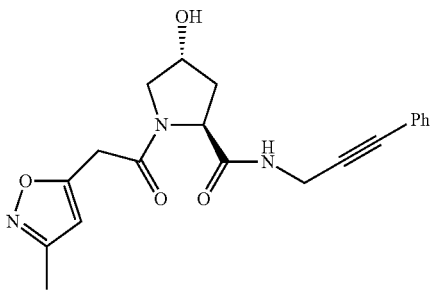 [SMILES: Cc1cc(CC(=O)N2C[C@H](O)C[C@H]2C(=O)NCC#Cc2ccccc2)on1] |
| VL248 | | | 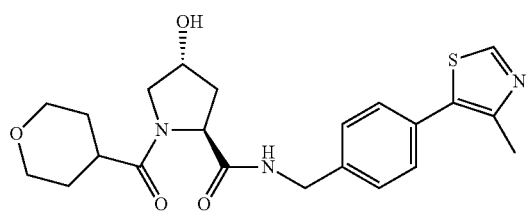 [SMILES: Cc1ncsc1-c1ccc(CNC(=O)[C@@H]2C[C@@H](O)CN2C(=O)C2CCOCC2)cc1] |
| VL249 | | | 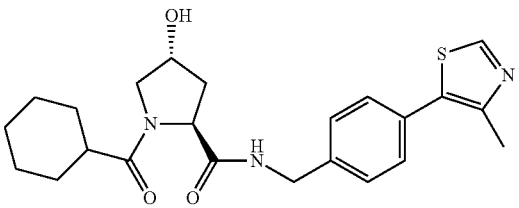 [SMILES: Cc1ncsc1-c1ccc(CNC(=O)[C@@H]2C[C@@H](O)CN2C(=O)C2CCCCC2)cc1] |
| VL250 | | | 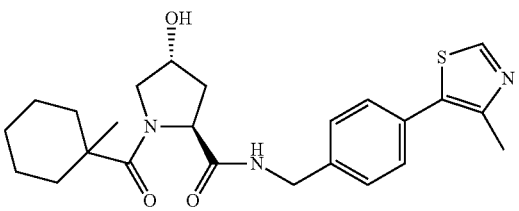 [SMILES: Cc1ncsc1-c1ccc(CNC(=O)[C@@H]2C[C@@H](O)CN2C(=O)C2(C)CCCCC2)cc1] |

TABLE 2-continued
Affinity Table.
(Most compounds showed activity within the range of about 200 μM or lower).
| VHL ligand No. | IC$_{50}$(μM) 10% DMSO | IC$_{50}$(μM) 1% DMSO | Chemical Structure |
|---|---|---|---|
| VL251 | | | 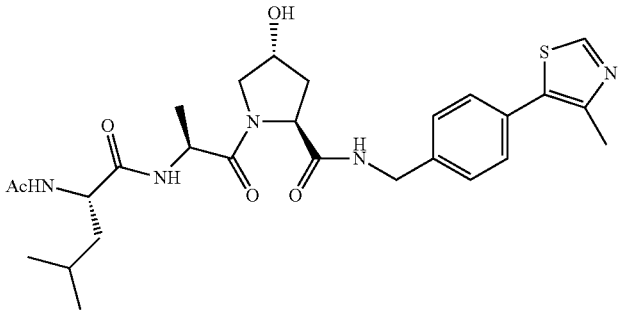 [SMILES: CC(=O)N[C@@H](CC(C)C)C(=O)N[C@@H](C)C(=O)N1C[C@H](O)C[C@H]1C(=O)NCc1ccc(-c2scnc2C)cc1] |
| VL252 | | | 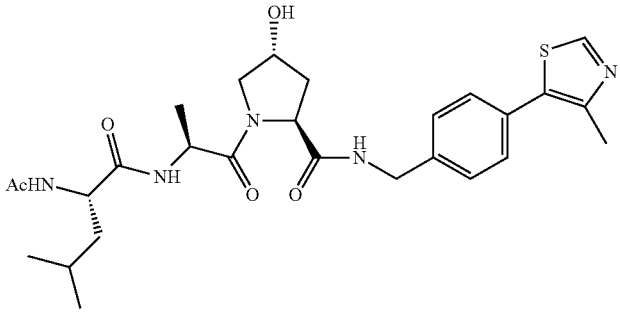 [SMILES: CC(=O)N[C@@H](CC(C)C)C(=O)N[C@@H](C)C(=O)N1C[C@H](O)C[C@H]1C(=O)NCc1ccc(-c2scnc2C)cc1] |
| VL253 | | | 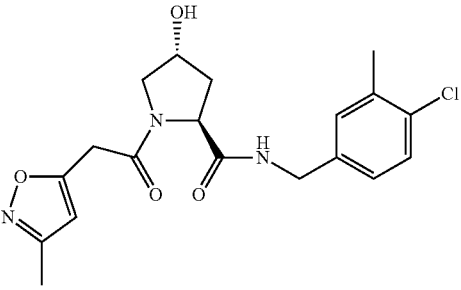 [SMILES: Cc1cc(CC(=O)N2C[C@H](O)C[C@H]2C(=O)NCc2ccc(Cl)c(C)c2)on1] |
| VL254 | | | 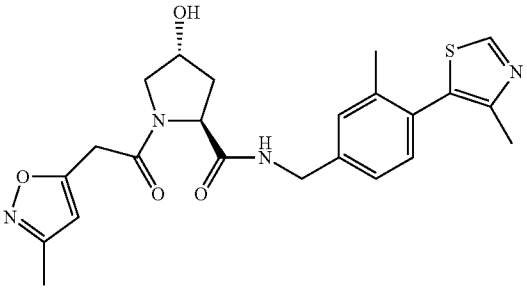 [SMILES: Cc1cc(CC(=O)N2C[C@H](O)C[C@H]2C(=O)NCc2ccc(-c3scnc3C)c(C)c2)on1] |
| VL255 | | | 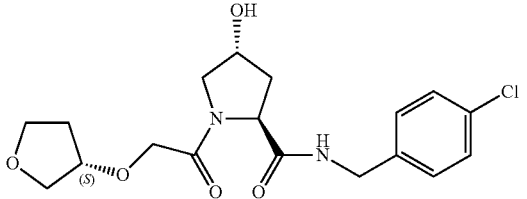 |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL256 | | | 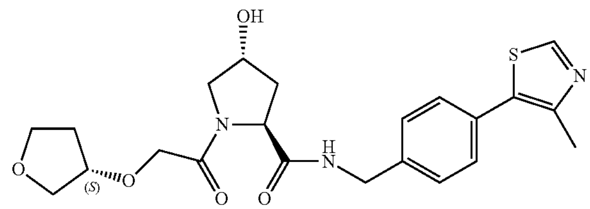 |
| VL257 | | | 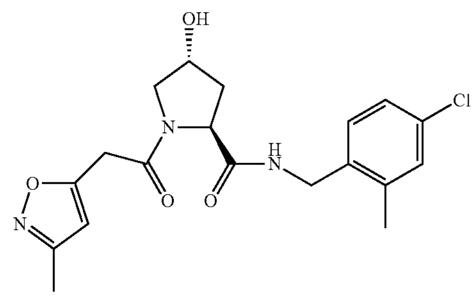 [SMILES: Cc1cc(CC(=O)N2C[C@H](O)C[C@H]2C(=O)NCc2ccc(Cl)cc2C)on1] |
| VL258 | | | 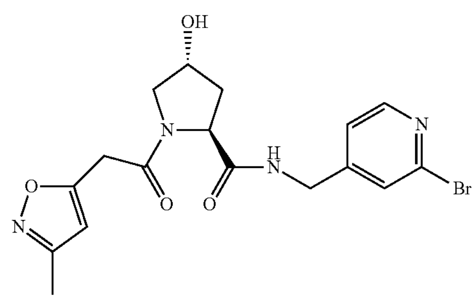 |
| VL259 | | | 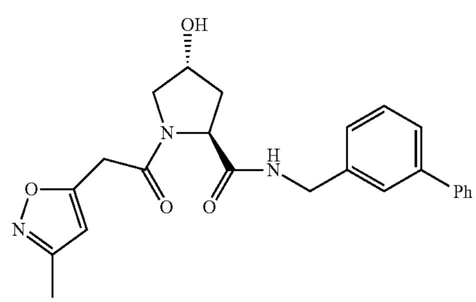 [SMILES: Cc1cc(CC(=O)N2C[C@H](O)C[C@H]2C(=O)NCc2cccc(-c3ccccc3)c2)on1] |
| VL260 | | | 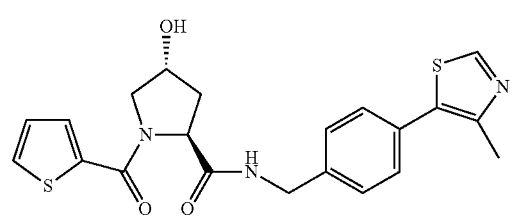 [SMILES: Cc1ncsc1-c1ccc(CNC(=O)[C@@H]2C[C@@H](O)CN2C(=O)c2cccs2)cc1] |

TABLE 2-continued

Affinity Table.
(Most compounds showed activity within the range of about 200 μM or lower).

| VHL ligand No. | IC$_{50}$(μM) 10% DMSO | IC$_{50}$(μM) 1% DMSO | Chemical Structure |
|---|---|---|---|
| VL261 | | | 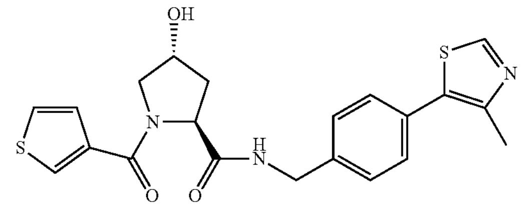 [SMILES: Cc1ncsc1-c1ccc(CNC(=O)[C@@H]2C[C@@H](O)CN2C(=O)c2ccsc2)cc1] |
| VL262 | | | 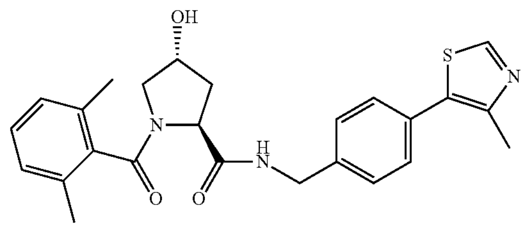 [SMILES: Cc1cccc(C)c1C(=O)N1C[C@H](O)C[C@H]1C(=O)NCc1ccc(-c2scnc2C)cc1] |
| VL263 | | | 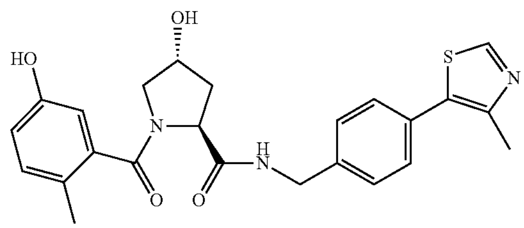 [SMILES: Cc1ccc(O)cc1C(=O)N1C[C@H](O)C[C@H]1C(=O)NCc1ccc(-c2scnc2C)cc1] |
| VL264 | | | 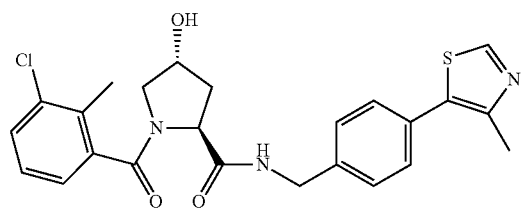 [SMILES: Cc1ncsc1-c1ccc(CNC(=O)[C@@H]2C[C@@H](O)CN2C(=O)c2cccc(Cl)c2C)cc1] |
| VL265 | | | 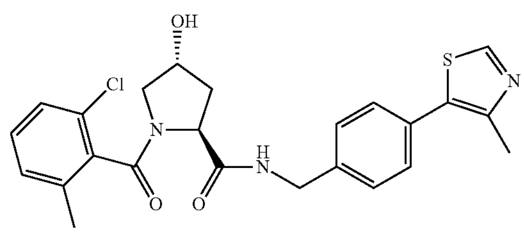 [SMILES: Cc1cccc(Cl)c1C(=O)N1C[C@H](O)C[C@H]1C(=O)NCc1ccc(-c2scnc2C)cc1] |
| VL266 | | | 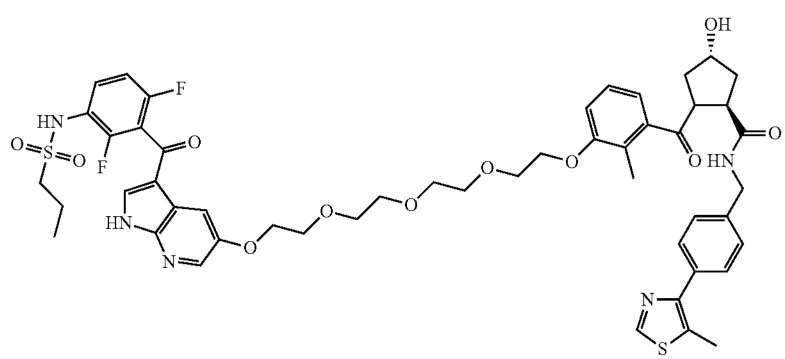 [SMILES: CCCS(=O)(=O)Nc1ccc(F)c(C(=O)c2c[nH]c3ncc(OCCOCCOCCOCCOc4cccc(C(=O)C5C[C@H](O)C[C@H]5C(=O)NCc5ccc(-c6ncsc6C)cc5)c4C)cc23)c1F] |

Synthetic Methods
General Chemistry

All reactions were performed in oven-dried or flame-dried glassware fitted with rubber septa under a positive pressure of nitrogen, unless otherwise noted. Air- and moisture-sensitive liquids were transferred via syringe or cannula. THF was distilled from sodium/benzophenone. Dichloromethane was distilled from calcium hydride. Analytical thin layer chromatography (TLC) was performed using glass plates precoated with silica gel (0.25 mm). TLC plates were visualized by exposure to UV light (UV) or $KMnO_4$. Flash column chromatography was performed using silica gel 60 (230-400 mesh, Merck) with the indicated solvents.

$^1H$ and $^{13}C$ spectra were recorded on Bruker Avance DPX-500 or Bruker Avance DPX-400 NMR spectrometers. $^1H$ NMR spectra are represented as follows: chemical shift, multiplicity (s=singlet, d=doublet, t=triplet, q=quartet, m=multiplet, br=broad), integration, and coupling constant (J) in Hertz (Hz). $^1H$ NMR chemical shifts are reported relative to $CDCl_3$ (7.26 ppm), $d_6$-DMSO (2.50 ppm) and $d_4$-MeOD (3.31 ppm). $^{13}C$ NMR was recorded relative to the central line of $CDCl_3$ (77.16 ppm), $d_6$-DMSO (39.52 ppm) and $d_4$-MeOD (49.00 ppm). In most cases, only peaks of the major rotamer are reported. Mass spectra were obtained using a Perkin-Elmer API 150 EX spectrometer. MALDI-TOF analyses of purified samples were performed in a Voyager-DE-PRO6268 (Applied Biosystems) using cyano-4-hydroxycinnamic acid matrices. Unless otherwise noted, HPLC was performed using a Dynamax SD200 solvent delivery system connected to a Dynamax UV-1 Absorbance Detector with a YMC-Pack ODS-AM preparative column (250×20 mm, 5 μm particle size, 12 nm pore size). A linear gradient of MeCN in $H_2O$ from 20% to 100% MeCN, with constant 0.1% TFA was run over 40 minutes.

General Methods of Chemical Synthesis

The following eight (8) general chemical synthetic methods (Methods A through F and Solid Phase Synthesis A and B, described hereinbelow) are provided for synthesizing numerous compounds according to the present invention which are set forth in Table 2 Affinity Table above. Each method is presented with reference to a specific compound, the synthetic details of which are presented hereinabove. All of the compounds numbered may be synthesized relatively easily using the straight-forward methods which are set forth hereinbelow. In certain instances, more synthetic details are provided for certain preferred embodiments in order to present that information such that it may serve as a template for synthesizing a number of other compounds as otherwise disclosed herein.

A

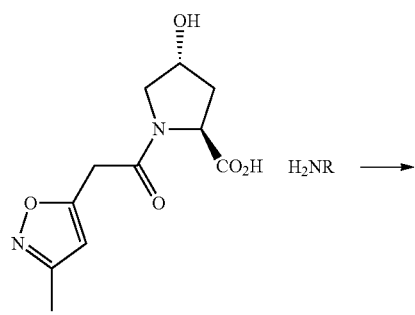

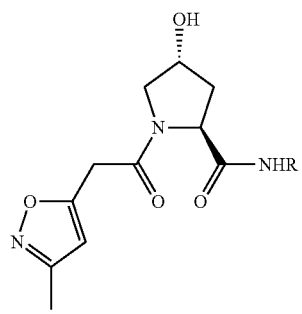

As an example, see the synthesis for compound VL133 of Table II, set forth below.

B

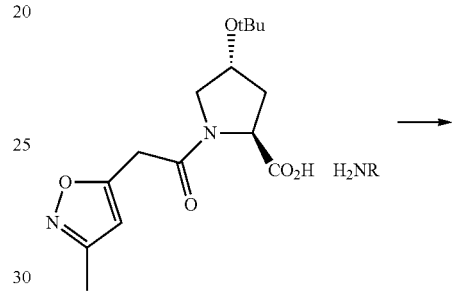

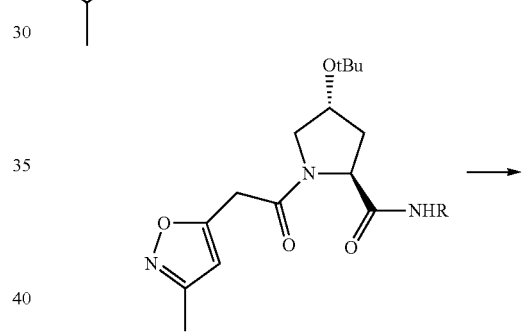

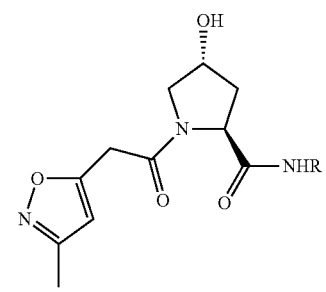

See the general synthesis for VL116 of Table II with protection of the hydroxyl group.

C

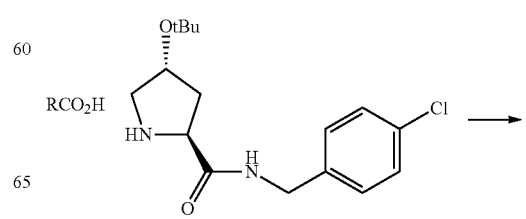

201
-continued

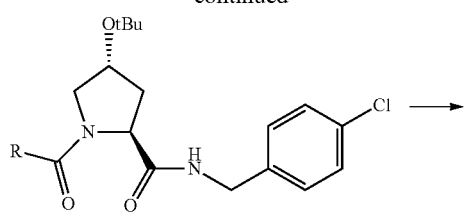

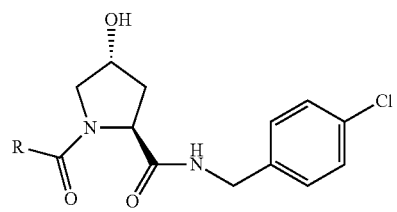

See the general synthesis for compound VL 156 of Table II, described below.

D

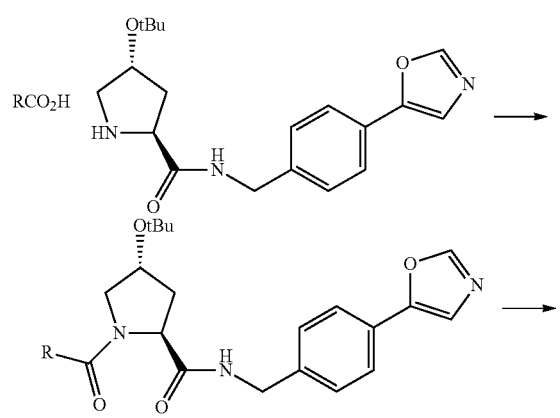

See the general synthesis for compound VL 217 of Table II, described below.

E

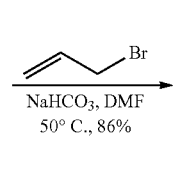

202
-continued

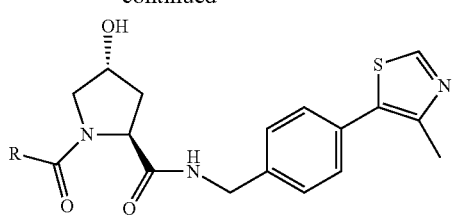

See the general synthesis for VL 219 of Table II, described below.

F

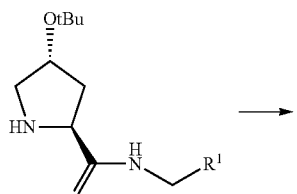

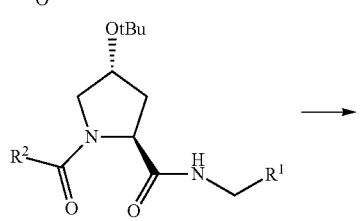

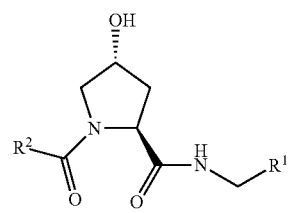

Method F subsumes methods C, D and E and is a general method which proceeds through commercially available amines.

Following the general synthetic methods set forth above and as previously described, the following compounds are synthesized by analogy.

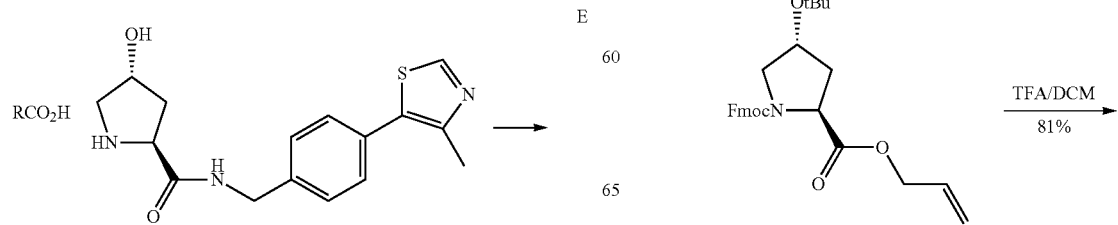

(2S,4R)-1-((9H-fluoren-9-yl)methyl) 2-allyl 4-(tert-butoxy)pyrrolidine-1,2-dicarboxylate (Fmoc-Hyp(OtBu)-OAllyl)

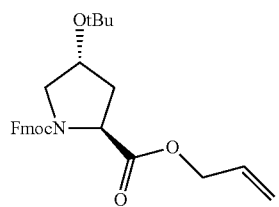

Fmoc-Hyp(OtBu)OH (24.9 g, 60.8 mmol, 1 eq) was dissolved in DMF (300 mL) at room temperature. Sodium bicarbonate (12.8 g, 152 mmol, 2.5 eq) was added, followed by allyl bromide (25.3 mL, 300 mmol, 4.9 eq). The solution was fitted with an air condenser and heated to 50° C. for 20 hours. It was then cooled to room temperature, diluted with EtOAc, washed with aqueous 1 M HCl, saturated sodium bicarbonate, water and brine. The organic layer was dried with sodium sulfate, filtered and condensed.[15] Purification by column chromatography (15 to 33% EtOAc/hexanes) gave Fmoc-Hyp(OtBu)OAllyl (23.42 g, 52.1 mmol, 86%) as a faint yellow oil. $^1$H NMR (500 MHz, CDCl$_3$) δ 7.76 (t, J=6.3 Hz, 2H), 7.63-7.54 (m, 2H), 7.43-7.37 (m, 2H), 7.31 (t, J=7.0 Hz, 2H), 5.99-5.79 (m, 1H), 5.39-5.18 (m, 2H), 4.66 (d, J=5.6 Hz, 1H), 4.63-4.13 (m, 6H), 3.81 (ddd, J=16.6, 10.7, 6.2 Hz, 1H), 3.48-3.33 (m, 1H), 2.31-2.18 (m, 1H), 2.18-2.08 (m, 1H), 1.21 (d, J=11.6 Hz, 9H). $^{13}$C NMR (126 MHz, CDCl$_3$) (mixture of rotamers) δ 172.49, 155.01, 154.49, 144.31, 144.18, 144.06, 143.84, 141.44, 141.41, 141.36, 131.91, 131.74, 127.80, 127.76, 127.20, 127.16, 125.31, 125.28, 125.11, 120.08, 120.05, 118.93, 118.61, 74.29, 69.37, 68.48, 67.73, 65.86, 58.09, 57.79, 54.01, 53.52, 47.40, 47.28, 38.90, 37.87, 28.41, 28.37. MS (ESI) 450.5 (M+H).

(2S,4R)-1-((9H-fluoren-9-yl)methyl) 2-allyl 4-hydroxypyrrolidine-1,2-dicarboxylate (Fmoc-Hyp(OH)-OAllyl)

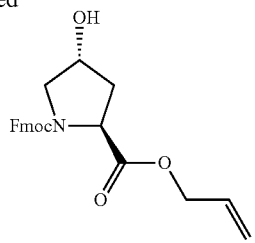

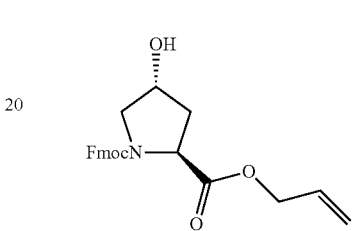

Fmoc-Hyp(OtBu)-OAllyl (23.42 g, 52.1 mmol) was dissolved in DCM (306 mL) at room temperature. TFA (54 mL, 15% vol/vol) was added and the solution was stirred for 13 hours. The solution was poured into water, neutralized by slow addition of saturated aqueous sodium bicarbonate and extracted twice with DCM and once with EtOAc. The combined organic layers were dried with sodium sulfate, filtered and condensed. Purification by column chromatography (30 to 80% EtOAc/hexanes) gave Fmoc-Hyp(OH)-OAllyl as a yellowish oil (16.7 g, 42.4 mmol, 81%). $^1$H and $^{13}$C NMR spectra matched those reported in the literature.[16]

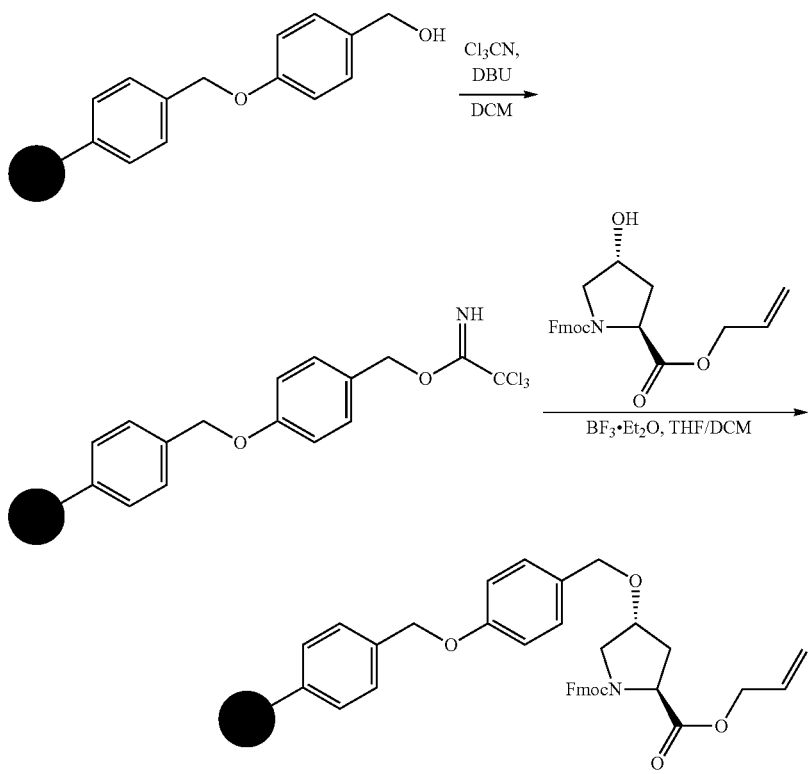

205

Fmoc-Hyp(OWang)-OAllyl

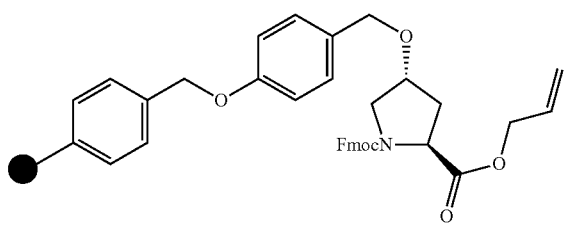

Wang Resin (12.1 g, 1.1 mmol/g loading, 13.3 mmol, 1 eq) was swelled with DCM (90 mL) in a glass reaction vessel and cooled to 4° C. Trichloroacetonitirle (20 mL, 200 mmol, 15 eq) was added, followed by the addition of DBU (3 mL, 20 mmol, 1.5 eq) in 3 portions over 3 minutes, manually shaking the reaction vessel in between additions. The reaction vessel was nutated at 4° C. for 1 hour, then washed with DCM, DMSO, THF, then twice with DCM at room temperature.[17] A solution of Fmoc-Hyp(OH)—OAllyl (26.15 g, 66.5 mmol, 5 eq) in DCM (40 mL) and THF (40 mL) was then added, and shaken for 30 minutes and then washed twice with DCM, thrice with DCM and then twice with MeOH followed by DCM. The initial DCM washes were condensed, and purified by column chromatography (33% to 80% EtOAc) to recover the Fmoc-Hyp(OH)—OAllyl starting material (21.51 g, 54.67 mmol, 82%). The resin was dried in air, then dried under vacuum to give 15.5 g of Fmoc-Hyp(OWang)-OAllyl.[18] The loading of the resin was estimated to be 0.53 mmol/g based upon the increase in mass.

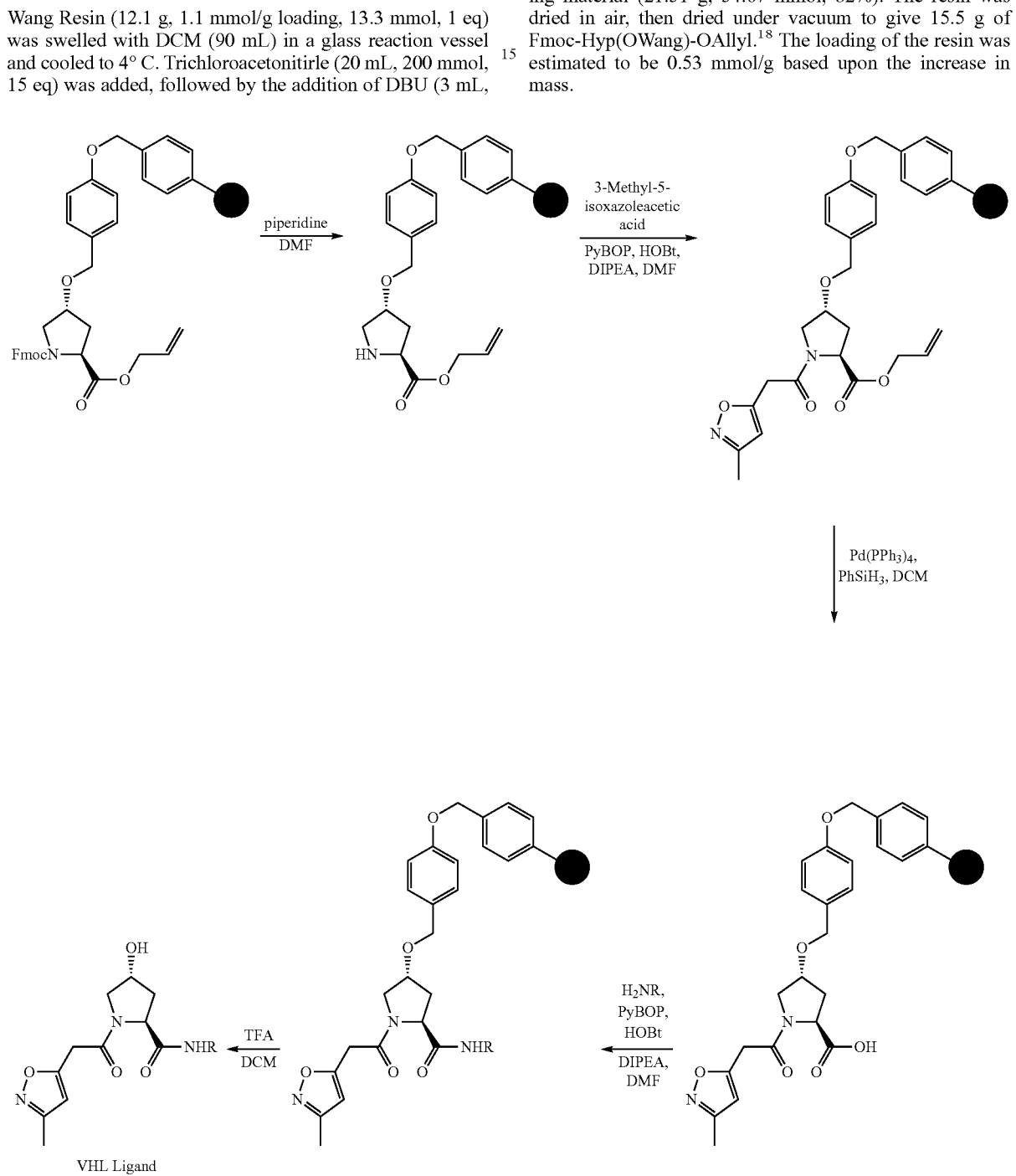

Solid Phase Synthesis General Method A

Fmoc-Hyp(OWang)-OAllyl resin (1 eq) was swelled DMF, then reacted with 20% piperidine in DMF for 30 minutes. The resin was then washed once with piperidine, and reacted again with 20% piperidine for 30 minutes to ensure complete deprotection. The resin was then washed twice with DMF and once with MeOH followed by DCM. The resulting free amine was then coupled with 3-methyl-5-isoxazoleacetic acid (4 eq), PyBOP (4 eq) HOBt (4 eq) and DIPEA (7 eq) in DMF for 4 hours. The resin was then washed thrice with DMF and twice with MeOH followed by DCM. The resin was then swelled with freshly distilled DCM, and reacted with Pd(PPh$_3$)$_4$ (0.1 eq) and PhSiH$_3$ (10 eq) for 30 minutes. The resin was then washed once with DCM, and reacted again with Pd(PPh$_3$)$_4$ (0.1 eq) and PhSiH$_3$ (10 eq) in distilled DCM for 30 minutes, after which the resin was washed twice with DMF and once with MeOH followed by DCM. The resulting carboxylic acid was then coupled with the appropriate amine (or a salt of the appropriate amine), RNH$_2$ (4 eq) with PyBOP (4 eq), HOBt (4 eq) and DIPEA (7 eq for free amines, 8 eq for amine salts) in DMF for 4 hours. The resin was then washed 5 times with DMF, thrice with MeOH and 5 times with DCM. The resin was then reacted with 20% TFA in DCM for 2 hours. The reaction mixture was then drained and the resin was washed with DCM. Condensation under reduced pressure, and purification by column chromatography (1% to 10% 0.5M NH$_3$ in MeOH/DCM or 1% to 10% MeOH in DCM) gave the desired VHL ligand.

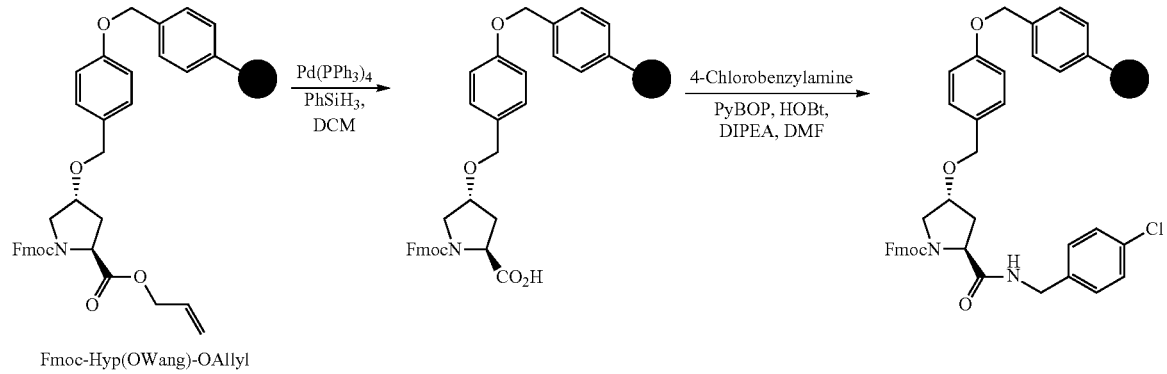

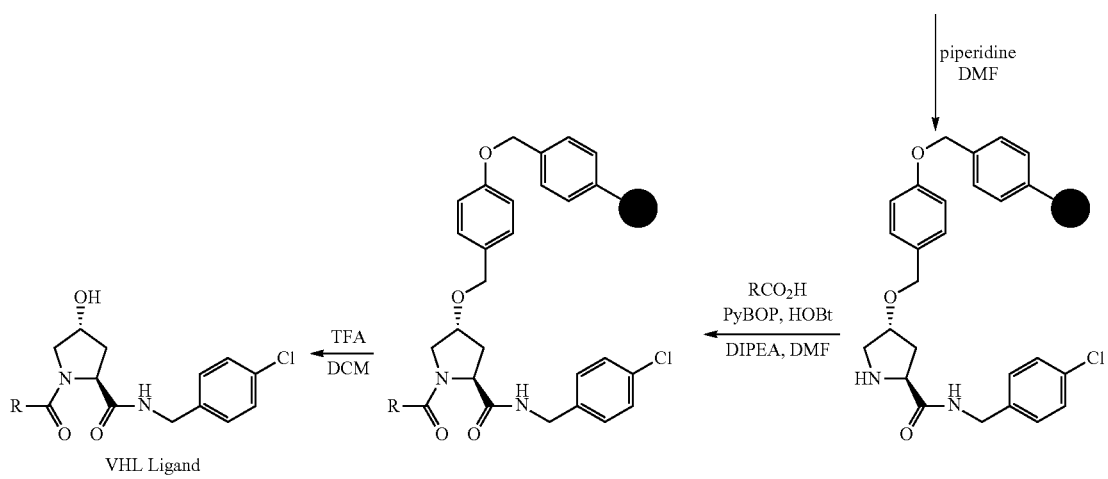

VHL Ligand

Solid Phase Synthesis General Method B

Briefly, Fmoc-Hyp-(OWang)-OAllyl resin (1 eq) was swelled with freshly distilled DCM, and reacted with Pd(PPh$_3$)$_4$ (0.1 eq) and PhSiH$_3$ (10 eq) for 30 minutes. The resin was then washed once with DCM, and reacted again with Pd(PPh$_3$)$_4$ (0.1 eq) and PhSiH$_3$ (10 eq) in distilled DCM for 30 minutes, after which the resin was washed twice with DMF and once with MeOH followed by DCM. The resulting carboxylic acid was then coupled with 4-chlorobenzylamine (4 eq), PyBOP (4 eq), HOBt (4 eq) and DIPEA (7 eq) in DMF for 4 hours. The resin was then reacted with 20% piperidine in DMF for 30 minutes. The resin was then washed once with DMF, and reacted again with 20% piperidine for 30 minutes to ensure complete deprotection. The resin was then coupled with the appropriate carboxylic acid (RCO$_2$H, 4 eq), PyBOP (4 eq), HOBt (4 eq) and DIPEA (7 eq) in DMF for 4 hours. The resin was then washed 4 times with DMF and twice with methanol followed by DCM. The resin was then reacted with 20% TFA in DCM for 2 hours. The reaction mixture was then drained and the resin was washed with DCM. Condensation under reduced pressure, and purification by column chromatography (1% to 10% 0.5M NH$_3$ in MeOH/DCM or 1% to 10% MeOH in DCM)

gave the desired VHL ligand. Yields are based upon the loading of the resin, which was estimated based upon its change in mass.

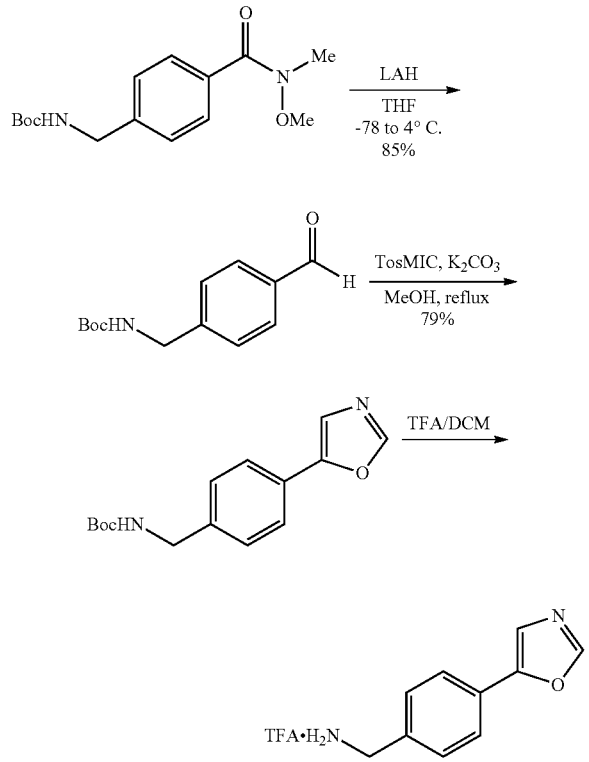

Tert-Butyl 4-(methoxy(methyl)carbamoyl)benzylcarbamate (Boc-Amb-N(OMe)Me)

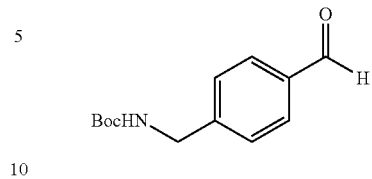

Boc-Amb-OH (2.55 g, 10.16 mmol, 1 eq) was dissolved in DCM (68 mL) and cooled to 4° C. in an ice bath. EDC (2.34 g, 12.2 mmol, 1.2 eq), HOBt (1.65 g, 12.2 mmol, 1.2 eq) and DIPEA (6.2 mL, 35.6 mmol, 3.5 eq) were added. The solution was stirred for 30 minutes and then N,O-Dimethylhydroxylamine hydrochloride (1.09 g, 11.2 mmol, 1.1 eq) was added. The solution warmed slowly to room temperature and after 21 hours was poured into brine, with a small amount of chloroform to break the resulting emulsion. After separation, the aqueous layer was extracted twice with EtOAc. The combined organic layer was dried over sodium sulfate, filtered and condensed. Purification by column chromatography (40 to 75% EtOAc/hexanes) gave a colorless oil (2.45 g, 8.33 mmol, 82%). $^1$H NMR (500 MHz, CDCl$_3$) δ 7.65 (d, J=8.2 Hz, 2H), 7.31 (d, J=8.1 Hz, 2H), 4.88 (s, 1H), 4.36 (d, J=5.1 Hz, 2H), 3.55 (s, 3H), 3.35 (d, J=4.7 Hz, 3H), 1.47 (s, 9H). $^{13}$C NMR (126 MHz, CDCl$_3$) δ 169.77, 156.04, 141.79, 133.21, 128.76, 127.03, 79.87, 61.20, 44.50, 33.88, 28.55. MS (ESI) 295.2 (M+H).

tert-Butyl 4-formylbenzylcarbamate (Boc-Amb-H)

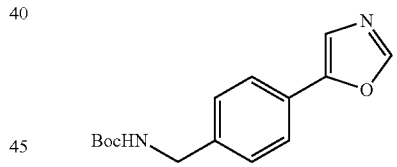

Boc-Amb-N(OMe)Me (2.45 g, 8.33 mmol, 1 eq) was dissolved in THF (83 mL) and cooled to −78° C. in a dry ice/acetone bath. Lithium aluminum hydride (0.41 g, 10.83 mmol, 1.3 eq) was added in 2 portions over 5 minutes. After 50 minutes, the suspension was warmed to 4° C. in an ice bath. After 3.5 hours, the reaction was deemed complete by TLC (mini workup in 10% potassium bisulfate and EtOAc, 50% EtOAc/hexanes) and the reaction was quenched by the slow addition of 10% potassium bisulfate at 4° C. The mixture was warmed to room temperature, and stirred for 30 minutes. Most of the THF was removed under reduced pressure and mixture was diluted with water and extracted thrice with EtOAc. The combined organic layer was washed once with brine, dried over sodium sulfate, filtered and condensed. Purification by column chromatography (40 to 50% EtOAc/hexanes) gave Boc-Amb-H as a white solid (1.66 g, 7.1 mmol, 85%). $^1$H NMR (500 MHz, CDCl$_3$) δ 9.96 (s, 1H), 7.81 (d, J=8.2 Hz, 2H), 7.41 (d, J=8.0 Hz, 2H), 5.12 (s, 1H), 4.37 (d, J=5.6 Hz, 2H), 1.44 (s, 9H). $^{13}$C NMR (126 MHz, CDCl$_3$) δ 191.94, 156.03, 146.30, 135.62, 130.14, 127.78, 79.92, 44.44, 28.46. MS (ESI) 235.9 (M+H), 180.2 (M-tBu).

tert-Butyl 4-(oxazol-5-yl)benzylcarbamate

Potassium carbonate (0.13 g, 0.94 mmol, 1.2 eq) and toluenesulfonylmethyl isocyanide (0.184 g, 0.94 mmol, 1.2 eq) were added to MeOH (7.8 mL) at room temperature. The round bottom was fitted with a reflux condenser and heated to 45° C. After 15 minutes, Boc-Amb-H (0.1835 g, 0.78 mmol, 1 eq) was added and the mixture was heated to 75° C. for 3 hours and then cooled to room temperature. The MeOH was removed under reduced pressure and the crude material was resuspended in EtOAc and 1:2 mixture of saturated sodium carbonate to water and separated. The aqueous layer was then extracted once with EtOAc. The combined organic layer was dried over sodium sulfate, filtered and condensed. Purification by column chromatography (20 to 35% EtOAc/hexanes) gave a white solid. $^1$H NMR (400 MHz, CDCl$_3$) δ 7.91 (s, 1H), 7.62 (d, J=8.3 Hz, 2H), 7.35 (ob d, 2H), 7.34 (ob s, 1), 4.88 (s, 1H), 1.47 (s, 9H). $^{13}$C NMR (126 MHz, CDCl$_3$) δ 156.02, 151.40, 150.47, 139.78, 128.01, 126.84, 124.67, 121.47, 79.68, 44.38, 28.47. MS (ESI) 275.5 (M+H).

(4-(Oxazol-5-yl)phenyl)methanamine trifluoroacetate salt

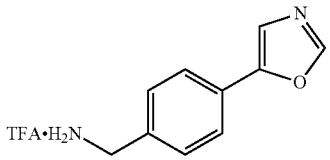

To a solution of tert-butyl 4-(oxazol-5-yl)benzylcarbamate (1.09 g) in DCM (40 mL), TFA (4 mL) was added at room temperature. The solution was stirred for 16 hours and concentrated under reduced pressure to yield the trifluoroacetate salt of (4-(oxazol-5-yl)phenyl)methanamine (1.984 g) as a cream colored solid, which was used without further purification. $^1$H NMR (400 MHz, MeOD) δ 8.29 (s, 1H), 7.83 (d, J=8.4 Hz, 2H), 7.60 (s, 1H), 7.56 (d, J=8.5 Hz, 2H), 4.16 (s, 2H). MS (ESI) 175.3 (M-CF$_3$CO$_2^-$).

(2S,4R)—N-(3-chlorobenzyl)-4-hydroxy-1-(2-(3-methylisoxazol-5-yl)acetyl)pyrrolidine-2-carboxamide (VL4)

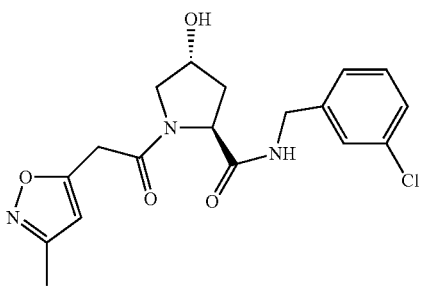 [SMILES: Cc1cc(CC(=O)N2C[C@H](O)C[C@H]2C(=O)NCc2cccc(Cl)c2)on1]

VL4 was synthesized according to General Method F as a white solid. $^1$H NMR (500 MHz, MeOD): δ8.684 (1H, s); 7.33-7.23 (4H, m); 6.24 (1H, s); 4.56-4.53 (1H, t, J=8 Hz); 4.51-4.50 (1H, m); 4.39-4.37 (2H, m); 3.96-3.92 (2H, m); 3.81-3.3.78 (1H, dd, J=9 Hz, 4 Hz); 3.64-3.62 (1H, m); 2.28-2.24 (4H, m); 2.09-2.04 (1H, m).$^{13}$C NMR (125 MHz, MeOD): δ174.56, 168.67, 167.68, 161.58, 142.25, 135.35, 131.04, 128.43, 128.19, 126.76, 105.37, 70.86, 60.78, 56.96, 43.60, 39.33, 33.90, 11.21. MS (ESI) 378.2 (M+H).

(2S,4R)-4-hydroxy-N-(4-hydroxyphenethyl)-1-(2-(3-methylisoxazol-5-yl)acetyl)pyrrolidine-2-carboxamide (VL2)

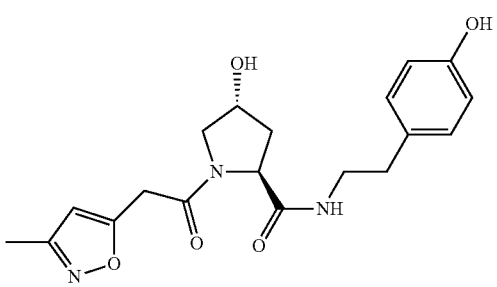 [SMILES: Cc1cc(CC(=O)N2C[C@H](O)C[C@H]2C(=O)NCCc2ccc(O)cc2)on1]

VL2 was synthesized according to General Method F. $^1$H NMR (500 MHz, MeOD) d 8.33 & 8.13 (due to the rotamers, both s, 1H), 7.02 (d, J=8.3 Hz, 2H), 6.69 & 6.65 (due to the rotamers, both d, J=8.3 Hz, 2H), 6.22 & 6.10 (due to the rotamers, both s, 1H), 4.43 (d, J=7.7 Hz, 2H), 3.89 (d, J=4.7 Hz, 2H), 3.74 (dd, J=11.0, 4.3 Hz, 1H), 3.57 (d, J=11.0 Hz, 1H), 3.42-3.36 (m, 2H), 2.73-2.63 (m, 2H), 2.25 (s, 3H), 2.16-2.12 (m, 1H), 1.96-1.91 (m, 1H). $^{13}$C NMR (asterisk denotes the signals of the minor rotamer, 125 MHz, MeOD) d 174.2, 174.1, *173.9, *173.8, *169.0, 168.6, 167.6, *167.4, 161.6, *161.5, *157.0, 156.9, *131.2, 130.8, *116.2, 116.1, *105.6, 105.4, 70.7, *69.2, *61.0, *60.9, 60.7, 60.6, 56.9, *56.2, 42.4, 42.3, *42.0, *41.9, 41.5, 39.3, 35.5, *35.3, 33.9, *32.9, 11.2. MS (ESI) [M+H] 374.1, [2M+Na] 769.6.

(2S,4R)-4-hydroxy-N-methyl-1-(2-(3-methylisoxazol-5-yl)acetyl)pyrrolidine-2-carboxamide (VL26)

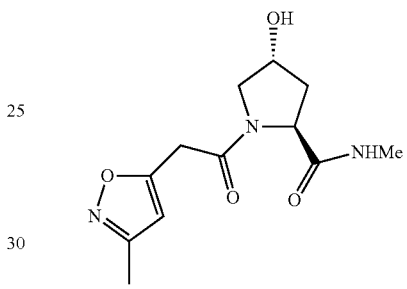

VL26 was synthesized according to General Method F and was isolated as a colorless oil (28 mg, 0.105 mmol, 80%). $^1$H NMR (500 MHz, MeOD) δ 6.23 (s, 1H), 4.47 (dt, J=16.3, 5.2 Hz, 2H), 3.91 (d, J=5.7 Hz, 2H), 3.78 (dd, J=10.9, 4.2 Hz, 1H), 3.61 (dd, J=11.0, 1.8 Hz, 1H), 2.73 (s, 3H), 2.26-2.18 (m, 4H), 2.05 (dd, J=8.3, 4.7 Hz, 1H). $^{13}$C NMR (126 MHz, MeOD) δ 174.82, 168.66, 167.67, 161.58, 105.40, 70.79, 60.67, 56.91, 39.30, 33.89, 26.35, 11.20. MS (ESI) 291.1 (M+Na), 268.7 (M+H).

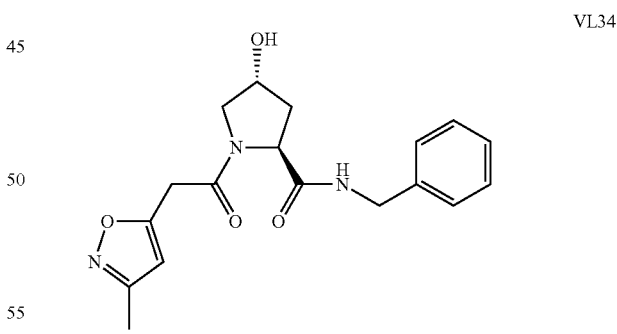

VL34 was synthesized from Fmoc-Hyp(OWang)-OAllyl (0.3 mmol) according to Solid Phase Synthesis General Method A. It was isolated as a white solid (14.7 mg). $^1$H NMR (400 MHz, MeOD) δ 7.31 (dd, J=5.9, 5.1 Hz, 4H), 7.27-7.17 (m, 1H), 6.23 (s, 1H), 4.55 (t, J=8.0 Hz, 1H), 4.50 (s, 1H), 4.39 (s, 2H), 3.92 (d, J=1.8 Hz, 2H), 3.80 (dd, J=10.9, 4.3 Hz, 1H), 3.61 (dd, J=7.3, 5.5 Hz, 1H), 2.33-2.19 (m, 4H), 2.12-2.03 (m, 1H). $^{13}$C NMR (101 MHz, MeOD) δ 174.29, 168.68, 167.68, 161.60, 139.73, 129.51, 128.40, 128.14, 105.36, 70.84, 60.73, 56.97, 44.05, 39.36, 33.95, 11.21.MS (ESI) 344.3 (M+H), 366.2 (M+Na).

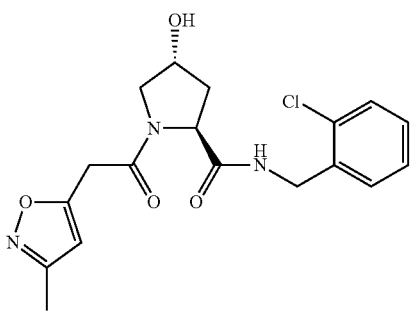

VL28

VL28 was synthesized from Fmoc-Hyp(OWang)-OAllyl (0.3 mmol) according to Solid Phase Synthesis General Method A. It was isolated as a yellow solid (19.1 mg). $^1$H NMR (500 MHz, MeOD) δ 8.66 (t, J=5.5 Hz, 1H), 7.48-7.34 (m, 2H), 7.31-7.21 (m, 2H), 6.23 (s, 1H), 4.58 (t, J=8.0 Hz, 1H), 4.48 (qd, J=15.8, 5.9 Hz, 3H), 3.99-3.87 (m, 2H), 3.80 (dd, J=10.9, 4.3 Hz, 1H), 3.66-3.60 (m, 1H), 2.31-2.22 (m, 4H), 2.09 (ddd, J=13.0, 8.2, 4.7 Hz, 1H). $^{13}$C NMR (126 MHz, MeOD) δ 174.60, 168.72, 167.65, 161.59, 136.79, 134.01, 130.29, 130.08, 129.67, 128.21, 105.37, 70.84, 60.74, 56.96, 42.08, 39.34, 33.95, 11.22. MS (ESI) 378.3 (M+H).

VL21

VL21 was synthesized from Fmoc-Hyp(OWang)-OAllyl (0.2 mmol) using Solid Phase Synthesis General Method A. It was isolated as a white solid (15.9 mg). $^1$H NMR (500 MHz, MeOD) δ 8.65 (s, 1H), 7.32-7.26 (m, 4H), 6.22 (s, 1H), 4.58-4.47 (m, 2H), 4.43-4.32 (m, 2H), 3.92 (d, J=4.2 Hz, 2H), 3.80 (dd, J=10.9, 4.3 Hz, 1-H), 3.66-3.58 (m, 1H), 2.30-2.22 (m, 4H), 2.08 (dd, J=8.3, 4.7 Hz, 1-H). $^{13}$C NMR (126 MHz, MeOD) δ 174.48, 168.71, 167.66, 161.60, 138.67, 133.85, 129.99, 129.53, 105.37, 70.85, 60.80, 56.99, 43.45, 39.33, 33.95, 11.20. MS (ESI) 378.4 (M+H).

VL20

VL20 was synthesized from Fmoc-Hyp(OWang)-OAllyl (0.15 mmol) using Solid Phase Synthesis General Method A. It was isolated as a white solid (9.9 mg). $^1$H NMR (400 MHz, MeOD) δ 8.64 (t, J=5.6 Hz, 1H), 7.37-7.26 (m, 2H), 7.07-6.99 (m, 2H), 6.23 (s, 1H), 4.57-4.47 (m, 2H), 4.37 (dd, J=8.4, 5.8 Hz, 2H), 3.93 (d, J=3.0 Hz, 2H), 3.80 (dd, J=11.0, 4.2 Hz, 1H), 3.66-3.58 (m, 1H), 2.28-2.22 (m, 4H), 2.08 (dd, J=8.3, 4.7 Hz, 1H). $^{13}$C NMR (126 MHz, MeOD) δ 174.31, 168.69, 167.67, 163.44 (d, J=243.5 Hz), 161.60, 135.78, 130.27 (d, J=8.1 Hz), 116.09 (d, J=21.6 Hz), 105.37, 70.85, 60.75, 56.99, 43.32, 39.33, 33.95, 11.20. MS (ESI) 362.3 (M+H).

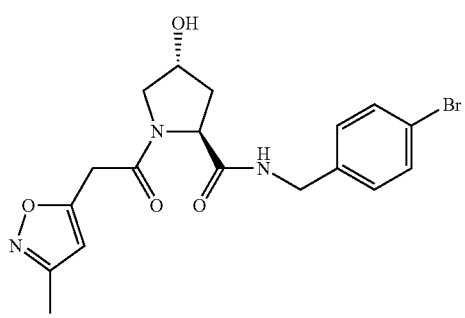

VL29

VL29 was synthesized from Fmoc-Hyp(OWang)-OAllyl (0.3 mmol) according to Solid Phase Synthesis General Method A. It was isolated as a light yellow solid (16.4 mg). $^1$H NMR (400 MHz, MeOD) δ 7.45 (dq, J=9.0, 2.2 Hz, 2H), 7.23 (d, J=8.5 Hz, 2H), 6.22 (s, 1H), 4.58-4.47 (m, 2H), 4.35 (dt, J=18.9, 15.4 Hz, 2H), 3.92 (d, J=2.6 Hz, 2H), 3.80 (dd, J=10.9, 4.2 Hz, 1H), 3.63 (d, J=11.0 Hz, 1H), 2.30-2.21 (m, 4H), 2.11-2.02 (m, 1H). $^{13}$C NMR (101 MHz, MeOD) δ 174.41, 168.71, 167.66, 161.61, 139.15, 132.55, 130.32, 121.77, 105.37, 70.85, 60.75, 56.99, 43.37, 39.33, 33.94, 11.22. MS (ESI) 424.1 (M+H).

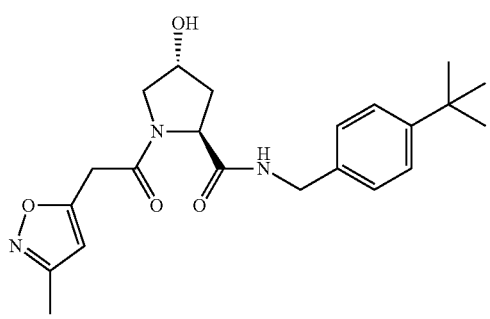

VL31

VL31 was synthesized from Fmoc-Hyp(OWang)-OAllyl (0.3 mmol) according to Solid Phase Synthesis General Method A. It was isolated as a white solid (19.8 mg). $^1$H NMR (500 MHz, MeOD) δ 8.56 (s, 1H), 7.35 (d, J=8.2 Hz, 2H), 7.22 (d, J=8.2 Hz, 2H), 6.24 (s, 1H), 4.53 (dd, J=18.3, 10.3 Hz, 2H), 4.36 (d, J=5.7 Hz, 2H), 3.92 (d, J=3.0 Hz, 2H), 3.80 (dd, J=10.9, 4.2 Hz, 1H), 3.62 (d, J=11.1 Hz, 1H), 2.29-2.21 (m, 4H), 2.12-2.02 (m, 1H), 1.29 (d, J=7.9 Hz, 9H). $^{13}$C NMR (126 MHz, MeOD) δ 174.29, 168.67, 167.68, 161.59, 151.18, 136.67, 128.19, 126.39, 105.38, 70.83, 60.77, 56.97, 43.88, 39.37, 35.28, 33.95, 31.79, 31.74, 11.23. MS (ESI) 400.5 (M+H).

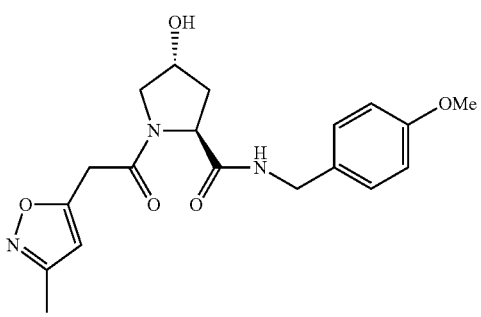

VL47

VL47 was synthesized from Fmoc-Hyp(OWang)-OAllyl (0.156 mmol) according to Solid Phase Synthesis General Method A. It was isolated as a white solid (9.1 mg). $^1$H NMR (500 MHz, MeOD) δ 7.22 (dd, J=8.4, 3.9 Hz, 2H), 6.86 (dd, J=8.8, 2.2 Hz, 2H), 6.22 (s, 1H), 4.63-4.45 (m, 2H), 4.37-4.26 (m, 2H), 3.92 (d, J=2.6 Hz, 2H), 3.83-3.70 (m, 4H), 3.61 (d, J=11.2 Hz, 1H), 2.28-2.20 (m, 4H), 2.06 (ddd, J=13.0, 8.1, 4.7 Hz, 1H). $^{13}$C NMR (126 MHz, MeOD) δ 174.13, 168.66, 167.68, 161.60, 160.39, 131.67, 129.76, 114.89, 105.37, 70.83, 60.74, 56.97, 55.67, 43.57, 39.34, 33.95, 11.21. MS (ESI) 374.5 (M+H).

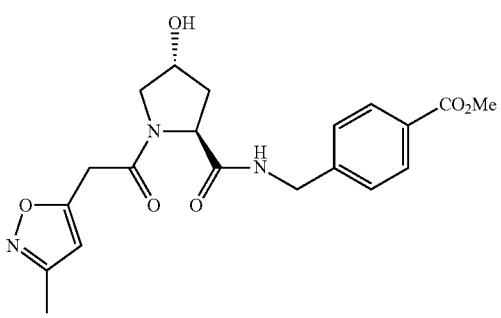

VL35

VL35 was synthesized from Fmoc-Hyp(OWang)-OAllyl (0.156 mmol) according to Solid Phase Synthesis General Method A. It was isolated as a white solid (14.1 mg). $^1$H NMR (500 MHz, DMSO) δ 7.90-7.85 (m, 2H), 7.39 (d, J=8.4 Hz, 2H), 6.23 (s, 1H), 5.17 (s, 1H), 4.37 (dd, J=17.9, 10.4 Hz, 4H), 3.88 (s, 2H), 3.84 (s, 3H), 3.70 (dd, J=10.5, 4.6 Hz, 1H), 3.47 (dd, J=10.4, 2.5 Hz, 1H), 2.20 (d, J=10.2 Hz, 3H), 2.11-2.03 (m, 1H), 1.92 (ddd, J=12.5, 7.2, 4.9 Hz, 1H). $^{13}$C NMR (126 MHz, DMSO) δ 171.66, 166.66, 166.10, 165.66, 159.35, 145.22, 129.08, 127.99, 127.06, 103.94, 68.62, 58.76, 55.20, 52.02, 41.49, 38.17, 32.73, 10.95. MS (ESI) 402.6 (M+H).

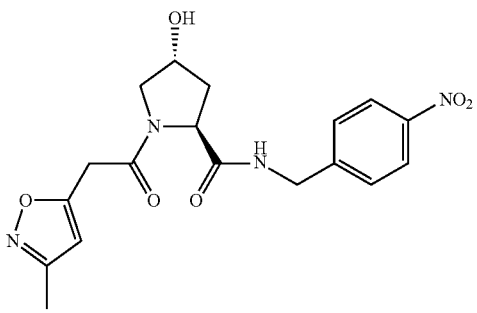

VL48

VL48 was synthesized from Fmoc-Hyp(OWang)-OAllyl (0.156 mmol) according to Solid Phase Synthesis General Method A. It was isolated as a white solid (11.4 mg). $^1$H NMR (400 MHz, MeOD) δ 8.28-8.05 (m, 2H), 7.55 (d, J=8.8 Hz, 2H), 6.23 (s, 1H), 4.64-4.36 (m, 4H), 3.94 (d, J=3.8 Hz, 2H), 3.81 (dd, J=10.9, 4.2 Hz, 1H), 3.65 (dt, J=11.0, 1.7 Hz, 1H), 2.34-2.21 (m, 4H), 2.09 (td, J=8.5, 4.2 Hz, 1H). $^{13}$C NMR (101 MHz, MeOD) δ 174.70, 168.79, 167.65, 161.63, 148.48, 147.72, 129.13, 124.56, 105.40, 70.88, 60.79, 57.03, 43.41, 39.32, 33.94, 11.20. MS (ESI) 389.3 (M+H), 411.4 (M+Na).

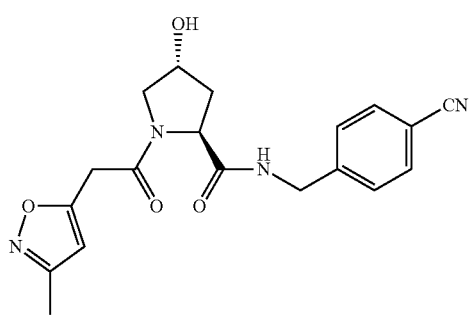

VL88

VL88 was synthesized from Fmoc-Hyp(OWang)-OAllyl (0.156 mmol) according to Solid Phase Synthesis General Method A. It was isolated as a clear oil (8.0 mg). $^1$H NMR (500 MHz, MeOD) δ 8.77 (s, 1H), 7.58 (dd, J=88.0, 8.1 Hz, 4H), 6.23 (d, J=4.4 Hz, 1H), 4.61-4.33 (m, 4H), 3.93 (d, J=9.7 Hz, 2H), 3.83-3.74 (m, 1H), 3.63 (dd, J=10.4, 9.0 Hz, 1H), 2.33-2.27 (m, 1H), 2.26 (d, J=3.7 Hz, 3H), 2.15-2.03 (m, 1H). $^{13}$C NMR (126 MHz, MeOD) δ 175.33, 168.76, 167.64, 161.61, 145.83, 133.39, 129.12, 119.74, 111.79, 105.28, 70.87, 70.87, 59.32, 57.02, 43.61, 38.79, 33.94, 11.21, 11.19. MS (ESI) 391.2 (M+Na).

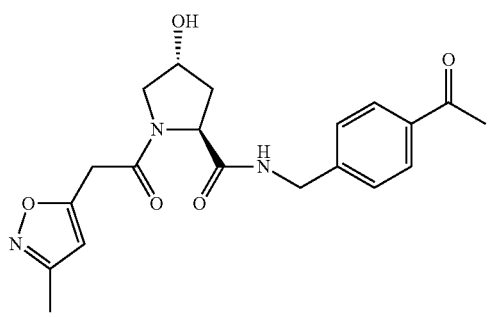

VL95

VL95 was synthesized from Fmoc-Hyp(OWang)-OAllyl (0.156 mmol) according to Solid Phase Synthesis General Method A. It was isolated as a white solid (23 mg). $^1$H NMR (400 MHz, MeOD) δ 8.71 (s, 1H), 7.96-7.91 (m, 2H), 7.43 (d, J=8.5 Hz, 2H), 6.22 (s, 1H), 4.56 (t, J=8.0 Hz, 1H), 4.49 (ddd, J=18.6, 8.6, 4.1 Hz, 3H), 3.91 (s, 2H), 3.80 (dd, J=10.9, 4.2 Hz, 1H), 3.65-3.58 (m, 1H), 2.58 (d, J=1.6 Hz, 3H), 2.28-2.22 (m, 4H), 2.10 (dd, J=8.3, 4.7 Hz, 1H). $^{13}$C NMR (101 MHz, MeOD) δ 200.08, 174.34, 168.43, 167.36, 161.39, 145.50, 136.96, 129.62, 128.28, 105.26, 70.65, 60.57, 56.83, 43.72, 39.14, 33.87, 26.73, 11.30. MS (ESI) 386.0 (M+H).

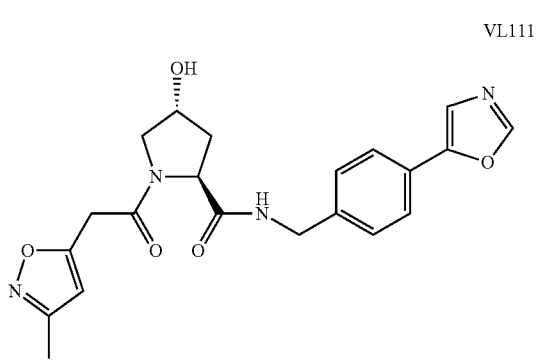 [SMILES: Cc1cc(CC(=O)N2C[C@H](O)C[C@H]2C(=O)NCc2ccc(-c3cnco3)cc2)on1]

VL111

VL111 was synthesized from Fmoc-Hyp(OWang)-OAllyl (0.2 mmol) according to Solid Phase Synthesis General Method A. It was isolated as a white solid (18.2 mg). $^1$H NMR (500 MHz, MeOD) δ 8.23 (s, 1H), 7.68 (d, J=8.1 Hz, 2H), 7.49 (s, 1H), 7.41 (d, J=8.1 Hz, 2H), 6.23 (s, 1H), 4.59-4.37 (m, 4H), 3.93 (d, J=3.4 Hz, 2H), 3.81 (dd, J=10.9, 4.1 Hz, 1H), 3.63 (d, J=11.0 Hz, 1H), 2.32-2.17 (m, 4H), 2.09 (ddd, J=13.0, 8.0, 4.6 Hz, 1H). $^{13}$C NMR (126 MHz, MeOD) δ 174.43, 168.72, 167.67, 161.60, 153.14, 152.75, 140.78, 129.06, 127.74, 125.61, 121.81, 105.37, 70.86, 60.78, 57.00, 43.72, 39.35, 33.96, 11.20. MS (ESI) 411.3 (M+H).

VL116 Right Hand Fragment (Representative Method B Synthesis)

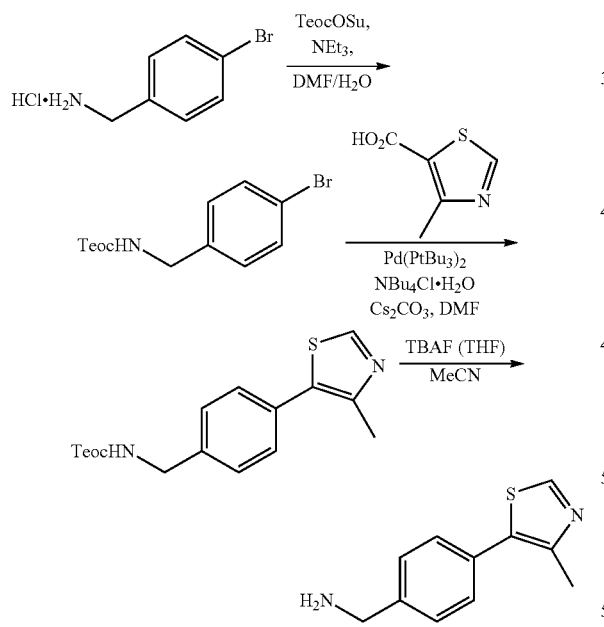

2-(trimethylsilyl)ethyl 4-bromobenzylcarbamate

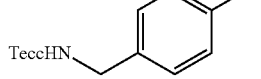

4-Bromobenzylamine hydrochloride (354 mg, 1.59 mmol, 1 eq) was dissolved in DMF (6.4 mL) and water (2.1 mL) and stirred at room temperature. Triethylamine (0.33 mL, 2.39 mmol, 1.5 eq) and TeocOSu (454 mg, 1.75 mmol, 1.1 eq) were then added. After 12 hours, the mixture was diluted with EtOAc, washed with 1M HCl, saturated sodium bicarbonate, water and brine. The organic layer was then dried over sodium sulfate, filtered, and concentrated under reduced pressure. Purification by column chromatography (10 to 20% EtOAc/hexanes) gave a colorless oil (0.4158 g, 1.26 mmol, 79%). $^1$H NMR (500 MHz, CDCl$_3$) δ 7.48-7.43 (m, 2H), 7.17 (d, J=8.1 Hz, 2H), 4.94 (s, 1H), 4.31 (d, J=6.0 Hz, 2H), 4.23-4.15 (m, 2H), 1.04-0.93 (m, 2H), 0.04 (s, 9H). $^{13}$C NMR (126 MHz, CDCl$_3$) 156.91, 137.95, 131.88, 129.32, 121.43, 63.53, 44.53, 17.92, −1.32. MS (ESI) 354.1 (M+H).

2-(trimethylsilyl)ethyl 4-(4-methylthiazol-5-yl)benzylcarbamate

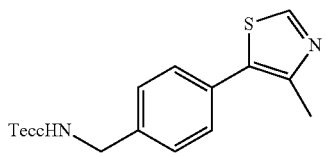

2-(trimethylsilyl)ethyl 4-bromobenzylcarbamate (132 mg, 0.4 mmol, 1 eq), 4-methylthiazole-5-carboxylic acid (114.5 mg, 0.8 mmol, 2 eq), tetrabutylammonium chloride hydrate (118 mg, 0.4 mmol, 1 eq), cesium carbonate (196 mg, 0.6 mmol, 1.5 eq) and Pd(P(tBu)$_3$)$_2$ (40.8 mg, 0.08 mmol, 0.2 eq) were dissolved in DMF (4 mL).$^1$ The reaction was heated to 170° C. in a microwave reactor for 16 minutes. The mixture was then cooled to room temperature, diluted with EtOAc and washed thrice with brine, once with saturated sodium bicarbonate, water, and then brine. The organic layer was dried over sodium sulfate, filtered and concentrated under reduced pressure. Purification by column chromatography (10 to 35% EtOAc/hexanes) gave a colorless oil (61.7 mg, 0.177 mmol, 44%). $^1$H NMR (400 MHz, CDCl$_3$) δ 8.67 (s, 1H), 7.43-7.37 (m, 2H), 7.34 (d, J=8.1 Hz, 2H), 5.09 (s, 1H), 4.39 (d, J=6.0 Hz, 2H), 4.28-4.02 (m, 2H), 2.52 (s, 3H), 1.10-0.90 (m, 2H), 0.14-0.09 (m, 9H). $^{13}$C NMR (101 MHz, CDCl$_3$) δ 156.98, 150.42, 148.66, 138.76, 131.67, 131.18, 129.66, 127.89, 63.46, 44.71, 17.90, 16.18, −1.34. MS (ESI) 349.0 (M+H).

(4-(4-methylthiazol-5-yl)phenyl)methanamine

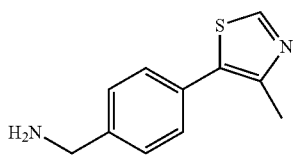

2-(trimethylsilyl)ethyl 4-(4-methylthiazol-5-yl)benzylcarbamate (51.8 mg, 0.149 mmol, 1 eq) was dissolved in acetonitrile (6 mL) at room temperature. A one molar solution of tetrabutylammonium fluoride in THF (0.45 mL, 0.45 mmol, 3 eq) was added and the solution was stirred for 24 hours. The mixture was concentrated under reduced pressure. Purification by column chromatography (0.5 to 4% 0.5N NH$_3$ (MeOH)/DCM) gave a light yellow oil (27.2 mg, 0.133 mmol, 89%). $^1$H NMR (500 MHz, MeOD) δ 8.87 (s, 1H), 7.44 (s, 4H), 3.85 (s, 2H), 2.47 (s, 3H). $^{13}$C NMR (126 MHz, MeOD) δ 152.77, 149.07, 143.63, 133.42, 131.46, 130.49, 129.05, 46.23, 15.79. MS (ESI) 205.0 (M+H).

Alternate Route:

4-bromobenzonitrile (5.1 g, 28 mmol, 1 eq), 4-methylthiazole (5.56 g, 56 mmol, 2 eq) potassium acetate (5.5 g, 56 mmol, 2 eq), palladium (II) acetate (63 mg, 0.28 mmol, 1 mol %) were dissolved in dimethylacetamide and stirred under argon. (CITE JOC, 2009, 74, 1179) The mixture was heated to 150° C. and stirred for 19 hours, then diluted with 500 mL EtOAc, and washed 4 times with 300 mL water. The first wash was then back extracted with 300 mL EtOAc, and then washed 4 times with 100 mL water. The combined organic layer was dried over sodium sulfate, filtered and concentrated under vacuum to give a beige solid (5.55 g, 27.7 mmol, 99%) that matched the reported spectral data.[8] The solid was then dissolved in MeOH (280 mL) and cooled to 4° C. Cobalt chloride (9.9 g, 41.6 mmol, 1.5 eq) was added, followed by the slow, portionwise addition of sodium borohydride (5.2 g, 139 mmol, 5 eq), which was accompanied by vigorous bubbling. After 90 minutes, the reaction was quenched by the addition of water and ammonium hydroxide. The mixture was extracted 4 times with chloroform, and purified by column chromatography (10 to 30% 0.5M NH$_3$ (MeOH)/DCM) to give a darker oil (4.12 g, 20.2 mmol, 73%).

General Solution Phase Synthesis (2S,4R)-allyl 4-(tert-butoxy)pyrrolidine-2-carboxylate

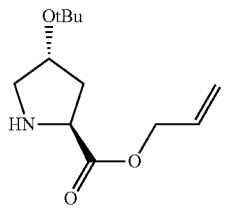 [SMILES: C=CCOC(=O)[C@@H]1C[C@@H](OC(C)(C)C)CN1]

(2S,4R)-1-((9H-fluoren-9-yl)methyl) 2-allyl-4-(tert-butoxy)pyrrolidine-1,2-dicarboxylate (7.0 g, 15.57 mmol, 1 eq) was dissolved in DCM (156 mL) and cooled to 4° C. Tris(2-aminoethyl)amine (5.8 mL, 38.9 mmol, 2.5 eq) was added, and the solution was stirred for 1 hour at 4° C. and 4.5 hours at room temperature. The mixture was then mixed with silica gel (roughly 20 g), and concentrated under reduced pressure, and purified by column chromatography (1 to 5% 0.5N NH$_3$ (MeOH)/DCM) to give an opaque oil (3.44 g, 15.1 mmol, 97%). $^1$H NMR (400 MHz, MeOH) δ 6.03-5.88 (m, 1H), 5.25 (dq, J=17.2, 1.8 Hz, 1H), 5.09 (dq, J=10.5, 1.6 Hz, 1-H), 4.33-4.23 (m, 1H), 4.06 (dt, J=5.1, 1.6 Hz, 2H), 3.86 (t, J=8.0 Hz, 1H), 3.18 (dd, J=11.4, 5.7 Hz, 1H), 2.70 (dd, J=11.4, 3.8 Hz, 1H), 2.00 (dd, J=8.0, 5.0 Hz, 2H), 1.19 (s, 9H). $^{13}$C NMR (101 MHz, MeOH) δ 175.89, 138.93, 114.88, 74.93, 72.93, 63.97, 59.77, 55.44, 40.18, 28.65. MS (ESI) 228.0 (M+H).

(2S,4R)-allyl 4-(tert-butoxy)-1-(2-(3-methylisoxazol-5-yl)acetyl)pyrrolidine-2-carboxylate

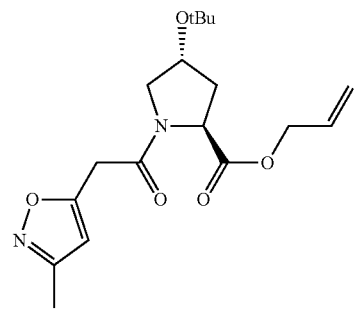 [SMILES: C=CCOC(=O)[C@@H]1C[C@@H](OC(C)(C)C)CN1C(=O)Cc1cc(C)no1]

(2S,4R)-allyl 4-(tert-butoxy)pyrrolidine-2-carboxylate (0.148 g, 0.65 mmol, 1 eq) was dissolved in DMF (6.5 mL) and cooled to 4° C. 2-(3-methylisoxazol-5-yl)acetic acid (0.12 g, 0.85 mmol, 1.3 eq), EDC (0.163 g, 0.85 mmol, 1.3 eq), HOBt (0.123 g, 0.91 mmol, 1.4 eq), and DIPEA (0.283 mL, 1.63 mmol, 2.5 eq) were added, and the solution was allowed to warm slowly to room temperature. After 12 hours, the mixture was poured into brine and extracted four times with EtOAc. The organic layer was dried over sodium sulfate, filtered and concentrated under reduced pressure. Purification by column chromatography (1 to 3% MeOH/DCM) gave a light yellow oil (0.2008 g, 0.573 mmol, 88%). $^1$H NMR (500 MHz, CDCl$_3$) δ 6.17 (s, 1H), 5.95-5.85 (m, 1H), 5.29 (ddd, J=13.8, 11.7, 1.3 Hz, 2H), 4.69-4.55 (m, 3H), 4.40-4.32 (m, 1H), 3.84-3.75 (m, 3H), 3.37 (dd, J=10.0, 4.7 Hz, 1H), 2.27 (s, 3H), 2.15 (ddd, J=18.5, 12.0, 5.9 Hz, 2H), 1.18 (s, 9H). $^{13}$C NMR (126 MHz, CDCl$_3$) δ 171.87, 165.94, 165.63, 160.30, 131.84, 118.72, 104.04, 74.53, 69.55, 65.98, 57.96, 54.53, 37.31, 33.58, 28.35, 11.62. MS (ESI) 351.5 (M+H).

(2S,4R)-4-(tert-butoxy)-1-(2-(3-methylisoxazol-5-yl)acetyl)pyrrolidine-2-carboxylic acid

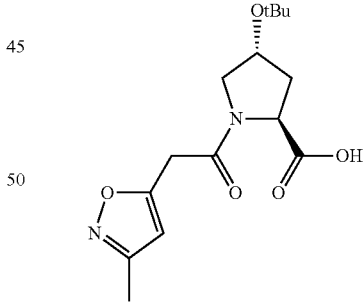

(2S,4R)-allyl 4-(tert-butoxy)-1-(2-(3-methylisoxazol-5-yl)acetyl)pyrrolidine-2-carboxylate (1.67 g, 4.77 mmol, 1 eq) was dissolved in THF (48 mL) at room temperature. Pd(PPh$_3$)$_4$ (0.55 g, 0.48 mmol, 0.1 eq) and morpholine (4.2 mL, 48 mmol, 10 eq) were then added. After 35 minutes, the solution was concentrated under reduced pressure, redissolved in DCM, and washed four times with 1M HCl (aq). The aqueous layer was then back extracted once with DCM. The combined organic layer was then dried over sodium sulfate, filtered and concentrated under reduced pressure. Purification by column chromatography (1 to 20% MeOH/DCM) gave a yellow solid (1.27 g, 4.1 mmol, 86%). $^1$H NMR (500 MHz, MeOH) δ 6.23 (s, 1H), 4.47 (t, J=6.0 Hz, 2H), 3.94-3.80 (m, 3H), 3.48 (dd, J=10.6, 3.8 Hz, 1H), 2.28-2.11 (m, 5H), 1.21 (s, 9H). $^{13}$C NMR (126 MHz, MeOH) δ 175.53, 168.41, 167.68, 161.59, 105.25, 75.57, 71.00, 59.36, 55.81, 38.49, 33.88, 28.48, 11.20. MS (ESI) 311.2 (M+H).

General Method B Representative Procedure (with Hydroxyl Group Protection): VL116

(2S,4R)-4-(tert-butoxy)-1-(2-(3-methylisoxazol-5-yl) acetyl)-N-(4-(4-methylthiazol-5-yl)benzyl)pyrrolidine-2-carboxamide

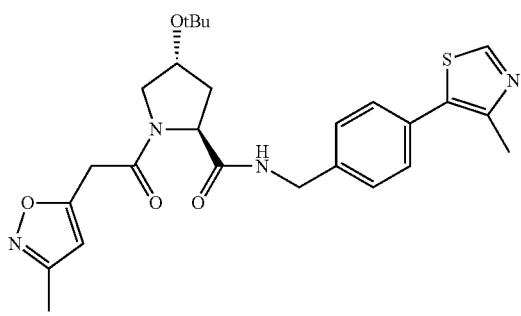 [SMILES: Cc1cc(CC(=O)N2C[C@H](OC(C)(C)C)C[C@H]2C(=O)NCc2ccc(-c3scnc3C)cc2)on1]

(2S,4R)-4-(tert-butoxy)-1-(2-(3-methylisoxazol-5-yl) acetyl)pyrrolidine-2-carboxylic acid (53.7 mg, 0.173 mmol, 1.3 eq), (4-(4-methylthiazol-5-yl)phenyl)methanamine (27.2 mg, 0.133 mmol, 1 eq), EDC (33.2 mg, 0.173 mmol, 1.3 eq), and HOBt (23.4 mg, 0.173 mmol, 1.3 eq) were dissolved in DMF (3.5 mL) at 4° C. DIPEA (0.07 mL, 0.4 mmol, 3 eq) was added, and the solution was allowed to slowly warm to room temperature. After 19 hours, the mixture was poured into brine and extracted four times with EtOAc. The organic layer was dried with sodium sulfate, filtered and concentrated under reduced pressure. Purification by column chromatography (1 to 5% MeOH/DCM) gave a colorless oil (58.1 mg, 0.117 mmol, 88%). $^1$H NMR (400 MHz, CDCl$_3$) δ 8.67 (s, 1H), 7.42-7.27 (m, 5H), 6.06 (s, 1H), 4.69 (dd, J=8.4, 2.6 Hz, 1H), 4.59-4.35 (m, 3H), 3.82-3.71 (m, 3H), 3.34 (dd, J=9.9, 6.3 Hz, 1H), 2.59-2.46 (m, 4H), 2.25 (s, 3H), 1.91 (dd, J=8.2, 4.4 Hz, 1H), 1.25-1.14 (m, 9H). $^{13}$C NMR (101 MHz, CDCl$_3$) δ 170.70, 167.35, 165.30, 160.24, 150.42, 148.59, 138.09, 131.74, 131.05, 129.66, 127.85, 104.19, 74.48, 70.02, 59.12, 54.20, 43.25, 35.59, 33.49, 28.38, 16.19, 11.57. MS (ESI) 497.4 (M+H).

(2S,4R)-4-hydroxy-1-(2-(3-methylisoxazol-5-yl) acetyl)-N-(4-(4-methylthiazol-5-yl)benzyl)pyrrolidine-2-carboxamide (VL116)

(2S,4R)-4-(tert-butoxy)-1-(2-(3-methylisoxazol-5-yl)acetyl)-N-(4-(4-methylthiazol-5-yl)benzyl)pyrrolidine-2-carboxamide (58.1 mg, 0.117 mmol) was dissolved in DCM (8 mL). TFA (2 mL, 20% vol/vol) was added and the solution was stirred for 12 hours at room temperature, after which it was concentrated under reduced pressure. Purification by column chromatography (1 to 10% 0.5N NH$_3$ (MeOH)/DCM) gave a colorless oil (28.4 mg, 0.065 mmol, 56%). $^1$H NMR (400 MHz, MeOH) δ 8.87 (d, J=2.1 Hz, 1H), 7.50-7.34 (m, 4H), 6.23 (s, 1H), 4.57 (t, J=8.0 Hz, 1H), 4.54-4.38 (m, 3H), 3.93 (d, J=2.4 Hz, 2H), 3.81 (dd, J=10.9, 4.3 Hz, 1H), 3.63 (dd, J=7.2, 5.5 Hz, 1H), 2.46 (d, J=8.8 Hz, 3H), 2.33-2.20 (m, 4H), 2.10 (ddd, J=13.1, 8.2, 4.7 Hz, 1H). $^{13}$C NMR (101 MHz, MeOH) δ 174.43, 168.71, 167.66, 161.58, 152.83, 149.04, 140.14, 133.39, 131.56, 130.43, 128.88, 105.39, 70.86, 60.78, 57.00, 43.65, 39.36, 33.96, 15.81, 11.22. MS (ESI) 441.3 (M+H).

General Method A Representative Procedure: VL133

(2S,4R)-4-hydroxy-1-(2-(3-methylisoxazol-5-yl) acetyl)pyrrolidine-2-carboxylic acid

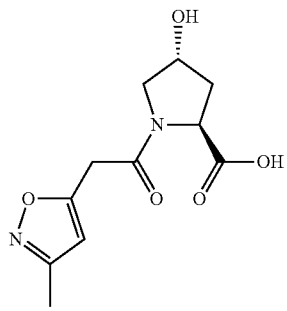

(2S,4R)-4-(tert-butoxy)-1-(2-(3-methylisoxazol-5-yl) acetyl)pyrrolidine-2-carboxylic acid (124.9 mg, 0.4 mmol, 1 eq) was dissolved in DCM (18 mL) at room temperature. TFA (2 mL, 10%) was added, and the solution was stirred for 12 hours. It was then concentrated under reduced pressure and purified by column chromatography (4 to 20% MeOH/DCM) to give a yellow oil (99.7 mg, 0.39 mmol, 98%). $^1$H NMR (500 MHz, MeOD) δ 6.24 (s, 1H), 4.55-4.46 (m, 2H), 3.89 (d, J=28.3 Hz, 2H), 3.77 (dd, J=10.9, 4.3 Hz, 1H), 3.62 (d, J=11.0 Hz, 1H), 2.36-2.22 (m, 4H), 2.10 (ddd, J=13.1, 8.0, 4.8 Hz, 1H). $^{13}$C NMR (126 MHz, CDCl$_3$) δ 175.33, 168.51, 167.61, 161.61, 105.28, 70.86, 59.33, 56.60, 38.78, 33.85, 11.20. MS (ESI) 255.1 (M+H).

(2S,4R)—N-(4-(1H-pyrrol-3-yl)benzyl)-4-hydroxy-1-(2-(3-methylisoxazol-5-yl)acetyl)pyrrolidine-2-carboxamide (VL133)

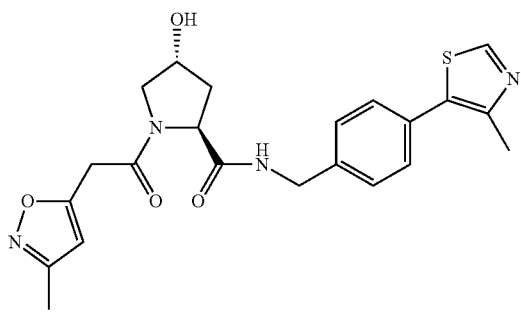 [SMILES: Cc1cc(CC(=O)N2C[C@H](O)C[C@H]2C(=O)NCc2ccc(-c3scnc3C)cc2)on1]

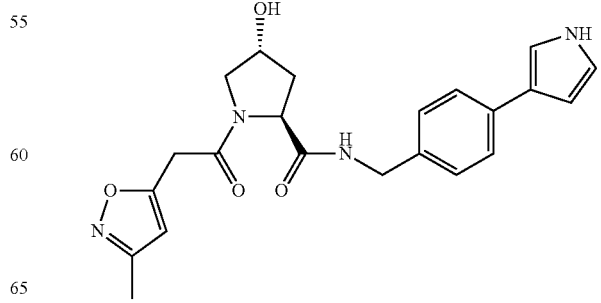

(2S,4R)-4-hydroxy-1-(2-(3-methylisoxazol-5-yl)acetyl)pyrrolidine-2-carboxylic acid (52.6 mg, 0.207 mmol, 1.3 eq), (4-(1H-pyrrol-3-yl)phenyl)methanamine (27.3 mg, 0.159 mmol, 1 eq), EDC (39.7 mg, 0.207 mmol, 1.3 eq) and HOBt (28 mg, 0.207 mmol, 1.3 eq) were dissolved in DMF (4.1 mL) and cooled to 4° C. DIPEA (0.083 mL, 0.477 mmol, 3 eq) was added and the solution was allowed to slowly warm to room temperature. After 16 hours, the mixture was poured into half saturated sodium chloride (aqueous) and extracted 3 times with EtOAc. The organic layer was dried over sodium sulfate, filtered and concentrated under reduced pressure. Purification by column chromatography (1 to 10% 0.5N $NH_3$ (MeOH)/DCM) gave an off white solid (41.5 mg, 0.102 mmol, 64%). $^1$HNMR (400 MHz, DMSO) δ 8.40 (d, J=6.0 Hz, 1H), 7.52-7.39 (m, 2H), 7.22-7.12 (m, 3H), 6.82-6.72 (m, 1H), 6.41 (d, J=1.7 Hz, 1H), 6.24 (s, 1H), 5.17 (d, J=3.9 Hz, 1H), 4.31 (ddd, J=17.1, 13.7, 6.4 Hz, 4H), 3.88 (s, 2H), 3.75-3.65 (m, 1H), 3.52-3.41 (m, 1H), 2.18 (d, J=18.0 Hz, 3H), 2.12-1.99 (m, 1H), 1.94-1.85 (m, 1H). $^{13}$C NMR (101 MHz, DMSO) δ 171.36, 166.69, 165.54, 159.38, 135.66, 134.68, 127.20, 124.21, 123.00, 118.86, 114.71, 105.22, 103.99, 68.61, 58.76, 55.18, 41.63, 38.27, 32.78, 11.00. MS (ESI) 431.5 (M+Na).

For further reference see the following articles and the references cited therein:

(1) Buckley D L et al. *J. Am. Chem. Soc* 2012, 134, 4465-4468.
(2) Van Molle I et al. A *Chemistry & Biology* 2012, 19, 1300-1312
(3) Buckley, D. *Angew. Chem. Int. Ed.*, 2012, 51, 11463-11467
(4) Buckley, D. L et al. *Angew. Chem.* 2012, 124, 11630-11634.

Examples Second Set

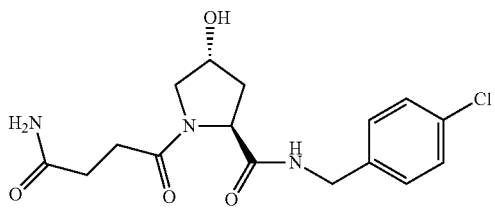

VL50

VL50 was synthesized from Fmoc-Hyp(OWang)-OAllyl resin (0.156 mmol) according to Solid Phase Synthesis General Method B. It was isolated as a white solid (29.8 mg, 0.084 mmol, 54%). $^1$H NMR (400 MHz, CD$_3$OD): δ7.34-7.27 (m, 4H); 5.43-5.35 (m, 4H); 3.81-3.78 (dd, J=8 Hz, 4 Hz, 1H); 3.61-3.57 (m, 1H); 2.65-2.61 (m, 2H); 2.57-2.51 (m, 2H); 2.28-2.21 (m, 1H); 2.08-2.02 (m, 1H). $^{13}$C NMR (100 MHz, CD$_3$OD): δ 177.53, 174.74, 173.76, 138.75, 133.76, 129.96, 129.49, 70.71, 60.55, 56.47, 43.25, 39.33, 30.97, 30.64. MS (ESI) 354.2 (M+H).

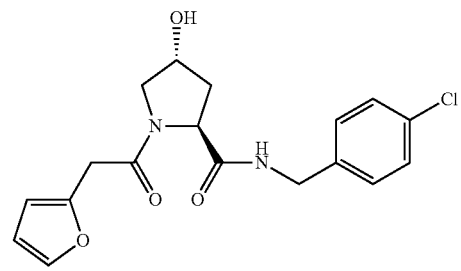

VL52

VL52 was synthesized from Fmoc-Hyp(OWang)-OAllyl resin (0.156 mmol) according to the Solid Phase Synthesis General Method B. It was isolated as a white solid (7.7 mg, 0.021 mmol, 14%). $^1$H NMR (500 MHz, CD$_3$OD): δ7.41 (d, J=2 Hz, 1H); 7.30 (s, 4H); 6.35-6.34 (dd, J=3 Hz, 2 Hz, 1H); 6.26-6.25 (d, J=3 Hz, 1H); 4.49-4.32 (m, 4H); 3.82-3.73 (m, 31-1); 3.65-2.62 (m, 1H); 2.23-2.22 (m, 1H); 2.09-2.06 (m, 1H).$^{13}$C NMR (125 MHz, CD$_3$OD): δ174.54, 170.58, 149.67, 143.24, 138.68, 133.84, 129.98, 129.53, 111.50, 108.98, 70.88, 60.75, 56.95, 43.31, 39.24, 35.58. MS (ESI) 365.2 (M+H), 385.3 (M+Na).

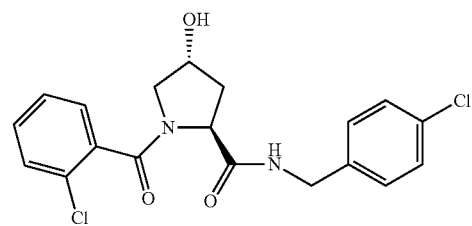

VL73

VL73 was synthesized from Fmoc-Hyp(OWang)-OAllyl resin (0.18 mmol) according to Solid Phase Synthesis General Method B. It was isolated as a clear oil (38.9 mg, 0.099 mmol, 55%).$^1$H NMR (500 MHz, CD$_3$OD) δ 7.51-6.99 (m, 8H), 4.72 (t, J=8.2, 1H), 4.55-4.33 (m, 3H), 3.60 (dd, J=3.7, 11.3, 1H), 3.19 (dd, J=1.5, 11.3, 1H), 2.36-2.25 (m, 1H), 2.21-2.03 (m, 1H).$^{13}$C NMR (126 MHz, CD$_3$OD) δ 174.03, 169.66, 138.62, 137.31, 133.87, 132.12, 130.92, 130.48, 129.98, 129.56, 129.16, 128.53, 70.64, 60.38, 43.39, 39.25, 24.21. MS (ESI) 395.3 (M+H).

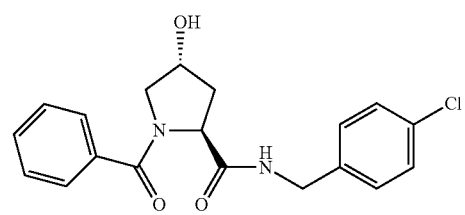

VL64

VL64 was synthesized from Fmoc-Hyp(OWang)-OAllyl resin (0.156 mmol) according to the Solid Phase Synthesis General Method B. It was isolated as a white solid (27.5 mg, 0.077 mmol, 49%).$^1$H NMR (500 MHz, CD$_3$OD) δ 7.66-7.59 (m, 2H), 7.54-7.22 (m, 7H), 4.75 (t, J=8.6, 1H), 4.55-4.33 (m, 3H), 3.85 (dd, J=3.0, 11.5, 1H), 3.43 (d, J=11.5, 1H), 2.38-2.26 (m, 1H), 2.14-2.05 (m, 1H).$^{13}$C NMR (126 MHz, CD$_3$OD) δ 174.72, 172.78, 138.73, 137.14, 133.83, 131.74, 129.93, 129.55, 129.49, 128.56, 71.04, 60.85, 59.80, 43.34, 39.28. MS (ESI) 359.1 (M+H).

VL69

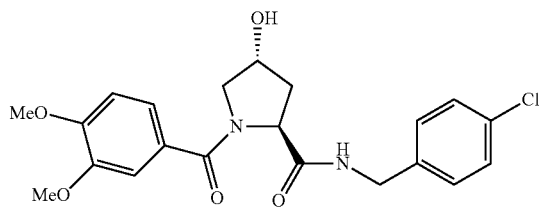

VL69 was synthesized from Fmoc-Hyp(OWang)-OAllyl resin (0.156 mmol) according to Solid Phase Synthesis General Method B. It was isolated as a white solid (26.1 mg, 0.62 mmol, 40%). $^1$H NMR (500 MHz, DMSO) δ 7.30 (dt, J=8.2, 25.1, 4H), 7.20 (dd, J=1.7, 8.3, 1H), 7.13 (d, J=1.7, 1H), 7.01 (d, J=8.4, 1H), 4.98 (s, 1H), 4.56 (t, J=8.6, 1H), 4.29 (d, J=2.6, 2H), 3.76 (dd, J=15.5, 30.6, 7H), 3.36 (d, J=11.1, 1H), 2.14 (dd, J=7.7, 12.8, 1H), 1.96-1.83 (m, 1H). $^{13}$C NMR (126 MHz, DMSO) δ 171.91, 168.82, 150.39, 148.08, 138.70, 131.10, 128.68, 128.09, 121.00, 111.44, 110.75, 99.56, 68.90, 59.33, 59.30, 58.68, 55.57, 41.17, 38.01. MS (ESI) 418.8 (M+H).

VL70

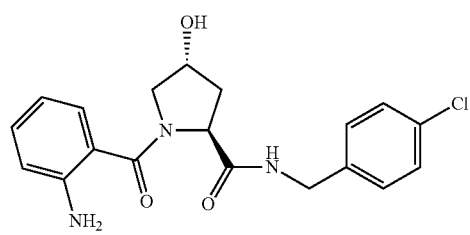

VL70 was synthesized from Fmoc-Hyp(OWang)-OAllyl resin (0.156 mmol) according to Solid Phase Synthesis General Method B. It was isolated as a colorless oil (31.1 mg, 0.083 mmol, 53%). $^1$H NMR (500 MHz, CD$_3$OD) δ 7.38-7.17 (m, 6H), 6.85-6.73 (m, 2H), 4.76 (t, J=8.5, 1H), 4.53-4.31 (m, 3H), 3.85 (dd, J=3.2, 11.6, 1H), 3.37 (d, J=11.6, 1H), 2.50-2.24 (m, 1H), 2.08 (ddd, J=4.3, 9.1, 13.3, 1H). $^{13}$C NMR (126 MHz, CD$_3$OD) δ 174.72, 172.14, 145.18, 138.67, 133.87, 132.18, 129.97, 129.56, 128.80, 122.39, 118.87, 117.94, 71.01, 60.29, 58.54, 43.40, 39.40. MS (ESI) 374.5 (M+H).

VL71

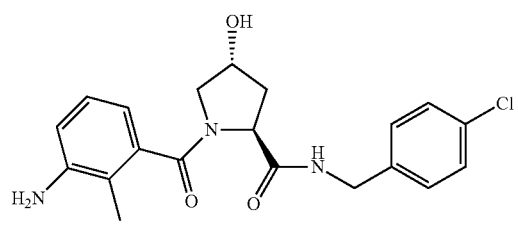

VL71 was synthesized from Fmoc-Hyp(OWang)-OAllyl resin (0.156 mmol) according to the Solid Phase Synthesis General Method B. It was isolated as a colorless oil (31.1 mg, 0.080 mmol, 51%). $^1$H NMR (500 MHz, CD$_3$OD) δ 7.40-7.32 (m, 4H), 7.24 (t, J=7.6, 1H), 7.09 (d, J=7.9, 1H), 7.03 (d, J=7.1, 1H), 4.74 (t, J=8.2, 1H), 4.59-4.33 (m, 3H), 3.54 (d, J=11.0, 1H), 3.20 (d, J=11.2, 1H), 2.35 (dd, J=8.7, 12.4, 1H), 2.26 (s, 3H), 2.14 (dd, J=4.3, 9.3, 1H). $^{13}$C NMR (126 MHz, CD$_3$OD) δ 174.37, 172.44, 140.91, 139.29, 138.69, 133.84, 129.93, 129.55, 128.37, 124.30, 121.45, 120.64, 70.73, 60.11, 43.36, 39.44, 13.89. MS (ESI) 388.1, 390.3 (M+H).

VL72

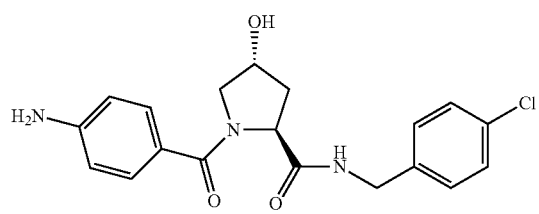

VL72 was synthesized from Fmoc-Hyp(OWang)-OAllyl resin (0.156 mmol) according to Solid Phase Synthesis General Method B. It was isolated as a yellow oil (31.3 mg, 0.084 mmol, 54%). $^1$H NMR (500 MHz, CD$_3$OD) δ 7.48 (d, J=8.3, 2H), 7.30 (s, 4H), 6.79 (d, J=8.3, 2H), 4.79-4.69 (m, 1H), 4.53-4.29 (m, 3H), 3.95-3.83 (m, 1H), 3.54 (d, J=11.4, 1H), 2.35-2.24 (m, 1H), 2.07 (ddd, J=3.9, 10.1, 13.5, 1H). $^{13}$C NMR (126 MHz, CD$_3$OD) δ 175.03, 173.02, 149.95, 138.75, 133.80, 130.79, 129.91, 129.54, 126.23, 115.89, 71.16, 61.03, 60.12, 43.31, 39.16. MS (ESI) 375.0 (M+H).

VL74


VL74 was synthesized from Fmoc-Hyp(OWang)-OAllyl resin (0.18 mmol) according to Solid Phase Synthesis General Method B. It was isolated as a white solid (36.3 mg, 0.092 mmol, 51%). $^1$H NMR (500 MHz, CD$_3$OD) δ 7.67-7.56 (m, 2H), 7.52-7.44 (m, 2H), 7.34-7.28 (m, 4H), 4.74 (dd, J=7.7, 9.6, 1H), 4.55-4.30 (m, 3H), 3.85 (dd, J=3.5, 11.4, 1H), 3.42 (d, J=11.4, 1H), 2.37-2.28 (m, 1H), 2.15-2.05 (m, 1H). $^{13}$C NMR (126 MHz, CD$_3$OD) δ 174.59, 171.54, 138.69, 137.75, 135.66, 133.84, 130.38, 129.92, 129.70, 129.55, 71.04, 60.92, 59.75, 43.34, 39.29. MS (ESI) 394.6 (M+H).

VL75

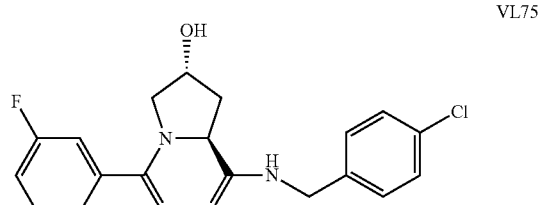

VL75 was synthesized from Fmoc-Hyp(OWang)-OAllyl resin (0.18 mmol) according to Solid Phase Synthesis General Method B. It was isolated as a white solid (25.0 mg, 0.066 mmol, 37%). ¹H NMR (500 MHz, CD₃OD) δ 7.64-6.87 (m, 8H), 4.73 (dd, J=7.7, 9.6, 1H), 4.54-4.31 (m, 3H), 3.84 (dd, J=3.5, 11.5, 1H), 3.42 (d, J=11.4, 1H), 2.33 (ddd, J=1.6, 7.6, 13.0, 1H), 2.13-2.05 (m, 1H). ¹³C NMR (126 MHz, CD₃OD) δ 174.64, 171.20, 163.83 (d, J=246.5), 139.35, 138.72, 133.86, 131.60, 129.94, 129.56, 124.51, 118.51 (d, J=21.3), 115.56 (d, J=23.4), 71.02, 60.94, 59.70, 43.47, 39.31. MS (ESI) 377.4 (M+H).

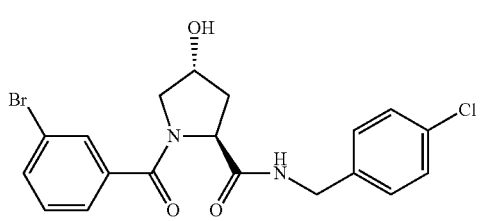

VL76

VL76 was synthesized from Fmoc-Hyp(OWang)-OAllyl resin (0.18 mmol) according to Solid Phase Synthesis General Method B. It was isolated as a white solid (29.6 mg, 0.067 mmol, 38%). ¹H NMR (400 MHz, CD₃OD) δ 7.82 (s, 1H), 7.70-7.58 (m, 2H), 7.40 (t, J=7.9, 1H), 7.36-7.18 (m, 4H), 4.73 (dd, J=7.9, 9.4, 1H), 4.53-4.31 (m, 3H), 3.82 (dt, J=5.2, 10.4, 1H), 3.40 (d, J=11.4, 1H), 2.33 (dd, J=7.6, 13.2, 1H), 2.09 (ddd, J=4.1, 9.7, 13.7, 1H). ¹³C NMR (101 MHz, CD₃OD) δ 174.53, 170.95, 139.22, 138.68, 134.68, 133.85, 131.56, 131.44, 129.92, 129.56, 127.31, 123.35, 71.02, 60.90, 59.70, 43.33, 39.31. MS (ESI) 439.4 (M+H).

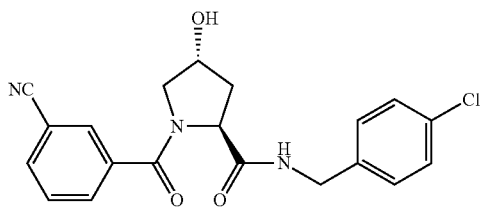

VL77

VL77 was synthesized from Fmoc-Hyp(OWang)-OAllyl resin (0.18 mmol) according to Solid Phase Synthesis General Method B. It was isolated as a white solid (31.0 mg, 0.081 mmol, 45%). ¹H NMR (500 MHz, DMSO) δ 8.07 (t, J=1.4, 1H), 8.01-7.95 (m, 1H), 7.93-7.88 (m, 1H), 7.69 (t, J=7.8, 1H), 7.40-7.23 (m, 4H), 4.56 (dd, J=8.3, 16.4, 1H), 4.30 (dd, J=8.1, 15.4, 3H), 3.79 (dd, J=3.6, 11.0, 1H), 3.24 (d, J=11.0, 1H), 2.23-2.15 (m, 1H), 1.92 (ddd, J=4.2, 9.3, 13.2, 1H). ¹³C NMR (126 MHz, DMSO) δ 171.51, 167.29, 138.64, 137.27, 133.88, 132.29, 131.16, 131.08, 129.73, 128.68, 128.15, 118.25, 111.40, 68.82, 59.39, 59.36, 58.28, 38.19. MS (ESI) 383.8 (M+H).

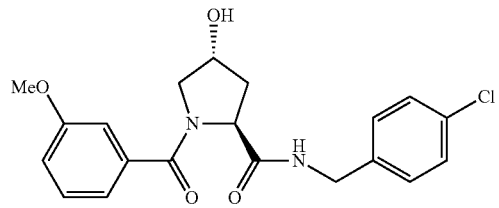

VL79

VL79 was synthesized from Fmoc-Hyp(OWang)-OAllyl resin (0.18 mmol) according to Solid Phase Synthesis General Method B. It was isolated as a white solid (34.9 mg, 0.090 mmol, 50%). ¹H NMR (500 MHz, CD₃OD) δ 7.41-7.15 (m, 6H), 7.08-6.90 (m, 2H), 4.73 (dd, J=7.7, 9.6, 1H), 4.54-4.31 (m, 3H), 3.87-3.74 (m, 4H), 3.43 (d, J=11.5, 1H), 2.37-2.27 (m, 1H), 2.14-2.05 (m, 1H). ¹³C NMR (126 MHz, CD₃OD) δ 174.72, 172.59, 161.07, 138.72, 138.40, 133.83, 130.67, 129.93, 129.56, 120.58, 117.52, 113.77, 71.01, 60.82, 59.80, 55.87, 43.33, 39.29. MS (ESI) 389.0 (M+H).

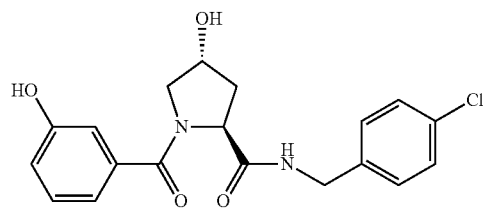

VL80

VL80 was synthesized from Fmoc-Hyp(OWang)-OAllyl resin (0.18 mmol) according to Solid Phase Synthesis General Method B. It was isolated as a white solid (41.2 mg, 0.110 mmol, 61%). ¹H NMR (500 MHz, CD₃OD) δ 7.36-6.76 (m, 8H), 4.72 (dd, J=7.8, 9.4, 1H), 4.53-4.31 (m, 3H), 3.82 (dd, J=3.5, 11.6, 1H), 3.45 (d, J=11.6, 1H), 2.34-2.27 (m, 1H), 2.14-2.03 (m, 1H). ¹³C NMR (126 MHz, CD₃OD) δ 174.81, 172.77, 158.73, 138.74, 138.36, 133.83, 130.64, 129.93, 129.56, 119.39, 118.62, 115.26, 71.01, 60.81, 59.80, 43.46, 39.24. MS (ESI) 375.4 (M+H).

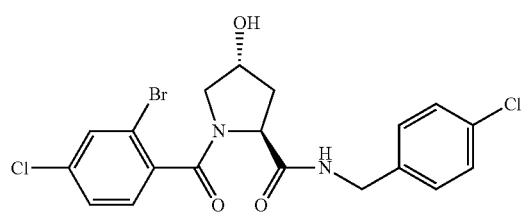

VL81

VL81 was synthesized from Fmoc-Hyp(OWang)-OAllyl resin (0.18 mmol) according to Solid Phase Synthesis General Method B. It was isolated as a colorless oil (42.9 mg, 0.091 mmol, 50%). ¹H NMR (500 MHz, CD₃OD) δ 7.77-7.27 (m, 6H), 7.04 (d, J=8.3, 1H), 4.71 (t, J=8.2, 1H), 4.56-4.30 (m, 3H), 3.59 (dd, J=3.7, 11.2, 1H), 3.17 (d, J=11.3, 1H), 2.37-2.25 (m, 1H), 2.19-2.09 (m, 1H). ¹³C NMR (126 MHz, CD₃OD) δ 173.87, 169.41, 138.18, 137.15, 133.71, 130.60, 130.36, 130.00, 129.69, 129.56, 129.40, 120.48, 70.62, 69.41, 60.48, 43.53, 39.23. MS (ESI) 472.1 (M+H).

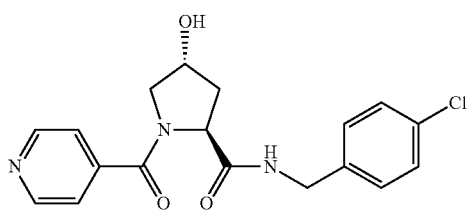

VL96

VL96 was synthesized from Fmoc-Hyp(OWang)-OAllyl resin (0.155 mmol) according to Solid Phase Synthesis General Method B. It was isolated as a light yellow oil (36.6 mg, 0.102 mmol, 66%). $^1$H NMR (500 MHz, CD$_3$OD) δ 8.81 (s, 1H), 8.66 (dd, J=4.6, 1.5 Hz, 2H), 7.60 (dd, J=4.5, 1.6 Hz, 2H), 7.32-7.25 (m, 4H), 4.70 (dd, J=9.3, 7.9 Hz, 1H), 4.46 (dd, J=15.3, 6.3 Hz, 1H), 4.39 (s, 1H), 4.33 (dd, J=15.4, 5.5 Hz, 1H), 3.78 (dd, J=11.4, 3.5 Hz, 1H), 3.27 (dt, J=3.2, 1.6 Hz, 1H), 2.31 (dd, J=13.2, 7.6 Hz, 1H), 2.08 (ddd, J=13.5, 9.6, 4.2 Hz, 1H). $^{13}$C NMR (126 MHz, CD$_3$OD) δ 174.32, 169.63, 150.65, 145.83, 138.68, 133.88, 129.96, 129.56, 123.32, 70.99, 60.88, 59.33, 43.49, 39.33. MS (ESI) 360.5 (M+H).

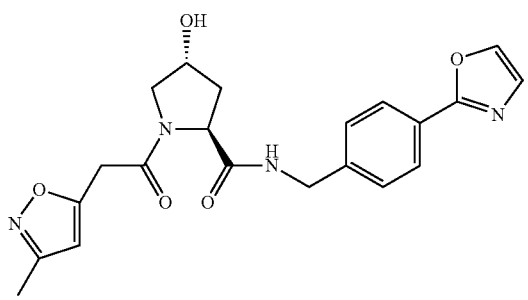

VL112

VL112 was synthesized from Fmoc-Hyp(OWang)-OAllyl resin (0.2 mmol) according to Solid Phase Synthesis General Method A. It was isolated as a cream colored solid (22.6 mg, 0.055 mmol, 28%). $^1$H NMR (500 MHz, CD$_3$OD) δ 7.98 (d, J=7.1 Hz, 3H), 7.46 (d, J=8.0 Hz, 2H), 7.28 (s, 1H), 6.23 (s, 1H), 4.62-4.39 (m, 4H), 3.93 (d, J=2.9 Hz, 2H), 3.81 (dd, J=10.9, 4.1 Hz, 1H), 3.64 (d, J=11.0 Hz, 1H), 2.33-2.17 (m, 4H), 2.15-2.04 (m, 1H). $^{13}$C NMR (126 MHz, CD$_3$OD) δ 174.50, 168.72, 167.68, 163.41, 161.60, 142.96, 140.75, 129.45, 128.96, 127.53, 127.15, 105.36, 70.87, 60.78, 56.99, 43.72, 39.36, 33.95, 11.20. MS (ESI) 410.9 (M+H).

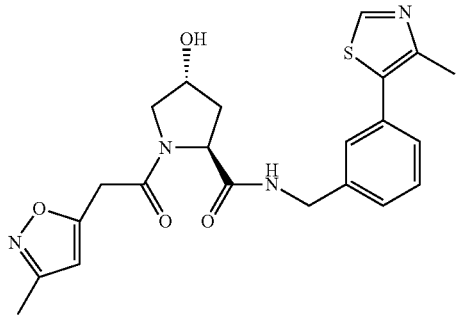

VL115

VL115 was synthesized according to General Method B. $^1$H NMR (500 MHz, CD$_3$OD) δ 8.87 (s, 1H), 7.46-7.40 (m, 2H), 7.36 (dd, J=8.8, 4.3 Hz, 2H), 6.20 (s, 1H), 4.55 (t, J=8.0 Hz, 1H), 4.50 (d, J=6.3 Hz, 1H), 4.48-4.42 (m, 2H), 3.92 (d, J=4.5 Hz, 2H), 3.80 (dd, J=10.9, 4.3 Hz, 1H), 3.62 (d, J=11.0 Hz, 1H), 2.48 (d, J=10.2 Hz, 3H), 2.31-2.21 (m, 4H), 2.08 (ddd, J=13.0, 8.2, 4.7 Hz, 1H). $^{13}$C NMR (126 MHz, CD$_3$OD) δ 174.48, 168.60, 167.70, 161.57, 152.92, 149.26, 140.81, 133.50, 133.09, 130.13, 129.24, 129.09, 128.34, 105.35, 70.86, 60.75, 56.95, 43.81, 39.38, 33.92, 15.87, 11.23. MS (ESI) 441.4 (M+H).

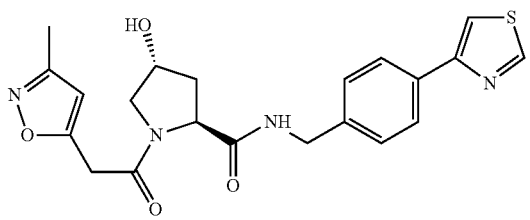

VL154

VL154 was synthesized according to General Method B. $^1$H NMR (500 MHz, CD$_3$OD) δ 8.95 (s, 1H), 8.44 (t, J=5.6, 1H), 7.84 (d, J=8.2, 2H), 7.70 (d, J=1.9, 1H), 7.35 (d, J=8.2, 2H), 6.19 (s, 1H), 4.56 (t, J=7.9, 1H), 4.51 (s, 1H), 4.43 (d, J=5.7, 2H), 3.87 (s, 2H), 3.78 (dd, J=10.9, 4.3, 1H), 3.58 (d, J=10.8, 1H), 2.24 (obscured s, 4H), 2.16-2.07 (m, 1H); $^{13}$C NMR (126 MHz, CD$_3$OD) δ 176.66, 170.98, 169.94, 164.15, 159.72, 157.62, 142.33, 136.89, 131.58, 130.33, 117.00, 108.05, 73.36, 63.27, 59.60, 46.75, 41.78, 36.80, 14.39; TLC: (EtOAC) R$_f$=0.5; LRMS (ESI) 427.6 (M+H)$^+$.

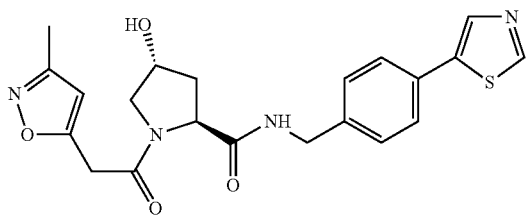

VL155

VL155 was synthesized according to General Method B. $^1$H NMR (500 MHz, CD$_3$OD) δ 8.87 (d, J=5.2, 1H), 8.54 (t, J=5.7, 1H), 8.07 (s, 1H), 7.56 (d, J=8.2, 2H), 7.36 (d, J=8.2, 2H), 6.20 (s, 1H), 4.56 (t, J=8.0, 1H), 4.51 (s, 1H), 4.42 (qd, J=5.5, 15.5, 2H), 3.78 (dt, J=9.2, 18.5, 1H), 3.60 (d, J=11.1, 1H), 2.28-2.21 (m, 4H), 2.10 (ddd, J=4.7, 8.0, 13.0, 1H); $^{13}$C NMR (126 MHz, CD$_3$OD) δ 176.72, 171.03, 169.98, 164.12, 142.98, 142.96, 133.45, 132.34 131.86, 130.07, 108.02, 100.0, 73.37, 63.29, 59.60, 46.52, 41.81, 36.74, 14.27. TLC: (EtOAC) R$_f$=0.5; LRMS (ESI) 427.4 (M+H)$^+$.

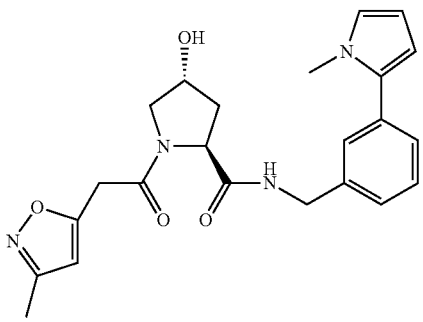

VL118

VL118 was synthesized according to General Method A. $^1$H NMR (500 MHz, CD$_3$OD) δ 7.37-7.31 (m, 2H), 7.27 (d, J=7.7 Hz, 1H), 7.22 (d, J=7.5 Hz, 1H), 6.74-6.68 (m, 1H), 6.20 (s, 1H), 6.14 (dd, J=3.5, 1.8 Hz, 1H), 6.10-6.05 (m, 1H), 4.55 (t, J=8.0 Hz, 1H), 4.49 (s, 1H), 4.45-4.39 (m, 2H), 3.89 (t, J=8.4 Hz, 1H), 3.79 (dd, J=10.9, 4.3 Hz, 1H), 3.67-3.55 (m, 5H), 2.26-2.22 (m, 4H), 2.07 (ddd, J=13.0, 8.1, 4.7 Hz, 1H). $^{13}$C NMR (126 MHz, CD$_3$OD) δ 174.35, 168.57, 167.66, 161.57, 139.94, 135.44, 135.24, 129.58, 128.35, 128.22, 126.62, 124.93, 109.56, 108.54, 105.37, 70.84, 60.72, 56.91, 44.04, 39.36, 35.34, 33.88, 11.23. MS (ESI) 422.8 (M+H).

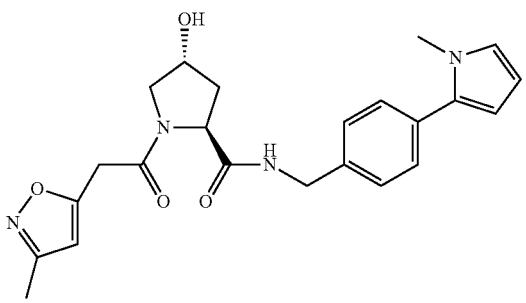

VL119

VL119 was synthesized according to General Method A. $^1$H NMR (500 MHz, CD$_3$OD) δ 7.38-7.30 (m, 4H), 6.76-6.67 (m, 1H), 6.23 (s, 1H), 6.10 (dd, J=3.5, 1.8 Hz, 1H), 6.09-6.05 (m, 1H), 4.56 (t, J=8.1 Hz, 1H), 4.51 (s, 1H), 4.47-4.39 (m, 2H), 3.93 (d, J=3.0 Hz, 2H), 3.81 (dd, J=10.9, 4.3 Hz, 1H), 3.63 (q, J=5.8 Hz, 4H), 2.31-2.22 (m, 4H), 2.10 (ddd, J=13.0, 8.1, 4.7 Hz, 1H). $^{13}$C NMR (101 MHz, ~1:1 CD$_3$OD:CDCl$_3$) δ 172.63, 167.39, 166.19, 160.68, 136.80, 132.70, 129.06, 128.99, 127.75, 124.09, 108.75, 107.93, 104.62, 69.88, 59.64, 56.15, 43.36, 37.98, 35.19, 33.53, 11.37. MS (ESI) 423.6 (M+H).

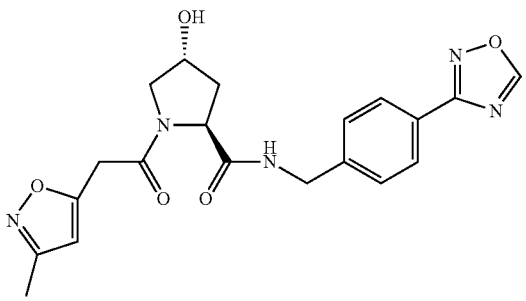

VL131

VL131 was synthesized according to General Method B. $^1$H NMR (400 MHz, CD$_3$OD) δ 9.02 (d, J=5.2 Hz, 1H), 8.02 (d, J=8.4 Hz, 2H), 7.41 (d, J=8.4 Hz, 2H), 6.17 (s, 1H), 4.52-4.38 (m, 4H), 3.84 (s, 2H), 3.76 (dd, J=10.8, 4.3 Hz, 1H), 3.56 (d, J=9.5 Hz, 1H), 2.30-2.18 (m, 4H), 2.14 (td, J=8.1, 3.9 Hz, 1H). $^{13}$C NMR (101 MHz, CD$_3$OD) δ 173.25, 167.86, 167.57, 166.44, 166.18, 160.85, 142.53, 128.33, 128.14, 125.56, 104.77, 70.04, 59.87, 56.31, 43.52, 38.30, 33.60, 11.39. MS (ESI) 413.3 (M+H).

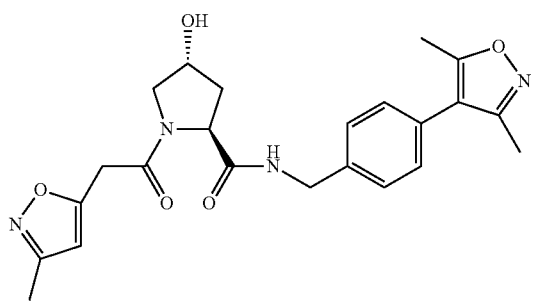

VL138

VL138 was synthesized according to General Method B. $^1$H NMR (400 MHz, CD$_3$OD) δ 7.42 (d, J=8.2 Hz, 2H), 7.32-7.24 (m, 2H), 6.24 (s, 1H), 4.69-4.33 (m, 5H), 3.94 (d, J=3.0 Hz, 1H), 3.82 (dd, J=10.9, 4.3 Hz, 1H), 3.64 (d, J=11.1 Hz, 1H), 2.38 (s, 3H), 2.31-2.24 (m, 4H), 2.23 (s, 3H), 2.10 (ddd, J=13.1, 8.2, 4.7 Hz, 1H). $^{13}$C NMR (126 MHz, CD$_3$OD) δ 174.41, 168.72, 167.67, 166.87, 161.59, 160.02, 139.46, 130.38, 129.37, 128.89, 117.72, 105.38, 70.87, 60.78, 57.01, 43.74, 39.37, 33.97, 11.38, 11.20, 10.66. MS (ESI) 438.6 (M+H).

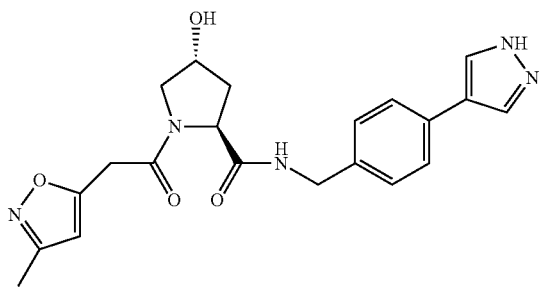

VL139

VL139 was synthesized according to General Method B. $^1$H NMR (400 MHz, ~1:1 CD$_3$OD:CDCl$_3$) δ 7.89 (s, 2H), 7.49 (d, J=8.1 Hz, 2H), 7.28 (d, J=7.9 Hz, 2H), 6.20 (s, 1H), 4.54 (dd, J=17.4, 9.5 Hz, 2H), 4.39 (d, J=5.3 Hz, 2H), 3.93-3.46 (m, 4H), 2.32-2.16 (m, 4H), 2.16-2.05 (m, 1H). $^{13}$C NMR (126 MHz, ~1:1 CD$_3$OD:CDCl$_3$) δ 173.80, 168.23, 167.21, 161.29, 137.35, 132.66, 129.24, 128.77, 126.60, 126.48, 105.16, 70.53, 60.42, 56.73, 43.71, 39.00, 33.85, 11.30. MS (ESI) 410.0 (M+H).

VL152

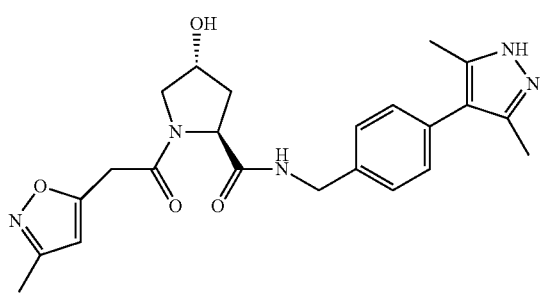

VL152 was synthesized according to General Method B. ¹H NMR (400 MHz, CD₃OD) δ 7.38 (d, J=8.2 Hz, 2H), 7.25 (d, J=8.2 Hz, 2H), 6.17 (d, J=55.2 Hz, 1H), 4.65-4.30 (m, 4H), 4.05-3.72 (m, 3H), 3.64 (d, J=11.1 Hz, 1H), 2.32-2.19 (m, 10H), 2.10 (ddd, J=13.1, 8.2, 4.7 Hz, 1H). ¹³C NMR (101 MHz, CD₃OD) δ 174.37, 168.72, 167.67, 161.59, 143.18, 138.27, 132.85, 130.54, 129.12, 128.64, 105.40, 70.86, 60.78, 57.01, 43.80, 39.38, 33.96, 11.21, 11.07. MS (ESI) 438.5 (M+H).

VL158

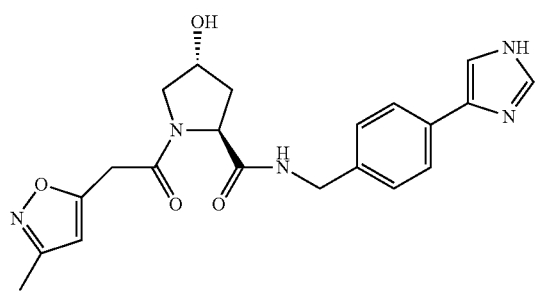

VL158 was synthesized according to General Method B. ¹H NMR (500 MHz, CD₃OD) δ 8.03 (s, 1H), 7.62 (t, J=8.7 Hz, 2H), 7.43 (d, J=6.6 Hz, 1H), 7.33 (t, J=6.5 Hz, 2H), 6.19 (s, 1H), 4.62-4.48 (m, 2H), 4.48-4.32 (m, 2H), 3.93-3.68 (m, 3H), 3.58 (s, 1H), 2.29-2.19 (m, 4H), 2.11 (ddd, J=13.0, 8.0, 4.8 Hz, 1-H). ¹³C NMR (126 MHz, CD₃OD) δ 173.59, 168.01, 166.92, 161.11, 138.84, 135.95, 130.48, 129.06, 128.64, 125.89, 116.23, 105.04, 70.35, 60.24, 56.60, 43.56, 38.76, 33.78, 11.33. MS (ESI) 410.1 (M+H).

VL160

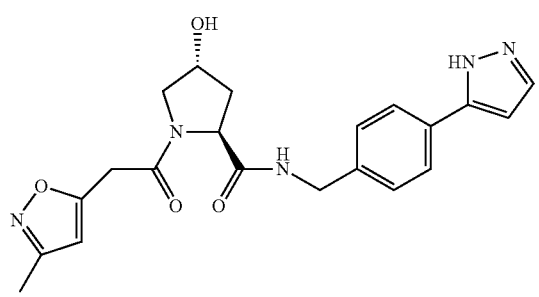

VL160 was synthesized according to General Method B. ¹H NMR (500 MHz, CD₃OD) δ 7.68 (d, J=8.1 Hz, 2H), 7.63 (s, 1H), 7.33 (d, J=8.0 Hz, 2H), 6.63 (s, 1H), 6.19 (s, 1H), 4.54 (t, J=8.0 Hz, 1H), 4.47 (s, 1H), 4.38 (d, J=4.6 Hz, 2H), 3.89 (d, J=3.1 Hz, 2H), 3.78 (dd, J=10.9, 4.3 Hz, 1H), 3.60 (d, J=11.1 Hz, 1H), 2.28-2.14 (m, 4H), 2.06 (ddd, J=13.0, 8.1, 4.7 Hz, 1H). ¹³C NMR (126 MHz, CD₃OD) δ 174.32, 168.69, 167.67, 161.61, 139.59, 132.31, 129.33, 128.86, 127.00, 126.87, 105.49, 105.38, 70.84, 60.78, 56.97, 43.80, 39.35, 33.95, 11.19. MS (ESI) 409.2 (M+H), 431.8 (M+Na).

(2S,4R)-(9H-fluoren-9-yl)methyl 4-(tert-butoxy)-2-((4-chlorobenzyl)carbamoyl)pyrrolidine-1-carboxylate

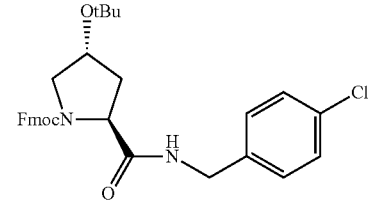

Fmoc-Hyp(OtBu)-OH (1.23 g, 3 mmol, 1 eq) was dissolved in DCM (15 mL) and cooled to 4° C. EDC (0.69 g, 3.6 mmol, 1.2 eq) and HOBt (0.49 g, 3.6 mmol, 1.2 eq) were then added. After 20 minutes, 4-chlorobenzylamine (0.48 mL, 3.9 mmol, 1.3 eq) was added and the solution was allowed to warm slowly to room temperature. After 15 hours, the mixture was diluted with EtOAc and washed with 1M HCl, sodium bicarbonate, water and brine. The organic layer was dried with sodium sulfate, filtered and condensed. Purification by column chromatography (25 to 100% EtOAc/hexanes) gave a white foam (1.42 g, 2.66 mmol, 89%). ¹H NMR (400 MHz, CDCl₃) δ 7.77 (d, J=7.2 Hz, 2H), 7.57 (s, 2H), 7.40 (t, J=7.3 Hz, 2H), 7.31 (t, J=7.3 Hz, 2H), 7.17 (dd, J=27.2, 19.5 Hz, 4H), 4.58-3.94 (m, 7H), 3.60 (d, J=6.7 Hz, 1H), 3.31 (d, J=6.6 Hz, Hz), 2.50 (s, 1-H), 1.96 (s, 1H), 1.28-1.10 (m, 9H). ¹³C NMR (101 MHz, CDCl₃) δ 171.54, 156.13, 143.74, 141.32, 136.81, 133.02, 128.79, 128.71, 127.83, 127.12, 125.04, 120.07, 74.15, 69.63, 67.87, 59.17, 53.26, 47.10, 42.72, 36.34, 28.31. MS (ESI) 534.8 (M+H).

(2S,4R)-4-(tert-butoxy)-N-(4-chlorobenzyl)pyrrolidine-2-carboxamide

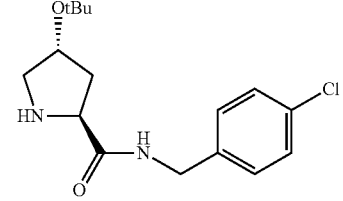 [SMILES: CC(C)(C)O[C@H]1CN[C@H](C(=O)NCc2ccc(Cl)cc2)C1]

(2S,4R)-(9H-fluoren-9-yl) methyl 4-(tert-butoxy)-2-((4-chlorobenzyl)carbamoyl)pyrrolidine-1-carboxylate (0.5 g, 0.94 mmol, 1 eq) was dissolved in DCM (15 mL) and cooled to 4° C. Tris(2-aminoethyl)amine (0.35 mL, 2.34 mmol, 2.5 eq) was added slowly, dropwise. After 30 minutes, the reaction was warmed to room temperature and stirred for an additional 14 hours. It was loaded directly onto a silica column, and purified by column chromatography (1 to 7% 0.5N methanolic ammonia/DCM) to give a white solid (0.2871 g, 0.92 mmol, 98%). $^1$H NMR (400 MHz, CD$_3$OD) δ 7.27 (dd, J=20.1, 8.4 Hz, 4H), 4.35 (s, 2H), 4.22 (s, 1H), 3.84 (t, J=8.0 Hz, 1H), 3.08 (dd, J=11.4, 5.1 Hz, 1H), 2.76 (dd, J=11.4, 2.8 Hz, 1H), 2.14-1.98 (m, 1H), 1.97-1.81 (m, 1H), 1.17 (s, 9H). $^{13}$C NMR (126 MHz, CD$_3$OD) δ 176.48, 138.81, 133.83, 130.00, 129.52, 74.76, 73.37, 60.80, 55.61, 43.04, 40.76, 28.67.

General Method C: Representative Procedure: VL156

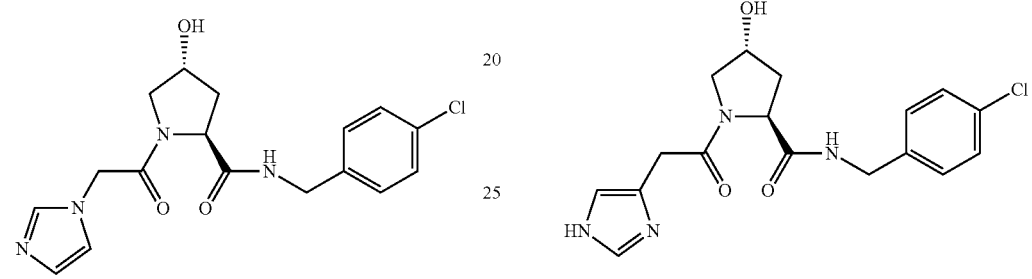

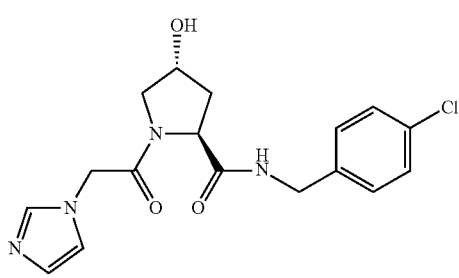 [SMILES: O=C(NCc1ccc(Cl)cc1)[C@@H]1C[C@@H](O)CN1C(=O)Cn1ccnc1]

1H-Imidazol-1-ylacetic acid (20.6 mg, 0.163 mmol, 1.3 eq), EDC (31.2 mg, 0.163 mmol, 1.3 eq) and HOBt (22 mg, 0.163 mmol, 1.3 eq) were dissolved in DCM (2.5 mL) and DMF (0.4 mL) at room temperature in a 1 dram vial. After stirring for 15 minutes, DIPEA (0.055 mL, 0.313 mmol, 2.5 eq) was added, followed by (2S,4R)-4-(tert-butoxy)-N-(4-chlorobenzyl)pyrrolidine-2-carboxamide (38.9 mg, 0.125 mmol, 1 eq) after an additional 30 minutes. The mixture was stirred for 14 hours, then diluted with EtOAc and washed with brine. The organic layer was dried over sodium sulfate, filtered and condensed. Purification by column chromatography (1 to 10% MeOH/DCM) gave a white solid, which was used directly in the following step. $^1$H NMR (400 MHz, CD$_3$OD) δ 7.65 (s, 1H), 7.28 (td, J=10.9, 8.4 Hz, 4H), 7.06 (d, J=43.6 Hz, 2H), 4.99 (dd, J=38.1, 17.1 Hz, 2H), 4.51 (t, J=6.6 Hz, 2H), 4.35 (q, J=15.4 Hz, 2H), 3.86 (dd, J=10.2, 5.6 Hz, 1H), 3.45 (dd, J=10.3, 4.1 Hz, 1H), 2.22-2.02 (m, 2H), 1.21 (d, J=13.8 Hz, 9H). MS (ESI) 419.7 (M+H).

The white solid was dissolved in DCM (9 mL) at room temperature. TFA (1 mL) was added and the mixture was stirred for 12 hours and condensed. Purification by column chromatography (1 to 20% 0.5 N methanolic ammonia/DCM) gave a white solid (39.8 mg, 0.11 mmol, 88% over 2 steps. $^1$H NMR (400 MHz, CD$_3$OD) δ 8.73 (s, 1H), 7.47 (d, J=16.9 Hz, 2H), 7.26 (s, 4H), 5.25 (dd, J=37.5, 16.9 Hz, 2H), 4.56 (t, J=7.9 Hz, 2H), 4.44-4.27 (m, 2H), 3.82 (dd, J=10.8, 4.1 Hz, 1H), 3.63 (d, J=10.8 Hz, 1H), 2.36-2.22 (m, 1H), 2.07 (ddd, J=13.1, 8.3, 4.6 Hz, 1H). $^{13}$C NMR (126 MHz, CD$_3$OD) δ 174.14, 166.34, 138.56, 138.20, 133.87, 129.97, 129.49, 124.55, 121.47, 70.94, 61.00, 55.75, 51.33, 43.35, 39.21. MS (ESI) 364.8 (M+H).

VL120

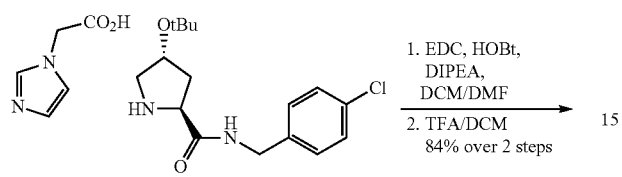

VL120 was synthesized according to General Method C. $^1$H NMR (500 MHz, CD$_3$OD) δ 8.67 (d, J=1.2 Hz, 1H), 7.36 (s, 1H), 7.29 (d, J=9.2 Hz, 4H), 4.62-4.47 (m, 2H), 4.47-4.24 (m, 2H), 3.87 (ddd, J=18.3, 15.1, 10.8 Hz, 3H), 3.66 (d, J=11.0 Hz, 1H), 2.37-2.20 (m, 1H), 2.07 (ddd, J=13.1, 8.4, 4.6 Hz, 1H). $^{13}$C NMR (126 MHz, CD$_3$OD) δ 174.56, 169.45, 138.62, 135.15, 133.89, 129.98, 129.72, 129.52, 118.80, 70.89, 60.70, 56.84, 43.35, 39.46, 31.70. MS (ESI) 362.3 (M+H).

VL157

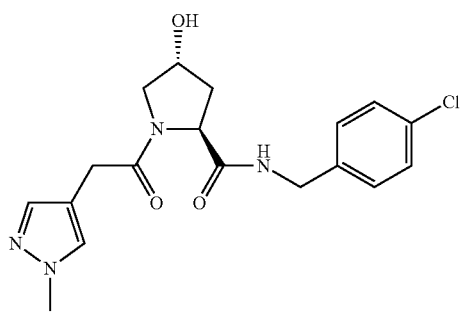

VL157 was synthesized according to General Method C. $^1$H NMR (500 MHz, CD$_3$OD) δ 7.49 (s, 1H), 7.39 (s, 1H), 7.34-7.22 (m, 4H), 4.52 (t, J=8.1 Hz, 1H), 4.50-4.45 (m, 1H), 4.37 (dt, J=22.8, 15.4 Hz, 2H), 3.87-3.80 (m, 3H), 3.77 (dd, J=11.0, 4.2 Hz, 1H), 3.66-3.52 (m, 3H), 2.30-2.18 (m, 1H), 2.04 (ddd, J=13.1, 8.3, 4.7 Hz, 1H). $^{13}$C NMR (126 MHz, CD$_3$OD) δ 174.67, 172.70, 140.18, 138.71, 133.81, 131.62, 129.95, 129.51, 115.17, 70.91, 60.65, 56.93, 43.29, 39.28, 38.76, 31.51. MS (ESI) 377.0 (M+H).

VL173

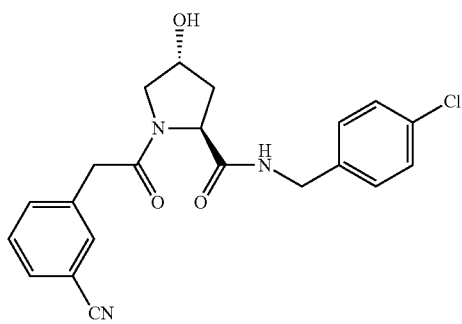

VL173 was synthesized according to General Method C. ¹H NMR (400 MHz, CDCl₃/CD₃OD) δ 7.63-7.53 (m, 3H); 7.49 (d, J=7.6 Hz, 1H); 7.26 (q, J=8.3 Hz, 4H); 4.60-4.51 (m, 2H); 4.42-4.32 (m, 2H); 3.84-3.75 (m, 3H); 3.59 (d, J=11.3 Hz, 1H); 3.42-3.32 (m, 1H); 2.29-2.19 (m, 1H); 2.17-2.08 (m, 1H). ¹³C NMR (100 MHz, CDCl₃/CD₃OD) δ 173.4, 170.7, 137.4, 136.8, 134.8, 133.6, 131.1, 129.9, 129.3, 129.0, 119.2, 112.7, 70.1, 59.8, 56.3, 43.0, 41.1, 38.4. TLC (10% MeOH in CH₂Cl₂), R$_f$ 0.38 (UV, CAM), MS (ESI+): calculated for C₂₁H₂₁N₃O₃Cl [M+H]⁺ 398.1. found 398.2.

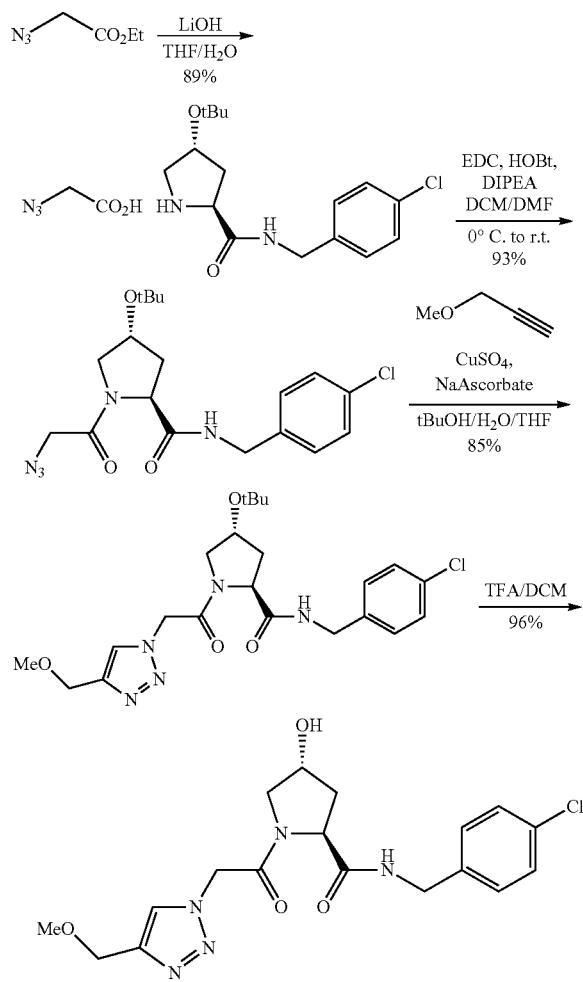

Azidoacetic Acid

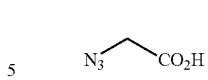

To a solution of ethyl azidoacetate (530 mg, 4.107 mmol) in THF—H₂O (12 mL/12 mL) at rt was added LiOH.H₂O (345 mg, 8.214 mmol). The reaction mixture was stirred at rt for 17 h, evaporated, and diluted with H₂O (10 mL), cooled to 0° C., and adjusted to pH 4 with 1N—HCl. The resulting mixture was extracted twice with diethyl ether, washed with brine, dried over anhydrous Na₂SO₄, and evaporated. The concentrate was purified by short column chromatography (eluting with 100% hexane initially, grading to 2% ethyl acetate in hexane) on silica gel to give azidoacetic acid 1 (372 mg, 89%) as a pale-yellow oil. ¹H NMR (500 MHz, CDCl₃) δ 9.73 (brs, 1H), 3.97 (s, 2H). ¹³C NMR (125 MHz, CD₃OD) δ 174.2, 50.0.

(2S,4R)-1-(2-azidoacetyl)-4-(tert-butoxy)-N-(4-chlorobenzyl)pyrrolidine-2-carboxamide

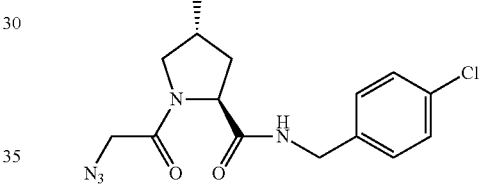

To a solution of azidoacetic acid (32 mg, 0.315 mmol) in CH₂Cl₂-DMF (1.5 mL/1.5 mL)) at room temperature were added (2S,4R)-4-(tert-butoxy)-N-(4-chlorobenzyl)pyrrolidine-2-carboxamide (93 mg, 0.300 mmol), DIPEA (0.19 mL, 1.080 mmol), and HOBt (48 mg, 0.360 mmol). The mixture was cooled to 0° C., and then EDC (69 mg, 0.360 mmol) was added to the mixture at 0° C. The reaction mixture was allowed to warm to rt, stirred at rt for 17 h, and cooled to 0° C. The resulting mixture was quenched with H₂O (5 mL) and extracted twice with ethylacetate. The combined extracts were washed with brine, dried over anhydrous Na₂SO₄, filtered, and evaporated. The concentrate was purified by column chromatography (eluting with 5% ethyl acetate in hexane initially, grading to 40% ethyl acetate in hexane) on silica gel to afford the coupled product (110 mg, 93%). ¹H NMR (400 MHz, CDCl₃) δ 7.31 (brs, 1H), 7.27 (d, J=8.5 Hz, 2H), 7.18 (d, J=8.5 Hz, 2H), 4.66 (dd, J=8.4, 2.2 Hz, 1H), 4.58-4.52 (m, 1H), 4.41 (dd, J=15.1, 6.1 Hz, 1H), 4.30 (dd, J=15.1, 5.8 Hz, 1H), 3.87 (dd, J=16.0, 16.0 Hz, 1H), 3.84 (dd, J=16.0, 16.0 Hz, 1H), 3.61 (dd, J=9.8, 7.0 Hz, 1H), 3.14 (dd, J=9.8, 6.4 Hz, 1H), 2.50 (ddd, J=12.6, 6.3, 2.3 Hz, 1H), 1.86 (dt, J=12.6, 8.2 Hz, 1H), 1.19 (s, 9H). ¹³C NMR, 100 MHz, CDCl₃) δ 170.3, 167.4, 162.5, 136.5, 133.1, 128.8, 128.7, 74.3, 69.9, 59.0, 52.7, 50.9, 42.8, 36.4, 35.1, 31.4, 28.2. MS (ESI) [M+H]⁺ 394.3.

239

(2S,4R)-4-(tert-butoxy)-N-(4-chlorobenzyl)-1-(2-(4-(methoxymethyl)-1H-1,2,3-triazol-1-yl)acetyl)pyrrolidine-2-carboxamide

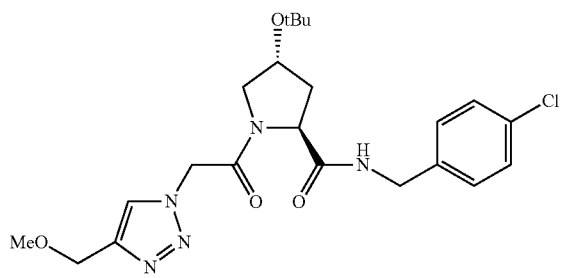 [SMILES: COCc1cn(CC(=O)N2C[C@H](OC(C)(C)C)C[C@H]2C(=O)NCc2ccc(Cl)cc2)nn1]

To a solution of methyl propargyl ether (7 mg, 0.067 mmol) and (2S,4R)-1-(2-azidoacetyl)-4-(tert-butoxy)-N-(4-chlorobenzyl)pyrrolidine-2-carboxamide (25 mg, 0.0636 mmol) in t-BuOH—H$_2$O (1:1, 1 mL) and THF (1 mL) at rt were added CuSO$_4$.5H$_2$O (1.5 mg, 0.006 mmol) and sodium ascorbate (1.0 M in H$_2$O, 2 drops). The reaction mixture was stirred at rt for 19 h and evaporated. The residue was diluted with H$_2$O (5 mL) and the mixture was extracted three times with ethyl acetate. The combined extracts were washed with brine, dried over Na$_2$SO$_4$, filtered, and concentrated. The crude residue was purified by flash chromatography on silica gel to give the desired triazole (25 mg, 85%). $^1$H NMR (500 MHz, CD$_3$OD) δ 7.91 (s, 1H), 7.30-7.22 (m, 4H), 5.43 (d, J=16.8 Hz, 1H), 5.34 (d, J=16.7 Hz, 1H), 4.54 (s, 2H), 4.53-4.49 (m, 2H), 4.37 (d, J=15.4 Hz, 1H), 4.31 (d, J=15.4 Hz, 1H), 3.90 (dd, J=10.3, 5.6 Hz, 1H), 3.49 (dd, J=10.4, 4.3 Hz, 1H), 3.37 (s, 3H), 2.19-2.13 (m, 1H), 2.11-2.07 (m, 1H), 1.22 (s, 9H). $^{13}$C NMR (asterisk denotes the signals of the minor rotamer, 125 MHz, CD$_3$OD) δ 174.1, *173.4, *166.9, 166.7, 145.7, *138.6, 138.5, *134.2, 133.8, *130.4, 129.9, *129.7, 129.5, 126.7, 75.6, *75.5, 71.1, *69.2, 66.3, *66.2, 60.8, *60.3, 58.4, *58.3, *55.5, 54.8, 52.6, *51.9, *43.7, 43.3, *41.1, 38.7, 28.5. MS (ESI) [M+H]$^+$464.2.

VL141

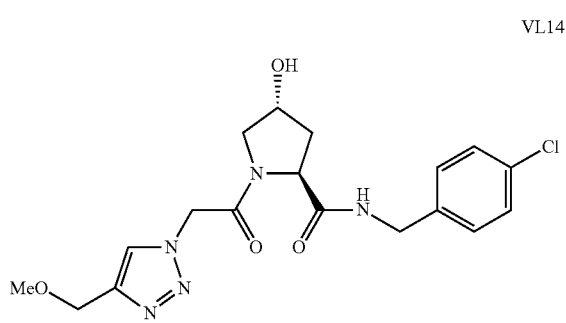

To a stirred solution of the corresponding t-butyl ether (22 mg, 0.0475 mmol) in CH$_2$Cl$_2$ (1.5 mL) at 0° C. was added TFA (0.2 mL). The reaction mixture was stirred at rt for 12 h and concentrated. The residue was chromatographed (eluting with 100% CH$_2$Cl$_2$ initially, grading to 7% CH$_3$OH in CH$_2$Cl$_2$) on silica gel to provide 5 (18.5 mg, 96%). $^1$H NMR (500 MHz, CD$_3$OD/CDCl$_3$=2:1) d 8.83 & 8.46 (due to the rotamers, both t, J=5.7 Hz, 1H), 7.85 & 7.76 (due to the rotamers, both s, 1H), 7.23 (d, J=8.5 Hz, 2H), 7.18 (d, J=8.5 Hz, 2H), 5.36 (d, J=16.6 Hz, 1H), 5.27 (d, J=16.6 Hz, 1H), 4.54 (s, 2H), 4.54-4.50 (m, 2H), 4.33 & 4.32 (due to the rotamers, both s, 2H), 3.77 (dd, J=10.8, 4.2 Hz, 1H), 3.60 (d, J=10.8 Hz, 1H), 3.37 & 3.36 (due to the rotamers, both s, 3H), 2.26-2.21 (m, 1H), 2.09-2.04 (m, 1H). $^{13}$C NMR (asterisk denotes the signals of the minor rotamer, 125 MHz, CD$_3$OD/CDCl$_3$=2:1) d *173.4, 173.3, *166.2, 165.9, 145.2, 137.5, *133.9, 133.5, 129.9, 129.4, 129.1, 126.0, *125.9, 70.4, *68.5, 66.0, *65.9, *60.4, 60.3, 58.4, *58.3, *56.1, 55.4, 52.2, *51.5, *43.2, 43.1, *41.1, 38.4. MS (ESI) [M+H]$^+$408.3. TLC (10% MeOH in CH$_2$Cl$_2$), R$_f$ 0.48 (UV, CAM).

VL167

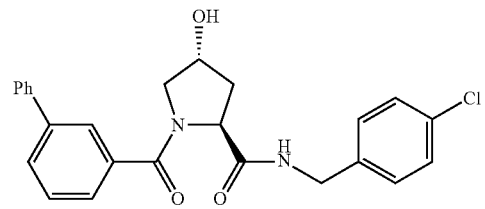

VL167 was synthesized according to General Method C. $^1$H NMR (500 MHz, CDCl$_3$) d 7.86 (s, 1H), 7.71 (d, J=9.5 Hz, 1H), 7.61 (d, J=7.4 Hz, 2H), 7.56 (d, J=7.6 Hz, 1H), 7.51 (d, J=7.6 Hz, 1H), 7.42 (dd, J=7.4, 7.4 Hz, 2H), 7.38-7.30 (m, 2H), 7.30-7.26 (m, 3H), 4.66-4.42 (m, 2H), 4.42-4.27 (m, 2H), 3.85 (dd, J=11.4, 3.5 Hz, 1H), 3.49 (d, J=11.4 Hz, 1H), 2.33-2.29 (m, 1H), 2.15-2.09 (m, 1H). $^{13}$C NMR (asterisk denotes the signals of the minor rotamer, 125 MHz, CDCl$_3$) d 172.5, 170.6, 162.7, 140.7, 139.3, 136.4, 135.6, 131.9, 128.2, *128.1, 128.0, 127.9, 127.6, *127.5, 126.8, 126.1, *126.0, 125.2, 125.1, 68.9, *67.4, *60.2, 58.7, 57.8, 41.5, *39.5, 37.2, 35.2, 30.0. MS (ESI) [M+H]$^+$435.5.

VL216

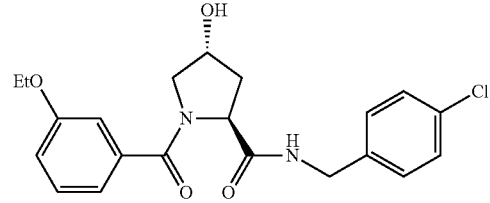

VL216 was synthesized according to General Method C.

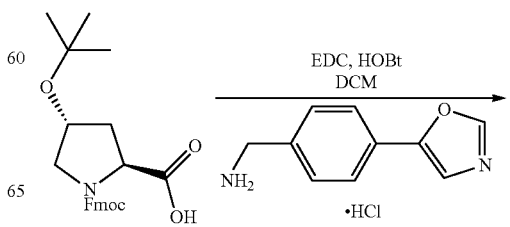

241

-continued

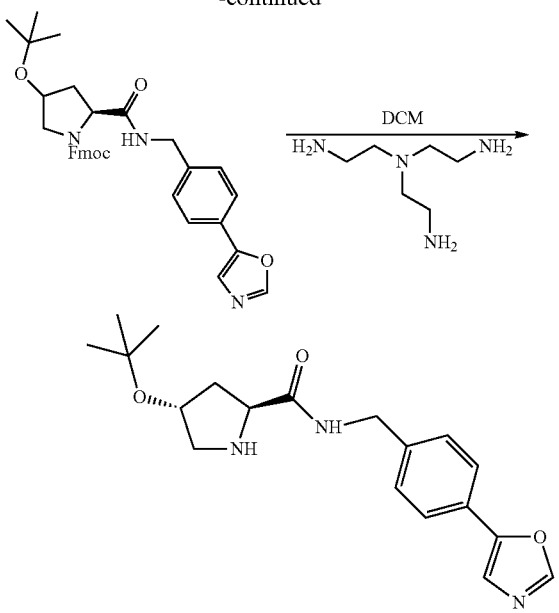

(2S,4R)-(9H-fluoren-9-yl)methyl 4-(tert-butoxy)-2-((4-(oxazol-5-yl)benzyl)carbamoyl)pyrrolidine-1-carboxylate

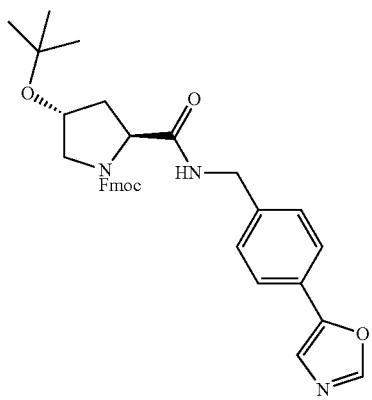

To a round bottom flask with stir bar was charged (2S,4R)-1-(((9H-fluoren-9-yl)methoxy)carbonyl)-4-(tert-butoxy) pyrrolidine-2-carboxylic acid (0.587, 1.4 mmol 1.0 equiv) EDC (380 mg, 2.0 mmol, 1.4 equiv), HOBt (310 mg, 2.0 mmol, 1.4 equiv) and (4-(oxazol-5-yl)phenyl)methanamine (250 mg, 1.4 mmol, 1.0 equiv). Upon stirring for 18 h the reaction was diluted with 25 ml DCM, and washed with citric acid (2×50 mL), and saturated NaHCO₃ (2×50 mL). The organic layer was dried with Na₂SO₄, concentrated down then purified via silica gel chromatography (DCM to 2% MeOH (0.5 N NH₃) to yield 515 mg (65% yield) of product as a viscous oil $^1$H NMR (400 MHz, CDCl₃) δ 7.89 (s, 1H), 7.85-7.70 (m, 2H), 7.68-7.49 (m, 4H), 7.47-7.37 (m, 2H), 7.35-7.20 (m, 5H), 4.54-4.35 (m, 4H), 4.35-4.14 (m, 2H), 3.72-3.58 (m, 1H), 3.49-3.27 (m, 1H), 2.53 (s, 1H), 2.00 (dd, J=8.1, 20.2, 1H), 1.25 (s, 9H); TLC: (9:1 DCM:MeOH (0.5 N NH₃)) $R_f$=0.5; LRMS (ESI) 565. 9 (M+H)⁺.

242

(2S,4R)-1-(3-ethoxybenzoyl)-4-hydroxy-N-(4-(4-methylthiazol-5-yl)benzyl)pyrrolidine-2-carboxamide

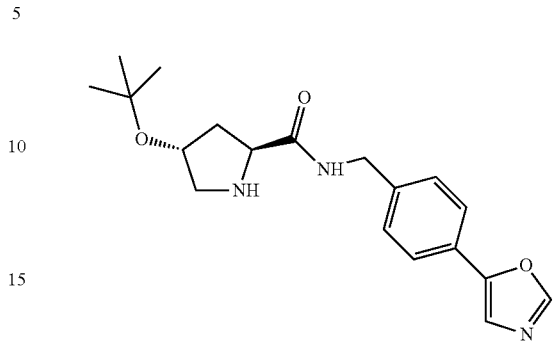

To (2S,4R)-(9H-fluoren-9-yl)methyl 4-(tert-butoxy)-2-((4-(oxazol-5-yl)benzyl)carbamoyl)pyrrolidine-1-carboxylate (2.5 g, 3.61 mmol, 1.0 equiv) in 36 mL DCM was charged tris(2-aminoethyl)amine mol, 9.0 mmol, 2.5 equiv).☐(400 upon stirring for 3 h the cloudy mixture was diluted with silica gel and concentrated down. The material was then dry loaded to a silica gel column and purified (DCM to 5% MeOH (0.5 N NH₃) in DCM) to yield 820 mg (67% yield) as a white solid. $^1$H NMR (501 MHz, CDCl₃) δ 8.02 (s, 1H), 7.90 (s, 1H), 7.60 (d, J=8.1, 2H), 7.33-7.29 (m, 3H), 4.44 (d, J=6.1, 2H), 4.21-4.07 (m, 1H), 3.97 (dd, J=7.2, 8.7, 1H), 2.87 (d, J=11.6, 1H), 2.80 (dd, J=4.3, 11.6, 1H), 2.17 (dd, J=10.2, 12.4, 1H), 2.11-1.94 (m, 1H), 1.16 (s, 9H); $^{13}$C NMR (126 MHz, CDCl₃) δ 174.88, 151.27, 150.40, 139.33, 128.07, 126.79, 124.63, 121.43, 73.65, 72.30, 59.95, 54.97, 42.51, 39.27, 28.38; TLC: (9:1 DCM:MeOH (0.5 N NH₃)) $R_f$=0.42; LRMS (ESI) 344.2 (M+H)⁺.

$^1$H NMR (400 MHz, CD₃OD) δ 7.42-7.28 (m, 4H), 7.28-7.12 (m, 2H), 7.10-6.77 (m, 2H), 4.71 (dt, J=30.7, 15.3 Hz, 1H), 4.58-4.30 (m, 3H), 4.18-3.92 (m, 2H), 3.87-3.77 (m, 1H), 3.44 (d, J=11.4 Hz, 1H), 2.38-2.24 (m, 1H), 2.15-2.03 (m, 1H), 1.55-1.23 (m, 314). $^{13}$C NMR (126 MHz, CD₃OD) δ 174.72, 172.63, 160.34, 138.72, 138.35, 133.82, 130.65, 130.11, 129.92, 129.55, 120.47, 118.08, 114.27, 113.89, 71.01, 64.71, 60.81, 59.80, 43.33, 39.29, 15.09. MS (ESI) 403.2 (M+H).

General Method D: Representative Procedure:

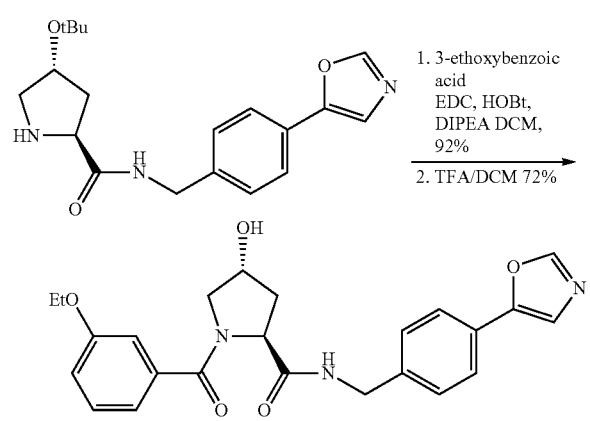

VL217

243

(2S,4R)-4-(tert-butoxy)-1-(3-ethoxybenzoyl)-N-(4-(oxazol-5-yl)benzyl)pyrrolidine-2-carboxamide

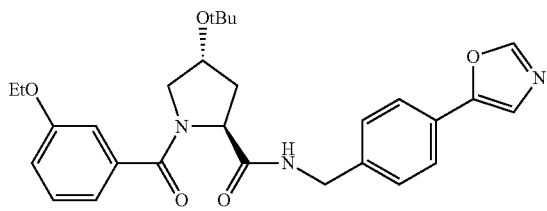 [SMILES: CCOc1cccc(C(=O)N2C[C@H](OC(C)(C)C)C[C@H]2C(=O)NCc2ccc(-c3cnco3)cc2)c1]

3-Ethoxybenzoic acid (13.3 mg, 0.08 mmol, 1 eq), EDC (16.9 mg, 0.088 mmol, 1.1 eq) and HOBt (11.9 mg, 0.88 mmol, 1.1 eq) were dissolved in DCM (0.8 mL) at room temperature. DIPEA (0.0279 mL, 0.16 mmol, 2 eq) was added, followed by (2S,4R)-4-(tert-butoxy)-N-(4-(oxazol-5-yl)benzyl)pyrrolidine-2-carboxamide (33.0 mg, 0.096 mmol, 1.2 eq). The solution was stirred for 21 hours then diluted with EtOAc and washed with 10% citric acid, saturated sodium bicarbonate and brine. The organic layer was dried over sodium sulfate, filtered and condensed. Purification by column chromatography (1 to 5% MeOH/DCM) gave a colorless oil (36.1 mg, 0.073 mmol, 92%). $^1$H NMR (400 MHz, CDCl$_3$) δ 7.90 (s, 1H), 7.61 (dd, J=16.6, 6.9 Hz, 3H), 7.38-7.27 (m, 4H), 6.98 (dd, J=16.0, 6.4 Hz, 3H), 4.92 (dd, J=8.3, 4.7 Hz, 1H), 4.48 (d, J=6.0 Hz, 2H), 4.43-4.31 (m, 1H), 4.03 (q, J=7.0 Hz, 2H), 3.61 (dd, J=10.9, 5.7 Hz, 1H), 3.31 (dd, J=10.9, 4.4 Hz, 1H), 2.73-2.55 (m, 1H), 2.05-1.92 (m, 1H), 1.40 (t, J=7.0 Hz, 3H), 1.13 (s, 9H). MS (ESI) 492.4 (M+H).

VL217

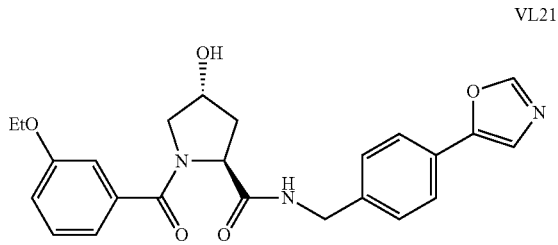

(2S,4R)-4-(tert-butoxy)-1-(3-ethoxybenzoyl)-N-(4-(oxazol-5-yl)benzyl)pyrrolidine-2-carboxamide (36.1 mg, 0.073 mmol, 1 eq) was dissolved in DCM (9 mL) at room temperature. TFA (1 mL) was added and the solution was stirred for 13 hours, then condensed. Purification by column chromatography (1 to 10% MeOH/DCM) gave a colorless oil (22.9 mg, 0.053 mmol, 72%). $^1$H NMR (400 MHz, CD$_3$OD) δ 8.24 (d, J=12.0 Hz, 1H), 7.65 (dd, J=28.0, 8.3 Hz, 2H), 7.47 (dd, J=18.8, 10.6 Hz, 3H), 7.23 (ddd, J=9.4, 4.6, 4.1 Hz, 3H), 7.09-6.87 (m, 2H), 4.75 (dd, J=9.6, 7.7 Hz, 1H), 4.48 (dd, J=49.7, 15.5 Hz, 3H), 4.06 (q, J=7.0 Hz, 2H), 3.84 (dd, J=11.5, 3.5 Hz, 1H), 3.44 (d, J=11.5 Hz, 1H), 2.42-2.29 (m, 1H), 2.21-2.05 (m, 1H), 1.36 (dt, J=24.0, 7.0 Hz, 3H). $^{13}$C NMR (101 MHz, CD$_3$OD) δ 174.78, 172.66, 160.35, 153.14, 152.74, 140.85, 138.38, 130.66, 129.00, 127.71, 125.62, 121.77, 120.50, 118.08, 114.30, 71.02, 64.71, 60.85, 59.82, 43.72, 39.32,

244

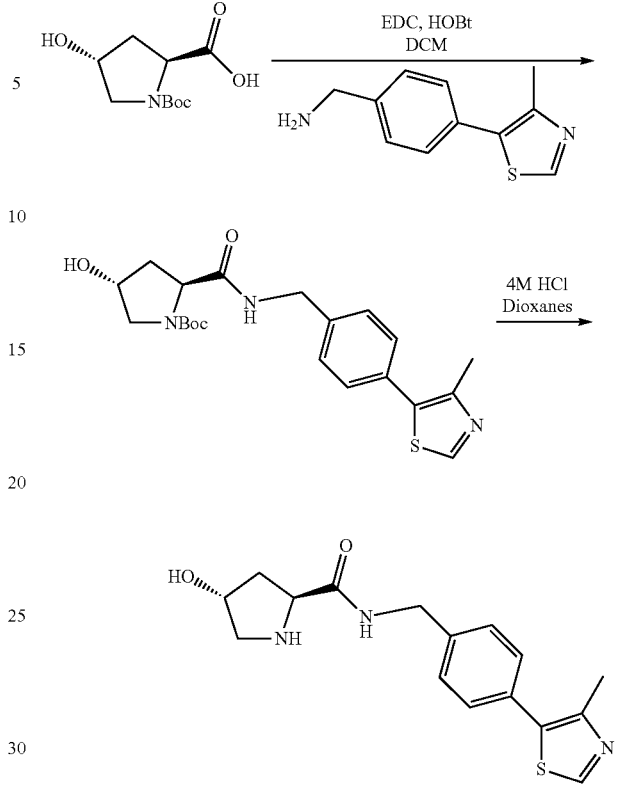

(2S,4R)-tert-butyl 4-hydroxy-2-((4-(4-methylthiazol-5-yl)benzyl)carbamoyl)pyrrolidine-1-carboxylate

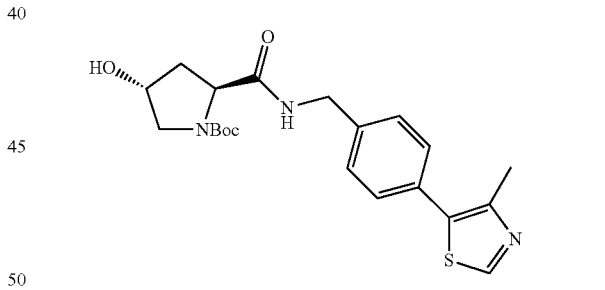

(2S,4R)-1-(tert-butoxycarbonyl)-4-hydroxypyrrolidine-2-carboxylic acid (366 mg, 1.58 mmol, 1 equiv.) was dissolved in 15 mL DMF and charged with EDC (380 mg, 2.0 mmol 1.3 equiv), and HOBt (310 mg, 2.0 mmol, 1.5 equiv) after 5 minutes of stirring (4-(4-methylthiazol-5-yl)phenyl)methanamine (325 mg, 1.58 mmol, 1 equiv) was added. Upon stirring for 15 h the reaction was diluted with 25 mL EtOAc, and washed with 25 mL brine (2×), followed by 25 mL Sat. NaHCO$_3$ (2×). The organic layer was concentrated down to yield 650 mg (98% yield) of the product as a yellow oil. $^1$H NMR (400 MHz, CDCl$_3$) δ 8.67 (s, 1H), 7.43-7.29 (m, 4H), 4.49 (d, J=16.7 Hz, 4H), 3.51 (dd, J=11.0, 4.7 Hz, 2H), 2.61-2.45 (m, 4H), 2.03 (d, J=7.4 Hz, 2H), 1.42 (s, 9H). TLC: (9:1 DCM:MeOH (0.5 N NH$_3$)) R$_f$=0.20; MS (ESI) 417.5 (M+H)$^+$.

(2S,4R)-4-hydroxy-N-(4-(4-methylthiazol-5-yl)benzyl)pyrrolidine-2-carboxamide

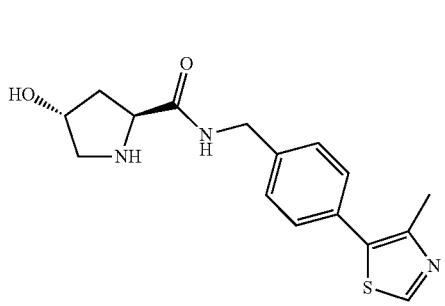 [SMILES: Cc1ncsc1-c1ccc(CNC(=O)[C@@H]2C[C@@H](O)CN2)cc1]

To (2S,4R)-tert-butyl 4-hydroxy-2-((4-(4-methylthiazol-5-yl)benzyl)carbamoyl)pyrrolidine-1-carboxylate (650 mg, 1.40 mmol, 1 equiv) in a round bottom flask was charged 9 mL 4M HCL in dioxanes (36 mmol, 26 equiv). The reaction was left to stir for 1 h upon which time $N_2$ was bubbled through for 1 h and the volatiles were removed by vacuum. The resulting viscous oil was washed dissolved in water and washed with 50 mL EtOAC. The aqueous layer was then basified to pH 12 with 1 M NaOH, and then extracted with 50 mL EtOAC (3×). The organic layer was dried and concentrated down to yield 250 mg (79% yield) of product as a brown viscous oil. $^1$H NMR (501 MHz, CDCl$_3$) δ 8.66 (s, 1H), 8.18 (t, J=6.0, 1H), 7.38 (d, J=8.1, 2H), 7.30 (d, J=8.1, 2H), 4.48-4.37 (m, 3H), 4.08 (t, J=8.4, 1H), 3.02 (d, J=13.3, 1H), 2.79 (dd, J=3.2, 12.3, 1H), 2.51 (s, 3H), 2.33 (dd, J=8.6, 13.9, 1H), 2.03-1.87 (m, 1H); $^{13}$C NMR (126 MHz, CDCl$_3$) δ 174.89, 150.35, 148.46, 138.30, 131.54, 130.95, 129.51, 127.92, 72.90, 59.72, 55.35, 42.53, 39.98, 16.06; TLC: (9:1 DCM:MeOH) R$_f$=0.1; LRMS (ESI) 317.4 (M+H)$^+$.

General Method E: Representative Procedure: VL219

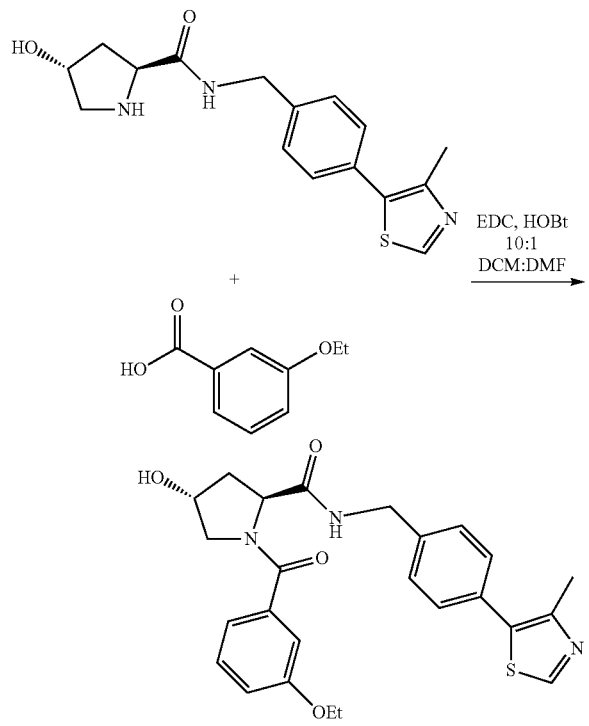

VL219

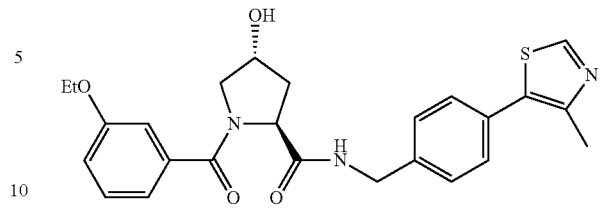

3-ethoxybenzoic acid (17 mg, 0.1 mmol, 1 equiv.) was dissolved in 1 mL 10:1 DCM:DMF and charged with EDC (25 mg, 0.13 mmol 1.3 equiv), and HOBt (21 mg, 0.13 mmol, 1.3 equiv). After 5 minutes of stirring (2S,4R)-4-hydroxy-N-(4-(4-methylthiazol-5-yl)benzyl)pyrrolidine-2-carboxamide (31 mg, 0.095 mmol, 1 equiv) was added. Upon stirring for 18 h the reaction was diluted with 15 mL EtOAc and washed with 25 mL 10% aqueous citric acid and 25 mL saturated NaHCO$_3$. The organic layer was dried with Na$_2$SO$_4$ and concentrated by vacuum. The resultant oil was purified by silica gel chromatography (DCM to 9% MeOH (0.5 N NH$_3$) in DCM) to yield 25 mg (56% yield) of the product as a white solid. $^1$H NMR (501 MHz, CD$_3$OD) δ 8.87 (s, 1H), 7.51-7.42 (m, 4H), 7.37 (t, J=8.1, 1H), 7.23-7.14 (m, 2H), 7.05 (dd, J=2.2, 8.4, 1H), 4.79 (dd, J=7.7, 9.5, 1H), 4.63-4.40 (m, 3H), 4.08 (q, J=7.0, 2H), 3.86 (dt, J=3.8, 7.6, 1H), 3.47 (d, J=11.5, 1H), 2.47 (s, 3H) 2.36 (dd, J=7.6, 13.2, 1H), 2.14 (ddd, J=5.3, 10.2, 16.4, 1H), 1.41 (t, J=7.0, 3H); $^{13}$C NMR (126 MHz, CD$_3$OD) δ 174.74, 172.64, 160.34, 152.78, 149.05, 140.21, 138.40, 133.39, 131.55, 130.65, 130.44, 128.83, 120.49, 118.07, 114.32, 71.02, 64.71, 60.83, 59.81, 43.67, 39.30, 15.79, 15.06; TLC: (9:1 DCM:MeOH (0.5 N NH$_3$)) R$_f$=0.25; LRMS (ESI) 466.1 (M+H)$^+$.

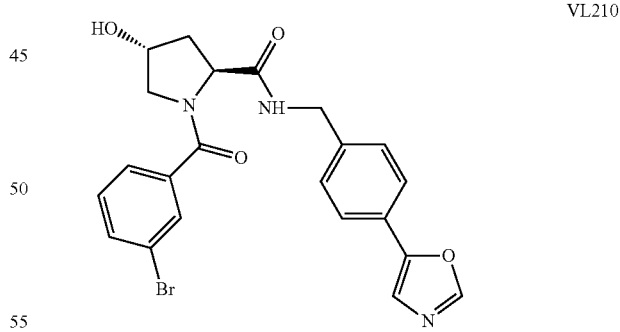

VL210

VL210 was synthesized according to General Method D. $^1$H NMR (500 MHz, CD$_3$OD) δ 8.23 (s, 1H), 7.82 (t, J=1.7, 1H), 7.73-7.58 (m, 4H), 7.49-7.33 (m, 4H), 4.76 (dd, J=7.6, 9.6, 1H), 4.59-4.32 (m, 3H), 3.84 (dd, J=3.5, 11.4, 1H), 3.41 (d, J=11.3, 1H), 2.43-2.30 (m, 1H), 2.18-2.07 (m, 1H); $^{13}$C NMR (126 MHz, CD$_3$OD) δ 173.14, 169.54, 151.35, 139.41, 137.87, 133.28, 130.18, 130.01, 127.92, 127.61, 126.31, 125.93, 124.23, 121.93, 120.36, 69.62, 59.53, 58.30, 42.31, 37.95; LRMS (ESI) 471.5 (M+H)$^+$.

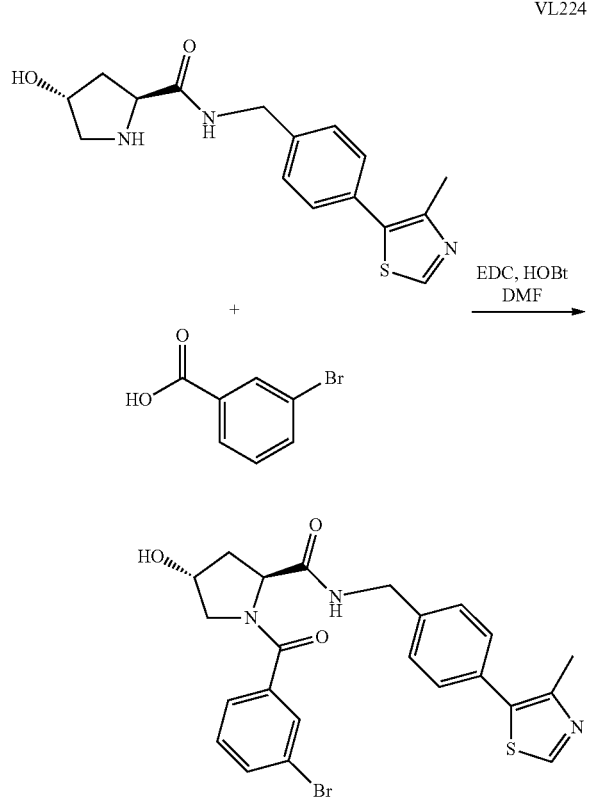

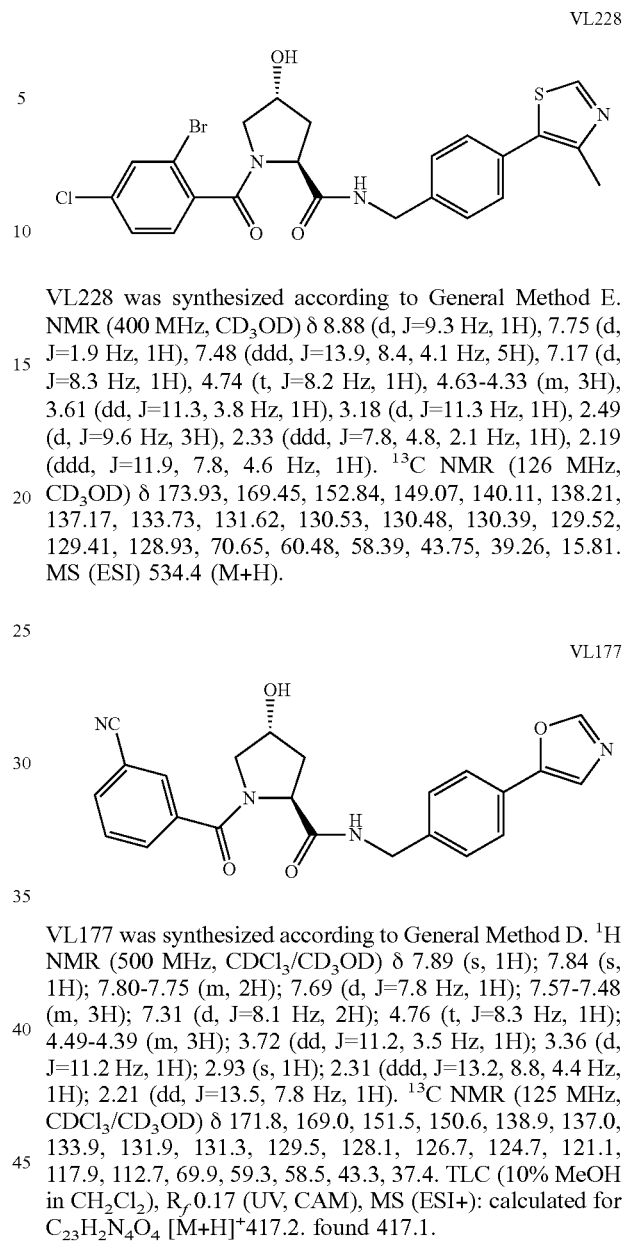

VL224 was synthesized according to General Method E. $^1$H NMR (501 MHz, CD$_3$OD) δ 8.87 (s, 1H), 7.83 (d, J=1.5, 1H), 7.67 (d, J=7.1, 1H), 7.61 (d, J=6.7, 1H), 7.48-7.36 (m, 5H), 4.77 (t, J=8.5, 1H), 4.60-4.39 (obscured m, 3H), 3.90-3.78 (m, 1H), 3.42 (d, J=11.4, 1H), 2.47 (s, 3H), 2.41-2.30 (m, 1H), 2.19-2.06 (m, 1H); $^{13}$C NMR (126 MHz, CD$_3$OD) δ 173.15, 169.55, 151.41, 147.64, 138.77, 137.85, 133.26, 132.78, 131.98, 130.16, 130.02, 129.05, 127.43, 125.91, 121.93, 69.64, 59.53, 58.32, 42.27, 37.94, 14.41; TLC: (9:1 DCM:MeOH (0.5 N NH$_3$)) R$_f$=0.7; LRMS (ESI) 499.8 (M+H)$^+$.

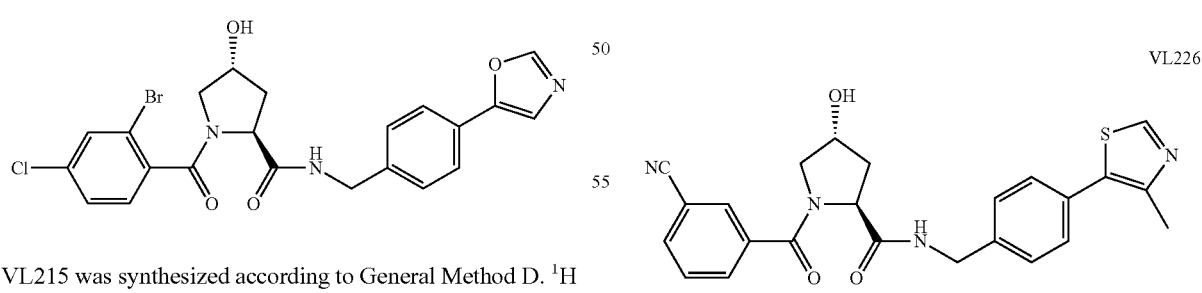

VL215 was synthesized according to General Method D. $^1$H NMR (501 MHz, CD$_3$OD) δ 8.24 (dd, J=13.4, 7.1 Hz, 1H), 7.87-7.58 (m, 3H), 7.58-7.31 (m, 4H), 7.16 (s, 1H), 4.73 (d, J=7.8 Hz, 1H), 4.63-4.50 (m, 1H), 4.49-4.29 (m, 2H), 3.80 (d, J=10.5 Hz, 1H), 3.60 (s, 1H), 2.31 (s, 1H), 2.17 (s, 1H). $^{13}$C NMR (126 MHz, CD$_3$OD) δ 179.37, 169.61, 153.12, 152.75, 140.72, 138.21, 137.16, 133.72, 130.38, 129.70, 129.40, 129.08, 127.76, 125.63, 121.80, 70.64, 60.46, 58.42, 43.80, 39.27. MS (ESI) 504.2 (M+H).

VL228 was synthesized according to General Method E. NMR (400 MHz, CD$_3$OD) δ 8.88 (d, J=9.3 Hz, 1H), 7.75 (d, J=1.9 Hz, 1H), 7.48 (ddd, J=13.9, 8.4, 4.1 Hz, 5H), 7.17 (d, J=8.3 Hz, 1H), 4.74 (t, J=8.2 Hz, 1H), 4.63-4.33 (m, 3H), 3.61 (dd, J=11.3, 3.8 Hz, 1H), 3.18 (d, J=11.3 Hz, 1H), 2.49 (d, J=9.6 Hz, 3H), 2.33 (ddd, J=7.8, 4.8, 2.1 Hz, 1H), 2.19 (ddd, J=11.9, 7.8, 4.6 Hz, 1H). $^{13}$C NMR (126 MHz, CD$_3$OD) δ 173.93, 169.45, 152.84, 149.07, 140.11, 138.21, 137.17, 133.73, 131.62, 130.53, 130.48, 130.39, 129.52, 129.41, 128.93, 70.65, 60.48, 58.39, 43.75, 39.26, 15.81. MS (ESI) 534.4 (M+H).

VL177 was synthesized according to General Method D. $^1$H NMR (500 MHz, CDCl$_3$/CD$_3$OD) δ 7.89 (s, 1H); 7.84 (s, 1H); 7.80-7.75 (m, 2H); 7.69 (d, J=7.8 Hz, 1H); 7.57-7.48 (m, 3H); 7.31 (d, J=8.1 Hz, 2H); 4.76 (t, J=8.3 Hz, 1H); 4.49-4.39 (m, 3H); 3.72 (dd, J=11.2, 3.5 Hz, 1H); 3.36 (d, J=11.2 Hz, 1H); 2.93 (s, 1H); 2.31 (ddd, J=13.2, 8.8, 4.4 Hz, 1H); 2.21 (dd, J=13.5, 7.8 Hz, 1H). $^{13}$C NMR (125 MHz, CDCl$_3$/CD$_3$OD) δ 171.8, 169.0, 151.5, 150.6, 138.9, 137.0, 133.9, 131.9, 131.3, 129.5, 128.1, 126.7, 124.7, 121.1, 117.9, 112.7, 69.9, 59.3, 58.5, 43.3, 37.4. TLC (10% MeOH in CH$_2$Cl$_2$), R$_f$ 0.17 (UV, CAM), MS (ESI+): calculated for C$_{23}$H$_2$N$_4$O$_4$ [M+H]$^+$417.2. found 417.1.

VL226 was synthesized according to General Method E. $^1$H NMR (500 MHz, CDCl$_3$/CD$_3$OD) δ 8.65 (s, 1H); 7.84 (s, 1H); 7.74 (dd, J=13.3, 7.8 Hz, 2H); 7.53 (t, J=7.8 Hz, 1H); 7.40-7.28 (m, 5H); 4.92 (t, J=8.1 Hz, 1H); 4.53 (s, 1H); 4.48 (d, J=5.9 Hz, 2H); 3.72 (dd, J=11.3, 3.5 Hz, 1H); 3.52-3.44 (m, 1H); 2.85 (br s, 1H); 2.67-2.56 (m, 1H); 2.48 (s, 3H); 2.21 (dd, J=13.5, 7.8 Hz, 1H). $^{13}$C NMR (125 MHz, CDCl$_3$/CD$_3$OD) δ 170.8, 169.4, 150.5, 148.6, 138.0, 137.0, 134.1, 131.9, 131.4, 129.7, 129.6, 127.0, 118.0, 113.0, 70.4, 59.1, 58.6, 43.5, 36.8, 16.2. TLC (10% MeOH in CH$_2$Cl$_2$), R$_f$ 0.32 (UV, CAM), MS (ESI$^+$): calculated for C$_{24}$H$_{23}$N$_4$O$_3$S [M+H]$^+$447.2. found 447.0.

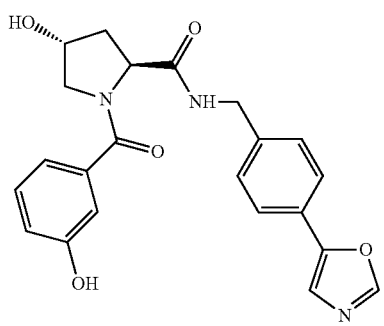

VL211 was synthesized according to General Method D. $^1$H NMR (500 MHz, CD$_3$OD) δ 8.11 (s, 1H), 7.58 (dd, J=2.3, 8.2, 2H), 7.42-7.30 (m, 3H), 7.16 (t, J=7.9, 1H), 6.96 (d, J=7.7, 1H), 6.92 (s, 1H), 6.80 (dd, J=2.3, 8.1, 1H), 4.65 (t, J=8.6, 1H), 4.47-4.26 (m, 3H), 3.71 (dt, J=4.0, 8.0, 1H), 3.36 (d, J=11.6, 1H), 2.32-2.16 (m, 1H), 2.08-1.94 (m, 1H); $^{13}$C NMR (126 MHz, CD$_3$OD) δ 174.74, 172.77, 158.71, 153.14, 152.70, 140.83, 138.38, 130.62, 128.98, 127.69, 125.62, 121.75, 119.39, 118.61, 115.27, 71.01, 60.77, 59.79, 43.73, 39.25; TLC: (9:1 DCM:MeOH R$_f$=0.15; LRMS (ESI) 408.3 (M+H)$^+$.

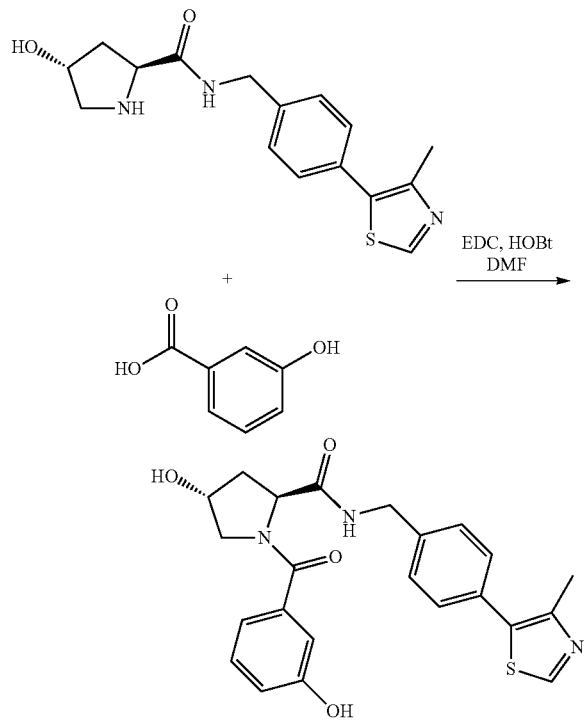

V1225 was synthesized according to General Method E. $^1$H NMR (501 MHz, CD$_3$OD) δ 8.86 (s, 1H), 7.49-7.34 (m, 4H), 7.27 (t, J=7.8, 1H), 7.11-7.00 (m, 2H), 6.93-6.84 (m, 1H), 4.77 (t, J=8.5, 1H), 4.57-4.38 (m, 3H), 3.84 (dd, J=3.3, 11.5, 1H), 3.47 (d, J=11.5, 1H), 2.46 (S, 3H) 2.34 (dd, J=7.1, 12.5, 1H), 2.18-2.06 (m, 1H); $^{13}$C NMR (126 MHz, CD$_3$OD) δ 173.35, 171.36, 157.31, 151.39, 147.62, 138.81, 136.95, 130.12, 129.21, 129.04, 127.62, 127.41, 117.97, 117.19, 113.84, 69.61, 59.37, 58.41, 42.24, 37.85, 14.37; TLC: (9:1 DCM:MeOH)R$_f$0.3; LRMS (ESI) 437.0 (M+H)$^+$.

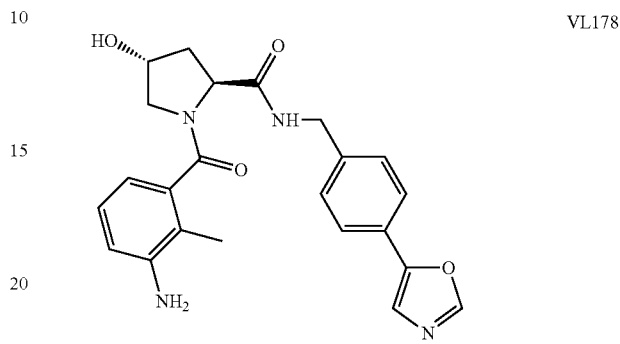

VL178 was synthesized according to General Method D. $^1$H NMR (400 MHz, CD$_3$OD) δ 8.84 (t, J=5.9, 1H), 8.26 (d, J=5.9, 1H), 7.73 (d, J=8.3, 2H), 7.55-7.45 (m, 3H), 7.06 (t, J=7.8, 1H), 6.86-6.76 (m, 1H), 6.68 (d, J=7.3, 1H), 4.75 (t, J=8.4, 1H), 4.66-4.35 (m, 3H), 3.55 (dd, J=3.5, 11.6, 1H), 3.24 (d, J=11.4, 1H), 2.41-2.26 (m, 1H), 2.21-2.10 (m, 4H); $^{13}$C NMR (126 MHz, CD$_3$OD) δ 173.21, 172.03, 151.32, 145.03, 139.46, 137.30, 130.95, 127.61, 126.53, 126.29, 124.22, 123.96, 120.35, 116.31, 115.97, 74.46, 69.35, 58.72, 42.46, 38.02, 23.61; LRMS (ESI) 420.4 (M+H)$^+$.

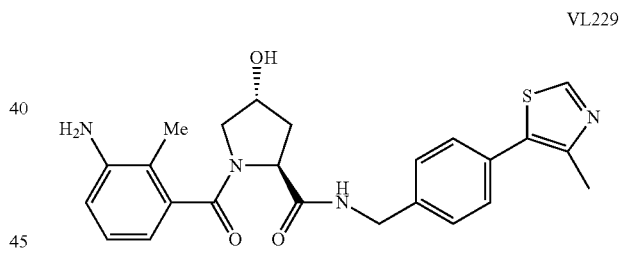

(2S,4R)-4-hydroxy-N-(4-(4-methylthiazol-5-yl)benzyl)pyrrolidine-2-carboxamide (24 mg, 0.0756 mmol, 1 eq), 3-amino-2-methylbenzoic acid (13 mg, 0.083 mmol, 1.1 eq), EDC (16 mg, 0.083 mmol, 1.1 eq) and HOBt (11 mg, 0.083 mmol, 1.1 eq) were dissolved in DMF (0.76 mL) at room temperature. DIPEA (0.02 mL, 0.113 mmol, 1.5 eq) was added, and the solution was stirred for 17 hours. The solution was then partitioned between 1M NaOH and EtOAc, separated, and extracted twice more with EtOAc. The combined organic layer was dried over sodium sulfate, filtered and condensed. Purification by column chromatography (1 to 10% 0.5N methanolic ammonia/DCM) gave a white solid (20.5 mg, 0.045 mmol, 60%). $^1$H NMR (501 MHz, CD$_3$OD) δ 8.87 (t, J=6.6 Hz, 1H), 7.45 (dt, J=20.5, 7.7 Hz, 4H), 7.03 (t, J=7.6 Hz, 1H), 6.78 (d, J=7.8 Hz, 1H), 6.65 (s, 1H), 4.74 (t, J=8.1 Hz, 1H), 4.67-4.34 (m, 3H), 3.53 (d, J=11.3 Hz, 1H), 3.21 (d, J=9.3 Hz, 1H), 2.48 (d, J=3.1 Hz, 3H), 2.32 (d, J=7.6 Hz, 1H), 2.14 (dd, J=31.4, 20.5 Hz, 4H). $^{13}$C NMR (126 MHz, CD$_3$OD) δ 174.56, 173.67, 152.89, 152.81, 149.04, 147.80, 140.23, 138.57, 133.44, 131.54, 130.46, 128.86, 127.83, 117.01, 116.36, 70.77, 69.66, 60.09, 43.70, 39.41, 15.81, 13.92. MS (ESI) 450.6 (M+H), 473.4 (M+Na).

For further reference see the following articles and the references cited therein:

(1) Buckley D L et al. J. Am. Chem. Soc 2012, 134, 4465-4468.

(2) Van Molle I et al. A Chemistry & Biology 2012, 19, 1300-1312

(3) Buckley, D *Angew. Chem. Int. Ed.,* 2012, 51, 11463-11467

(4) Buckley, D. L et al. Angew. Chem. 2012, 124, 11630-11634.

Examples

Compounds 165-266 of Affinity Table II

The following compounds were synthesized according to the stated General Method, were purified by standard chromatographic methods and had $^1$H and $^{13}$C NMR and MS data consistent with the desired structure.

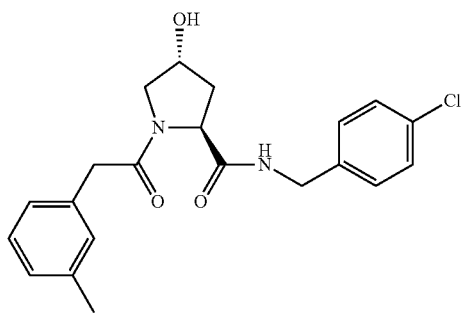

VL165

VL165 was synthesized according to General Method B.

VL168 & 169

The chiral RHS amine fragment was synthesized using the procedure from Surya Prakash, G. K.; Mandal, M.; Olah, G. A. *Angew. Chem. Int. Ed* 2001, 40, 589-690.

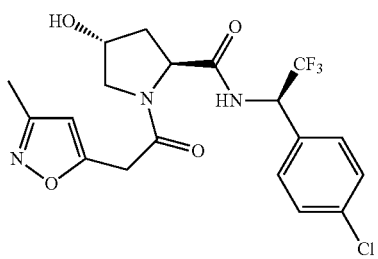

VL168

VL168 was synthesized according to General Method F

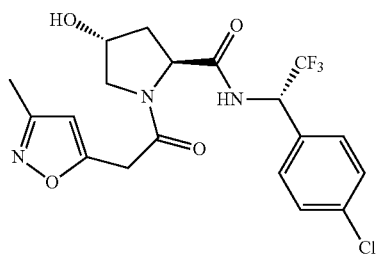

VL169

VL169 was synthesized according to General Method F

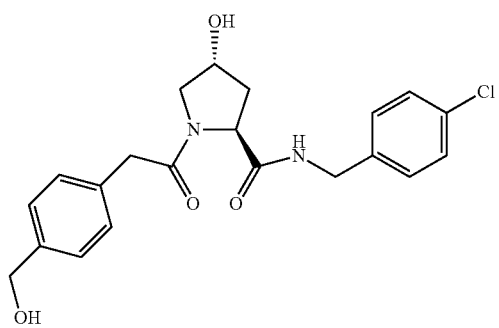

VL174

VL174 General Method C
VL175: General Method C

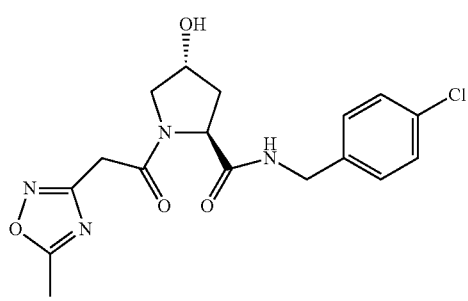 [SMILES: Cc1nc(CC(=O)N2C[C@H](O)C[C@H]2C(=O)NCc2ccc(Cl)cc2)no1]

VL170: General Method C

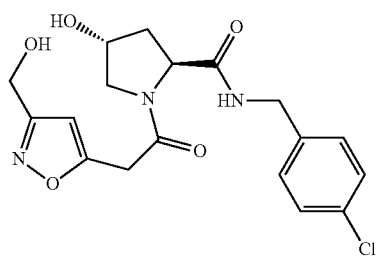 [SMILES: O=C(NCc1ccc(Cl)cc1)[C@@H]1C[C@@H](O)CN1C(=O)Cc1cc(CO)no1]

VL190: General Method B
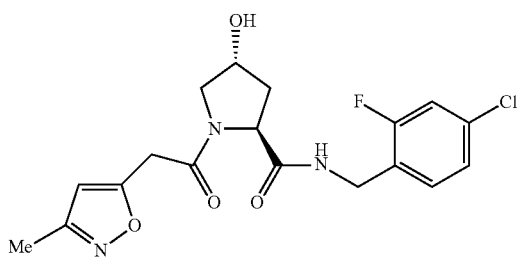
VL191: General Method B
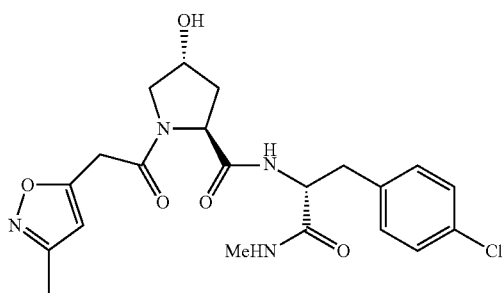 [SMILES: CNC(=O)[C@@H](Cc1ccc(Cl)cc1)NC(=O)[C@@H]1C[C@@H](O)CN1C(=O)Cc1cc(C)no1]
VL182: General Method B
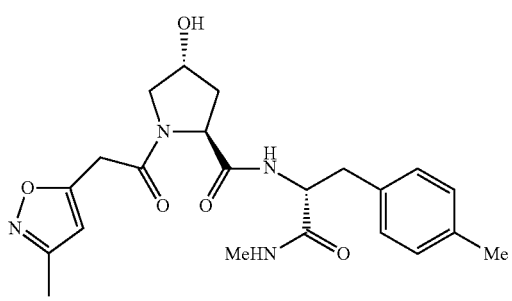 [SMILES: CNC(=O)[C@@H](Cc1ccc(C)cc1)NC(=O)[C@@H]1C[C@@H](O)CN1C(=O)Cc1cc(C)no1]
VL183: General Method B
VL184: General Method C
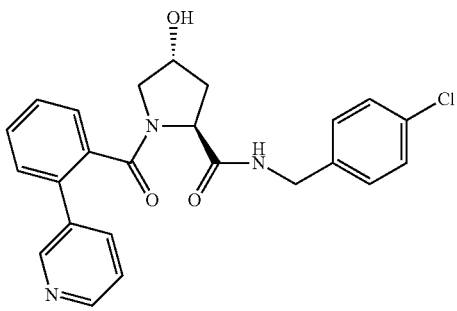 [SMILES: O=C(NCc1ccc(Cl)cc1)[C@@H]1C[C@@H](O)CN1C(=O)c1ccccc1-c1cccnc1]
VL185: General Method C
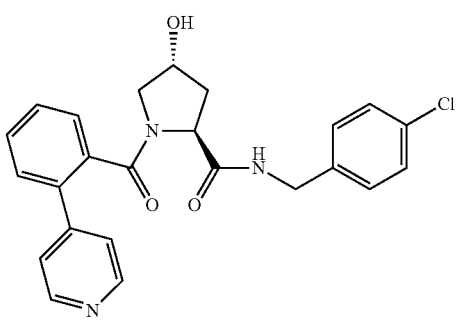 [SMILES: O=C(NCc1ccc(Cl)cc1)[C@@H]1C[C@@H](O)CN1C(=O)c1ccccc1-c1ccncc1]
VL187: General Method B
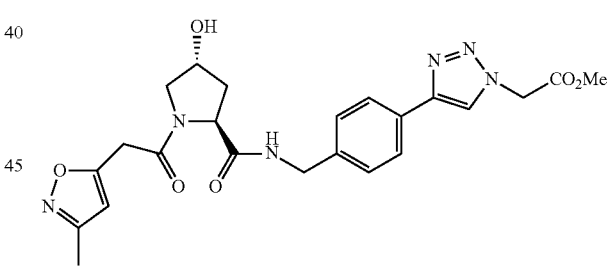
VL188: General Method B
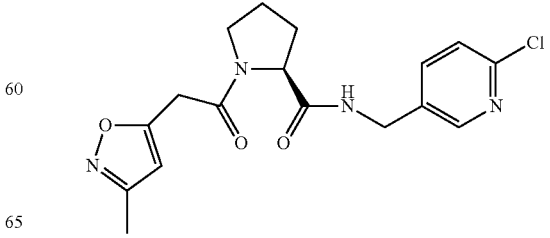

VL189: General Method B
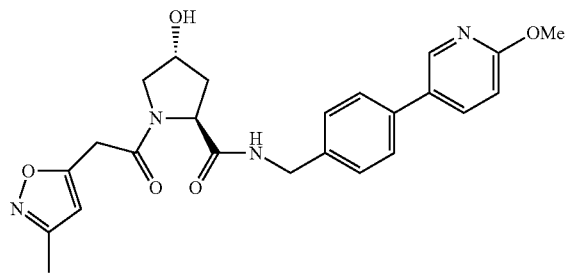 [SMILES: COc1ccc(-c2ccc(CNC(=O)[C@@H]3C[C@@H](O)CN3C(=O)Cc3cc(C)no3)cc2)cn1]
VL192-VL205: Solid Phase Synthesis General Method B
VL206: General Method C
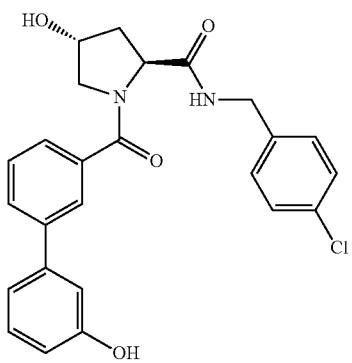 [SMILES: O=C(NCc1ccc(Cl)cc1)[C@@H]1C[C@@H](O)CN1C(=O)c1cccc(-c2cccc(O)c2)c1]
VL207 General Method C
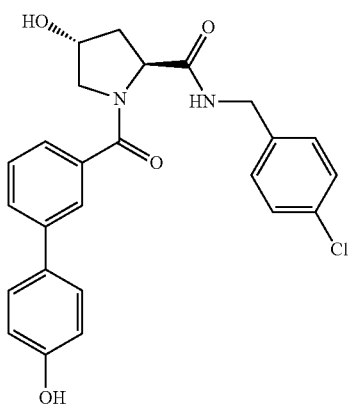 [SMILES: O=C(NCc1ccc(Cl)cc1)[C@@H]1C[C@@H](O)CN1C(=O)c1cccc(-c2ccc(O)cc2)c1]
VL212 General Method C
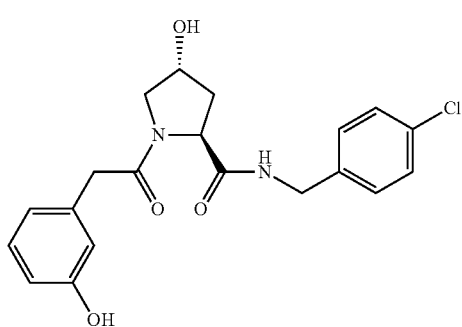
VL214 General Method C
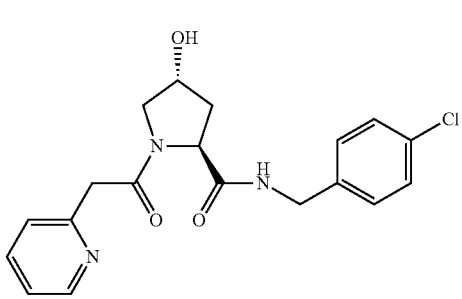 [SMILES: O=C(NCc1ccc(Cl)cc1)[C@@H]1C[C@@H](O)CN1C(=O)Cc1ccccn1]
VL218 General Method C
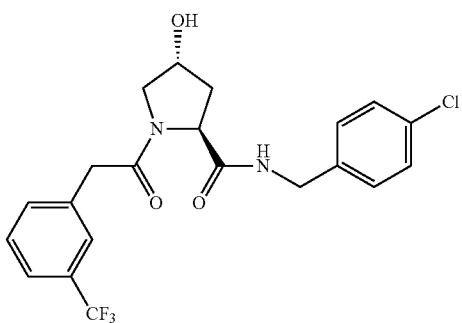 [SMILES: O=C(NCc1ccc(Cl)cc1)[C@@H]1C[C@@H](O)CN1C(=O)Cc1cccc(C(F)(F)F)c1]
VL220 General Method C
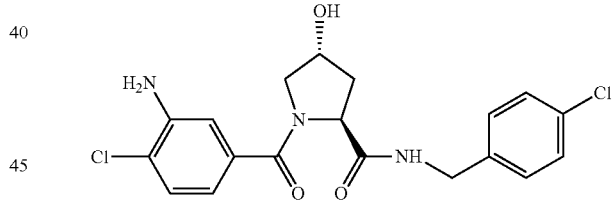
VL221 General Method C
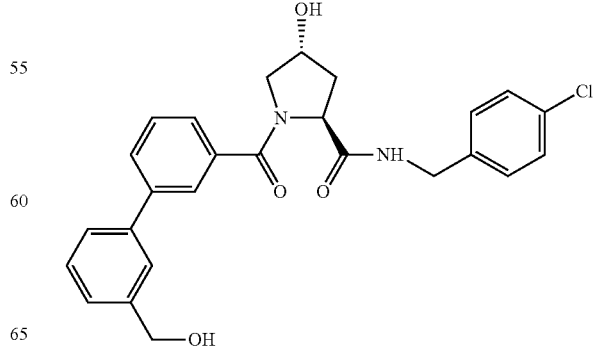

VL222 General Method C
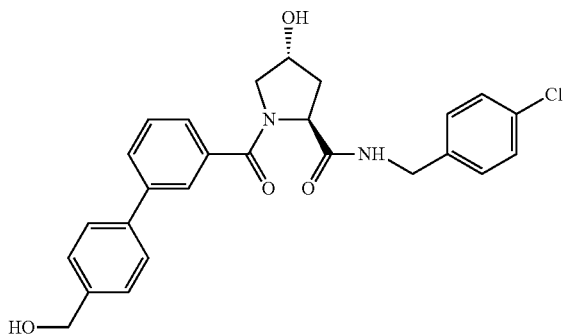 [SMILES: O=C(NCc1ccc(Cl)cc1)[C@@H]1C[C@@H](O)CN1C(=O)c1cccc(-c2ccc(CO)cc2)c1]
VL255 General Method C
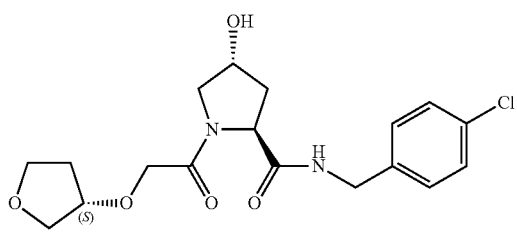
VL256 General Method E
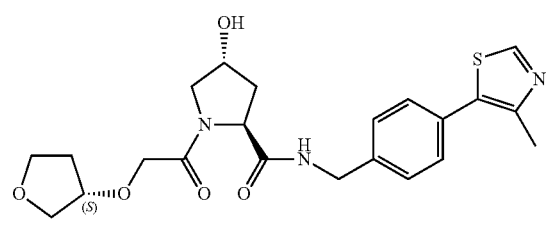
VL223: General Method D
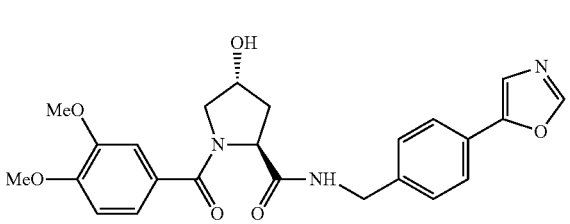 [SMILES: COc1ccc(C(=O)N2C[C@H](O)C[C@H]2C(=O)NCc2ccc(-c3cnco3)cc2)cc1OC]
VL230: General Method D
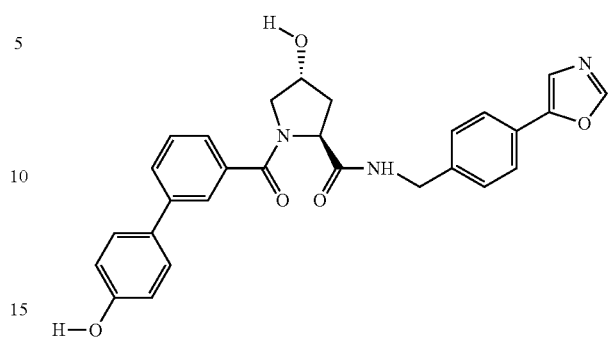
VL231: General Method E
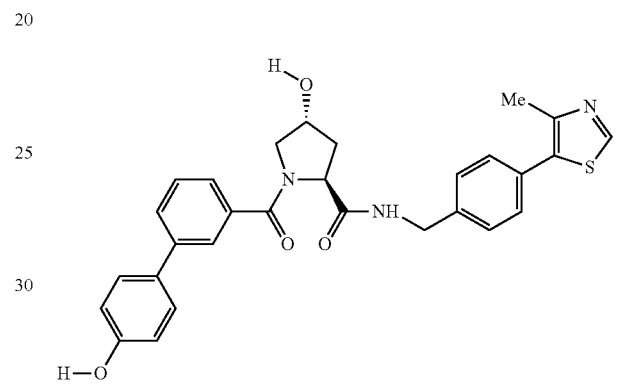
VL238: General Method B
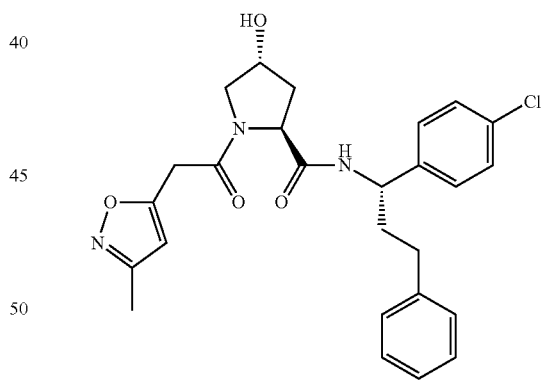
VL240: General Method E
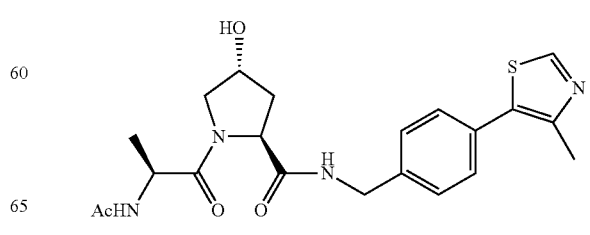

VL241: General Method B

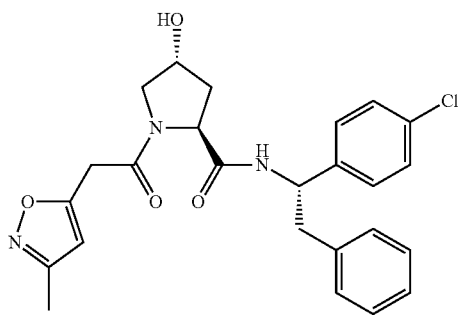 [SMILES: Cc1cc(CC(=O)N2C[C@H](O)C[C@H]2C(=O)N[C@@H](Cc2ccccc2)c2ccc(Cl)cc2)on1]

VL242: General Method E

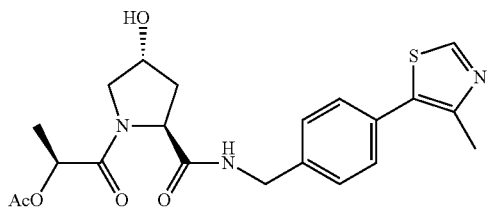 [SMILES: CC(=O)O[C@@H](C)C(=O)N1C[C@H](O)C[C@H]1C(=O)NCc1ccc(-c2scnc2C)cc1]

VL243: General Method E

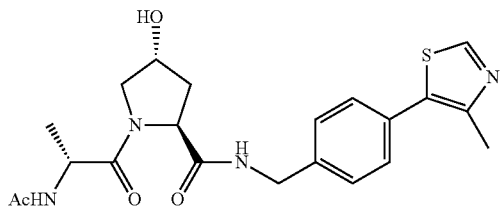 [SMILES: CC(=O)N[C@H](C)C(=O)N1C[C@H](O)C[C@H]1C(=O)NCc1ccc(-c2scnc2C)cc1]

VL244: General Method B

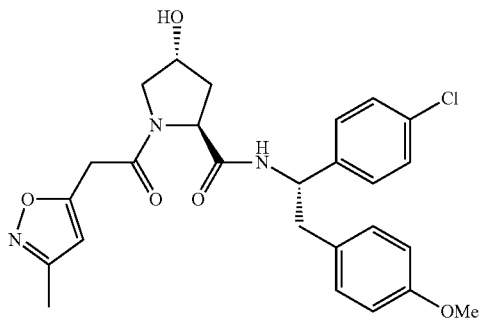 [SMILES: COc1ccc(C[C@H](NC(=O)[C@@H]2C[C@@H](O)CN2C(=O)Cc2cc(C)no2)c2ccc(Cl)cc2)cc1]

VL245: General Method E

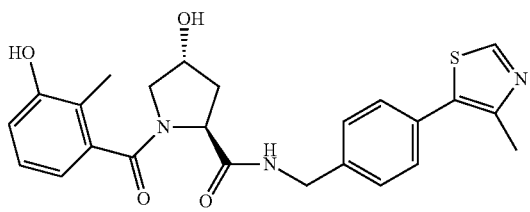 [SMILES: Cc1ncsc1-c1ccc(CNC(=O)[C@@H]2C[C@@H](O)CN2C(=O)c2cccc(O)c2C)cc1]

3-hydroxy-2-methylbenzoic acid (26.3 mg, 0.173 mmol, 1.1 eq), EDC (33.2 mg) and HOBt (23.4 mg) were dissolved in DCM (0.8 mL) and DMF (0.1 mL) at 4° C. After 10 minutes, (2S,4R)-4-hydroxy-N-(4-(4-methylthiazol-5-yl)benzyl)pyrrolidine-2-carboxamide (0.5 mL of a 100 mg/mL solution in DCM) was added and the mixture was warmed to room temperature. After 21 hours, the mixture was diluted with 10 mL of half saturated sodium chloride and extracted thrice with 10 mL of EtOAc. The combined organic layer was dried over sodium sulfate, filtered and condensed. Purification by column chromatography (1 to 10% MeOH/DCM) gave a white solid (29.2 mg, 0.0647, 41%). $^1$H NMR (400 MHz, MeOD) δ 8.93-8.82 (m, 1H), 7.55-7.36 (m, 4H), 7.10 (t, J=7.8 Hz, 1H), 6.83 (dd, J=10.3, 7.9 Hz, 2H), 4.76 (t, J=8.4 Hz, 1H), 4.66-4.38 (m, 3H), 3.56 (dd, J=11.6, 3.6 Hz, 1H), 3.22 (d, J=11.6 Hz, 1H), 2.54-2.47 (m, 3H), 2.41-2.31 (m, 1H), 2.19 (dt, J=11.3, 10.9 Hz, 4H). $^{13}$C NMR (126 MHz, MeOD) δ 174.50, 173.09, 157.22, 152.89, 152.80, 149.01, 140.21, 139.18, 133.42, 131.52, 130.44, 128.85, 127.94, 117.84, 116.42, 70.73, 69.62, 60.12, 43.69, 39.38, 15.79, 12.70. MS (ESI) 452.5 (M+H).

VL247: General Method C

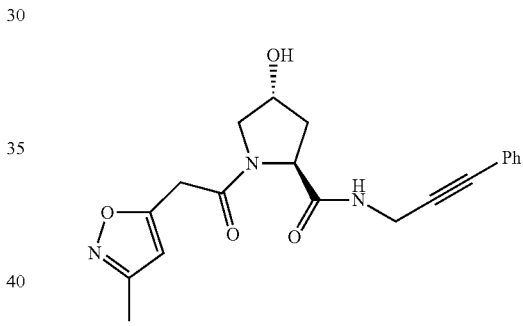

VL248: General Method E

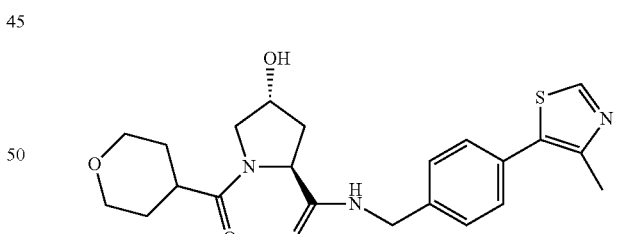

VL249: General Method E

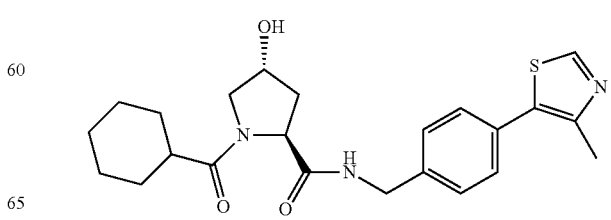

VL250: General Method E
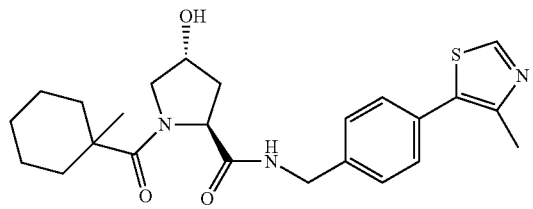 [SMILES: Cc1ncsc1-c1ccc(CNC(=O)[C@@H]2C[C@@H](O)CN2C(=O)C2(C)CCCCC2)cc1]
VL253: General Method C
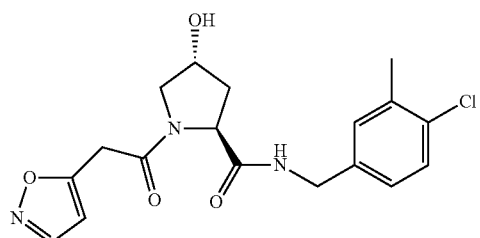
VL254: General Method C
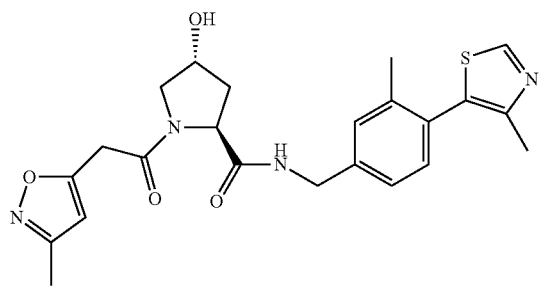 [SMILES: Cc1cc(CC(=O)N2C[C@H](O)C[C@H]2C(=O)NCc2ccc(-c3scnc3C)c(C)c2)on1]
VL257: General Method C
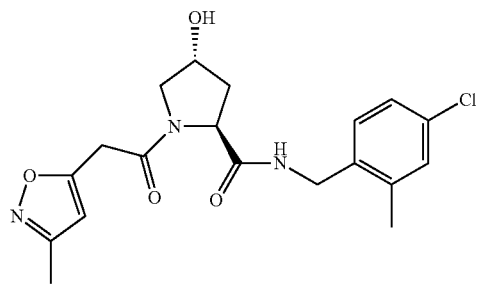 [SMILES: Cc1cc(CC(=O)N2C[C@H](O)C[C@H]2C(=O)NCc2ccc(Cl)cc2C)on1]
VL258: General Method C
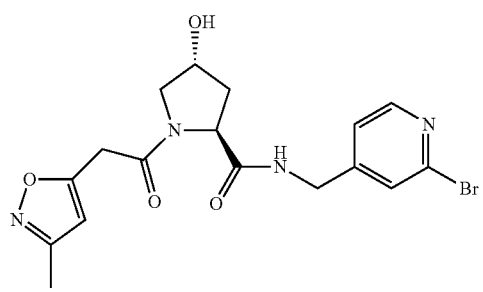
VL259: General Method C
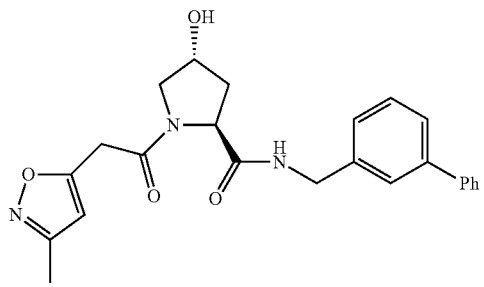 [SMILES: Cc1cc(CC(=O)N2C[C@H](O)C[C@H]2C(=O)NCc2cccc(-c3ccccc3)c2)on1]
VL260: General Method E
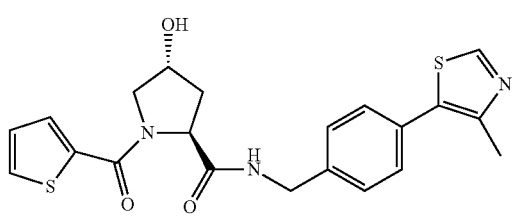 [SMILES: Cc1ncsc1-c1ccc(CNC(=O)[C@@H]2C[C@@H](O)CN2C(=O)c2cccs2)cc1]
VL261: General Method E
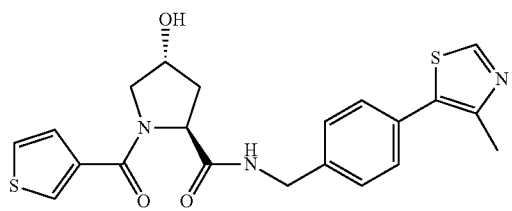 [SMILES: Cc1ncsc1-c1ccc(CNC(=O)[C@@H]2C[C@@H](O)CN2C(=O)c2ccsc2)cc1]
VL262: General Method E
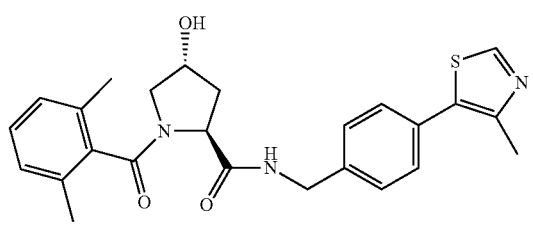 [SMILES: Cc1cccc(C)c1C(=O)N1C[C@H](O)C[C@H]1C(=O)NCc1ccc(-c2scnc2C)cc1]
VL263: General Method E
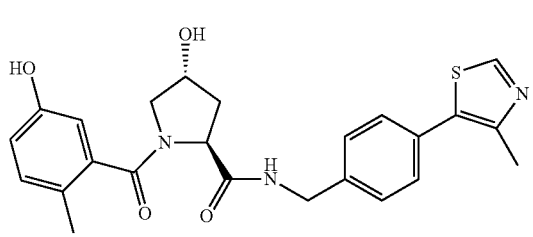 [SMILES: Cc1ccc(O)cc1C(=O)N1C[C@H](O)C[C@H]1C(=O)NCc1ccc(-c2scnc2C)cc1]

VL264: General Method E

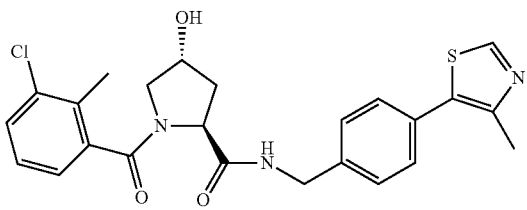 [SMILES: Cc1ncsc1-c1ccc(CNC(=O)[C@@H]2C[C@@H](O)CN2C(=O)c2cccc(Cl)c2C)cc1]

VL265: General Method E

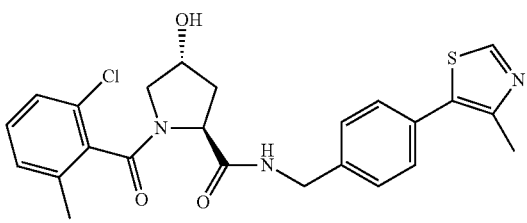 [SMILES: Cc1cccc(Cl)c1C(=O)N1C[C@H](O)C[C@H]1C(=O)NCc1ccc(-c2scnc2C)cc1]

VL251

(2S,4R)-1-((S)-2-((S)-2-acetamido-4-methylpentana-mido)propanoyl)-4-hydroxy-N-(4-(4-methylthiazol-5-yl)benzyl)pyrrolidine-2-carboxamide

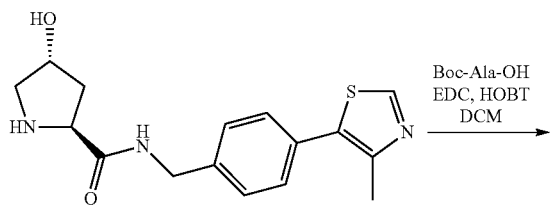

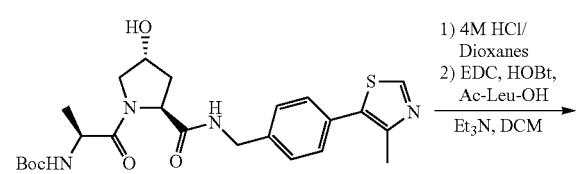

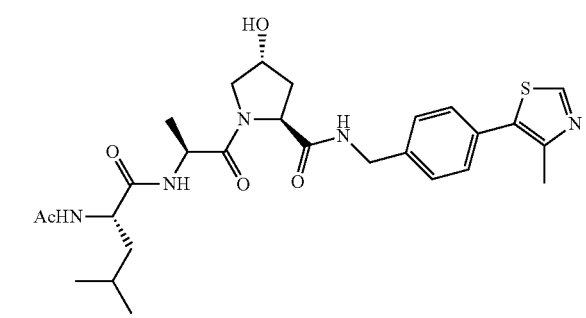 [SMILES: CC(=O)N[C@@H](CC(C)C)C(=O)N[C@@H](C)C(=O)N1C[C@H](O)C[C@H]1C(=O)NCc1ccc(-c2scnc2C)cc1]

tert-butyl ((S)-142S,4R)-4-hydroxy-2-((4-(4-methyl-thiazol-5-yl)benzyl)carba-moyl)pyrrolidin-1-yl)-1-oxopropan-2-yl)carbamate

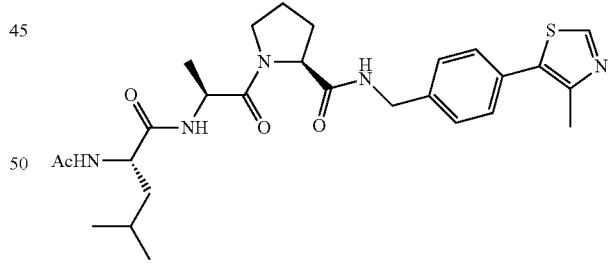

Boc-Ala-OH (189 mg, 1.0-mmol) was dissolved in 10 mL DCM and charged with EDC (248 mg, 1.2 mmol), and HOBt (202 mg, 1.3 mmol) after 5 minutes of stirring (2S,4R)-4-hydroxy-N-(4-(4-methylthiazol-5-yl)benzyl)pyrrolidine-2-carb-oxamide (317 mg, 1.0 mmol) was added. Upon stirring for 18 h the reaction was diluted with 10 mL DCM and washed with 10 mL 10% aqueous citric acid followed by 5 mL saturated NaHCO$_3$. The mixture was concentrated down and purified by silica gel chromatography (DCM/MeOH gradient) to yield 210 mg (43% yield) of the product as a white solid. $^1$H NMR (501 MHz, CDCl$_3$) δ 8.65 (s, 1H), 7.58 (s, 1H), 7.31 (d, J=8.1, 2H), 7.26 (d, J=8.0, 2H), 5.44 (d, J=7.4, 1H), 4.66 (t, J=7.6, 1H), 4.52 (s, 1H), 4.39 (m, 3H), 3.78 (d, J=10.9, 1H), 3.59 (d, J=7.0, 1H), 2.47 (s, 3H), 2.30 (s, 1H), 2.10 (s, 1H), 1.54-1.31 (m, 9H), 1.26 (d, J=6.9, 3H); $^{13}$C NMR (126 MHz, CDCl$_3$) δ 173.1, 171.2, 155.5, 150.5, 148.2, 138.2, 130.7, 129.4, 127.6, 80.1, 70.1, 58.8, 55.2, 48.0, 42.3, 36.5, 28.3, 18.0, 16.0; LRMS (ESI) 489.4 (M+H)$^+$.

VL251

(2S,4R)-1-((S)-2-((S)-2-acetamido-4-methylpentana-mido)propanoyl)-4-hydroxy-N-(4-(4-methylthiazol-5-yl)benzyl)pyrrolidine-2-carboxamide Boc-Ala-Hyp-benzyl thiazole (116 mg, 0.225 mmol) was dissolved in 1 mL DCM and charged with 2.3 mL 4M HCL in dioxanes. Upon stirring for one hour Nitrogen gas was sparged through the mixture for 15 minutes and the remaining volatiles removed by roto vap. The resultant foam was then dissolved in 5 mL 1:1 DCM: DMF and charged with EDC (56 mg, 0.29 mmol), HOBt (45 mg, 0.29 mmol), and Ac-Leu-OH (43 mg, 0.25 mmol) were added. After stirring for 5 minutes triethyl amine was added. Upon stirring for 18 h the reaction was diluted with 10 mL EtOAc and washed with 10 mL 10% aqueous citric acid followed by 5 mL saturated NaHCO$_3$ The aqueous layer was then back extracted 2×10 mL DCM. The organic layers were combined and the mixture was concentrated down and purified by silica gel chromatography (DCM/MeOH gradient) to yield 35 mg (29% yield) of the product as a white solid. ¹H NMR (501 MHz, CDCl₃) δ 8.68 (s, 1H), 8.05 (s, 1H), 7.70 (s, 1H), 7.36 (d, J=7.3, 2H), 7.28 (d, J=8.6, 2H), 6.50 (s, 1H), 4.85-4.73 (m, 2H), 4.68 (s, 1H), 4.59 (s, 1H), 4.40 (d, J=32.4, 2H), 3.84 (d, J=10.7, 1H), 3.70 (d, J=10.5, 1H), 2.51 (s, 3H), 2.30 (s, 1H), 2.21 (s, 1H), 1.85 (s, 3H), 1.59 (s, 1H), 1.50 (s, 2H), 1.34 (d, J=6.7, 3H), 0.86 (t, J=6.7, 6H); ¹³C NMR (126 MHz, CDCl₃) δ 172.1, 172.0, 171.2, 170.8, 150.4, 148.4, 138.1, 129.5, 129.4, 127.8, 110.0, 70.36, 58.9, 55.5, 51.8, 46.9, 43.1, 41.8, 36.9, 24.7, 23.2, 23.1, 21.8, 17.9, 16.0; LRMS (ESI) 545.1 (M+H)⁺.

VL252

(2S,4R)-1-((S)-2-((S)-2-amino-4-methylpentanamido)propanoyl)-4-hydroxy-N-(4-(4-methylthiazol-5-yl)benzyl)pyrrolidine-2-carboxamide the mixture was concentrated to yield 55 mg (40% yield) of the product as a white solid. LRMS (ESI) 602.0 (M+H)⁺. Upon confirmation by mass spec the product was dissolved in 2 mL 1:1 DCM:MeOH and charged with 3 mL 4M HCl in dioxanes. Upon stirring for 45 minutes the reaction was quenched with 5 ml 0.5 N ammonia in methanol. The solvents were evaporated down and purified by silica gel chromatography (gradient of DCM/MeOH (0.5 N NH₃) to yield 50 mg of pure product as a white solid. ¹H NMR (501 MHz, CDCl₃) δ 8.25 (s, 1H), 6.91 (dd, J=7.3, 18.0, 4H), 4.17 (d, J=7.5, 2H), 4.06 (d, J=22.4, 2H), 3.95 (d, J=15.3, 1H), 3.56-3.42 (m, 2H), 3.24 (d, J=7.8, 1H), 2.05 (s, 3H), 1.86-1.77 (m, 1H), 1.77-1.65 (m, 1H), 1.35-1.19 (m, 2H), 1.13 (s, 1H), 0.93 (d, J=6.8, 3H), 0.50 (dd, J=6.3, 9.8, 6H); ¹³C NMR (126 MHz, CDCl₃) δ 171.6, 171.5, 150.3, 147.7, 137.9, 131.4, 130.1, 129.0, 127.3, 109.9, 69.7, 58.6, 55.11, 46.9, 42.5, 36.7, 24.1, 22.4, 22.2, 16.2, 15.3; LRMS (ESI) 502.0 (M+H)⁺.

VL253: General Method C

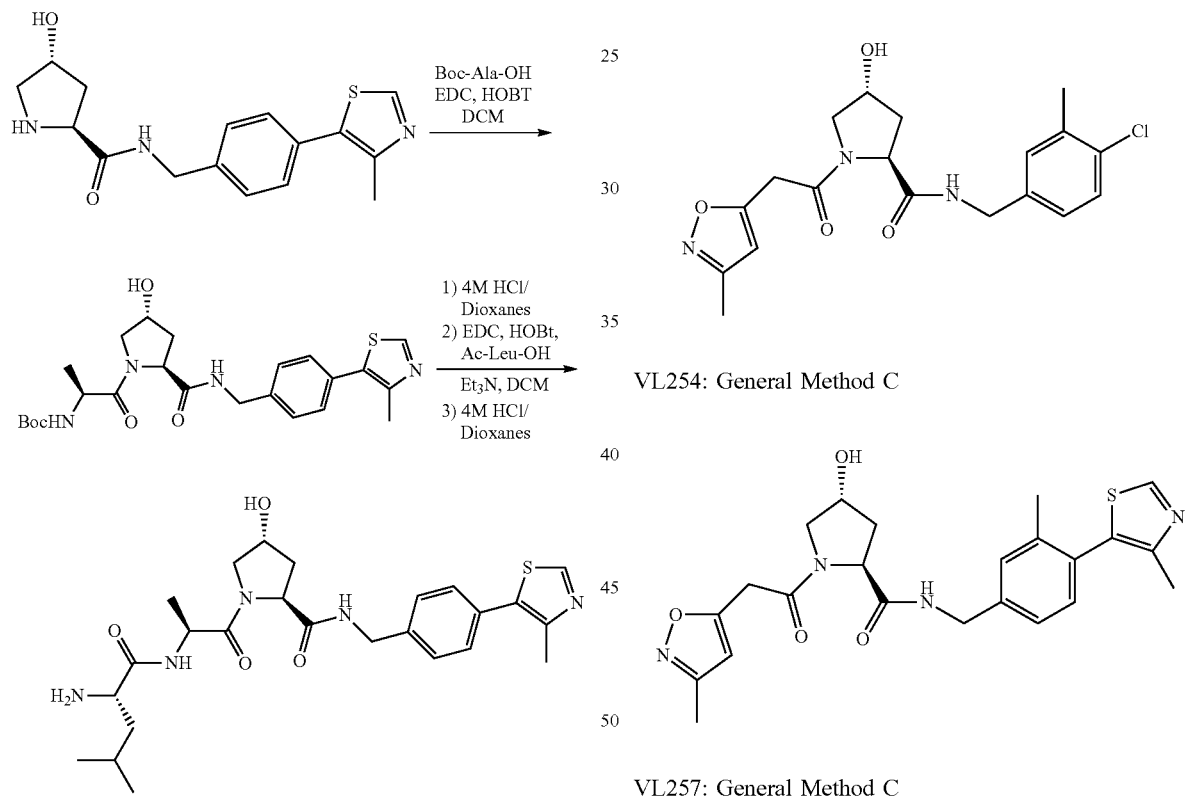

VL254: General Method C

VL257: General Method C

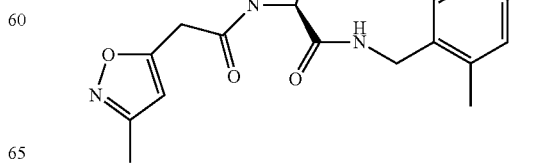

Boc-Ala-Hyp-benzyl thiazole (116 mg, 0.225 mmol) was dissolved in 1 mL DCM and charged with 2.3 mL 4M HCL in dioxanes. Upon stirring for one hour Nitrogen gas was sparged through the mixture for 15 minutes and the remaining volatiles removed by roto vap. The resultant foam was then dissolved in 5 mL 1:1 DCM: DMF and charged with EDC (56 mg, 0.29 mmol), HOBt (45 mg, 0.29 mmol), and Boc-Leu-OH (62 mg, 0.25 mmol) were added. After stirring for 5 minutes triethyl amine was added. Upon stirring for 18 h the reaction was diluted with 10 mL EtOAc and washed with 10 mL 10% aqueous citric acid followed by 5 mL saturated NaHCO₃. The organic layers were combined and VL258: General Method C

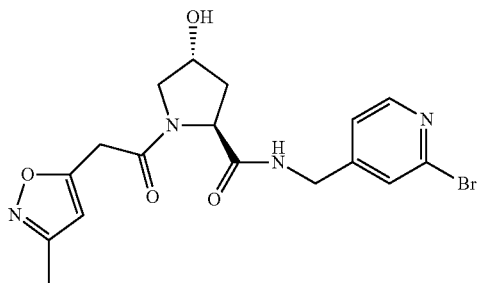

VL259: General Method C

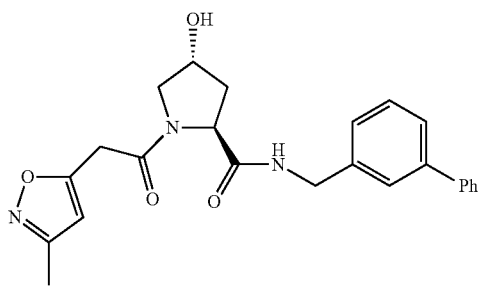 [SMILES: Cc1cc(CC(=O)N2C[C@H](O)C[C@H]2C(=O)NCc2cccc(-c3ccccc3)c2)on1]

VL260: General Method E

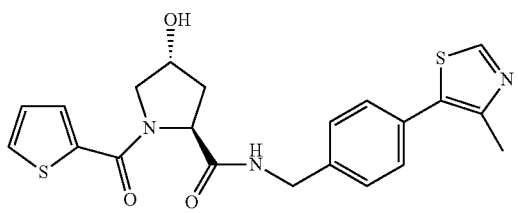 [SMILES: Cc1ncsc1-c1ccc(CNC(=O)[C@@H]2C[C@@H](O)CN2C(=O)c2cccs2)cc1]

VL261: General Method E

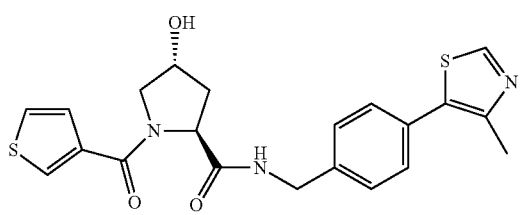 [SMILES: Cc1ncsc1-c1ccc(CNC(=O)[C@@H]2C[C@@H](O)CN2C(=O)c2ccsc2)cc1]

VL262: General Method E

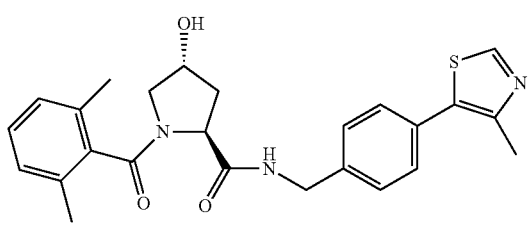 [SMILES: Cc1cccc(C)c1C(=O)N1C[C@H](O)C[C@H]1C(=O)NCc1ccc(-c2scnc2C)cc1]

VL263: General Method E

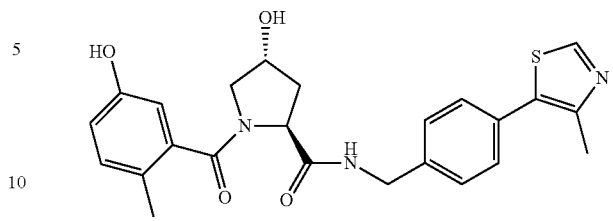

VL264: General Method E

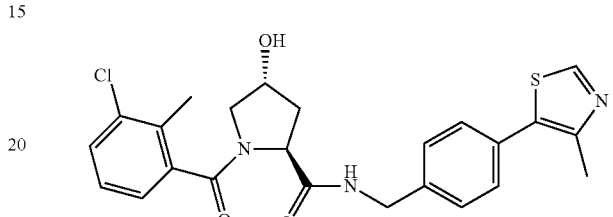

VL265: General Method E

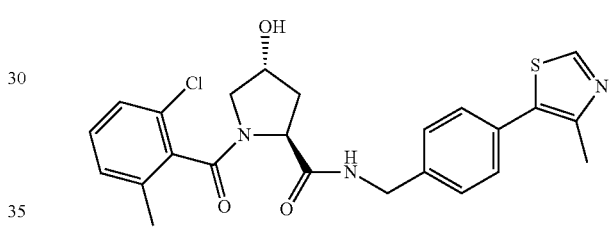

Figure 15:
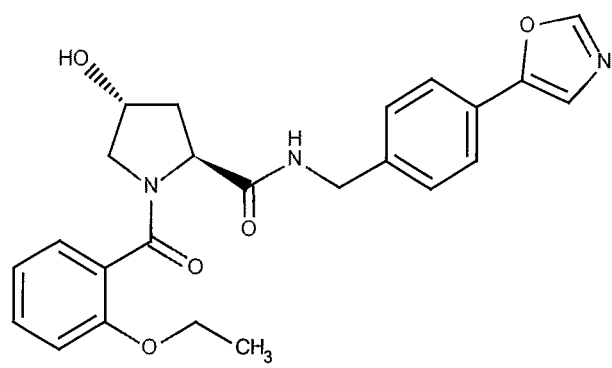
FIG. 15 shows a further number of compounds according to the present invention and their activity. Most compounds are active below concentrations of 100 μM.
Figure 15:
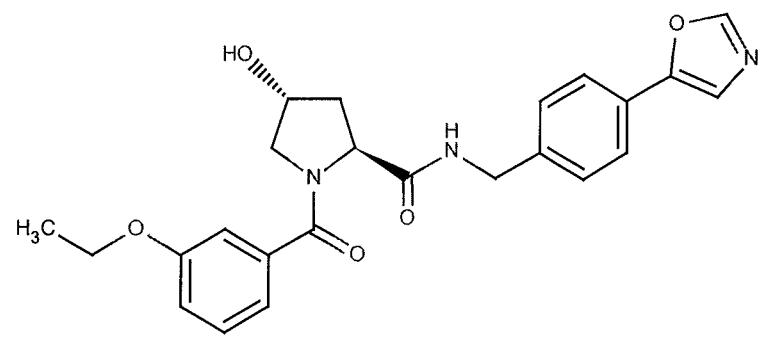
Figure 15:
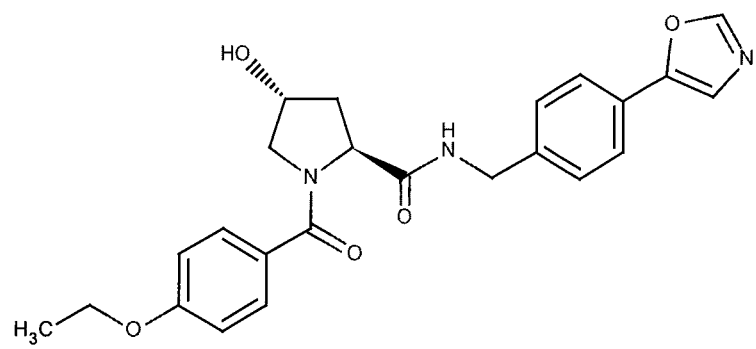
Figure 15:
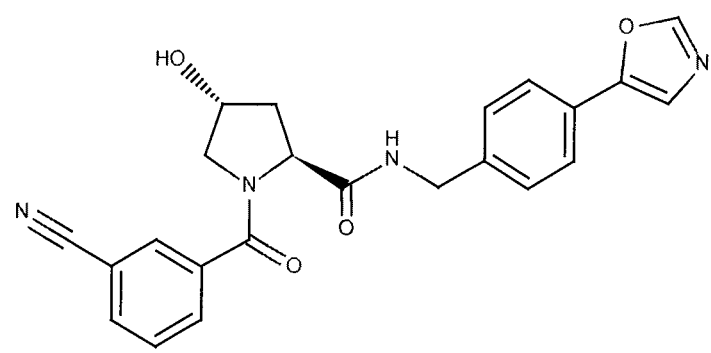
Figure 15:
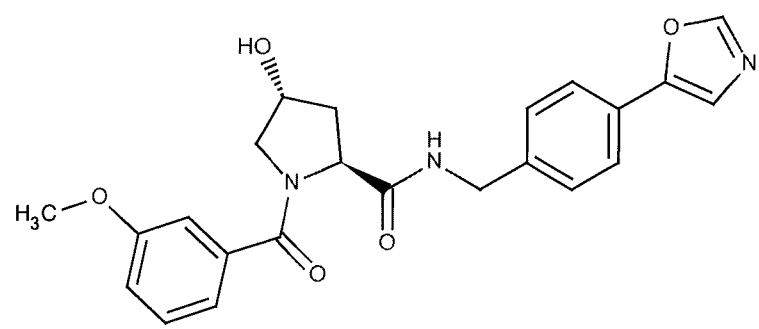
Figure 15:
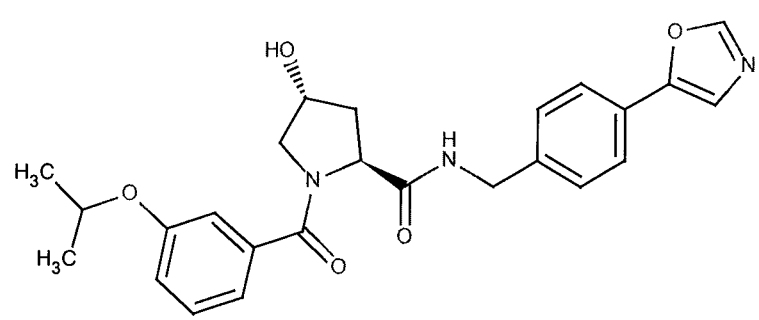
Figure 15:
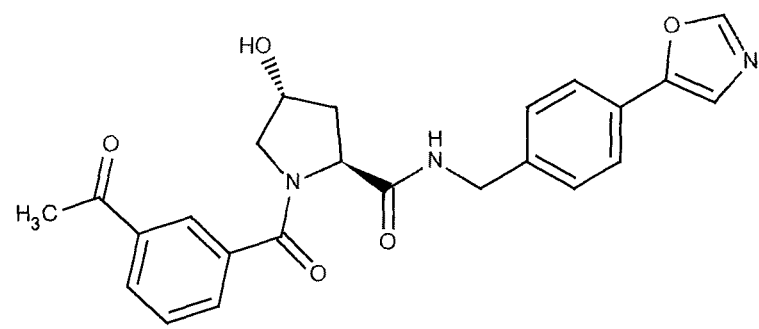
Figure 15:
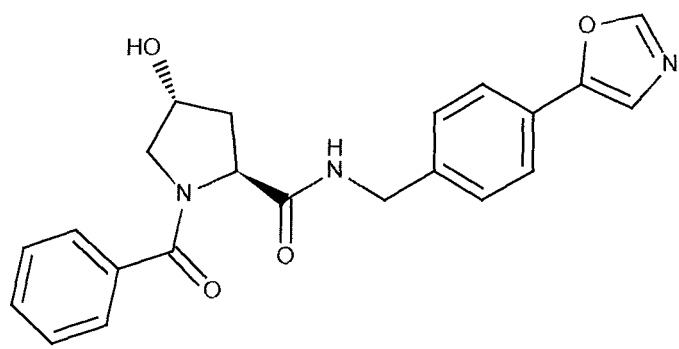
Figure 15:
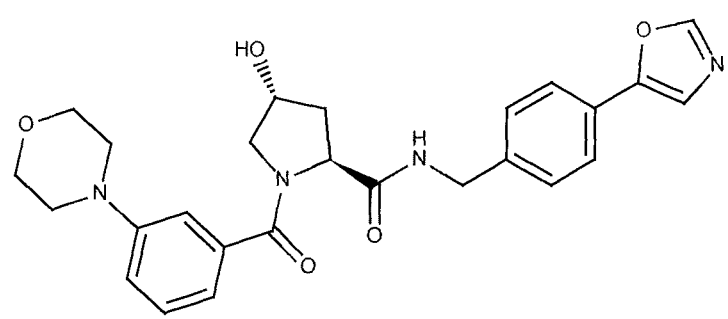
Figure 15:
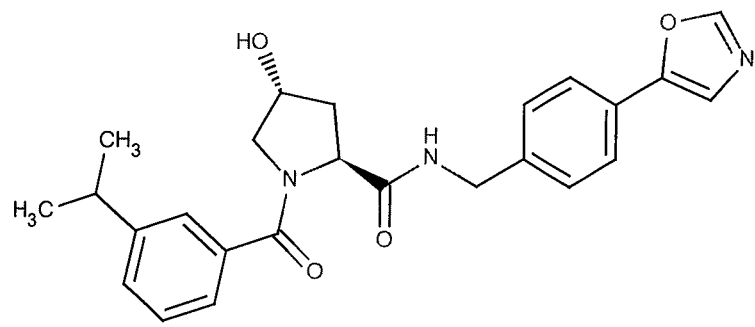
Figure 15:
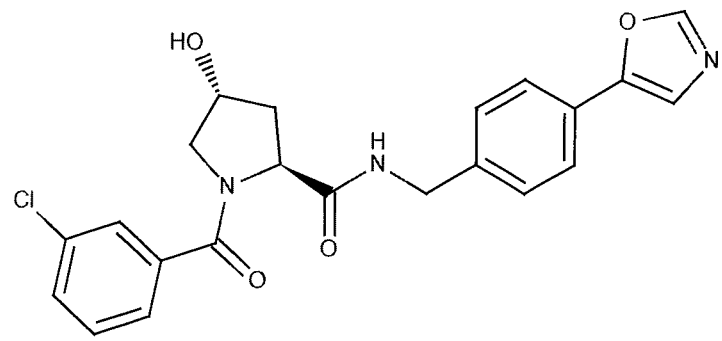
Figure 15:
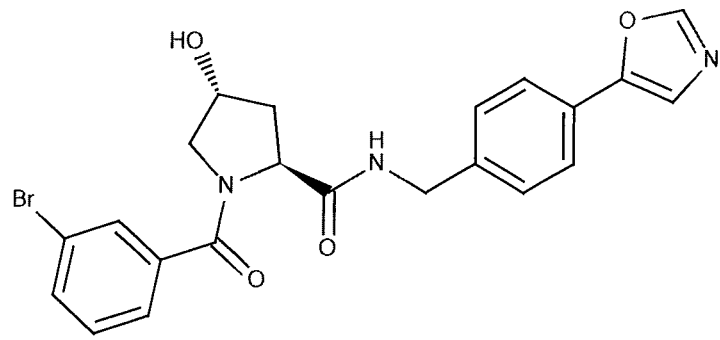
Figure 15:
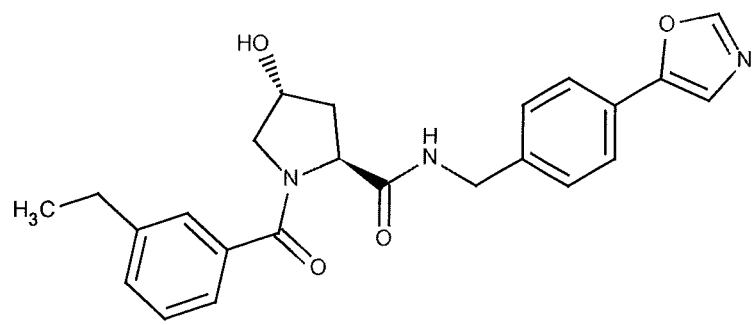
Figure 15:
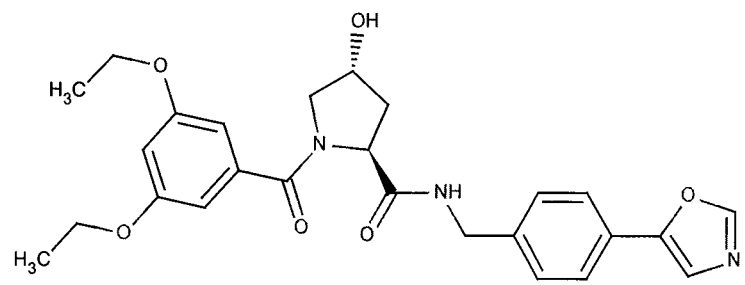
Figure 15:
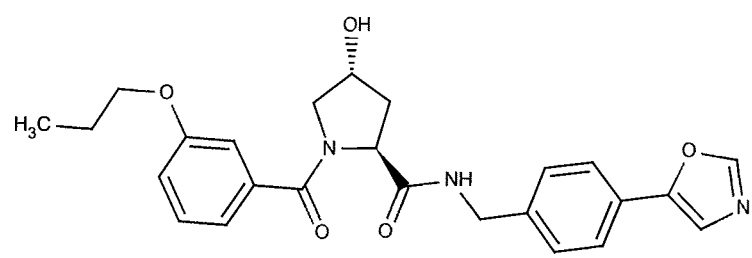
Figure 15:
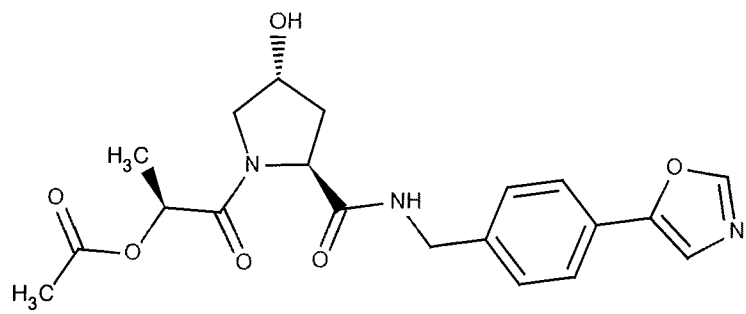
Figure 15:
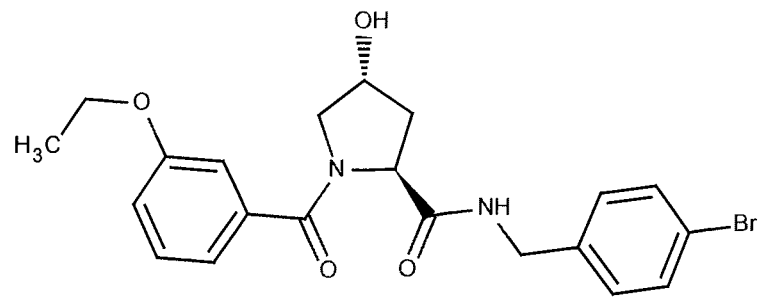
Figure 15:
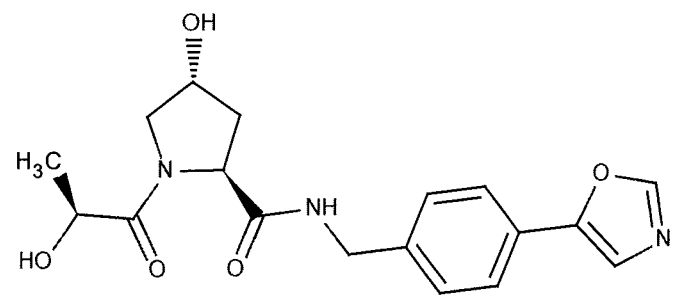
Figure 15:
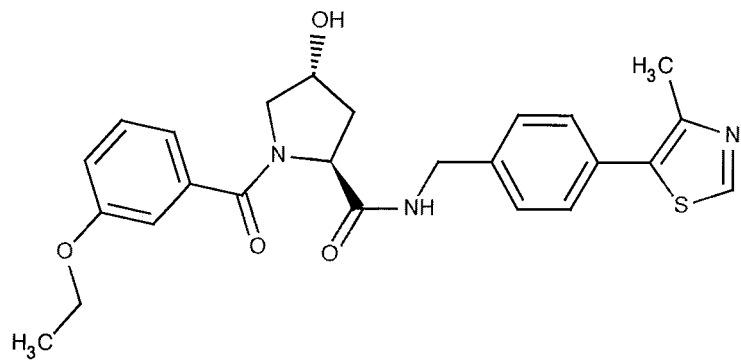
Figure 15:
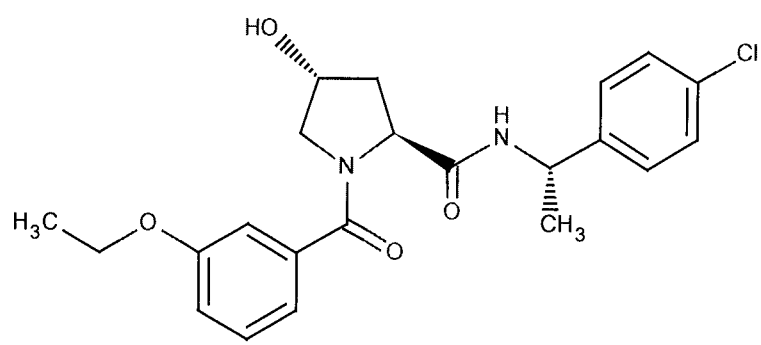
Figure 15:
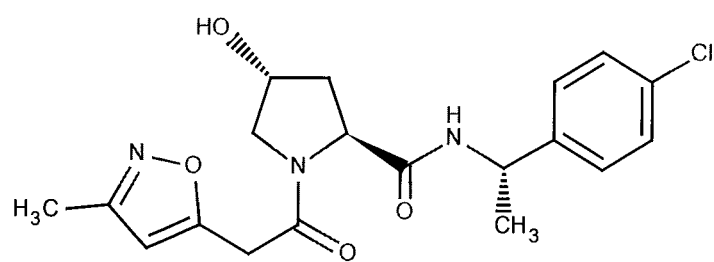
Figure 15:
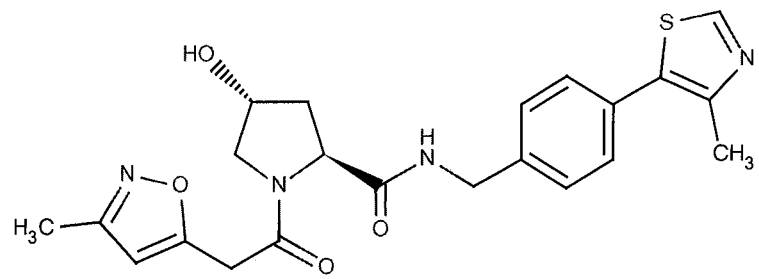
Figure 15:
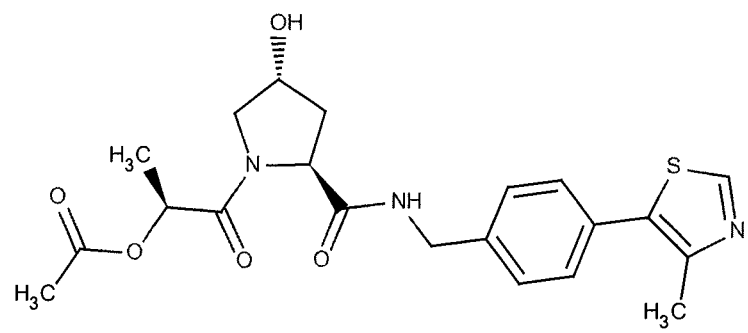
Figure 15:
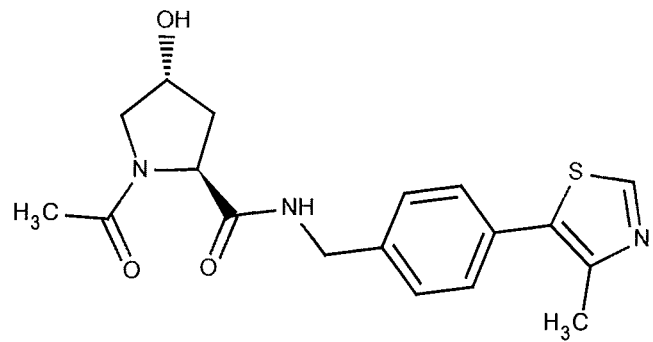
Figure 15:
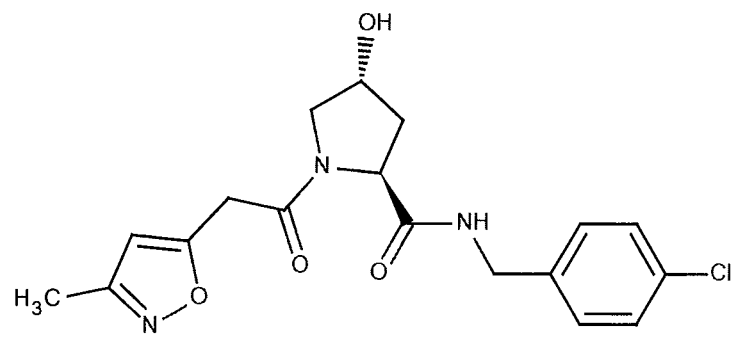
Figure 15:
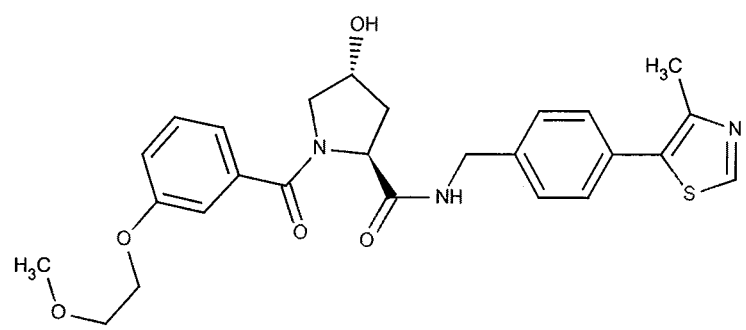
Figure 15:
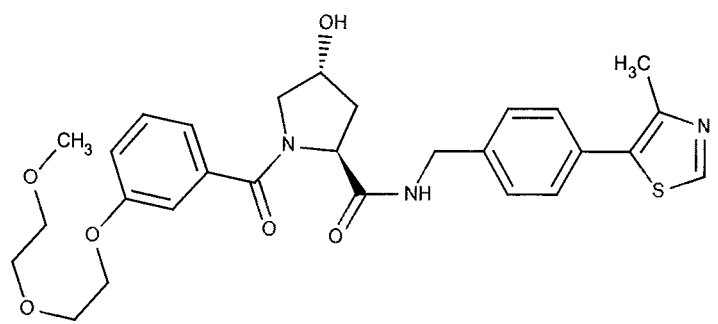
Figure 15:
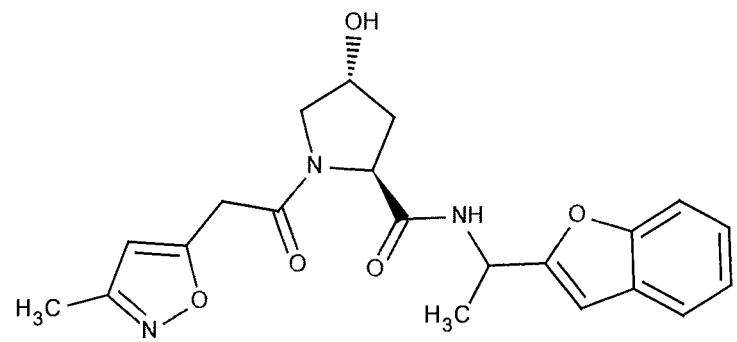
Figure 15:
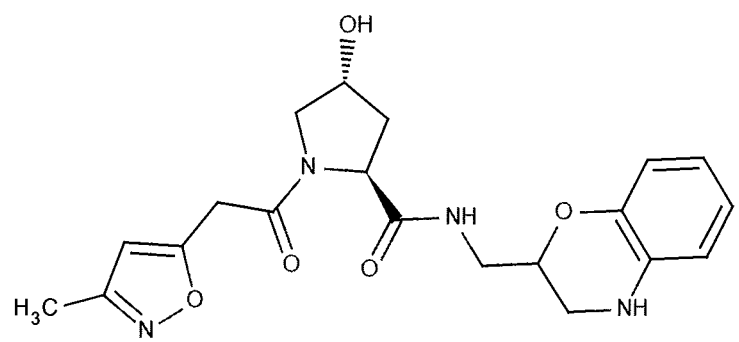
Figure 15:
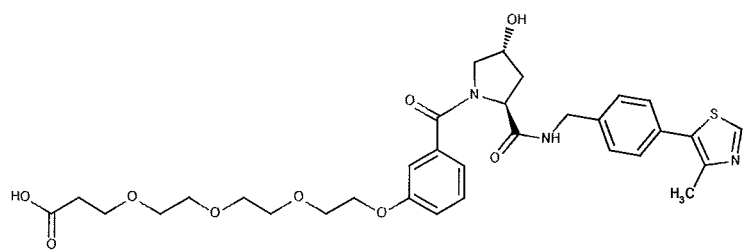
Figure 15:
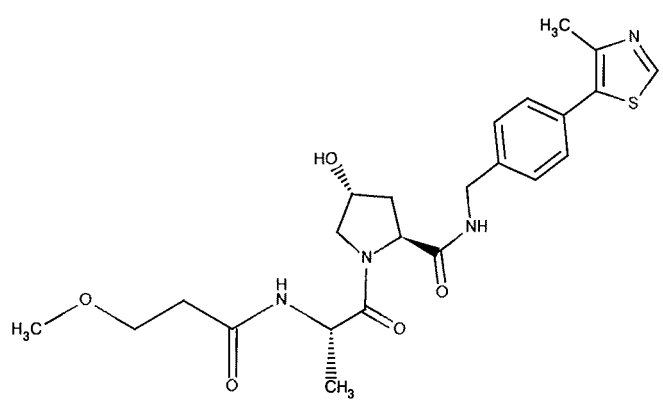
Figure 15:
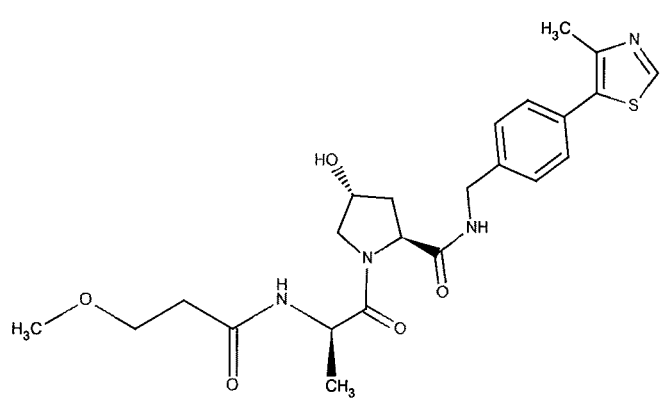
Figure 15:
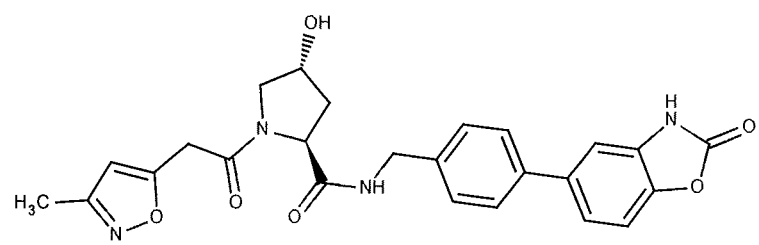
Figure 15:
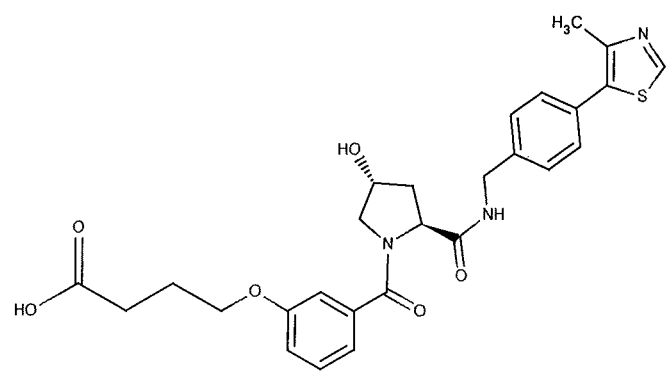
Figure 15:
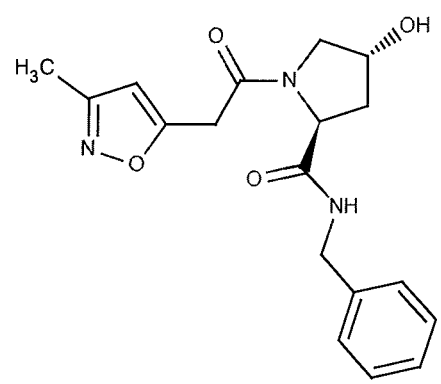
Figure 15:
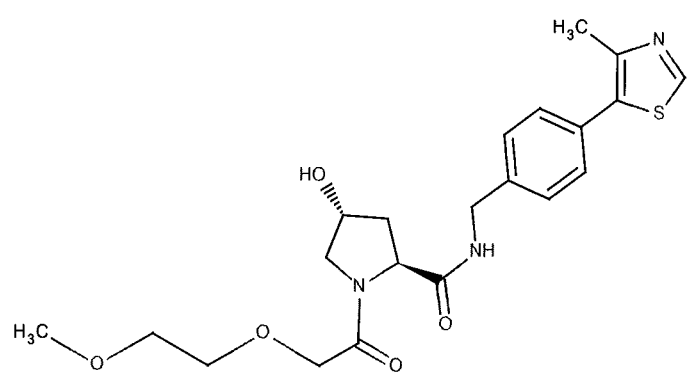
Figure 15:
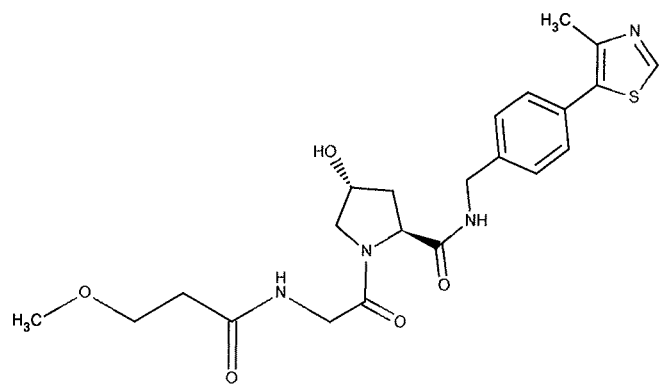
Figure 15:
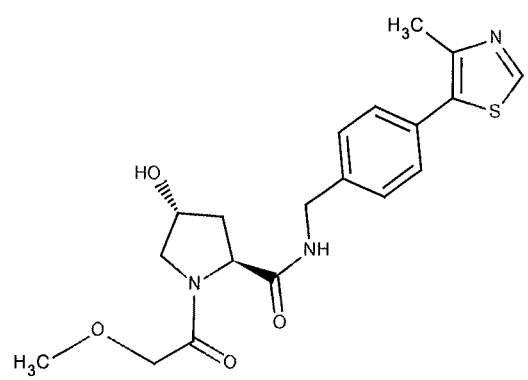
Figure 15:
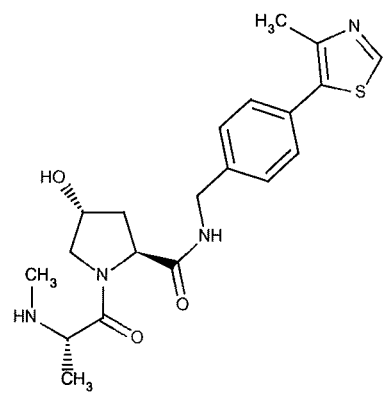
Figure 15:
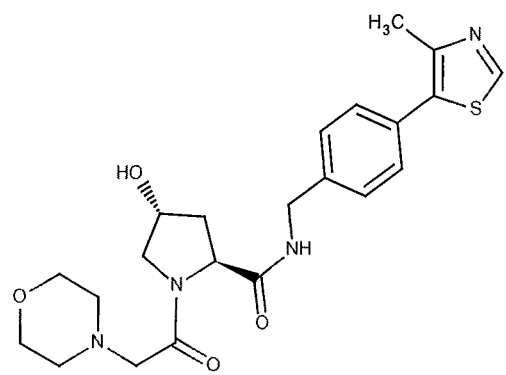
Figure 15:
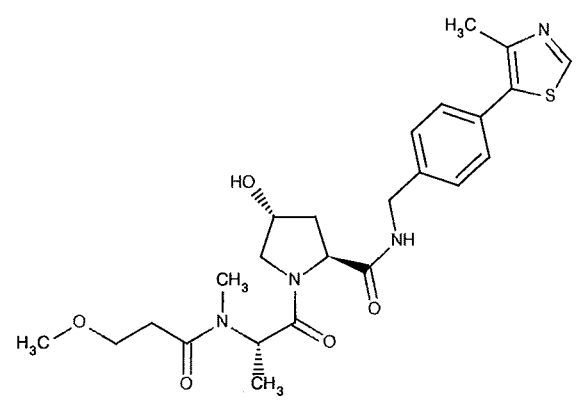
Figure 15:
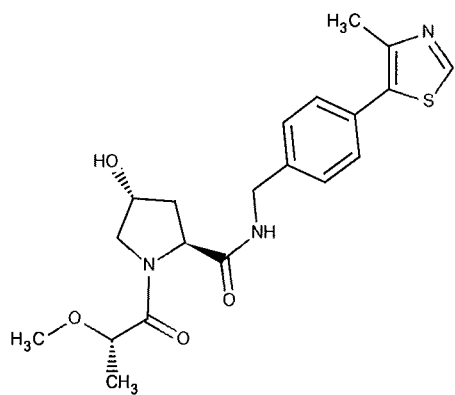
Figure 15:
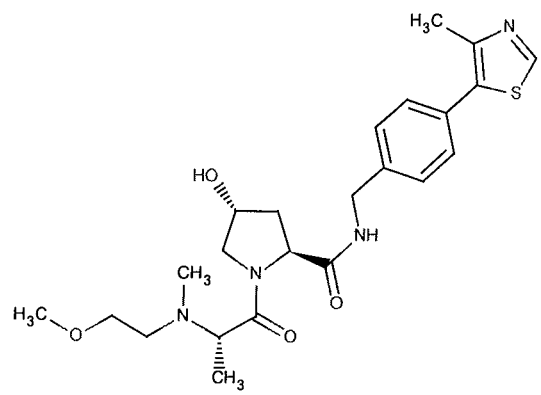
Figure 15:
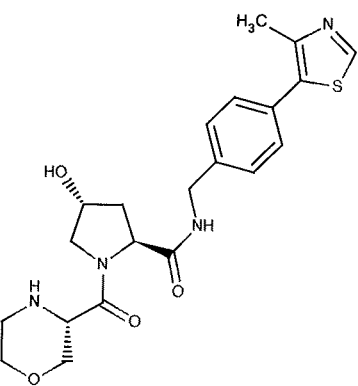
Figure 15:
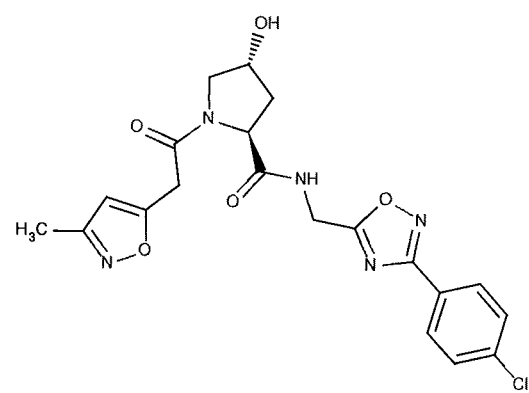
Figure 15:
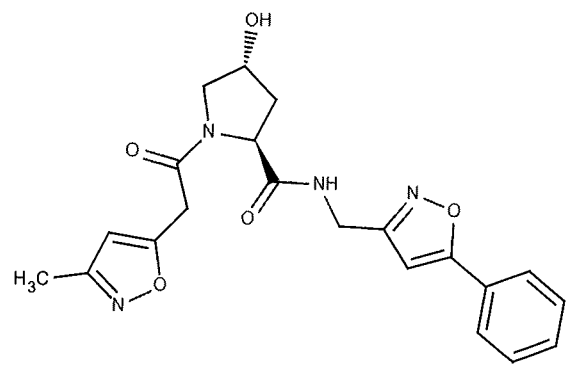
Figure 15:
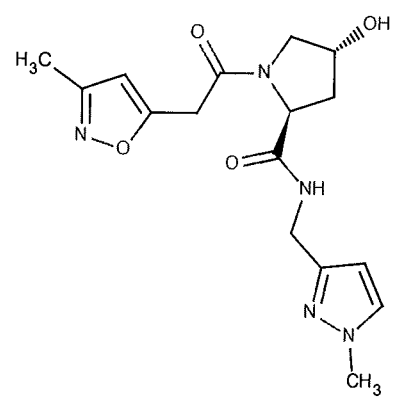
Figure 15:
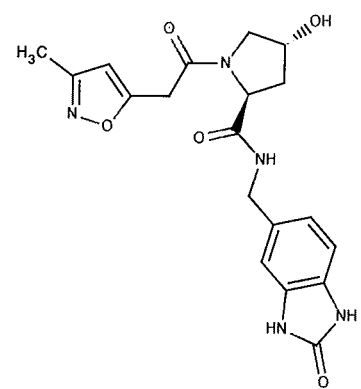
Figure 15:
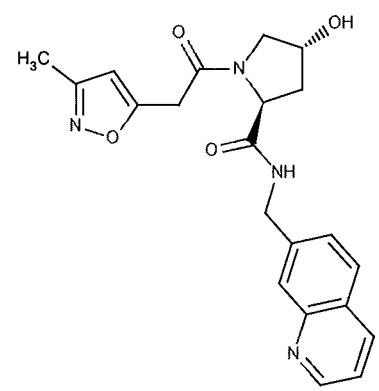
Figure 15:
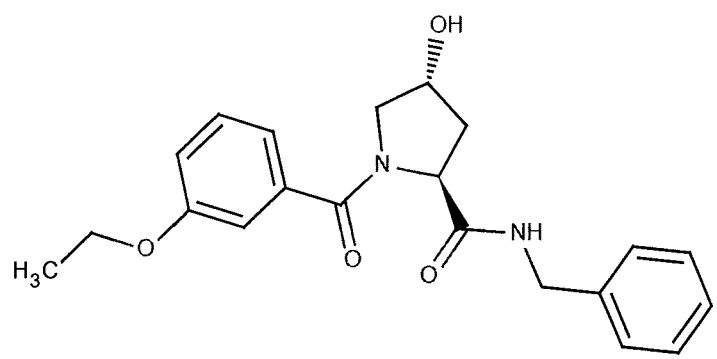
Figure 15:
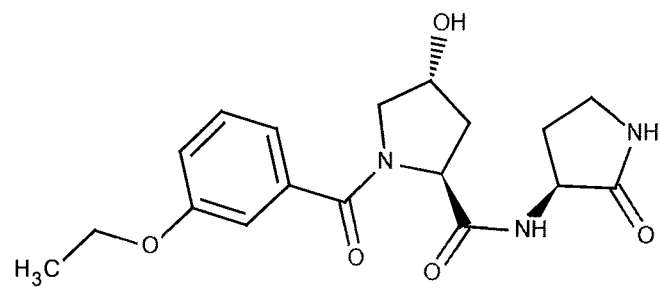
Figure 15:
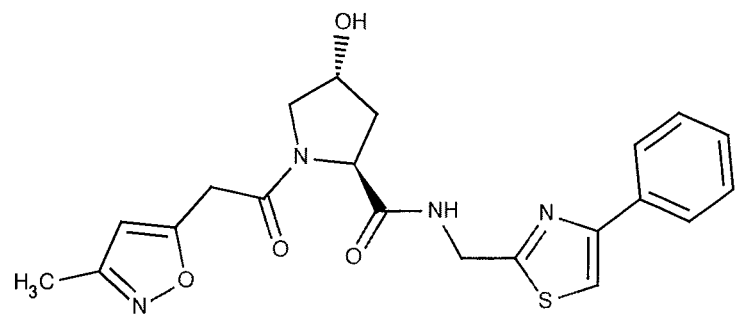
Figure 15:
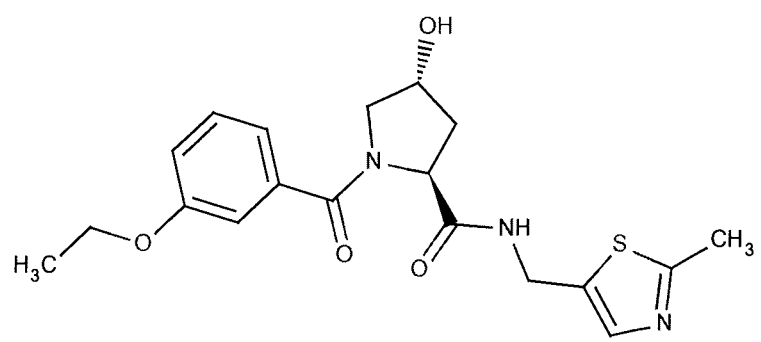
Figure 15:
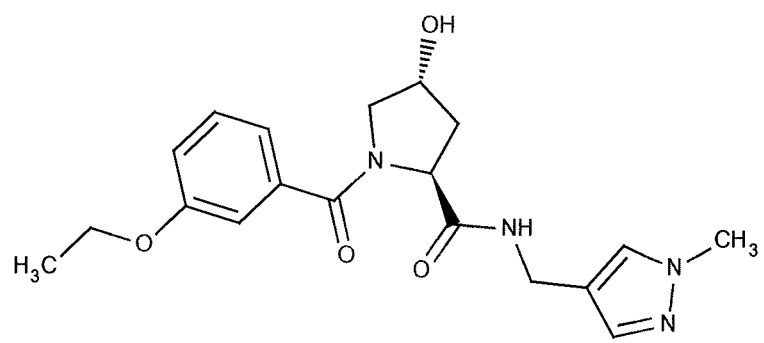
Figure 15:
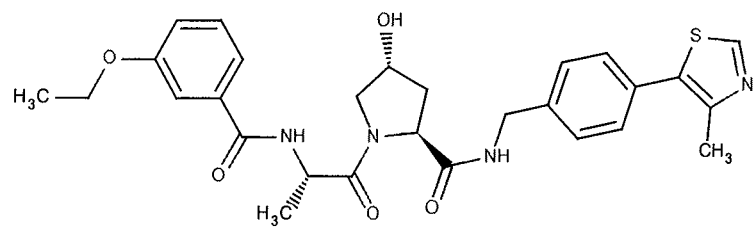
Figure 15:
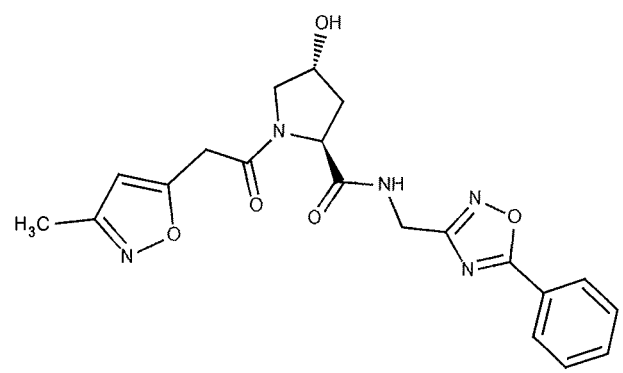
Figure 15:
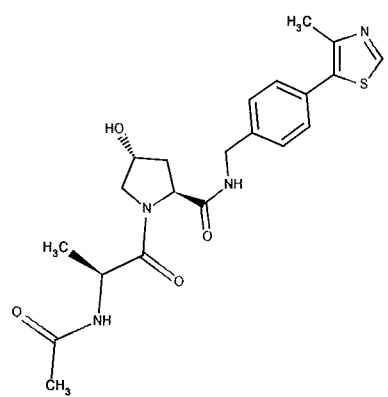
Figure 15:
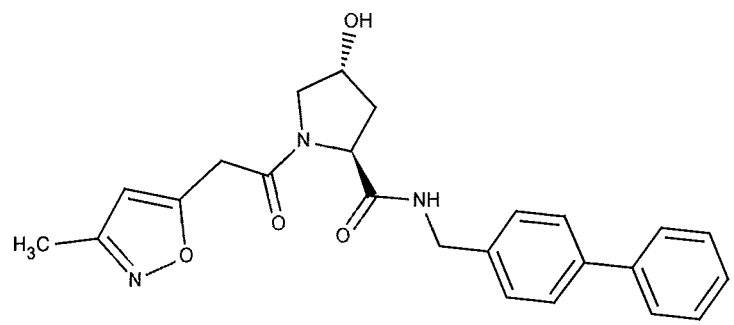
Figure 15:
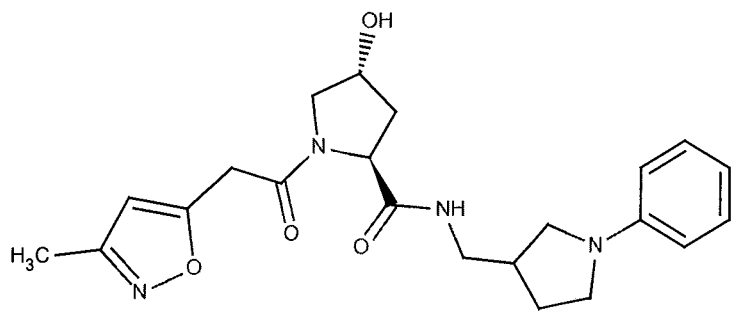
Figure 15:
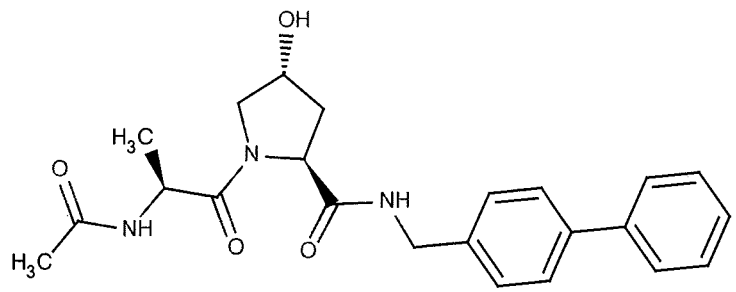
Figure 15:
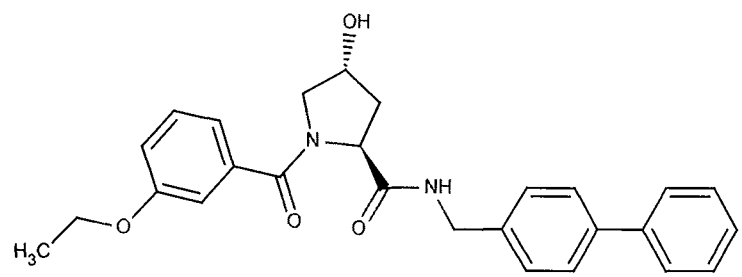
Figure 15:
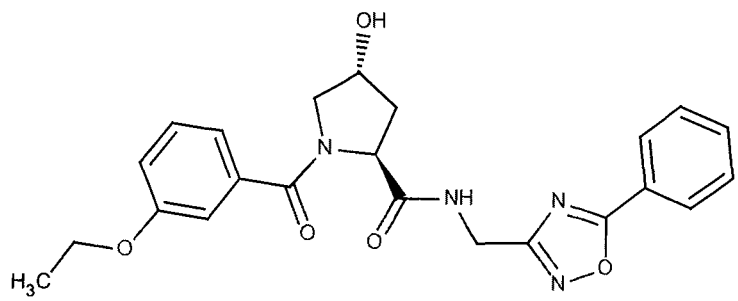
Figure 15:
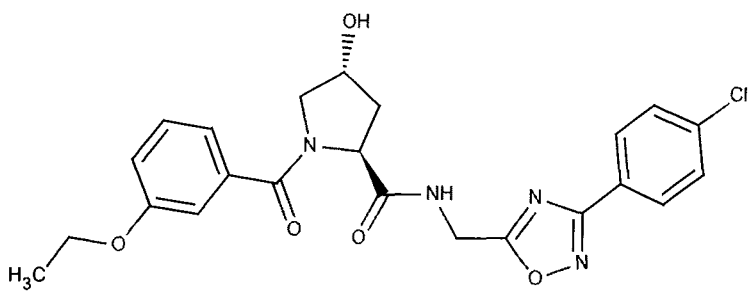
Figure 15:
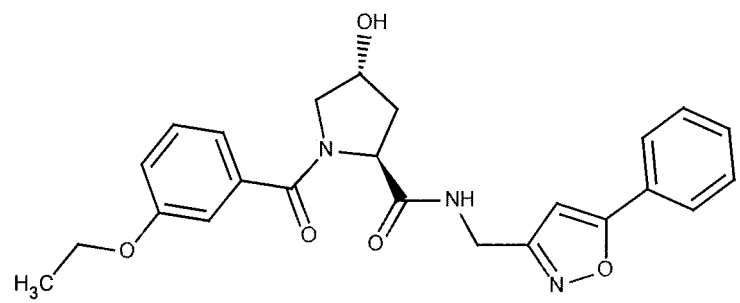
Figure 15:
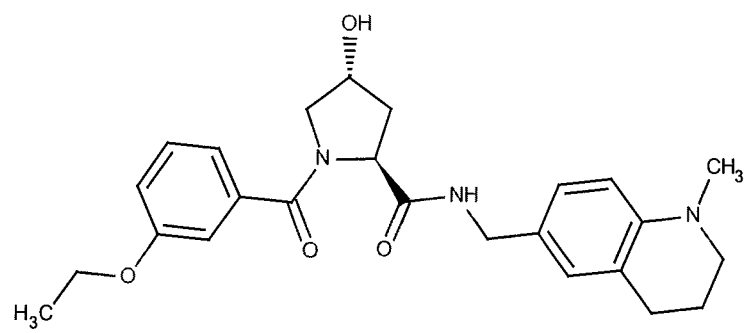
Figure 15:
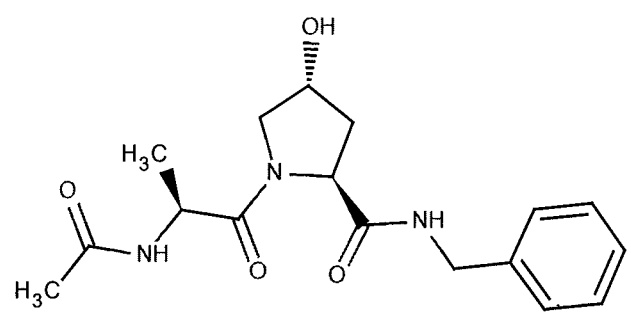
Figure 15:
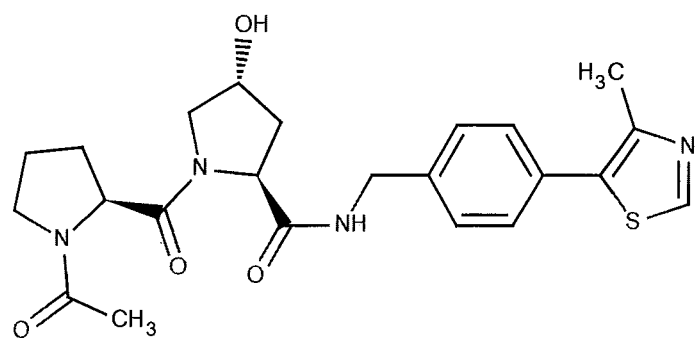
Figure 15:
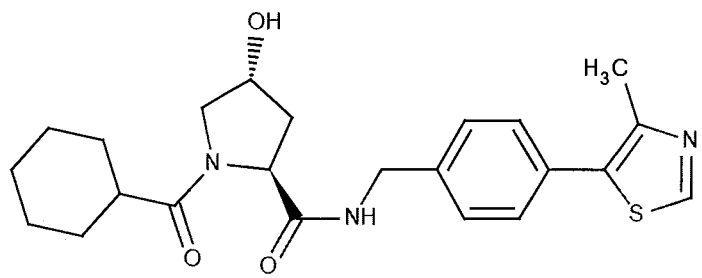
Figure 15:
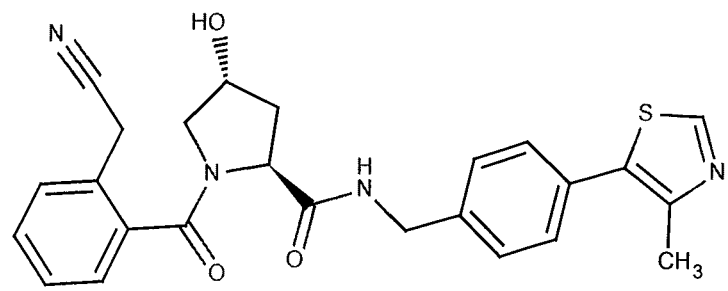
Figure 15:
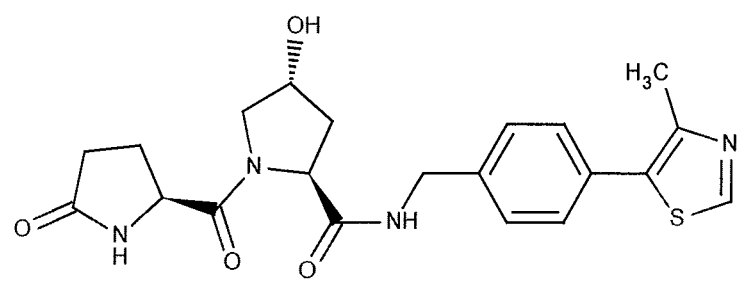
Figure 15:
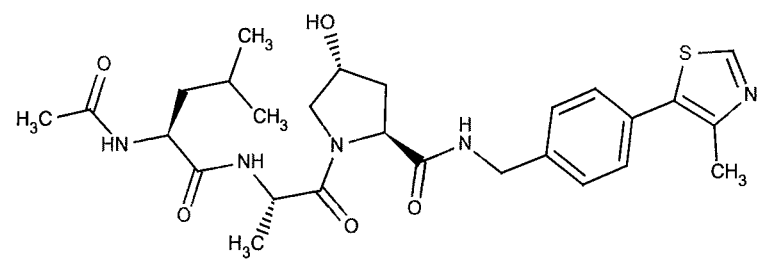
Figure 15:
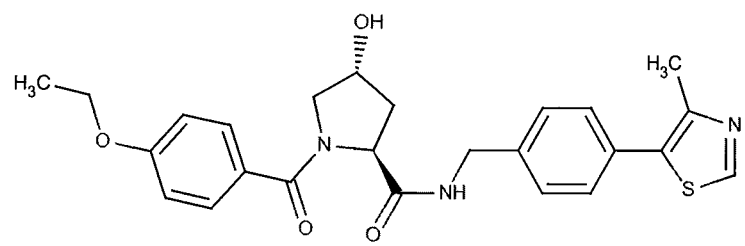
Figure 15:
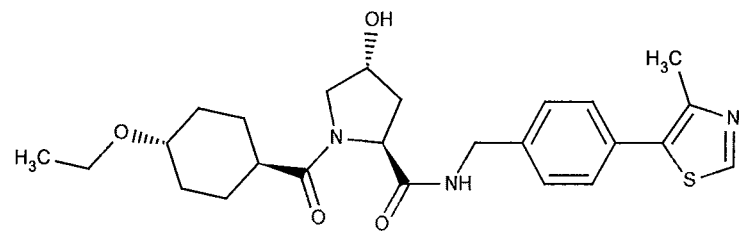
Figure 15:
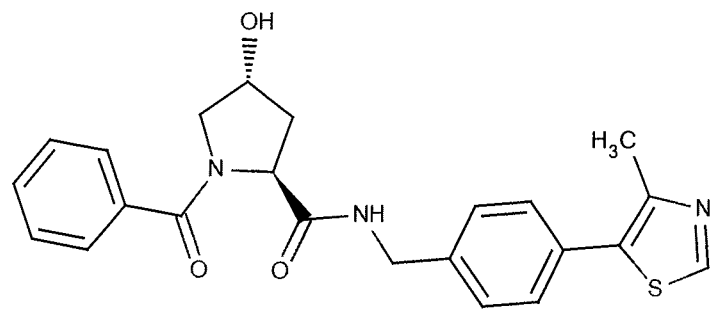
Figure 15:
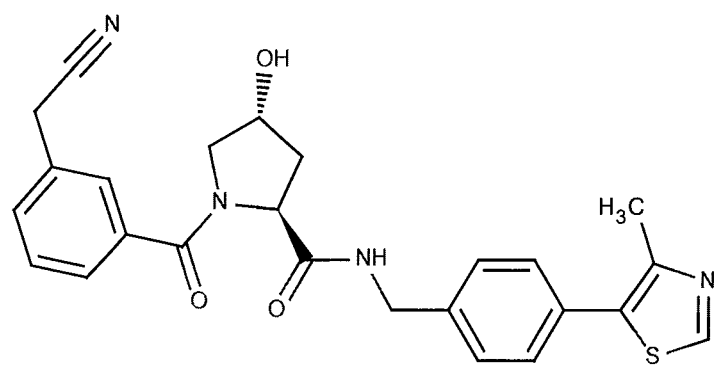
Figure 15:
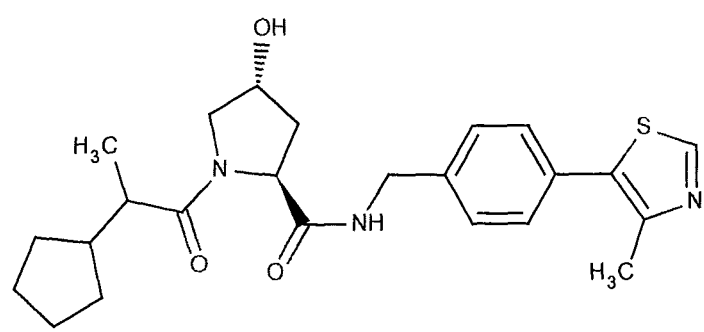
Figure 15:
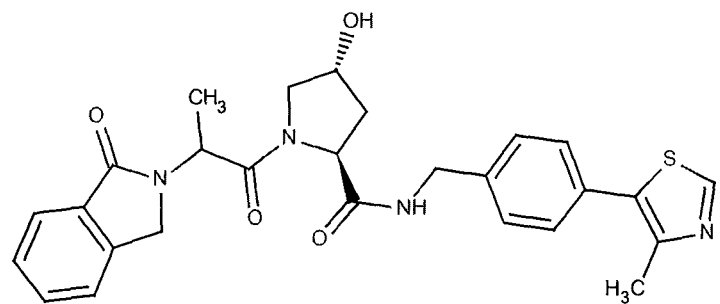
Figure 15:
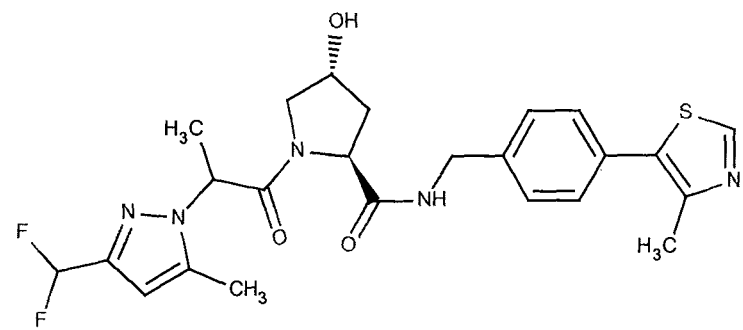
Figure 15:
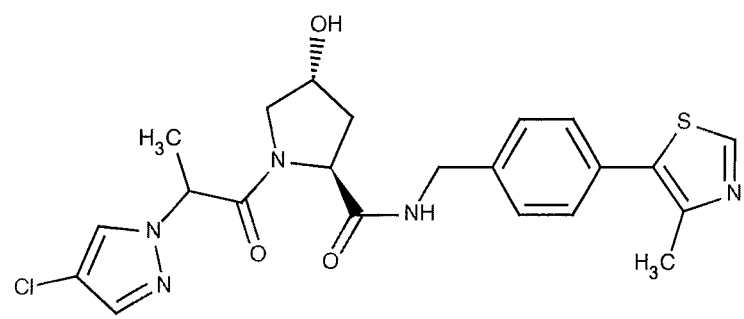
Figure 15:
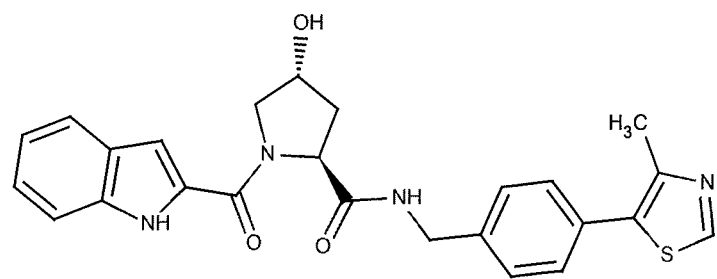
Figure 15:
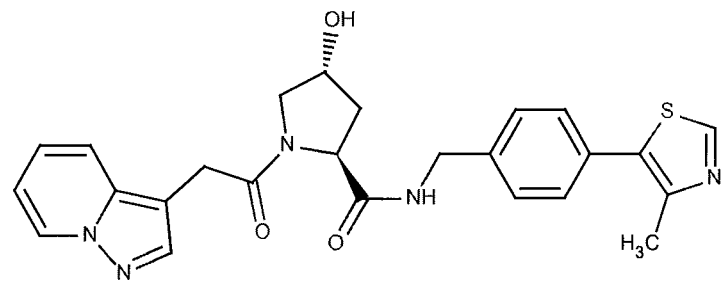
Figure 15:
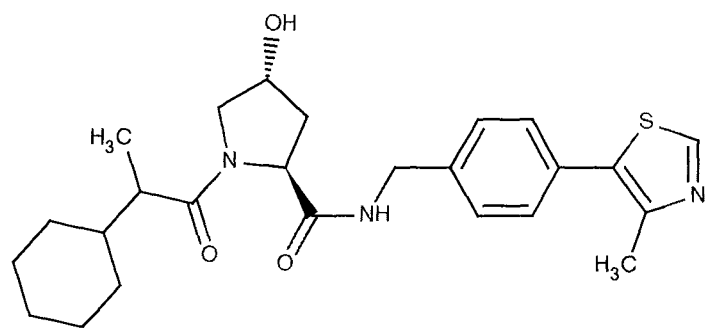
Figure 15:
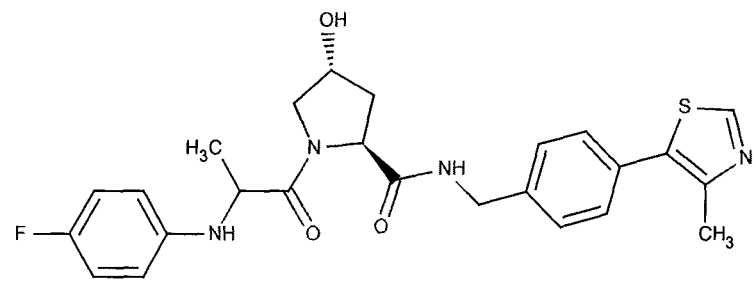
Figure 15:
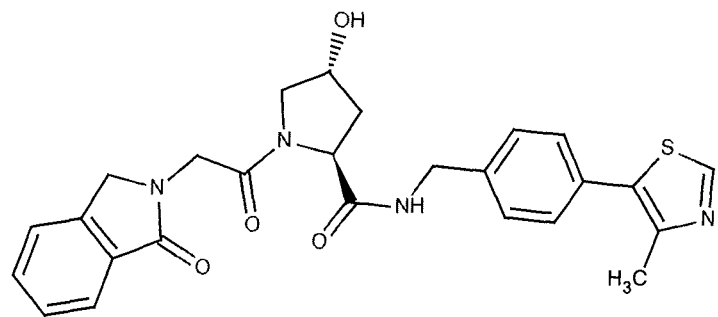
Figure 15:
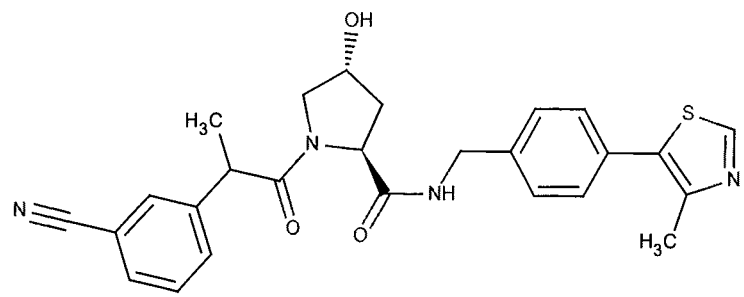
Figure 15:
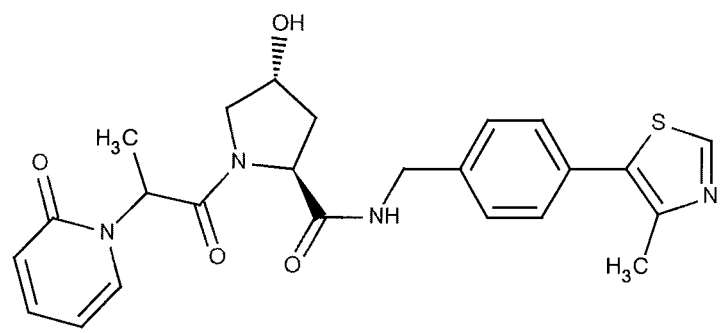
Figure 15:
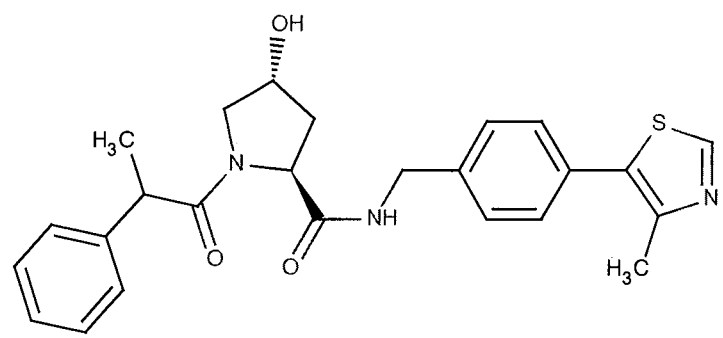
Figure 15:
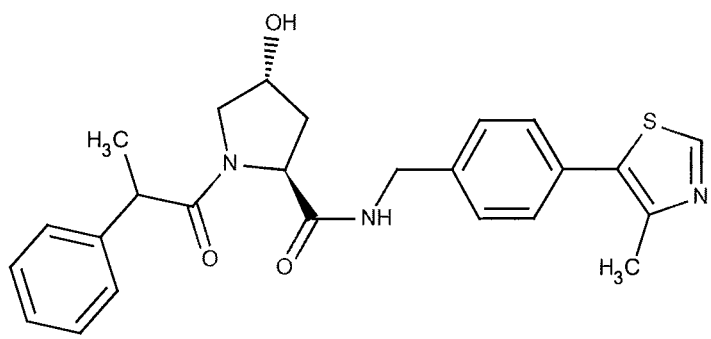
Figure 15:
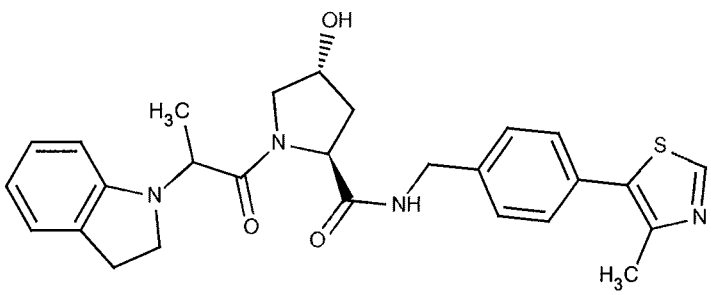
Figure 15:
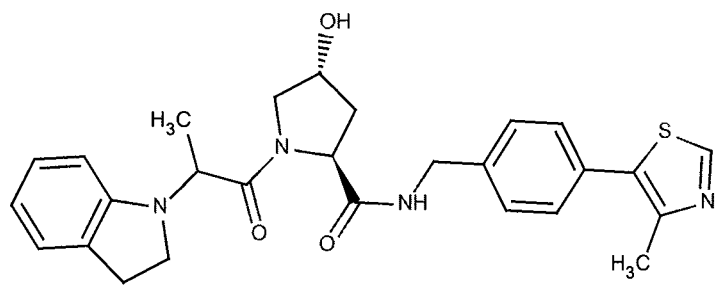
Figure 15:
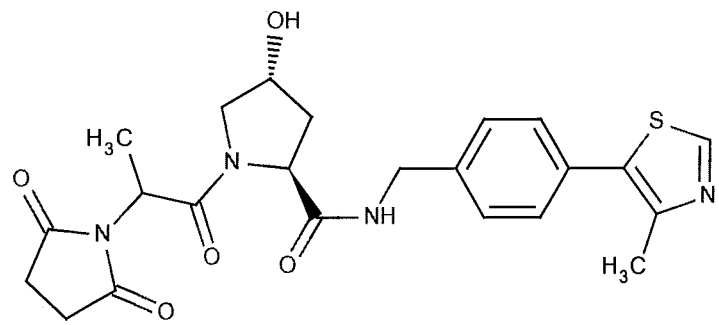
Figure 15:
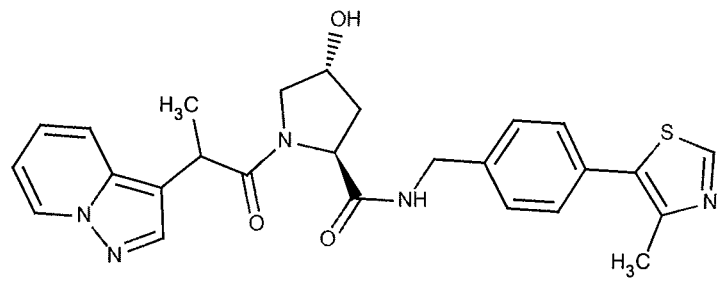
Figure 15:
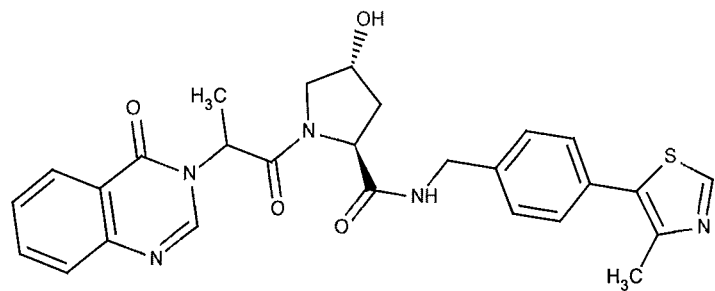
Figure 15:
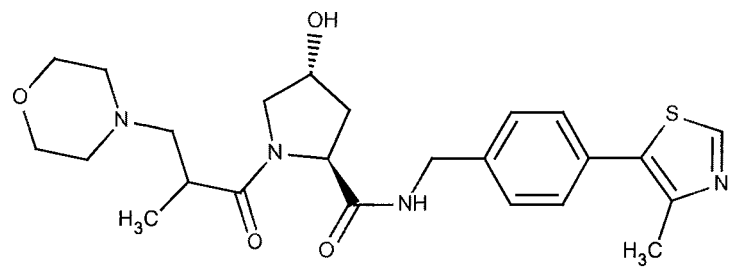
Figure 15:
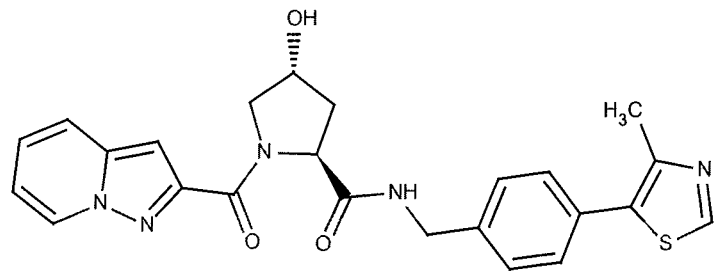
Figure 15:
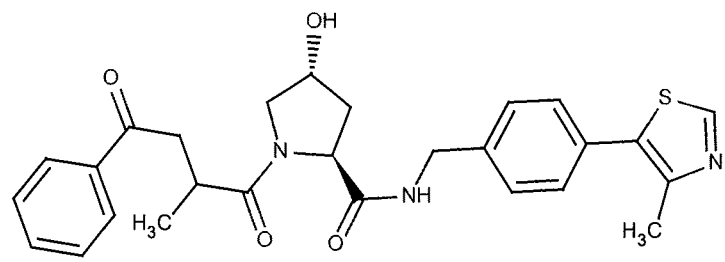
Figure 15:
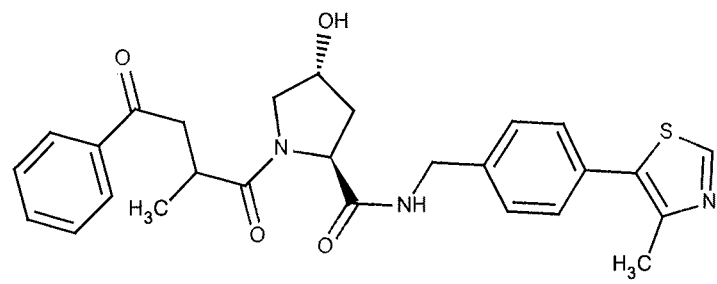
Figure 15:
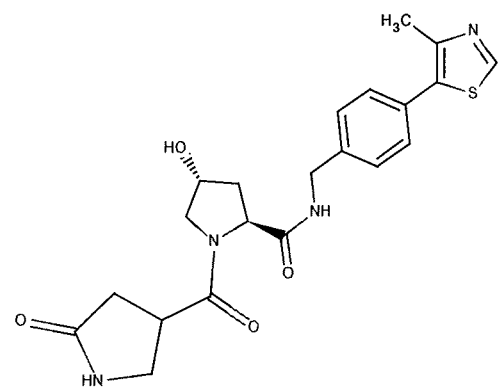
Figure 15:
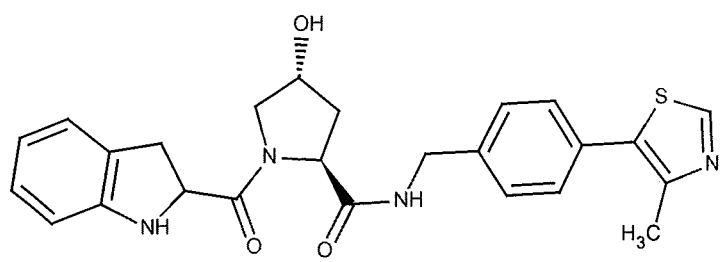
Figure 15:
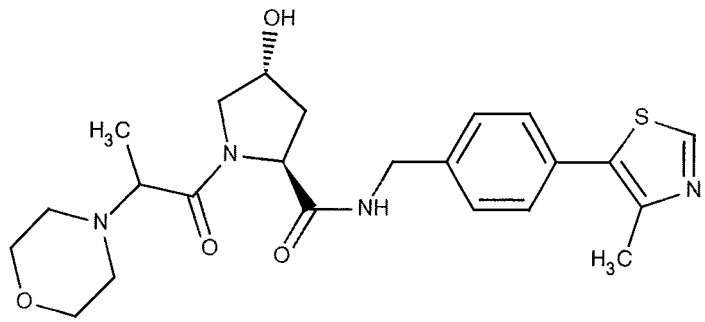
Figure 15:
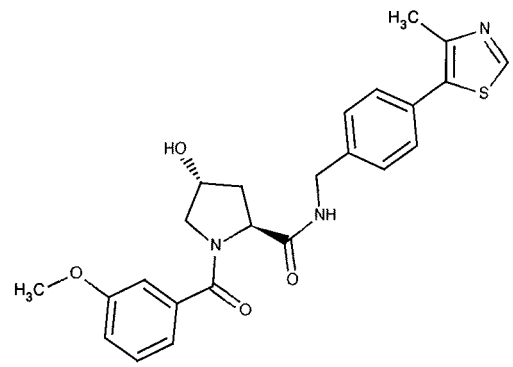
Figure 15:
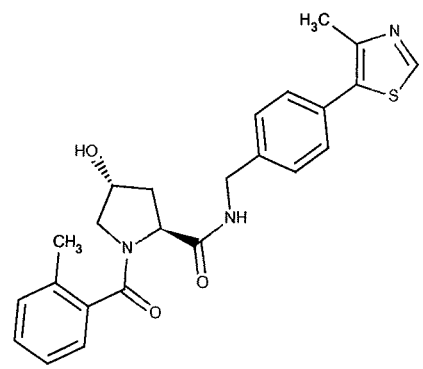
Figure 15:
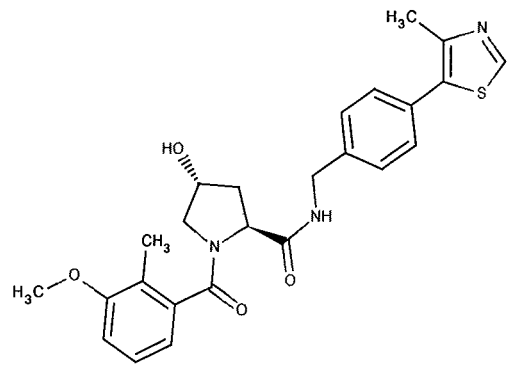
Figure 15:
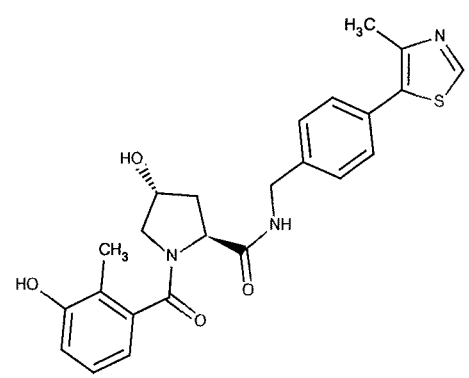
Figure 15:
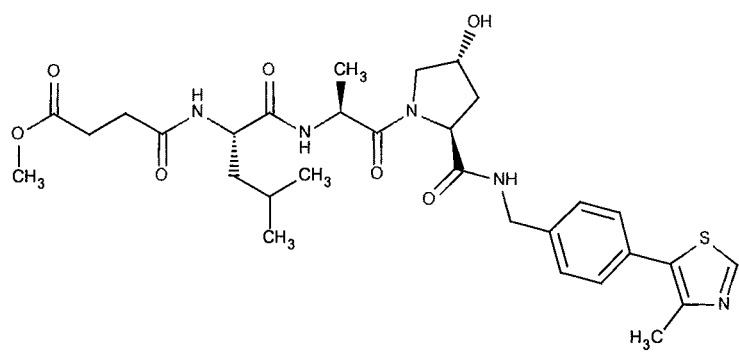
Figure 15:
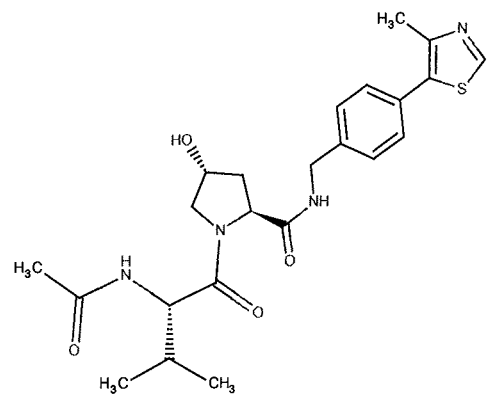
Figure 15:
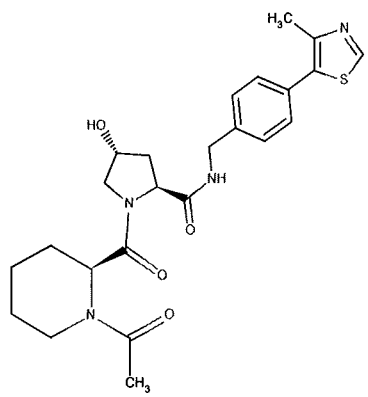
Figure 15:
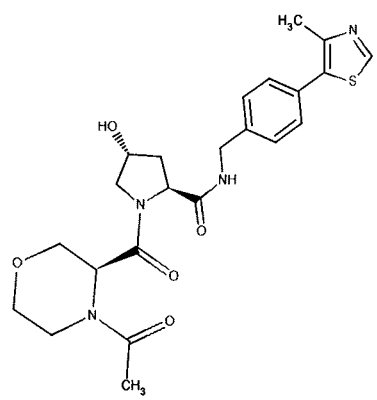
Figure 15:
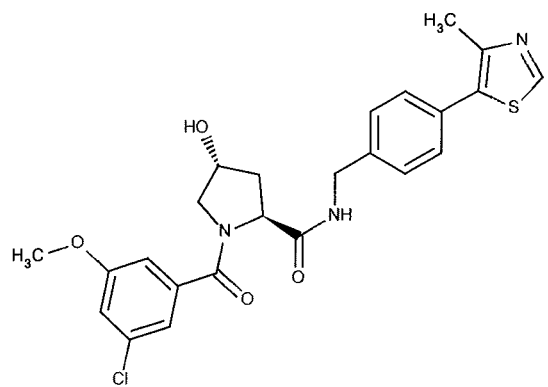
Figure 15:
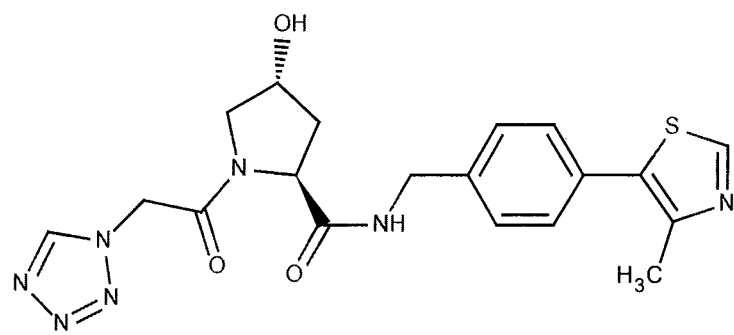
Figure 15:
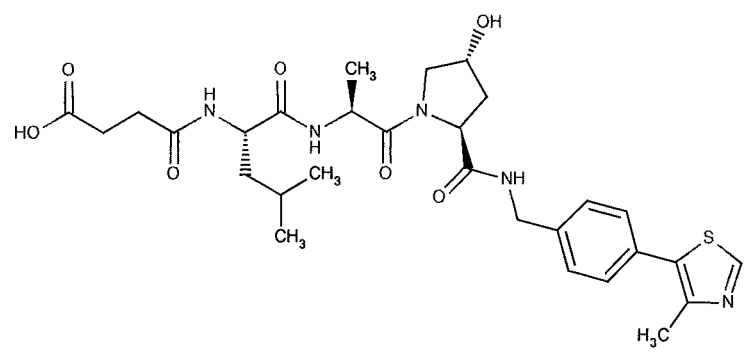
Figure 15:
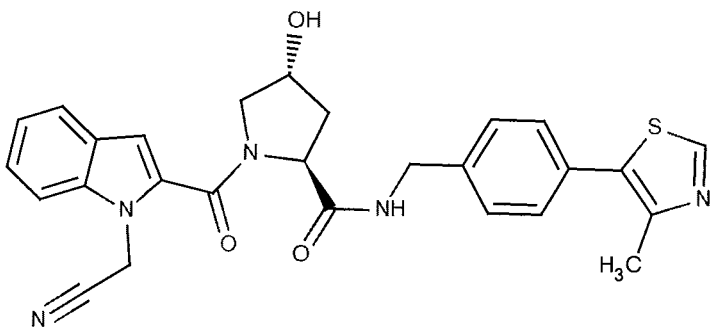
Figure 15:
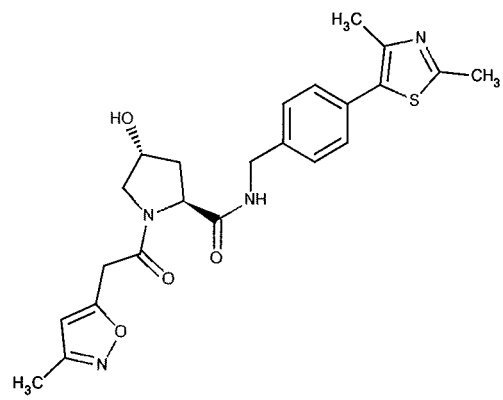
Figure 15:
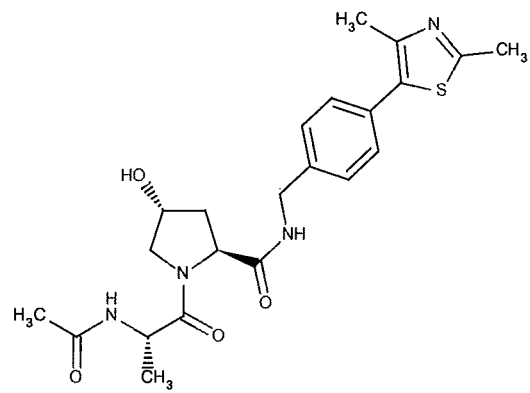
Figure 15:
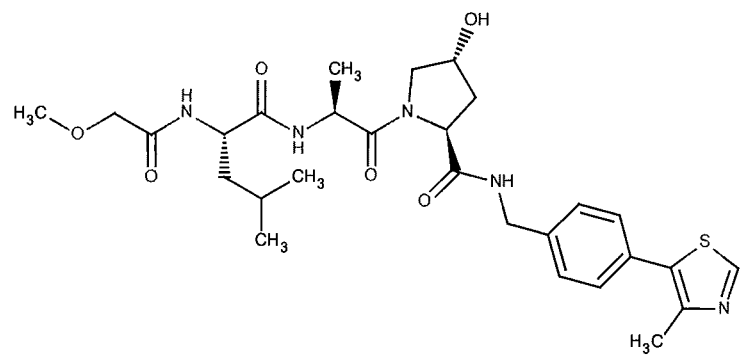
Figure 15:
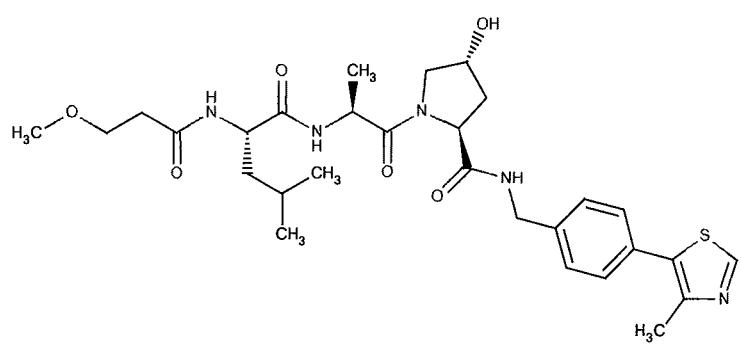
Figure 15:
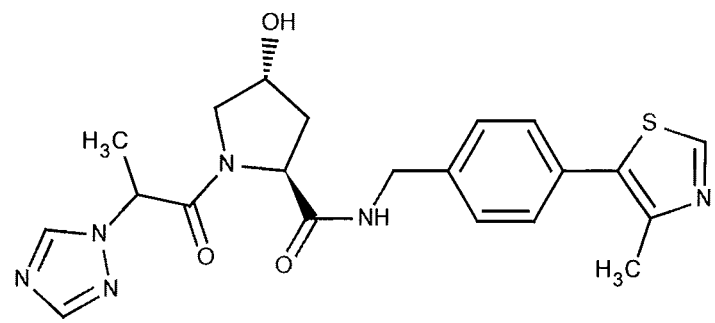
Figure 15:
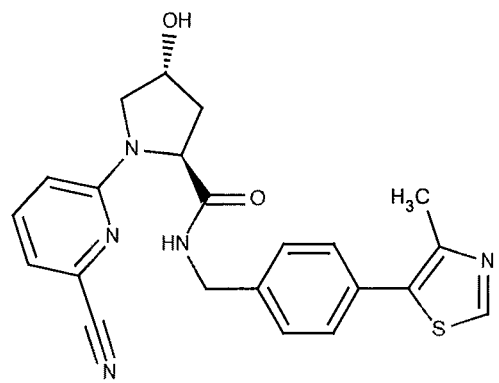
Figure 15:
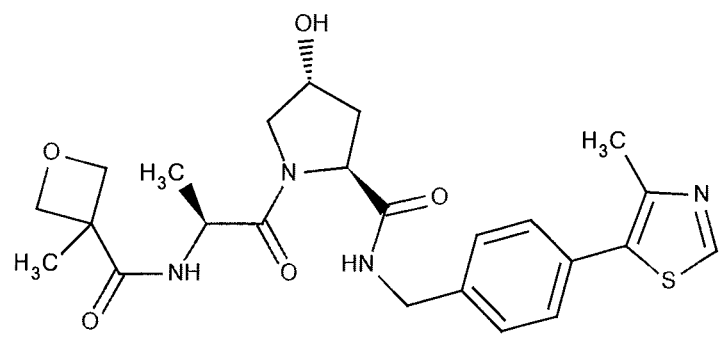
Figure 15:
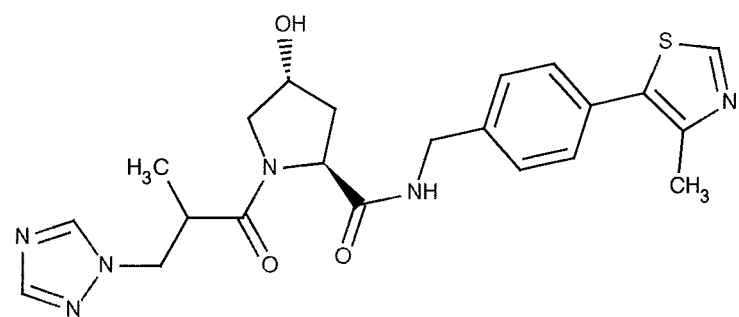
Figure 15:
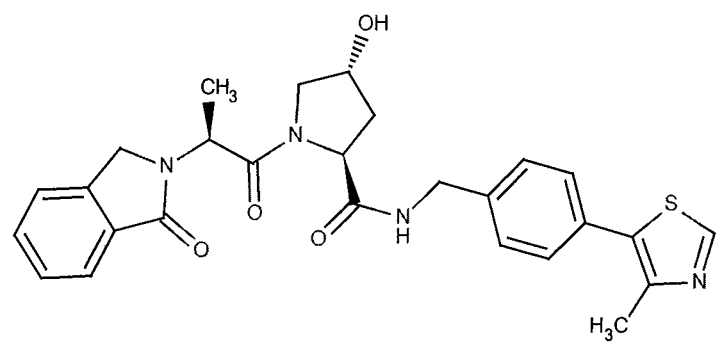
Figure 15:
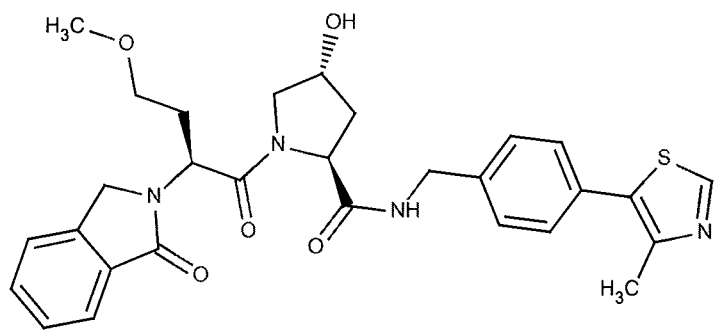
Figure 15:
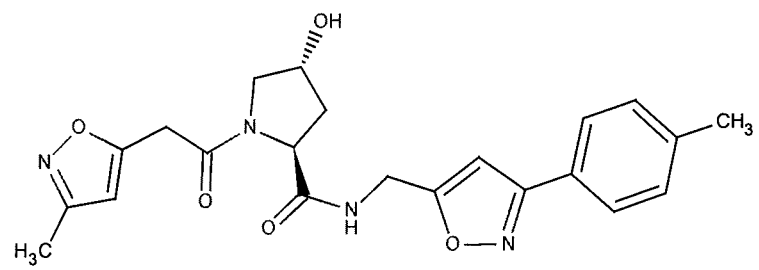
Figure 15:
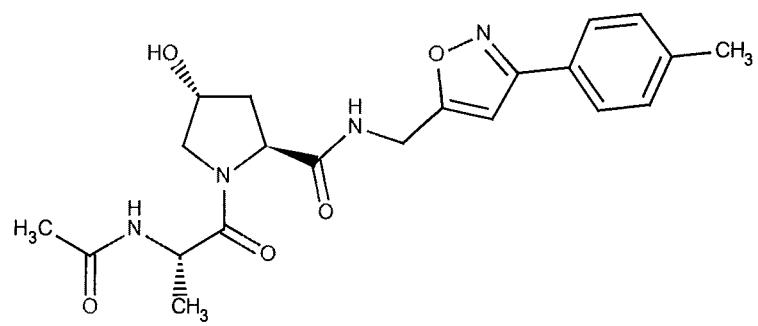
Figure 15:
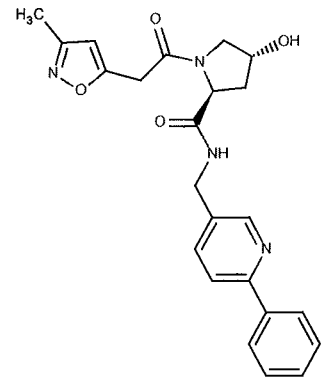
Figure 15:
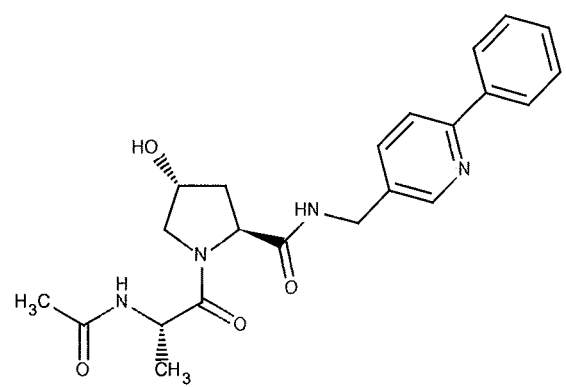
Figure 15:
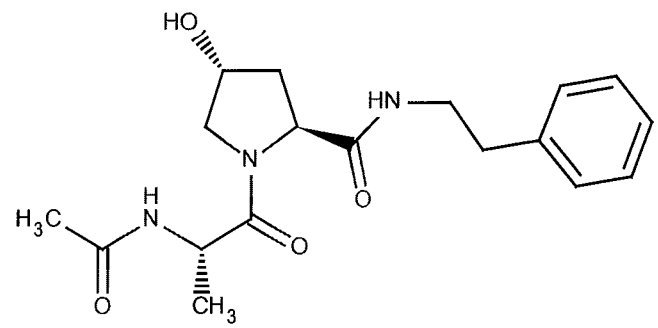
Figure 15:
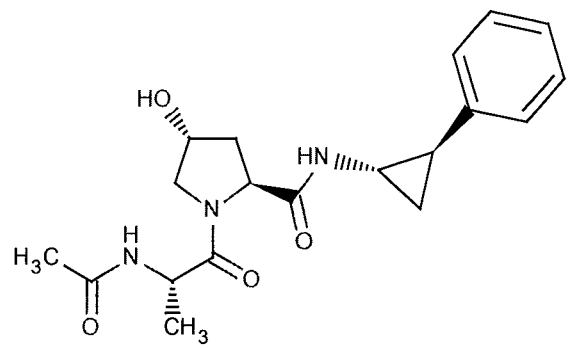
Figure 15:
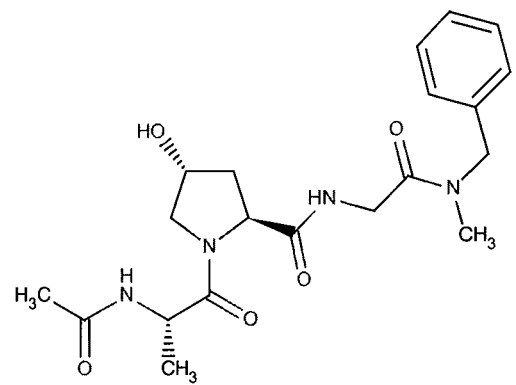
Figure 15:
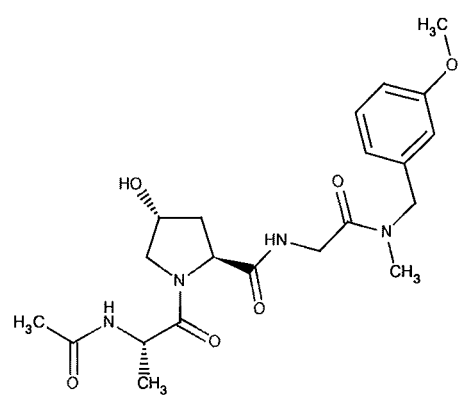
Figure 15:
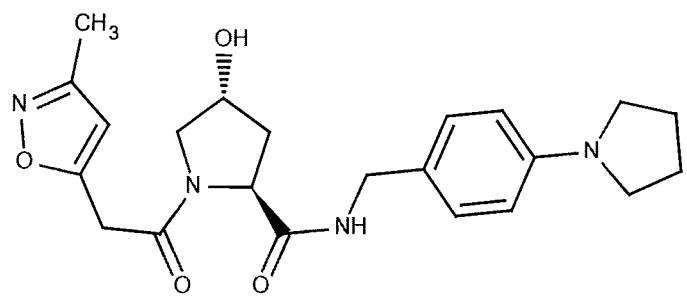
Figure 15:
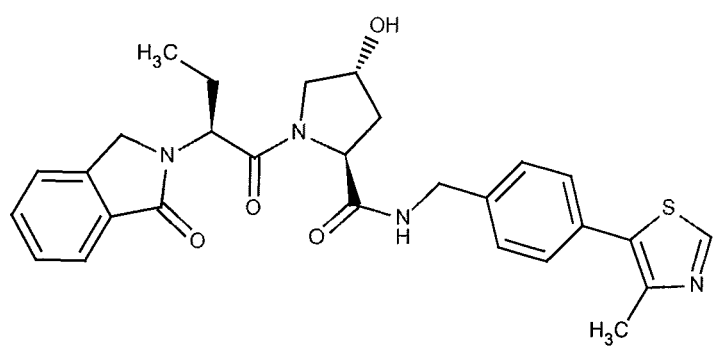
Figure 15:
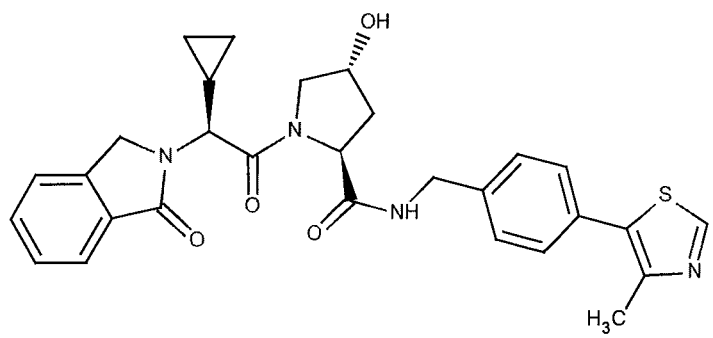
Figure 15:
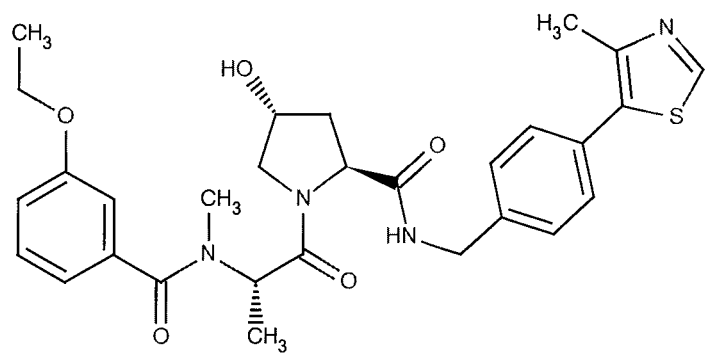
Figure 15:
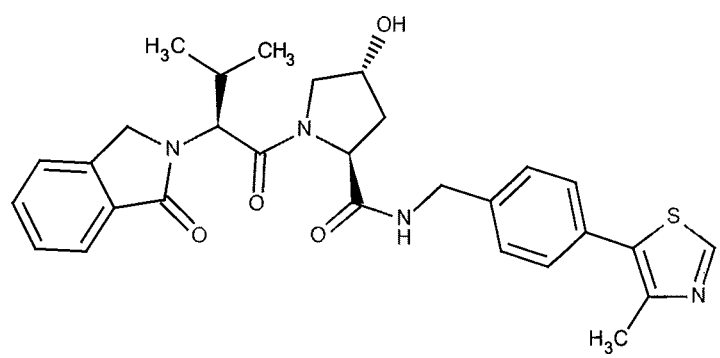
Figure 15:

Figure 15:
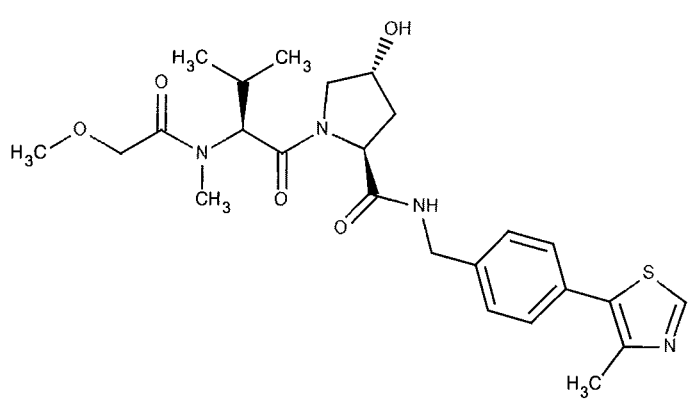
Figure 15:
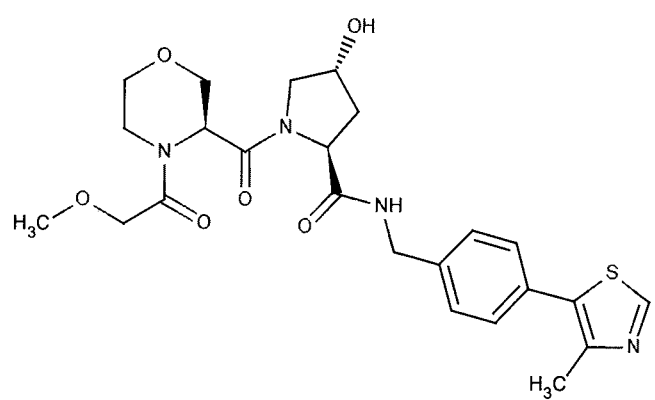
Figure 15:
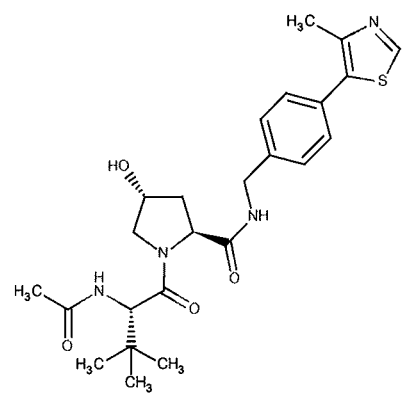
Figure 15:
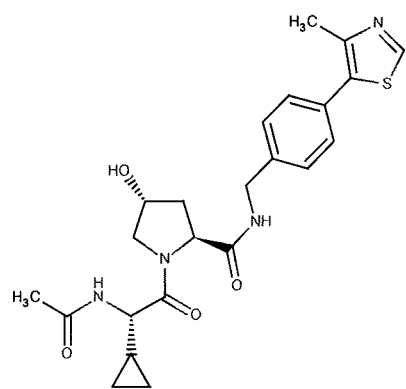
Figure 15:
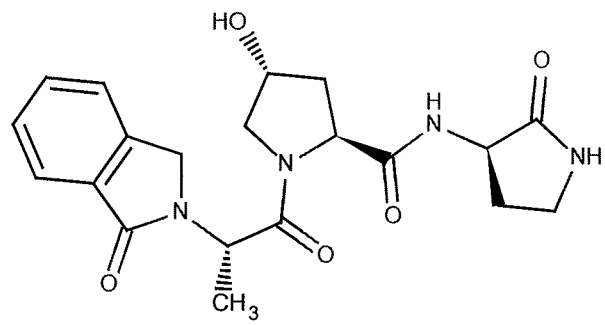
Figure 15:
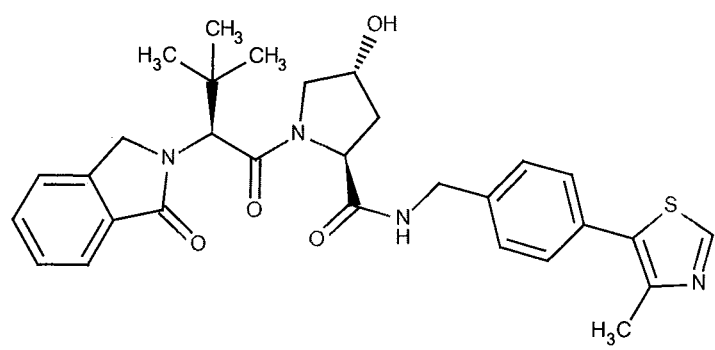
Figure 15:
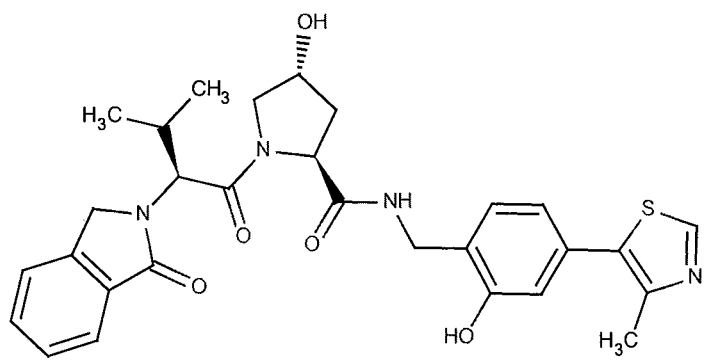
Figure 15:
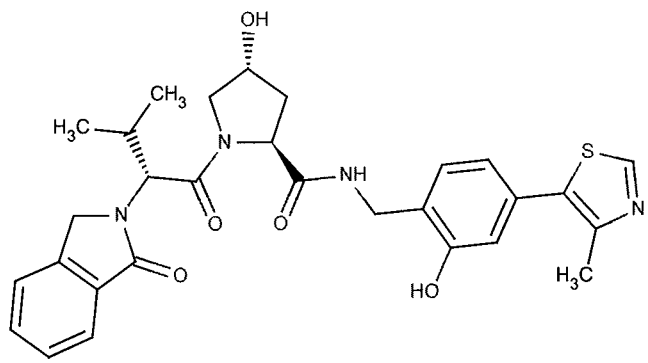
Figure 15:
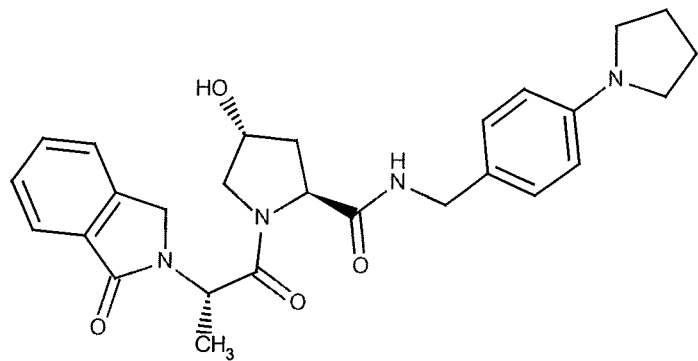
Figure 15:
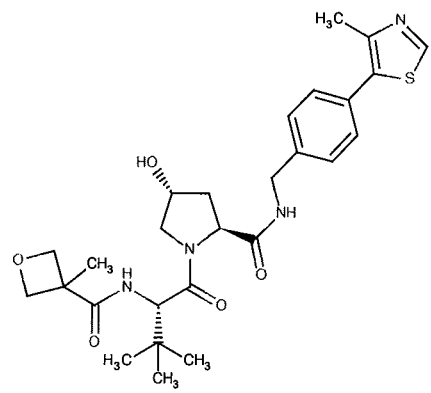
Figure 15:
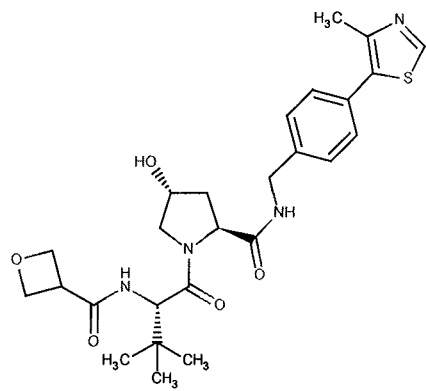
Figure 15:
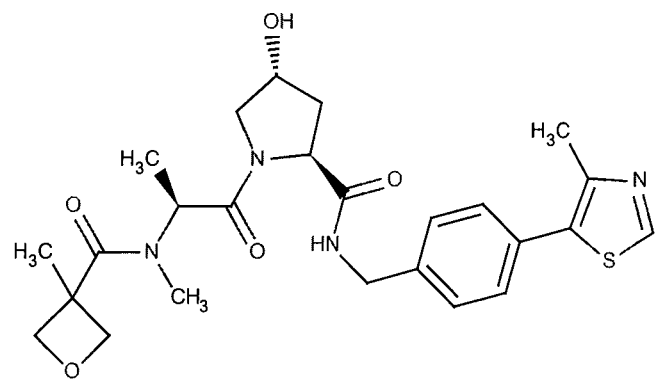
Figure 15:
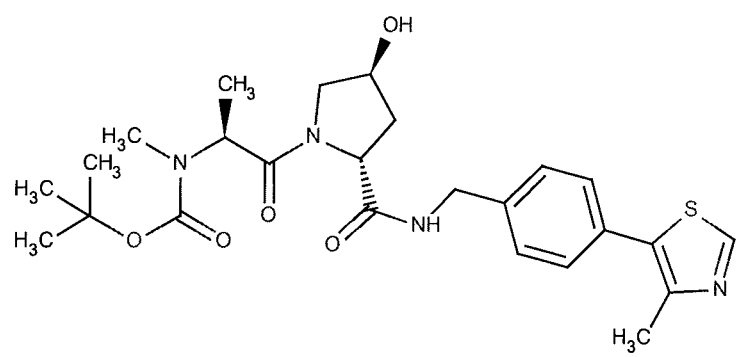
Figure 15:
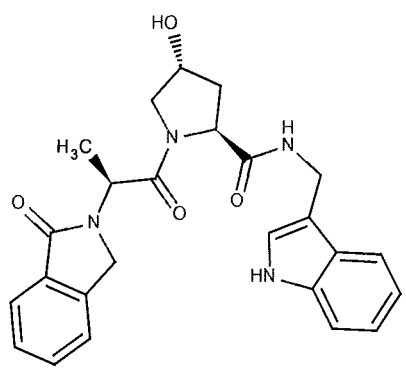
Figure 15:
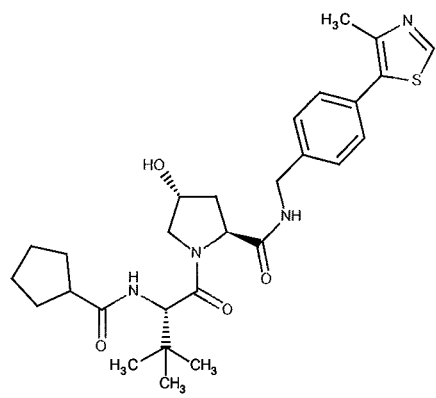
Figure 15:
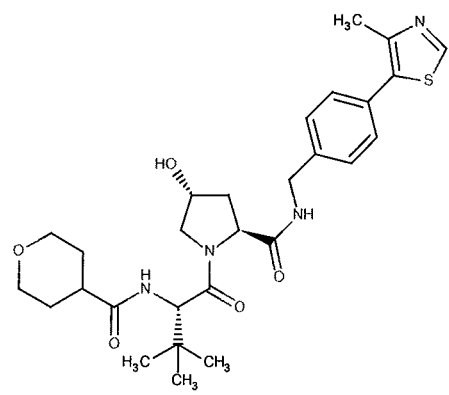
Figure 15:
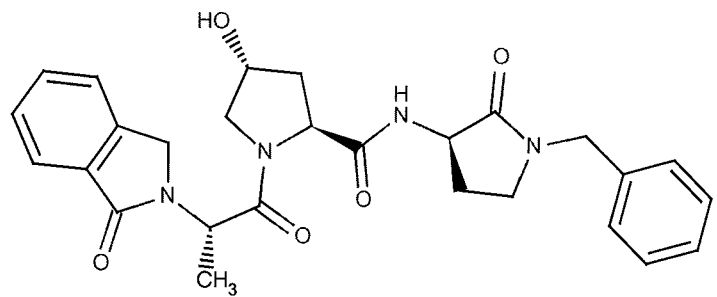
Figure 15:
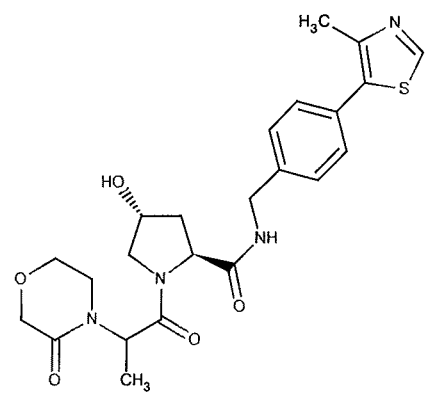
Figure 15:
Figure 15:
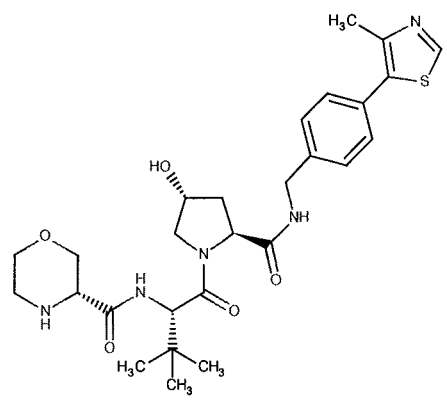
Figure 15:
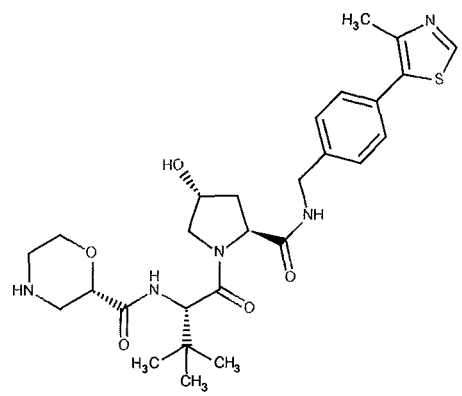
Figure 15:
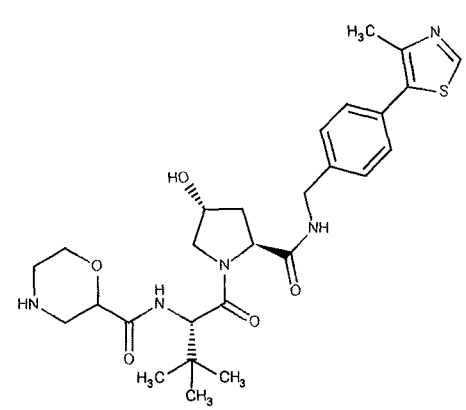
Figure 15:
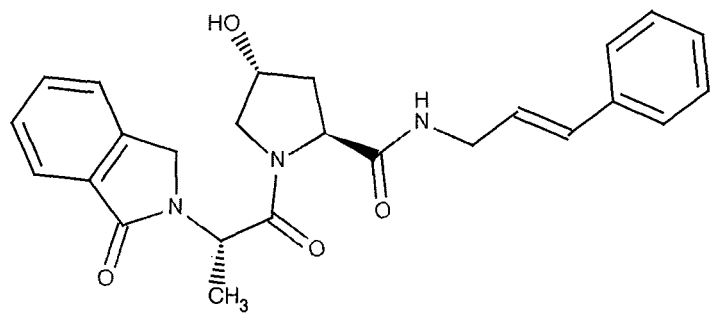
Figure 15:
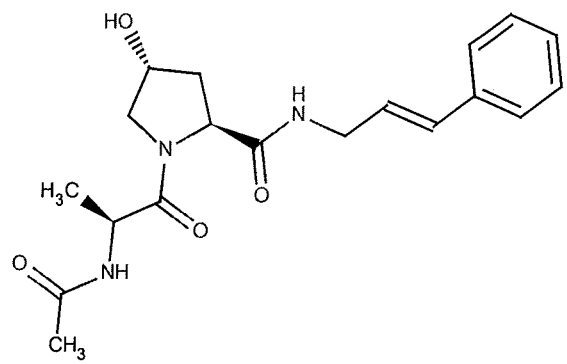
Figure 15:
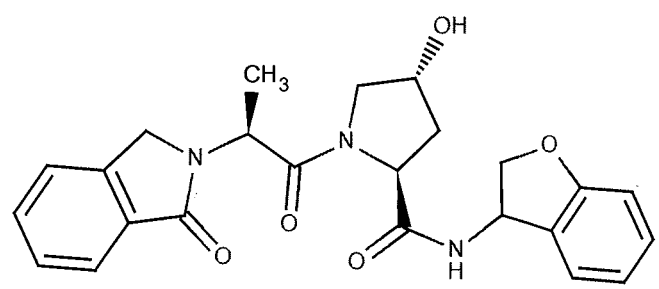
Figure 15:
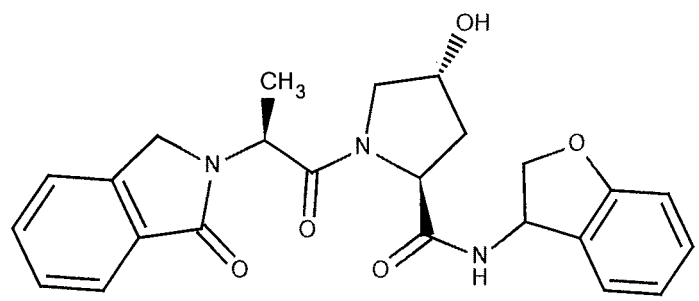
Figure 15:
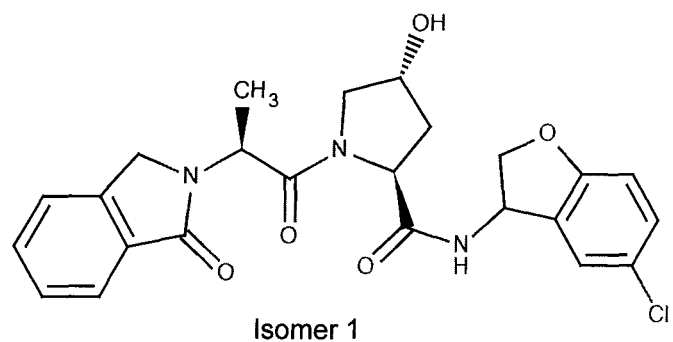
Figure 15:
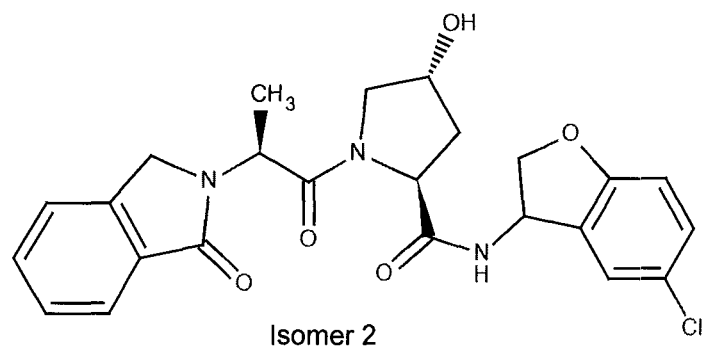
Figure 15:
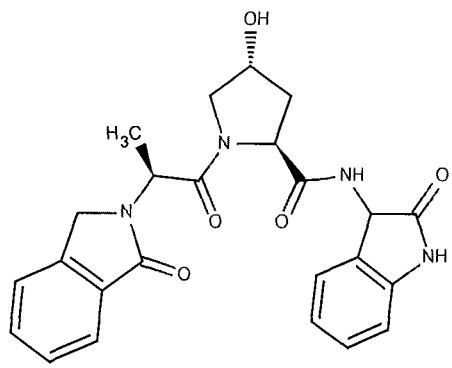
Figure 15:
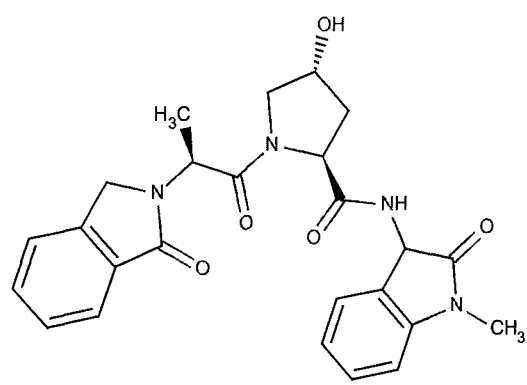
Figure 15:
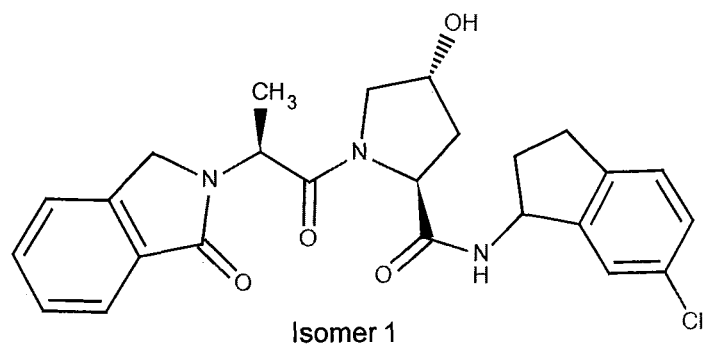
Figure 15:
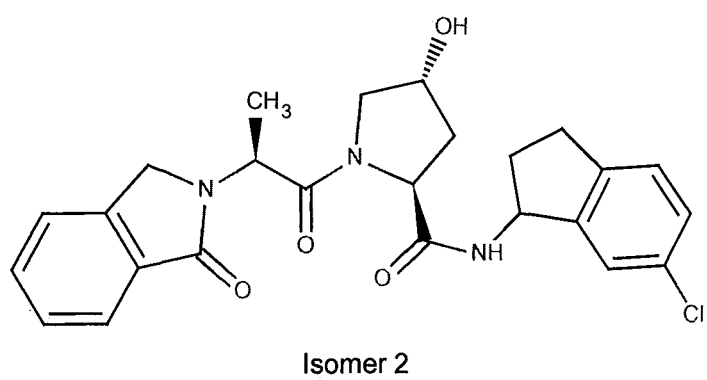
Figure 15:
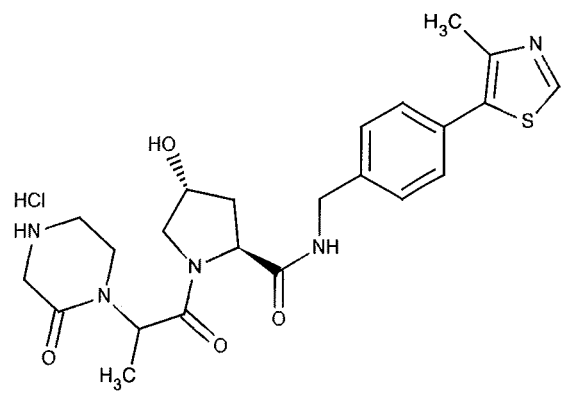
Figure 15:
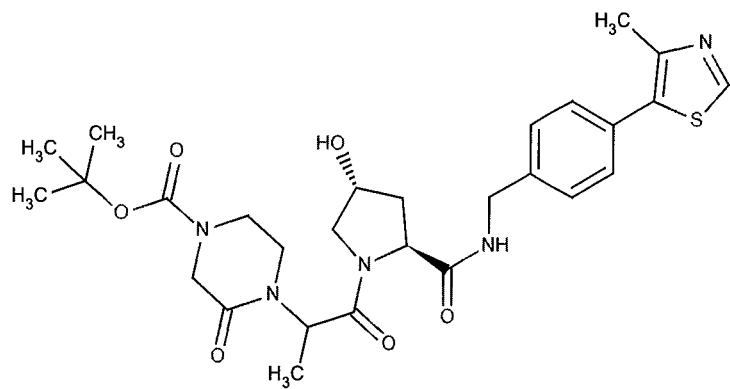
Figure 15:
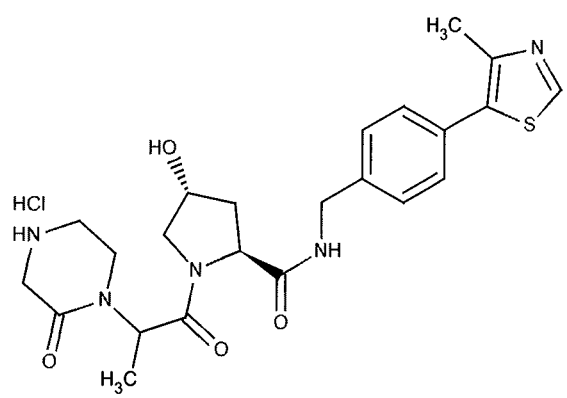
Figure 15:
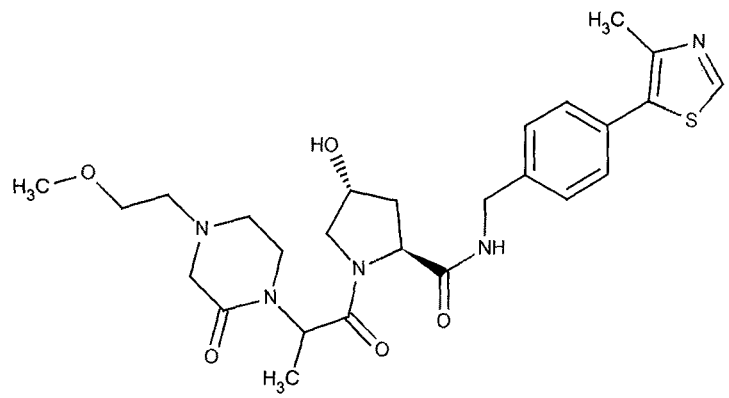
Figure 15:
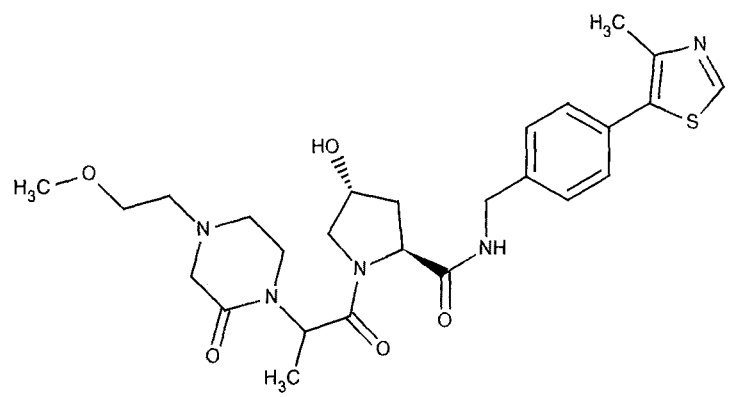
Figure 15:
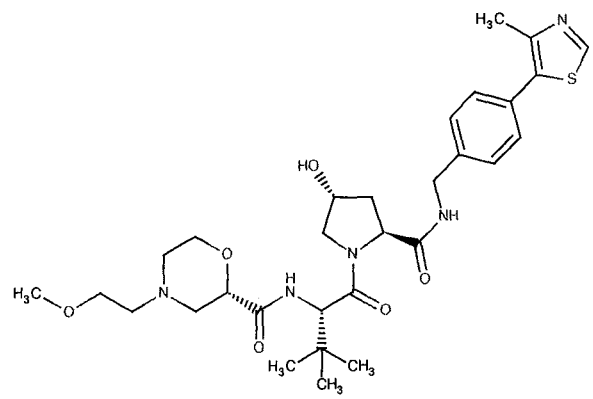
Figure 15:
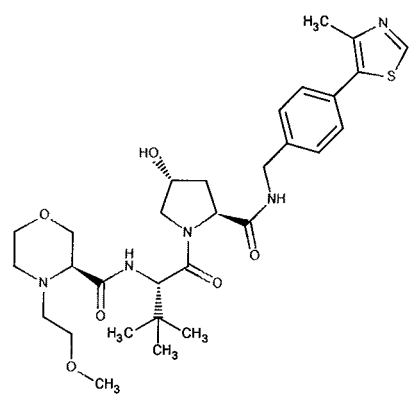
Figure 15:
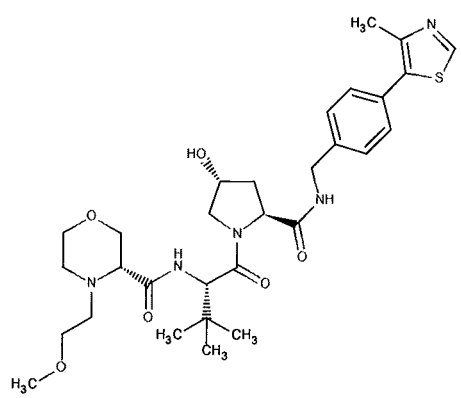
Figure 15:
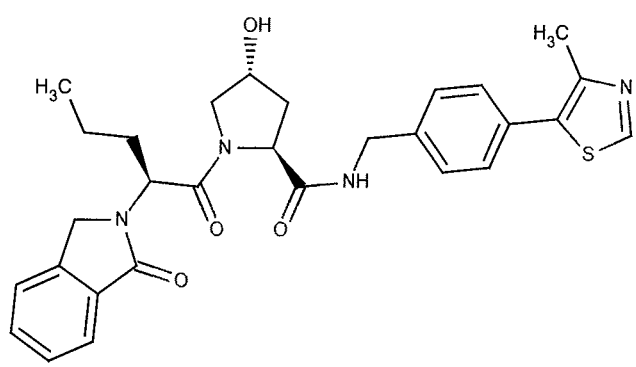
Figure 15:
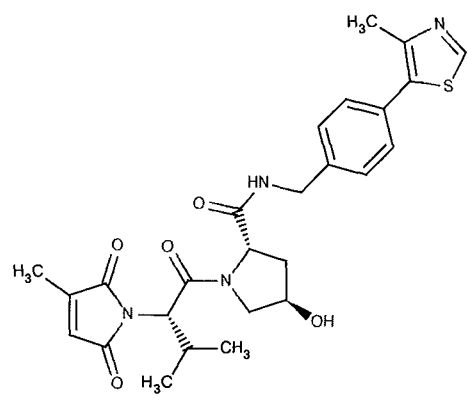
Figure 15:
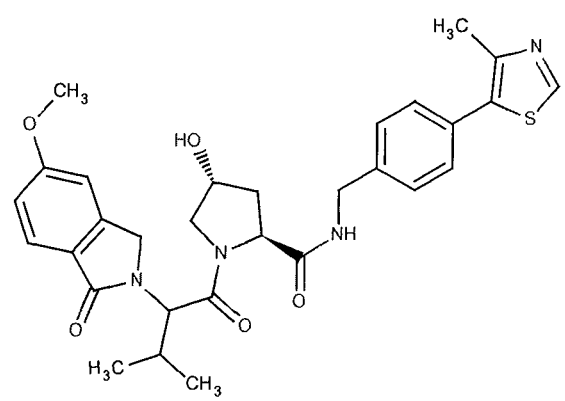
Figure 15:
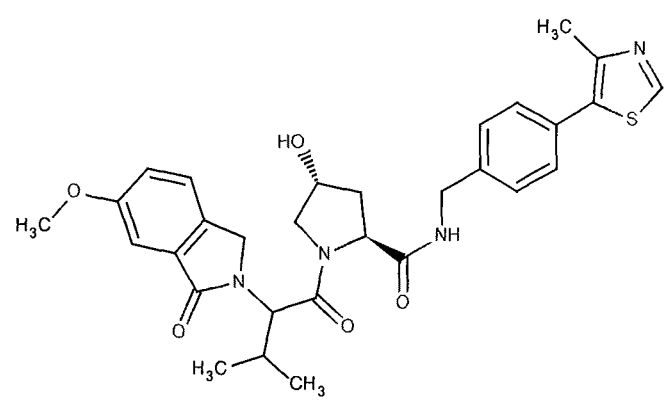
Figure 15:
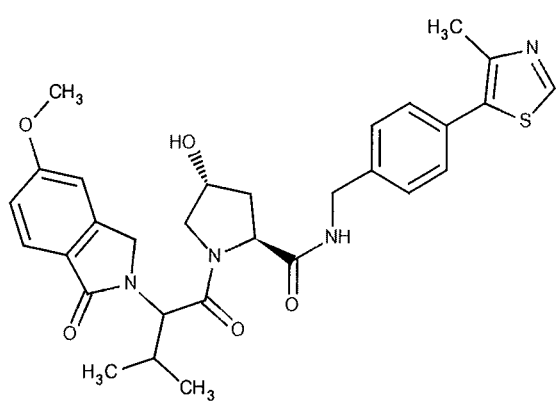
Figure 15:
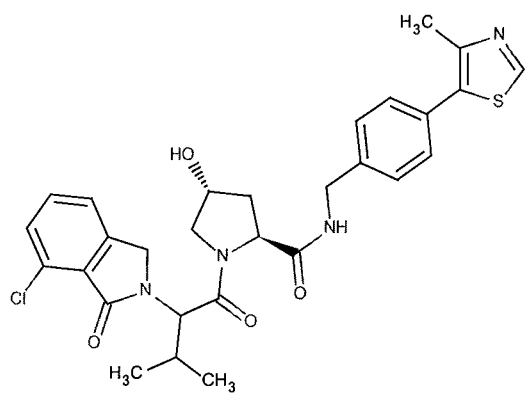
Figure 16:
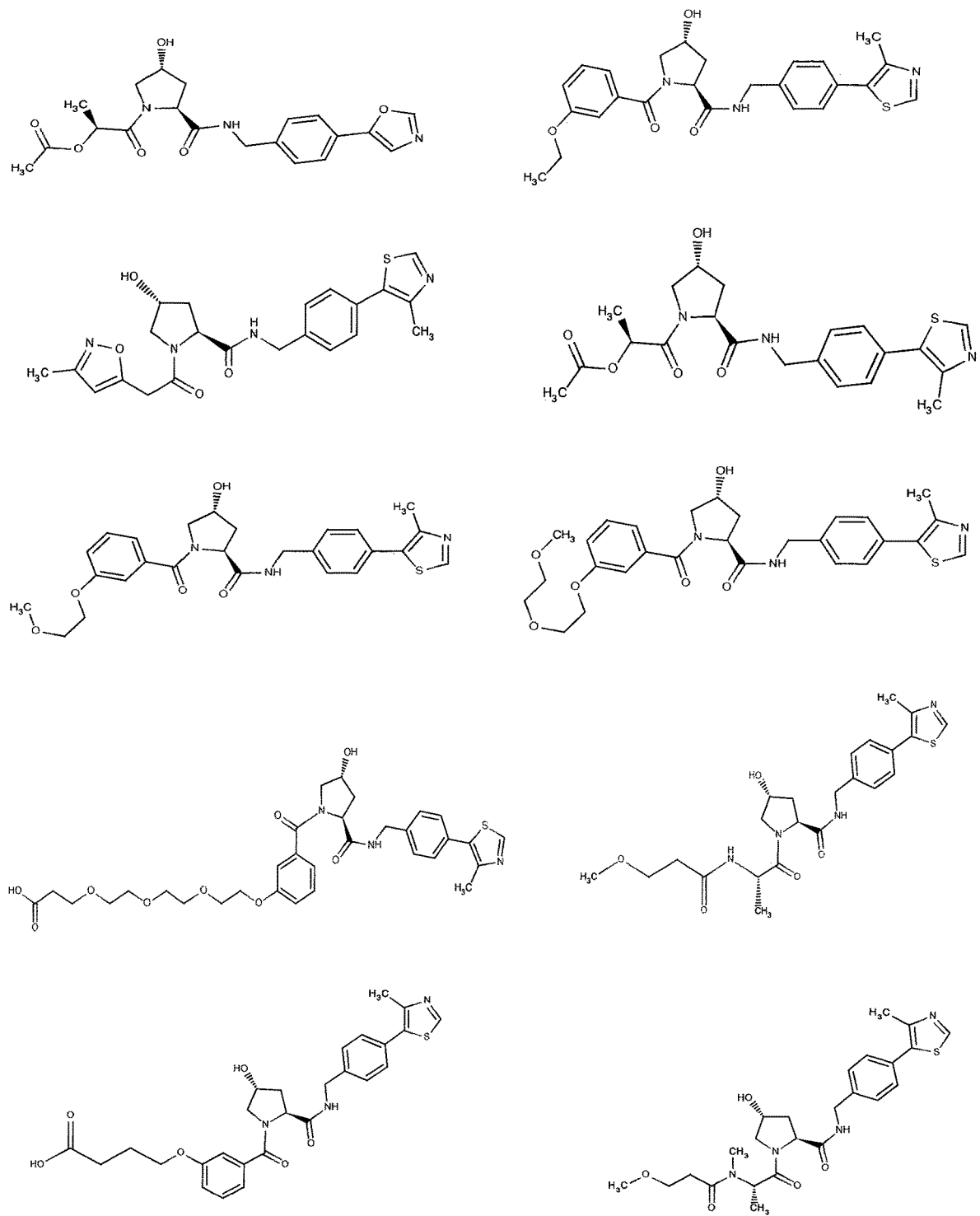
FIG. 16 shows numerous preferred compounds from FIG. 15 according to the present invention.
Figure 16:
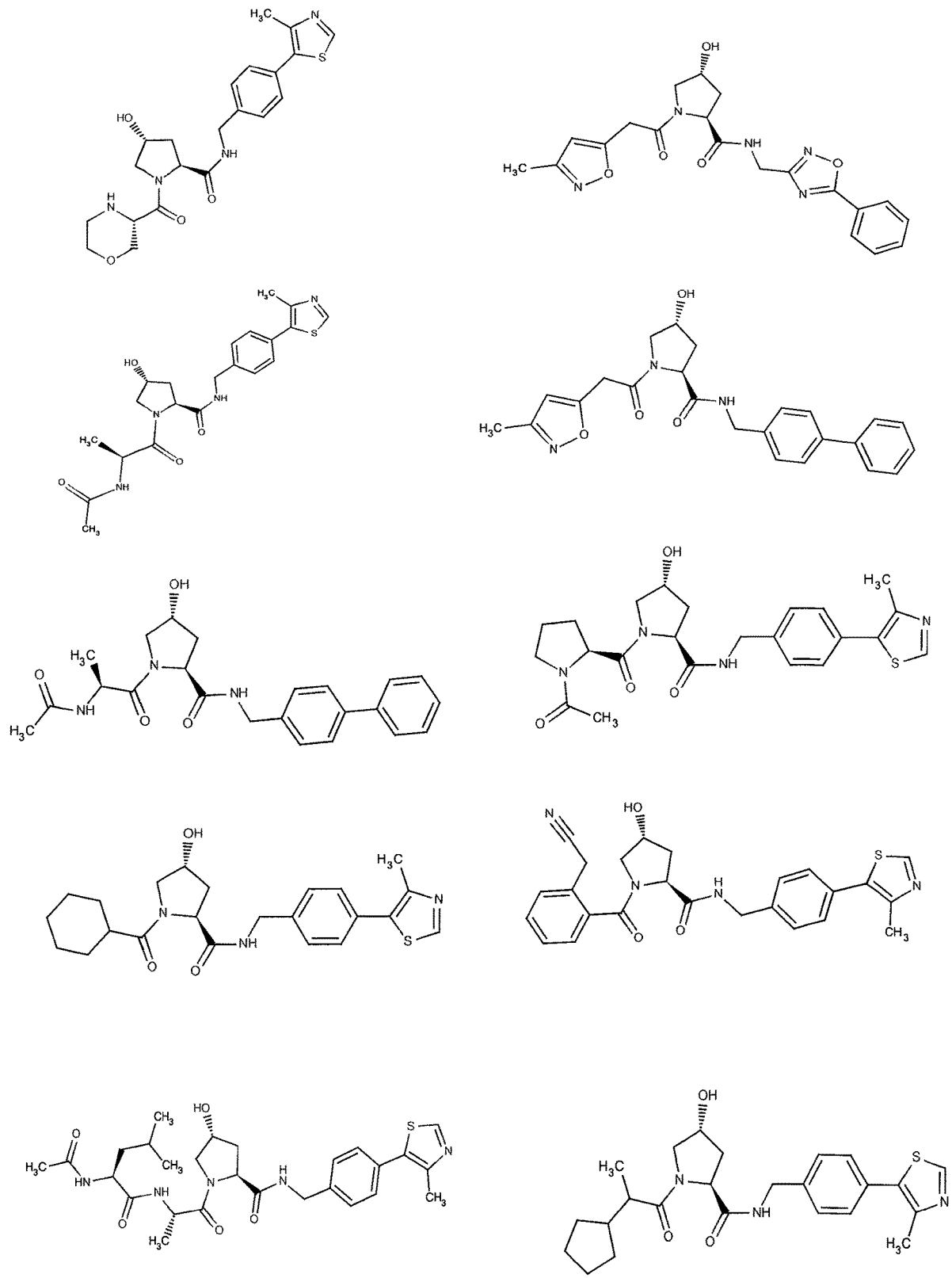
Figure 16:
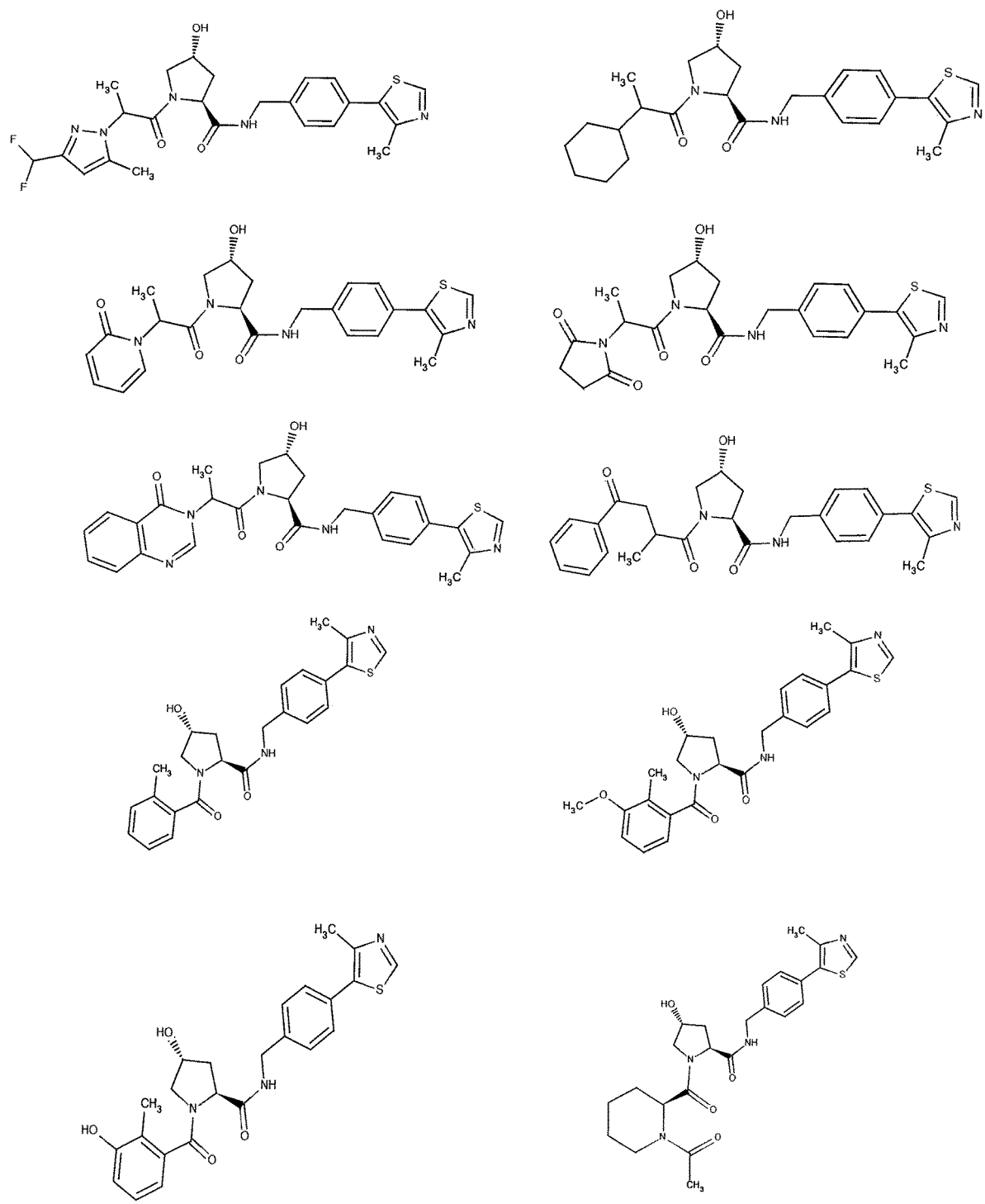
Figure 16:
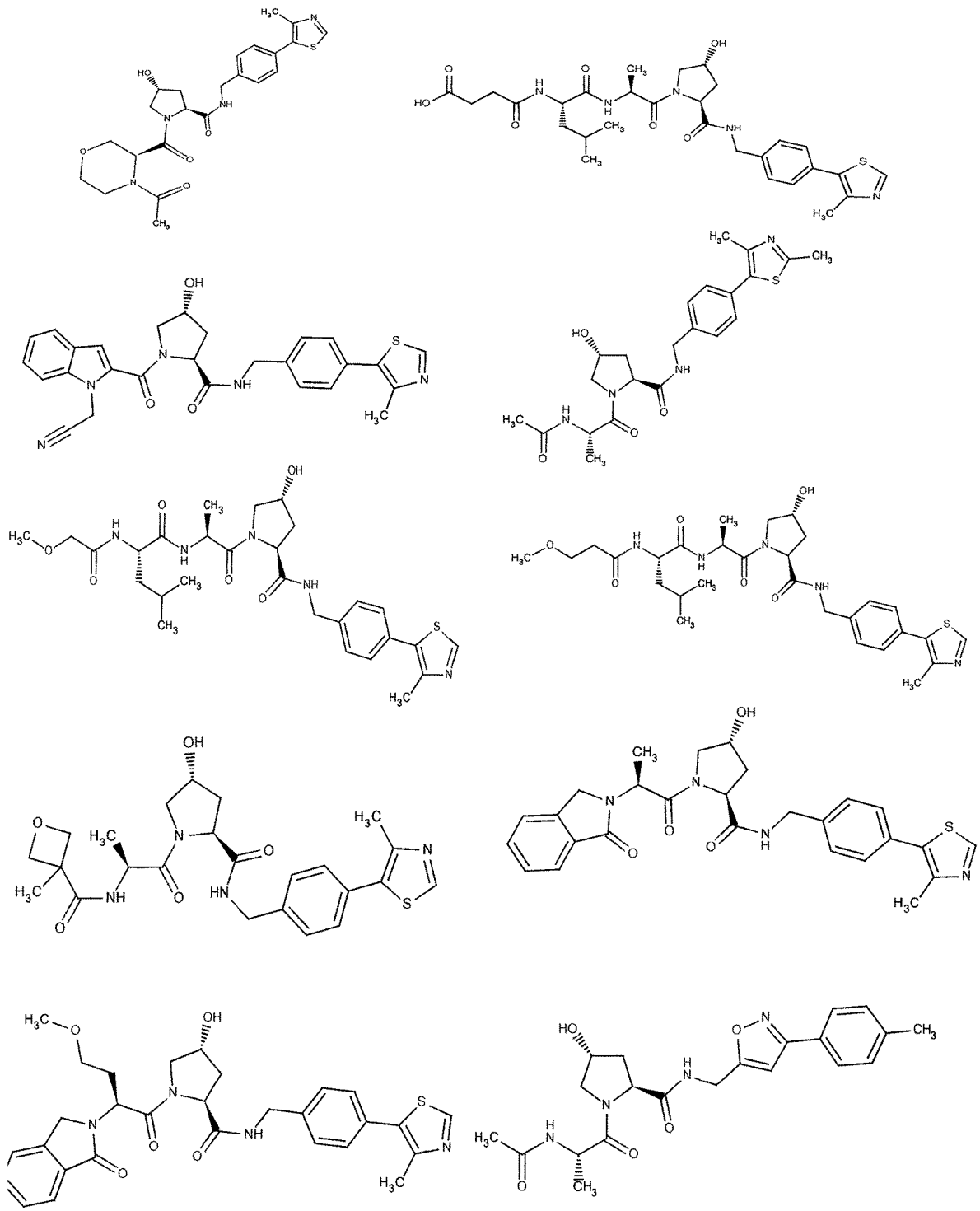
Figure 16:
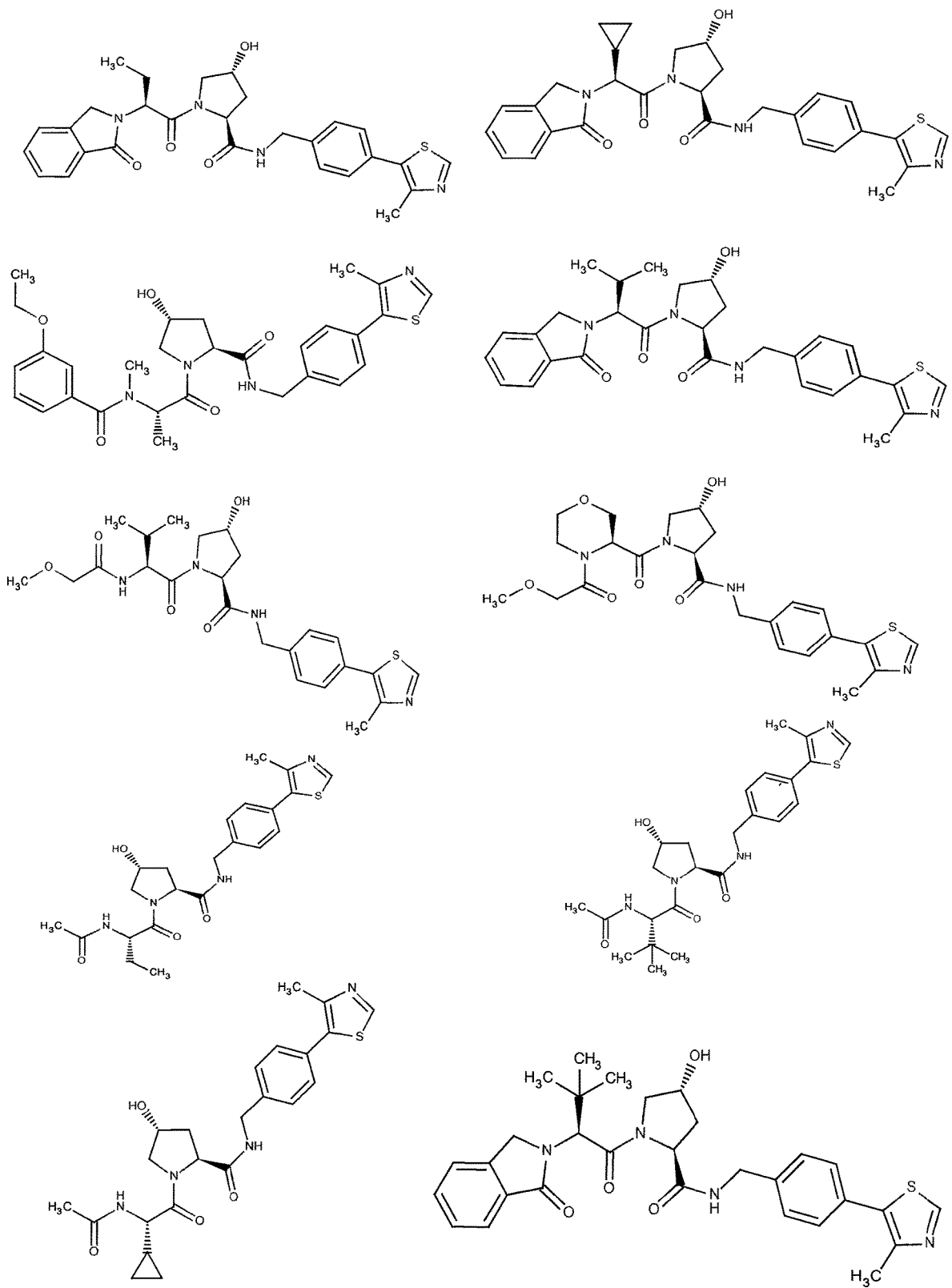
Figure 16:
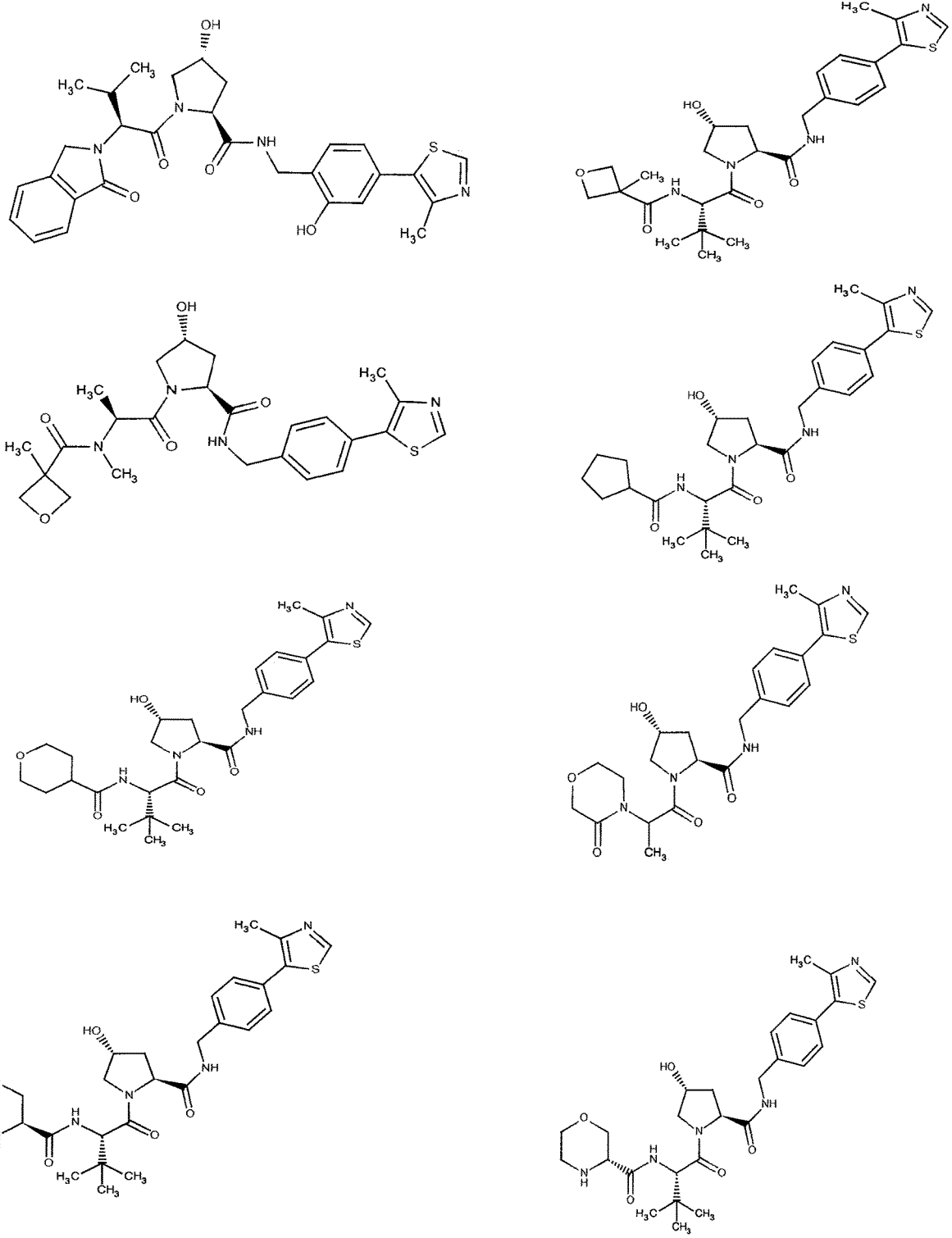
Figure 16:
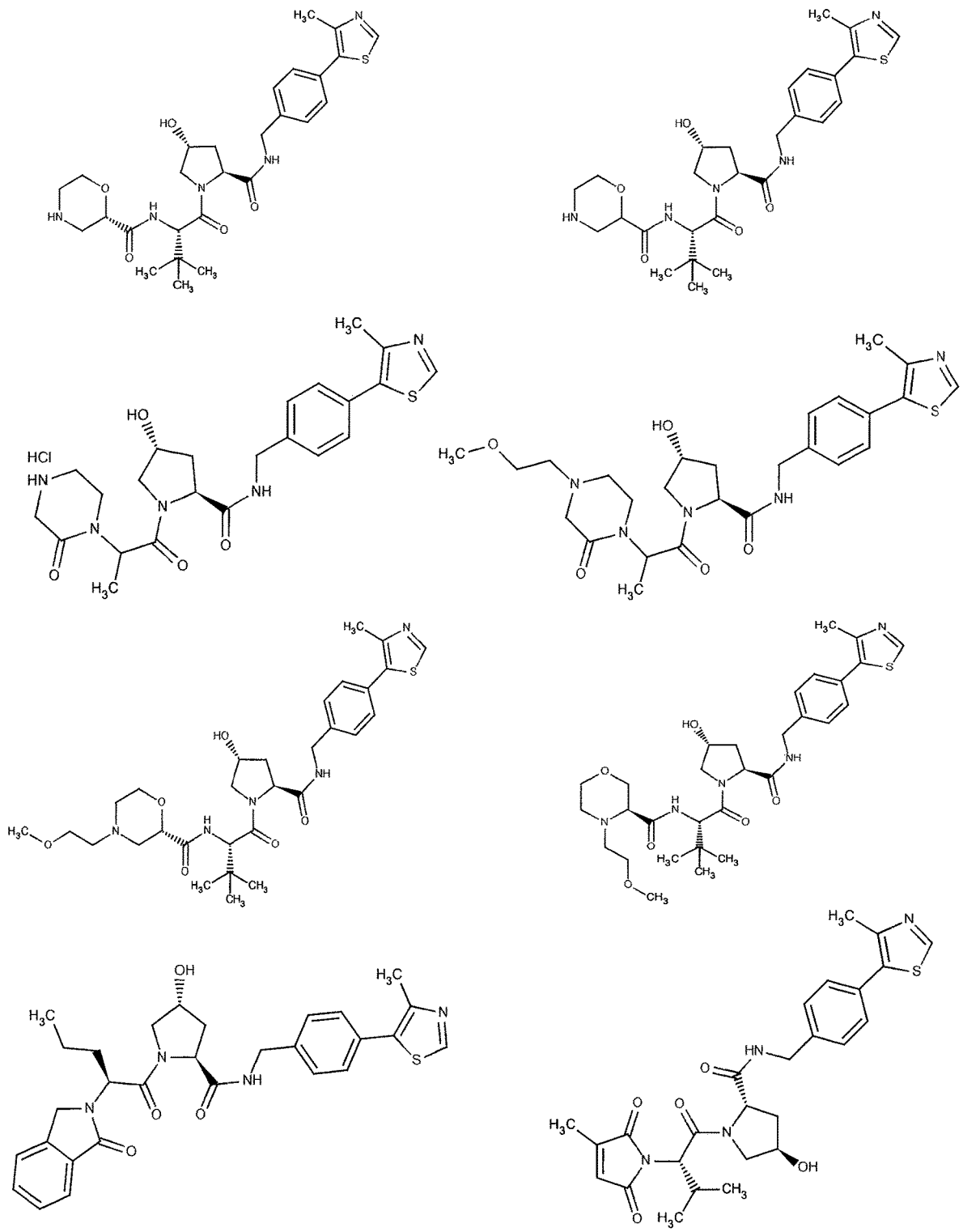
Figure 16:
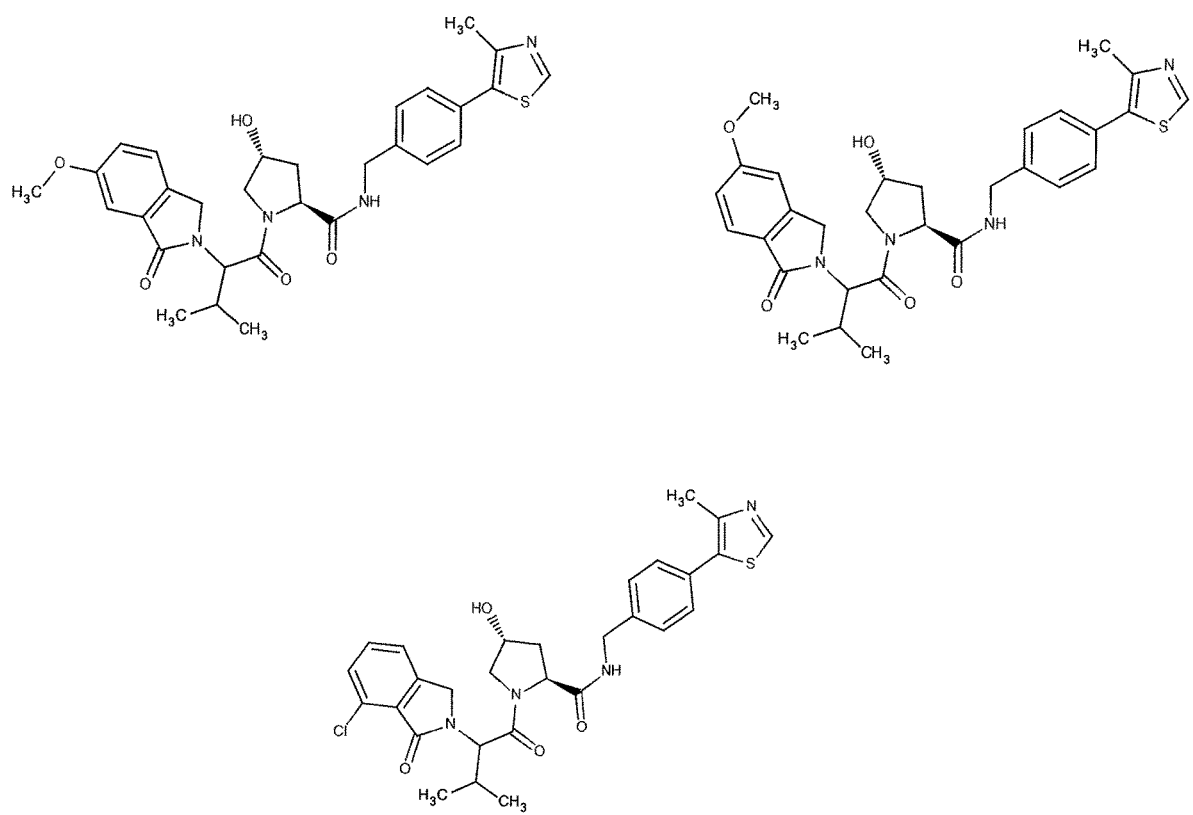
Figure 17:
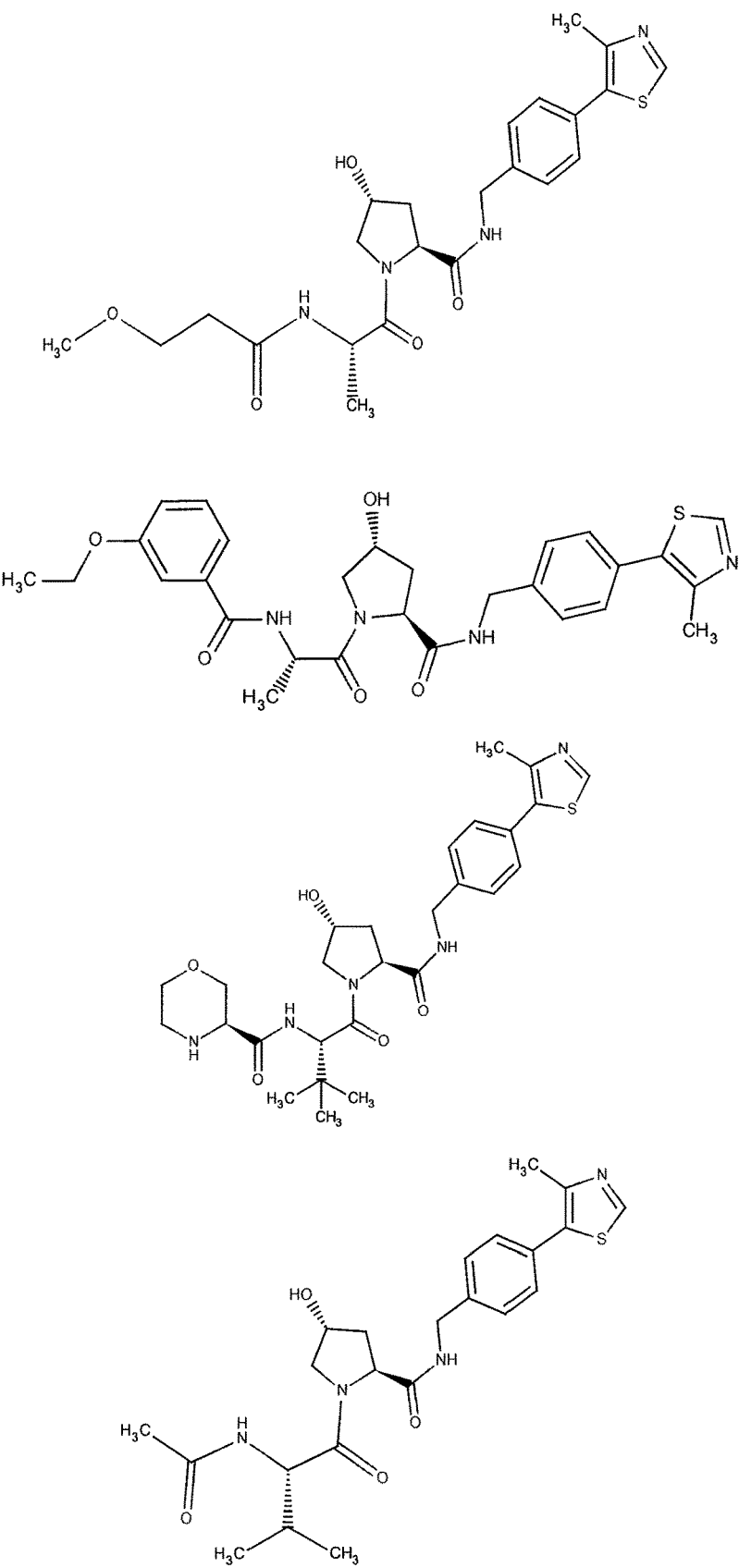
FIG. 17 shows eight particularly preferred compounds from FIG. 15 according to the present invention.
Figure 17:
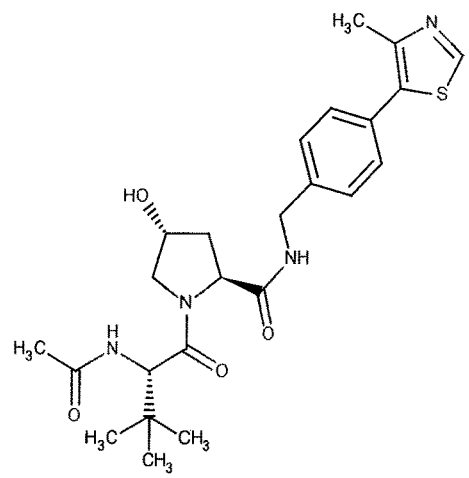
Figure 17:
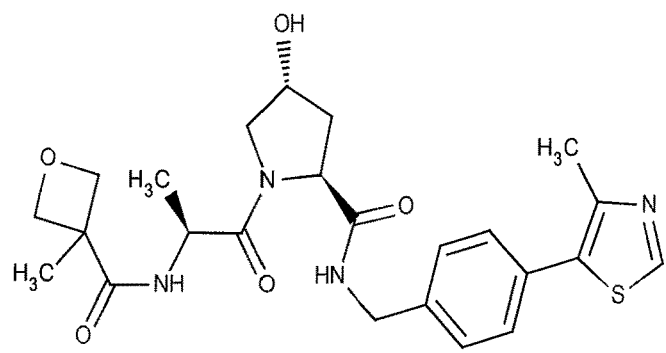
Figure 17:
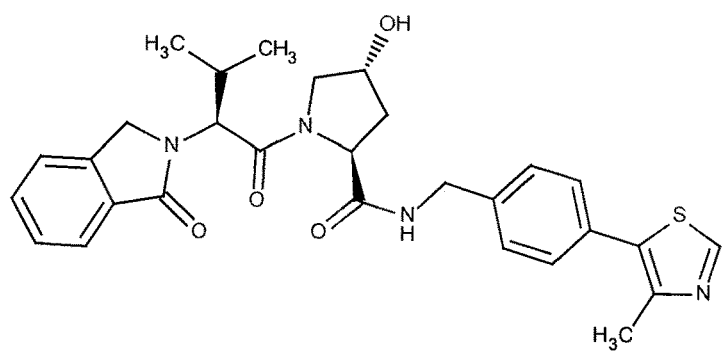
Figure 17:
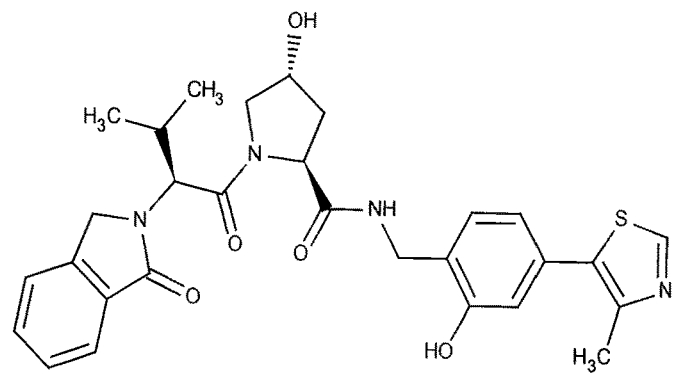
Figure 18:
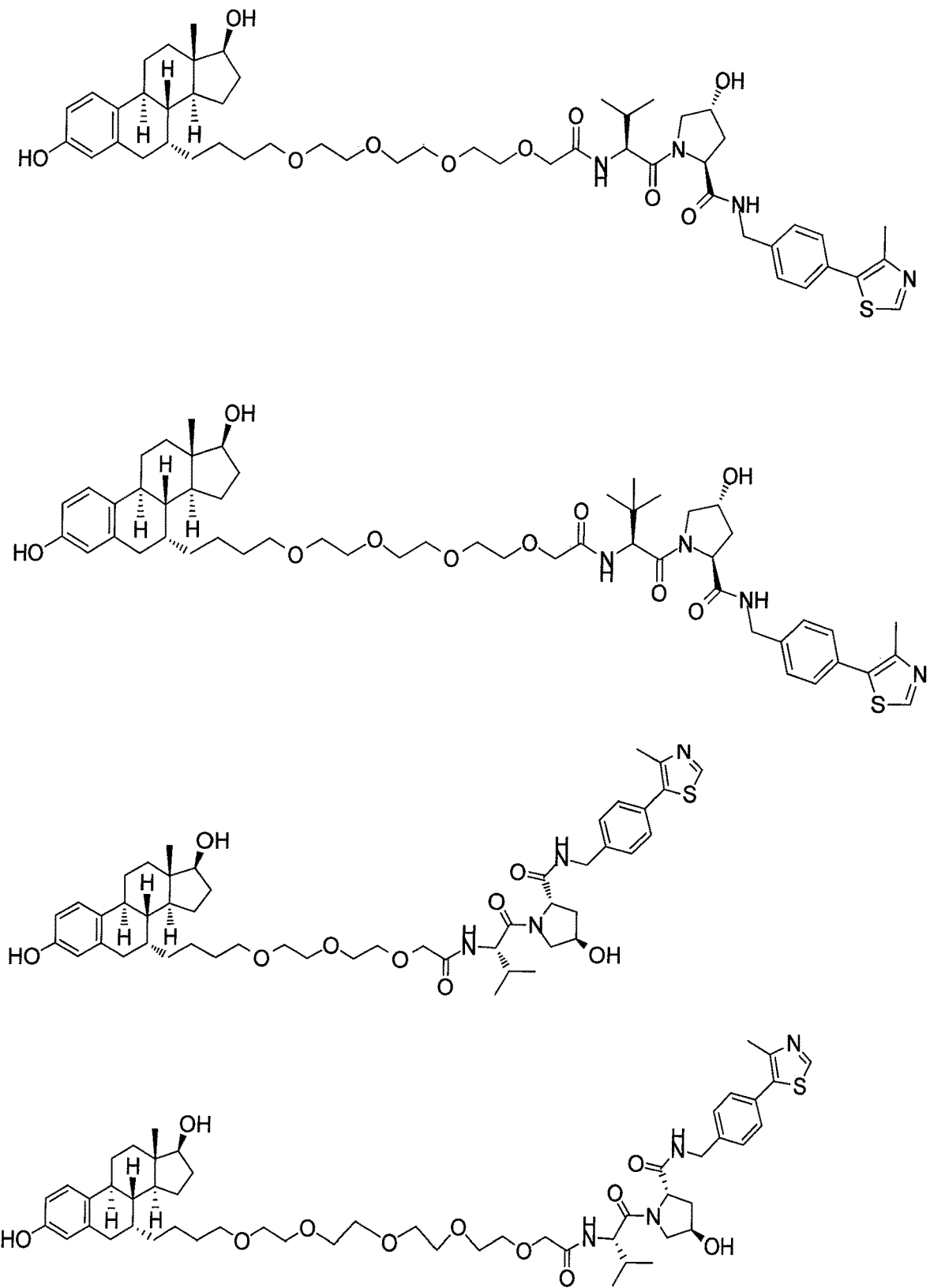
FIG. 18 shows six preferred compounds according to the present invention which contain estrogen binding protein targeting moieties linked to preferred ubiquitin ligand binding moieties.
Figure 18:
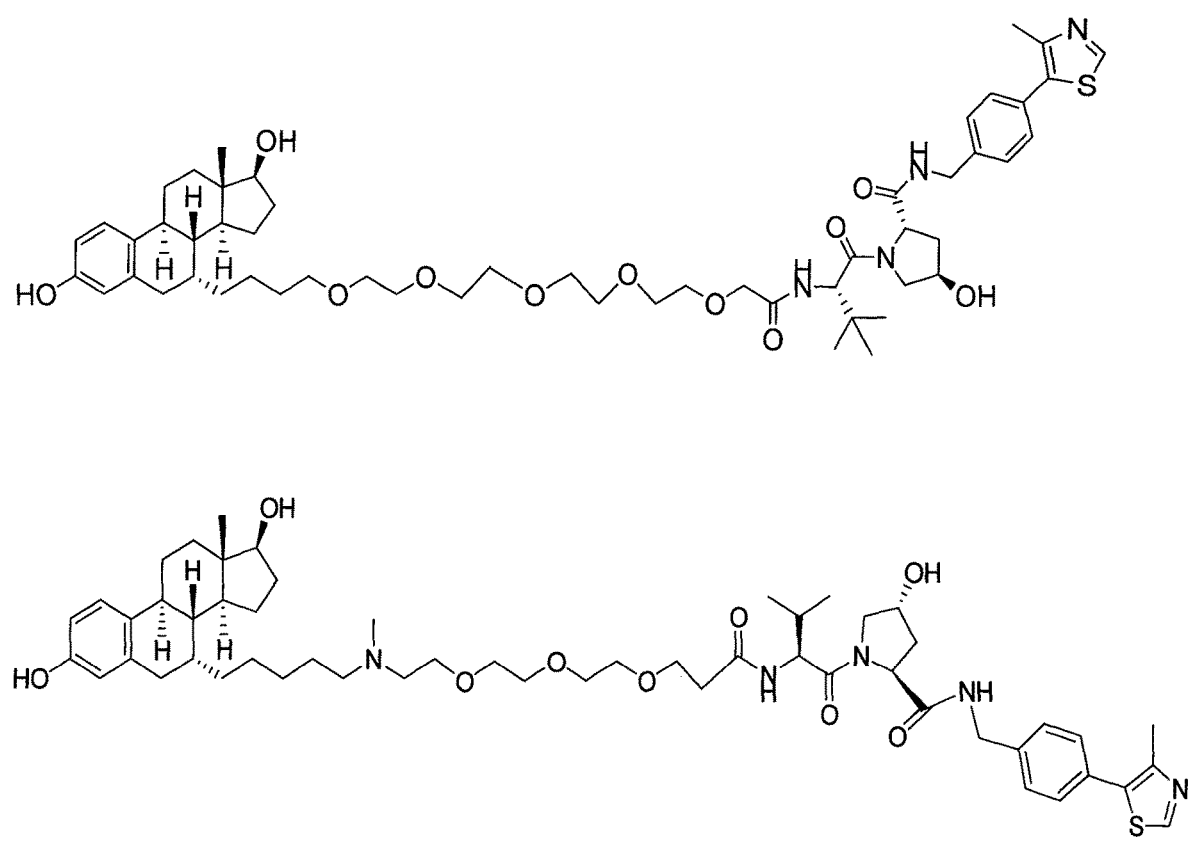

Examples for Compounds of FIG. 15 the Following Procedures were Used to Synthesize and/or Characterize Compounds According to the Present Invention as Indicated LCMS Method:
The analysis was conducted on an Acquity UPLC BEH C18 column (50 mm×2.1 mm internal diameter 1.7 μm packing diameter) at 40° C.
The solvents employed were:
A=0.1% v/v solution of formic acid in water.
B=0.1% v/v solution of formic acid in acetonitrile.
The gradient employed was as follows:

| Time (minutes) | Flow Rate (mL/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.
The following illustrates the mobile phases and gradients used when compounds underwent purification by mass-directed autopreparative HPLC.

Mass-Directed Autopreparative HPLC (Formic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of formic acid in water.
B=0.1% v/v solution of formic acid in acetonitrile.
Mass-Directed Autopreparative HPLC (Trifluoroacetic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of trifluoroacetic acid in water.
B=0.1% v/v solution of trifluoroacetic acid in acetonitrile.
Mass-Directed Autopreparative HPLC (Ammonium Bicarbonate Modifier)
The HPLC analysis was conducted on an XBridge C18 column (150 mm×30 mm internal diameter, 5 μm packing diameter) at ambient temperature.
The solvents employed were:
A=10 mM ammonium bicarbonate in water adjusted to pH 10 with ammonia solution.
B=acetonitrile.
For each of the mass-directed autopreparative purifications, irrespective of the modifier used, the gradient employed was dependent upon the retention time of the particular compound undergoing purification as recorded in the analytical LCMS, and was as follows:
For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ACD Name Pro version 6.02 from Advanced Chemistry Development, Inc.

EXAMPLES (2S,4R)-1-(2-ethoxybenzoyl)-4-hydroxy-N-(4-(oxazol-5-yl)benzyl)pyrrolidine-2-carboxamide A solution of 2-ethoxybenzoic acid (commercially available from for example Aldrich) (29 mg, 0.17 mmol), (2S,4R)-4-hydroxy-N-(4-(oxazol-5-yl)benzyl)pyrrolidine-2-carboxamide (50 mg, 0.17 mmol) and DIPEA (0.061 mL, 0.35 mmol) in DMF (1 mL) was treated with HATU (80 mg, 0.21 mmol) and the mixture was stirred at ambient temperature for 2 hours. The product was then subjected to purification by mass-directed automated preparative HPLC (formic acid modifier) to afford the title compound (38 mg, 0.087 mmol, 50% yield). LCMS RT=0.72 min, ES+ve m/z 436 [M+H]$^+$.

Using a method analogous to that for (2S,4R)-1-(2-ethoxybenzoyl)-4-hydroxy-N-(4-(oxazol-5-yl)benzyl)pyrrolidine-2-carboxamide, the following compounds were prepared:

| Name | Structure | Yield | RT | [M + H]+ |
|---|---|---|---|---|
| (2S,4R)-1-benzoyl-4-hydroxy-N-(4-(oxazol-5-yl)benzyl)pyrrolidine-2-carboxamide | 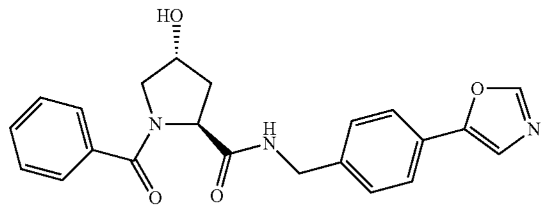 [SMILES: O=C(NCc1ccc(-c2cnco2)cc1)[C@@H]1C[C@@H](O)CN1C(=O)c1ccccc1] | 82% | 0.65 min | 392 |
| (2S,4R)-4-hydroxy-1-(3-methoxybenzoyl)-N-(4-(oxazol-5-yl)benzyl)pyrrolidine-2-carboxamide | 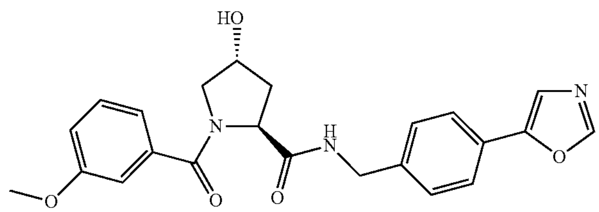 [SMILES: COc1cccc(C(=O)N2C[C@H](O)C[C@H]2C(=O)NCc2ccc(-c3cnco3)cc2)c1] | 66% | 0.67 min | 422 |
| (2S,4R)-1-(3-ethoxybenzoyl)-4-hydroxy-N-(4-(oxazol-5-yl)benzyl)pyrrolidine-2-carboxamide | 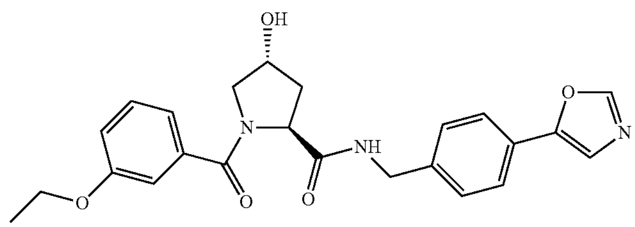 [SMILES: CCOc1cccc(C(=O)N2C[C@H](O)C[C@H]2C(=O)NCc2ccc(-c3cnco3)cc2)c1] | 54% | 0.72 min | 436 |
| (2S,4R)-1-(4-ethoxybenzoyl)-4-hydroxy-N-(4-(oxazol-5-yl)benzyl)pyrrolidine-2-carboxamide | 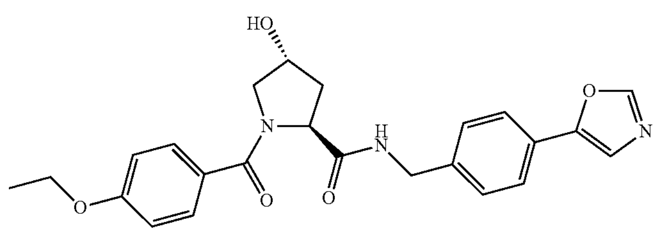 [SMILES: CCOc1ccc(C(=O)N2C[C@H](O)C[C@H]2C(=O)NCc2ccc(-c3cnco3)cc2)cc1] | 46% | 0.71 min | 436 |
| (2S,4R)-1-(3-cyanobenzoyl)-4-hydroxy-N-(4-(oxazol-5-yl)benzyl)pyrrolidine-2-carboxamide | 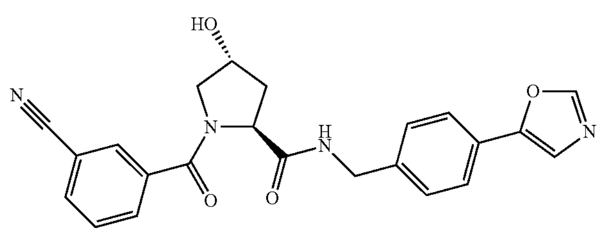 [SMILES: N#Cc1cccc(C(=O)N2C[C@H](O)C[C@H]2C(=O)NCc2ccc(-c3cnco3)cc2)c1] | 57% | 0.64 min | 417 |
| (2S,4R)-4-hydroxy-1-(3-isopropoxybenzoyl)-N-(4-(oxazol-5-yl)benzyl)pyrrolidine-2-carboxamide | 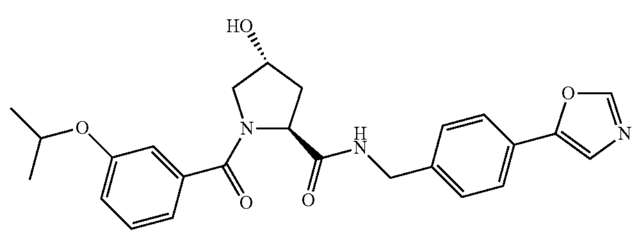 [SMILES: CC(C)Oc1cccc(C(=O)N2C[C@H](O)C[C@H]2C(=O)NCc2ccc(-c3cnco3)cc2)c1] | 53% | 0.78 min | 450 |
| (2S,4R)-1-(3-acetylbenzoyl)-4-hydroxy-N-(4-(oxazol-5-yl)benzyl)pyrrolidine-2-carboxamide | 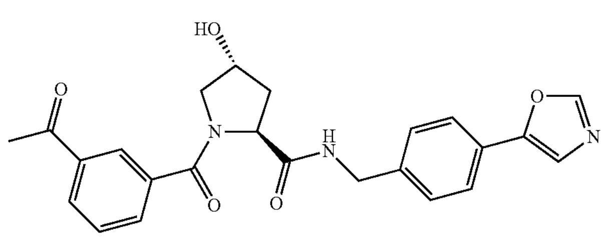 [SMILES: CC(=O)c1cccc(C(=O)N2C[C@H](O)C[C@H]2C(=O)NCc2ccc(-c3cnco3)cc2)c1] | 47% | 0.63 min | 434 |

-continued

| Name | Structure | Yield | RT | [M + H]+ |
|---|---|---|---|---|
| (2S,4R)-4-hydroxy-1-(3-morpholinobenzoyl)-N-(4-(oxazol-5-yl)benzyl)pyrrolidine-2-carboxamide | 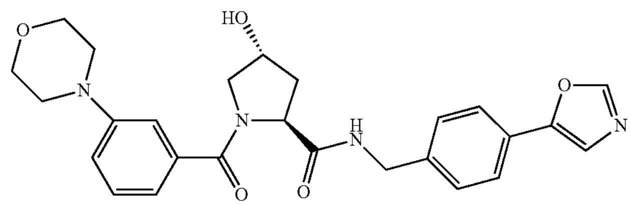 [SMILES: O=C(NCc1ccc(-c2cnco2)cc1)[C@@H]1C[C@@H](O)CN1C(=O)c1cccc(N2CCOCC2)c1] | 63% | 0.66 min | 477 |
| (2S,4R)-4-hydroxy-1-(3-isopropylbenzoyl)-N-(4-(oxazol-5-yl)benzyl)pyrrolidine-2-carboxamide | | 69% | 0.82 min | 434 |
| (2S,4R)-1-(3-chlorobenzoyl)-4-hydroxy-N-(4-(oxazol-5-yl)benzyl)pyrrolidine-2-carboxamide | 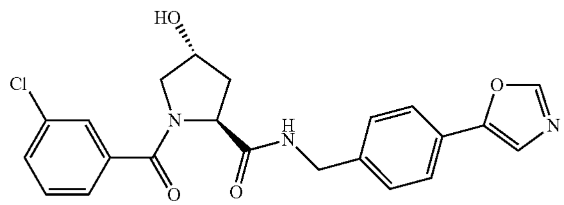 [SMILES: O=C(NCc1ccc(-c2cnco2)cc1)[C@@H]1C[C@@H](O)CN1C(=O)c1cccc(Cl)c1] | 65% | 0.73 min | 426 |
| (2S,4R)-1-(3-bromobenzoyl)-4-hydroxy-N-(4-(oxazol-5-yl)benzyl)pyrrolidine-2-carboxamide | 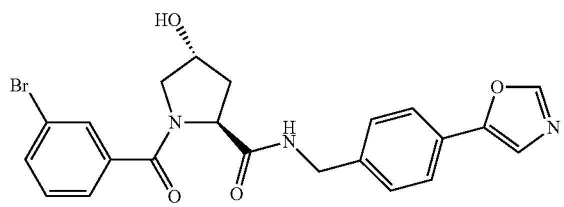 [SMILES: O=C(NCc1ccc(-c2cnco2)cc1)[C@@H]1C[C@@H](O)CN1C(=O)c1cccc(Br)c1] | 66% | 0.75 min | 470, 472 |
| (2S,4R)-1-(3-ethylbenzoyl)-4-hydroxy-N-(4-(oxazol-5-yl)benzyl)pyrrolidine-2-carboxamide | 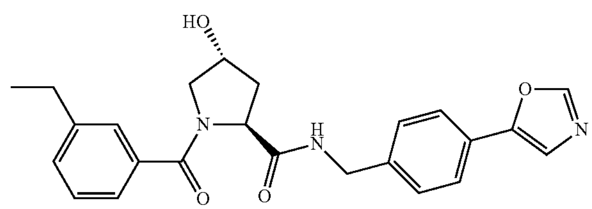 [SMILES: CCc1cccc(C(=O)N2C[C@H](O)C[C@H]2C(=O)NCc2ccc(-c3cnco3)cc2)c1] | 55% | 0.77 min | 420 |
| (2S,4R)-1-(3,5-diethoxybenzoyl)-4-hydroxy-N-(4-(oxazol-5-yl)benzyl)pyrrolidine-2-carboxamide | 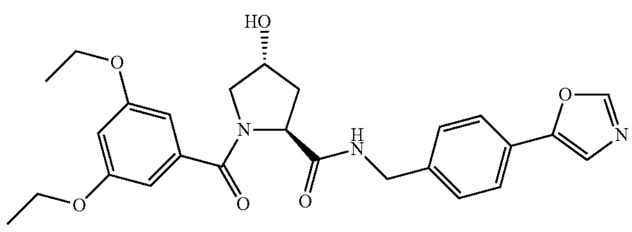 [SMILES: CCOc1cc(OCC)cc(C(=O)N2C[C@H](O)C[C@H]2C(=O)NCc2ccc(-c3cnco3)cc2)c1] | 65% | 0.81 min | 480 |
| (2S,4R)-4-hydroxy-N-(4-(oxazol-5-yl)benzyl)-1-(3-propoxybenzoyl)pyrrolidine-2-carboxamide | 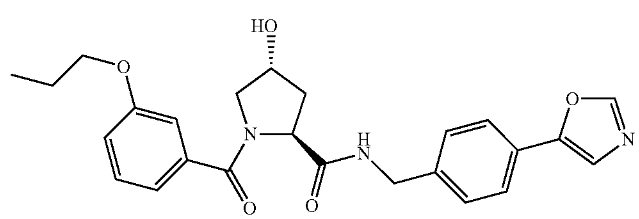 [SMILES: CCCOc1cccc(C(=O)N2C[C@H](O)C[C@H]2C(=O)NCc2ccc(-c3cnco3)cc2)c1] | 52% | 0.80 min | 450 |

(S)-1-((2S,4R)-4-hydroxy-2-((4-(oxazol-5-yl)benzyl)carbamoyl)pyrrolidin-1-yl)-1-oxopropan-2-yl acetate and (2S,4R)-4-hydroxy-1((S)-2-hydroxypropanoyl)-N-(4-(oxazol-5-yl)benzyl)pyrrolidine-2-carboxamide

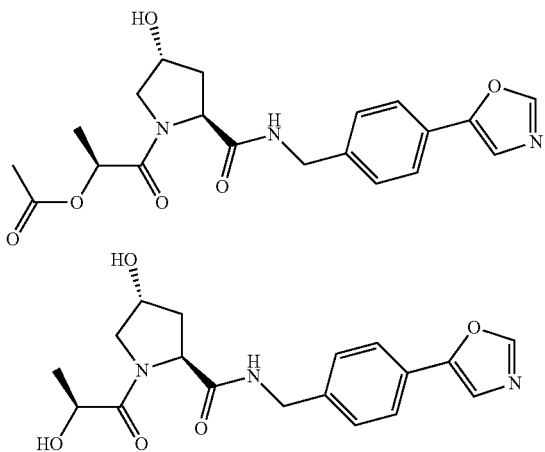

A stirred mixture of (2S,4R)-4-hydroxy-N-(4-(oxazol-5-yl)benzyl)pyrrolidine-2-carboxamide hydrochloride (60 mg, 0.19 mmol) and (S)-2-acetoxypropanoic acid (commercially available from for example Aldrich) (25 mg, 0.19 mmol) in DMF (1.2 mL) was treated with DIPEA (0.13 mL, 0.74 mmol) and then with HATU (85 mg, 0.22 mmol) and the mixture was stirred at ambient temperature for 30 minutes. Half of the reaction mixture was then subjected to purification by mass-directed automated preparative HPLC (formic acid modifier) to afford (S)-1-((2S,4R)-4-hydroxy-2-((4-(oxazol-5-yl)benzyl)carbamoyl)pyrrolidin-1-yl)-1-oxopropan-2-yl acetate (21 mg, 0.052 mmol, 28% yield). LCMS RT=0.58 min, ES+ve m/z 402 [M+H]$^+$.

The remaining half of the reaction mixture was treated with ammonia (2M solution in methanol) (2 mL), sealed and allowed to stand for 1 day. The solution was then evaporated to dryness and the product was subjected to purification by mass-directed automated preparative HPLC (formic acid modifier) to afford (2S,4R)-4-hydroxy-1-((S)-2-hydroxypropanoyl)-N-(4-(oxazol-5-yl)benzyl)pyrrolidine-2-carboxamide (18 mg, 0.050 mmol, 27% yield). LCMS RT=0.53 min, ES+ve m/z 360 [M+H]$^+$.

(2S,4R)-benzyl 4-hydroxy-1-(2-(3-methylisoxazol-5-yl)acetyl)pyrrolidine-2-carboxylate

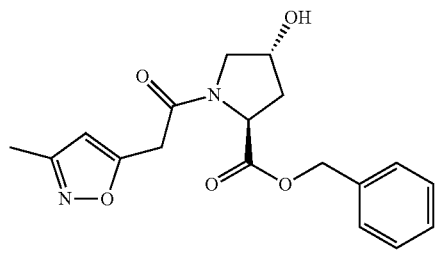 [SMILES: Cc1cc(CC(=O)N2C[C@H](O)C[C@H]2C(=O)OCc2ccccc2)on1]

An ice-cooled mixture of 2-(3-methylisoxazol-5-yl)acetic acid (commercially available from for example Aldrich) (0.91 g, 6.4 mmol) and (2S,4R)-benzyl 4-hydroxypyrrolidine-2-carboxylate, hydrochloride (1.67 g, 6.5 mmol) in DMF (9 mL) was treated with DIPEA (3.4 mL, 19 mmol) and then with HATU (2.56 g, 6.7 mmol) over 20 minutes. The mixture was stirred with cooling for 30 minutes and then overnight at ambient temperature. The mixture was then treated with saturated aqueous sodium bicarbonate (50 mL), extracted with dichloromethane (4×60 mL) and the combined organic phase was filtered through a hydrophobic frit and evaporated to dryness The product was purified by flash chromatography (100 g cartridge) using a gradient elution from 0% to 15% methanol in dichloromethane to afford the title compound (2.3 g, 6.7 mmol, quantitative). LCMS RT=0.75 min, ES+ve m/z 345 [M+H]$^+$.

(2S,4R)—N-((3,4-dihydro-2H-benzo[b][1,4]oxazin-2-yl)methyl)-4-hydroxy-1-(2-(3-methylisoxazol-5-yl)acetyl)pyrrolidine-2-carboxamide

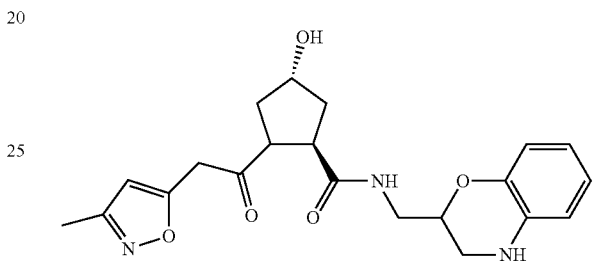

A solution of (2S,4R)-4-hydroxy-1-(2-(3-methylisoxazol-5-yl)acetyl)pyrrolidine-2-carboxylic acid (90 mg, 0.35 mmol), (3,4-dihydro-2H-benzo[b][1,4]oxazin-2-yl)methanamine (commercially available from for example Fluorochem) (58 mg, 0.35 mmol) and DIPEA (0.155 mL, 0.89 mmol) in DMF (2 mL) was treated with HATU (139 mg, 0.37 mmol) and stirred for 1 hour. The product was subjected to purification by mass-directed automated preparative HPLC (formic acid modifier) to afford the title compound (84 mg, 0.21 mmol, 60% yield) LCMS RT=0.61 min, ES+ve m/z 401 [M+H]$^+$.

(2S,4R)—N-(4-chlorobenzyl)-4-hydroxy-1-(2-(3-methylisoxazol-5-yl)acetyl)pyrrolidine-2-carboxamide

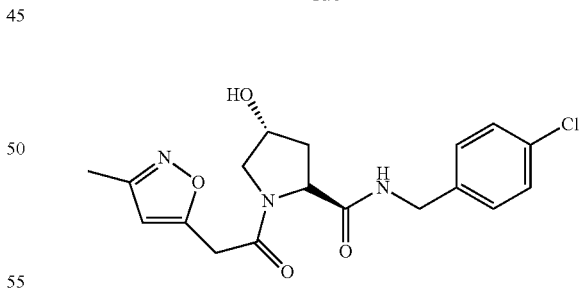

A solution of (4-chlorophenyl)methanamine (commercially available from for example Aldrich) (0.021 mL, 0.17 mmol) and (2S,4R)-4-hydroxy-1-(2-(3-methylisoxazol-5-yl)acetyl)pyrrolidine-2-carboxylic acid (40 mg, 0.16 mmol) in DMF (1 mL) was treated with DIPEA (0.082 mL, 0.47 mmol) then with HATU (66 mg, 0.17 mmol) and the mixture was stirred at ambient temperature for 2 hours. The product was subjected to purification by mass-directed automated preparative HPLC (formic acid modifier) to afford the title compound (24 mg, 0.064 mmol, 40% yield). LCMS RT=0.73 min, ES+ve m/z 378 [M+H]$^+$.

(2S,4R)-4-hydroxy-1-(2-(3-methylisoxazol-5-yl)acetyl)-N-(4-(2-oxo-2,3-dihydrobenzo[d]oxazol-5-yl)benzyl)pyrrolidine-2-carboxamide

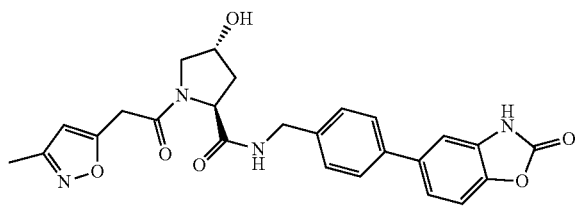 [SMILES: Cc1cc(CC(=O)N2C[C@H](O)C[C@H]2C(=O)NCc2ccc(-c3ccc4oc(=O)[nH]c4c3)cc2)on1]

A mixture of (2S,4R)-4-hydroxy-1-(2-(3-methylisoxazol-5-yl)acetyl)pyrrolidine-2-carboxylic acid (60 mg, 0.24 mmol) and 5-(4-(aminomethyl)phenyl)benzo[d]oxazol-2(3H)-one, hydrochloride (65 mg, 0.24 mmol) in DMF (1.6 mL) was treated with DIPEA (0.124 mL, 0.71 mmol) and HATU (99 mg, 0.26 mmol) and the mixture was stirred for 30 minutes. The product was then subjected to purification by mass-directed automated preparative HPLC (formic acid modifier) to afford the title compound (64 mg, 0.13 mmol, 57% yield). LCMS RT=0.70 min, ES+ve m/z 477 [M+H]$^+$.

(2S,4R)—N-(1-(benzofuran-2-yl)ethyl)-4-hydroxy-1-(2-(3-methylisoxazol-5-yl)acetyl)pyrrolidine-2-carboxamide

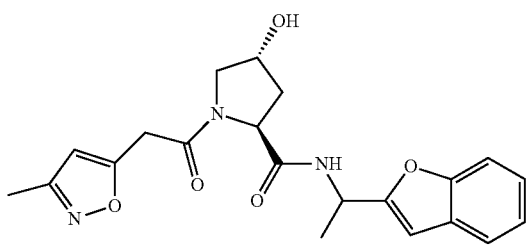 [SMILES: Cc1cc(CC(=O)N2C[C@H](O)C[C@H]2C(=O)NC(C)c2cc3ccccc3o2)on1]

A stirred solution of (2S,4R)-4-hydroxy-1-(2-(3-methylisoxazol-5-yl)acetyl)pyrrolidine-2-carboxylic acid (90 mg, 0.35 mmol), 1-(benzofuran-2-yl)ethanamine (commercially available from for example Enamine) (57 mg, 0.35 mmol) and DIPEA (0.155 mL, 0.89 mmol) in DMF (2 mL) was treated with HATU (139 mg, 0.37 mmol). After 1 hour the product was subjected to purification by mass-directed automated preparative HPLC (formic acid modifier) to afford the title compound (91 mg, 0.21 mmol, 65% yield) LCMS RT=0.79 min, ES+ve m/z 398 [M+H]$^+$.

(2S,4R)—N-([1,1'-biphenyl]-4-ylmethyl)-4-hydroxy-1-(2-(3-methylisoxazol-5-yl)acetyl)pyrrolidine-2-carboxamide

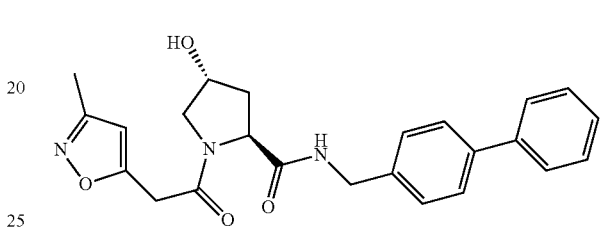

A stirred mixture of (2S,4R)-4-hydroxy-1-(2-(3-methylisoxazol-5-yl)acetyl)pyrrolidine-2-carboxylic acid (30 mg, 0.12 mmol) and [1,1'-biphenyl]-4-ylmethanamine (commercially available from for example Aldrich) (22 mg, 0.12 mmol) in DMF (0.8 mL) was treated with DIPEA (0.08 mL, 0.47 mmol) and then with HATU (49 mg, 0.13 mmol) and the mixture was stirred at ambient temperature for 30 minutes. The product was subjected to purification by mass-directed automated preparative HPLC (formic acid modifier) to afford the title compound (40 mg, 81% yield). LCMS RT=0.86 min, ES+ve m/z 420 [M+H]$^+$. Using a method analogous to that for (2S,4R)—N-([1,1'-biphenyl]-4-ylmethyl)-4-hydroxy-1-(2-(3-methylisoxazol-5-yl)acetyl)pyrrolidine-2-carboxamide the following compounds were prepared:

| Name | Structure | Yield | RT | [M + H]+ |
|---|---|---|---|---|
| (2S,4R)-N-benzyl-4-hydroxy-1-(2-(3-methylisoxazol-5-yl)acetyl)pyrrolidine-2-carboxamide | 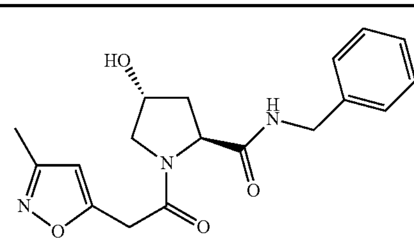 | 61% | 0.62 min | 344 |
| (2S,4R)-4-hydroxy-N-((1-methyl-1H-pyrazol-3-yl)methyl)-1-(2-(3-methylisoxazol-5-yl)acetyl)pyrrolidine-2-carboxamide | 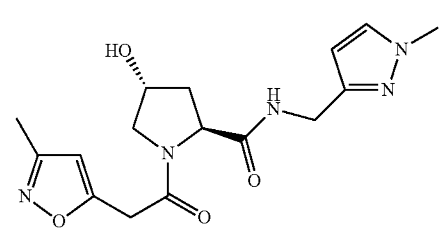 | 75% | 0.40 min | 348 |

| Name | Structure | Yield | RT | [M + H]+ |
|---|---|---|---|---|
| (2S,4R)-4-hydroxy-1-(2-(3-methylisoxazol-5-yl)acetyl)-N-((6-phenylpyridin-3-yl)methyl)pyrrolidine-2-carboxamide | 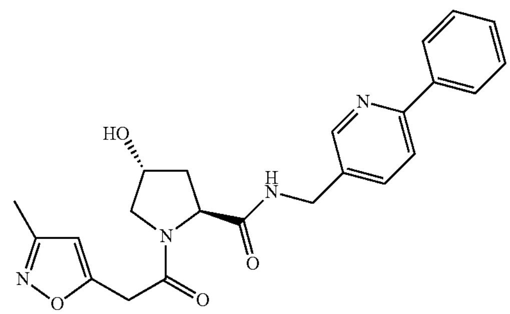 [SMILES: Cc1cc(CC(=O)N2C[C@H](O)C[C@H]2C(=O)NCc2ccc(-c3ccccc3)nc2)on1] | 41% | 0.57 min | 421 |
| (2S,4R)-4-hydroxy-1-(2-(3-methylisoxazol-5-yl)acetyl)-N-((2-oxo-2,3-dihydro-1H-benzo[d]imidazol-5-yl)methyl)pyrrolidine-2-carboxamide | 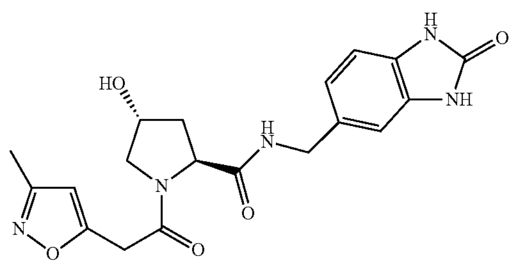 [SMILES: Cc1cc(CC(=O)N2C[C@H](O)C[C@H]2C(=O)NCc2ccc3[nH]c(=O)[nH]c3c2)on1] | 24% | 0.42 min | 400 |
| (2S,4R)-4-hydroxy-1-(2-(3-methylisoxazol-5-yl)acetyl)-N-(quinolin-7-ylmethyl)pyrrolidine-2-carboxamide | 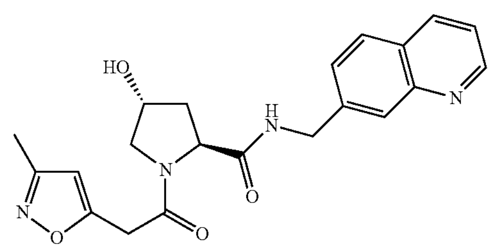 [SMILES: Cc1cc(CC(=O)N2C[C@H](O)C[C@H]2C(=O)NCc2ccc3cccnc3c2)on1] | 19% | 0.39 min | 395 |
| (2S,4R)-4-hydroxy-1-(2-(3-methylisoxazol-5-yl)acetyl)-N-((4-phenylthiazol-2-yl)methyl)pyrrolidine-2-carboxamide | 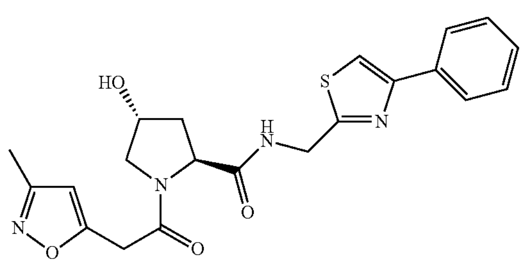 [SMILES: Cc1cc(CC(=O)N2C[C@H](O)C[C@H]2C(=O)NCc2nc(-c3ccccc3)cs2)on1] | 34% | 0.72 min | 427 |
| (2S,4R)-4-hydroxy-1-(2-(3-methylisoxazol-5-yl)acetyl)-N-((1-phenylpyrrolidin-3-yl)methyl)pyrrolidine-2-carboxamide | 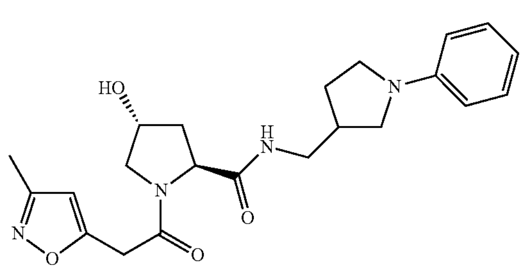 [SMILES: Cc1cc(CC(=O)N2C[C@H](O)C[C@H]2C(=O)NCC2CCN(c3ccccc3)C2)on1] | 35% | 0.72 min | 413 |
| (2S,4R)-4-hydroxy-1-(2-(3-methylisoxazol-5-yl)acetyl)-N-((5-phenyl-1,2,4-oxadiazol-3-yl)methyl)pyrrolidine-2-carboxamide | 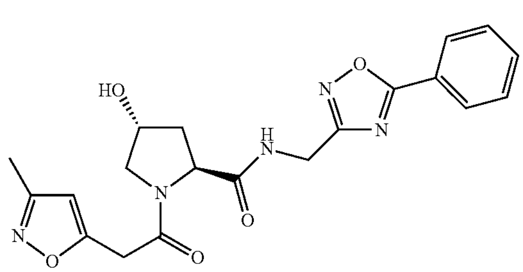 [SMILES: Cc1cc(CC(=O)N2C[C@H](O)C[C@H]2C(=O)NCc2noc(-c3ccccc3)n2)on1] | 31% | 0.67 min | 412 |

| Name | Structure | Yield | RT | [M + H]+ |
|---|---|---|---|---|
| (2S,4R)-4-hydroxy-1-(2-(3-methylisoxazol-5-yl)acetyl)-N-((3-(p-tolyl)isoxazol-5-yl)methyl)pyrrolidine-2-carboxamide | 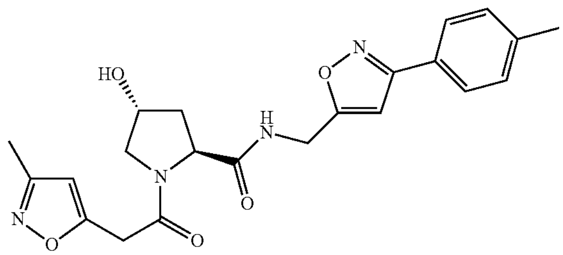 | 56% | 0.78 min | 426 |
| (2S,4R)-N-((S)-1-(4-chlorophenyl)ethyl)-4-hydroxy-1-(2-(3-methylisoxazol-5-yl)acetyl)pyrrolidine-2-carboxamide | 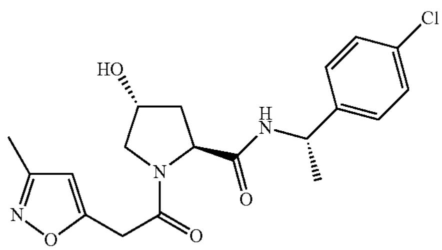 [SMILES: Cc1cc(CC(=O)N2C[C@H](O)C[C@H]2C(=O)N[C@@H](C)c2ccc(Cl)cc2)on1] | 58% | 0.78 min | 392 |
| (2S,4R)-N-((3-(4-chlorophenyl)-1,2,4-oxadiazol-5-yl)methyl)-4-hydroxy-1-(2-(3-methylisoxazol-5-yl)acetyl)pyrrolidine-2-carboxamide | 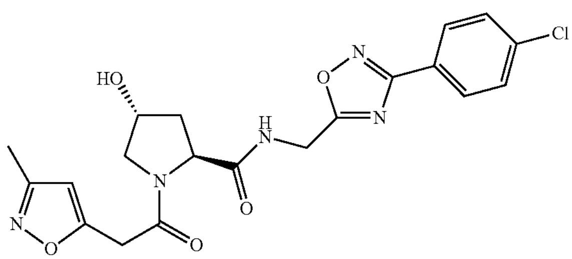 [SMILES: Cc1cc(CC(=O)N2C[C@H](O)C[C@H]2C(=O)NCc2nc(-c3ccc(Cl)cc3)no2)on1] | 57% | 0.81 min | 446 |
| (2S,4R)-4-hydroxy-1-(2-(3-methylisoxazol-5-yl)acetyl)-N-((5-phenylisoxazol-3-yl)methyl)pyrrolidine-2-carboxamide | 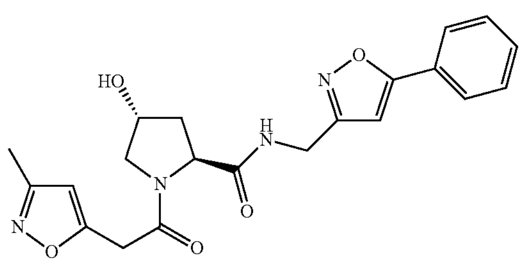 [SMILES: Cc1cc(CC(=O)N2C[C@H](O)C[C@H]2C(=O)NCc2cc(-c3ccccc3)on2)on1] | 66% | 0.72 min | 411 |
| (2S,4R)-4-hydroxy-1-(2-(3-methylisoxazol-5-yl)acetyl)-N-(4-(pyrrolidin-1-yl)benzyl)pyrrolidine-2-carboxamide | 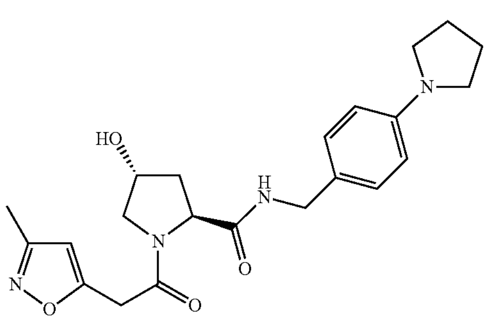 [SMILES: Cc1cc(CC(=O)N2C[C@H](O)C[C@H]2C(=O)NCc2ccc(N3CCCC3)cc2)on1] | 43% | 0.60 min | 413 |

(2S,4R)-1-((S)-2-acetamidopropanoyl)-4-hydroxy-N-phenethylpyrrolidine-2-carboxamide

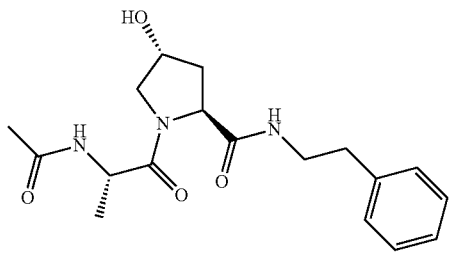 [SMILES: CC(=O)N[C@@H](C)C(=O)N1C[C@H](O)C[C@H]1C(=O)NCCc1ccccc1]

A stirred mixture of (2S,4R)-1-((S)-2-acetamidopropanoyl)-4-hydroxypyrrolidine-2-carboxylic acid (24 mg, 0.10 mmol) and 2-phenylethanamine (commercially available from for example Aldrich) (0.012 mL, 0.10 mmol) in DMF (0.8 mL) was treated with DIPEA (0.07 mL, 0.39 mmol) and then with HATU (45 mg, 0.12 mmol), and the mixture was stirred at ambient temperature for 30 minutes. The product was subjected to purification by mass-directed automated preparative HPLC (formic acid modifier) to afford the title compound (25 mg, 72% yield). LCMS RT=0.56 min, ES+ve m/z 348 [M+H]$^+$.

Using a method analogous to that for (2S,4R)-1-((S)-2-acetamidopropanoyl)-4-hydroxy-N-phenethylpyrrolidine-2-carboxamide the following compounds were prepared:

| Name | Structure | Yield | RT | [M+H]+ |
|---|---|---|---|---|
| (2S,4R)-1-((S)-2-acetamidopropanoyl)-4-hydroxy-N-((6-phenylpyridin-3-yl)methyl)pyrrolidine-2-carboxamide | 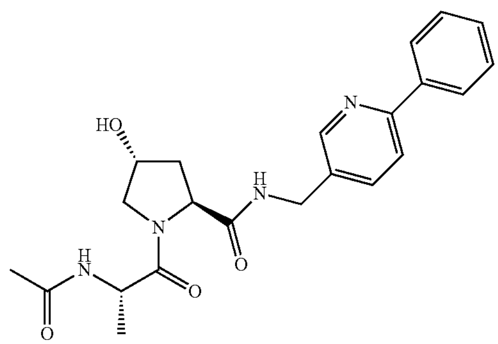 [SMILES: CC(=O)N[C@@H](C)C(=O)N1C[C@H](O)C[C@H]1C(=O)NCc1ccc(-c2ccccc2)nc1] | 10% | 0.49 min | 411 |
| (2S,4R)-N-([1,1'-biphenyl]-4-ylmethyl)-1-((S)-2-acetamidopropanoyl)-4-hydroxypyrrolidine-2-carboxamide | 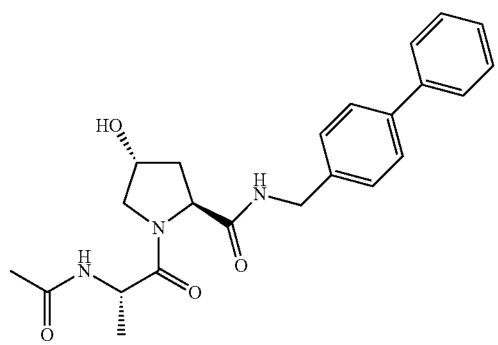 [SMILES: CC(=O)N[C@@H](C)C(=O)N1C[C@H](O)C[C@H]1C(=O)NCc1ccc(-c2ccccc2)cc1] | 40% | 0.79 min | 411 |
| (2S,4R)-1-((S)-2-acetamidopropanoyl)-N-benzyl-4-hydroxypyrrolidine-2-carboxamide | 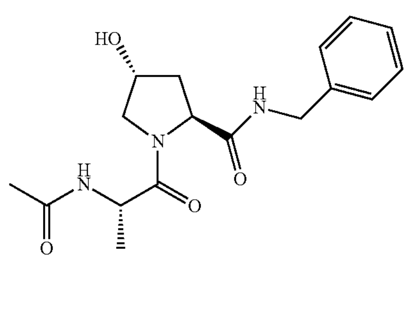 [SMILES: CC(=O)N[C@@H](C)C(=O)N1C[C@H](O)C[C@H]1C(=O)NCc1ccccc1] | 12% | 0.51 min | 334 |

-continued

| Name | Structure | Yield | RT | [M + H]+ |
|---|---|---|---|---|
| (2S,4R)-1-((S)-2-acetamidopropanoyl)-4-hydroxy-N-((3-(p-tolyl)isoxazol-5-yl)methyl)pyrrolidine-2-carboxamide | 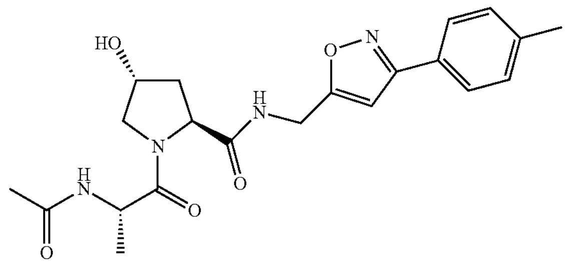 [SMILES: CC(=O)N[C@@H](C)C(=O)N1C[C@H](O)C[C@H]1C(=O)NCc1cc(-c2ccc(C)cc2)no1] | 70% | 0.70 min | 415 |
| (2S,4R)-1-((S)-2-acetamidopropanoyl)-N-cinnamyl-4-hydroxypyrrolidine-2-carboxamide | 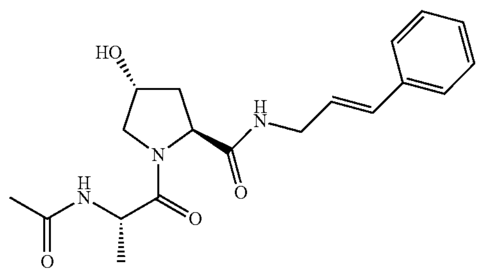 [SMILES: CC(=O)N[C@@H](C)C(=O)N1C[C@H](O)C[C@H]1C(=O)NC/C=C/c1ccccc1] | 50% | 0.64 min | 360 |
| (2S,4R)-1-((S)-2-acetamidopropanoyl)-N-(2-(benzyl(methyl)amino)-2-oxoethyl)-4-hydroxypyrrolidine-2-carboxamide | 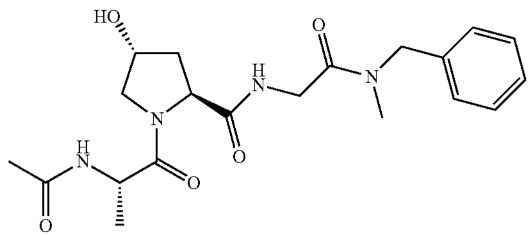 [SMILES: CC(=O)N[C@@H](C)C(=O)N1C[C@H](O)C[C@H]1C(=O)NCC(=O)N(C)Cc1ccccc1] | 27% | 0.56 min | 405 |
| (2S,4R)-1-((S)-2-acetamidopropanoyl)-4-hydroxy-N-(2-((3-methoxybenzyl)(methyl)amino)-2-oxoethyl)pyrrolidine-2-carboxamide | 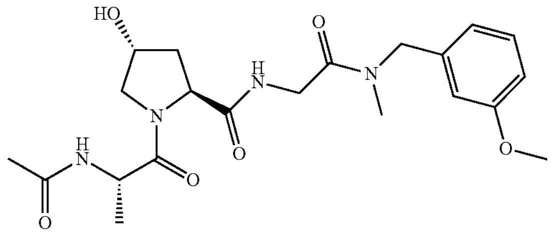 [SMILES: COc1cccc(CN(C)C(=O)CNC(=O)[C@@H]2C[C@@H](O)CN2C(=O)[C@H](C)NC(C)=O)c1] | 28% | 0.58 min | 435 |
| (2S,4R)-1-((S)-2-acetamidopropanoyl)-4-hydroxy-N-((1S,2R)-2-phenylcyclopropyl)pyrrolidine-2-carboxamide | 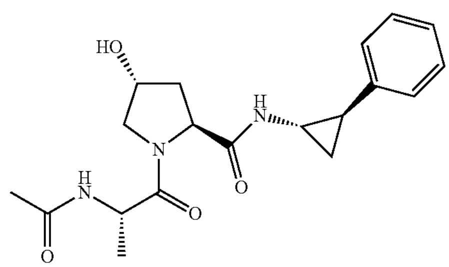 [SMILES: CC(=O)N[C@@H](C)C(=O)N1C[C@H](O)C[C@H]1C(=O)N[C@H]1C[C@@H]1c1ccccc1] | 44% | 0.62 min | 360 |
| (2S,4R)-1-((S)-2-acetamidopropanoyl)-N-((R)-1-benzyl-2-oxopyrrolidin-3-yl)-4-hydroxypyrrolidine-2-carboxamide | 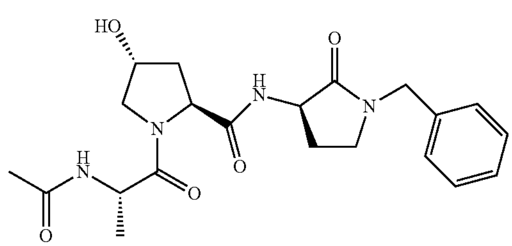 [SMILES: CC(=O)N[C@@H](C)C(=O)N1C[C@H](O)C[C@H]1C(=O)N[C@@H]1CCN(Cc2ccccc2)C1=O] | 76% | 0.58 min | 417 |

287

(S)-1-((2S,4R)-4-hydroxy-2-((4-(4-methylthiazol-5-yl)benzyl)carbamoyl)pyrrolidin-1-yl)-1-oxopropan-2-yl acetate & (2S,4R)-1-acetyl-4-hydroxy-N-(4-(4-methylthiazol-5-yl)benzyl)pyrrolidine-2-carboxamide

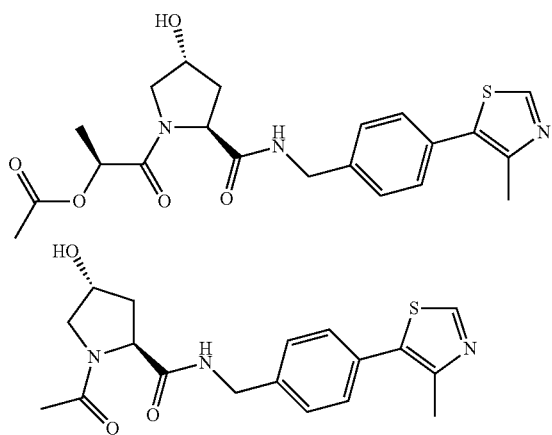

An ice-cooled mixture of (2S,4R)-4-hydroxy-N-(4-(4-methylthiazol-5-yl)benzyl)pyrrolidine-2-carboxamide, hydrochloride (31 mg, 0.088 mmol) and (S)-2-acetoxypropanoic acid (commercially available from for example Aldrich) (8 μL, 0.09 mmol) in DMF (0.8 mL) was treated with DIPEA (0.074 mL, 0.42 mmol). HATU (34 mg, 0.088 mmol) was then added portion-wise over 10 minutes and the mixture was stirred at ambient temperature for 1 hour. The products were separated and purified by mass-directed automated preparative HPLC (formic acid modifier) to afford (S)-1-((2S,4R)-4-hydroxy-2-((4-(4-methylthiazol-5-yl)benzyl) carbamoyl)pyrrolidin-1-yl)-1-oxopropan-2-yl acetate (15 mg, 0.035 mmol, 41% yield) LCMS RT=0.64 min, ES+ve m/z 432 [M+H]+ and (2S,4R)-1-acetyl-4-hydroxy-N-(4-(4-methylthiazol-5-yl)benzyl)pyrrolidine-2-carboxamide (9 mg, 0.025 mmol, 30% yield) LCMS RT=0.57 min, ES+ve m/z 360 [M+H]+.

(2S,4R)-1-(2-(cyanomethyl)benzoyl)-4-hydroxy-N-(4-(4-methylthiazol-5-yl)benzyl)pyrrolidine-2-carboxamide

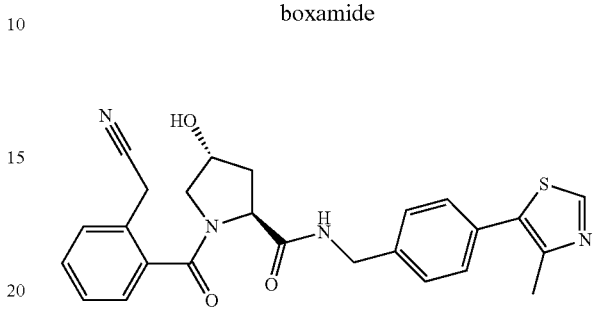

A stirred mixture of (2S,4R)-4-hydroxy-N-(4-(thiazol-5-yl)benzyl)pyrrolidine-2-carboxamide (50 mg, 0.17 mmol) and 2-(cyanomethyl)benzoic acid (commercially available from for example Aldrich) (29 mg, 0.18 mmol) in DMF (0.7 mL) was treated with DIPEA (0.086 mL, 0.49 mmol) and then with HATU (69 mg, 0.18 mmol) and the mixture was stirred at ambient temperature for 10 minutes. The product was subjected to purification by mass-directed automated preparative HPLC (formic acid modifier) to afford the title compound (31 mg, 0.067 mmol, 41% yield). LCMS RT=0.73 min, ES+ve m/z 461 [M+H]+.

Using a method analogous to that for (2S,4R)-1-(2-(cyanomethyl)benzoyl)-4-hydroxy-N-(4-(4-methylthiazol-5-yl)benzyl)pyrrolidine-2-carboxamide the following compounds were prepared:

| Name | Structure | Stereochemistry Comment | Yield | RT | [M+H]+ |
|---|---|---|---|---|---|
| (2S,4R)-4-hydroxy-1-(2-(2-methoxyethoxy)acetyl)-N-(4-(4-methylthiazol-5-yl)benzyl)pyrrolidine-2-carboxamide | 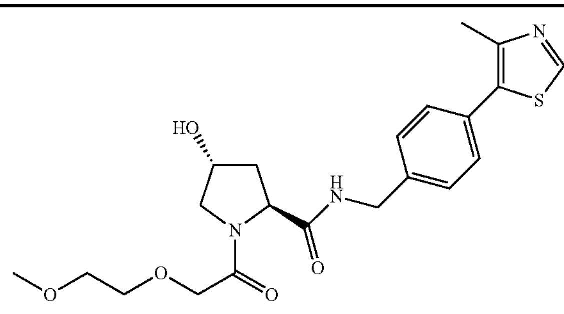 | | 59% | 0.57 min | 434 |
| (2S,4R)-1-((S)-2-acetamidopropanoyl)-4-hydroxy-N-(4-(4-methylthiazol-5-yl)benzyl)pyrrolidine-2-carboxamide | 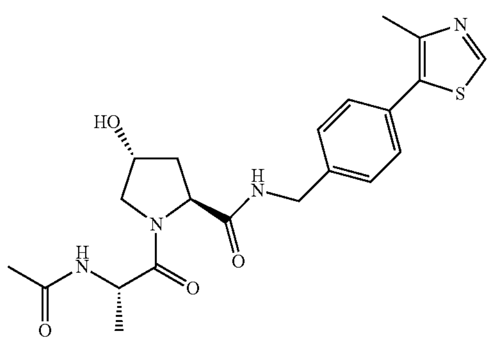 [SMILES: CC(=O)N[C@@H](C)C(=O)N1C[C@H](O)C[C@H]1C(=O)NCc1ccc(-c2scnc2C)cc1] | | 71% | 0.56 min | 431 |

-continued

| Name | Structure | Stereo-chemistry Comment | Yield | RT | [M + H]+ |
|---|---|---|---|---|---|
| (2S,4R)-1-((S)-1-acetylpyrrolidine-2-carbonyl)-4-hydroxy-N-(4-(4-methylthiazol-5-yl)benzyl)pyrrolidine-2-carboxamide | 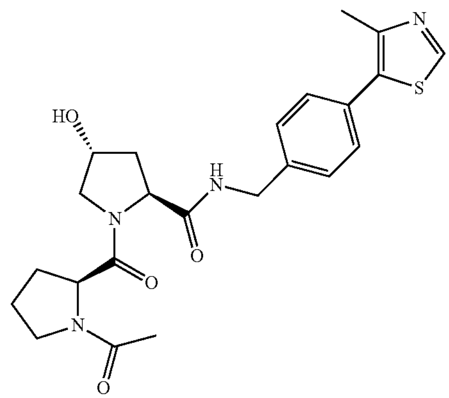 [SMILES: CC(=O)N1CCC[C@H]1C(=O)N1C[C@H](O)C[C@H]1C(=O)NCc1ccc(-c2scnc2C)cc1] | | 57% | 0.54 min | 457 |
| (2S,4R)-4-hydroxy-N-(4-(4-methylthiazol-5-yl)benzyl)-1-((S)-5-oxopyrrolidine-2-carbonyl)pyrrolidine-2-carboxamide | 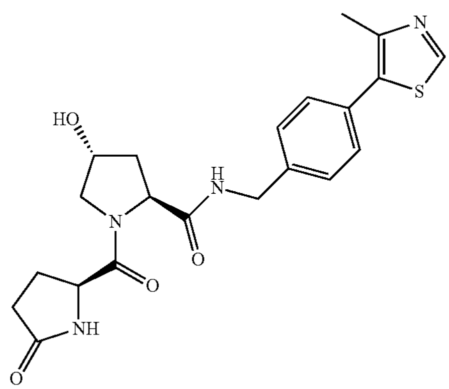 [SMILES: Cc1ncsc1-c1ccc(CNC(=O)[C@@H]2C[C@@H](O)CN2C(=O)[C@@H]2CCC(=O)N2)cc1] | | 58% | 0.53 min | 429 |
| (2S,4R)-1-(cyclohexanecarbonyl)-4-hydroxy-N-(4-(4-methylthiazol-5-yl)benzyl)pyrrolidine-2-carboxamide | 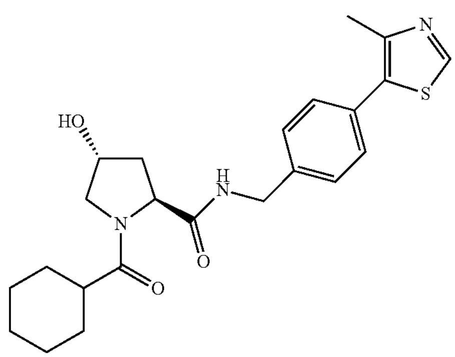 [SMILES: Cc1ncsc1-c1ccc(CNC(=O)[C@@H]2C[C@@H](O)CN2C(=O)C2CCCCC2)cc1] | | 61% | 0.76 min | 428 |
| (2S,4R)-1-(4-ethoxybenzoyl)-4-hydroxy-N-(4-(4-methylthiazol-5-yl)benzyl)pyrrolidine-2-carboxamide | 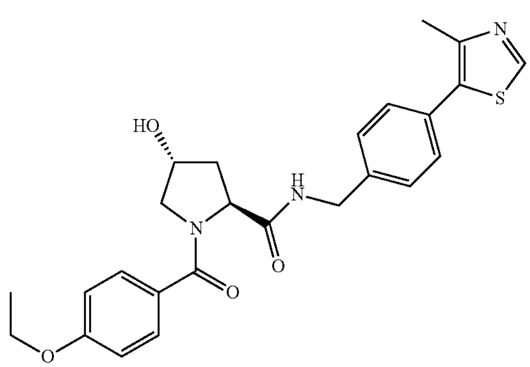 [SMILES: CCOc1ccc(C(=O)N2C[C@H](O)C[C@H]2C(=O)NCc2ccc(-c3scnc3C)cc2)cc1] | | 73% | 0.78 min | 466 |

| Name | Structure | Stereochemistry Comment | Yield | RT | [M + H]+ |
|---|---|---|---|---|---|
| (2S,4R)-4-hydroxy-N-(4-(4-methylthiazol-5-yl)benzyl)-1-(5-oxopyrrolidine-3-carbonyl)pyrrolidine-2-carboxamide | 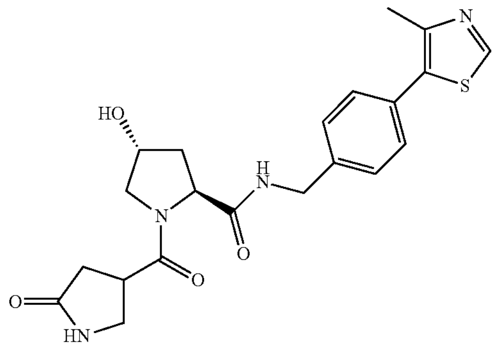 [SMILES: Cc1ncsc1-c1ccc(CNC(=O)[C@@H]2C[C@@H](O)CN2C(=O)C2CNC(=O)C2)cc1] | | 85% | 0.53 min | 429 |
| (2S,4R)-4-hydroxy-N-(4-(4-methylthiazol-5-yl)benzyl)-1-(2-morpholinoacetyl)pyrrolidine-2-carboxamide | 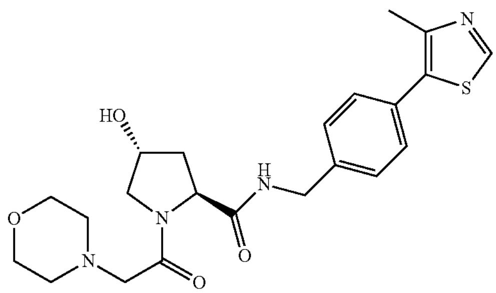 [SMILES: Cc1ncsc1-c1ccc(CNC(=O)[C@@H]2C[C@@H](O)CN2C(=O)CN2CCOCC2)cc1] | | 40% | 0.48 min | 445 |
| (2S,4R)-4-hydroxy-1-(2-methoxyacetyl)-N-(4-(4-methylthiazol-5-yl)benzyl)pyrrolidine-2-carboxamide | 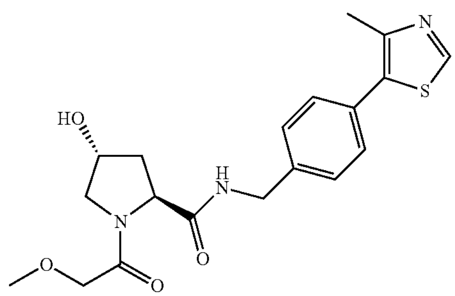 [SMILES: COCC(=O)N1C[C@H](O)C[C@H]1C(=O)NCc1ccc(-c2scnc2C)cc1] | | 68% | 0.55 min | 390 |
| (2S,4R)-4-hydroxy-1-((S)-2-methoxypropanoyl)-N-(4-(4-methylthiazol-5-yl)benzyl)pyrrolidine-2-carboxamide | 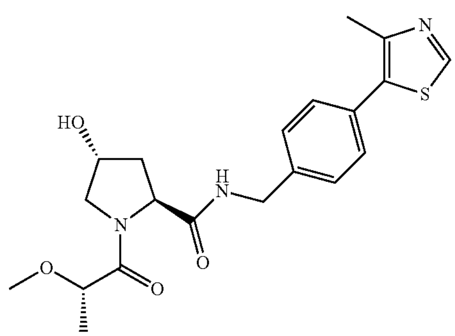 [SMILES: CO[C@@H](C)C(=O)N1C[C@H](O)C[C@H]1C(=O)NCc1ccc(-c2scnc2C)cc1] | | 69% | 0.57 min | 404 |

| Name | Structure | Stereo-chemistry Comment | Yield | RT | [M + H]+ |
|---|---|---|---|---|---|
| (2S,4R)-4-hydroxy-1-(3-methoxybenzoyl)-N-(4-(4-methylthiazol-5-yl)benzyl)pyrrolidine-2-carboxamide | 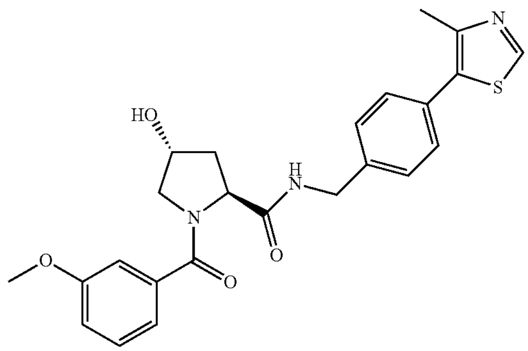 [SMILES: COc1cccc(C(=O)N2C[C@H](O)C[C@H]2C(=O)NCc2ccc(-c3scnc3C)cc2)c1] | | 67% | 0.71 min | 452 |
| (2S,4R)-4-hydroxy-1-(2-methylbenzoyl)-N-(4-(4-methylthiazol-5-yl)benzyl)pyrrolidine-2-carboxamide | 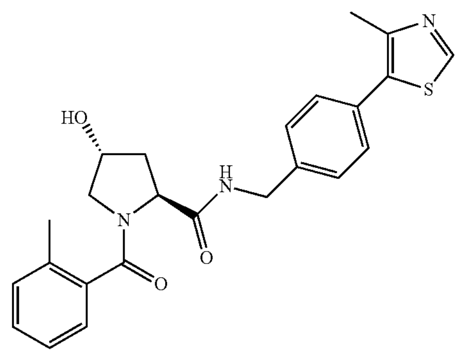 [SMILES: Cc1ccccc1C(=O)N1C[C@H](O)C[C@H]1C(=O)NCc1ccc(-c2scnc2C)cc1] | | 77% | 0.74 min | 436 |
| (2S,4R)-4-hydroxy-1-(3-methoxy-2-methylbenzoyl)-N-(4-(4-methylthiazol-5-yl)benzyl)pyrrolidine-2-carboxamide | 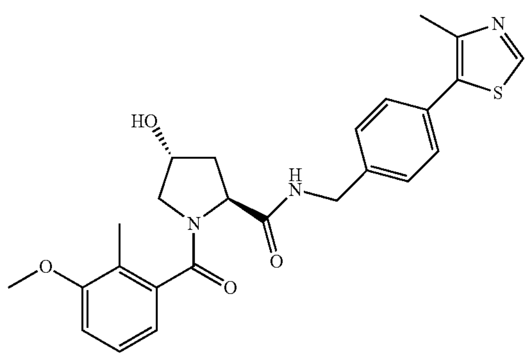 [SMILES: COc1cccc(C(=O)N2C[C@H](O)C[C@H]2C(=O)NCc2ccc(-c3scnc3C)cc2)c1C] | | 61% | 0.76 min | 466 |
| (2S,4R)-1-(3-chloro-5-methoxybenzoyl)-4-hydroxy-N-(4-(4-methylthiazol-5-yl)benzyl)pyrrolidine-2-carboxamide | 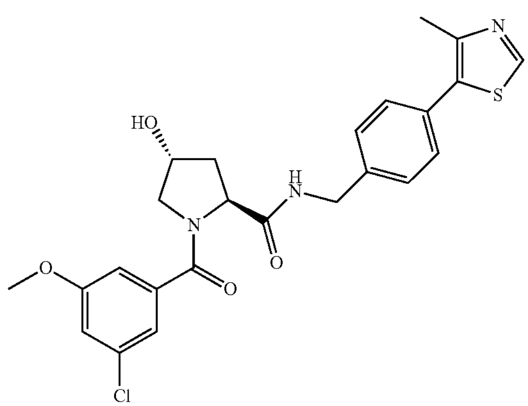 [SMILES: COc1cc(Cl)cc(C(=O)N2C[C@H](O)C[C@H]2C(=O)NCc2ccc(-c3scnc3C)cc2)c1] | | 69% | 0.80 min | 486 |

| Name | Structure | Stereo-chemistry Comment | Yield | RT | [M + H]+ |
|---|---|---|---|---|---|
| (2S,4R)-4-hydroxy-1-(3-hydroxy-2-methylbenzoyl)-N-(4-(4-methylthiazol-5-yl)benzyl)pyrrolidine-2-carboxamide | 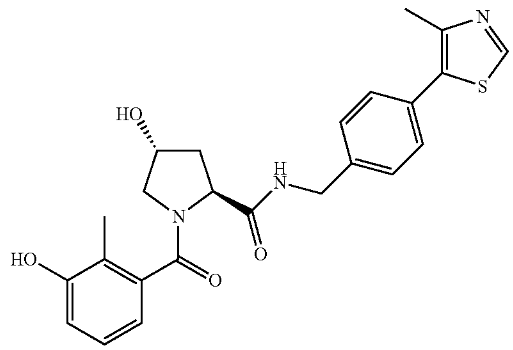 [SMILES: Cc1ncsc1-c1ccc(CNC(=O)[C@@H]2C[C@@H](O)CN2C(=O)c2cccc(O)c2C)cc1] | | 84% | 0.64 min | 452 |
| (2S,4R)-4-hydroxy-N-(4-(4-methylthiazol-5-yl)benzyl)-1-(2-(3-oxomorpholino)propanoyl)pyrrolidine-2-carboxamide | 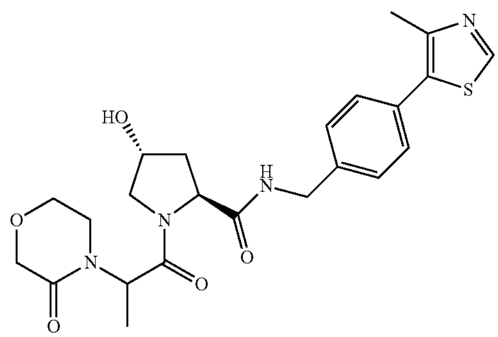 [SMILES: Cc1ncsc1-c1ccc(CNC(=O)[C@@H]2C[C@@H](O)CN2C(=O)C(C)N2CCOCC2=O)cc1] | Single enantiomer, stereochemistry unknown at the unspecified chiral centre, eluted first during HPLC purification (formic acid modifier) | 32% | 0.59 min | 473 |
| (2S,4R)-4-hydroxy-N-(4-(4-methylthiazol-5-yl)benzyl)-1-((S)-2-(1-oxoisoindolin-2-yl)pentanoyl)pyrrolidine-2-carboxamide | 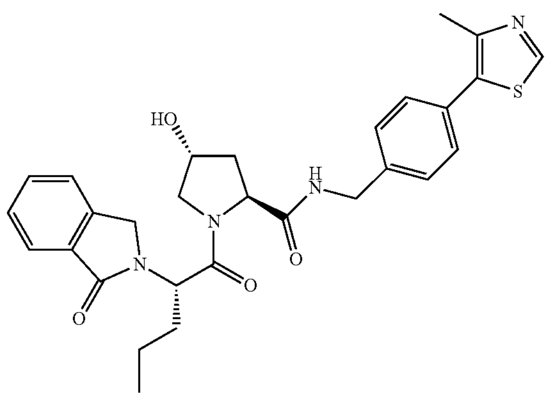 [SMILES: CCC[C@@H](C(=O)N1C[C@H](O)C[C@H]1C(=O)NCc1ccc(-c2scnc2C)cc1)N1Cc2ccccc2C1=O] | | 69% | 0.84 min | 533 |
| (2S,4R)-4-hydroxy-1-(2-(6-methoxy-1-oxoisoindolin-2-yl)-3-methylbutanoyl)-N-(4-(4-methylthiazol-5-yl)benzyl)pyrrolidine-2-carboxamide | 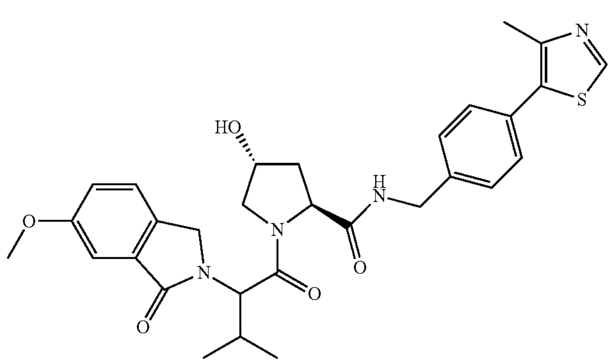 [SMILES: COc1ccc2c(c1)C(=O)N(C(C(=O)N1C[C@H](O)C[C@H]1C(=O)NCc1ccc(-c3scnc3C)cc1)C(C)C)C2] | Single enantiomer, stereochemistry unknown at the unspecified chiral centre, eluted first during HPLC purification (formic acid modifier) | 35% | 0.84 min | 563 |

| Name | Structure | Stereochemistry Comment | Yield | RT | [M + H]+ |
|---|---|---|---|---|---|
| (2S,4R)-4-hydroxy-1-(2-(6-methoxy-1-oxoisoindolin-2-yl)-3-methylbutanoyl)-N-(4-(4-methylthiazol-5-yl)benzyl)pyrrolidine-2-carboxamide | 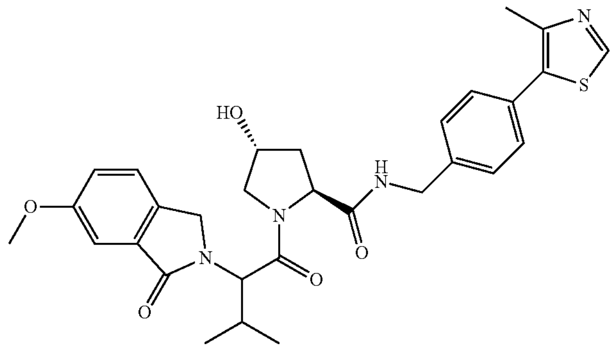 [SMILES: COc1ccc2c(c1)C(=O)N(C(C(=O)N1C[C@H](O)C[C@H]1C(=O)NCc1ccc(-c3scnc3C)cc1)C(C)C)C2] | Single enantiomer, stereochemistry unknown at the unspecified chiral centre, eluted second during HPLC purification (formic acid modifier) | 34% | 0.85 min | 563 |
| (2S,4R)-4-hydroxy-1-(2-(5-methoxy-1-oxoisoindolin-2-yl)-3-methylbutanoyl)-N-(4-(4-methylthiazol-5-yl)benzyl)pyrrolidine-2-carboxamide | 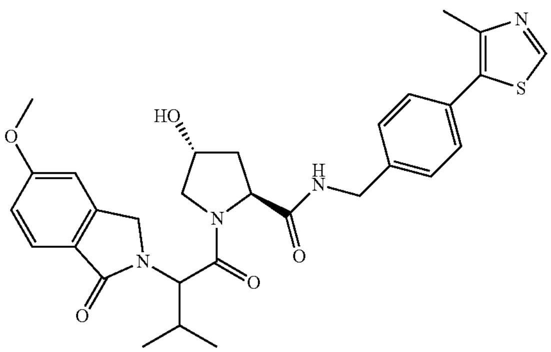 [SMILES: COc1ccc2c(c1)CN(C(C(=O)N1C[C@H](O)C[C@H]1C(=O)NCc1ccc(-c3scnc3C)cc1)C(C)C)C2=O] | Single enantiomer, stereochemistry unknown at the unspecified chiral centre, eluted second during HPLC purification (formic acid modifier) | 28% | 0.84 min | 536 |
| (2S,4R)-1-(2-(7-chloro-1-oxoisoindolin-2-yl)-3-methylbutanoyl)-4-hydroxy-N-(4-(4-methylthiazol-5-yl)benzyl)pyrrolidine-2-carboxamide | 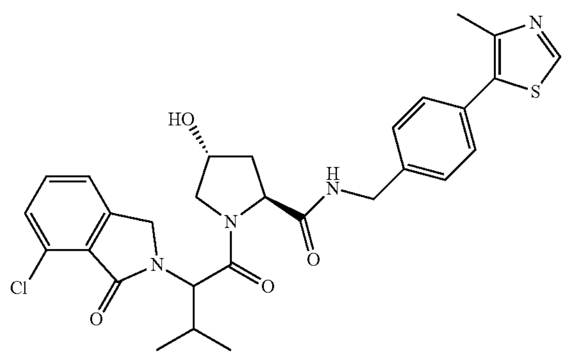 [SMILES: Cc1ncsc1-c1ccc(CNC(=O)[C@@H]2C[C@@H](O)CN2C(=O)C(C(C)C)N2Cc3cccc(Cl)c3C2=O)cc1] | Single enantiomer, stereochemistry unknown at the unspecified chiral centre, eluted second during HPLC purification (formic acid modifier) | 35% | 0.93 min | 567, 569 |
| (2S,4R)-1-((S)-2-acetamido-4-methylpentanoyl)-4-hydroxy-N-(4-(4-methylthiazol-5-yl)benzyl)pyrrolidine-2-carboxamide | 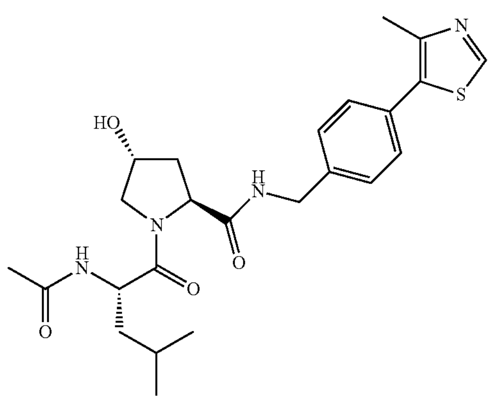 [SMILES: CC(=O)N[C@@H](CC(C)C)C(=O)N1C[C@H](O)C[C@H]1C(=O)NCc1ccc(-c2scnc2C)cc1] | | 71% | 0.71 min | 473 |

-continued

| Name | Structure | Stereo-chemistry Comment | Yield | RT | [M + H]+ |
|---|---|---|---|---|---|
| (2S,4R)-1-((S)-2-acetamido-3-phenylpropanoyl)-4-hydroxy-N-(4-(4-methylthiazol-5-yl)benzyl)pyrrolidine-2-carboxamide | 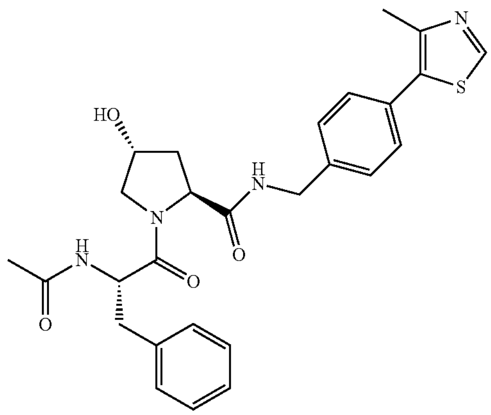 [SMILES: CC(=O)N[C@@H](Cc1ccccc1)C(=O)N1C[C@H](O)C[C@H]1C(=O)NCc1ccc(-c2scnc2C)cc1] | | 77% | 0.75 min | 507 |
| (2S,4R)-4-hydroxy-1-((S)-3-methyl-2-(3-methyl-2,5-dioxo-2,5-dihydro-1H-pyrrol-1-yl)butanoyl)-N-(4-(4-methylthiazol-5-yl)benzyl)pyrrolidine-2-carboxamide | 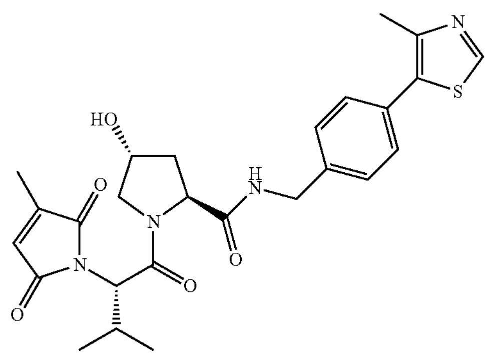 [SMILES: CC1=CC(=O)N([C@H](C(=O)N2C[C@H](O)C[C@H]2C(=O)NCc2ccc(-c3scnc3C)cc2)C(C)C)C1=O] | | 17% | 0.80 min | 511 |
| (2S,4R)-1-benzoyl-4-hydroxy-N-(4-(4-methylthiazol-5-yl)benzyl)pyrrolidine-2-carboxamide | 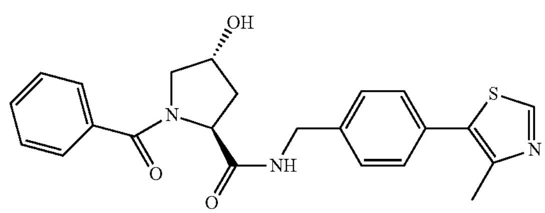 [SMILES: Cc1ncsc1-c1ccc(CNC(=O)[C@@H]2C[C@@H](O)CN2C(=O)c2ccccc2)cc1] | | 57% | 0.69 min | 422 |
| (2S,4R)-1-(3-(cyanomethyl)benzoyl)-4-hydroxy-N-(4-(4-methylthiazol-5-yl)benzyl)pyrrolidine-2-carboxamide | 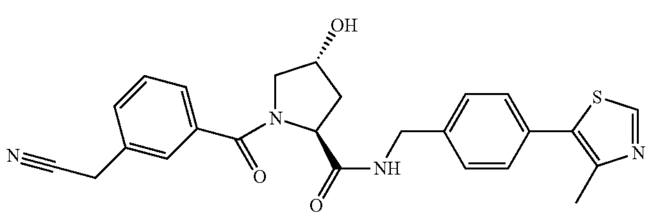 [SMILES: Cc1ncsc1-c1ccc(CNC(=O)[C@@H]2C[C@@H](O)CN2C(=O)c2cccc(CC#N)c2)cc1] | | 74% | 0.68 min | 461 |
| (2S,4R)-1-(1-(cyanomethyl)-1H-indole-2-carbonyl)-4-hydroxy-N-(4-(4-methylthiazol-5-yl)benzyl)pyrrolidine-2-carboxamide | 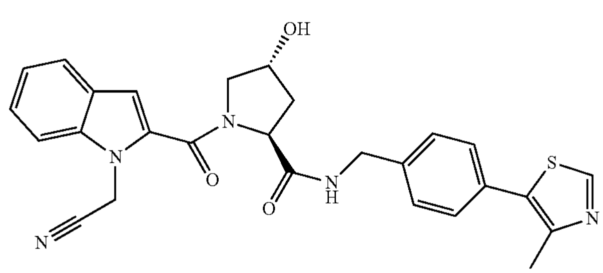 [SMILES: Cc1ncsc1-c1ccc(CNC(=O)[C@@H]2C[C@@H](O)CN2C(=O)c2cc3ccccc3n2CC#N)cc1] | | 62% | 0.82 min | 500 |

| Name | Structure | Stereochemistry Comment | Yield | RT | [M + H]+ |
| --- | --- | --- | --- | --- | --- |
| (2S,4R)-1-(4-ethoxycyclohexanecarbonyl)-4-hydroxy-N-(4-(4-methylthiazol-5-yl)benzyl)pyrrolidine-2-carboxamide | 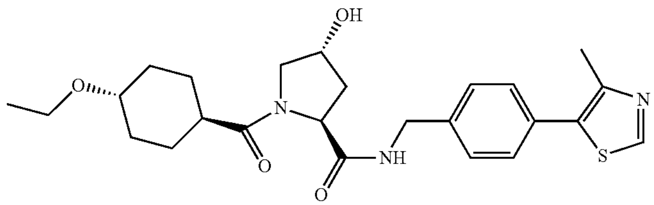 [SMILES: CCO[C@H]1CC[C@H](C(=O)N2C[C@H](O)C[C@H]2C(=O)NCc2ccc(-c3scnc3C)cc2)CC1] | | 74% | 0.74 min | 472 |
| (2S,4R)-1-(2-cyclopentylpropanoyl)-4-hydroxy-N-(4-(4-methylthiazol-5-yl)benzyl)pyrrolidine-2-carboxamide | 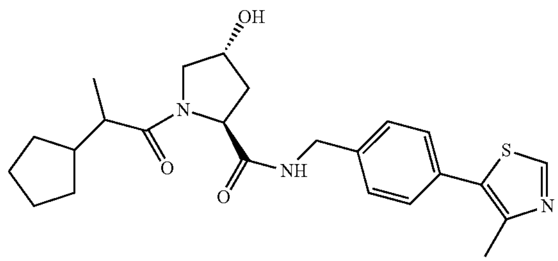 [SMILES: Cc1ncsc1-c1ccc(CNC(=O)[C@@H]2C[C@@H](O)CN2C(=O)C(C)C2CCCC2)cc1] | Mixture of diastereoisomers | 67% | 0.82 min | 442 |
| (2S,4R)-4-hydroxy-N-(4-(4-methylthiazol-5-yl)benzyl)-1-(2-morpholinopropanoyl)pyrrolidine-2-carboxamide | 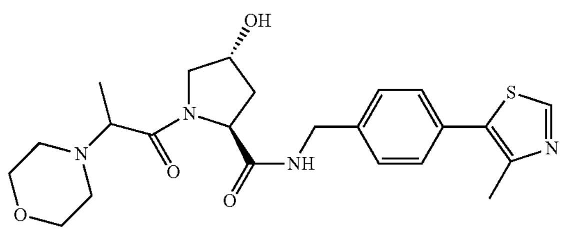 [SMILES: Cc1ncsc1-c1ccc(CNC(=O)[C@@H]2C[C@@H](O)CN2C(=O)C(C)N2CCOCC2)cc1] | Mixture of diastereoisomers | 53% | 0.68 min | 459 |
| (2S,4R)-4-hydroxy-1-(indoline-2-carbonyl)-N-(4-(4-methylthiazol-5-yl)benzyl)pyrrolidine-2-carboxamide | 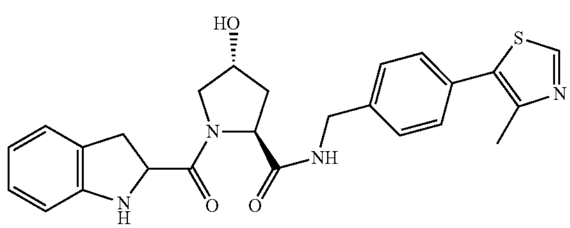 [SMILES: Cc1ncsc1-c1ccc(CNC(=O)[C@@H]2C[C@@H](O)CN2C(=O)C2Cc3ccccc3N2)cc1] | Single enantiomer, stereochemistry unknown at the unspecified chiral centre, eluted first during HPLC purification (formic acid modifier) | 64% | 0.70 min | 463 |
| (2S,4R)-1-(2-(4-chloro-1H-pyrazol-1-yl)propanoyl)-4-hydroxy-N-(4-(4-methylthiazol-5-yl)benzyl)pyrrolidine-2-carboxamide | 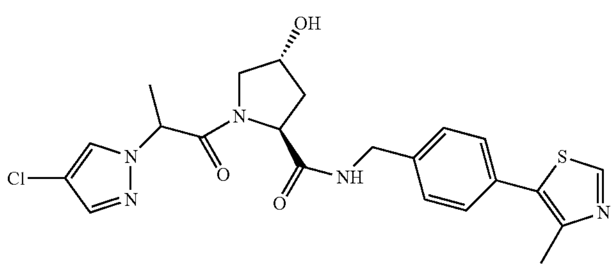 [SMILES: Cc1ncsc1-c1ccc(CNC(=O)[C@@H]2C[C@@H](O)CN2C(=O)C(C)n2cc(Cl)cn2)cc1] | Single enantiomer, stereochemistry unknown at the unspecified chiral centre, eluted first during HPLC purification (formic acid modifier) | 39% | 0.74 min | 474 |

-continued

| Name | Structure | Stereo-chemistry Comment | Yield | RT | [M + H]+ |
|---|---|---|---|---|---|
| (2S,4R)-4-hydroxy-N-(4-(4-methylthiazol-5-yl)benzyl)-1-(2-(1-oxoisoindolin-2-yl)propanoyl)pyrrolidine-2-carboxamide | 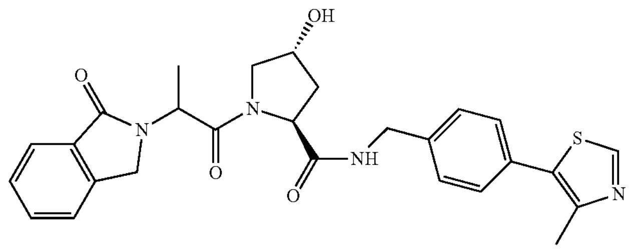 [SMILES: Cc1ncsc1-c1ccc(CNC(=O)[C@@H]2C[C@@H](O)CN2C(=O)C(C)N2Cc3ccccc3C2=O)cc1] | Mixture of diastereo-isomers | 51% | 0.73 min | 505 |
| (2S,4R)-1-(2-(3-(difluoromethyl)-5-methyl-1H-pyrazol-1-yl)propanoyl)-4-hydroxy-N-(4-(4-methylthiazol-5-yl)benzyl)pyrrolidine-2-carboxamide | | Single enantiomer, stereo-chemistry unknown at the unspecified chiral centre, eluted second during HPLC purifi-cation (formic acid modifier) | 31% | 0.76 min | 504 |
| (2S,4R)-4-hydroxy-1-(1H-indole-2-carbonyl)-N-(4-(4-methylthiazol-5-yl)benzyl)pyrrolidine-2-carboxamide | 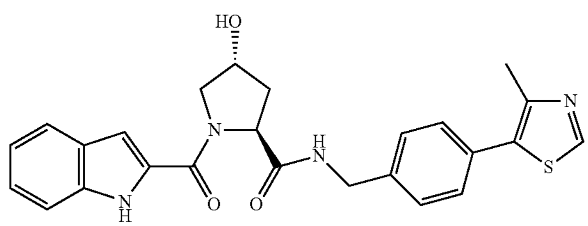 [SMILES: Cc1ncsc1-c1ccc(CNC(=O)[C@@H]2C[C@@H](O)CN2C(=O)c2cc3ccccc3[nH]2)cc1] | | 65% | 0.78 min | 461 |
| (2S,4R)-4-hydroxy-N-(4-(4-methylthiazol-5-yl)benzyl)-1-(2-(pyrazolo[1,5-a]pyridin-3-yl)acetyl)pyrrolidine-2-carboxamide | 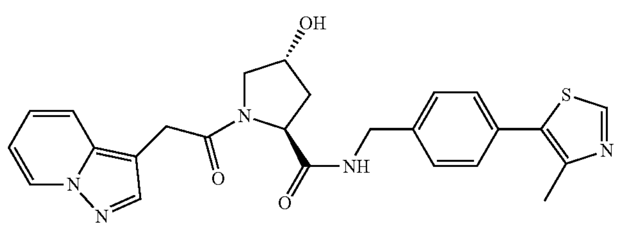 [SMILES: Cc1ncsc1-c1ccc(CNC(=O)[C@@H]2C[C@@H](O)CN2C(=O)Cc2cnn3ccccc23)cc1] | | 51% | 0.65 min | 476 |
| (2S,4R)-1-(2-cyclohexylpropanoyl)-4-hydroxy-N-(4-(4-methylthiazol-5-yl)benzyl)pyrrolidine-2-carboxamide | 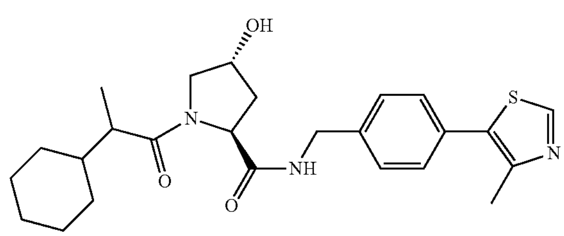 [SMILES: Cc1ncsc1-c1ccc(CNC(=O)[C@@H]2C[C@@H](O)CN2C(=O)C(C)C2CCCCC2)cc1] | Mixture of diastereo-isomers | 68% | 0.87 min | 456 |
| (2S,4R)-1-(2-((4-fluorophenyl)amino)propanoyl)-4-hydroxy-N-(4-(4-methylthiazol-5-yl)benzyl)pyrrolidine-2-carboxamide | 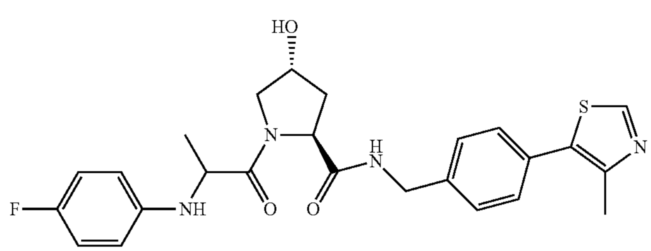 [SMILES: Cc1ncsc1-c1ccc(CNC(=O)[C@@H]2C[C@@H](O)CN2C(=O)C(C)Nc2ccc(F)cc2)cc1] | Mixture of diastereo-isomers | 41% | 0.70 min | 483 |

-continued

| Name | Structure | Stereochemistry Comment | Yield | RT | [M + H]+ |
|---|---|---|---|---|---|
| (2S,4R)-4-hydroxy-N-(4-(4-methylthiazol-5-yl)benzyl)-1-(2-(1-oxoisoindolin-2-yl)acetyl)pyrrolidine-2-carboxamide | 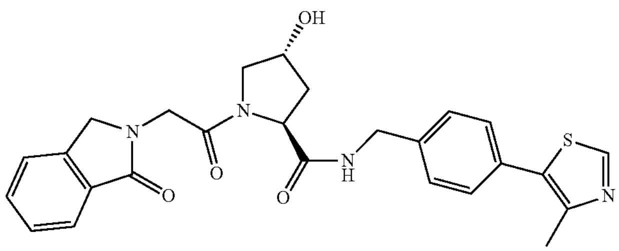 [SMILES: Cc1ncsc1-c1ccc(CNC(=O)[C@@H]2C[C@@H](O)CN2C(=O)CN2Cc3ccccc3C2=O)cc1] | | 49% | 0.69 min | 491 |
| (2S,4R)-4-hydroxy-N-(4-(4-methylthiazol-5-yl)benzyl)-1-(2-(pyrazolo[1,5-a]pyridin-3-yl)propanoyl)pyrrolidine-2-carboxamide | 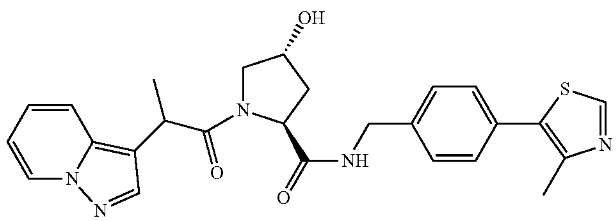 | Mixture of diastereoisomers | 61% | 0.70 min | 490 |
| (2S,4R)-1-(2-(3-cyanophenyl)propanoyl)-4-hydroxy-N-(4-(4-methylthiazol-5-yl)benzyl)pyrrolidine-2-carboxamide | 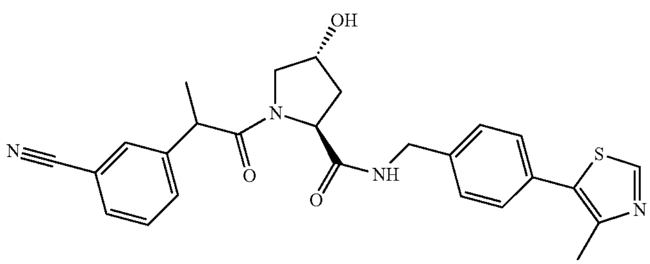 [SMILES: Cc1ncsc1-c1ccc(CNC(=O)[C@@H]2C[C@@H](O)CN2C(=O)C(C)c2cccc(C#N)c2)cc1] | Mixture of diastereoisomers | 54% | 0.77 min | 475 |
| (2S,4R)-4-hydroxy-1-(2-methyl-4-oxo-4-phenylbutanoyl)-N-(4-(4-methylthiazol-5-yl)benzyl)pyrrolidine-2-carboxamide | | Single enantiomer, stereochemistry unknown at the unspecified chiral centre, eluted first during HPLC purification (formic acid modifier) | 35% | 0.80 min | 492 |
| (2S,4R)-4-hydroxy-1-(2-methyl-4-oxo-4-phenylbutanoyl)-N-(4-(4-methylthiazol-5-yl)benzyl)pyrrolidine-2-carboxamide | | Single enantiomer, stereochemistry unknown at the unspecified chiral centre, eluted second during HPLC purification (formic acid modifier) | 26% | 0.82 min | 492 |

| Name | Structure | Stereochemistry Comment | Yield | RT | [M + H]+ |
|---|---|---|---|---|---|
| (2S,4R)-4-hydroxy-N-(4-(4-methylthiazol-5-yl)benzyl)-1-(2-phenylpropanoyl)pyrrolidine-2-carboxamide | | Single enantiomer, stereochemistry unknown at the unspecified chiral centre, eluted first during HPLC purification (formic acid modifier) | 44% | 0.78 min | 450 |
| (2S,4R)-4-hydroxy-N-(4-(4-methylthiazol-5-yl)benzyl)-1-(2-phenylpropanoyl)pyrrolidine-2-carboxamide | | Single enantiomer, stereochemistry unknown at the unspecified chiral centre, eluted second during HPLC purification (formic acid modifier) | 41% | 0.80 min | 450 |
| (2S,4R)-4-hydroxy-N-(4-(4-methylthiazol-5-yl)benzyl)-1-(2-(2-oxopyridin-1(2H)-yl)propanoyl)pyrrolidine-2-carboxamide | 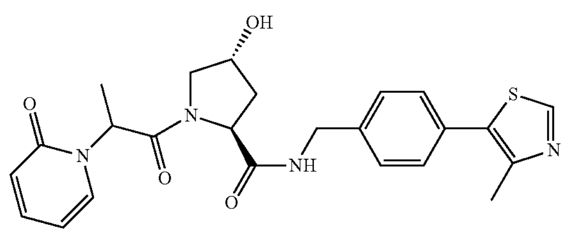 [SMILES: Cc1ncsc1-c1ccc(CNC(=O)[C@@H]2C[C@@H](O)CN2C(=O)C(C)n2ccccc2=O)cc1] | Single enantiomer, stereochemistry unknown at the unspecified chiral centre, eluted first during HPLC purification (formic acid modifier) | 33% | 0.62 min | 467 |
| (2S,4R)-4-hydroxy-1-(2-(indolin-1-yl)propanoyl)-N-(4-(4-methylthiazol-5-yl)benzyl)pyrrolidine-2-carboxamide | 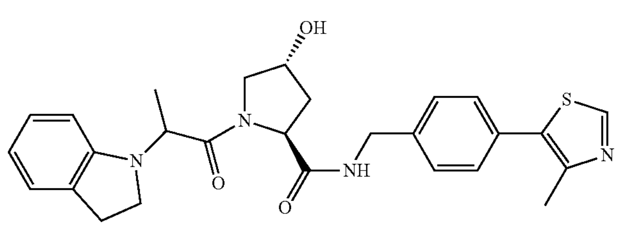 [SMILES: Cc1ncsc1-c1ccc(CNC(=O)[C@@H]2C[C@@H](O)CN2C(=O)C(C)N2CCc3ccccc32)cc1] | Single enantiomer, stereochemistry unknown at the unspecified chiral centre, eluted first during HPLC purification (formic acid modifier) | 35% | 0.86 min | 491 |

-continued

| Name | Structure | Stereochemistry Comment | Yield | RT | [M + H]+ |
|---|---|---|---|---|---|
| (2S,4R)-4-hydroxy-1-(2-(indolin-1-yl)propanoyl)-N-(4-(4-methylthiazol-5-yl)benzyl)pyrrolidine-2-carboxamide | 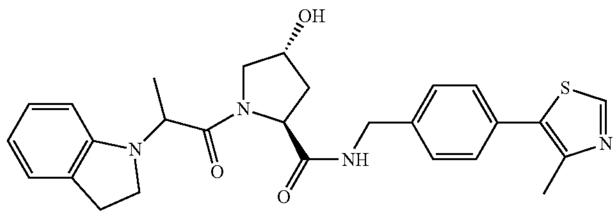 [SMILES: Cc1ncsc1-c1ccc(CNC(=O)[C@@H]2C[C@@H](O)CN2C(=O)C(C)N2CCc3ccccc32)cc1] | Single enantiomer, stereochemistry unknown at the unspecified chiral centre, eluted second during HPLC purification (formic acid modifier) | 40% | 0.88 min | 491 |
| (2S,4R)-4-hydroxy-1-(2-methyl-3-morpholinopropanoyl)-N-(4-(4-methylthiazol-5-yl)benzyl)pyrrolidine-2-carboxamide | 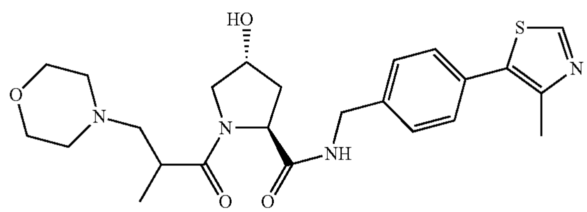 [SMILES: Cc1ncsc1-c1ccc(CNC(=O)[C@@H]2C[C@@H](O)CN2C(=O)C(C)CN2CCOCC2)cc1] | Mixture of diastereoisomers | 57% | 0.52 min | 472 |
| (2S,4R)-4-hydroxy-N-(4-(4-methylthiazol-5-yl)benzyl)-1-(pyrazolo[1,5-a]pyridine-2-carbonyl)pyrrolidine-2-carboxamide | 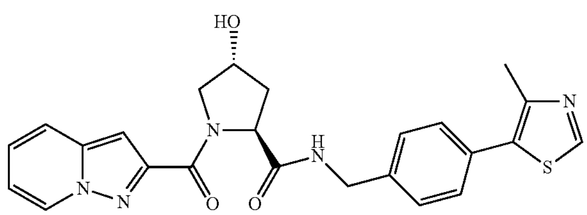 [SMILES: Cc1ncsc1-c1ccc(CNC(=O)[C@@H]2C[C@@H](O)CN2C(=O)c2cc3ccccn3n2)cc1] | | 64% | 0.68 min | 463 |
| (2S,4R)-4-hydroxy-N-(4-(4-methylthiazol-5-yl)benzyl)-1-(2-(4-oxoquinazolin-3(4H)-yl)propanoyl)pyrrolidine-2-carboxamide | 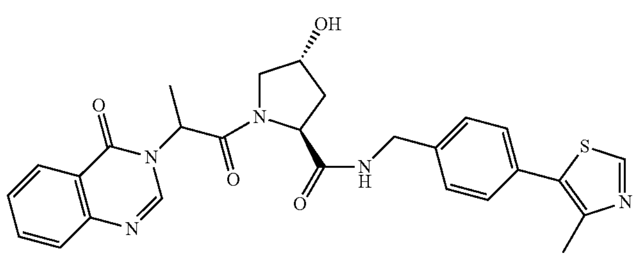 [SMILES: Cc1ncsc1-c1ccc(CNC(=O)[C@@H]2C[C@@H](O)CN2C(=O)C(C)n2cnc3ccccc3c2=O)cc1] | Mixture of diastereoisomers | 49% | 0.71 min | 518 |
| (2S,4R)-1-(2-(2,5-dioxopyrrolidin-1-yl)propanoyl)-4-hydroxy-N-(4-(4-methylthiazol-5-yl)benzyl)pyrrolidine-2-carboxamide | 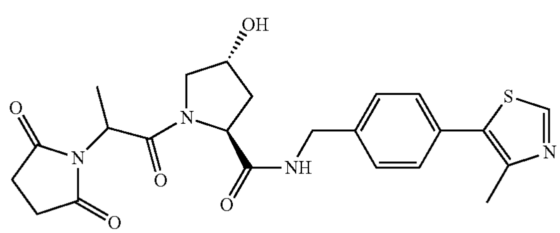 [SMILES: Cc1ncsc1-c1ccc(CNC(=O)[C@@H]2C[C@@H](O)CN2C(=O)C(C)N2C(=O)CCC2=O)cc1] | Single enantiomer, stereochemistry unknown at the unspecified chiral centre, eluted first during HPLC purification (formic acid modifier) | 27% | 0.60 min | 472 |

-continued

| Name | Stereochemistry Comment | Yield | RT | [M + H]+ |
|---|---|---|---|---|
| (2S,4R)-1-(2-(1H-tetrazol-1-yl)acetyl)-4-hydroxy-N-(4-(4-methylthiazol-5-yl)benzyl)pyrrolidine-2-carboxamide | | 73% | 0.58 min | 428 |
| (2S,4R)-1-(2-(1H-1,2,4-triazol-1-yl)propanoyl)-4-hydroxy-N-(4-(4-methylthiazol-5-yl)benzyl)pyrrolidine-2-carboxamide | Single enantiomer, stereochemistry unknown at the unspecified chiral centre, eluted first during HPLC purification (formic acid modifier) | 35% | 0.58 min | 441 |
| (2S,4R)-4-hydroxy-1-(2-methyl-3-(1H-1,2,4-triazol-1-yl)propanoyl)-N-(4-(4-methylthiazol-5-yl)benzyl)pyrrolidine-2-carboxamide | Mixture of diastereoisomers | 53% | 0.60 min | 455 |
| (2S,4R)-4-hydroxy-N-(4-(4-methylthiazol-5-yl)benzyl)-1-((S)-2-(1-oxoisoindolin-2-yl)propanoyl)pyrrolidine-2-carboxamide | Single enantiomer | 65% | 0.74 min | 505 |
| (2S,4R)-4-hydroxy-N-(4-(4-methylthiazol-5-yl)benzyl)-1-((S)-2-(1-oxoisoindolin-2-yl)propanoyl)pyrrolidine-2-carboxamide | Single enantiomer | 80% | 0.76 min | 549 |
| (2S,4R)-4-hydroxy-N-(4-(4-methylthiazol-5-yl)benzyl)-1-((S)-2-(1-oxoisoindolin-2-yl)butanoyl)pyrrolidine-2-carboxamide | Single enantiomer | 57% | 0.67 min | 519 |

| Name | Structure | Stereochemistry Comment | Yield | RT | [M + H]+ |
|---|---|---|---|---|---|
| (2S,4R)-1-((S)-2-cyclopropyl-2-(1-oxoisoindolin-2-yl)acetyl)-4-hydroxy-N-(4-(4-methylthiazol-5-yl)benzyl)pyrrolidine-2-carboxamide | 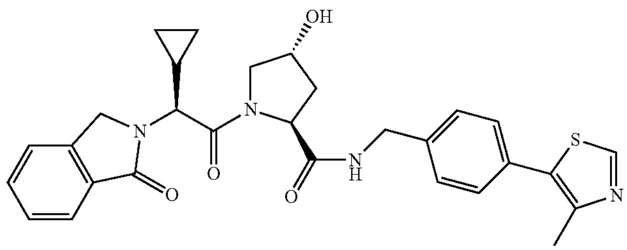 [SMILES: Cc1ncsc1-c1ccc(CNC(=O)[C@@H]2C[C@@H](O)CN2C(=O)[C@H](C2CC2)N2Cc3ccccc3C2=O)cc1] | Single enantiomer | 62% | 0.80 min | 531 |
| (2S,4R)-4-hydroxy-1-((S)-3-methyl-2-(1-oxoisoindolin-2-yl)butanoyl)-N-(4-(4-methylthiazol-5-yl)benzyl)pyrrolidine-2-carboxamide | 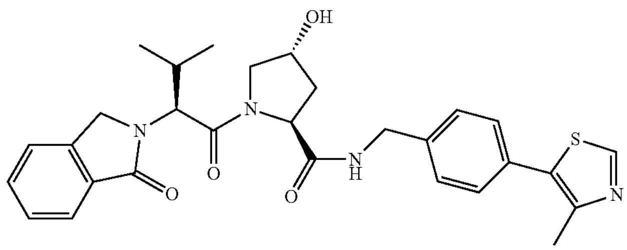 [SMILES: Cc1ncsc1-c1ccc(CNC(=O)[C@@H]2C[C@@H](O)CN2C(=O)[C@H](C(C)C)N2Cc3ccccc3C2=O)cc1] | Single enantiomer | 58% | 0.83 min | 533 |
| (2S,4R)-1-((S)-3,3-dimethyl-2-(1-oxoisoindolin-2-yl)butanoyl)-4-hydroxy-N-(4-(4-methylthiazol-5-yl)benzyl)pyrrolidine-2-carboxamide | | Single enantiomer | 52% | 0.91 min | 547 |

3-(2-(2-(2-(3-((2S,4R)-4-hydroxy-2-((4-(4-methylthiazol-5-yl)benzyl)carbamoyl)pyrrolidine-1-carbonyl)phenoxy)ethoxy)ethoxy)ethoxy)propanoic acid

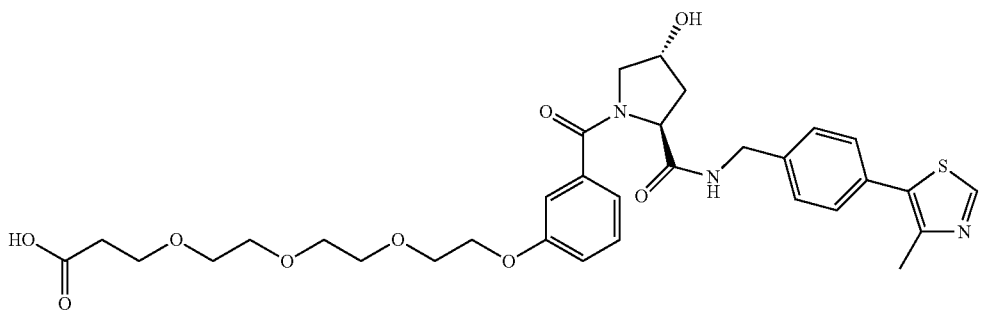 [SMILES: Cc1ncsc1-c1ccc(CNC(=O)[C@@H]2C[C@@H](O)CN2C(=O)c2cccc(OCCOCCOCCOCCC(=O)O)c2)cc1]

An ice-cooled mixture of (2S,4R)-4-hydroxy-N-(4-(4-methylthiazol-5-yl)benzyl)pyrrolidine-2-carboxamide, hydrochloride (682 mg, 2.2 mmol), 3-((14,14-dimethyl-12-oxo-3,6,9,13-tetraoxapentadecyl)oxy)benzoic acid (778 mg, 2.0 mmol), DIPEA (1.36 mL, 7.8 mmol) in DMF (12 mL) was treated with HATU (817 mg, 2.2 mmol). The mixture was allowed to warm to ambient temperature and stirred for 30 minutes then treated with water (70 mL) and extracted with ethyl acetate (3×70 mL). The combined organic phase was washed with saturated aqueous sodium bicarbonate (100 mL), water (100 mL), brine (100 mL), dried over magnesium sulfate, filtered and evaporated to dryness. The crude product was dissolved in dichloromethane (6 mL) and treated with TFA (2.0 mL). After 1 hour, the reaction mixture was evaporated to dryness and the product was purified by flash chromatography (60 g C18 cartridge) using a gradient elution from 10 to 95% acetonitrile (+0.1% formic acid) in water (+0.1% formic acid) to afford the title compound (568 mg, 45% yield). LCMS RT=0.73 min, ES+ve m/z 642 [M+H]+.

315

(2S,4R)-4-hydroxy-1-(3-(2-methoxyethoxy)benzoyl)-N-(4-(4-methylthiazol-5-yl)benzyl)pyrrolidine-2-carboxamide

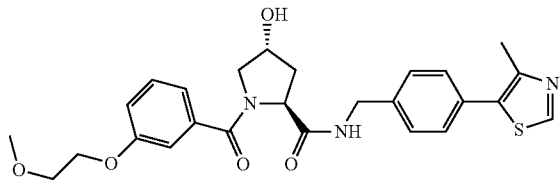 [SMILES: COCCOc1cccc(C(=O)N2C[C@H](O)C[C@H]2C(=O)NCc2ccc(-c3scnc3C)cc2)c1]

A mixture of (2S,4R)-4-hydroxy-1-(3-hydroxybenzoyl)-N-(4-(4-methylthiazol-5-yl)benzyl)pyrrolidine-2-carboxamide (55 mg, 0.13 mmol) and potassium carbonate (55 mg, 0.40 mmol) in DMF (0.8 mL) was treated with 1-bromo-2-methoxyethane (commercially available from for example Aldrich) (0.024 mL, 0.25 mmol) and stirred at 50° C. for 2.5 hours. Additional 1-bromo-2-methoxyethane (0.024 mL, 0.25 mmol) was added and the mixture stirred at 50° C. overnight. The product was subjected to purification by mass-directed automated preparative HPLC (formic acid modifier) to afford the title compound (41 mg, 0.083 mmol, 66% yield) LCMS RT=0.74 min, ES+ve m/z 496 [M+H]+

(2S,4R)-4-hydroxy-1-(3-(2-(2-methoxyethoxy)ethoxy)benzoyl)-N-(4-(4-methylthiazol-5-yl)benzyl)pyrrolidine-2-carboxamide

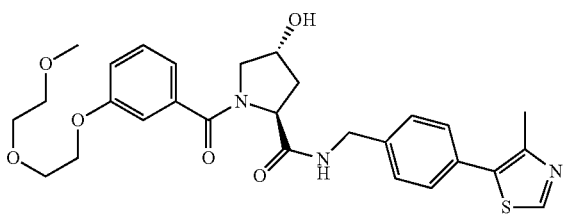 [SMILES: COCCOCCOc1cccc(C(=O)N2C[C@H](O)C[C@H]2C(=O)NCc2ccc(-c3scnc3C)cc2)c1]

A mixture of (2S,4R)-4-hydroxy-1-(3-hydroxybenzoyl)-N-(4-(4-methylthiazol-5-yl)benzyl)pyrrolidine-2-carboxamide (55 mg, 0.13 mmol) and potassium carbonate (55 mg, 0.40 mmol) in DMF (0.8 mL) was treated with 1-bromo-2-(2-methoxyethoxy)ethane (commercially available from for example Aldrich) (0.034 mL, 0.25 mmol) and the reaction stirred at 50° C. for 2.5 hours. Additional 1-bromo-2-(2-methoxyethoxy)ethane (0.034 mL, 0.25 mmol) was added and the mixture stirred at 50° C. overnight. The product was subjected to purification by mass-directed automated preparative HPLC (formic acid modifier) to afford the title compound (40 mg, 0.074 mmol, 59% yield) LCMS RT=0.74 min, ES+ve m/z 540 [M+H]+.

316

(2S,4R)-1-((S)-2-((S)-2-acetamido-4-methylpentanamido)propanoyl)-4-hydroxy-N-(4-(4-methylthiazol-5-yl)benzyl)pyrrolidine-2-carboxamide

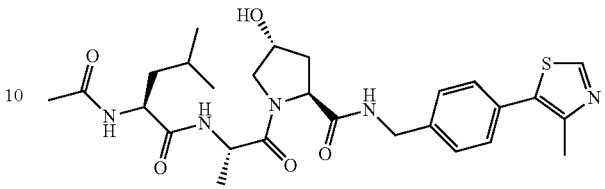

A stirred mixture of (2S,4R)-1-((S)-2-aminopropanoyl)-4-hydroxy-N-(4-(4-methylthiazol-5-yl)benzyl)pyrrolidine-2-carboxamide, hydrochloride (50 mg, 0.12 mmol) and (S)-2-acetamido-4-methylpentanoic acid (commercially available from for example Aldrich) (22 mg, 0.12 mmol) in DMF (0.7 mL) was treated with DIPEA (0.062 mL, 0.35 mmol) and then with HATU (49 mg, 0.13 mmol) and the mixture was stirred at ambient temperature for 10 minutes. The product was subjected to purification by mass-directed automated preparative HPLC (formic acid modifier) to afford the title compound (42 mg, 0.077 mmol, 66% yield). LCMS RT=0.68 min, ES+ve m/z 544 [M+H]+.

(2S,4R)-1-((S)-2-acetamido-3-methylbutanoyl)-4-hydroxy-N-(4-(4-methylthiazol-5-yl)benzyl)pyrrolidine-2-carboxamide

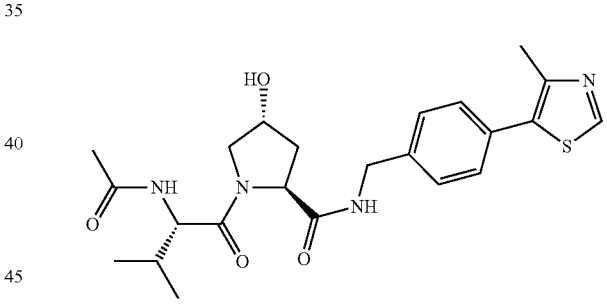

A solution of tert-butyl ((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate (120 mg, 0.23 mmol) in dichloromethane (2 mL) and treated with 4 M hydrochloric acid in 1,4-dioxane (1 mL). The mixture was stirred at ambient temperature for 30 minutes and was then evaporated to dryness. The residue was dissolved in DMF (1 mL) and treated with triethylamine (0.08 mL, 0.58 mmol), followed by acetic anhydride (0.02 mL, 0.21 mmol) and the mixture was stirred at ambient temperature for 1 hour. The product was subjected to purification by mass-directed automated preparative HPLC (formic acid modifier) to afford the title compound (53 mg, 49% yield). LCMS RT=0.65 min, ES+ve m/z 460 [M+H]+.

Using a method analogous to that for (2S,4R)-1-((S)-2-acetamido-3-methylbutanoyl)-4-hydroxy-N-(4-(4-methylthiazol-5-yl)benzyl)pyrrolidine-2-carboxamide, the following compounds were prepared:

| Name | Structure | Yield | RT | [M + H]+ |
|---|---|---|---|---|
| (2S,4R)-1-((S)-1-acetylpiperidine-2-carbonyl)-4-hydroxy-N-(4-(4-methylthiazol-5-yl)benzyl)pyrrolidine-2-carboxamide | 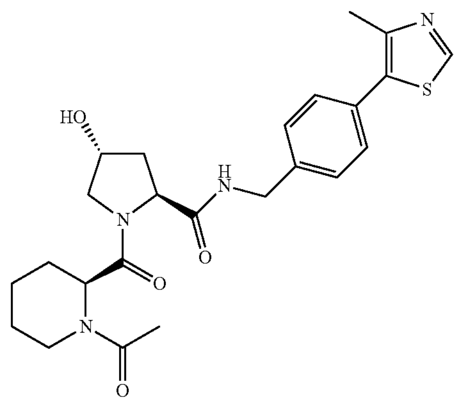 [SMILES: CC(=O)N1CCCC[C@H]1C(=O)N1C[C@H](O)C[C@H]1C(=O)NCc1ccc(-c2scnc2C)cc1] | 49% | 0.67 min | 471 |
| (2S,4R)-1-((S)-4-acetylmorpholine-3-carbonyl)-4-hydroxy-N-(4-(4-methylthiazol-5-yl)benzyl)pyrrolidine-2-carboxamide | 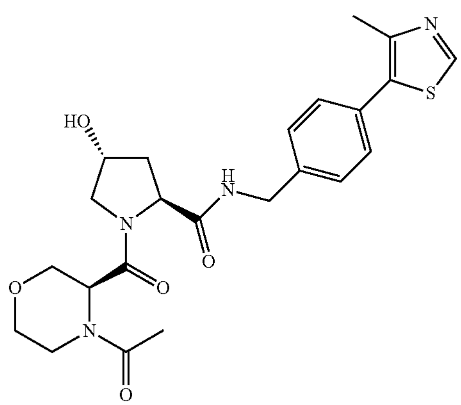 [SMILES: CC(=O)N1CCOC[C@H]1C(=O)N1C[C@H](O)C[C@H]1C(=O)NCc1ccc(-c2scnc2C)cc1] | 57% | 0.59 min | 473 |
| (2S,4R)-1-((S)-2-acetamidobutanoyl)-4-hydroxy-N-(4-(4-methylthiazol-5-yl)benzyl)pyrrolidine-2-carboxamide | 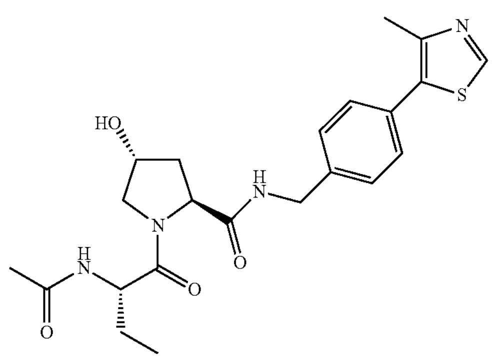 [SMILES: CC[C@H](NC(C)=O)C(=O)N1C[C@H](O)C[C@H]1C(=O)NCc1ccc(-c2scnc2C)cc1] | 82% | 0.61 min | 445 |
| (2S,4R)-1-((S)-2-acetamido-3,3-dimethylbutanoyl)-4-hydroxy-N-(4-(4-methylthiazol-5-yl)benzyl)pyrrolidine-2-carboxamide | 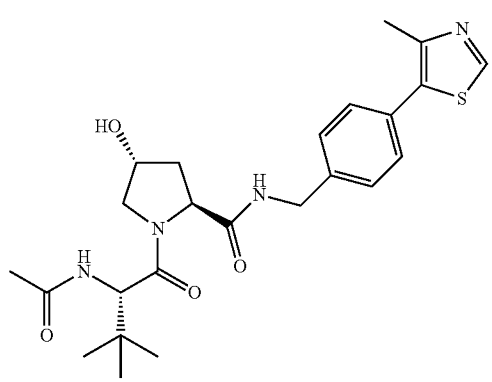 [SMILES: CC(=O)N[C@H](C(=O)N1C[C@H](O)C[C@H]1C(=O)NCc1ccc(-c2scnc2C)cc1)C(C)(C)C] | 68% | 0.71 min | 473 |

| Name | Structure | Yield | RT | [M + H]+ |
|---|---|---|---|---|
| (2S,4R)-1-((S)-2-acetamido-2-cyclopropylacetyl)-4-hydroxy-N-(4-(4-methylthiazol-5-yl)benzyl)pyrrolidine-2-carboxamide | 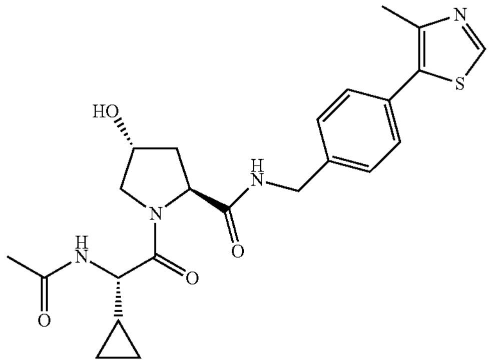 [SMILES: CC(=O)N[C@H](C(=O)N1C[C@H](O)C[C@H]1C(=O)NCc1ccc(-c2scnc2C)cc1)C1CC1] | 67% | 0.62 min | 457 |

(2S,4R)-1-((S)-2-(3-ethoxy-N-methylbenzamido)propanoyl)-4-hydroxy-N-(4-(4-methylthiazol-5-yl)benzyl)pyrrolidine-2-carboxamide

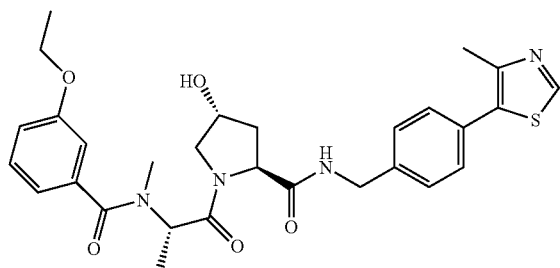 [SMILES: CCOc1cccc(C(=O)N(C)[C@@H](C)C(=O)N2C[C@H](O)C[C@H]2C(=O)NCc2ccc(-c3scnc3C)cc2)c1]

A mixture of (2S,4R)-4-hydroxy-1-((S)-2-(methylamino)propanoyl)-N-(4-(4-methylthiazol-5-yl)benzyl)pyrrolidine-2-carboxamide (20 mg, 0.05 mmol), DIPEA (0.043 mL, 0.25 mmol) and 3-ethoxybenzoic acid (commercially available from for example Aldrich) (8 mg, 0.05 mmol) in DMF (1 mL) was treated with HATU (19 mg, 0.05 mmol) and the mixture was stirred for 20 minutes. The product was purified by mass-directed automated preparative HPLC (formic acid modifier) to afford the title compound (14 mg, 0.025 mmol, 50% yield). LCMS RT=0.82 min, ES+ve m/z 551 [M+H]+.

(2S,4R)-4-hydroxy-1-((S)-2-(3-methoxypropanamido)propanoyl)-N-(4-(4-methylthiazol-5-yl)benzyl)pyrrolidine-2-carboxamide

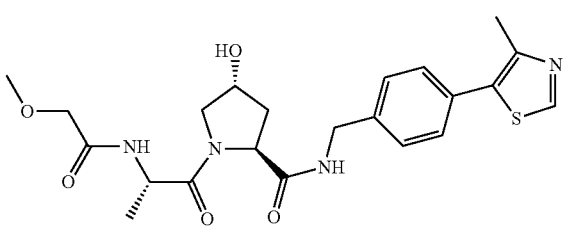 [SMILES: COCC(=O)N[C@@H](C)C(=O)N1C[C@H](O)C[C@H]1C(=O)NCc1ccc(-c2scnc2C)cc1]

A solution of a mixture of (2S,4R)-1-((S)-2-aminopropanoyl)-4-hydroxy-N-(4-(4-methylthiazol-5-yl)benzyl)pyrrolidine-2-carboxamide, hydrochloride (107 mg, 0.25 mmol), 3-methoxypropionic acid (commercially available from for example Aldrich) (0.028 mL, 0.30 mmol) and DIPEA (0.2 mL, 1.15 mmol) in dry DMF (3 mL) was treated with HATU (115 mg, 0.30 mmol). The mixture was stirred at ambient temperature for 30 minutes. The mixture was loaded onto a methanol-preconditioned aminopropyl solid-phase extraction cartridge (2 g), which was eluted with methanol (3 column volumes). The resulting eluant was evaporated to dryness and the product was subjected to purification by mass-directed automated preparative HPLC (formic acid modifier) to afford the title compound (57 mg, 0.12 mmol, 48% yield). LCMS RT=0.62 min, ES+ve m/z 475 [M+H]+.

(2S,4R)-4-hydroxy-1-(2-(3-methoxypropanamido)-2-methylpropanoyl)-N-(4-(4-methylthiazol-5-yl)benzyl)pyrrolidine-2-carboxamide

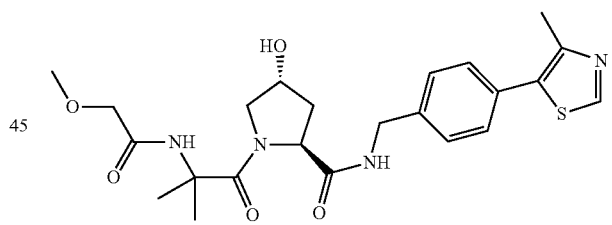

A solution of a mixture of (2S,4R)-1-(2-amino-2-methylpropanoyl)-4-hydroxy-N-(4-(4-methylthiazol-5-yl)benzyl)pyrrolidine-2-carboxamide (95 mg, 0.24 mmol), 3-methoxypropionic acid (0.028 mL, 0.30 mmol) and DIPEA (0.2 mL, 1.15 mmol) in dry DMF (3 mL) was treated with HATU (115 mg, 0.30 mmol) and the mixture was stirred at ambient temperature for 30 minutes The mixture was loaded onto a methanol-preconditioned aminopropyl solid-phase extraction cartridge (NH2) which was eluted with methanol (3 column volumes). The resulting eluant was evaporated to dryness and the product was subjected to purification by mass-directed automated preparative HPLC (formic acid modifier) to afford the title compound (45 mg, 0.09 mmol, 37% yield). LCMS RT=0.68 min, ES+ve m/z 489 [M+H]+.

321

(2S,4R)-4-hydroxy-1-((S)-2-(2-methoxyacetamido)-3-methylbutanoyl)-N-(4-(4-methylthiazol-5-yl)benzyl)pyrrolidine-2-carboxamide

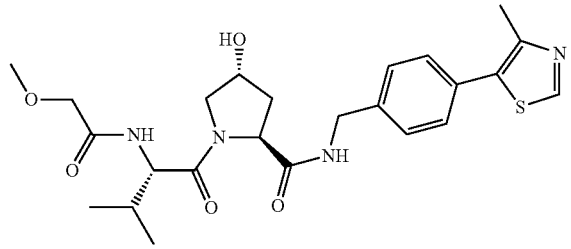 [SMILES: COCC(=O)N[C@H](C(=O)N1C[C@H](O)C[C@H]1C(=O)NCc1ccc(-c2scnc2C)cc1)C(C)C]

A mixture of (2S,4R)-1-((S)-2-amino-3-methylbutanoyl)-4-hydroxy-N-(4-(4-methylthiazol-5-yl)benzyl)pyrrolidine-2-carboxamide, hydrochloride (20 mg, 0.044 mmol), 2-methoxyacetic acid (3 µL, 0.039 mmol) and DIPEA (0.035 mL, 0.20 mmol) in DMF (1 mL) was treated with HATU (18 mg, 0.047 mmol) and stirred at ambient temperature for 30 minutes. The product was subjected to purification by mass-directed automated preparative HPLC (formic acid modifier) to afford the title compound (14 mg, 0.029 mmol, 73% yield). LCMS RT=0.70 min, ES+ve m/z 489 [M+H]+.

(2S,4R)-4-hydroxy-1-((S)-2-(2-methoxy-N-methylacetamido)-3-methylbutanoyl)-N-(4-(4-methylthiazol-5-yl)benzyl)pyrrolidine-2-carboxamide

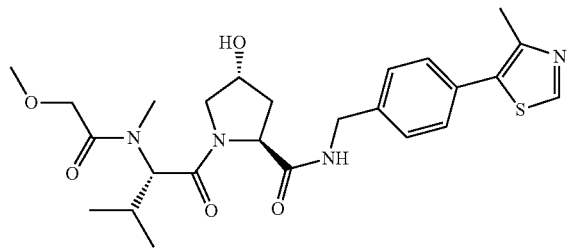 [SMILES: COCC(=O)N(C)[C@H](C(=O)N1C[C@H](O)C[C@H]1C(=O)NCc1ccc(-c2scnc2C)cc1)C(C)C]

A mixture of (2S,4R)-4-hydroxy-1-((S)-3-methyl-2-(methylamino)butanoyl)-N-(4-(4-methylthiazol-5-yl)benzyl)pyrrolidine-2-carboxamide, hydrochloride (19 mg, 0.041 mmol), 2-methoxyacetic acid (3 µL, 0.039 mmol) and DIPEA (0.035 mL, 0.20 mmol) in DMF (1 mL) was treated with HATU (18 mg, 0.047 mmol) and stirred at ambient temperature for 30 minutes. The product was subjected to purification by mass-directed automated preparative HPLC (formic acid modifier) to afford the title compound (16 mg, 0.032 mmol, 81% yield). LCMS RT=0.70 min, ES+ve m/z 503 [M+H]+.

322

(2S,4R)-1-((S)-2-(N,3-dimethyloxetane-3-carboxamido)propanoyl)-4-hydroxy-N-(4-(4-methylthiazol-5-yl)benzyl)pyrrolidine-2-carboxamide

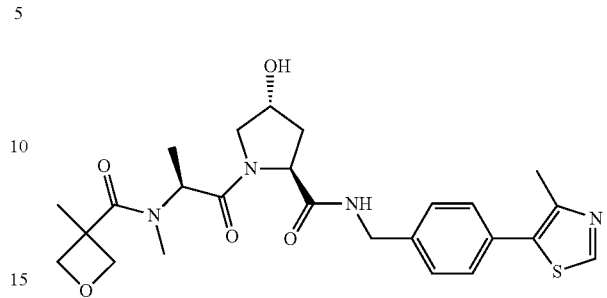

A mixture of (2S,4R)-4-hydroxy-1-((S)-2-(methylamino)propanoyl)-N-(4-(4-methylthiazol-5-yl)benzyl)pyrrolidine-2-carboxamide (15 mg, 0.037 mmol), DIPEA (0.032 mL, 0.18 mmol) and 3-methyloxetane-3-carboxylic acid (commercially available from for example Fluorochem) (3 µL, 0.037 mmol) in DMF (1 mL) was treated with HATU (14 mg, 0.037 mmol) and the mixture was stirred for 1 hour. The product was purified by mass-directed automated preparative HPLC (formic acid modifier) to afford the title compound (9 mg, 0.019 mmol, 51% yield). LCMS RT=0.62 min, ES+ve m/z 501 [M+H]+.

(2S,4R)-4-hydroxy-1-((S)-2-(3-methyloxetane-3-carboxamido)propanoyl)-N-(4-(4-methylthiazol-5-yl)benzyl)pyrrolidine-2-carboxamide

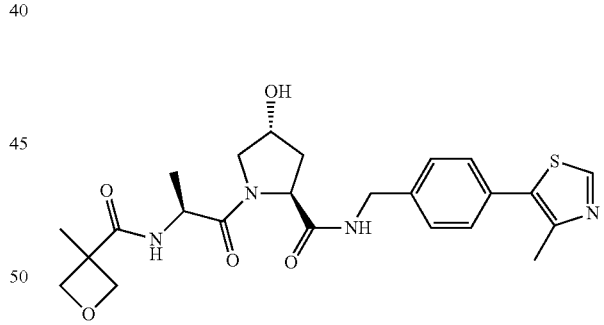

A stirred mixture of (2S,4R)-1-((S)-2-aminopropanoyl)-4-hydroxy-N-(4-(4-methylthiazol-5-yl)benzyl)pyrrolidine-2-carboxamide (21 mg, 0.043 mmol), DIPEA (0.043 mL, 0.25 mmol) and 3-methyloxetane-3-carboxylic acid (commercially available from for example Fluorochem) (6 mg, 0.05 mmol) in DMF (2 mL) was treated with HATU (19 mg, 0.05 mmol) and stirred for 30 minutes. The product was purified by mass-directed automated preparative HPLC (formic acid modifier) to afford the title compound (14 mg, 0.029 mmol, 60% yield). LCMS RT=0.59 min, ES+ve m/z 487 [M+H]+.

(2S,4R)-1-((S)-2-(3-ethoxybenzamido)propanoyl)-4-hydroxy-N-(4-(4-methylthiazol-5-yl)benzyl)pyrrolidine-2-carboxamide

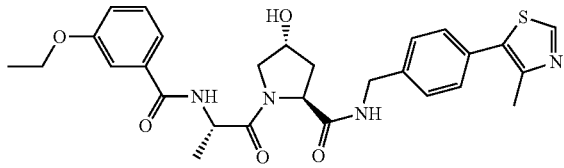 [SMILES: CCOc1cccc(C(=O)N[C@@H](C)C(=O)N2C[C@H](O)C[C@H]2C(=O)NCc2ccc(-c3scnc3C)cc2)c1]

A stirred mixture of 3-ethoxybenzoic acid (commercially available from for example Aldrich) (20 mg, 0.12 mmol) and (2S,4R)-1-((S)-2-aminopropanoyl)-4-hydroxy-N-(4-(4-methylthiazol-5-yl)benzyl)pyrrolidine-2-carboxamide, hydrochloride (56 mg, 0.13 mmol) in DMF (3.2 mL) was treated with DIPEA (0.063 mL, 0.36 mmol) and then with HATU (50 mg, 0.13 mmol) and the mixture was stirred at ambient temperature for 30 minutes. The product was then subjected to purification by mass-directed automated preparative HPLC (formic acid modifier) to afford the title compound (36 mg, 0.067 mmol, 56% yield). LCMS RT=0.80 min, ES+ve m/z 537 [M+H]+.

(2S,4R)-N-((1H-indol-3-yl)methyl)-4-hydroxy-1-((S)-2-(1-oxoisoindolin-2-yl)propanoyl)pyrrolidine-2-carboxamide

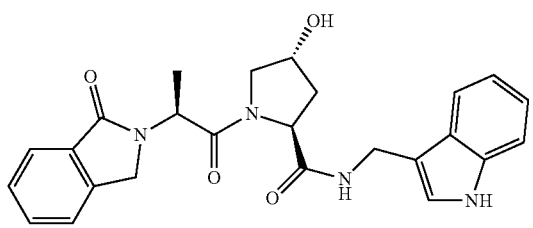 [SMILES: C[C@@H](C(=O)N1C[C@H](O)C[C@H]1C(=O)NCc1c[nH]c2ccccc12)N1Cc2ccccc2C1=O]

A solution of (2S,4R)-4-hydroxy-1-((S)-2-(1-oxoisoindolin-2-yl)propanoyl)pyrrolidine-2-carboxylic acid (10 mg, 0.031 mmol), DIPEA (0.038 mL, 0.22 mmol) and (1H-indol-3-yl)methanamine (commercially available from for example Fluorochem) (6 mg, 0.041 mmol) in DMF (0.8 mL) was treated with HATU (15 mg, 0.039 mmol) and stirred for 1 hour. The product was purified by mass-directed automated preparative HPLC (formic acid modifier) to afford the title compound (3.1 mg, 6.9 μmol, 22% yield). LCMS RT=0.75 min, ES+ve m/z 447 [M+H]+.

(2S,4R)—N—((R)-2,3-dihydrobenzofuran-3-yl)-4-hydroxy-1-((S)-2-(1-oxoisoindolin-2-yl)propanoyl)pyrrolidine-2-carboxamide & (2S,4R)—N—((S)-2,3-dihydrobenzofuran-3-yl)-4-hydroxy-1-((S)-2-(1-oxoisoindolin-2-yl)propanoyl)pyrrolidine-2-carboxamide

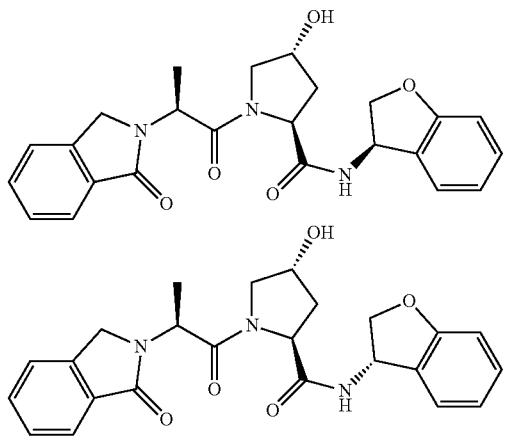

A mixture of 2,3-dihydrobenzofuran-3-amine (commercially available from for example Chem-Impex International, Inc.) (13 mg, 0.094 mmol) and (2S,4R)-4-hydroxy-1-((S)-2-(1-oxoisoindolin-2-yl)propanoyl)pyrrolidine-2-carboxylic acid (25 mg, 0.079 mmol) in DMF (0.8 mL) was treated with DIPEA (0.055 mL, 0.31 mmol) and then HATU (33 mg, 0.086 mmol) and the mixture was stirred at ambient temperature for 30 minutes. The product mixture was subjected to purification by mass-directed automated preparative HPLC (formic acid modifier) to afford the title compounds: Isomer 1 (first-eluting) (12 mg, 0.027 mmol, 35% yield). LCMS RT=0.73 min, ES+ve m/z 436 [M+H]+. Isomer 2 (second-eluting) (13 mg, 0.030 mmol, 38% yield). LCMS RT=0.74 min, ES+ve m/z 436 [M+H]+.

Using a method analogous to that for the two diastereoisomers of (2S,4R)—N-(2,3-dihydrobenzofuran-3-yl)-4-hydroxy-1-((S)-2-(1-oxoisoindolin-2-yl)propanoyl)pyrrolidine-2-carboxamide, the following compounds were prepared:

| Name | Structure | Yield | RT | [M + H]+ |
|---|---|---|---|---|
| (2S,4R)-N-((S)-1-(4-chlorophenyl)ethyl)-1-(3-ethoxybenzoyl)-4-hydroxypyrrolidine-2-carboxamide | 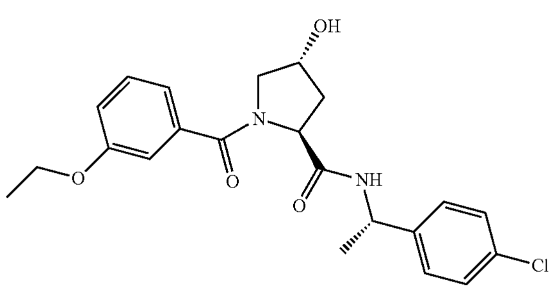 [SMILES: CCOc1cccc(C(=O)N2C[C@H](O)C[C@H]2C(=O)N[C@@H](C)c2ccc(Cl)cc2)c1] | 56% | 0.92 min | 417 |

| Name | Structure | Yield | RT | [M + H]+ |
|---|---|---|---|---|
| (2S,4R)-N-benzyl-1-(3-ethoxybenzoyl)-4-hydroxypyrrolidine-2-carboxamide | 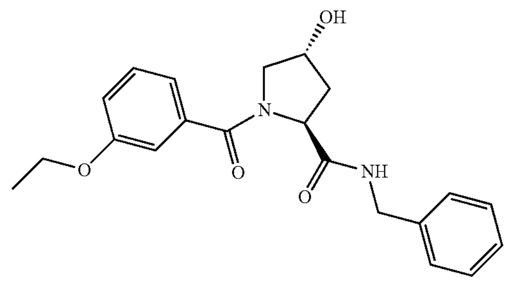 [SMILES: CCOc1cccc(C(=O)N2C[C@H](O)C[C@H]2C(=O)NCc2ccccc2)c1] | 64% | 0.76 min | 369 |
| (2S,4R)-1-(3-ethoxybenzoyl)-4-hydroxy-N-((S)-2-oxopyrrolidin-3-yl)pyrrolidine-2-carboxamide | 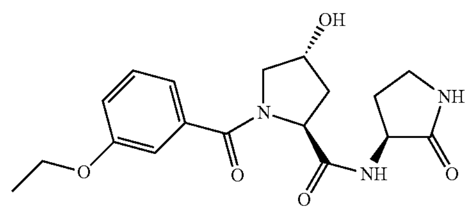 [SMILES: CCOc1cccc(C(=O)N2C[C@H](O)C[C@H]2C(=O)N[C@H]2CCNC2=O)c1] | 77% | 0.50 min | 362 |
| (2S,4R)-1-(3-ethoxybenzoyl)-4-hydroxy-N-((2-methylthiazol-5-yl)methyl)pyrrolidine-2-carboxamide | 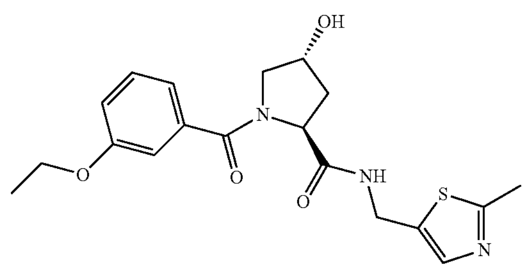 [SMILES: CCOc1cccc(C(=O)N2C[C@H](O)C[C@H]2C(=O)NCc2cnc(C)s2)c1] | 69% | 0.57 min | 390 |
| (2S,4R)-1-(3-ethoxybenzoyl)-4-hydroxy-N-((1-methyl-1H-pyrazol-4-yl)methyl)pyrrolidine-2-carboxamide | 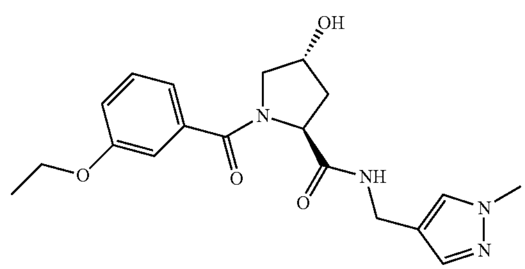 [SMILES: CCOc1cccc(C(=O)N2C[C@H](O)C[C@H]2C(=O)NCc2cnn(C)c2)c1] | 70% | 0.55 min | 375 |
| (2S,4R)-N-([1,1'-biphenyl]-4-ylmethyl)-1-(3-ethoxybenzoyl)-4-hydroxypyrrolidine-2-carboxamide | 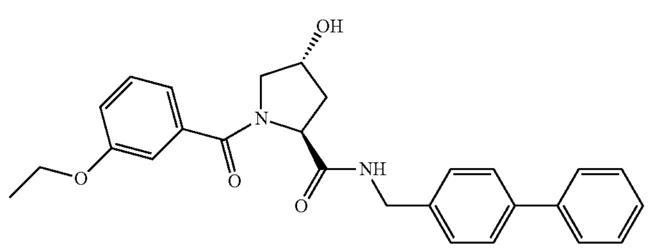 [SMILES: CCOc1cccc(C(=O)N2C[C@H](O)C[C@H]2C(=O)NCc2ccc(-c3ccccc3)cc2)c1] | 55% | 0.98 min | 445 |
| (2S,4R)-1-(3-ethoxybenzoyl)-4-hydroxy-N-((5-phenyl-1,2,4-oxadiazol-3-yl)methyl)pyrrolidine-2-carboxamide | 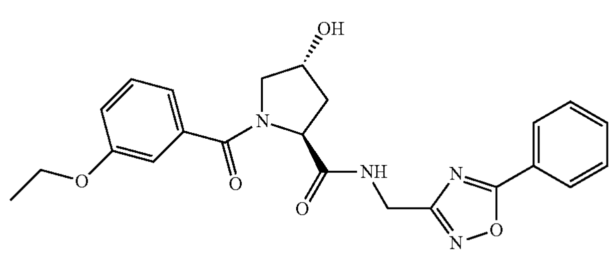 [SMILES: CCOc1cccc(C(=O)N2C[C@H](O)C[C@H]2C(=O)NCc2noc(-c3ccccc3)n2)c1] | 60% | 0.82 min | 437 |

-continued

| Name | Structure | Yield | RT | [M + H]+ |
|---|---|---|---|---|
| (2S,4R)-N-((3-(4-chlorophenyl)-1,2,4-oxadiazol-5-yl)methyl)-1-(3-ethoxybenzoyl)-4-hydroxypyrrolidine-2-carboxamide | 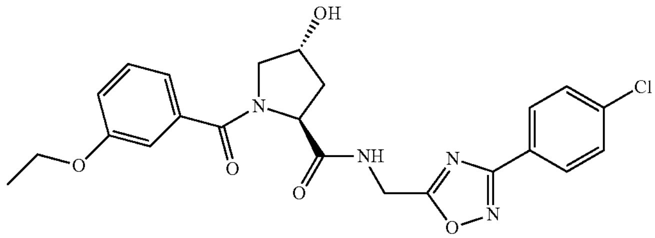 [SMILES: CCOc1cccc(C(=O)N2C[C@H](O)C[C@H]2C(=O)NCc2nc(-c3ccc(Cl)cc3)no2)c1] | 47% | 0.95 min | 471 |
| (2S,4R)-1-(3-ethoxybenzoyl)-4-hydroxy-N-((5-phenylisoxazol-3-yl)methyl)pyrrolidine-2-carboxamide | 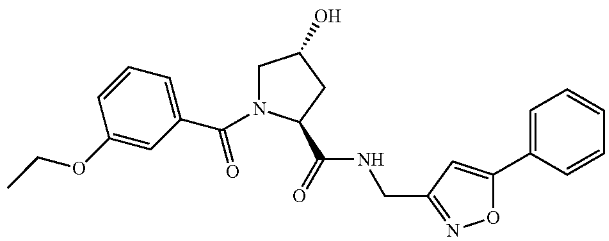 [SMILES: CCOc1cccc(C(=O)N2C[C@H](O)C[C@H]2C(=O)NCc2cc(-c3ccccc3)on2)c1] | 60% | 0.86 min | 436 |
| (2S,4R)-1-(3-ethoxybenzoyl)-4-hydroxy-N-((1-methyl-1,2,3,4-tetrahydroquinolin-6-yl)methyl)pyrrolidine-2-carboxamide | 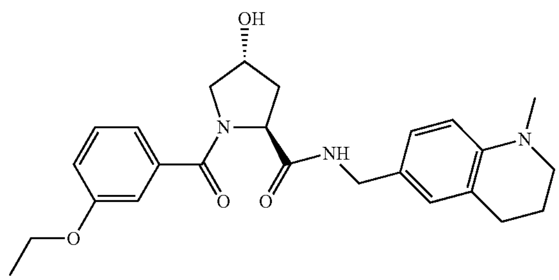 [SMILES: CCOc1cccc(C(=O)N2C[C@H](O)C[C@H]2C(=O)NCc2ccc3c(c2)CCCN3C)c1] | 30% | 0.67 min | 438 |

(2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (2S,4R)-4-hydroxy-N-(2-hydroxy-4-(4-methylthiazol-5-yl)benzyl)-1-((R)-3-methyl-2-(1-oxoisoindolin-2-yl)butanoyl)pyrrolidine-2-carboxamide

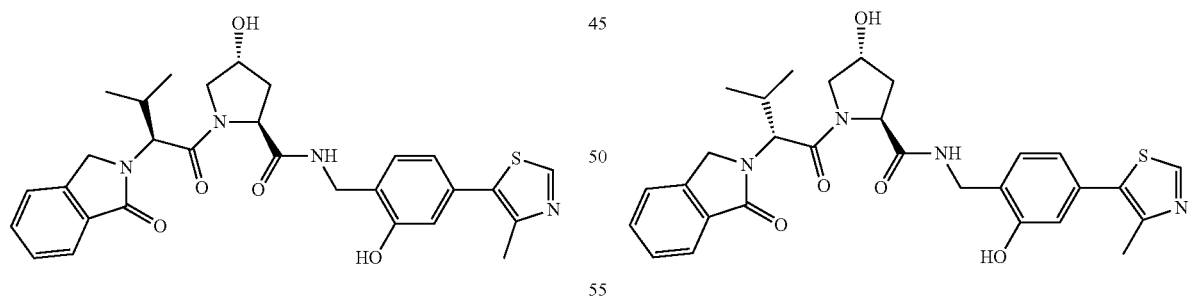

A mixture of (2S,4R)-4-hydroxy-N-(2-hydroxy-4-(4-methylthiazol-5-yl)benzyl)pyrrolidine-2-carboxamide, hydrochloride (125 mg, 0.34 mmol) and (S)-3-methyl-2-(1-oxoisoindolin-2-yl)butanoic acid (83 mg, 0.36 mmol) in DMF (1.6 mL) was treated with DIPEA (0.24 mL, 1.4 mmol) and HATU (140 mg, 0.37 mmol) and the mixture was stirred at ambient temperature for 30 minutes. The product was subjected to purification by mass-directed automated preparative HPLC (formic acid modifier) to afford the title compound (120 mg, 0.22 mmol, 65% yield). LCMS RT=0.81 min, ES+ve m/z 549 [M±H]+.

A mixture of (2S,4R)-4-hydroxy-N-(2-hydroxy-4-(4-methylthiazol-5-yl)benzyl)pyrrolidine-2-carboxamide, hydrochloride (65 mg, 0.18 mmol) and (R)-3-methyl-2-(1-oxoisoindolin-2-yl)butanoic acid (43 mg, 0.19 mmol) in DMF (1.6 mL) was treated with DIPEA (0.123 mL, 0.70 mmol) and HATU (74 mg, 0.19 mmol) and the mixture was stirred at ambient temperature for 30 minutes. The product was subjected to purification by mass-directed automated preparative HPLC (formic acid modifier) to afford the title compound (64 mg, 0.12 mmol, 66% yield). LCMS RT=0.80 min, ES+ve m/z 549 [M+H]+.

329 tert-butyl ((S)-1-(2R,4S)-4-hydroxy-2-((4-(4-methylthiazol-5-yl)benzyl)carbamoyl)pyrrolidin-1-yl)-1-oxopropan-2-yl)(methyl)carbamate

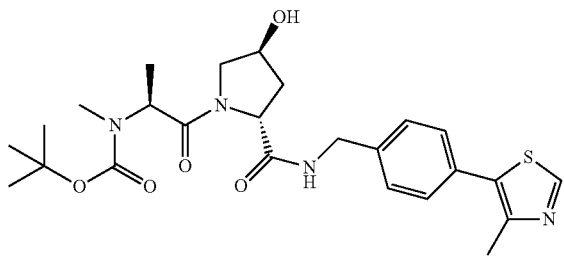 [SMILES: Cc1ncsc1-c1ccc(CNC(=O)[C@H]2C[C@H](O)CN2C(=O)[C@H](C)N(C)C(=O)OC(C)(C)C)cc1]

A stirred mixture of (S)-2-((tert-butoxycarbonyl)(methyl) amino)propanoic acid (115 mg, 0.57 mmol) and (2R,4S)-4-hydroxy-N-(4-(4-methylthiazol-5-yl)benzyl)pyrrolidine-2-carboxamide, hydrochloride (200 mg, 0.57 mmol) in DMF (0.7 mL) was treated with DIPEA (0.4 mL, 2.3 mmol) and then with HATU (215 mg, 0.57 mmol) and the mixture was stirred at ambient temperature for 30 minutes. The product was subjected to purification by mass-directed automated preparative HPLC (formic acid modifier) to afford the title compound (146 mg, 0.29 mmol, 51% yield). LCMS RT=0.84 min, ES+ve m/z 503 [M+H]+.

(2S,4R)-4-hydroxy-1-((S)-2-(3-methoxy-N-methylpropanamido)propanoyl)-N-(4-(4-methylthiazol-5-yl)benzyl)pyrrolidine-2-carboxamide

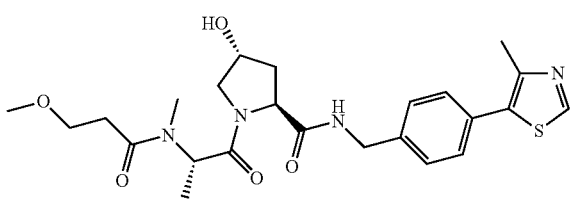 [SMILES: COCCC(=O)N(C)[C@@H](C)C(=O)N1C[C@H](O)C[C@H]1C(=O)NCc1ccc(-c2scnc2C)cc1]

A stirred mixture of (2S,4R)-4-hydroxy-1-((S)-2-(methylamino)propanoyl)-N-(4-(4-methylthiazol-5-yl)benzyl)pyrrolidine-2-carboxamide (50 mg, 0.12 mmol) and 3-methoxypropanoic acid (commercially available from for example Aldrich) (0.013 mL, 0.14 mmol) in DMF (0.8 mL) was treated with DIPEA (0.087 mL, 0.50 mmol) and then with HATU (52 mg, 0.14 mmol). The mixture was stirred at ambient temperature for 30 minutes. The product was subjected to purification by mass-directed automated preparative HPLC (formic acid modifier) to afford the title compound (43 mg, 71% yield). LCMS RT=0.61 min, ES+ve m/z 489 [M+H]+.

330

(2S,4R)-4-hydroxy-1-((S)-2-(2-methoxyethyl)(methyl)amino)propanoyl)-N-(4-(4-methylthiazol-5-yl)benzyl)pyrrolidine-2-carboxamide

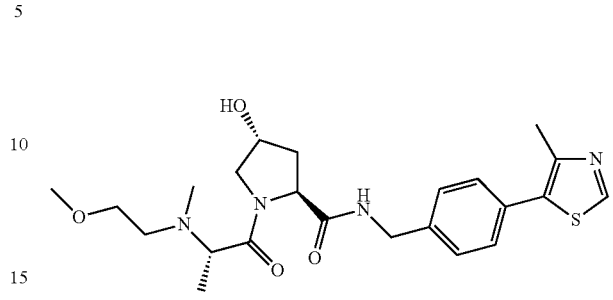

A stirred mixture of 1-bromo-2-methoxyethane (commercially available from for example Aldrich) (0.013 mL, 0.14 mmol) and (2S,4R)-4-hydroxy-1-((S)-2-(methylamino)propanoyl)-N-(4-(4-methylthiazol-5-yl)benzyl)pyrrolidine-2-carboxamide (50 mg, 0.12 mmol) in DMF (0.8 mL) was treated with DIPEA (0.054 mL, 0.31 mmol) and the mixture was stirred at 85° C. for 18 hours. The reaction mixture was cooled and the product was subjected to purification by mass-directed automated preparative HPLC (ammonium bicarbonate modifier) to afford the title compound (44 mg, 77% yield). LCMS RT=0.51 min, ES+ve m/z 461 [M+H]+.

(2S,4R)-4-hydroxy-1-((S)-4-(2-methoxyacetyl)morpholine-3-carbonyl)-N-(4-(4-methylthiazol-5-yl)benzyl)pyrrolidine-2-carboxamide

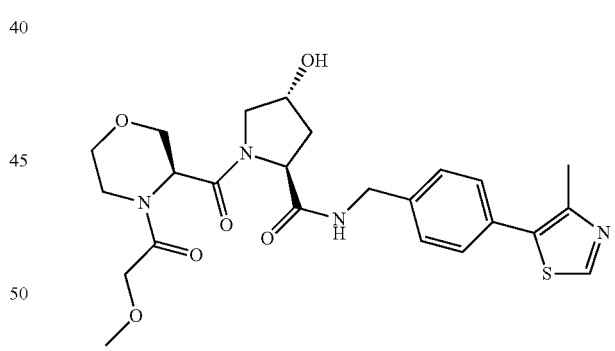

A mixture of (2S,4R)-4-hydroxy-N-(4-(4-methylthiazol-5-yl)benzyl)-1-((S)-morpholine-3-carbonyl)pyrrolidine-2-carboxamide, hydrochloride (19 mg, 0.041 mmol), 2-methoxyacetic acid (3 μL, 0.039 mmol) and DIPEA (0.035 mL, 0.20 mmol) in DMF (1 mL) was treated with HATU (18 mg, 0.047 mmol) and stirred at ambient temperature for 30 minutes. The product was subjected to purification by mass-directed automated preparative HPLC (formic acid modifier) to afford the title compound (13 mg, 0.026 mmol, 66% yield). LCMS RT=0.60 min, ES+ve m/z 503 [M+H]+.

331

(2S,4R)—N-(4-(2,4-dimethylthiazol-5-yl)benzyl)-4-hydroxy-1-(2-(3-methylisoxazol-5-yl)acetyl)pyrrolidine-2-carboxamide

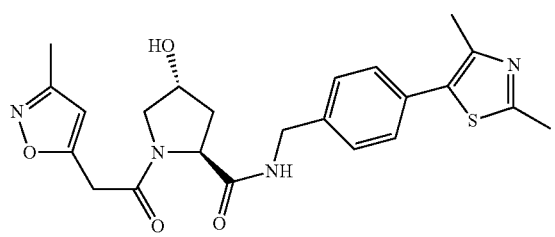 [SMILES: Cc1cc(CC(=O)N2C[C@H](O)C[C@H]2C(=O)NCc2ccc(-c3sc(C)nc3C)cc2)on1]

A stirred mixture of (2S,4R)—N-(4-(2,4-dimethylthiazol-5-yl)benzyl)-4-hydroxypyrrolidine-2-carboxamide (30 mg, 0.09 mmol) and 2-(3-methylisoxazol-5-yl)acetic acid (commercially available from for example Aldrich) (13 mg, 0.09 mmol) in DMF (0.8 mL) was treated with DIPEA (0.063 mL, 0.36 mmol) and then with HATU (41 mg, 0.11 mmol) and stirred at ambient temperature for 30 minutes. The product was subjected to purification by mass-directed automated preparative HPLC (formic acid modifier) to afford the title compound (26 mg, 63% yield). LCMS RT=0.66 min, ES+ve m/z 455 [M+H]$^+$.

(2S,4R)-1-((S)-2-acetamidopropanoyl)-N-(4-(2,4-dimethylthiazol-5-yl)benzyl)-4-hydroxypyrrolidine-2-carboxamide

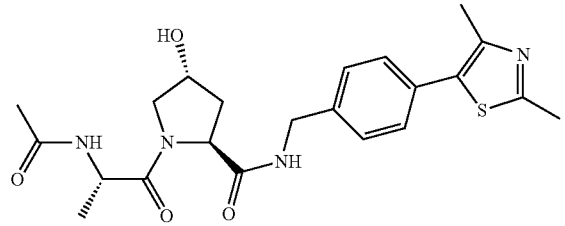 [SMILES: CC(=O)N[C@@H](C)C(=O)N1C[C@H](O)C[C@H]1C(=O)NCc1ccc(-c2sc(C)nc2C)cc1]

A stirred mixture of (2S,4R)—N-(4-(2,4-dimethylthiazol-5-yl)benzyl)-4-hydroxypyrrolidine-2-carboxamide (30 mg, 0.09 mmol) and (S)-2-acetamidopropanoic acid (commercially available from for example Aldrich) (12 mg, 0.09 mmol) in DMF (0.8 mL) was treated with DIPEA (0.063 mL, 0.36 mmol) and then with HATU (41 mg, 0.11 mmol), and the mixture was stirred at ambient temperature for 30 minutes. The product was subjected to purification by mass-directed automated preparative HPLC (formic acid modifier) to afford the title compound (30 mg, 75% yield). LCMS RT=0.58 min, ES+ve m/z 445 [M+H]$^+$.

332

(2S,4R)—N-(4-bromobenzyl)-1-(3-ethoxybenzoyl)-4-hydroxypyrrolidine-2-carboxamide

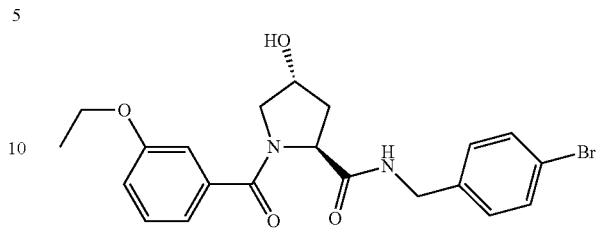

An ice-cooled mixture of (2S,4R)-1-(3-ethoxybenzoyl)-4-hydroxypyrrolidine-2-carboxylic acid (73 mg, 0.26 mmol) and (4-bromophenyl)methanamine, hydrochloride (commercially available from for example Aldrich) (58 mg, 0.26 mmol) in DMF (0.5 mL) was treated with a solution of DIPEA (0.145 mL, 0.83 mmol) in DMF (1 mL) and then with HATU (105 mg, 0.28 mmol) and stirred overnight at ambient temperature. The product was then subjected to purification by mass-directed automated preparative HPLC (formic acid modifier) to afford the title compound (62 mg, 53% yield). LCMS RT=0.90 min, ES+ve m/z 447,449 [M+H]$^+$.

(2S,4R)—N-([1,1'-biphenyl]-4-ylmethyl)-1-(3-ethoxybenzoyl)-4-hydroxypyrrolidine-2-carboxamide

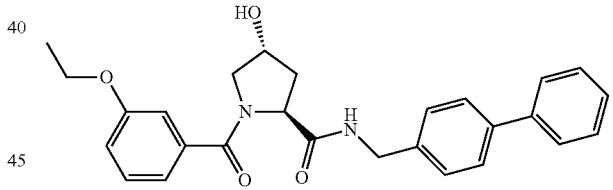

A mixture of (2S,4R)-1-(3-ethoxybenzoyl)-4-hydroxypyrrolidine-2-carboxylic acid (30 mg, 0.11 mmol) and [1,1'-biphenyl]-4-ylmethanamine (commercially available from for example Aldrich) (20 mg, 0.11 mmol) in DMF (0.8 mL) was treated with DIPEA (0.075 mL, 0.43 mmol) and then with HATU (45 mg, 0.12 mmol) and stirred at ambient temperature for 30 minutes. The product was subjected to purification by mass-directed automated preparative HPLC (formic acid modifier) to afford the title compound (26 mg, 55% yield). LCMS RT=0.98 min, ES+ve m/z 445 [M+H]$^+$. Using a method analogous to that for 2S,4R)—N-([1,1'-biphenyl]-4-ylmethyl)-1-(3-ethoxybenzoyl)-4-hydroxypyrrolidine-2-carboxamide, the following compounds were prepared:

| Name | Structure | Yield | RT | [M + H]+ |
|---|---|---|---|---|
| (2S,4R)-N-((S)-1-(4-chlorophenyl)ethyl)-1-(3-ethoxybenzoyl)-4-hydroxypyrrolidine-2-carboxamide | 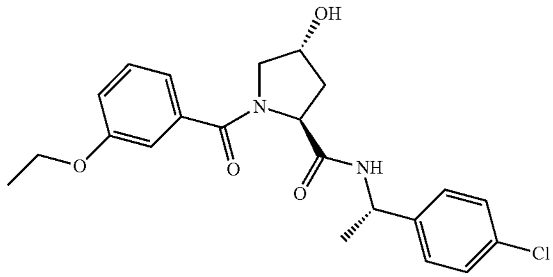 [SMILES: CCOc1cccc(C(=O)N2C[C@H](O)C[C@H]2C(=O)N[C@@H](C)c2ccc(Cl)cc2)c1] | 56% | 0.92 min | 417 |
| (2S,4R)-N-benzyl-1-(3-ethoxybenzoyl)-4-hydroxypyrrolidine-2-carboxamide | 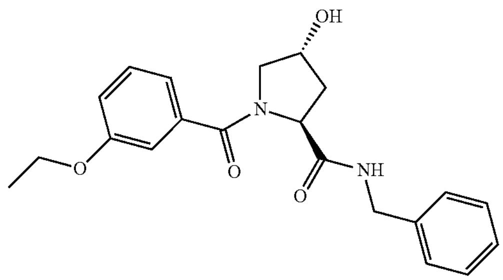 [SMILES: CCOc1cccc(C(=O)N2C[C@H](O)C[C@H]2C(=O)NCc2ccccc2)c1] | 64% | 0.76 min | 369 |
| (2S,4R)-1-(3-ethoxybenzoyl)-4-hydroxy-N-((S)-2-oxopyrrolidin-3-yl)pyrrolidine-2-carboxamide | 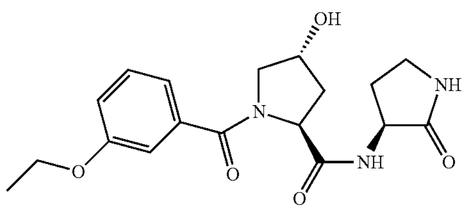 [SMILES: CCOc1cccc(C(=O)N2C[C@H](O)C[C@H]2C(=O)N[C@H]2CCNC2=O)c1] | 77% | 0.50 min | 362 |
| (2S,4R)-1-(3-ethoxybenzoyl)-4-hydroxy-N-((2-methylthiazol-5-yl)methyl)pyrrolidine-2-carboxamide | 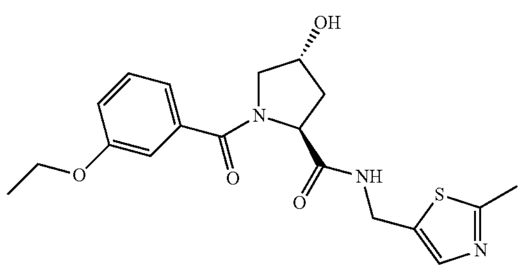 [SMILES: CCOc1cccc(C(=O)N2C[C@H](O)C[C@H]2C(=O)NCc2cnc(C)s2)c1] | 69% | 0.57 min | 390 |
| (2S,4R)-1-(3-ethoxybenzoyl)-4-hydroxy-N-((1-methyl-1H-pyrazol-4-yl)methyl)pyrrolidine-2-carboxamide | 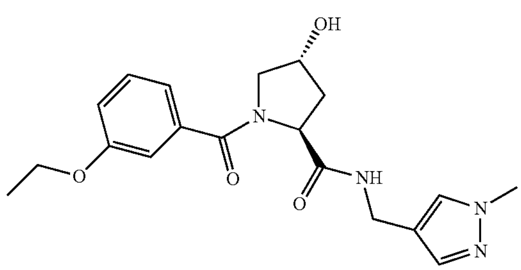 [SMILES: CCOc1cccc(C(=O)N2C[C@H](O)C[C@H]2C(=O)NCc2cnn(C)c2)c1] | 70% | 0.55 min | 375 |
| (2S,4R)-N-([1,1'-biphenyl]-4-ylmethyl)-1-(3-ethoxybenzoyl)-4-hydroxypyrrolidine-2-carboxamide | 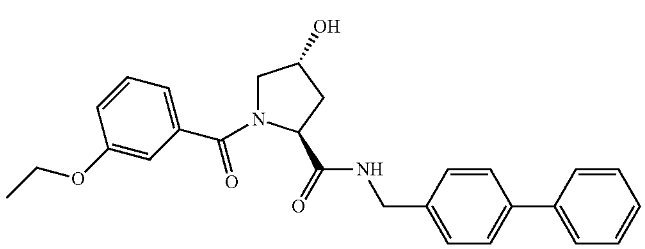 [SMILES: CCOc1cccc(C(=O)N2C[C@H](O)C[C@H]2C(=O)NCc2ccc(-c3ccccc3)cc2)c1] | 55% | 0.98 min | 445 |

| Name | Structure | Yield | RT | [M + H]+ |
|---|---|---|---|---|
| (2S,4R)-1-(3-ethoxybenzoyl)-4-hydroxy-N-((5-phenyl-1,2,4-oxadiazol-3-yl)methyl)pyrrolidine-2-carboxamide | 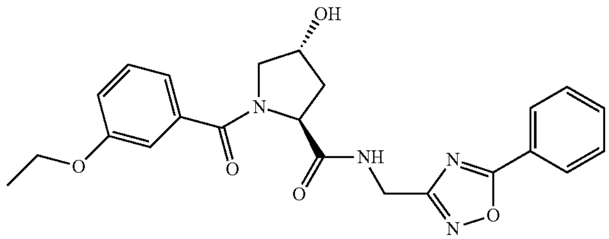 | 60% | 0.82 min | 437 |
| (2S,4R)-N-((3-(4-chlorophenyl)-1,2,4-oxadiazol-5-yl)methyl)-1-(3-ethoxybenzoyl)-4-hydroxypyrrolidine-2-carboxamide | 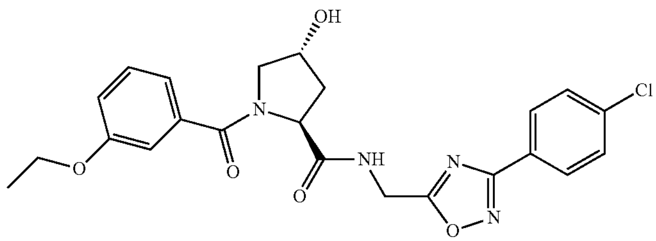 [SMILES: CCOc1cccc(C(=O)N2C[C@H](O)C[C@H]2C(=O)NCc2nc(-c3ccc(Cl)cc3)no2)c1] | 47% | 0.95 min | 471 |
| (2S,4R)-1-(3-ethoxybenzoyl)-4-hydroxy-N-((5-phenylisoxazol-3-yl)methyl)pyrrolidine-2-carboxamide | 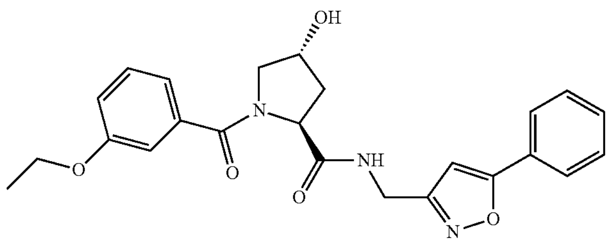 [SMILES: CCOc1cccc(C(=O)N2C[C@H](O)C[C@H]2C(=O)NCc2cc(-c3ccccc3)on2)c1] | 60% | 0.86 min | 436 |
| (2S,4R)-1-(3-ethoxybenzoyl)-4-hydroxy-N-((1-methyl-1,2,3,4-tetrahydroquinolin-6-yl)methyl)pyrrolidine-2-carboxamide | 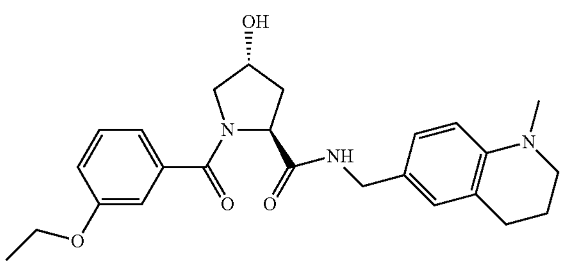 [SMILES: CCOc1cccc(C(=O)N2C[C@H](O)C[C@H]2C(=O)NCc2ccc3c(c2)CCCN3C)c1] | 30% | 0.67 min | 438 |

(2S,4R)-4-hydroxy-1-(2-(3-methoxypropanamido)acetyl)-N-(4-(4-methylthiazol-5-yl)benzyl)pyrrolidine-2-carboxamide

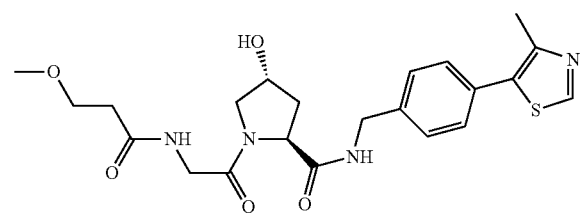 [SMILES: COCCC(=O)NCC(=O)N1C[C@H](O)C[C@H]1C(=O)NCc1ccc(-c2scnc2C)cc1]

A mixture of (2S,4R)-1-(2-aminoacetyl)-4-hydroxy-N-(4-(4-methylthiazol-5-yl)benzyl)pyrrolidine-2-carboxamide (134 mg, 0.33 mmol) and 3-methoxypropanoic acid (commercially available from for example Aldrich) (37 mg, 0.36 mmol) in DMF (0.8 mL) was treated with DIPEA (0.23 mL, 1.3 mmol) and then with HATU (136 mg, 0.36 mmol) and stirred at ambient temperature for 30 minutes. The product was subjected to purification by mass-directed automated preparative HPLC (formic acid modifier) to afford the title compound (36 mg, 24% yield). LCMS RT=0.56 min, ES+ve m/z 461 [M+H]+.

(2S,4R)-1-((S)-3,3-dimethyl-2-(3-methyloxetane-3-carboxamido)butanoyl)-4-hydroxy-N-(4-(4-methylthiazol-5-yl)benzyl)pyrrolidine-2-carboxamide

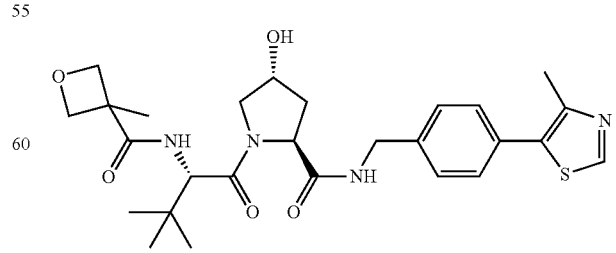

A stirred mixture of (2S,4R)-1-((S)-2-amino-3,3-dimethylbutanoyl)-4-hydroxy-N-(4-(4-methylthiazol-5-yl)benzyl)

pyrrolidine-2-carboxamide, hydrochloride (20 mg, 0.04 mmol) and 3-methyloxetane-3-carboxylic acid (commercially available from for example Chemgenx) (5 mg, 0.04 mmol) in DMF (0.6 mL) was treated with DIPEA (0.03 mL, 0.17 mmol) and then with HATU (20 mg, 0.05 mmol), and the mixture was stirred at ambient temperature for 1 hour. The product was subjected to purification by mass-directed automated preparative HPLC (formic acid modifier) to give the title compound (18 mg, 80% yield). LCMS RT=0.76 min, ES+ve m/z 529 [M+H]$^+$.

Using a method analogous to that for (2S,4R)-1-((S)-3,3-dimethyl-2-(3-methyloxetane-3-carboxamido)butanoyl)-4-hydroxy-N-(4-(4-methylthiazol-5-yl)benzyl)pyrrolidine-2-carboxamide, the following compounds were prepared:

| Name | Structure | Yield | RT | [M + H]+ |
|---|---|---|---|---|
| (2S,4R)-1-((S)-3,3-dimethyl-2-(oxetane-3-carboxamido)butanoyl)-4-hydroxy-N-(4-(4-methylthiazol-5-yl)benzyl)pyrrolidine-2-carboxamide | | 41% | 0.72 min | 515 |
| (2S,4R)-1-((S)-2-(cyclopentanecarboxamido)-3,3-dimethylbutanoyl)-4-hydroxy-N-(4-(4-methylthiazol-5-yl)benzyl)pyrrolidine-2-carboxamide | | 58% | 0.89 min | 527 |
| (2S54R)-1-((S)-3,3-dimethyl-2-(tetrahydro-2H-pyran-4-carboxamido)butanoyl)-4-hydroxy-N-(4-(4-methylthiazol-5-yl)benzyl)pyrrolidine-2-carboxamide | | 52% | 0.76 min | 543 |

339

(S)—N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)morpholine-3-carboxamide, hydrochloride

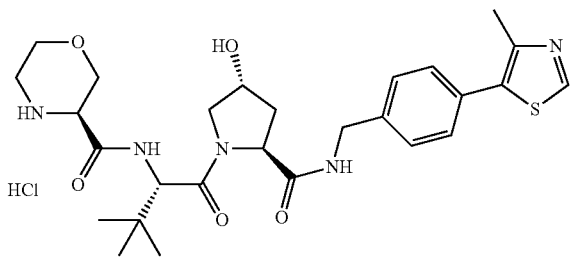 [SMILES: Cl ; Cc1ncsc1-c1ccc(CNC(=O)[C@@H]2C[C@@H](O)CN2C(=O)[C@@H](NC(=O)[C@@H]2COCCN2)C(C)(C)C)cc1]

A mixture of (2S,4R)-1-((S)-2-amino-3,3-dimethylbutanoyl)-4-hydroxy-N-(4-(4-methylthiazol-5-yl)benzyl)pyrrolidine-2-carboxamide (40 mg, 0.086 mmol) and (S)-4-(tert-butoxycarbonyl)morpholine-3-carboxylic acid (commercially available from for example Astatech, Inc.) (20 mg, 0.086 mmol) in DMF (0.6 mL) was treated with DIPEA (0.06 mL, 0.35 mmol) and then with HATU (40 mg, 0.10 mmol) and stirred at ambient temperature for 1 hour. The product was subjected to purification by mass-directed automated preparative HPLC (formic acid modifier) to give the intermediate Boc-protected product. The intermediate was then dissolved in a mixture of dichloromethane (1 mL) and methanol (0.5 mL) and treated with 4M hydrochloric acid in 1,4-dioxane (0.4 mL, 1.6 mmol), After stirring at ambient temperature for 1 hour, the mixture was evaporated to dryness to afford the title compound (31 mg, 62% yield). LCMS RT=0.60 min, ES+ve m/z 544 [M+H]$^+$.

Using a method analogous to that for (S)—N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)morpholine-3-carboxamide, hydrochloride, the following compounds were prepared:

| | | | | |
|---|---|---|---|---|
| (R)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)morpholine-3-carboxamide, hydrochloride | 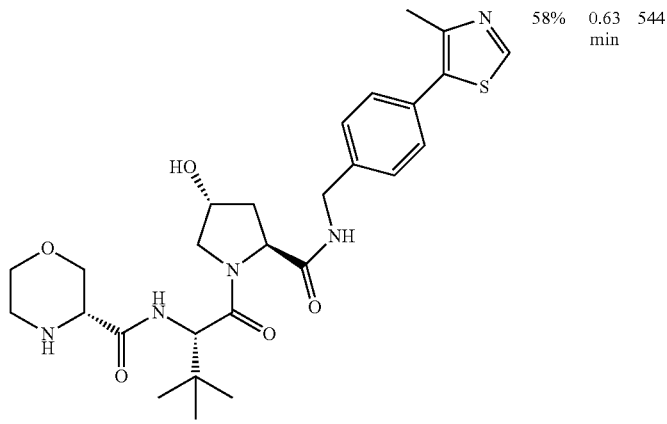 | 58% | 0.63 min | 544 |
| (S)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)morpholine-2-carboxamide, hydrochloride | 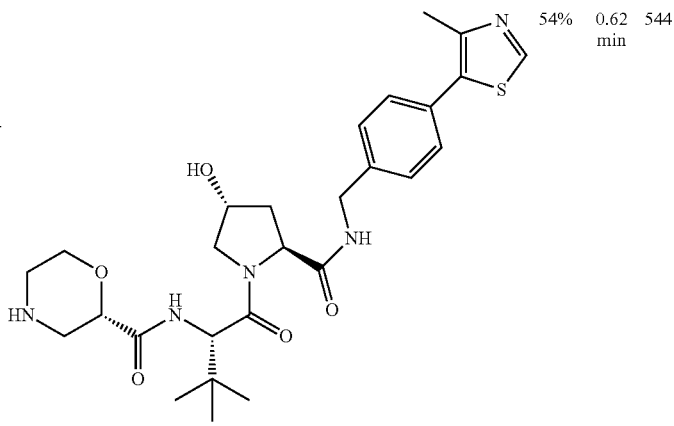 | 54% | 0.62 min | 544 |

-continued

| | | | |
|---|---|---|---|
| N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)morpholine-2-carboxamide, hydrochloride | 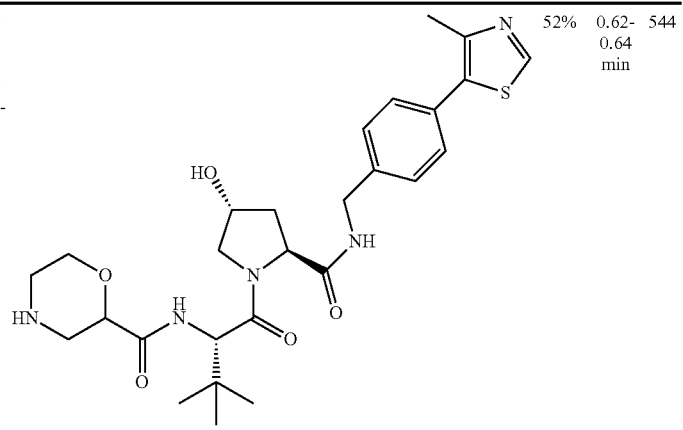 | 52% | 0.62-0.64 min | 544 | tert-butyl 4-((S)-1-((2S,4R)-4-hydroxy-2-((4-(4-methylthiazol-5-yl)benzyl)carbamoyl)pyrrolidin-1-yl)-1-oxopropan-2-yl)piperazine-1-carboxylate & tert-butyl 4((R)-1-((2S,4R)-4-hydroxy-2-((4-(4-methylthiazol-5-yl)benzyl)carbamoyl)pyrrolidin-1-yl)-1-oxopropan-2-yl)piperazine-1-carboxylate

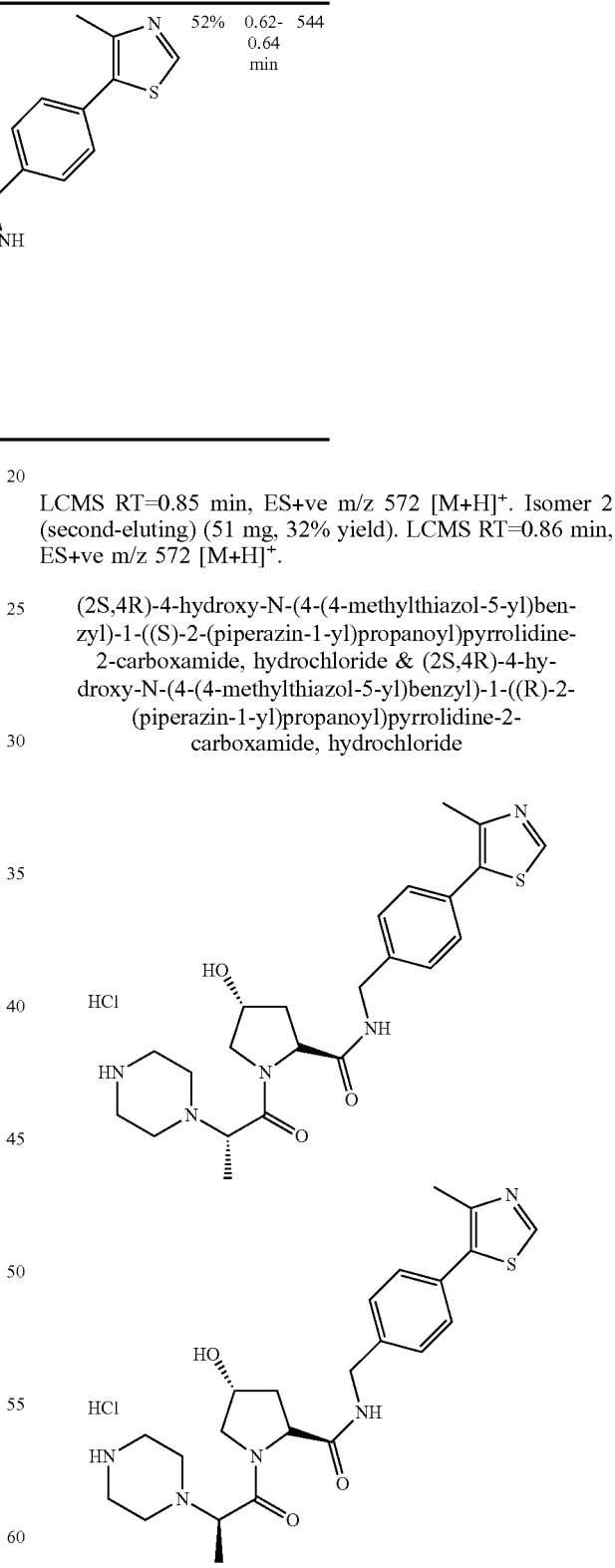

A stirred mixture of (2S,4R)-4-hydroxy-N-(4-(4-methylthiazol-5-yl)benzyl)pyrrolidine-2-carboxamide, hydrochloride (100 mg, 0.28 mmol) and 2-(4-(tert-butoxycarbonyl)-2-oxopiperazin-1-yl)propanoic acid (85 mg, 0.31 mmol) in DMF (0.8 mL) was treated with DIPEA (0.20 mL, 1.13 mmol) and then with HATU (129 mg, 0.34 mmol) and then stirred at ambient temperature for 30 minutes. The product was subjected to purification by mass-directed automated preparative HPLC (ammonium bicarbonate modifier) to afford the title compounds: Isomer 1 (first-eluting) (48 mg, 30% yield).

LCMS RT=0.85 min, ES+ve m/z 572 [M+H]$^+$. Isomer 2 (second-eluting) (51 mg, 32% yield). LCMS RT=0.86 min, ES+ve m/z 572 [M+H]$^+$.

(2S,4R)-4-hydroxy-N-(4-(4-methylthiazol-5-yl)benzyl)-1-((S)-2-(piperazin-1-yl)propanoyl)pyrrolidine-2-carboxamide, hydrochloride & (2S,4R)-4-hydroxy-N-(4-(4-methylthiazol-5-yl)benzyl)-1-((R)-2-(piperazin-1-yl)propanoyl)pyrrolidine-2-carboxamide, hydrochloride Isomer 1 and isomer 2 of tert-butyl 4-(1-((2S,4R)-4-hydroxy-2-((4-(4-methylthiazol-5-yl)benzyl)carbamoyl)pyrrolidin-1-yl)-1-oxopropan-2-yl)piperazine-1-carboxylate (48 mg, 0.08 mmol) were separately dissolved in a mixture of dichloromethane (0.3 mL) and methanol (0.1 mL) and treated with 4M hydrochloric acid in 1,4-dioxane (0.3 mL, 1.2 mmol) respectively. After stirring at ambient temperature for 1 hour, the reaction mixtures were evaporated to dryness to afford the title compounds as hydrochloride salts. Isomer 1 (42 mg, 99% yield). LCMS RT=0.62 min, ES+ve m/z 472 [M+H]⁺. Isomer 2 (42 mg, 99% yield). LCMS RT=0.60 min, ES+ve m/z 472 [M+H]⁺.

(S)—N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4-(2-methoxyethyl)morpholine-2-carboxamide

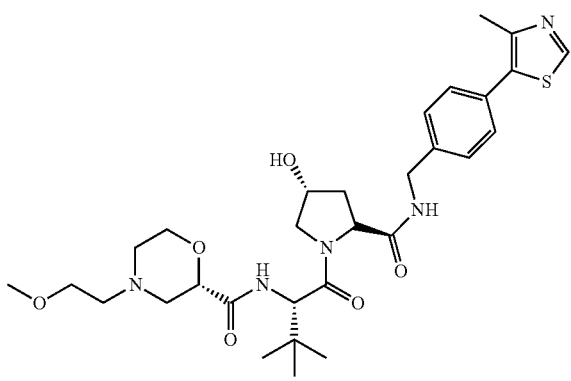

A mixture of 1-bromo-2-methoxyethane (4 μL, 0.04 mmol), (S)—N—((S)-1-(2S,4R)-4-hydroxy-2-((4-(4-methylthiazol-5-yl)benzyl)carbamoyl)pyrrolidin-1-yl)-3,3-dimethyl-1-oxobutan-2-yl)morpholine-2-carboxamide, hydrochloride (20 mg, 0.04 mmol) and DIPEA (0.019 mL, 0.11 mmol) in DMF (0.5 mL) was stirred at 85° C. for 6 hours. The cooled product was subjected to purification by mass-directed automated preparative HPLC (ammonium bicarbonate modifier) to afford the title compound (9 mg, 41% yield). LCMS RT=0.88 min, ES+ve m/z 602 [M+H]⁺.

Using a method analogous to that for (S)—N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4-(2-methoxyethyl)morpholine-2-carboxamide the following compounds were prepared:

| Name | Structure | Stereochemistry Comments | Yield | RT | [M + H]+ |
|---|---|---|---|---|---|
| (2S,4R)-4-hydroxy-1-(2-(4-(2-methoxyethyl)-2-oxopiperazin-1-yl)propanoyl)-N-(4-(4-methylthiazol-5-yl)benzyl)pyrrolidine-2-carboxamide | | Single enantiomer, stereochemistry unknown at the unspecified chiral centre | 20% | 0.68 min | 530 |
| (2S,4R)-4-hydroxy-1-(2-(4-(2-methoxyethyl)-2-oxopiperazin-1-yl)propanoyl)-N-(4-(4-methylthiazol-5-yl)benzyl)pyrrolidine-2-carboxamide | | Single enantiomer, stereochemistry unknown at the unspecified chiral centre | 32% | 0.69 min | 530 |

| Name | Structure | Stereo-chemistry Comments | Yield | RT | [M + H]+ |
|---|---|---|---|---|---|
| (S)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4-(2-methoxyethyl)morpholine-3-carboxamide | 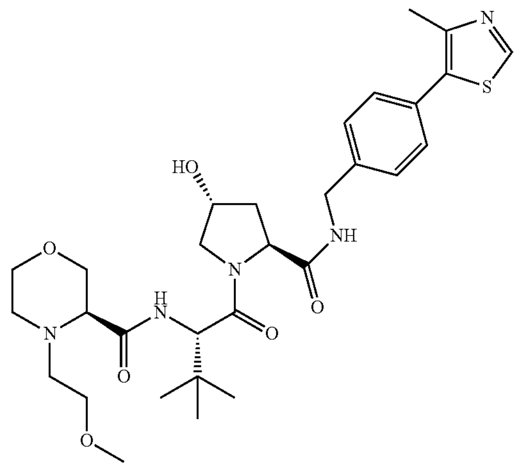 [SMILES: COCCN1CCOC[C@H]1C(=O)N[C@H](C(=O)N1C[C@H](O)C[C@H]1C(=O)NCc1ccc(-c2scnc2C)cc1)C(C)(C)C] | | 41% | 0.86 min | 602 |
| (R)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4-(2-methoxyethyl)morpholine-3-carboxamide | 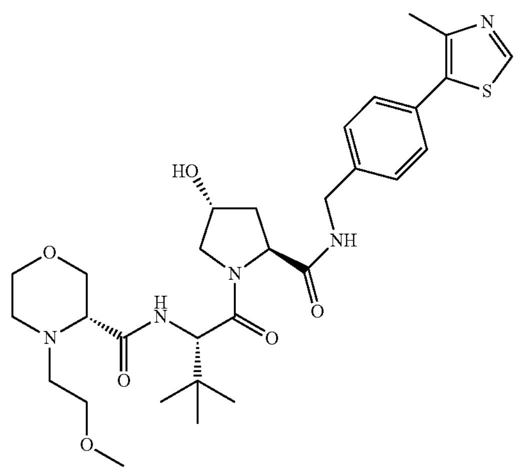 [SMILES: COCCN1CCOC[C@@H]1C(=O)N[C@H](C(=O)N1C[C@H](O)C[C@H]1C(=O)NCc1ccc(-c2scnc2C)cc1)C(C)(C)C] | | 45% | 0.86 min | 602 |

50

Methyl 4-(((S)-1-(((S)-1-((2S,4R)-4-hydroxy-2-((4-(4-methylthiazol-5-yl)benzyl)carbamoyl)pyrrolidin-1-yl)-1-oxopropan-2-yl)amino)-4-methyl-1-oxopentan-2-yl)amino)-4-oxobutanoate

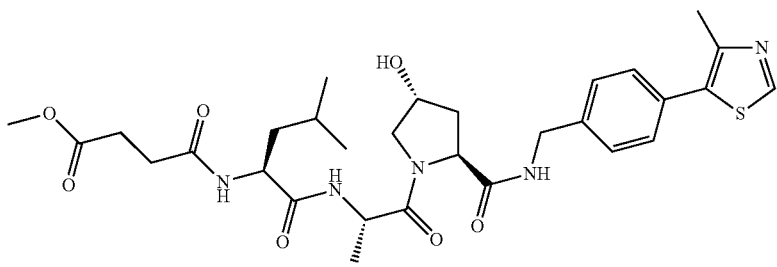 [SMILES: COC(=O)CCC(=O)N[C@@H](CC(C)C)C(=O)N[C@@H](C)C(=O)N1C[C@H](O)C[C@H]1C(=O)NCc1ccc(-c2scnc2C)cc1]

A mixture of (2S,4R)-1-((S)-2-((S)-2-amino-4-methylpentanamido)propanoyl)-4-hydroxy-N-(4-(4-methylthiazol-5-yl)benzyl)pyrrolidine-2-carboxamide, hydrochloride (102 mg, 0.19 mmol), DIPEA (0.165 mL, 0.95 mmol) and 4-methoxy-4-oxobutanoic acid (commercially available from for example Aldrich) (25 mg, 0.19 mmol) in DMF (2 mL) was treated with HATU (64 mg, 0.17 mmol) and the mixture was stirred at ambient temperature for 20 minutes. Brine (10 mL) was added and the product was extracted with ethyl acetate (20 mL). The organic phase was washed with brine (2×20 mL), dried using a hydrophobic frit and evaporated to dryness. The product was purified by chromatography on reverse phase silica using a gradient elution from 5% to 70% acetonitrile (+0.1% formic acid) in water (+0.1% formic acid) to afford the title compound (73 mg, 0.12 mmol, 63% yield). LCMS RT=0.74 min, ES+ve m/z 616 [M+H]$^+$.

4-(3-((2S,4R)-4-Hydroxy-2-((4-(4-methylthiazol-5-yl)benzyl)carbamoyl)pyrrolidine-1-carbonyl)phenoxy)butanoic acid

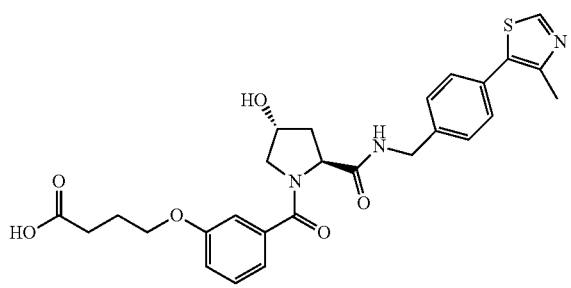 [SMILES: Cc1ncsc1-c1ccc(CNC(=O)[C@@H]2C[C@@H](O)CN2C(=O)c2cccc(OCCCC(=O)O)c2)cc1]

A solution of tert-butyl 4-(3-((2S,4R)-4-hydroxy-2-((4-(4-methylthiazol-5-yl)benzyl)carbamoyl)pyrrolidine-1-carbonyl)phenoxy)butanoate (130 mg, 0.22 mmol) in dichloromethane (3 mL) was treated with TFA (0.5 mL, 6.5 mmol) and stirred at ambient temperature for 5 hours. The solvent was evaporated to dryness and the product was subjected to purification by mass-directed automated preparative HPLC (formic acid modifier) to afford the title compound (65 mg, 0.12 mmol, 55% yield). LCMS RT=0.70 min, ES+ve m/z 524 [M+H]$^+$.

4-(((S)-1-(((S)-1-((2S,4R)-4-hydroxy-2-((4-(4-methylthiazol-5-yl)benzyl)carbamoyl)pyrrolidin-1-yl)-1-oxopropan-2-yl)amino)-4-methyl-1-oxopentan-2-yl)amino)-4-oxobutanoic acid A solution of methyl 4-(((S)-1-(((S)-1-((2S,4R)-4-hydroxy-2-((4-(4-methylthiazol-5-yl)benzyl)carbamoyl)pyrrolidin-1-yl)-1-oxopropan-2-yl)amino)-4-methyl-1-oxopentan-2-yl)amino)-4-oxobutanoate (73 mg, 0.12 mmol) in methanol (3 mL) was treated with aqueous sodium hydroxide (2M, 0.6 mL, 1.2 mmol) and the mixture was stirred at ambient temperature for 2 hours. The mixture was evaporated to dryness and the product was purified by chromatography on reverse phase silica using a gradient elution from 5% to 60% acetonitrile (+0.1% formic acid) in water (+0.1% formic acid) to afford the title compound (53 mg, 0.088 mmol, 74% yield). LCMS RT=0.69 min, ES+ve m/z 602 [M+H]$^+$.

(2S,4R)-4-hydroxy-1-((S)-2-((S)-2-(2-methoxyacetamido)-4-methylpentanamido)propanoyl)-N-(4-(4-methylthiazol-5-yl)benzyl)pyrrolidine-2-carboxamide

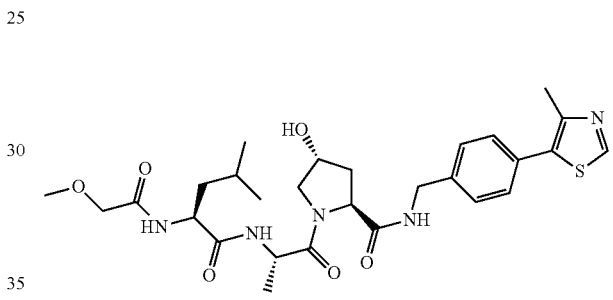

A mixture of (2S,4R)-1-((S)-2-((S)-2-amino-4-methylpentanamido)propanoyl)-4-hydroxy-N-(4-(4-methylthiazol-5-yl)benzyl)pyrrolidine-2-carboxamide, hydrochloride (30 mg, 0.056 mmol), 2-methoxyacetic acid (commercially available from for example Aldrich) (4.3 uL, 0.056 mmol) and DIPEA (0.05 mL, 0.29 mmol) in DMF (1 mL) was treated with HATU (25 mg, 0.066 mmol) and stirred at ambient temperature for 30 minutes. The product was subjected to purification by mass-directed automated preparative HPLC (formic acid modifier) to afford the title compound (18 mg, 0.031 mmol, 56% yield). LCMS RT=0.73 min, ES+ve m/z 574 [M+H]$^+$.

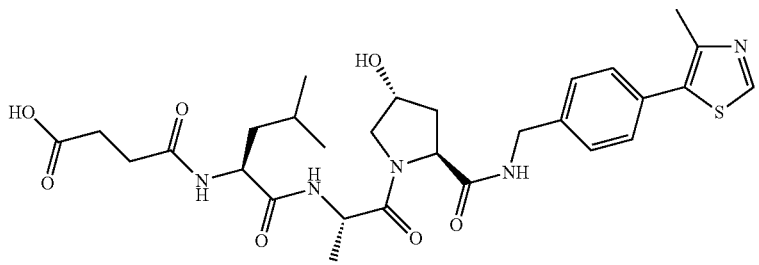 [SMILES: Cc1ncsc1-c1ccc(CNC(=O)[C@@H]2C[C@@H](O)CN2C(=O)[C@H](C)NC(=O)[C@H](CC(C)C)NC(=O)CCC(=O)O)cc1]

(2S,4R)-4-hydroxy-1-((S)-2-((S)-2-(3-methoxypropanamido)-4-methylpentanamido)propanoyl)-N-(4-(4-methylthiazol-5-yl)benzyl)pyrrolidine-2-carboxamide

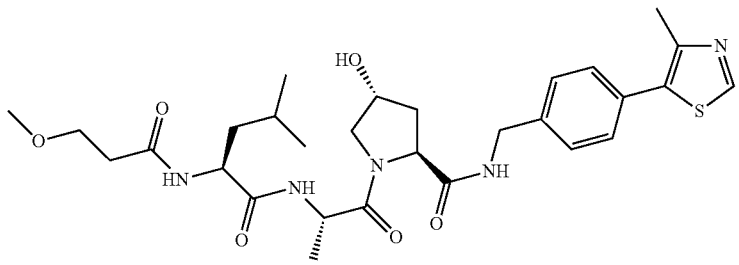 [SMILES: COCCC(=O)N[C@@H](CC(C)C)C(=O)N[C@@H](C)C(=O)N1C[C@H](O)C[C@H]1C(=O)NCc1ccc(-c2scnc2C)cc1]

A mixture of (2S,4R)-1-((S)-2-(S)-2-amino-4-methylpentanamido)propanoyl)-4-hydroxy-N-(4-(4-methylthiazol-5-yl)benzyl)pyrrolidine-2-carboxamide, hydrochloride (30 mg, 0.056 mmol), 3-methoxypropanoic acid (commercially available from for example Aldrich) (5.2 uL, 0.056 mmol) and DIPEA (0.05 mL, 0.29 mmol) in DMF (1 mL) and stirred at ambient temperature for 30 minutes. The product was subjected to purification by mass-directed automated preparative HPLC (formic acid modifier) to afford the title compound (20 mg, 0.034 mmol, 61% yield). LCMS RT=0.72 min, ES+ve m/z 588 [M+H]+.

(2S,4R)-1-(6-cyanopyridin-2-yl)-4-hydroxy-N-(4-(4-methylthiazol-5-yl)benzyl)pyrrolidine-2-carboxamide

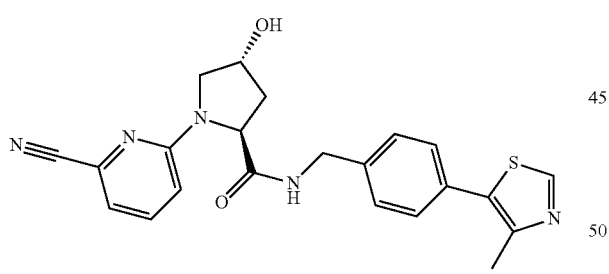

A mixture of (2S,4R)-4-hydroxy-N-(4-(4-methylthiazol-5-yl)benzyl)pyrrolidine-2-carboxamide, hydrochloride (58 mg, 0.16 mmol) and 6-fluoropicolinonitrile (commercially available from for example Aldrich) (20 mg, 0.16 mmol) in DMSO (1 mL) was treated with DIPEA (0.10 mL, 0.57 mmol), sealed and heated in a Biotage "Initiator" microwave at 100° C. for 60 minutes. The product was purified by mass-directed automated preparative HPLC (formic acid modifier) to afford the title compound (23 mg, 0.055 mmol, 34% yield). LCMS RT=0.74 min, ES+ve m/z 420 [M+H]+.

Intermediates 4-(oxazol-5-yl)benzonitrile

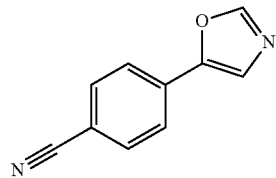 [SMILES: N#Cc1ccc(-c2cnco2)cc1]

A mixture of 4-formylbenzonitrile (commercially available from for example Aldrich) (5.32 g, 41 mmol), 1-((isocyanomethyl)sulfonyl)-4-methylbenzene (commercially available from for example Aldrich) (8.83 g, 45 mmol) and potassium carbonate (7.3 g, 53 mmol) in methanol (200 mL) was stirred at ambient temperature for 80 minutes. The mixture was then evaporated to dryness; the residue was treated with saturated aqueous sodium bicarbonate (100 mL) and extracted with dichloromethane (3×100 mL). The combined organics were washed with brine (75 mL), passed through a hydrophobic frit and then evaporated to dryness to afford the title compound (7.19 g, 42 mmol, quantitative). LCMS RT=0.48 min, ES+ve m/z 171 [M+H]+.

(4-(oxazol-5-yl)phenyl)methanamine

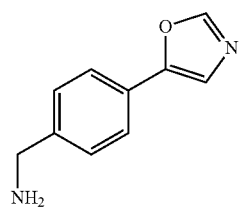 [SMILES: NCc1ccc(-c2cnco2)cc1]

Under an atmosphere of nitrogen, an ice-cooled mixture of 4-(oxazol-5-yl)benzonitrile (900 mg, 5.29 mmol) and cobalt (II) chloride hexahydrate (commercially available from for example Aldrich) (1.8 g, 7.9 mmol) in methanol (50 mL) was treated portion-wise over 5 minutes with sodium borohydride (1 g, 26 mmol). The mixture was stirred for 30 minutes and then treated with water (50 mL) and concentrated aqueous ammonia (20 mL). The mixture was extracted with chloroform (3×150 mL), the combined organics were evaporated to dryness and the product was purified by chromatography on silica using a gradient elution from 0% to 30% methanol in dichloromethane (+0.1% triethylamine) to afford the title compound (580 mg, 3.3 mmol, 63% yield). LCMS RT=0.35 min, ES+ve m/z 175 [M+H]⁺.

(2S,4R)-tert-butyl 4-hydroxy-2-((4-(oxazol-5-yl)benzyl)carbamoyl)pyrrolidine-1-carboxylate

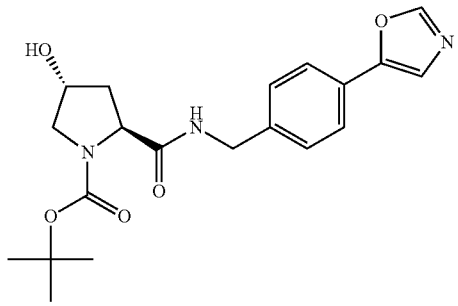 [SMILES: CC(C)(C)OC(=O)N1C[C@H](O)C[C@H]1C(=O)NCc1ccc(-c2cnco2)cc1]

To a stirred solution of (2S,4R)-1-(tert-butoxycarbonyl)-4-hydroxypyrrolidine-2-carboxylic acid (0.66 g, 2.9 mmol) in dry DMF (20 mL) were added (4-(oxazol-5-yl)phenyl)methanamine (0.5 g, 2.87 mmol) and DIPEA (1 mL, 5.7 mmol). This solution was then ice-cooled and HATU (1.09 g, 2.9 mmol) was added. The reaction mixture was stirred with cooling for an additional hour then treated with water (30 mL) and extracted with ethyl acetate (3×100 mL). The combined organic phase was washed with saturated aqueous sodium bicarbonate (60 mL), brine (60 mL), dried over magnesium sulfate, filtered and evaporated to dryness. The product was purified by chromatography on silica using a gradient elution from 0% to 25% methanol in dichloromethane to afford the title compound (758 mg, 1.96 mmol, 68% yield). LCMS RT=0.73 min, ES+ve m/z 388 [M+H]⁺.

(2S,4R)-4-hydroxy-N-(4-(oxazol-5-yl)benzyl)pyrrolidine-2-carboxamide, hydrochloride

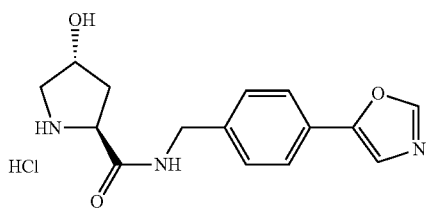 [SMILES: Cl ; O=C(NCc1ccc(-c2cnco2)cc1)[C@@H]1C[C@@H](O)CN1]

A solution of (2S,4R)-tert-butyl 4-hydroxy-2-((4-(oxazol-5-yl)benzyl)carbamoyl)pyrrolidine-1-carboxylate (2.74 g, 7.1 mmol) in methanol (10 mL) and dichloromethane (15 mL) was treated with hydrochloric acid (4 M in 1,4-dioxane) (8.8 mL, 35 mmol) and the mixture was stirred at ambient temperature for 24 hours. The mixture was evaporated to dryness. The residue was suspended in methanol, filtered and dried under vacuum to afford the title compound (2.24 g, 6.9 mmol, 98% yield). LCMS RT=0.44 min, ES+ve m/z 288 [M+H]⁺.

(2S,4R)-tert-butyl 2-((4-bromobenzyl)carbamoyl)-4-hydroxypyrrolidine-1-carboxylate

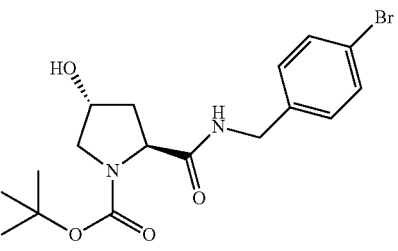 [SMILES: CC(C)(C)OC(=O)N1C[C@H](O)C[C@H]1C(=O)NCc1ccc(Br)cc1]

An ice-cooled mixture of (2S,4R)-1-(tert-butoxycarbonyl)-4-hydroxypyrrolidine-2-carboxylic acid (commercially available from for example Aldrich) (7.95 g, 34 mmol) and (4-bromophenyl)methanamine (commercially available from for example Fluorochem) (6.4 g, 34 mmol) in DMF (200 mL) was treated with DIPEA (18 mL, 103 mmol) and then with HATU (14.4 g, 38 mmol) and the mixture was stirred at ambient temperature for 30 minutes. The mixture was treated with water (200 mL) and extracted with ethyl acetate (2×200 mL). The combined organic phase was washed with saturated aqueous sodium bicarbonate (2×300 mL), water (100 mL), brine (200 mL), dried over magnesium sulfate and evaporated to dryness. The product was purified by flash chromatography (750 g silica cartridge) using a gradient elution from 0% to 10% methanol in dichloromethane to afford the title compound (12.9 g, 94% yield). LCMS RT=0.87 min, ES+ve m/z 401 [M+H]⁺.

(2S,4R)-tert-butyl 4-hydroxy-2-((4-(4-methylthiazol-5-yl)benzyl)carbamoyl)pyrrolidine-1-carboxylate

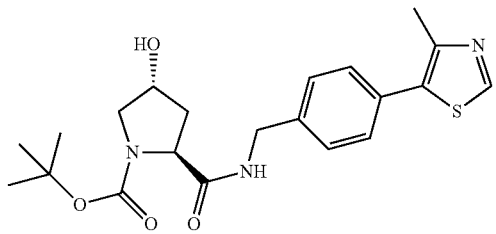 [SMILES: Cc1ncsc1-c1ccc(CNC(=O)[C@@H]2C[C@@H](O)CN2C(=O)OC(C)(C)C)cc1]

Under an atmosphere of nitrogen, a mixture of (2S,4R)-tert-butyl 2-((4-bromobenzyl)carbamoyl)-4-hydroxypyrrolidine-1-carboxylate (12.9 g, 32 mmol), 4-methylthiazole (commercially available from for example Aldrich) (5.9 mL, 65 mmol), palladium(II) acetate (commercially available from for example Aldrich) (0.145 g, 0.65 mmol) and potassium acetate (6.34 g, 65 mmol) in N-methyl-2-pyrrolidone (80 mL) was stirred at 120° C. for 18 hours. After cooling to ambient temperature, water (100 ml) was added and the product was extracted with ethyl acetate (4×300 mL). The combined organic phase was washed with brine (5×200 mL), dried over magnesium sulfate and evaporated to dryness. The product was purified by flash chromatography (750 g silica cartridge) using a gradient elution from 0% to 10% methanol in dichloromethane to afford the title compound (8.0 g, 59% yield). LCMS RT=0.75 min, ES+ve m/z 418 [M+H]⁺.

353

(2S,4R)-4-hydroxy-N-(4-(4-methylthiazol-5-yl)benzyl)pyrrolidine-2-carboxamide, hydrochloride

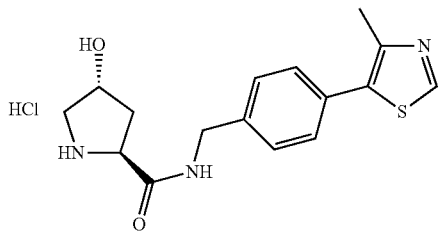 [SMILES: Cl ; Cc1ncsc1-c1ccc(CNC(=O)[C@@H]2C[C@@H](O)CN2)cc1]

A solution of (2S,4R)-tert-butyl 4-hydroxy-2-((4-(4-methylthiazol-5-yl)benzyl)carbamoyl)pyrrolidine-1-carboxylate (8 g, 19 mmol) in a mixture of methanol (30 mL) and dichloromethane (20 mL) was treated with 4M hydrochloric acid in 1,4-dioxane (8 mL, 32 mmol). The mixture was stirred at ambient temperature for 2 hours. The solvent was evaporated to dryness and the residue was triturated in dichloromethane, filtered and dried under vacuum to afford the title compound (6.7 g, 99% yield). LCMS RT=0.51 min, ES+ve m/z 318 [M+H]+.

(2S,4R)-1-(3-ethoxybenzoyl)-4-hydroxypyrrolidine-2-carboxylic acid

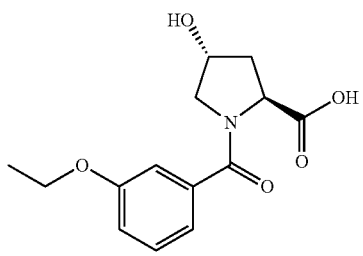 [SMILES: CCOc1cccc(C(=O)N2C[C@H](O)C[C@H]2C(=O)O)c1]

3-Ethoxybenzoic acid (commercially available from for example Aldrich) (4 g, 24 mmol) was dissolved in thionyl chloride (24 mL, 329 mmol) and stirred at 60° C. for 1 hour and then at 50° C. for 18 hours. After cooling to ambient temperature the mixture was evaporated to dryness and the residue was treated with diethyl ether (5 mL). The mixture was then ice-cooled and treated with a solution of (2S,4R)-4-hydroxypyrrolidine-2-carboxylic acid, hydrochloride (commercially available from for example Aldrich) (4.44 g, 27 mmol) in 1M aqueous sodium hydroxide (27 mL, 27 mmol). The reaction was warmed to ambient temperature and stirred for 18 hours. The mixture was separated; the aqueous phase was washed with diethyl ether and then acidified with 2M aqueous hydrochloric acid. The product was extracted in diethyl ether (2×70 mL) and the combined ethereal phase was evaporated to dryness. The product was purified by flash chromatography (340 g C18 cartridge), using a gradient elution from 10 to 30% acetonitrile (+0.1% formic acid) in water (+0.1% formic acid) to afford the title compound (3.5 g, 52% yield). LCMS RT=0.55 min, ES+ve m/z 280 [M+H]+.

354

(2S,4R)-benzyl 1-((S)-2-acetamidopropanoyl)-4-hydroxypyrrolidine-2-carboxylate

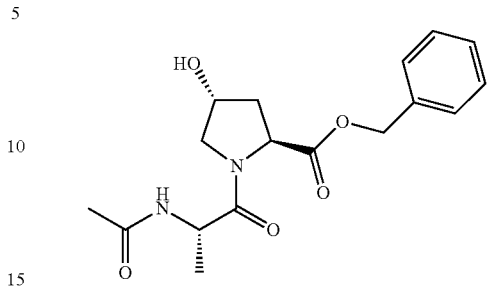

An ice-cooled mixture of (S)-2-acetamidopropanoic acid (commercially available from for example Aldrich) (2.80 g, 21 mmol) and (2S,4R)-benzyl 4-hydroxypyrrolidine-2-carboxylate, hydrochloride (commercially available from for example Aldrich) (5 g, 19 mmol) in DMF (5 mL) was treated with DIPEA (14 mL, 78 mmol), followed by HATU (8.11 g, 21 mmol) over 10 min. The mixture was warmed to ambient temperature and stirred for 1 hour then treated with saturated aqueous sodium bicarbonate (30 mL) and stirred for 5 min. The mixture was then extracted with ethyl acetate (3×100 mL) and the combined organic phase was washed with water (100 mL), brine (100 mL), dried over magnesium sulfate and evaporated to dryness. The product was purified by flash chromatography (330 g silica cartridge) using a gradient elution from 0 to 10% methanol in dichloromethane to afford the title compound (2.0 g, 31% yield). LCMS RT=0.63 min, ES+ve m/z 335 [M+H]+.

(2S,4R)-1-((S)-2-acetamidopropanoyl)-4-hydroxypyrrolidine-2-carboxylic acid

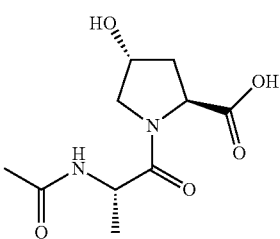 [SMILES: CC(=O)N[C@@H](C)C(=O)N1C[C@H](O)C[C@H]1C(=O)O]

A solution of (2S,4R)-benzyl-1-((S)-2-acetamidopropanoyl)-4-hydroxypyrrolidine-2-carboxylate (2 g, 6.0 mmol) in ethanol (10 mL) was added to a flask containing palladium on carbon (1.27 g, 1.2 mmol) (10%, Degussa type) under an atmosphere of nitrogen. The flask was filled with hydrogen and the solution was stirred at ambient temperature for 2 hours. The catalyst was removed by filtration through celite and the filtrate was evaporated under reduced pressure to afford the title compound (1.37 g, 94% yield). LCMS RT=0.28 min, ES+ve m/z 244 [M+H]+.

355

(2S,4R)-4-hydroxy-1-(2-(3-methylisoxazol-5-yl)acetyl)pyrrolidine-2-carboxylic acid

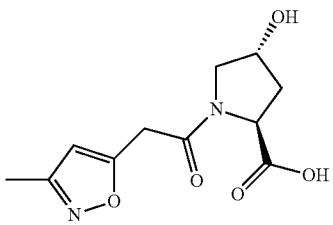 [SMILES: Cc1cc(CC(=O)N2C[C@H](O)C[C@H]2C(=O)O)on1]

Under an atmosphere of nitrogen, a solution of (2S,4R)-benzyl 4-hydroxy-1-(2-(3-methylisoxazol-5-yl)acetyl)pyrrolidine-2-carboxylate (2.3 g, 6.7 mmol) in ethanol (60 mL) was added to palladium on carbon (0.071 g, 0.67 mmol) (10%, Degussa type) and then stirred under an atmosphere of hydrogen. After 2 hours, the mixture was filtered through celite. The filtrate was evaporated to dryness and the residue was triturated with cyclohexane and dried under vacuum to afford a white solid. The product was purified by mass-directed automated preparative HPLC (TFA modifier) to afford the title compound (650 mg, 2.6 mmol, 38% yield). LCMS RT=0.38 min, ES+ve m/z 255 [M+H]$^+$.

(2S,4R)-methyl 4-hydroxy-1-((S)-2-(1-oxoisoindolin-2-yl)propanoyl)pyrrolidine-2-carboxylate

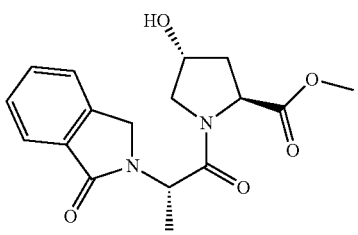 [SMILES: COC(=O)[C@@H]1C[C@@H](O)CN1C(=O)[C@H](C)N1Cc2ccccc2C1=O]

A mixture of (2S,4R)-methyl 4-hydroxypyrrolidine-2-carboxylate, hydrochloride (commercially available from for example Aldrich) (1.77 g, 9.8 mmol) and (S)-2-(1-oxoisoindolin-2-yl)propanoic acid (2 g, 9.8 mmol) in DMF (4 mL) was treated with DIPEA (5.11 mL, 29 mmol) and then with HATU (4.08 g, 10.7 mmol), and stirred at ambient temperature for 30 minutes. The mixture was treated with saturated aqueous sodium bicarbonate (100 mL) and extracted with ethyl acetate (2×200 mL). The combined organic phase was washed with water (100 mL), brine 100 mL), dried over magnesium sulfate and evaporated to dryness. The product was purified by flash chromatography (120 g C18 cartridge), using a gradient elution from 10% to 50% acetonitrile (+0.1% formic acid) in water (+0.1% formic acid) to afford the title compound (1.0 g, 31% yield). LCMS RT=0.60 min, ES+ve m/z 333 [M+H]$^+$.

356

(2S,4R)-4-hydroxy-1-((S)-2-(1-oxoisoindolin-2-yl)propanoyl)pyrrolidine-2-carboxylic acid

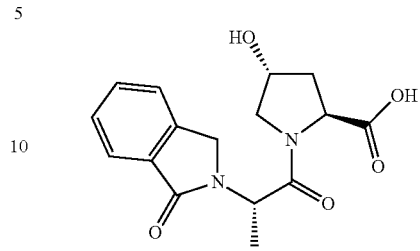

A solution of (2S,4R)-methyl 4-hydroxy-1-((S)-2-(1-oxoisoindolin-2-yl)propanoyl)pyrrolidine-2-carboxylate (1 g, 3.0 mmol) in methanol (2 mL) was treated with 2M aqueous sodium hydroxide (5 mL, 10 mmol) and the mixture was stirred at ambient temperature for 2 hours then acidified with 2M aqueous hydrochloric acid (6 mL). The mixture was then evaporated to about one half of the original volume and then ice-cooled. The resulting precipitate was filtered off and dried under vacuum to afford the title compound (615 mg, 64% yield). LCMS RT=0.51 min, ES+ve m/z 319 [M+H]$^+$.

Methyl 3-(4-(tert-butoxy)-4-oxobutoxy)benzoate

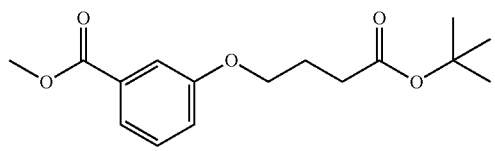 [SMILES: COC(=O)c1cccc(OCCCC(=O)OC(C)(C)C)c1]

A solution of methyl 3-hydroxybenzoate (commercially available from for example Aldrich) (1 g, 6.6 mmol) and K$_2$CO$_3$ (1.82 g, 13.2 mmol) in DMF (10 mL) was treated with tert-butyl 4-bromobutanoate (commercially available from for example Aldrich) (2.2 g, 9.9 mmol) and the mixture was stirred at 60° C. for 16 hours. A further aliquot of K$_2$CO$_3$ (1.82 g, 13.2 mmol) and tert-butyl 4-bromobutanoate (2.2 g, 9.9 mmol) were added and the mixture was heated at 60° C. for further 6 hours. The mixture was cooled to ambient temperature and partitioned between ethyl acetate (50 mL) and water (50 mL). The organic phase was washed with brine (2×50 mL), dried (hydrophobic fit) and evaporated to dryness. The product was purified by chromatography on silica using a gradient elution from 0% to 100% methyl tert-butyl ether in cyclohexane to afford the title compound (1.4 g, 4.8 mmol, 72% yield). LCMS RT=1.26 min, ES+ve m/z 312 [M+H]$^+$.

3-(4-(Tert-butoxy)-4-oxobutoxy)benzoic acid

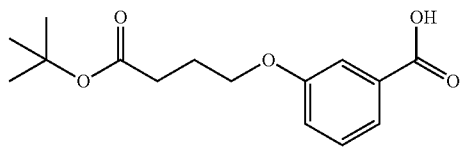 [SMILES: CC(C)(C)OC(=O)CCCOc1cccc(C(=O)O)c1]

A mixture of methyl 3-(4-(tert-butoxy)-4-oxobutoxy)benzoate (1.4 g, 4.8 mmol) and aqueous sodium hydroxide (2M, 4.8 mL, 9.6 mmol) in methanol (10 mL) was stirred at ambient temperature for 5 hours. The methanol was removed under reduced pressure (no heat) and the aqueous phase was acidified to pH 3 with saturated aqueous citric acid. The product was extracted with ethyl acetate (60 mL) and the organic extract was washed with brine (20 mL), dried using a hydrophobic frit and evaporated to dryness. The product was purified by chromatography on silica using a gradient elution from 0% to 25% methanol in dichloromethane to afford the title compound (625 mg, 2.2 mmol, 47% yield). LCMS RT=1.06 min, ES+ve m/z 279 [M−H]$^-$.

Methyl 3-((14,14-dimethyl-12-oxo-3,6,9,13-tetraoxapentadecyl)oxy)benzoate

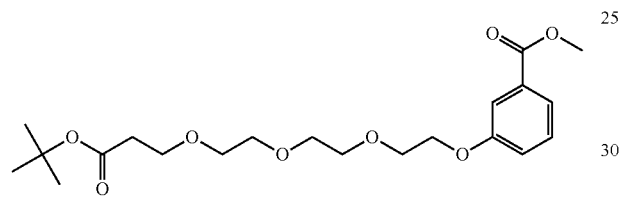

An ice-cooled mixture of tert-butyl 3-(2-(2-(2-hydroxyethoxy)ethoxy)ethoxy)propanoate (commercially available from for example Aldrich) (2.0 g, 7.2 mmol), triphenylphosphine (2.3 g, 8.6 mmol) and methyl 3-hydroxybenzoate (commercially available from for example Aldrich) (1.2 g, 7.9 mmol) in THF (40 mL) was treated dropwise over 5 minutes with diisopropyl azodicarboxylate (1.68 mL, 8.6 mmol). The mixture was warmed to ambient temperature and stirred for 18 hours. The mixture was then evaporated to dryness and purified by flash column chromatography (100 g silica cartridge) using a gradient elution from 0 to 100% methyl tert-butyl ether in cyclohexane over 40 minutes to afford the title compound (2.53 g, 85% yield). LCMS RT=1.14 min, ES+ve m/z 430 [M+NH$_4$]$^+$.

3-((14,14-dimethyl-12-oxo-3,6,9,13-tetraoxapentadecyl)oxy)benzoic acid

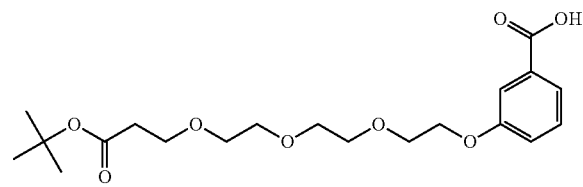 [SMILES: CC(C)(C)OC(=O)CCOCCOCCOCCOc1cccc(C(=O)O)c1]

A solution of methyl 3-((14,14-dimethyl-12-oxo-3,6,9,13-tetraoxapentadecyl)oxy)benzoate (2.53 g, 4.9 mmol) in methanol (25 mL) was treated with 1M aqueous sodium hydroxide (0.3 g, 7.6 mmol) in water (7 mL), and the mixture was stirred at ambient temperature for 1 hour. Acetic acid (0.45 mL, 7.9 mmol) was slowly added and the mixture was evaporated to dryness and purified by flash chromatography (100 g silica cartridge) using a gradient elution from 0% to 15% methanol in dichloromethane (+1% triethylamine) to afford the title compound (1.37 g, 70% yield). LCMS RT=0.99 min, ES+ve m/z 399 [M+H]$^+$.

tert-butyl ((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate

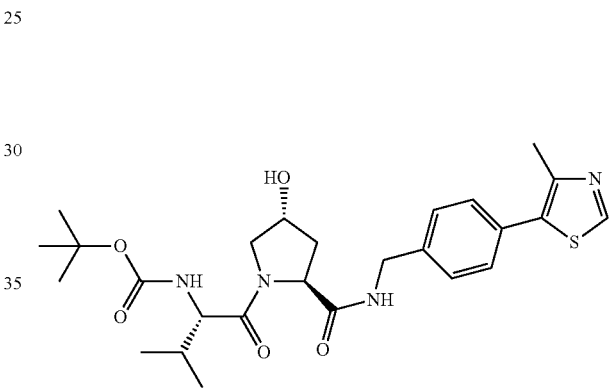

A stirred mixture of (2S,4R)-4-hydroxy-N-(4-(4-methylthiazol-5-yl)benzyl)pyrrolidine-2-carboxamide, hydrochloride (125 mg, 0.35 mmol) and (S)-2-((tert-butoxycarbonyl)amino)-3-methylbutanoic acid (commercially available from for example Aldrich) (77 mg, 0.35 mmol) in DMF (0.9 mL) was treated with DIPEA (0.22 mL, 1.3 mmol) and then with HATU (134 mg, 0.35 mmol) and the mixture was stirred at ambient temperature for 1 hour. The product was subjected to purification by mass-directed automated preparative HPLC (formic acid modifier) to afford the title compound (120 mg, 72% yield). LCMS RT=0.87 min, ES+ve m/z 517 [M+H]$^+$.

Using a method analogous to that for tert-butyl-((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate, the following compounds were prepared:

| Name | Structure | Yield | RT | [M + H]+ |
|---|---|---|---|---|
| (S)-tert-butyl 2-((2S,4R)-4-hydroxy-2-((4-(4-methylthiazol-5-yl)benzyl)carbamoyl)pyrrolidine-1-carbonyl)piperidine-1-carboxylate | 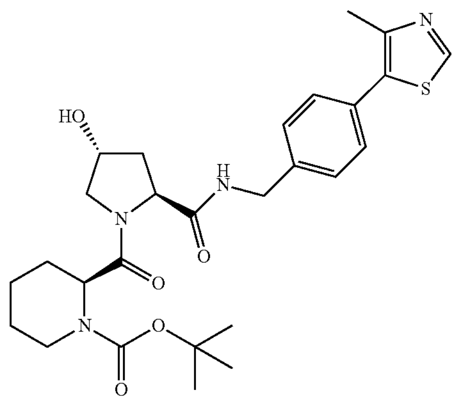 [SMILES: Cc1ncsc1-c1ccc(CNC(=O)[C@@H]2C[C@@H](O)CN2C(=O)[C@@H]2CCCCN2C(=O)OC(C)(C)C)cc1] | 67% | 0.88 min | 529 |
| (S)-tert-butyl 3-((2S,4R)-4-hydroxy-2-((4-(4-methylthiazol-5-yl)benzyl)carbamoyl)pyrrolidine-1-carbonyl)morpholine-4-carboxylate | 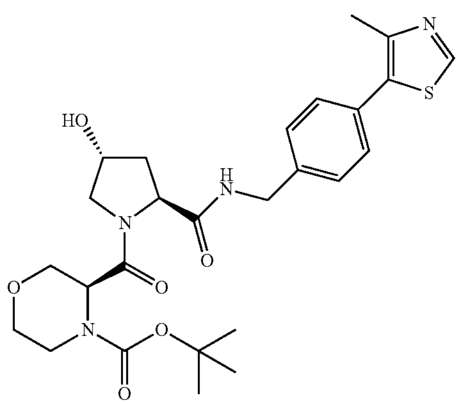 [SMILES: Cc1ncsc1-c1ccc(CNC(=O)[C@@H]2C[C@@H](O)CN2C(=O)[C@@H]2COCCN2C(=O)OC(C)(C)C)cc1] | 67% | 0.78 min | 531 |
| tert-butyl ((S)-1-((2S,4R)-4-hydroxy-2-((4-(4-methylthiazol-5-yl)benzyl)carbamoyl)pyrrolidin-1-yl)-1-oxobutan-2-yl)carbamate | 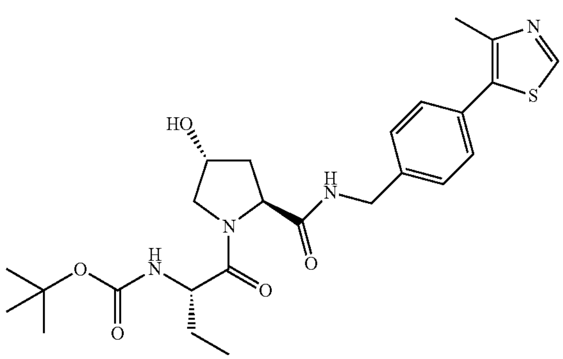 [SMILES: CC[C@H](NC(=O)OC(C)(C)C)C(=O)N1C[C@H](O)C[C@H]1C(=O)NCc1ccc(-c2scnc2C)cc1] | 85% | 0.81 min | 503 |
| tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate | 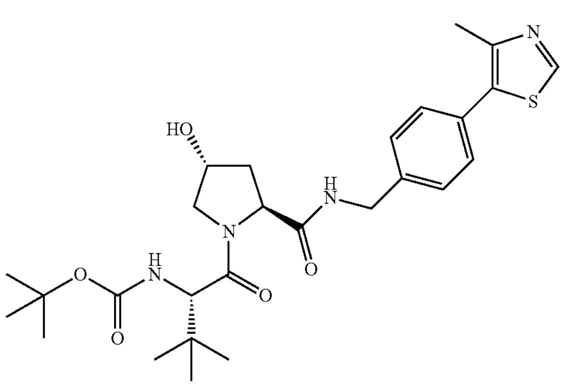 [SMILES: Cc1ncsc1-c1ccc(CNC(=O)[C@@H]2C[C@@H](O)CN2C(=O)[C@@H](NC(=O)OC(C)(C)C)C(C)(C)C)cc1] | 85% | 0.94 min | 531 |

-continued

| Name | Structure | Yield | RT | [M + H]+ |
|---|---|---|---|---|
| tert-butyl ((S)-1-cyclopropyl-2-((2S,4R)-4-hydroxy-2-((4-(4-methylthiazol-5-yl)benzyl)carbamoyl)pyrrolidin-1-yl)-2-oxoethyl)carbamate | 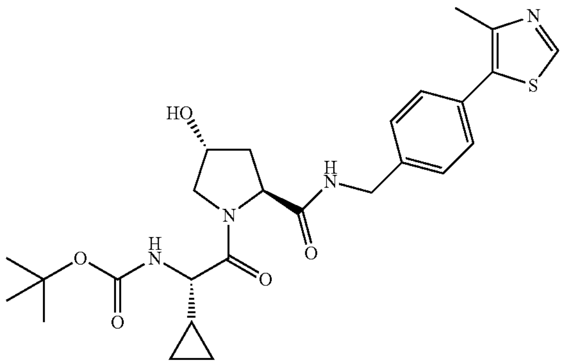 [SMILES: Cc1ncsc1-c1ccc(CNC(=O)[C@@H]2C[C@@H](O)CN2C(=O)[C@@H](NC(=O)OC(C)(C)C)C2CC2)cc1] | 82% | 0.83 min | 515 |

(2S,4R)-1-(2-aminoacetyl)-4-hydroxy-N-(4-(4-methylthiazol-5-yl)benzyl)pyrrolidine-2-carboxamide

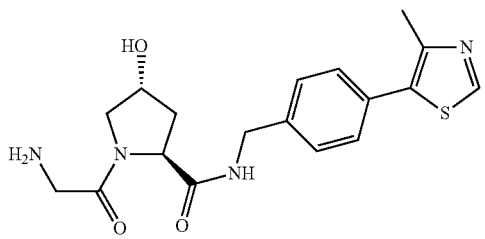 [SMILES: Cc1ncsc1-c1ccc(CNC(=O)[C@@H]2C[C@@H](O)CN2C(=O)CN)cc1]

A stirred mixture of (2S,4R)-4-hydroxy-N-(4-(4-methylthiazol-5-yl)benzyl)pyrrolidine-2-carboxamide, hydrochloride (100 mg, 0.28 mmol) and 2-((tert-butoxycarbonyl)amino)acetic acid (commercially available from for example Aldrich) (49 mg, 0.28 mmol) in DMF (3 mL) was treated with DIPEA (0.20 mL, 1.1 mmol) and then with HATU (118 mg, 0.31 mmol) and the mixture was stirred at ambient temperature for 30 minutes. Water (20 ml) was added and the product was extracted with ethyl acetate (3×20 mL). The combined organic phase was washed with saturated aqueous sodium bicarbonate (20 mL), water (20 mL), brine (20 mL) filtered through a hydrophobic frit and evaporated to dryness. The residue was then dissolved in dichloromethane (3 mL) and treated with TFA (1 mL, 13 mmol). After stirring at ambient temperature for 10 minutes, the reaction mixture was evaporated to dryness. The residue was dissolved in the minimum amount of methanol and then loaded onto a pre-conditioned (methanol) aminopropyl solid-phase extraction cartridge (5 g). The column was eluted with methanol (3 volumes) and the product-containing fractions were evaporated to dryness to afford the title compound (104 mg, 99% yield). LCMS RT=0.44 min, ES+ve m/z 375 [M+H]+.

(2S,4R)-4-hydroxy-N-(4-(4-methylthiazol-5-yl)benzyl)-1-((S)-morpholine-3-carbonyl)pyrrolidine-2-carboxamide

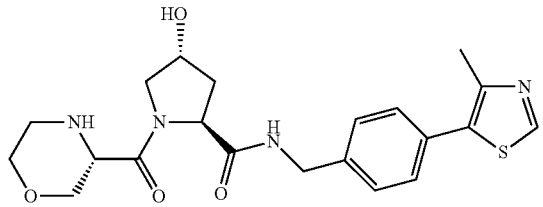 [SMILES: Cc1ncsc1-c1ccc(CNC(=O)[C@@H]2C[C@@H](O)CN2C(=O)[C@@H]2COCCN2)cc1]

A solution of (S)-tert-butyl 3-((2S,4R)-4-hydroxy-2-((4-(4-methylthiazol-5-yl)benzyl)carbamoyl)pyrrolidine-1-carbonyl)morpholine-4-carboxylate (115 mg, 0.22 mmol) in dichloromethane (0.5 mL) was treated with TFA (0.5 mL) and the reaction mixture was stirred at ambient temperature for 1 hour. The mixture was evaporated to dryness and the residue was then dissolved in the minimum amount of a mixture of methanol:dichloromethane (1:1), and loaded onto a pre-conditioned (methanol) aminopropyl solid-phase extraction cartridge (2 g). The column was eluted with methanol (3 volumes) and the product-containing fractions were evaporated under reduced pressure to afford the title compound (89 mg, 94% yield). LCMS RT=0.47 min, ES+ve m/z 431 [M+H]+.

(2S,4R)-4-hydroxy-1-((S)-3-methyl-2-(methylamino)butanoyl)-N-(4-(4-methylthiazol-5-yl)benzyl)pyrrolidine-2-carboxamide, hydrochloride

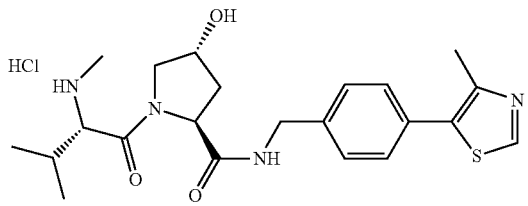 [SMILES: CN[C@H](C(=O)N1C[C@H](O)C[C@H]1C(=O)NCc1ccc(-c2scnc2C)cc1)C(C)C ; Cl]

A mixture of (2S,4R)-4-hydroxy-N-(4-(4-methylthiazol-5-yl)benzyl)pyrrolidine-2-carboxamide, hydrochloride (100 mg, 0.28 mmol), (S)-2-((tert-butoxycarbonyl)(methyl) amino)-3-methylbutanoic acid (commercially available from for example Aldrich) (65 mg, 0.28 mmol) and DIPEA (0.247 mL, 1.41 mmol) in DMF (2 mL) was treated with HATU (118 mg, 0.31 mmol) and stirred at ambient temperature for 30 minutes. The Boc protected intermediate was subjected to purification by mass-directed automated preparative HPLC (formic acid modifier). The purified intermediate was dissolved in methanol:dichloromethane (1:1, 3 mL), treated with hydrochloric acid in 1,4-dioxane (4M, 3 mL, 12 mmol) and allowed to stand for 1 hour. The mixture was then evaporated to dryness to afford the title compound (107 mg, 0.23 mmol, 81% yield). LCMS RT=0.55 min, ES+ve m/z 431 [M+H]+.

(2S,4R)-1-((S)-2-amino-3-methylbutanoyl)-4-hydroxy-N-(4-(4-methylthiazol-5-yl)benzyl)pyrrolidine-2-carboxamide, hydrochloride

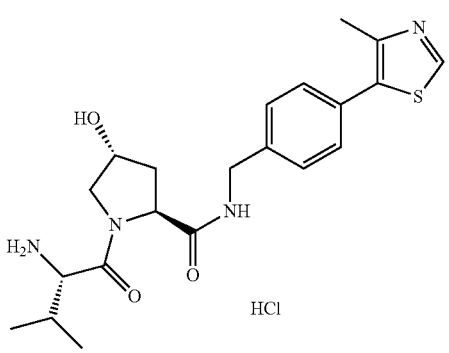 [SMILES: Cc1ncsc1-c1ccc(CNC(=O)[C@@H]2C[C@@H](O)CN2C(=O)[C@@H](N)C(C)C)cc1 ; Cl]

A solution of tert-butyl ((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate (287 mg, 0.56 mmol) in THF (5 mL) and treated with 4M hydrochloric acid in 1,4-dioxan (10 mL) and stirred at ambient temperature for 2 hours. The mixture was evaporated to dryness to afford the title compound (224 mg, 0.49 mmol, quantitative). LCMS RT=0.55 min, ES+ve m/z 417 [M+H]+.

(2S,4R)-1-((S)-2-amino-3,3-dimethylbutanoyl)-4-hydroxy-N-(4-(4-methylthiazol-5-yl)benzyl)pyrrolidine-2-carboxamide, hydrochloride

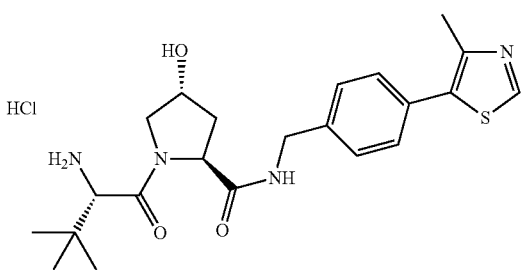 [SMILES: Cl ; Cc1ncsc1-c1ccc(CNC(=O)[C@@H]2C[C@@H](O)CN2C(=O)[C@@H](N)C(C)(C)C)cc1]

A stirred mixture of (2S,4R)-4-hydroxy-N-(4-(4-methylthiazol-5-yl)benzyl)pyrrolidine-2-carboxamide, hydrochloride (70 mg, 0.20 mmol) and (S)-2-((tert-butoxycarbonyl) amino)-3,3-dimethylbutanoic acid (commercially available from for example Fluka) (50 mg, 0.22 mmol) in DMF (1 mL) was treated with DIPEA (0.14 mL, 0.79 mmol) and then with HATU (90 mg, 0.24 mmol), and stirred at ambient temperature for 30 minutes. The product was subjected to purification by mass-directed automated preparative HPLC (formic acid modifier) to give the intermediate boc-protected product. The intermediate was then dissolved in a mixture of dichloromethane (0.5 mL) and methanol (0.1 mL) and treated with 4M hydrochloric acid in 1,4-dioxane (0.25 mL, 1.0 mmol), After stirring at ambient temperature for 1 hour, the reaction mixture was evaporated to dryness and the residue triturated to a solid with dichloromethane and dried under vacuum to afford the title compound (76 mg, 82% yield). LCMS RT=0.58 min, ES+ve m/z 431 [M+H]+.

(2S,4R)-1-((S)-2-((S)-2-amino-4-methylpentanamido)propanoyl)-4-hydroxy-N-(4-(4-methylthiazol-5-yl)benzyl)pyrrolidine-2-carboxamide, hydrochloride

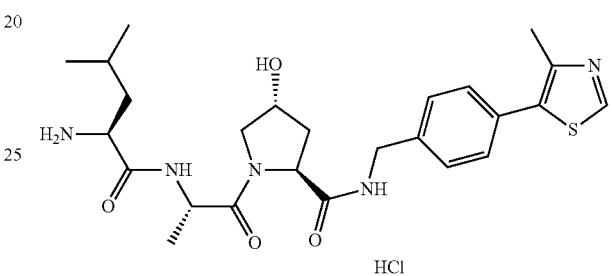

A solution of a mixture of (2S,4R)-1-((S)-2-aminopropanoyl)-4-hydroxy-N-(4-(4-methylthiazol-5-yl)benzyl)pyrrolidine-2-carboxamide, hydrochloride (507 mg, 1.2 mmol), DIPEA (0.868 mL, 4.97 mmol) and (S)-2-((tert-butoxycarbonyl)amino)-4-methylpentanoic acid (commercially available from for example Aldrich) (230 mg, 0.99 mmol) in DMF (5 mL) was treated with HATU (416 mg, 1.1 mmol) and stirred at ambient temperature for 2 hours. Water (50 mL) was added and the product was extracted with ethyl acetate (50 mL). The organic phase was washed with brine (2×50 mL), dried using a hydrophobic fit and evaporated to dryness. The residue was dissolved in methanol:dichloromethane (1:1, 15 mL), treated with hydrochloric acid in 1,4-dioxane (4M, 5 mL, 20 mmol) and stirred at ambient temperature for 3 hours. The mixture was evaporated to dryness and the residue was suspended in dichloromethane (10 mL), sonicated, filtered and dried under vacuum to afford the title compound (280 mg, 0.56 mmol, 56% yield). LCMS RT=0.55 min, ES+ve m/z 502 [M+H]+.

(2S,4R)-tert-butyl 2-((4-(2,4-dimethylthiazol-5-yl) benzyl)carbamoyl)-4-hydroxypyrrolidine-1-carboxylate

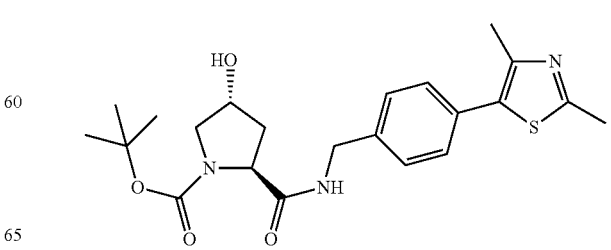

Under an atmosphere of nitrogen, a mixture of (2S,4R)-tert-butyl 24(4-bromobenzyl)carbamoyl)-4-hydroxypyrrolidine-1-carboxylate (200 mg, 0.50 mmol), 2,4-dimethylthiazole (commercially available from for example Avocado) (113 mg, 1.0 mmol), palladium(II) acetate (commercially available from for example Aldrich) (2 mg, 10 μmol) and potassium acetate (98 mg, 1.0 mmol) in N-methyl-2-pyrrolidone (2 mL) was stirred at 120° C. for 18 hours. The cooled mixture was treated with water (25 ml) and the product was extracted with ethyl acetate (4×30 mL). The combined organic phase was washed with brine (5×20 mL), filtered through a hydrophobic fit and evaporated to dryness. The product was subjected to purification by mass-directed automated preparative HPLC (formic acid modifier) to afford the title compound (142 mg, 66% yield). LCMS RT=0.77 min, ES+ve m/z 432 [M+H]$^+$.

(2S,4R)—N-(4-(2,4-dimethylthiazol-5-yl)benzyl)-4-hydroxypyrrolidine-2-carboxamide, hydrochloride

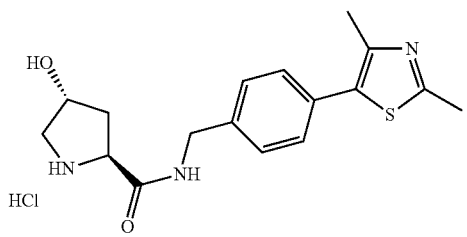 [SMILES: Cl ; Cc1nc(C)c(-c2ccc(CNC(=O)[C@@H]3C[C@@H](O)CN3)cc2)s1]

A solution of (2S,4R)-tert-butyl 2-((4-(2,4-dimethylthiazol-5-yl)benzyl)carbamoyl)-4-hydroxypyrrolidine-1-carboxylate (142 mg, 0.33 mmol) in a mixture of methanol (0.5 mL) and dichloromethane (1.5 mL) was treated with 4M hydrochloric acid in 1,4-dioxane (0.63 mL, 2.5 mmol) and stirred at ambient temperature for 2 hours. The solvent was evaporated to dryness and the residue was triturated to a solid with diethyl ether and dried under vacuum to afford the title compound (120 mg, 99% yield). LCMS RT=0.49 min, ES+ve m/z 332 [M+H]$^+$.

(S)-3-methyl-2-(3-methyl-2,5-dioxo-2,5-dihydro-1H-pyrrol-1-yl)butanoic acid

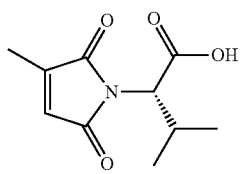

A mixture of 3-methylfuran-2,5-dione (commercially available from for example Aldrich) (0.12 mL, 1.3 mmol) and (S)-2-amino-3-methylbutanoic acid (commercially available from for example Apollo Scientific) (150 mg, 1.3 mmol). in acetic acid (1 mL) was sealed and heated in a Biotage "Initiator" microwave at 120° C. for 1 hour. The mixture was evaporated to dryness to afford the title compound (253 mg, 94% yield). LCMS RT=0.75 min, ES+ve m/z 212 [M+H]$^+$ benzyl 2-(3-oxomorpholino)propanoate

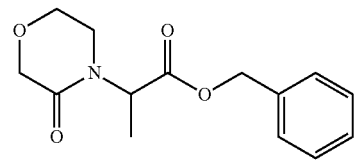 [SMILES: CC(C(=O)OCc1ccccc1)N1CCOCC1=O]

Under an atmosphere of nitrogen, an ice-cooled solution of morpholin-3-one (commercially available from for example Aldrich) (100 mg, 1.0 mmol) in DMF (2 mL) was treated with sodium hydride (60% w/w in mineral oil) (40 mg, 1.0 mmol). After 5 minutes, benzyl 2-bromopropanoate (commercially available from for example Aldrich) (240 mg, 1.0 mmol) was added and the mixture was stirred with cooling for 30 minutes and then at ambient temperature for a further 18 hours. The reaction mixture was cautiously treated with saturated aqueous sodium bicarbonate (10 mL) and then extracted with ethyl acetate (2×40 mL). The combined organic phase was washed with brine (25 mL), filtered through a hydrophobic frit, and evaporated to dryness. The product was subjected to purification by mass-directed automated preparative HPLC (formic acid modifier) to give the title compound (105 mg, 40% yield). LCMS RT=0.80 min, ES+ve m/z 264 [M+H]$^+$.

2-(3-oxomorpholino)propanoic acid

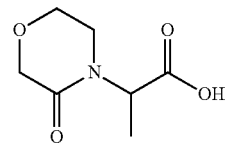

Under an atmosphere of nitrogen, a solution of benzyl 2-(3-oxomorpholino)propanoate (90 mg, 0.34 mmol) in ethanol (3 mL) was added to a flask containing palladium on carbon (36 mg, 0.034 mmol) (10%, Degussa type). The flask was then filled with hydrogen and the mixture was stirred at ambient temperature for 1 hour. The catalyst was removed by filtration through celite and the filtrate was evaporated under reduced pressure to afford the title compound (55 mg, 93% yield). LCMS RT=0.33 min, ES+ve m/z 174 [M+H]$^+$.

tert-butyl 4-(1-(benzyloxy)-1-oxopropan-2-yl)-3-oxopiperazine-1-carboxylate

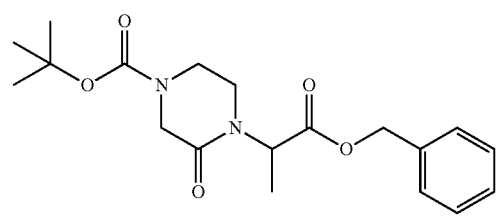 [SMILES: CC(C(=O)OCc1ccccc1)N1CCN(C(=O)OC(C)(C)C)CC1=O]

Under an atmosphere of nitrogen, an ice-cooled solution of tert-butyl 3-oxopiperazine-1-carboxylate (commercially available from for example Aldrich) (200 mg, 1.0 mmol) in DMF (4 mL) was treated with sodium hydride (60% w/w in mineral oil) (44 mg, 1.1 mmol). After 5 minutes, benzyl 2-bromopropanoate (commercially available from for example Aldrich) (255 mg, 1.05 mmol) was added. The mixture was stirred at 0° C. for 30 minutes and then at ambient temperature for a further 18 hours. The mixture was cautiously treated with saturated aqueous sodium bicarbonate (20 mL) and then extracted with ethyl acetate (2×40 mL). The combined organic phase was washed with brine (25 mL), filtered through a hydrophobic frit, and evaporated to dryness. The product was purified by flash column chromatography (20 g silica cartridge) using a gradient elution from 0% to 100% ethyl acetate in cyclohexane to afford the title compound (230 mg, 64% yield). LCMS RT=1.05 min, ES+ve m/z 363 [M+H]+.

2-(4-(tert-butoxycarbonyl)-2-oxopiperazin-1-yl)propanoic acid

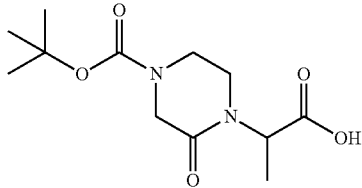 [SMILES: CC(C(=O)O)N1CCN(C(=O)OC(C)(C)C)CC1=O]

Under an atmosphere of nitrogen, a solution of tert-butyl 4-(1-(benzyloxy)-1-oxopropan-2-yl)-3-oxopiperazine-1-carboxylate (230 mg, 0.64 mmol) in ethanol (3 mL) was added to a flask containing palladium on carbon (68 mg, 0.063 mmol) (10%, Degussa type). The flask was filled with hydrogen and the mixture was stirred at ambient temperature for 1 hour. The catalyst was removed by filtration through celite and the filtrate was evaporated under reduced pressure to afford the title compound (171 mg, 99% yield). LCMS RT=0.62 min, ES+ve m/z 290 [M+H]+.

tert-butyl 4-(2-oxo-2,3-dihydrobenzo[d]oxazol-5-yl)benzylcarbamate

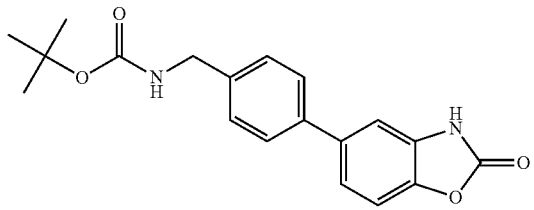 [SMILES: CC(C)(C)OC(=O)NCc1ccc(-c2ccc3oc(=O)[nH]c3c2)cc1]

Under an atmosphere of nitrogen, a mixture of (4-(((tert-butoxycarbonyl)amino)methyl)phenyl)boronic acid (commercially available from for example Aldrich) (387 mg, 1.54 mmol), 5-bromobenzo[d]oxazol-2(3H)-one (commercially available from for example Aldrich) (300 mg, 1.40 mmol) and sodium carbonate (446 mg, 4.21 mmol) in DMF (4 mL) was treated with dicholoro[1,1'-bis(diphenylphosphino)ferrocene]palladium(II) (commercially available from for example Aldrich) (72 mg, 0.098 mmol) then sealed and heated in a Biotage "Initiator" microwave at 110° C. for 1 hr. The cooled product mixture was treated with dichloromethane (50 mL) and water (10 mL). The mixture was separated and the organic fraction was evaporated to dryness. The product was subjected to purification by mass-directed automated preparative HPLC (formic acid modifier) to afford the title compound (178 mg, 0.52 mmol, 37% yield). LCMS RT=1.03 min, ES+ve m/z 341 [M+H]+.

5-(4-(aminomethyl)phenyl)benzo[d]oxazol-2(3H)-one, hydrochloride

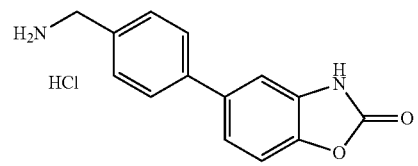 [SMILES: NCc1ccc(-c2ccc3oc(=O)[nH]c3c2)cc1 ; Cl]

A solution of tert-butyl 4-(2-oxo-2,3-dihydrobenzo[d]oxazol-5-yl)benzylcarbamate (130 mg, 0.38 mmol) in THF (10 mL) was treated with hydrochloric acid (4M in 1,4-dioxan) (1 mL, 4 mmol) and the mixture was stirred at ambient temperature overnight. The mixture was treated with diethyl ether (40 mL); the resulting precipitate was filtered off and dried under vacuum to afford the title compound (87 mg, 0.31 mmol, 82% yield). LCMS RT=0.49 min, ES+ve m/z 241 [M+H]+.

(2S,4R)-4-hydroxy-1-(3-hydroxybenzoyl)-N-(4-(4-methylthiazol-5-yl)benzyl)pyrrolidine-2-carboxamide

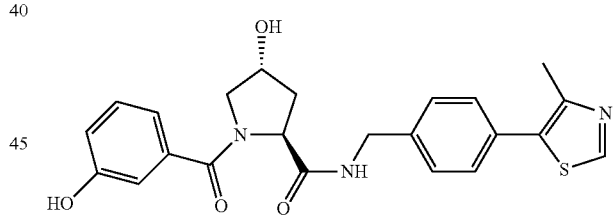

An ice-cooled solution of (2S,4R)-4-hydroxy-N-(4-(4-methylthiazol-5-yl)benzyl)pyrrolidine-2-carboxamide, hydrochloride (217 mg, 0.61 mmol), 3-hydroxybenzoic acid (85 mg, 0.61 mmol) and DIPEA (0.321 mL, 1.84 mmol) in DMF (4 mL) was treated portion-wise with HATU (240 mg, 0.63 mmol) over 1 minute and then stirred at ambient temperature for 1 hour. The mixture was treated with saturated aqueous sodium bicarbonate (20 mL) and extracted with ethyl acetate (3×20 mL). The combined organic phase was washed with brine (3×30 mL), filtered through a hydrophobic frit and then evaporated to dryness. The product was purified by flash chromatography (50 g silica cartridge) using a gradient elution from 0 to 25% methanol in dichloromethane to afford the title compound (234 mg, 0.53 mmol, 87% yield). LCMS RT=0.49 min, ES+ve m/z 241 [M+H]+.

(S)-2-(1-oxoisoindolin-2-yl)propanoic acid

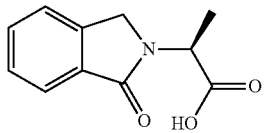

A mixture of phthalaldehyde (commercially available from for example Aldrich) (4 g, 30 mmol) and (S)-2-aminopropanoic acid (commercially available from for example Aldrich) (2.39 g, 27 mmol) in acetonitrile (150 mL) was heated at reflux for 5 hr then allowed to cool to ambient temperature and stood overnight. The resulting crystalline precipitate was filtered off, washed with acetonitrile and dried under vacuum to afford the title compound (4.46 g, 22 mmol, 73% yield). LCMS RT=0.59 min, ES+ve m/z 206 [M+H]+.

Using a method analogous to that for (S)-2-(1-oxoisoindolin-2-yl)propanoic acid, the following compounds were prepared:

| Name | Structure | Yield | RT | [M + H]+ |
|---|---|---|---|---|
| (S)-4-methoxy-2-(1-oxoisoindolin-2-yl)butanoic acid | 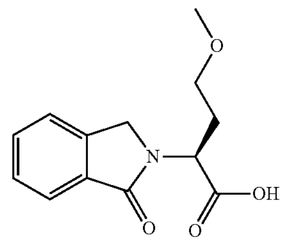 [SMILES: COCC[C@@H](C(=O)O)N1Cc2ccccc2C1=O] | 46% | 0.62 min | 250 |
| (S)-2-(1-oxoisoindolin-2-yl)butanoic acid | 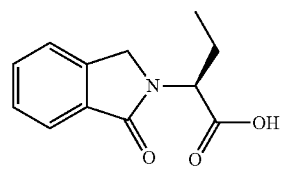 [SMILES: CC[C@@H](C(=O)O)N1Cc2ccccc2C1=O] | 60% | 0.67 min | 220 |
| (S)-2-(1-oxoisoindolin-2-yl)pentanoic acid | 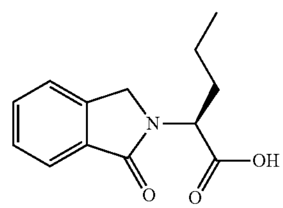 [SMILES: CCC[C@@H](C(=O)O)N1Cc2ccccc2C1=O] | 60% | 0.77 min | 234 |
| (S)-2-cyclopropyl-2-(1-oxoisoindolin-2-yl)acetic acid | 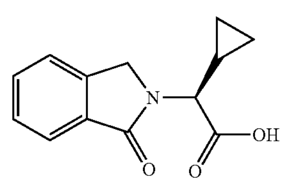 [SMILES: O=C(O)[C@H](C1CC1)N1Cc2ccccc2C1=O] | 54% | 0.69 min | 232 |
| (S)-3-methyl-2-(1-oxoisoindolin-2-yl)butanoic acid | 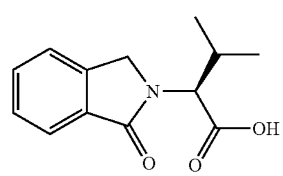 | 59% | 0.74 min | 234 |
| (S)-3,3-dimethyl-2-(1-oxoisoindolin-2-yl)butanoic acid | 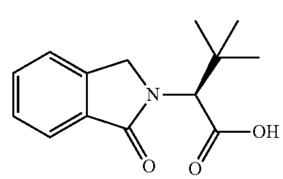 [SMILES: CC(C)(C)[C@@H](C(=O)O)N1Cc2ccccc2C1=O] | 69% | 0.82 min | 248 |

Ethyl 2-(5-methoxy-1-oxoisoindolin-2-yl)-3-methylbutanoate

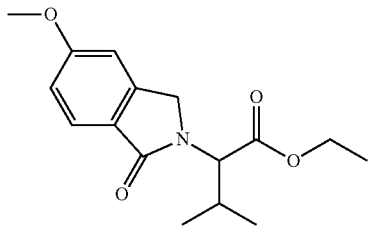 [SMILES: CCOC(=O)C(C(C)C)N1Cc2cc(OC)ccc2C1=O]

Under an atmosphere of nitrogen, an ice-cooled solution of 5-methoxyisoindolin-1-one (commercially available from for example Chem Impex) (105 mg, 0.64 mmol) in DMF (2.5 mL) was treated with sodium hydride (60% w/w in mineral oil) (31 mg, 0.77 mmol). The mixture was warmed to ambient temperature, treated with ethyl 2-bromo-3-methylbutanoate (commercially available from for example Alfa Aesar) (135 mg, 0.64 mmol), stirred at ambient temperature for 2 hours and then heated to 70° C. for a further 18 hours. The mixture was then ice-cooled and treated with additional sodium hydride (60% w/w in mineral oil) (31 mg, 0.77 mmol), followed by ethyl 2-bromo-3-methylbutanoate (135 mg, 0.64 mmol) and stirred at 70° C. for a further 24 hours. The cooled mixture was then cautiously treated with saturated aqueous ammonium chloride (20 mL) and the product was extracted with ethyl acetate (2×25 mL). The combined organic phase was washed with water (20 mL), brine (20 mL), filtered through a hydrophobic fit and evaporated to dryness. The product was purified by flash chromatography (20 g silica cartridge) using a gradient elution from 0% to 50% ethyl acetate in cyclohexane to afford the title compound (44 mg, 23% yield). LCMS RT=1.01 min, ES+ve m/z 292 [M+H]+

Ethyl 2-(6-methoxy-1-oxoisoindolin-2-yl)-3-methylbutanoate

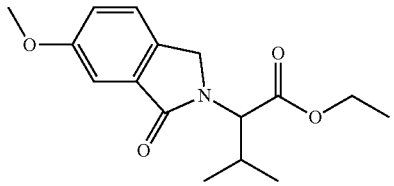 [SMILES: CCOC(=O)C(C(C)C)N1Cc2ccc(OC)cc2C1=O]

Under an atmosphere of nitrogen, an ice-cooled solution of 6-methoxyisoindolin-1-one (commercially available from for example Astatech) (105 mg, 0.64 mmol) in DMF (2.5 mL) was treated with sodium hydride (60% w/w in mineral oil) (31 mg, 0.77 mmol) and the mixture was allowed to warm to ambient temperature. The mixture was then treated with ethyl 2-bromo-3-methylbutanoate (commercially available from for example Alfa Aesar) (135 mg, 0.64 mmol) and the mixture was stirred for 18 hours then cautiously treated with saturated aqueous ammonium chloride (20 mL). The product was extracted with ethyl acetate (2×25 mL) and the combined organic phase was washed with water (20 mL), brine (20 mL), filtered through a hydrophobic fit and evaporated to dryness. The product was purified by flash chromatography (20 g silica cartridge) using a gradient elution from 0 to 50% ethyl acetate in cyclohexane to afford the title compound (40 mg, 21% yield). LCMS RT=1.03 min, ES+ve m/z 292 [M+H]+

2-(6-methoxy-1-oxoisoindolin-2-yl)-3-methylbutanoic acid

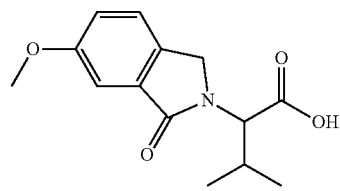 [SMILES: COc1ccc2c(c1)C(=O)N(C(C(=O)O)C(C)C)C2]

A solution of ethyl 2-(6-methoxy-1-oxoisoindolin-2-yl)-3-methylbutanoate (40 mg, 0.14 mmol) in ethanol (0.4 mL) was treated with 2M aqueous sodium hydroxide (0.20 mL, 0.41 mmol) and the mixture was stirred at ambient temperature for 2 hours. The reaction mixture was evaporated to dryness, treated with water (10 mL) and acidified to pH 3 using 2M aqueous hydrochloric acid. The product was extracted with ethyl acetate (2×10 mL), and the combined organic phase was filtered through a hydrophobic frit and evaporated to dryness to afford the title compound (34 mg, 94% yield). LCMS RT=0.80 min, ES+ve m/z 264 [M+H]+.

2-(5-methoxy-1-oxoisoindolin-2-yl)-3-methylbutanoic acid

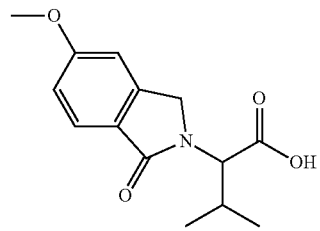 [SMILES: COc1ccc2c(c1)CN(C(C(=O)O)C(C)C)C2=O]

A solution of ethyl 2-(5-methoxy-1-oxoisoindolin-2-yl)-3-methylbutanoate (40 mg, 0.14 mmol) in ethanol (0.4 mL) was treated with 2M aqueous sodium hydroxide (0.20 mL, 0.41 mmol) and the mixture was stirred at ambient temperature for 2 hours. The mixture was then evaporated to dryness; the residue was treated with water (10 mL) and acidified to pH 3 using 2M aqueous hydrochloric acid. The product was extracted with ethyl acetate (2×10 mL), and the combined organic phase was filtered through a hydrophobic frit and evaporated to dryness to afford the title compound (33 mg, 93% yield). LCMS RT=0.76 min, ES+ve m/z 264 [M+H]+.

Ethyl 2-(7-chloro-1-oxoisoindolin-2-yl)-3-methylbutanoate

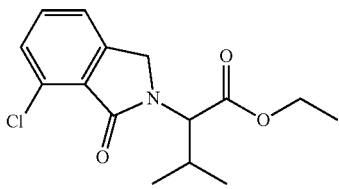 [SMILES: CCOC(=O)C(C(C)C)N1Cc2cccc(Cl)c2C1=O]

Under a nitrogen atmosphere, an ice-cooled solution of 7-chloroisoindolin-1-one (commercially available from for example JW Pharm) (150 mg, 0.90 mmol) in DMF (2.5 mL) was treated with sodium hydride (60% w/w in mineral oil) (50 mg, 1.25 mmol). The mixture was allowed to warm to ambient temperature, then treated with ethyl 2-bromo-3-methylbutanoate (commercially available from for example Alfa Aesar) (187 mg, 0.90 mmol) and stirred for 5 hours. The mixture was then ice-cooled, treated with additional sodium hydride (60% w/w in mineral oil) (50 mg, 1.25 mmol) and ethyl 2-bromo-3-methylbutanoate (187 mg, 0.90 mmol) and the mixture was stirred at ambient temperature for a further 24 hours. The mixture was then cautiously treated with saturated aqueous ammonium chloride (20 mL), and the product was extracted with ethyl acetate (2×25 mL). The combined organic phase was washed with water (20 mL), brine (20 mL), filtered through a hydrophobic fit and evaporated to dryness. The product was purified by flash chromatography (20 g silica cartridge) using a gradient elution from 0 to 50% ethyl acetate in cyclohexane to afford the title compound (40 mg, 15% yield). LCMS RT=1.07 min, ES+ve m/z 296 [M+H]$^+$.

2-(7-chloro-1-oxoisoindolin-2-yl)-3-methylbutanoic acid

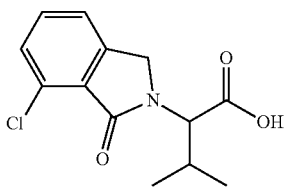 [SMILES: CC(C)C(C(=O)O)N1Cc2cccc(Cl)c2C1=O]

A solution of ethyl 2-(7-chloro-1-oxoisoindolin-2-yl)-3-methylbutanoate (40 mg, 0.14 mmol) in ethanol (0.4 mL) was treated with 2M aqueous sodium hydroxide (0.22 mL, 0.45 mmol) and the mixture was stirred at ambient temperature for 2 hours. The mixture was then evaporated to dryness, treated with water (10 mL) and then acidified to pH 3 using 2M aqueous hydrochloric acid. The product was extracted with ethyl acetate (2×10 mL) and the combined organic phase was filtered through a hydrophobic frit and evaporated to dryness to afford the title compound (34 mg, 94% yield). LCMS RT=0.82 min, ES+ve m/z 268 [M+H]$^+$.

2-Hydroxy-4-(4-methylthiazol-5-yl)benzonitrile

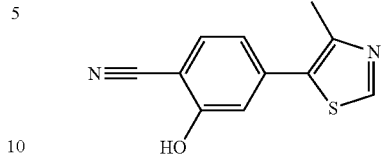

Under an atmosphere of nitrogen, a mixture of 4-bromo-2-hydroxybenzonitrile (commercially available from for example Fluorochem) (15 g, 76 mmol), 4-methylthiazole (commercially available from for example Aldrich) (14 mL, 152 mmol), potassium acetate (14.9 g, 152 mmol) and palladium(II) acetate (0.34 g, 1.52 mmol) in 1-methyl-2-pyrrolidone (125 mL) was heated at 110° C. for 3 hours. The mixture was then cooled to 50° C., poured into water (300 mL) and extracted with ethyl acetate (3×350 mL). The combined organic fraction was filtered and the filtrate was then washed with brine (3×400 mL), filtered through a hydrophobic frit and evaporated to dryness. The residue was re-evaporated from toluene then from diethyl ether and then slurried in methanol to precipitate a yellow solid which was filtered off. The filtrate was evaporated to dryness and slurried in ice-cooled methanol to afford a second batch of yellow solid. The combined solid was dried under vacuum to afford the title compound (12 g, 56 mmol, 73% yield). LCMS RT=0.75 min, ES+ve m/z 217 [M+H]$^+$.

2-(Aminomethyl)-5-(4-methylthiazol-5-yl)phenol

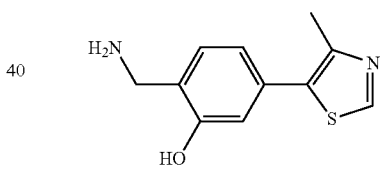

An ice-cooled solution of 2-hydroxy-4-(4-methylthiazol-5-yl)benzonitrile (12 g, 56 mmol) in THF (550 mL) was treated dropwise with lithium aluminium hydride (1M in THF, 140 mL, 140 mmol) over 5 minutes. The resulting mixture was then heated at 50° C. for 30 minutes and additional lithium aluminium hydride (1M in THF, 20 mL, 20 mmol) was added. After a further 30 minutes the mixture was cooled in an ice bath and treated cautiously with water (14 mL), followed by aqueous sodium hydroxide (4M, 42 mL, 168 mmol) and finally water (14 mL). After standing for 3 days, the mixture was filtered and the filtered solid was washed with THF. The combined filtrate was evaporated to dryness and the residue was slurried in dichloromethane:methanol (4:1) with Celite (about 20 g) and filtered. The filtered solid was washed three times with dichloromethane/methanol (4:1) and the combined filtrate was evaporated to dryness. The product was purified by flash chromatography (330 g silica cartridge) using a gradient elution from 0 to 15% methanol in dichloromethane (+1% triethylamine) to afford the title compound (6.2 g, 28 mmol, 51% yield). LCMS RT=0.41 min, ES+ve m/z 221 [M+H]$^+$.

(2S,4R)-tert-Butyl 4-hydroxy-2-((2-hydroxy-4-(4-methylthiazol-5-yl)benzyl)carbamoyl)pyrrolidine-1-carboxylate

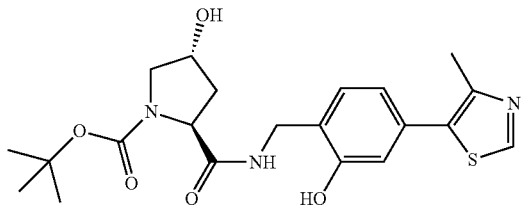 [SMILES: Cc1ncsc1-c1ccc(CNC(=O)[C@@H]2C[C@@H](O)CN2C(=O)OC(C)(C)C)c(O)c1]

An ice-cooled solution of 2-(aminomethyl)-5-(4-methylthiazol-5-yl)phenol (3.05 g, 13.8 mmol) and (2S,4R)-1-(tert-butoxycarbonyl)-4-hydroxypyrrolidine-2-carboxylic acid (2.94 mL, 13.8 mmol) in DMF (35 mL) was treated with DIPEA (7.25 mL, 42 mmol) followed by HATU (5.79 g, 15.2 mmol) and the mixture was stirred at ambient temperature for 1 hour. The mixture was treated with saturated aqueous sodium bicarbonate (50 mL) and extracted with ethyl acetate (3×80 mL). The combined organic phase was washed with brine (60 mL), filtered through a hydrophobic fit and evaporated to dryness. The product was purified by flash chromatography (330 g silica cartridge) using a gradient from 0 to 15% methanol in dichloromethane to afford the title product (4.8 g, 11 mmol, 80% yield). LCMS RT=0.76 min, ES+ve m/z 434 [M+H]⁺.

(2S,4R)-4-Hydroxy-N-(2-hydroxy-4-(4-methylthiazol-5-yl)benzyl)pyrrolidine-2-carboxamide, hydrochloride

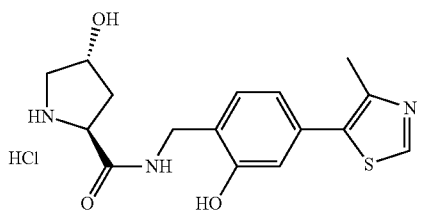 [SMILES: Cl ; Cc1ncsc1-c1ccc(CNC(=O)[C@@H]2C[C@@H](O)CN2)c(O)c1]

A solution of (2S,4R)-tert-butyl 4-hydroxy-2-((2-hydroxy-4-(4-methylthiazol-5-yl)benzyl)carbamoyl)pyrrolidine-1-carboxylate (4.8 g, 11 mmol) in dichloromethane:methanol 20:1 (50 mL) was treated with hydrochloric acid (4M in 1,4-dioxane) (35 mL, 140 mmol) and the mixture was stirred overnight at ambient temperature. The mixture was then evaporated to dryness and the residual solid was suspended in dichloromethane and filtered. The filtered solid was washed with further dichloromethane and dried under vacuum to afford the title compound (4 g, 10.8 mmol, 98% yield). LCMS RT=0.46 min, ES+ve m/z 334 [M+H]⁺.

(2S,4R)-1-((S)-2-Aminopropanoyl)-4-hydroxy-N-(4-(4-methylthiazol-5-yl)benzyl)pyrrolidine-2-carboxamide, hydrochloride

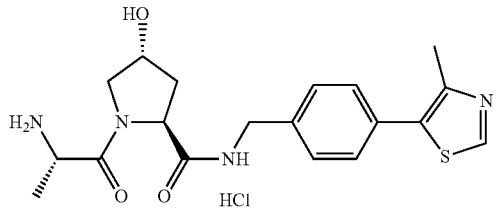 [SMILES: Cc1ncsc1-c1ccc(CNC(=O)[C@@H]2C[C@@H](O)CN2C(=O)[C@H](C)N)cc1 ; Cl]

A stirred mixture of (2S,4R)-4-hydroxy-N-(4-(4-methylthiazol-5-yl)benzyl)pyrrolidine-2-carboxamide, hydrochloride (100 mg, 0.28 mmol), (S)-2-((tert-butoxycarbonyl)amino)propanoic acid (commercially available from for example Aldrich) (64 mg, 0.34 mmol) and DIPEA (0.197 mL, 1.13 mmol) in dry DMF (3 mL) was treated with HATU (129 mg, 0.34 mmol and stirred at ambient temperature for 30 minutes. The mixture was then partitioned between ethyl acetate (30 mL) and water (30 mL) and the organic phase was washed with brine (30 mL), dried (hydrophobic frit) and evaporated to dryness. The residue was dissolved in methanol and added to a methanol-preconditioned aminopropyl solid-phase extraction cartridge (2 g) eluting with methanol (3 column volumes). The resulting eluant was evaporated to dryness and the residue was dissolved in dichloromethane:methanol (1:1, 8 mL) and treated with hydrochloric acid, (4M in 1,4-dioxane) (1 mL, 4 mmol). The mixture was stirred at ambient temperature for 16 hours and then evaporated to dryness to afford the title compound (107 mg, 0.25 mmol, 89% yield). LCMS RT=0.51 min, ES+ve m/z 389 [M+H]⁺.

(2S,4R)-1-(2-Amino-2-methylpropanoyl)-4-hydroxy-N-(4-(4-methylthiazol-5-yl)benzyl)pyrrolidine-2-carboxamide

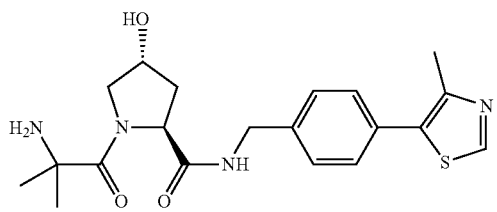 [SMILES: Cc1ncsc1-c1ccc(CNC(=O)[C@@H]2C[C@@H](O)CN2C(=O)C(C)(C)N)cc1]

A solution of a mixture of (2S,4R)-4-hydroxy-N-(4-(4-methylthiazol-5-yl)benzyl)pyrrolidine-2-carboxamide, hydrochloride (100 mg, 0.28 mmol), 2-((tert-butoxycarbonyl)amino)-2-methylpropanoic acid (commercially available from for example Aldrich) (69 mg, 0.34 mmol) and DIPEA (0.197 mL, 1.13 mmol) in dry DMF (3 mL) was treated with HATU (129 mg, 0.34 mmol, stirred at ambient temperature for 30 minutes and then partitioned between ethyl acetate (30 mL) and water (30 mL). The organic phase was washed with brine (30 mL), dried (hydrophobic fit) and evaporated to dryness. The residue was dissolved in methanol and added to a methanol-preconditioned aminopropyl solid-phase extraction cartridge (2 g) eluting with methanol. The resulting eluant was evaporated to dryness and the residue was dissolved in dichloromethane:methanol (1:1, 8 mL) and treated with hydrochloric acid, 4M in 1,4-dioxane (1 mL, 4 mmol). The reaction mixture was stirred at ambient temperature for 16 hours and then evaporated to dryness. The residue was suspended in dichloromethane (4 mL) and treated with TFA (1 mL) and the mixture was stirred at ambient temperature for 4 hours. The mixture was evaporated to dryness and the residue was dissolved in methanol and added to a methanol-preconditioned sulfonic acid solid-phase extraction cartridge (2 g) and eluted with methanol (3 column volumes) and then with ammonia in methanol (2M, 3 column volumes). The product-containing fractions were evaporated to dryness to afford the title compound (95 mg, 0.24 mmol, 84% yield). LCMS RT=0.53 min, ES+ve m/z 403 [M+H]+.

(2S,4R)-4-Hydroxy-1-((S)-2-(methylamino)propanoyl)-N-(4-(4-methylthiazol-5-yl)benzyl)pyrrolidine-2-carboxamide

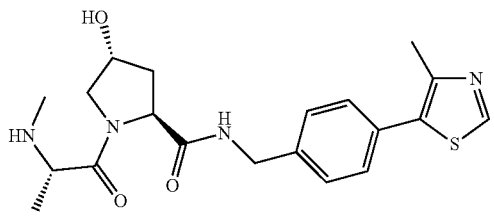 [SMILES: CN[C@@H](C)C(=O)N1C[C@H](O)C[C@H]1C(=O)NCc1ccc(-c2scnc2C)cc1]

A stirred mixture of (2S,4R)-4-hydroxy-N-(4-(4-methylthiazol-5-yl)benzyl)pyrrolidine-2-carboxamide, hydrochloride (120 mg, 0.34 mmol) and (S)-2-((tert-butoxycarbonyl)(methyl)amino)propanoic acid (commercially available from for example Aldrich) (76 mg, 0.37 mmol) in DMF (2 mL) was treated with DIPEA (0.24 mL, 1.36 mmol) and then with HATU (155 mg, 0.41 mmol), and the mixture was stirred at ambient temperature for 30 minutes. The crude product was subjected to purification by mass-directed automated preparative HPLC (formic acid modifier) to give the intermediate Boc-protected product. The intermediate was suspended in dichloromethane (0.5 mL) and treated with TFA (0.5 mL). The mixture was stirred at ambient temperature for 1 hour and was then evaporated to dryness. The residue was dissolved in the minimum amount of a mixture of methanol:dichloromethane (1:1), and then loaded onto a pre-conditioned (methanol) aminopropyl solid-phase extraction cartridge (5 g). The column was eluted with methanol (3 volumes) and the product-containing fractions were combined and evaporated to dryness to afford the title compound (103 mg, 75% yield). LCMS RT=0.47 min, ES+ve m/z 403 [M+H]+.

(2S,4R)-4-Hydroxy-N-(4-(4-methylthiazol-5-yl)benzyl)-1-((S)-morpholine-3-carbonyl)pyrrolidine-2-carboxamide, hydrochloride

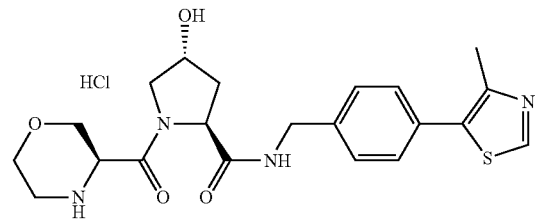 [SMILES: Cc1ncsc1-c1ccc(CNC(=O)[C@@H]2C[C@@H](O)CN2C(=O)[C@@H]2COCCN2)cc1 ; Cl]

A mixture of (2S,4R)-4-hydroxy-N-(4-(4-methylthiazol-5-yl)benzyl)pyrrolidine-2-carboxamide, hydrochloride (100 mg, 0.28 mmol), (S)-4-(tert-butoxycarbonyl)morpholine-3-carboxylic acid (commercially available from for example Astatech) (65 mg, 0.28 mmol) and DIPEA (0.247 mL, 1.41 mmol) in DMF (2 mL) was treated with HATU (118 mg, 0.311 mmol) and stirred at ambient temperature for 30 minutes. The Boc protected intermediate was subjected to purification by mass-directed automated preparative HPLC (formic acid modifier). The intermediate was dissolved in methanol:dichloromethane (1:1, 3 mL), treated with hydrochloric acid in 1,4-dioxane (4M, 3 mL, 12 mmol) and allowed to stand for 1 hour. The mixture was evaporated to dryness to afford the title compound (110 mg, 0.24 mmol, 83% yield). LCMS RT=0.50 min, ES+ve m/z 431/432 [M+H]+.

Tert-butyl 4-(3-((2S,4R)-4-hydroxy-2-((4-(4-methylthiazol-5-yl)benzyl)carbamoyl)pyrrolidine-1-carbonyl)phenoxy)butanoate

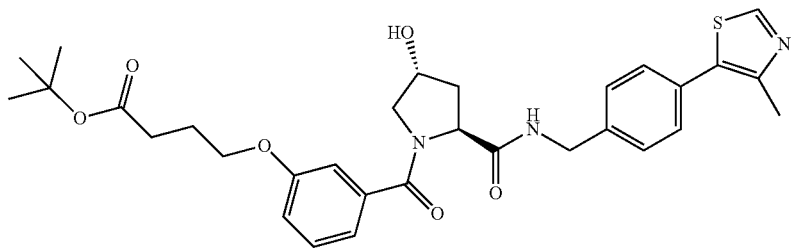 [SMILES: Cc1ncsc1-c1ccc(CNC(=O)[C@@H]2C[C@@H](O)CN2C(=O)c2cccc(OCCCC(=O)OC(C)(C)C)c2)cc1]

A solution of a mixture of 3-(4-(tert-butoxy)-4-oxobutoxy) benzoic acid (95 mg, 0.34 mmol), (2S,4R)-4-hydroxy-N-(4-(4-methylthiazol-5-yl)benzyl)pyrrolidine-2-carboxamide, hydrochloride (100 mg, 0.28 mmol) and DIPEA (0.2 mL, 1.15 mmol) in dry DMF (3 mL) was treated with HATU (129 mg, 0.34 mmol) and the mixture was stirred at ambient temperature for 30 minutes. The mixture was added to an aminopropyl solid-phase extraction cartridge and eluted with methanol (3 column volumes). The resulting eluant was evaporated to dryness and the product was subjected to purification by mass-directed automated preparative HPLC (formic acid modifier) to afford the title compound (130 mg, 0.22 mmol, 79% yield). LCMS RT=0.98 min, ES+ve m/z 580 [M+H]$^+$.

Example

VHL Protac which Binds Estrogen Receptor (Estrogen Protacts)

Abbreviations:
DCM: dichloromethane.
DIPEA: N,N-diisopropylethylamine.
DMF: N,N-dimethylformamide.
HATU: 2-(7-aza-1H-benzotriazole-1-yl)-1,1,3,3-tetramethyluronium hexafluorophosphate.
HPLC: high-performance liquid chromatography.
LCMS: liquid chromatography-mass spectrometry
Min: minutes.
RT: retention time.
tBu: tert-butoxide.
TFA: trifluoroacetic acid.
THF: tetrahydrofuran.
LCMS Method:
The analysis was conducted on an Acquity UPLC BEH C18 column (50 mm×2.1 mm internal diameter 1.7 μm packing diameter) at 40° C.
The solvents employed were:
A=0.1% v/v solution of formic acid in water.
B=0.1% v/v solution of formic acid in acetonitrile.
The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.
The following illustrates the mobile phases and gradients used when compounds underwent purification by mass-directed autopreparative HPLC.
Mass-Directed Autopreparative HPLC (Formic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of formic acid in water.
B=0.1% v/v solution of formic acid in acetonitrile.
Mass-Directed Autopreparative HPLC (Trifluoroacetic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of trifluoroacetic acid in water.
B=0.1% v/v solution of trifluoroacetic acid in acetonitrile.
Mass-Directed Autopreparative HPLC (Ammonium Bicarbonate Modifier)
The HPLC analysis was conducted on an XBridge C18 column (150 mm×30 mm internal diameter, 5 μm packing diameter) at ambient temperature.
The solvents employed were:
A=10 mM ammonium bicarbonate in water adjusted to pH 10 with ammonia solution.
B=acetonitrile.
For each of the mass-directed autopreparative purifications, irrespective of the modifier used, the gradient employed was dependent upon the retention time of the particular compound undergoing purification as recorded in the analytical LCMS, and was as follows:
For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ACD Name Pro version 6.02 from Advanced Chemistry Development, Inc.

8R,9S,13S,14S,17S)-3,17-bis(methoxymethoxy)-13-methyl-7,8,9,11,12,13,14,15,16,17-decahydro-6H-cyclopenta[a]phenanthren-6-one

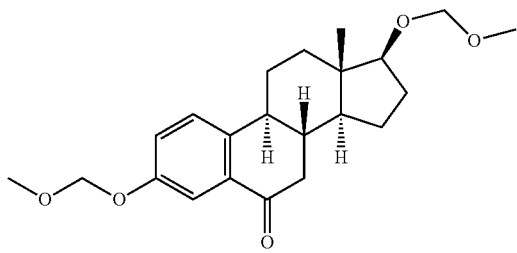

(8R,9S,13S,14S,17S)-3,17-bis(methoxymethoxy)-13-methyl-7,8,9,11,12,13,14,15,16,17-decahydro-6H-cyclopenta[a]phenanthren-6-one can be prepared according to the process described by Xiang-Rong Jiang, J. Walter Sowell, Bao Ting Zhu, Steroids, 2006, 71, 334-342. (doi:10.1016/j.steroids.2005.11.008).

15-Bromo-1-phenyl-2,5,8,11-tetraoxapentadecane

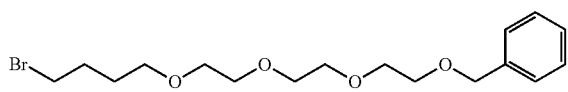 [SMILES: BrCCCCOCCOCCOCCOCc1ccccc1]

To a suspension of sodium hydride, 60% w/w in mineral oil (0.250 g, 6.24 mmol) in DMF (2 mL) was added a solution of 2-(2-(2-(benzyloxy)ethoxy)ethoxy)ethanol (1 g, 4.16 mmol) (commercially available from for example Fluorochem) in DMF (2 mL) at 0° C. After stirring for 25 minutes, 1,4-dibromobutane (commercially available from for example Aldrich) (4.04 g, 18.73 mmol) dissolved in DMF (2 mL) was added dropwise to the mixture. The reaction was stirred under an atmosphere of nitrogen for 2.5 hours. A further aliquot of sodium hydride, 60% w/w in mineral oil (0.250 g, 6.24 mmol) was added and the reaction was stirred at 0° C. for 30 minutes. The reaction was warmed to room temperature and stirred for 30 minutes. A final aliquot of sodium hydride, 60% w/w in mineral oil (0.250 g, 6.24 mmol) was added and the reaction stirred at room temperature for 2 hours then left standing over the weekend. The reaction mixture was filtered through celite and the solid washed with DCM. The filtrate was partitioned between DCM (30 mL) and water (30 mL). The organic extract was washed with brine (2×30 mL), dried using a hydrophobic frit and concentrated under reduced pressure. The product was purified by chromatography on silica using a gradient elution from 0% to 100% methyl tert-butyl ether in cyclohexane to afford the title compound (711 mg, 1.89 mmol, 46% yield). LCMS RT=1.16 min, ES+ve m/z 375.2/377.1 [M+H]$^+$.

15-Iodo-1-phenyl-2,5,8,11-tetraoxapentadecane

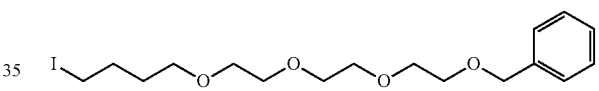

A mixture of 15-bromo-1-phenyl-2,5,8,11-tetraoxapentadecane (711 mg, 1.894 mmol) and sodium iodide (568 mg, 3.79 mmol) in acetone (10 mL) was heated under reflux conditions for 4 hours. The reaction was cooled to room temperature. The mixture was filtered through celite and the solid washed with acetone. The solvent was removed under reduced pressure. The residue was dissolved in ethyl acetate (30 mL) and washed with water (30 mL) and brine (2×30 mL). The organic extract was dried using a hydrophobic frit and concentrated under reduced pressure to afford the title compound (759 mg, 1.797 mmol, 95% yield). LCMS RT=1.23 min, ES+ve m/z 440.0 [M+NH$_4$]$^+$.

(7S,8R,9S,13S,14S,17S)-3,17-Bis(methoxymethoxy)-13-methyl-7-(1-phenyl-2,5,8,11-tetraoxapentadecan-15-yl)-7,8,9,11,12,13,14,15,16,17-decahydro-6H-cyclopenta[a]phenanthren-6-one

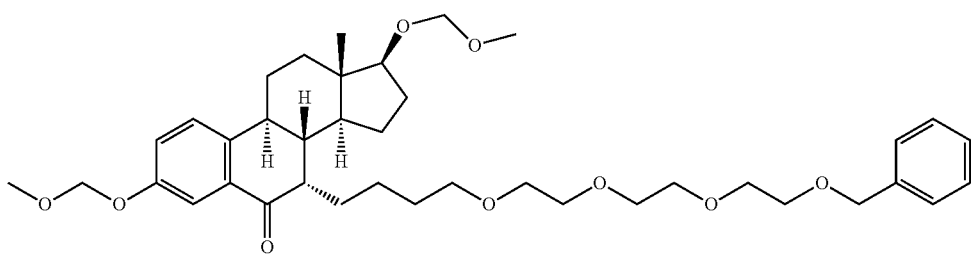

A solution of KOtBu in THF (1M, 1.282 mL, 1.282 mmol) was added to a cooled solution (0° C.) of (8R,9S,13S,14S,17S)-3,17-bis(methoxymethoxy)-13-methyl-7,8,9,11,12,13,14,15,16,17-decahydro-6H-cyclopenta[a]phenanthren-6-one (240 mg, 0.641 mmol) in anhydrous THF (2 mL). The reaction mixture was stirred at 0° C. for 45 minutes and then cooled to −78° C. A solution of 15-iodo-1-phenyl-2,5,8,11-tetraoxapentadecane (789 mg, 1.868 mmol) in THF (1 mL) was added dropwise. The solution was stirred at −78° C. for 2 minutes, allowed to warm to 0° C. and stirred for 1.5 hours at that temperature. The reaction was partitioned between water (30 mL) and ethyl acetate (30 mL). The organic extract was dried using a hydrophobic frit and concentrated under reduced pressure. The product was purified by chromatography on silica using a gradient elution from 0% to 100% ethyl acetate in cyclohexane to afford the title compound (234 mg, 0.350 mmol, 55% yield). LCMS RT=1.48 min, ES+ve m/z 669.3 [M+H]$^+$, 686.4 [M+NH$_4$]$^+$.

(7S,8R,9S,13S,14S,17S)-3,17-Dihydroxy-13-methyl-7-(1-phenyl-2,5,8,11-tetraoxapentadecan-15-yl)-7,8,9,11,12,13,14,15,16,17-decahydro-6H-cyclopenta[a]phenanthren-6-one

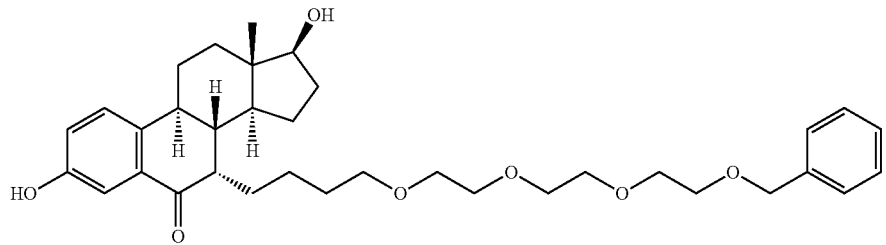

A solution of aqueous HCl (6M, 2.3 mL, 13.80 mmol) was added to a solution of (7S,8R,9S,13S,14S,17S)-3,17-bis(methoxymethoxy)-13-methyl-7-(1-phenyl-2,5,8,11-tetraoxapentadecan-15-yl)-7,8,9,11,12,13,14,15,16,17-decahydro-6H-cyclopenta[a]phenanthren-6-one (234 mg, 0.350 mmol) in THF (2.3 mL). The reaction mixture was stirred at room temperature for 16 hours. Water (30 mL) was added and the product was extracted with ethyl acetate (50 mL). The organic extract was washed with brine (2×30 mL), dried using a hydrophobic frit and concentrated under reduced pressure to afford the title compound (200 mg, 0.344 mmol, 98% yield). LCMS RT=1.07 min, ES+ve m/z 581.3 [M+H]$^+$, 598.3 [M+NH$_4$]$^+$.

(7R,8R,9S,13S,14S,17S)-13-Methyl-7-(1-phenyl-2,5,8,11-tetraoxapentadecan-15-yl)-7,8,9,11,12,13,14,15,16,17-decahydro-6H-cyclopenta[a]phenanthrene-3,17-diol

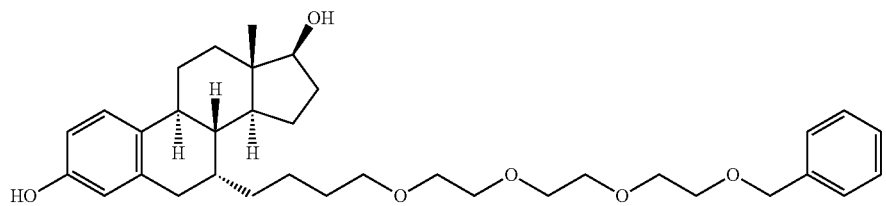

Triethylsilane (commercially available from for example Aldrich) (0.550 mL, 3.44 mmol) was added to a solution of (7S,8R,9S,13S,14S,17S)-3,17-dihydroxy-13-methyl-7-(1-phenyl-2,5,8,11-tetraoxapentadecan-15-yl)-7,8,9,11,12,13,14,15,16,17-decahydro-6H-cyclopenta[a]phenanthren-6-one (200 mg, 0.344 mmol) in TFA (2 mL, 26.0 mmol). The reaction was stirred at room temperature under an atmosphere of nitrogen for 16 hours. The mixture was partitioned between ethyl acetate (30 mL) and brine (30 mL). The organic extract was washed with brine (2×30 mL), dried using a hydrophobic fit and concentrated under reduced pressure. The residue was dissolved in MeOH (5 mL) and treated with aqueous NaOH (2M, 5 mL, 10.00 mmol). The reaction mixture was stirred at room temperature for 3 hours. The solvent was removed under reduced pressure. The residue was partitioned between ethyl acetate (30 mL) and a 10% citric acid solution (30 mL). The organic extract was washed with brine (30 mL), dried using a hydrophobic fit and concentrated under reduced pressure. The product was purified by reverse phase chromatography using a gradient elution from 5% to 95% acetonitrile (+0.1% formic acid) in water (+0.1% formic acid) to afford the title compound (150 mg, 0.265 mmol, 77% yield). LCMS RT=1.18 min, ES+ve m/z 567.3 [M+H]$^+$, 584.3 [M+NH$_4$]$^+$.

15-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)-1-phenyl-2,5,8,11-tetraoxapentadecane

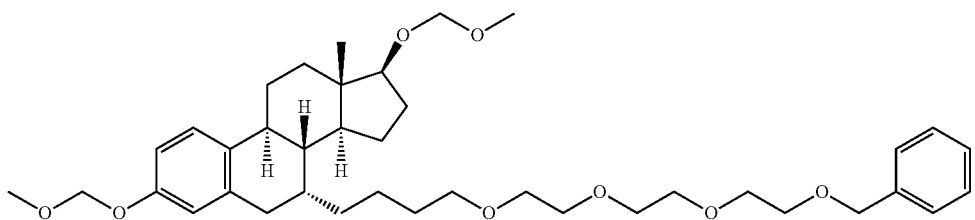

A vial was charged with (7R,8R,9S,13S,14S,17S)-13-methyl-7-(1-phenyl-2,5,8,11-tetraoxapentadecan-15-yl)-7,8,9,11,12,13,14,15,16,17-decahydro-6H-cyclopenta[a]phenanthrene-3,17-diol (150 mg, 0.265 mmol) and DIPEA (0.555 mL, 3.18 mmol) in THF (10 mL). The vial was sealed, the solution was cooled to 0° C. and chloro(methoxy)methane (commercially available from for example Aldrich) (0.2 mL, 2.63 mmol) was added. The reaction mixture was warmed to room temperature, stirred for 1 hour and heated at 70° C. for 40 hours. The reaction was cooled to room temperature. The reaction was partitioned between ethyl acetate (100 mL) and water (100 mL). The organic extract was washed with brine (2×50 mL), dried using a hydrophobic fit and concentrated under reduced pressure. The product was purified by chromatography on silica using a gradient elution from 0% to 100% methyl tert-butyl ether in cyclohexane to afford the title compound (122 mg, 0.186 mmol, 70% yield). LCMS RT=1.60 min, ES+ve m/z 672.5 [M+NH$_4$]$^+$.

2-(2-(2-(4-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)butoxy)ethoxy)ethoxy)ethanol

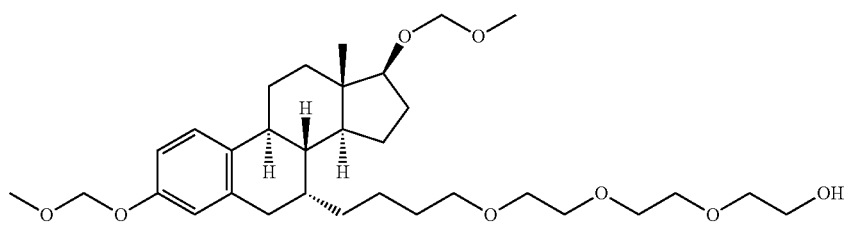

A mixture of 15-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-1-phenyl-2,5,8,11-tetraoxapentadecane (115 mg, 0.176 mmol) and 10% w/w palladium on carbon (100 mg, 0.094 mmol) in ethanol (4 mL) was stirred at room temperature under an atmosphere of hydrogen for 1.5 hours. The palladium on carbon was filtered through celite and the filtrate evaporated under reduced pressure. The residue was partitioned between ethyl acetate (15 mL) and brine (15 mL). The organic extract was dried using a hydrophobic frit and concentrated under reduced pressure to afford the title compound (81 mg, 0.143 mmol, 82% yield). LCMS RT=1.36 min, ES+ve m/z 582.4 [M+NH$_4$]$^+$.

Tert-butyl 16-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-3,6,9,12-tetraoxahexadecan-1-oate

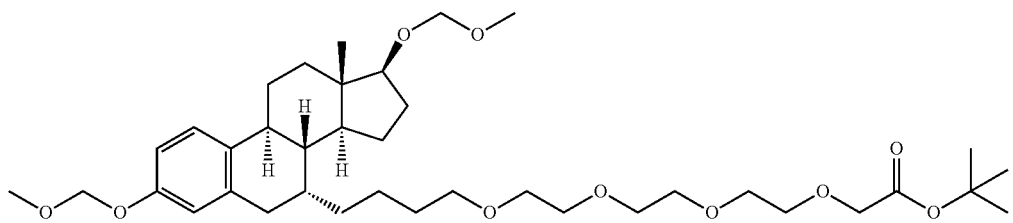

Sodium hydride, 60% w/w in mineral oil (10 mg, 0.250 mmol) was added to a cooled solution (0° C.) of 2-(2-(2-(4-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)butoxy)ethoxy)ethoxy)ethanol (81 mg, 0.143 mmol) in DMF (2 mL) The reaction was stirred at that temperature for 10 minutes and tert-butyl 2-bromoacetate (commercially available from for example Aldrich) (32 µL, 0.217 mmol) was added. The reaction was stirred at 0° C. for 1 hour and at room temperature for further 2 hours. The reaction mixture was partitioned between ethyl acetate (30 mL) and water (30 mL). The organic layer was washed with brine (30 mL), dried (hydrophobic frit) and concentrated under reduced pressure. The product was purified by chromatography on silica using a gradient elution from 0% to 100% methyl tert-butyl ether in cyclohexane to afford the title compound (60 mg, 0.088 mmol, 62% yield). LCMS RT=1.57 min, ES+ve m/z 696.5 [M+NH$_4$]$^+$.

16-((7R,8R,9S,13S,14S,17S)-3,17-Dihydroxy-13-methyl-7,8,9,11,12,13,14,15,16,17-decahydro-6H-cyclopenta[a]phenanthren-7-yl)-3,6,9,12-tetraoxahexadecan-1-oic acid

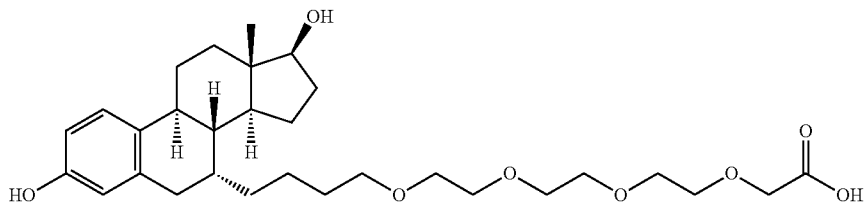

Tert-butyl 16-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-3,6,9,12-tetraoxahexadecan-1-oate (133 mg, 0.196 mmol) was dissolved in THF (1.5 mL) and treated with aqueous HCl (6M, 1.5 mL, 9.00 mmol). The reaction mixture was stirred at room temperature for 8 hours. The reaction mixture was subjected directly to purification by mass-directed automated preparative HPLC (formic acid modifier) to afford the title compound (60 mg, 0.112 mmol, 57% yield). LCMS RT=0.89 min, ES+ve m/z 535.3 [M+H]$^+$, 552.3 [M+NH$_4$]$^+$.

(2S,4R)-1-((S)-19-((7R,8R,9S,13S,14S,17S)-3,17-Dihydroxy-13-methyl-7,8,9,11,12,13,14,15,16,17-decahydro-6H-cyclopenta[a]phenanthren-7-yl)-2-isopropyl-4-oxo-6,9,12,15-tetraoxa-3-azanonadecan-1-oyl)-4-hydroxy-N-(4-(4-methylthiazol-5-yl)benzyl)pyrrolidine-2-carboxamide

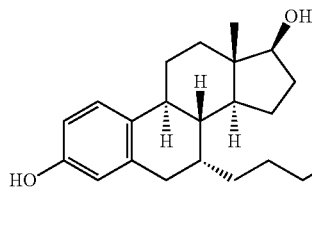
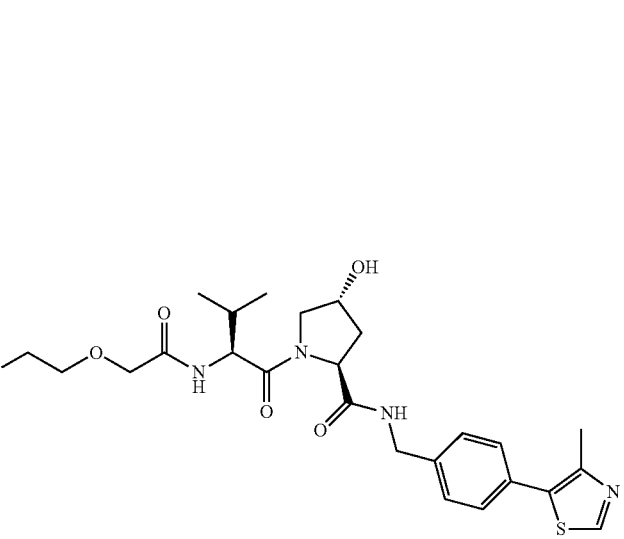

HATU (16 mg, 0.042 mmol) was added to a mixture of (2S,4R)-1-((S)-2-amino-3-methylbutanoyl)-4-hydroxy-N-(4-(4-methylthiazol-5-yl)benzyl)pyrrolidine-2-carboxamide, hydrochloride (25 mg, 0.055 mmol), 16-((7R,8R,9S,13S,14S,17S)-3,17-dihydroxy-13-methyl-7,8,9,11,12,13,14,15,16,17-decahydro-6H-cyclopenta[a]phenanthren-7-yl)-3,6,9,12-tetraoxahexadecan-1-oic acid (15 mg, 0.028 mmol) and DIPEA (0.05 mL, 0.286 mmol) in DMF (1 mL). The reaction was stirred at room temperature for 30 minutes. The reaction mixture was subjected directly to purification by mass-directed automated preparative HPLC (formic acid modifier) to afford the title compound (20 mg, 0.021 mmol, 76% yield). LCMS RT=0.99 min, ES+ve m/z 933.3 [M+H]$^+$.

(2S,4R)-1-((S)-2-(Tert-butyl)-19-((7R,8R,9S,13S,14S,17S)-3,17-dihydroxy-13-methyl-7,8,9,11,12,13,14,15,16,17-decahydro-6H-cyclopenta[a]phenanthren-7-yl)-4-oxo-6,9,12,15-tetraoxa-3-azanonadecan-1-oyl)-4-hydroxy-N-(4-(4-methylthiazol-5-yl)benzyl)pyrrolidine-2-carboxamide

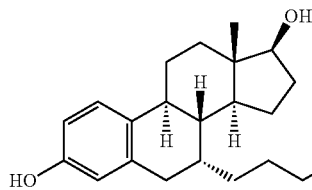
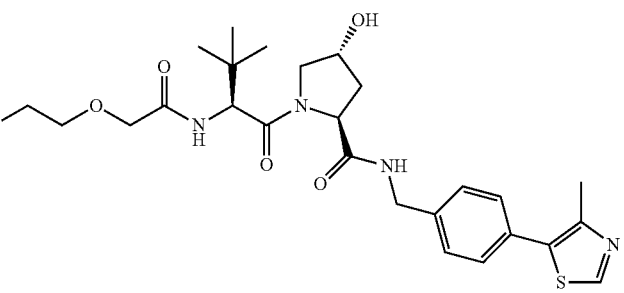

HATU (22 mg, 0.058 mmol) was added to a mixture of (2S,4R)-1-((S)-2-amino-3,3-dimethylbutanoyl)-4-hydroxy-N-(4-(4-methylthiazol-5-yl)benzyl)pyrrolidine-2-carboxamide, hydrochloride (25 mg, 0.054 mmol), 16-((7R,8R,9S,13S,14S,17S)-3,17-dihydroxy-13-methyl-7,8,9,11,12,13,14,15,16,17-decahydro-6H-cyclopenta[a]phenanthren-7-yl)-3,6,9,12-tetraoxahexadecan-1-oic acid (23 mg, 0.043 mmol) and DIPEA (0.040 mL, 0.229 mmol) in DMF (1 mL). The reaction was stirred at room temperature for 10 minutes. The reaction mixture was subjected directly to purification by mass-directed automated preparative HPLC (formic acid modifier) to afford the title compound (26 mg, 0.027 mmol, 64% yield). LCMS RT=1.02 min, ES+ve m/z 947.8 [M+H]$^+$.

((2(2-(4-Bromobutoxy)ethoxy)ethoxy)methyl)benzene

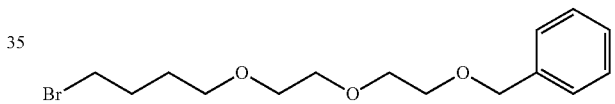

To a suspension of sodium hydride, 60% w/w in mineral oil (0.92 g, 22.9 mmol) in DMF (5 mL) was added a solution of 2-(2-(benzyloxy)ethoxy)ethanol (commercially available from for example Aldrich) (2.74 mL, 15.29 mmol) in DMF (5 mL) at 0° C. After stirring for 25 min, 1,4-dibromobutane (commercially available from for example Aldrich) (14.9 g, 68.8 mmol) dissolved in DMF (5 mL) was added dropwise to the mixture. The reaction was warmed to ambient temperature and stirred under an atmosphere of nitrogen for 2.5 hours. A further aliquot of sodium hydride, 60% w/w in mineral oil (0.92 g, 22.9 mmol) was added and the reaction was stirred at 0° C. for 30 minutes and at ambient temperature for 30 minutes. A final aliquot of sodium hydride, 60% w/w in mineral oil (0.92 g, 22.9 mmol) was added and the reaction stirred at ambient temperature for 2 hours then left standing overnight. The reaction mixture was filtered through celite and the solid washed with DCM. The filtrate was partitioned between DCM (30 mL) and water (30 mL).

The organic extract was washed with brine (2×30 mL), dried using a hydrophobic frit, and concentrated under reduced pressure. The product was purified by chromatography on silica using a using a gradient elution from 0% to 80% methyl tert-butyl ether in cyclohexane to afford the title compound (3 g, 9.06 mmol, 59% yield). LCMS RT=1.19 min, ES+ve m/z 331.2/333.2 [M+H]$^+$.

((2-(2-(4-Iodobutoxy)ethoxy)ethoxy)methyl)benzene

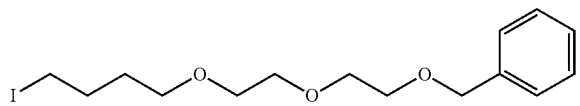 [SMILES: ICCCCOCCOCCOCc1ccccc1]

A mixture of ((2-(2-(4-bromobutoxy)ethoxy)ethoxy)methyl)benzene (3 g, 9.06 mmol) and sodium iodide (2.72 g, 18.11 mmol) in acetone (10 mL) was heated under reflux conditions for 3 hours. The reaction was cooled to room temperature. The mixture was filtered through celite and the solid washed with acetone. The solvent was removed under reduced pressure and the residue was dissolved in ethyl acetate (30 mL) and washed with water (30 mL) and brine (2×30 mL). The organic extract was dried using a hydrophobic fit and concentrated under reduced pressure. The product was purified by chromatography on silica using a using a gradient elution from 0% to 50% methyl tert-butyl ether in cyclohexane to afford the title compound (3.1 g, 8.2 mmol, 90% yield). LCMS RT=1.25 min, ES+ve m/z 379.2 [M+H]$^+$.

(7S,8R,9S,13S,14S,17S)-7-(4-(2-(2-(Benzyloxy)ethoxy)ethoxy)butyl)-3,17-bis(methoxymethoxy)-13-methyl-7,8,9,11,12,13,14,15,16,17-decahydro-6H-cyclopenta[a]phenanthren-6-one

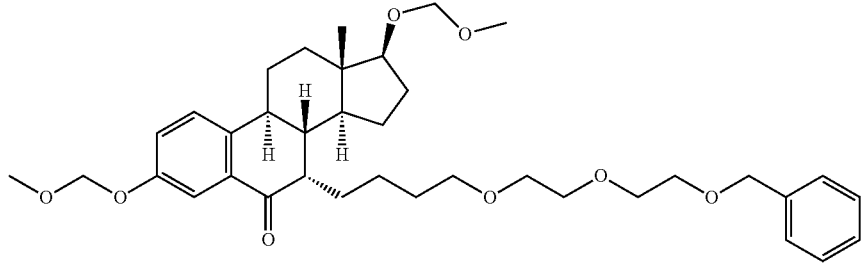

A solution of KOtBu, in THF (1M, 3.2 mL, 3.2 mmol) was added to a cooled solution (0° C.) of (8R,9S,13S,14S,17S)-3,17-bis(methoxymethoxy)-13-methyl-7,8,9,11,12,13,14,15,16,17-decahydro-6H-cyclopenta[a]phenanthren-6-one (600 mg, 1.6 mmol) in anhydrous THF (6 mL). The reaction mixture was stirred at 0° C. for 45 minutes and then cooled to −78° C. A solution of ((2-(2-(4-Iodobutoxy)ethoxy)methyl)benzene (910 mg, 2.4 mmol) in THF (3 mL) was added dropwise. The solution was stirred at −78° C. for 2 minutes then allowed to warm to 0° C. and stirred for 1.5 hours at that temperature. The reaction was partitioned between water (30 mL) and ethyl acetate (30 mL). The organic extract was separated, dried using a hydrophobic frit and concentrated under reduced pressure. The product was purified by chromatography on silica using a gradient elution from 0% to 50% ethyl acetate in cyclohexane to afford the title compound (450 mg, 0.72 mmol, 45% yield). LCMS RT=1.49 min, ES+ve m/z 625.5 [M+H]$^+$.

(7S,8R,9S,13S,14S,17S)-7-(4-(2-(2-(Benzyloxy)ethoxy)ethoxy)butyl)-3,17-dihydroxy-13-methyl-7,8,9,11,12,13,14,15,16,17-decahydro-6H-cyclopenta[a]phenanthren-6-one

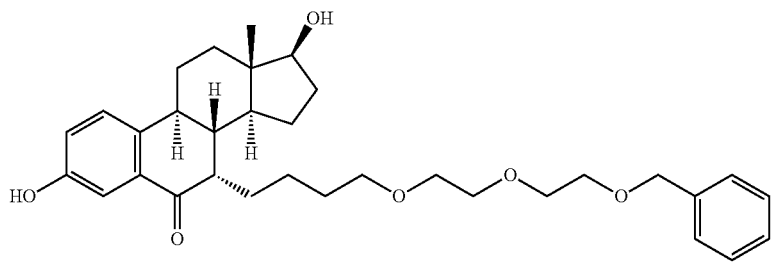

A solution of aqueous HCl (6M, 4.6 mL, 27.6 mmol) was added to a solution of (7S,8R,9S,13S,14S,17S)-7-(4-(2-(2-(benzyloxy)ethoxy)ethoxy)butyl)-3,17-bis(methoxymethoxy)-13-methyl-7,8,9,11,12,13,14,15,16,17-decahydro-6H-cyclopenta[a]phenanthren-6-one (470 mg, 0.752 mmol) in THF (4.6 mL). The reaction mixture was stirred at room temperature for 18 hours. Water (30 mL) was added and the product was extracted with ethyl acetate (50 mL). The organic extract was washed with brine (2×30 mL), dried using a hydrophobic frit and concentrated under reduced pressure to afford the title compound (390 mg, 0.727 mmol, 97% yield). LCMS RT=1.08 min, ES+ve m/z 537.2 [M+H]+, 554.2 [M+NH4]+.

(7R,8R,9S,13S,14S,17S)-7-(4-(2-(2-(Benzyloxy)ethoxy)ethoxy)butyl)-13-methyl-7,8,9,11,12,13,14,15,16,17-decahydro-6H-cyclopenta[a]phenanthrene-3,17-diol

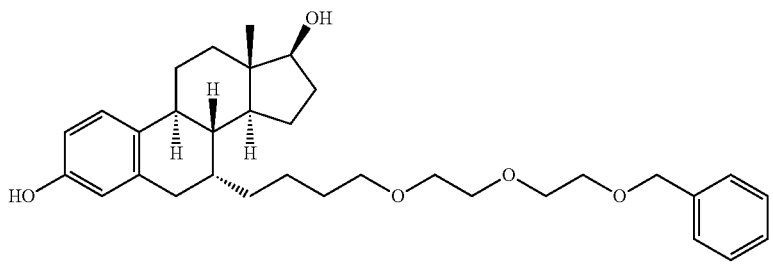

Triethylsilane (commercially available from for example Aldrich) 1.161 mL, 7.27 mmol) was added to a solution of (7S,8R,9S,13S,14S,17S)-7-(4-(2-(2-(benzyloxy)ethoxy)ethoxy)butyl)-3,17-dihydroxy-13-methyl-7,8,9,11,12,13,14,15,16,17-decahydro-6H-cyclopenta[a]phenanthren-6-one (390 mg, 0.727 mmol) in TFA (4.2 mL, 54.5 mmol). The reaction was stirred at room temperature under an atmosphere of nitrogen for 18 hours. The mixture was partitioned between ethyl acetate (50 mL) and brine (50 mL). The organic extract was washed with brine (2×30 mL), saturated sodium bicarbonate (30 mL), dried using a hydrophobic frit and concentrated under reduced pressure. The residue was dissolved in MeOH (10 mL) and treated with aqueous NaOH (2M, 5 mL, 10.0 mmol). The reaction mixture was stirred at room temperature for 1 hour. The solvent was removed under reduced pressure. The residue was partitioned between ethyl acetate (30 mL) and aqueous HCl solution (1M, 20 mL). The organic extract was washed with brine (20 mL), dried using a hydrophobic frit and concentrated under reduced pressure. The product was purified by reverse phase chromatography using a gradient elution from 5% to 95% acetonitrile (+0.1% formic acid) in water (+0.1% formic acid) to afford the title compound (270 mg, 0.517 mmol, 71% yield). LCMS RT=1.18 min, ES+ve m/z 523.5 [M+H]+, 540.5 [M+NH4]+.

(7R,8R,9S,13S,14S,17S)-7-(4-(2-(2-(Benzyloxy)ethoxy)ethoxy)butyl)-3,17-bis(methoxymethoxy)-13-methyl-7,8,9,11,12,13,14,15,16,17-decahydro-6H-cyclopenta[a]phenanthrene Chloro(methoxy)methane (commercially available from for example Aldrich) (0.390 mL, 5.14 mmol) was added to a cooled (0° C.) solution of (7R,8R,9S,13S,14S,17S)-7-(4-(2-(2-(benzyloxy)ethoxy)ethoxy)butyl)-13-methyl-7,8,9,11,12,13,14,15,16,17-decahydro-6H-cyclopenta[a]phenanthrene-3,17-diol (270 mg, 0.517 mmol) and DIPEA (1.083 mL, 6.20 mmol) in THF (16 mL). The reaction mixture was warmed to room temperature, stirred for 1 hour and then heated at 70° C. for 40 hours. The reaction mixture was cooled to 0° C., additional DIPEA (0.271 mL, 1.550 mmol) and chloro(methoxy)methane (0.098 mL, 1.291 mmol) was added. The reaction was heated to 70° C. and stirred for a further 24 hours. The reaction was cooled to room temperature, and was partitioned between ethyl acetate (100 mL) and water (100 mL). The organic extract was washed with brine (2×50 mL), dried using a hydrophobic frit and concentrated under reduced pressure. The product was purified by chromatography on silica using a gradient elution from 0% to 100% methyl tert-butyl ether in cyclohexane to afford the title compound (220 mg, 0.36 mmol, 70% yield). LCMS RT=1.62 min, ES+ve m/z 628.6 [M+NH4]+.

2-(2-(4-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)butoxy)ethoxy)ethanol

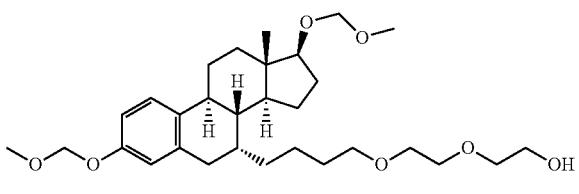

A mixture of (7R,8R,9S,13S,14S,17S)-7-(4-(2-(2-(benzyloxy)ethoxy)ethoxy)butyl)-3,17-bis(methoxymethoxy)-13-

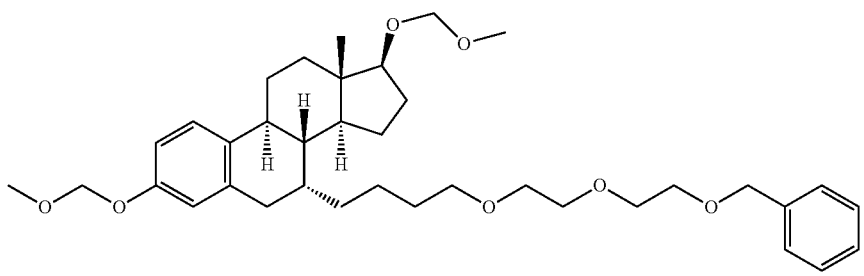

methyl-7,8,9,11,12,13,14,15,16,17-decahydro-6H-cyclopenta[a]phenanthrene (220 mg, 0.36 mmol) and 10% w/w palladium on carbon (100 mg, 0.094 mmol) in ethanol (4 mL) was stirred at room temperature under an atmosphere of hydrogen for 1 hour. The palladium on carbon was filtered through celite, washed with ethanol (50 ml) and the filtrate was evaporated under reduced pressure to afford the title compound (186 mg, 0.357 mmol, 99% yield) LCMS RT=1.36 min, ES+ve m/z 521.5 [M+H]$^+$, 538.5 [M+NH$_4$]$^+$.

Tert-butyl 2-(2-(2-(4-((7R,8R,9S,13S,14S,17S)-3,17-is(methoxymethoxy)-13-methyl-7,8,9,11,12,13,14,15,16,17-decahydro-6H-cyclopenta[a]phenanthren-7-yl)butoxy)ethoxy)ethoxy)acetate

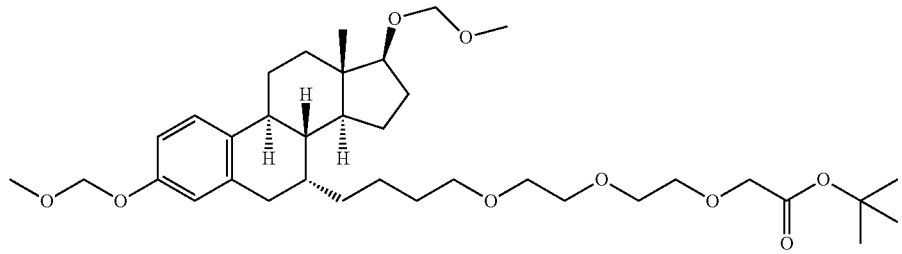

Sodium hydride, 60% w/w mineral oil (25.0 mg, 0.625 mmol) was added to a cooled solution (0° C.) of 2-(2-(4-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)butoxy)ethoxy)ethanol (186 mg, 0.357 mmol) in DMF (4.5 mL). The reaction was stirred at 0° C. for 10 minutes and tert-butyl 2-bromoacetate (commercially available from for example Aldrich) (79 µL, 0.536 mmol) was added. The reaction was stirred at 0° C. for 1 hour and at room temperature for a further 6 hours. The reaction was cooled to 0° C. and additional sodium hydride, 60% w/w in mineral oil (15.72 mg, 0.393 mmol), followed by tert-butyl 2-bromoacetate (0.053 mL, 0.357 mmol) was added. The reaction was stirred at room temperature for a further 18 hours. The reaction mixture was partitioned between ethyl acetate (30 mL) and water (30 mL). The organic layer separated, washed with brine (30 mL), dried using a hydrophobic frit and concentrated under reduced pressure. The product was purified by chromatography on silica using a gradient elution from 0% to 100% methyl tert-butyl ether in cyclohexane to afford the title compound (90 mg, 0.142 mmol, 40% yield). LCMS RT=1.56 min, ES+ve m/z 652.6 [M+NH$_4$]$^+$, 657.5 [M+Na]$^+$.

2-(2-(2-(4-((7R,8R,9S,13S,14S,17S)-3,17-Dihydroxy-13-methyl-7,8,9,11,12,13,14,15,16,17-decahydro-6H-cyclopenta[a]phenanthren-7-yl)butoxy)ethoxy)ethoxy)acetic acid

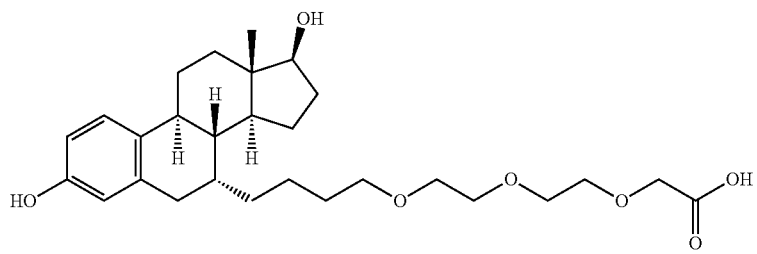

Tert-butyl 2-(2-(2-(4-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)butoxy)ethoxy)ethoxy)acetate (80 mg, 0.126 mmol) was dissolved in THF (1 mL) and treated with aqueous HCl (6M, 1 mL, 6.0 mmol). The reaction mixture was stirred at room temperature for 4 hours. The reaction mixture was subjected directly to purification by mass-directed automated preparative HPLC (formic acid modifier) to afford the title compound (23 mg, 0.047 mmol, 37% yield). LCMS RT=0.89 min, ES+ve m/z 491.4 [M+H]$^+$.

(2S,4R)-1-((S)-16-((7R,8R,9S,13S,14S,17S)-3,17-
Dihydroxy-13-methyl-7,8,9,11,12,13,14,15,16,17-
decahydro-6H-cyclopenta[a]phenanthren-7-yl)-2-
isopropyl-4-oxo-6,9,12-trioxa-3-azahexadecan-1-
oyl)-4-hydroxy-N-(4-(4-methylthiazol-5-yl)benzyl)
pyrrolidine-2-carboxamide

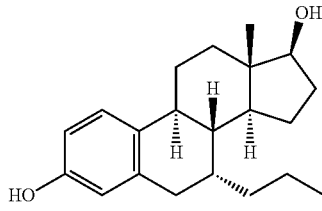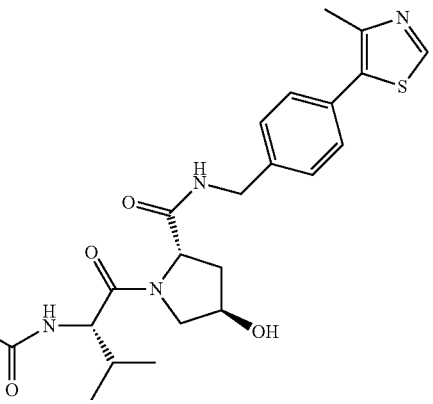

HATU (12 mg, 0.03 mmol) was added to a mixture of (2S,4R)-1-((S)-2-amino-3-methylbutanoyl)-4-hydroxy-N-(4-(4-methylthiazol-5-yl)benzyl)pyrrolidine-2-carboxamide, hydrochloride (23 mg, 0.05 mmol), 2-(2-(2-(4-((7R,8R,9S,13S,14S,17S)-3,17-dihydroxy-13-methyl-7,8,9,11,12,13,14,15,16,17-decahydro-6H-cyclopenta[a]phenanthren-7-yl)butoxy)ethoxy)ethoxy)acetic acid (10 mg, 0.02 mmol) and DIPEA (0.04 mL, 0.20 mmol) in DMF (0.8 mL). The reaction was stirred at room temperature for 30 min. The reaction mixture was subjected directly to purification by mass-directed automated preparative HPLC (formic acid modifier) to afford the title compound (15 mg, 0.017 mmol, 84% yield). LCMS RT=0.98 min, ES+ve m/z 889.7 [M+H]$^+$.

18-Bromo-1-phenyl-2,5,8,11,14-pentaoxaoctadecane

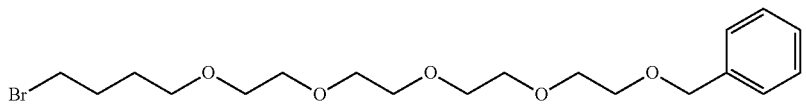 [SMILES: BrCCCCOCCOCCOCCOCCOCc1ccccc1]

To a suspension of sodium hydride, 60% w/w in mineral oil (0.85 g, 21.3 mmol) in DMF (8 mL) was added a solution of 1-phenyl-2,5,8,11-tetraoxamidecan-13-ol (commercially available from for example TCI Europe Fine Chemicals) (4.0 g, 14.2 mmol) in DMF (8 mL) at 0° C. After stirring for 25 minutes, 1,4-dibromobutane (commercially available from for example Aldrich) (7.62 mL, 63.8 mmol) dissolved in DMF (8 mL) was added dropwise to the mixture. The reaction was warmed to room temperature and stirred under an atmosphere of nitrogen for 30 minutes. A further aliquot of sodium hydride, 60% w/w in mineral oil (0.85 g, 21.3 mmol) was added and the reaction was stirred at room temperature overnight. Another aliquot of sodium hydride, 60% w/w in mineral oil (0.85 g, 21.3 mmol) was added and the reaction stirred at room temperature for 2 hours. A final aliquot of sodium hydride, 60% w/w in mineral oil (0.43 g, 10.6 mmol) was added and the reaction stirred at room temperature for 1 hour. The reaction mixture was filtered through celite and the solid washed with DCM. The filtrate was partitioned between DCM (50 mL) and water (50 mL). The organic extract was washed with brine (2×50 mL), dried using a hydrophobic frit and concentrated under reduced pressure. The product was purified by chromatography on silica using a gradient elution from 0% to 85% methyl tert-butyl ether in cyclohexane to afford the title compound (3.93 g, 9.37 mmol, 63% yield). LCMS RT=1.16 min, ES+ve m/z 419.3/421.2 [M+H]$^+$.

18-Iodo-1-phenyl-2,5,8,11,14-pentaoxaoctadecane

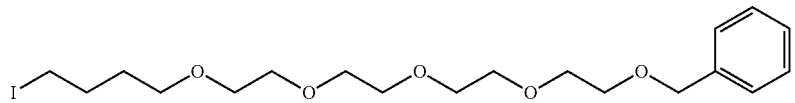 [SMILES: ICCCCOCCOCCOCCOCCOCc1ccccc1]

A mixture of 18-bromo-1-phenyl-2,5,8,11,14-pentaoxaoctadecane (2.08 g, 4.91 mmol) and sodium iodide (1.47 g, 9.82 mmol) in acetone (10 mL) was heated under reflux conditions for 3 hours. The reaction was cooled to room temperature, filtered through celite and the solid was washed with acetone. The solvent was removed under reduced pressure. The residue was dissolved in ethyl acetate (30 mL), and washed with water (30 mL) and brine (2×30 mL). The organic extract was dried using a hydrophobic frit and concentrated under reduced pressure to afford the title compound (759 mg, 1.80 mmol, 95% yield). LCMS RT=1.21 min, ES+ve m/z 467.0 [M+H]$^+$, 484.0 [M+NH$_4$]$^+$.

(7S,8R,9S,13S,14S,17S)-3,17-Bis(methoxymethoxy)-13-methyl-7-(1-phenyl-2,5,8,11,14-pentaoxaoctadecan-18-yl)-7,8,9,11,12,13,14,15,16,17-decahydro-6H-cyclopenta[a]phenanthren-6-one

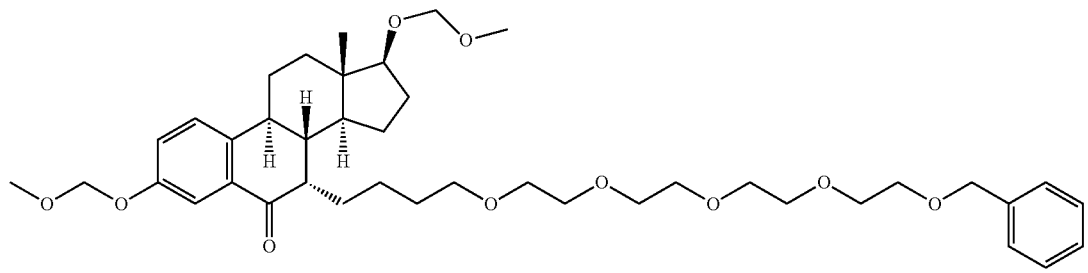

A solution of KOtBu in THF (1M, 5.34 mL, 5.34 mmol) was added to a cooled solution (0° C.) of (8R,9S,13S,14S,17S)-3,17-bis(methoxymethoxy)-13-methyl-7,8,9,11,12,13,14,15,16,17-decahydro-6H-cyclopenta[a]phenanthren-6-one (1 g, 2.67 mmol) in anhydrous THF (10 mL). The reaction mixture was stirred at 0° C. for 45 minutes and then cooled to −78° C. 18-Iodo-1-phenyl-2,5,8,11,14-pentaoxaoctadecane (1.87 g, 4.01 mmol) in THF (5 mL) was added dropwise. The solution was stirred at −78° C. for 2 minutes, allowed to warm to 0° C. and stirred for 1.5 hours at that temperature. The reaction was partitioned between water (50 mL) and ethyl acetate (2×50 mL). The organic extracts were dried using a hydrophobic frit and concentrated under reduced pressure. The product was purified by chromatography on silica using a gradient elution from 0% to 100% ethyl acetate in cyclohexane to afford the title compound (883 mg, 1.24 mmol, 46% yield). LCMS RT=1.47 min, ES+ve m/z 713.5 [M+H]$^+$.

(7S,8R,9S,13S,14S,17S)-3,17-Dihydroxy-13-methyl-7-(1-phenyl-2,5,8,11,14-pentaoxaoctadecan-18-yl)-7,8,9,11,12,13,14,15,16,17-decahydro-6H-cyclopenta[a]phenanthren-6-one

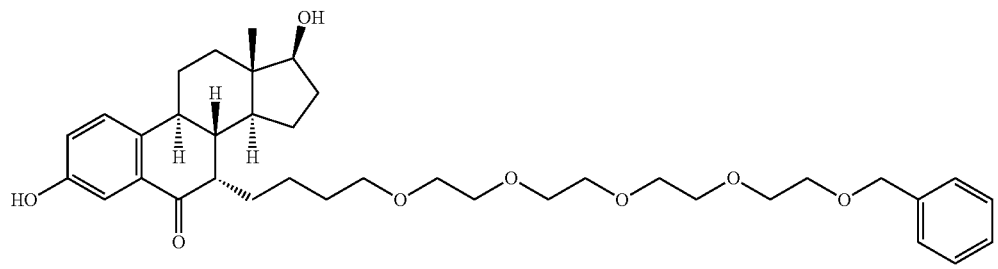

A solution of aqueous HCl (6M, 9.2 mL, 55.2 mmol) was added to a solution of (7S,8R,9S,13S,14S,17S)-3,17-bis(methoxymethoxy)-13-methyl-7-(1-phenyl-2,5,8,11,14-pentaoxaoctadecan-18-yl)-7,8,9,11,12,13,14,15,16,17-decahydro-6H-cyclopenta[a]phenanthren-6-one (883 mg, 1.24 mmol) in THF (9.2 mL). The reaction mixture was stirred at room temperature for 18 hours. Water (30 mL) was added and the product was extracted with ethyl acetate (50 mL). The organic extract was washed with brine (2×30 mL), dried using a hydrophobic fit and concentrated under reduced pressure to afford the title compound (772 mg, 1.23 mmol, 99% yield). LCMS RT=1.06 min, ES+ve m/z 625.3 [M+H]$^+$, 642.3 [M+NH$_4$]$^+$.

(7R,8R,9S,13S,14S,17S)-13-Methyl-7-(1-phenyl-2,5,8,11,14-pentaoxaoctadecan-18-yl)-7,8,9,11,12,13,14,15,16,17-decahydro-6H-cyclopenta[a]phenanthrene-3,17-diol

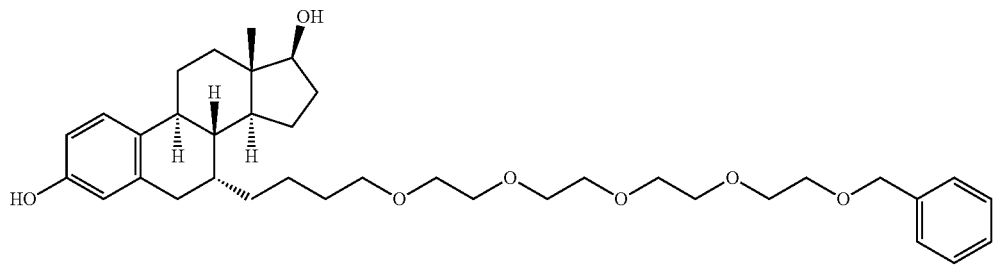

Triethylsilane (commercially available from for example Aldrich) (2.0 mL, 12.9 mmol) was added to a solution of (7S,8R,9S,13S,14S,17S)-3,17-dihydroxy-13-methyl-7-(1-phenyl-2,5,8,11,14-pentaoxaoctadecan-18-yl)-7,8,9,11,12,13,14,15,16,17-decahydro-6H-cyclopenta[a]phenanthren-6-one (830 mg, 1.29 mmol) in TFA (8.5 mL, 110 mmol). The reaction was stirred at room temperature under an atmosphere of nitrogen for 16 hours. The mixture was partitioned between ethyl acetate (50 mL) and brine (50 mL). The organic extract was washed with brine (2×50 mL), saturated sodium bicarbonate (50 mL), dried using a hydrophobic frit and concentrated under reduced pressure. The residue was dissolved in MeOH (10 mL) and treated with aqueous NaOH (2M, 10 mL, 20.0 mmol). The reaction mixture was stirred at room temperature for 1 hour. The solvent was removed under reduced pressure. The residue was partitioned between ethyl acetate (40 mL) and 1M HCl solution (20 mL). The organic extract was washed with brine (20 mL), dried using a hydrophobic frit and concentrated under reduced pressure. The product was purified by reverse phase chromatography using a gradient elution from 5% to 90% acetonitrile (+0.1% formic acid) in water (+0.1% formic acid) to afford the title compound (375 mg, 0.614 mmol, 47% yield). LCMS RT=1.17 min, ES+ve m/z 611.5 [M+H]$^+$, 628.6 [M+NH$_4$]$^+$.

18-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)-1-phenyl-2,5,8,11,14-pentaoxaoctadecane

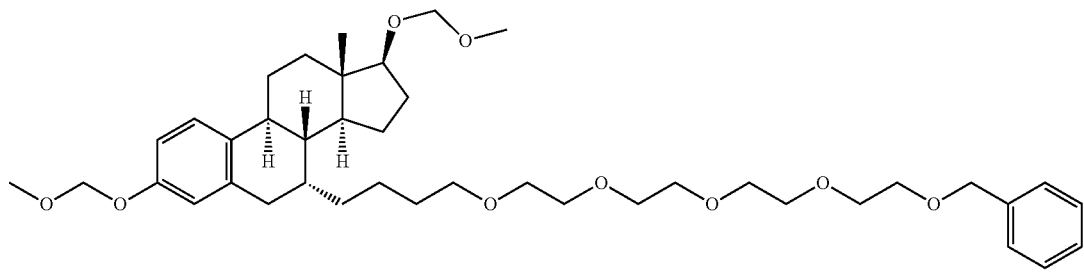

Chloro(methoxy)methane (commercially available from for example Aldrich) (0.5 mL, 6.58 mmol) was added to a cooled (0° C.) solution of (7R,8R,9S,13S,14S,17S)-13-methyl-7-(1-phenyl-2,5,8,11,14-pentaoxaoctadecan-18-yl)-7,8,9,11,12,13,14,15,16,17-decahydro-6H-cyclopenta[a]phenanthrene-3,17-diol (375 mg, 0.614 mmol) and DIPEA (1.5 mL, 8.59 mmol) in THF (20 mL). The reaction mixture was warmed to room temperature, stirred for 1 hour and heated at 70° C. for 72 hours. The reaction was cooled to room temperature. The reaction was partitioned between ethyl acetate (100 mL) and water (100 mL). The organic extract was washed with brine (2×50 mL), dried using a hydrophobic frit and concentrated under reduced pressure. The product was purified by chromatography on silica using a gradient elution from 0% to 100% methyl tert-butyl ether in cyclohexane to afford the title compound (357 mg, 0.51 mmol, 72% yield). LCMS RT=1.60 min, ES+ve m/z 716.7 [M+NH$_4$]$^+$, 721.7 [M+Na]$^+$.

16-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)-3,6,9,12-tetraoxahexadecan-1-ol

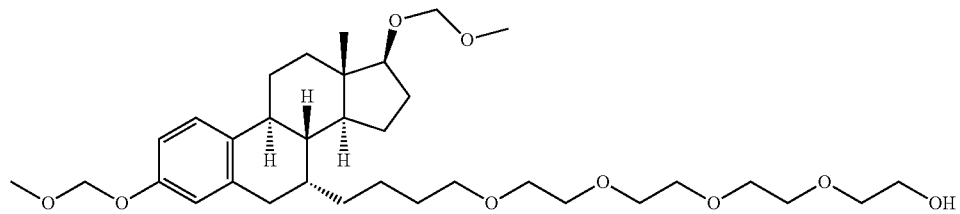

A mixture of 18-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-1-phenyl-2,5,8,11,14-pentaoxaoctadecane (357 mg, 0.444 mmol) and 10% w/w palladium on carbon (157 mg, 0.148 mmol) in ethanol (5 mL) was stirred at room temperature under an atmosphere of hydrogen for 1.5 hours. The palladium on carbon was filtered through celite and the filtrate evaporated under reduced pressure to afford the title compound (300 mg, 0.41 mmol, 93% yield) LCMS RT=1.37 min, ES+ve m/z 609.6 [M+H]$^+$, 631.6 [M+Na]$^+$.

Tert-butyl 19-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-3,6,9,12,15-pentaoxanonadecan-1-oate

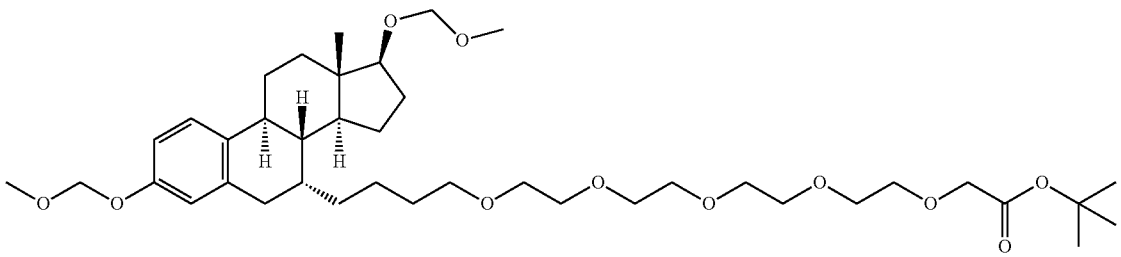

Sodium hydride, 60% w/w in mineral oil (30 mg, 0.75 mmol) was added to a cooled solution (0° C.) of 16-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-3,6,9,12-tetraoxahexadecan-1-ol (300 mg, 0.43 mmol) in DMF (5 mL). The reaction was stirred at that temperature for 10 minutes and tert-butyl 2-bromoacetate (0.095 mL, 0.643 mmol) was added. The reaction was stirred at 0° C. for 1 hour and then at room temperature for a further 18 hours. The reaction mixture was partitioned between ethyl acetate (30 mL) and water (30 mL). The water layer was extracted with additional ethyl acetate (2×30 mL), and the combined organic layers were washed with brine (2×30 mL), dried (hydrophobic frit) and concentrated under reduced pressure. The product was purified by chromatography on silica using a gradient elution from 0% to 100% methyl tert-butyl ether in cyclohexane to afford the title compound (177 mg, 0.245 mmol, 57% yield). LCMS RT=1.58 min, ES+ve m/z 740.6 [M+NH$_4$]$^+$, 745.6 [M+Na]$^+$.

19-((7R,8R,9S,13S,14S,17S)-3,17-Dihydroxy-13-methyl-7,8,9,11,12,13,14,15,16,17-decahydro-6H-cyclopenta[a]phenanthren-7-yl)-3,6,9,12,15-pentaoxanonadecan-1-oic acid

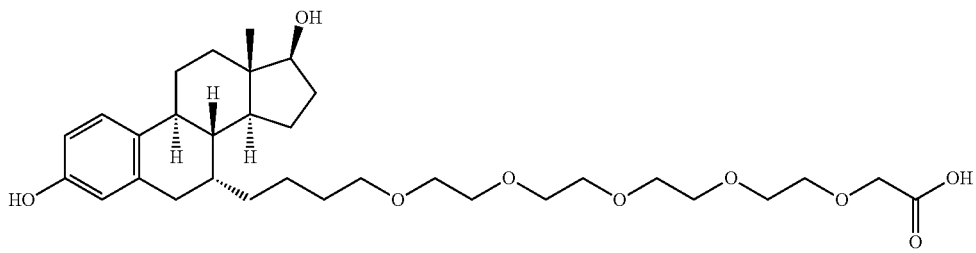

Tert-butyl 19-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-3,6,9,12,15-pentaoxanonadecan-1-oate (177 mg, 0.189 mmol) was dissolved in THF (2 mL) and treated with aqueous HCl (6M, 2 mL, 12.0 mmol). The reaction mixture was stirred at room temperature for 7 hours. The reaction mixture was subjected directly to purification by mass-directed automated preparative HPLC (formic acid modifier) to afford the title compound (64 mg, 0.111 mmol, 59% yield). LCMS RT=0.92 min, ES+ve m/z 579.4 [M+H]$^+$, 596.5 [M+NH$_4$]$^+$.

(2S,4R)-1-((S)-22-((7R,8R,9S,13S,14S,17S)-3,17-Dihydroxy-13-methyl-7,8,9,11,12,13,14,15,16,17-decahydro-6H-cyclopenta[a]phenanthren-7-yl)-2-isopropyl-4-oxo-6,9,12,15,18-pentaoxa-3-azadocosan-1-oyl)-4-hydroxy-N-(4-(4-methylthiazol-5-yl)benzyl)pyrrolidine-2-carboxamide

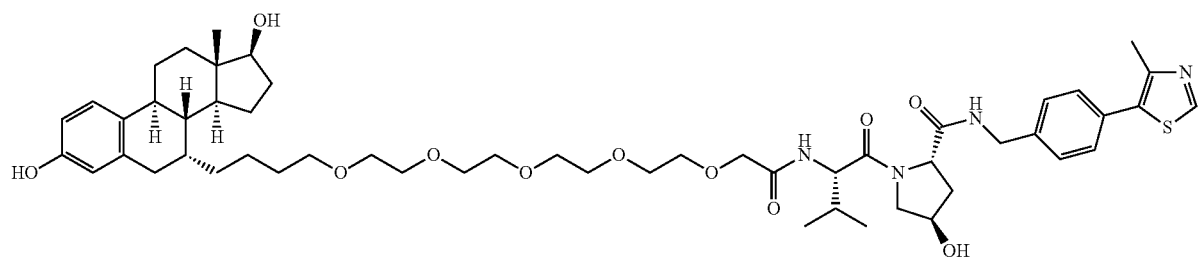

HATU (16 mg, 0.04 mmol) was added to a mixture of (2S,4R)-1-((S)-2-amino-3-methylbutanoyl)-4-hydroxy-N-(4-(4-methylthiazol-5-yl)benzyl)pyrrolidine-2-carboxamide, hydrochloride (25 mg, 0.06 mmol), 19-((7R,8R,9S,13S,14S,17S)-3,17-dihydroxy-13-methyl-7,8,9,11,12,13,14,15,16,17-decahydro-6H-cyclopenta[a]phenanthren-7-yl)-3,6,9,12,15-pentaoxanonadecan-1-oic acid (16 mg, 0.03 mmol) and DIPEA (0.048 mL, 0.28 mmol) in DMF (0.8 mL). The reaction was stirred at room temperature for 30 minutes. The reaction mixture was subjected directly to purification by mass-directed automated preparative HPLC (formic acid modifier) to afford the title compound (17.7 mg, 0.018 mmol, 65% yield). LCMS RT=0.99 min, ES+ve m/z 977.4 [M+H]$^+$.

(2S,4R)-1-((S)-2-(Tert-butyl)-22-((7R,8R,9S,13S,14S,17S)-3,17-dihydroxy-13-methyl-7,8,9,11,12,13,14,15,16,17-decahydro-6H-cyclopenta[a]phenanthren-7-yl)-4-oxo-6,9,12,15,18-pentaoxa-3-azadocosan-1-oyl)-4-hydroxy-N-(4-(4-methylthiazol-5-yl)benzyl)pyrrolidine-2-carboxamide

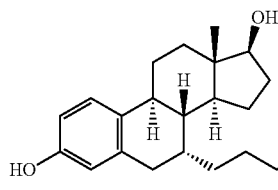
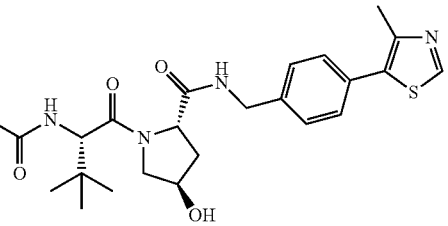

HATU (16 mg, 0.04 mmol) was added to a mixture of (2S,4R)-1-((S)-2-amino-3,3-dimethylbutanoyl)-4-hydroxy-N-(4-(4-methylthiazol-5-yl)benzyl)pyrrolidine-2-carboxamide, hydrochloride (25 mg, 0.05 mmol), 19-((7R,8R,9S,13S,14S,17S)-3,17-dihydroxy-13-methyl-7,8,9,11,12,13,14,15,16,17-decahydro-6H-cyclopenta[a]phenanthren-7-yl)-3,6,9,12,15-pentaoxanonadecan-1-oic acid (16 mg, 0.03 mmol) and DIPEA (0.048 mL, 0.28 mmol) in DMF (0.8 mL). The reaction was stirred at room temperature for 30 minutes. The reaction mixture was subjected directly to purification by mass-directed automated preparative HPLC (formic acid modifier) to afford the title compound (17.5 mg, 0.017 mmol, 63% yield). LCMS RT=1.03 min, ES+ve m/z 991.4 [M+H]⁺.

(7S,8R,9S,13S,14S,17S)-7-(5-(Benzyloxy)pentyl)-3,17-dihydroxy-13-methyl-7,8,9,11,12,13,14,15,16,17-decahydro-6H-cyclopenta[a]phenanthren-6-one

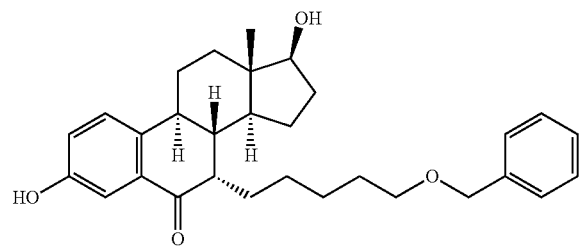

A solution of KOtBu in THF (1M, 4.81 mL, 4.81 mmol) was added to a cooled solution (0° C.) of (8R,9S,13S,14S,17S)-3,17-bis(methoxymethoxy)-13-methyl-7,8,9,11,12,13,14,15,16,17-decahydro-6H-cyclopenta[a]phenanthren-6-one (900 mg, 2.403 mmol) in anhydrous THF (10 mL). The reaction mixture was stirred at 0° C. for 45 minutes and then cooled to −78 0° C. (((5-Iodopentyl)oxy)methyl)benzene (can be prepared following the procedure described in *J. Chem. Soc., Perkin Trans.* 11990, 129-132) (2.193 g, 7.21 mmol) in THF (0.5 mL) was added dropwise. The solution was stirred at −78° C. for 2 minutes and allowed to warm to room temperature and stirred for 1 hour at that temperature. The reaction was partitioned between water (70 mL) and ethyl acetate (70 mL). The organic extract was dried using a hydrophobic fit and concentrated under reduced pressure.

The intermediate was purified by chromatography on silica using a gradient elution from 0% to 50% ethyl acetate in cyclohexane. The residue was dissolved in THF (16 mL) and aqueous HCl (6M, 16 mL, 96 mmol) was added. The reaction was stirred at room temperature for 16 hours. The reaction mixture was partitioned between ethyl acetate (20 mL) and water (20 mL). The organic extract was dried (hydrophobic frit) and concentrated under reduced pressure. The product was purified by reverse phase chromatography using a gradient elution from 5% to 85% acetonitrile (+0.1% formic acid) in water (+0.1% formic acid) to afford the title compound (487 mg, 1.053 mmol, 44% yield). LCMS RT=1.16 min, ES+ve m/z 463.4 [M+H]⁺.

(7R,8R,9S,13S,14S,17S)-7-(5-(Benzyloxy)pentyl)-13-methyl-7,8,9,11,12,13,14,15,16,17-decahydro-6H-cyclopenta[a]phenanthrene-3,17-diol

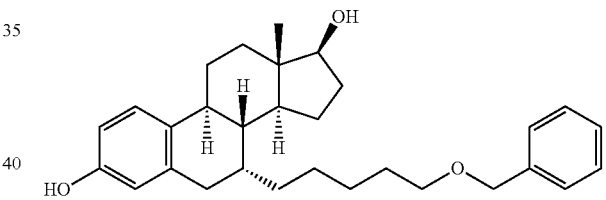

Triethylsilane (1.681 mL, 10.53 mmol) was added to a solution of (7S,8R,9S,13S,14S,17S)-7-(5-(benzyloxy)pentyl)-3,17-dihydroxy-13-methyl-7,8,9,11,12,13,14,15,16,17-decahydro-6H-cyclopenta[a]phenanthren-6-one (487 mg, 1.053 mmol) in TFA (6 mL, 78 mmol). The reaction was stirred at room temperature under an atmosphere of nitrogen for 16 hours. The mixture was partitioned between ethyl acetate (30 mL) and brine (30 mL). The organic extract was washed with brine (2×30 mL), dried using a hydrophobic fit and concentrated under reduced pressure. The residue was dissolved in MeOH (4 mL) and treated with aqueous NaOH (2M, 4 mL, 8.00 mmol). The reaction mixture was stirred at room temperature for 3 hours. The solvent was removed under reduced pressure. The residue was partitioned between ethyl acetate (30 mL) and water (30 mL). The organic extract was washed with brine (30 mL), dried (hydrophobic frit) and concentrated under reduced pressure. The product was purified by reverse phase chromatography using a gradient elution from 10% to 95% acetonitrile (+0.1% formic acid) in water (+0.1% formic acid) to afford the title compound (410 mg, 0.914 mmol, 87% yield). LCMS RT=1.30 min, ES+ve m/z 449.1 [M+H]⁺.

(7R,8R,9S,13S,14S,17S)-7-(5-(Benzyloxy)pentyl)-3,17-bis(methoxymethoxy)-13-methyl-7,8,9,11,12,13,14,15,16,17-decahydro-6H-cyclopenta[a]phenanthrene

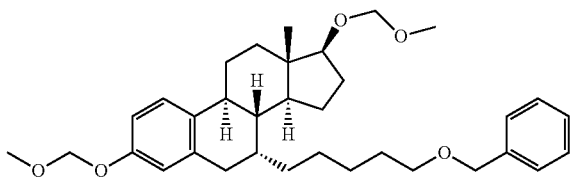

Chloro(methoxy)methane (0.7 mL, 9.22 mmol) was added to solution of (7R,8R,9S,13S,14S,17S)-7-(5-(benzyloxy)pentyl)-13-methyl-7,8,9,11,12,13,14,15,16,17-decahydro-6H-cyclopenta[a]phenanthrene-3,17-diol (410 mg, 0.914 mmol) and DIPEA (2 mL, 11.45 mmol) in THF (8 mL). The reaction vessel was sealed, placed under an atmosphere of nitrogen and heated at 70° C. for 2 days. The reaction was cooled to room temperature. The reaction was partitioned between ethyl acetate (50 mL) and brine (50 mL). The organic extract was washed with brine (2×50 mL), dried using a hydrophobic fit and concentrated under reduced pressure. The product was purified by chromatography on silica using a gradient elution from 0% to 100% methyl tert-butyl ether in cyclohexane to afford the title compound (474 mg, 0.883 mmol, 97% yield). LCMS RT=1.72 min, ES+ve m/z 554.5 [M+NH$_4$]$^+$.

5-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)pentan-1-ol

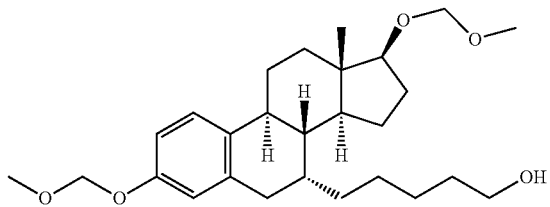

A mixture of (7R,8R,9S,13S,14S,17S)-7-(5-(benzyloxy)pentyl)-3,17-bis(methoxymethoxy)-13-methyl-7,8,9,11,12,13,14,15,16,17-decahydro-6H-cyclopenta[a]phenanthrene (474 mg, 0.883 mmol) and 10% w/w palladium on carbon (100 mg, 0.094 mmol) in ethanol (5 mL) and methyl tert-butyl ether (2 mL) was stirred at room temperature under an atmosphere of hydrogen for 1.5 hours. The palladium was filtered through celite and the filtrate concentrated under reduced pressure to afford the title compound (371 mg, 0.831 mmol, 94% yield). LCMS RT=1.39 min, ES+ve m/z 447.5 [M+H]$^+$ (weak ionisation).

5-((7R,8R,9S,13S,14S,17S)-3,17-Bis(methoxymethoxy)-13-methyl-7,8,9,11,12,13,14,15,16,17-decahydro-6H-cyclopenta[a]phenanthren-7-yl)pentyl 4-methylbenzenesulfonate

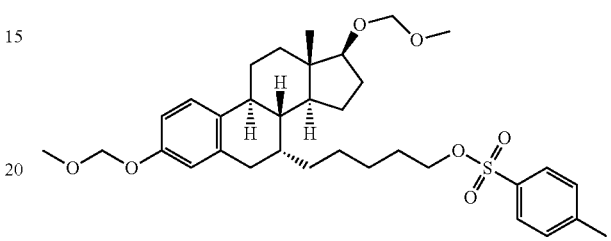

4-Methylbenzene-1-sulfonyl chloride (400 mg, 2.098 mmol) was added to 5-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)pentan-1-ol (371 mg, 0.831 mmol) in pyridine (5 mL). The reaction mixture was stirred at room temperature for 20 hours. The reaction mixture was partitioned between ethyl acetate (30 mL) and aqueous HCl (2M, 30 mL). The organic extract was washed with sat Na$_2$CO$_3$ (30 mL), brine (30 mL), dried (hydrophobic frit) and concentrated under reduced pressure. The product was purified by chromatography on silica using a gradient elution from 0% to 100% methyl tert-butyl ether in cyclohexane to afford the title compound (401 mg, 0.667 mmol, 80% yield). LCMS RT=1.60 min, ES+ve m/z 623.4 [M+Na]$^+$.

Tert-butyl 18-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-13-methyl-4,7,10-trioxa-13-azaoctadecan-1-oate, formic acid salt

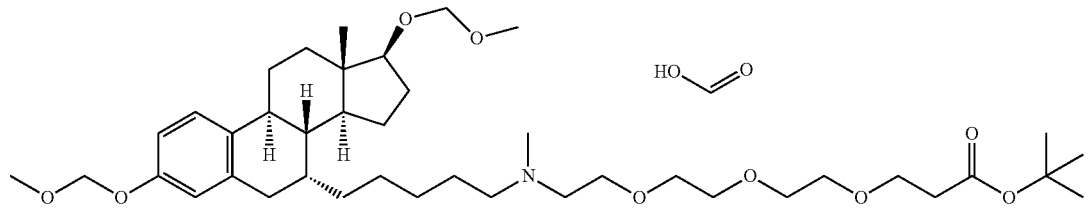

A microwave vial was charged with 5-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)pentyl 4-methylbenzenesulfonate (100 mg, 0.166 mmol), tert-butyl 5,8,11-trioxa-2-azatetradecan-14-oate (can be prepared following the procedure described in WO2012054110A2) (145 mg, 0.499 mmol) and DIPEA (0.291 mL, 1.664 mmol) in THF (2 mL). The vial was sealed and placed under an atmosphere of nitrogen using a vacuum purge. The reaction was heated at 75° C. for 48 hours. The reaction was cooled to room temperature. The reaction mixture was subjected directly to purification by mass-directed automated preparative HPLC (formic acid modifier) to afford the title compound (102 mg, 0.133 mmol, 80% yield). LCMS RT=1.22 min, ES+ve m/z 720.6 [M+H]$^+$.

18-((7R,8R,9S,13S,14S,17S)-3,17-Dihydroxy-13-methyl-7,8,9,11,12,13,14,15,16,17-decahydro-6H-cyclopenta[a]phenanthren-7-yl)-13-methyl-4,7,10-trioxa-13-azaoctadecan-1-oic acid, formic acid salt 14,15,16,17-decahydro-6H-cyclopenta[a]phenanthren-7-yl)-13-methyl-4,7,10-trioxa-13-azaoctadecan-1-oic acid, formic acid salt (12 mg, 0.019 mmol) and DIPEA (0.03 mL, 0.172 mmol) in DMF (0.8 mL). The reaction was stirred at room temperature for 10 minutes. The reaction mixture was subjected directly to two purifications by mass-directed automated preparative HPLC (formic acid modifier followed by ammonium carbonate modifier) to afford the title compound (13 mg, 0.013 mmol, 68% yield). LCMS RT=0.84 min, ES+ve m/z 988.8 [M+H]$^+$.

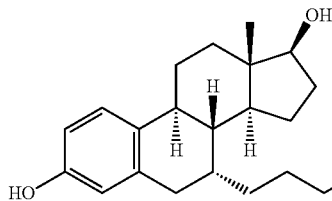
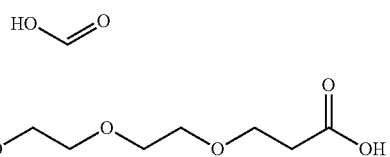

Tert-butyl 18-((7R,8R,9S,13S,14S,17S)-3,17-bis(methoxymethoxy)-13-methyl-7,8,9,11,12,13,14,15,16,17-decahydro-6H-cyclopenta[a]phenanthren-7-yl)-13-methyl-4,7,10-trioxa-13-azaoctadecan-1-oate, formic acid salt (100 mg, 0.131 mmol) was dissolved in THF (1 mL) and treated with aqueous HCl (6M, 1 mL, 6.00 mmol). The reaction was stirred at room temperature for 6 hours. The reaction mixture was subjected directly to purification by mass-directed automated preparative HPLC (formic acid modifier) to afford the title compound (24 mg, 0.039 mmol, 30% yield). LCMS RT=0.74 min, ES+ve m/z 576.5 [M+H]$^+$.

(2S,4R)-1-((S)-2-(Tert-butyl)-21-((7R,8R,9S,13S,14S,17S)-3,17-dihydroxy-13-methyl-7,8,9,11,12,13,14,15,16,17-decahydro-6H-cyclopenta[a]phenanthren-7-yl)-16-methyl-4-oxo-7,10,13-trioxa-3,16-diazahenicosan-1-oyl)-4-hydroxy-N-(4-(4-methylthiazol-5-yl)benzyl)pyrrolidine-2-carboxamide

The invention claimed is:
1. A compound according to the chemical structure:
L-ULM,
wherein:
L is selected from the group consisting of absent and a chemical linker group, and
ULM is a small molecule Von Hippel Lindau E3 ubiquitin ligase (VHL) binding moiety,
wherein the ULM has the structure:

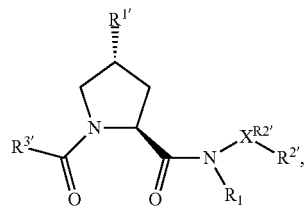

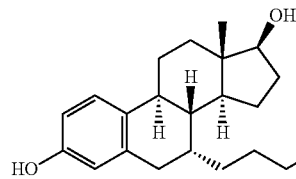
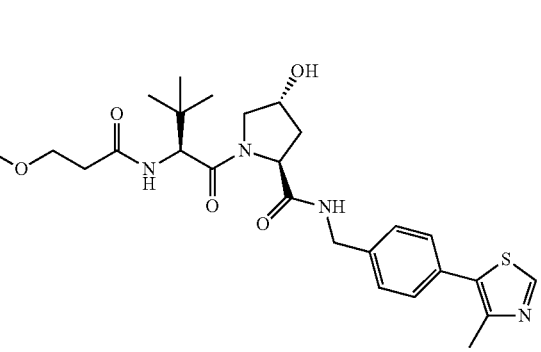

HATU (13 mg, 0.034 mmol) was added to a mixture of (2S,4R)-1-((S)-2-amino-3,3-dimethylbutanoyl)-4-hydroxy-N-(4-(4-methylthiazol-5-yl)benzyl)pyrrolidine-2-carboxamide, hydrochloride (13 mg, 0.028 mmol), 18-((7R,8R,9S,13S,14S,17S)-3,17-dihydroxy-13-methyl-7,8,9,11,12,13, wherein
$R^{1'}$ is selected from the group consisting of —OH and a group that can be metabolized in a patient or subject to —OH;

R²' is selected from the group consisting of optionally substituted -Aryl-HET and optionally substituted -HET-Aryl,
  wherein HET as defined in R²' is an optionally substituted substituent selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, benzofuran, indole, indolizine, azaindolizine, and quinolone, wherein the HET substitution is independently selected from the group consisting of $C_1$-$C_3$ alkyl and halo; or HET as defined in R²' is

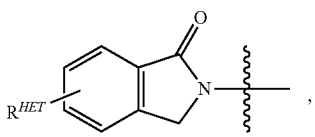

wherein $R^{HET}$ is selected from the group consisting of H, CN, $NO_2$, halogen, optionally substituted $C_1$-$C_6$ alkyl, optionally substituted —O($C_1$-$C_6$ alkyl), and optionally substituted —C≡C—$R^a$, wherein $R^a$ is selected from the group consisting of H and $C_1$-$C_6$ alkyl;
$X^{R2'}$ is selected from the group consisting of —(CH₂)ₙ— and optionally substituted —(CH₂)ₙ—C(X_v)=C(X_v)—, wherein in $X^{R2'}$ n is an integer from 1 to 6;
R³' is selected from the group consisting of:
  (a) optionally substituted —(CH₂)ₙ—N(R₁·)(C=O)_{m'}—(V)ₙ—$R^{S3'}$, optionally substituted —$X^{R3'}$-Aryl-HET, or optionally substituted —$X^{R3'}$-HET-Aryl;
    wherein HET is an optionally substituted substituent selected from the group consisting of oxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, benzofuran, indole, indolizine, azaindolizine, and quinolone, wherein the HET substitution is independently selected from the group consisting of $C_1$-$C_3$ alkyl and halo; or HET is

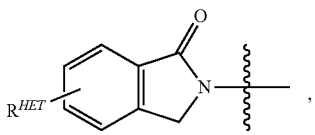

wherein $R^{HET}$ is selected from the group consisting of H, CN, $NO_2$, halogen, optionally substituted $C_1$-$C_6$ alkyl, optionally substituted —O($C_1$-$C_6$ alkyl), and optionally substituted —C≡C—$R^a$, wherein $R^a$ is selected from the group consisting of H and $C_1$-$C_6$ alkyl; and
  (b) optionally substituted —$X^{R3'}$-HET, wherein HET is

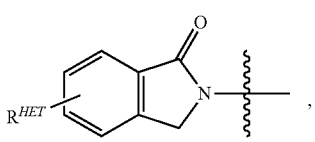

wherein $R^{HET}$ is selected from the group consisting of H, CN, $NO_2$, halogen, optionally substituted $C_1$-$C_6$ alkyl, optionally substituted —O($C_1$-$C_6$ alkyl), and optionally substituted —C≡C—$R^a$, wherein $R^a$ is selected from the group consisting of H and $C_1$-$C_6$ alkyl;
V is selected from the group consisting of O, S, and NR₁·;
each occurrence of n' is selected from the group consisting of 0 and 1;
each occurrence of m' is selected from the group consisting of 0 and 1;
Aryl is selected from the group consisting of optionally substituted phenyl and optionally substituted naphthyl;
$R^{S3'}$ is selected from the group consisting of optionally substituted alkyl, optionally substituted Aryl, and optionally substituted HET;
  wherein the alkyl or Aryl as defined in $R^{S3'}$ is independently optionally substituted with at least one selected from the group consisting of halogen, cyano, nitro, —OH, $C_1$-$C_6$ alkyl optionally substituted with at least one halogen, $C_1$-$C_6$ alkyl optionally substituted with at least one OH, $C_1$-$C_6$ alkoxy optionally substituted with at least one halogen, —(CH₂)ₙSH, —S($C_1$-$C_6$ alkyl), —S(=O)($C_1$-$C_6$ alkyl), —S(=O)₂($C_1$-$C_6$ alkyl), —S(=O)₂NH₂, —S(=O)₂NH($C_1$-$C_6$ alkyl), —S(=O)₂N($C_1$-$C_6$ alkyl)($C_1$-$C_6$ alkyl), —NHNH₂, —NH₂, —NH($C_1$-$C_6$ alkyl optionally substituted with 1-2 OH), —N($C_1$-$C_6$ alkyl optionally substituted with 1-2 OH)($C_1$-$C_6$ alkyl optionally substituted with 1-2 OH), —NHC(=O)($C_1$-$C_6$ alkyl), —N($C_1$-$C_6$ alkyl)C(=O)($C_1$-$C_6$ alkyl), —CHO, —(CH₂)ₙC(=O)OH, —(CH₂)ₙC(=O)O($C_1$-$C_6$ alkyl), —C(=O)S($C_1$-$C_6$ alkyl), —(CH₂)ₙC(=O)NH₂, —(CH₂)ₙC(=O)NH($C_1$-$C_6$ alkyl), —(CH₂)ₙC(=O)N($C_1$-$C_6$ alkyl)($C_1$-$C_6$ alkyl), —(CH₂)ₙC(=O)($C_1$-$C_6$ alkyl), —OC(=O)NH₂, —OC(=O)NH($C_1$-$C_6$ alkyl), —OC(=O)($C_1$-$C_6$ alkyl)($C_1$-$C_6$ alkyl), —(CH₂), NHC(=O)($C_1$-$C_6$ alkyl), —(CH₂), N($C_1$-$C_6$ alkyl)C(=O)($C_1$-$C_6$ alkyl), benzyl, and an aromatic substituent selected from the group consisting of phenyl, naphthyl, quinolinyl, indolyl, diazolyl, triazolyl, oxazolyl, isoxazolyl, thiazolyl, isothiazolyl, imidazolyl, pyrrolyl, furyl, indolyl, isoindolyl, indolizinyl, pyridinyl, pyrimidinyl, benzimidazolyl, benzodiazolyl, benzoxofuryl, benzofuryl, and thiophenyl; wherein the aromatic substituent is independently optionally substituted with at least one selected from the group consisting of $C_1$-$C_6$ alkyl and halogen;
  wherein HET as defined in $R^{S3'}$ is an optionally substituted substituent selected from the group consisting of oxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, benzofuran, indole, indolizine, azaindolizine, and quinolone, wherein the HET substitution is independently selected from the group consisting of $C_1$-$C_3$ alkyl and halogen, or HET as defined in R²' is

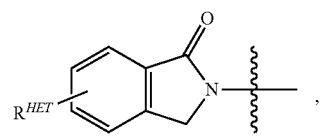

wherein R$^{HET}$ is selected from the group consisting of
H, CN, NO$_2$, halogen, optionally substituted C$_1$-C$_6$ alkyl, optionally substituted —O(C$_1$-C$_6$ alkyl), and optionally substituted —C≡C—R$^a$, wherein R$^a$ is selected from the group consisting of H and C$_1$-C$_6$ alkyl;

R$_1$ is selected from the group consisting of H and C$_1$-C$_3$ alkyl;

R$_{1'}$ is selected from the group consisting of H and C$_1$-C$_3$ alkyl;

X$^{R3'}$ is selected from the group consisting of optionally substituted —(CH$_2$)$_n$—, optionally substituted —(CH$_2$CH$_2$O)$_n$—, optionally substituted —(CH$_2$)$_n$—CH(X$_v$)=CH(X$_v$)—, optionally substituted —(CH$_2$)$_n$—CH=CH—, and optionally substituted C$_3$-C$_6$ cycloalkyl;

X$_v$ is selected from the group consisting of H, halogen, and C$_1$-C$_3$ alkyl optionally substituted with one or two hydroxyl groups or with one, two, or three independently selected halogen groups;

each occurrence of R$_1$ is independently selected from the group consisting of H and C$_1$-C$_3$ alkyl; and each occurrence of n is independently selected from the group consisting of 0, 1, 2, 3, 4, 5, and 6;

or a pharmaceutically acceptable salt, solvate, or polymorph thereof.

2. A compound according to the chemical structure:

L-ULM, wherein:

L is selected from the group consisting of absent and a chemical linker group,

ULM is a small molecule Von Hippel Lindau E3 ubiquitin ligase (VHL) binding moiety selected from the group consisting of:

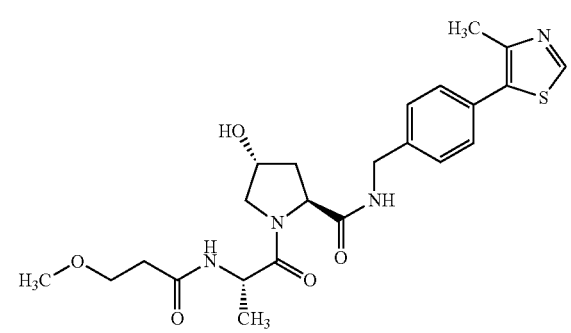

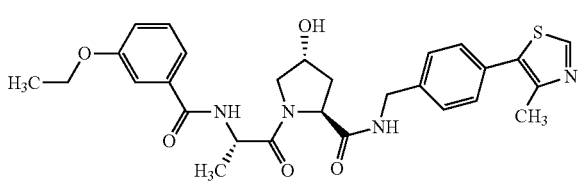

-continued

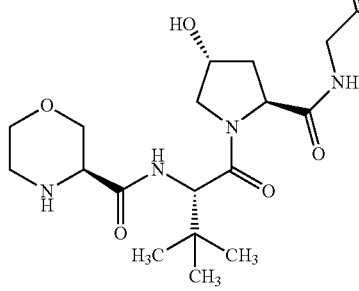

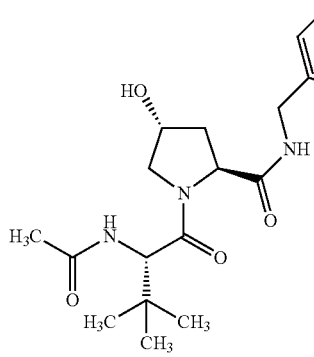

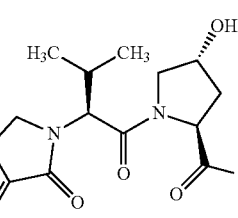

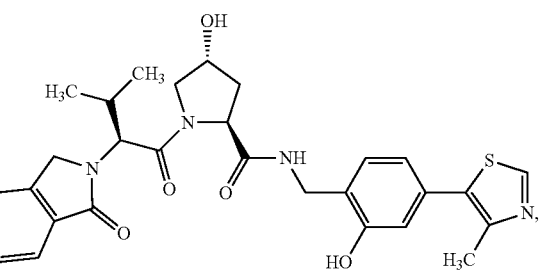

or a pharmaceutically acceptable salt, solvate, or polymorph thereof.

3. The compound of claim 1, wherein L is at least one member selected from the group consisting of a bond, —(CH$_2$)$_i$—O—, —(CH$_2$—CH$_2$—O)$_i$—, —(CH$_2$)$_i$—S—, —(CH$_2$)$_i$—NR—, —(CH$_2$)$_i$—X$_1$Y$_1$—,

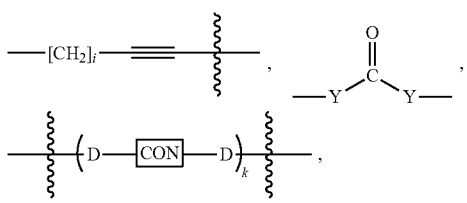

and any combinations thereof, wherein
each i is independently an integer ranging from 0 to 100;
R is H, a $C_1$-$C_3$ alkyl, an alkanol group or a heterocyclic group;
Y is independently a bond, O, S or N—R;
$X_1Y_1$ forms an amide group, a urethane group, ester or thioester group;
D is independently a bond (absent),

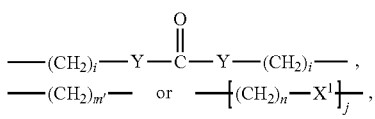

each j is independently an integer ranging from 1 to 100;
each k is independently an integer ranging from 1 to 100;
each m' is independently an integer ranging from 1 to 100;
each n is independently an integer ranging from 1 to 100; and
$X^1$ is O, S or N—R; and
CON is a bond (absent), a piperazinyl group, optionally substituted alkylene, heterocycle,

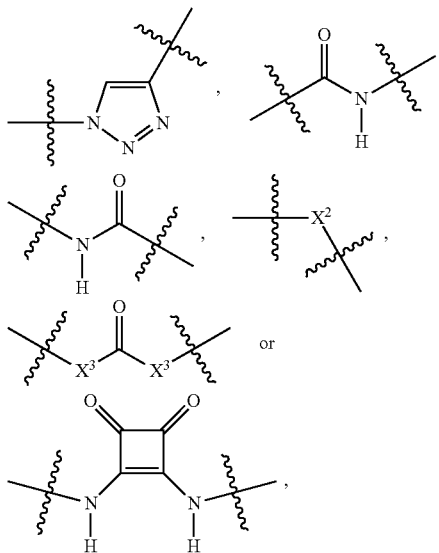

$X^2$ is O, S, $NR^4$, S(O), $S(O)_2$, —$S(O)_2O$, —$OS(O)_2$, or $OS(O)_2O$;
$X^3$ is O, S, $CHR^4$, or $NR^4$; and
$R^4$ is H or a $C_1$-$C_3$ alkyl group, which is optionally substituted with one or two hydroxyl groups.

4. The compound of claim 3, wherein each i is independently an integer ranging from 1 to 10.

5. The compound of claim 3, wherein L is a (poly) ethyleneglycol having from 2 to 100 ethylene glycol units.

6. The compound of claim 3, wherein R is morpholino, piperidinyl, or piperazinyl.

7. The compound of claim 3, wherein CON is a

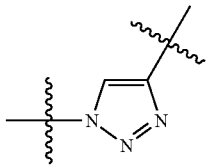 [SMILES: *c1cn(*)nn1]

group,

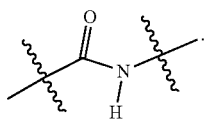 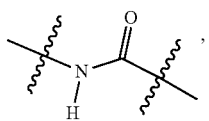

or a piperazinyl group.

8. The compound of claim 1, wherein the ULM is selected from the group consisting of:

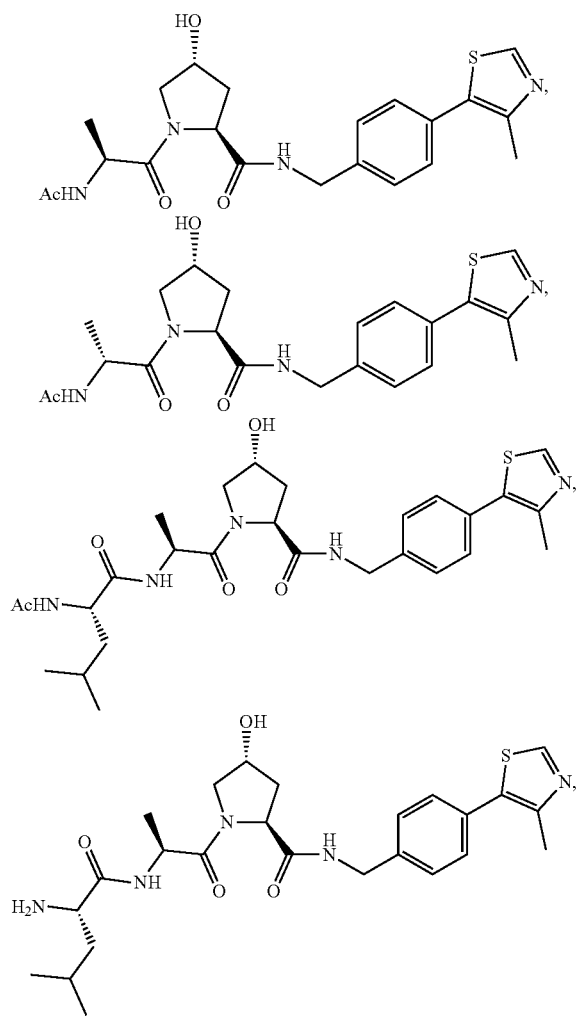

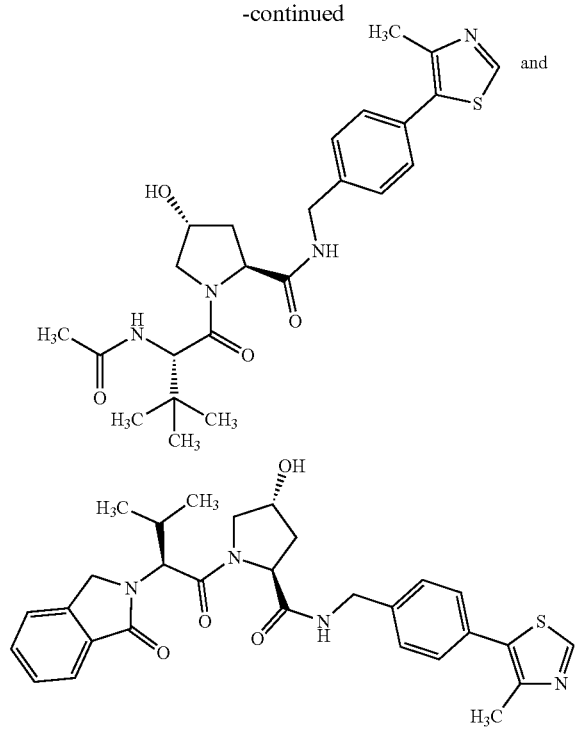
or a pharmaceutically acceptable salt, solvate, or polymorph thereof.
9. The compound of claim 1, wherein the ULM is a member selected from the group consisting of:
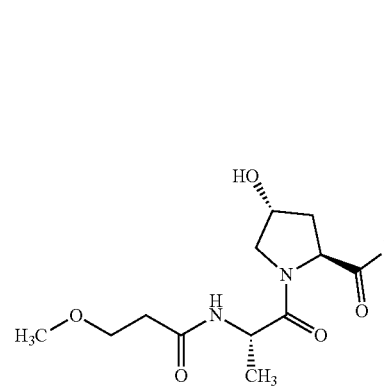
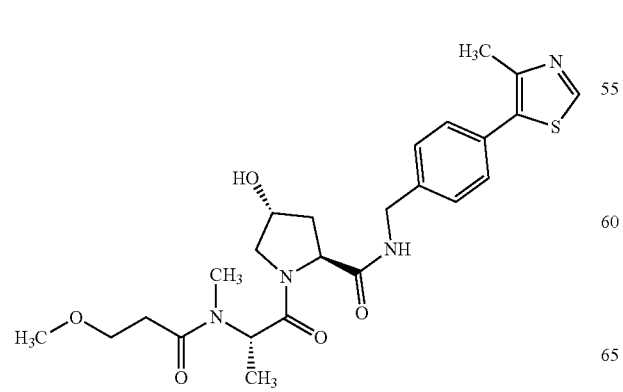
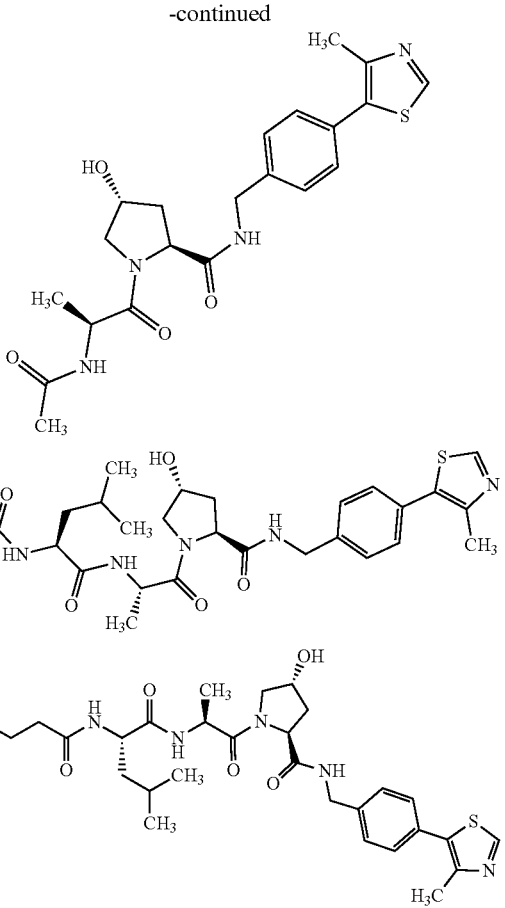
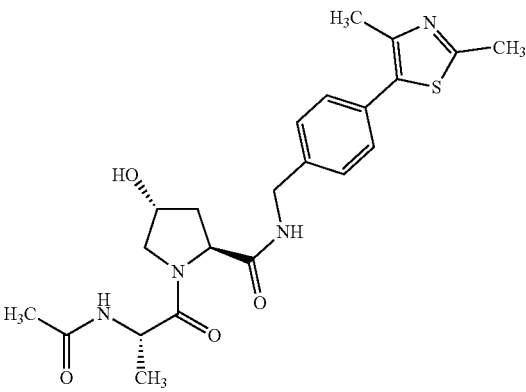

421
-continued
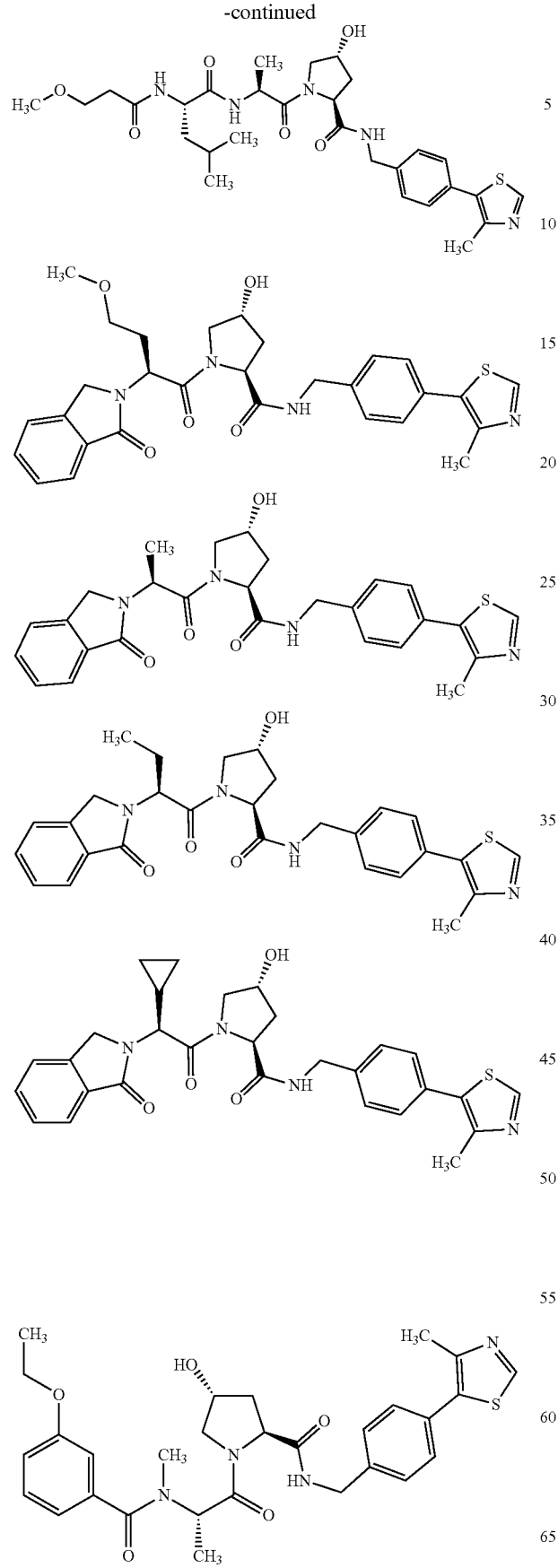
422
-continued
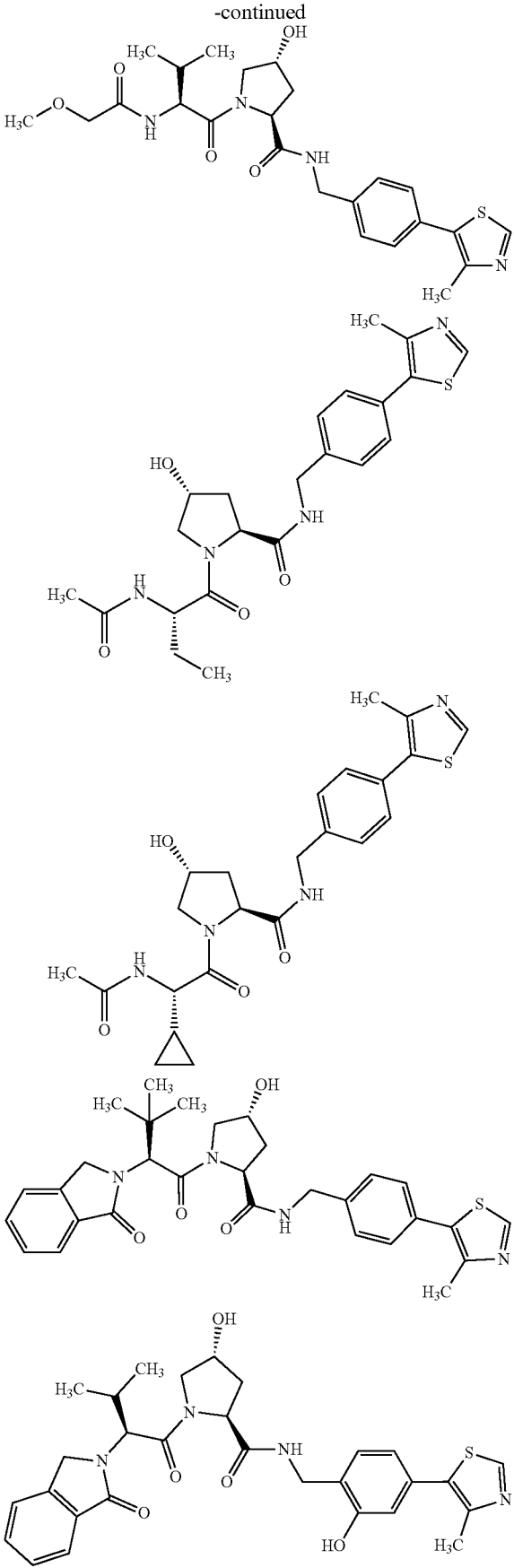

423
-continued
424
-continued
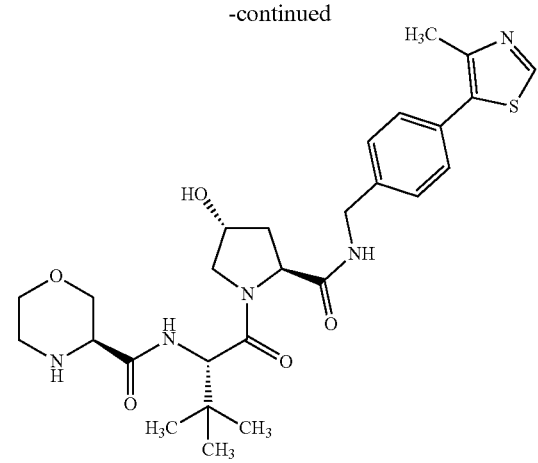
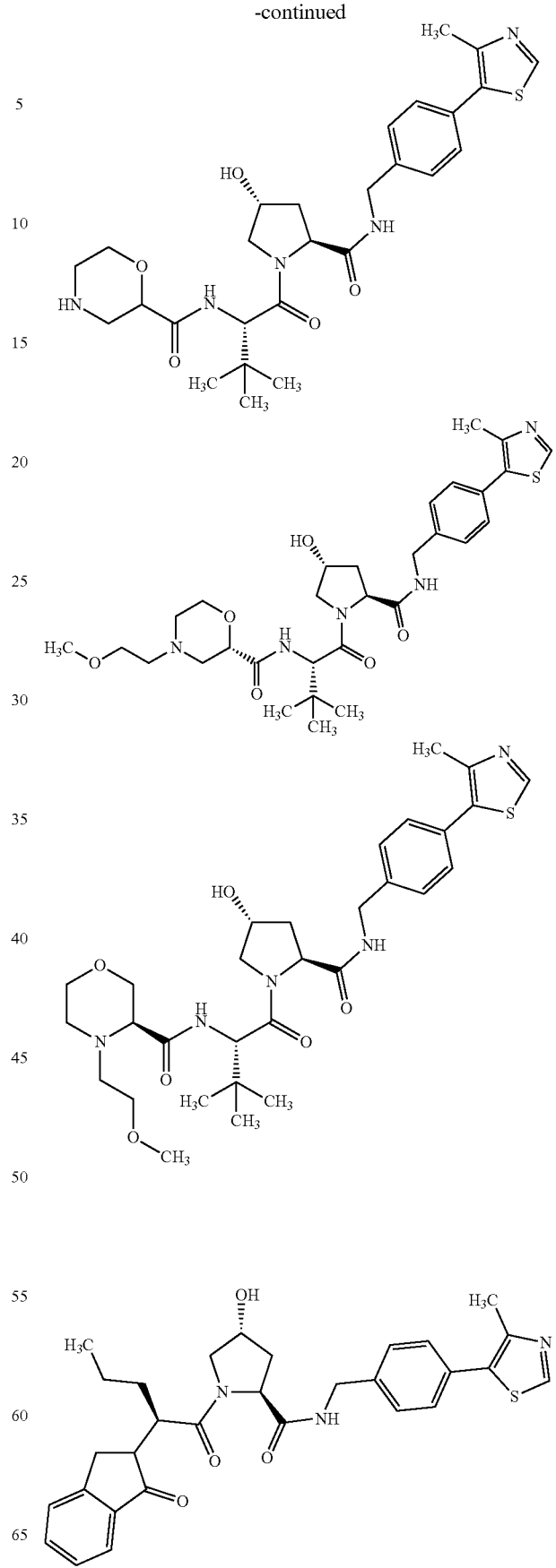

-continued

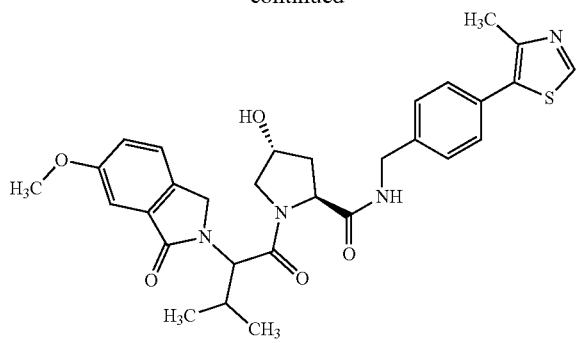

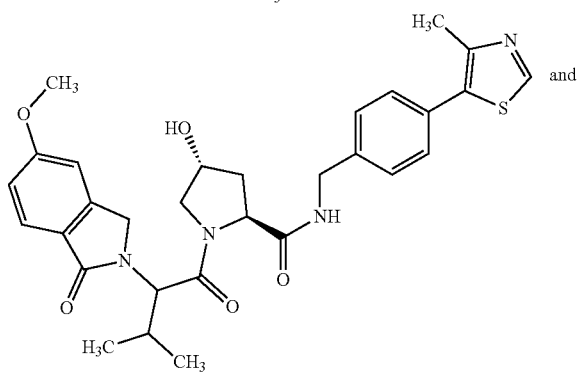

and

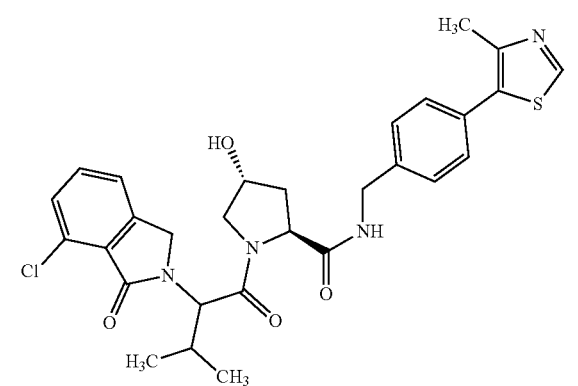

or a pharmaceutically acceptable salt, solvate, or polymorph thereof.

10. A compound selected from the group consisting of

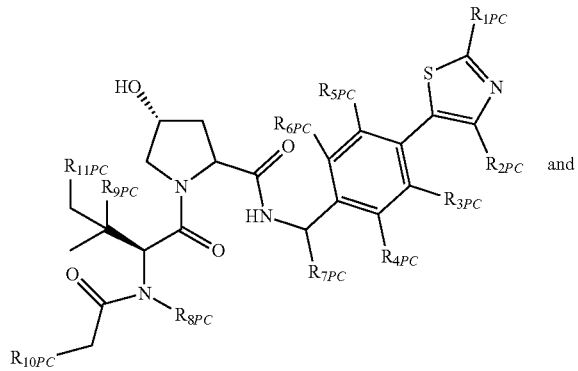

-continued

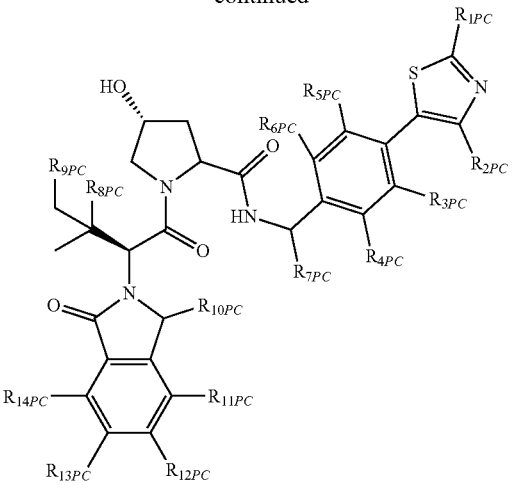

wherein each of $R_{1PC}$, $R_{2PC}$, $R_{3PC}$, $R_{4PC}$, $R_{5PC}$, $R_{6PC}$, $R_{8PC}$, $R_{9PC}$, $R_{10PC}$, $R_{11PC}$, $R_{12PC}$, $R_{13PC}$ and $R_{14PC}$ is independently H, optionally substituted alkyl, or a

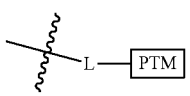

group
wherein $R_{7PC}$ is H or a

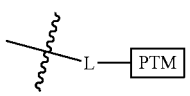

group; and
wherein L is a linker group and PTM is a protein targeting moiety, or a pharmaceutically acceptable salt, solvate, or polymorph thereof.

11. The compound of claim 10, according to the chemical structure:

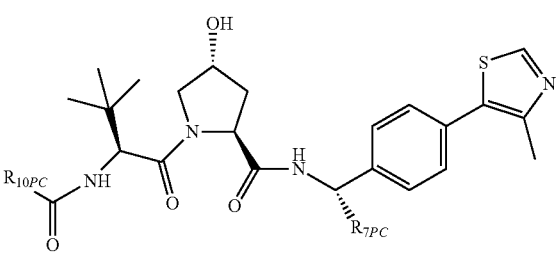

wherein $R_{10PC}$ is a

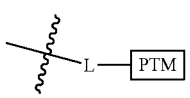

group, optionally substituted alkyl or H, or a pharmaceutically acceptable salt, solvate, or polymorph thereof.

12. The compound of claim 10, according to the chemical structure:

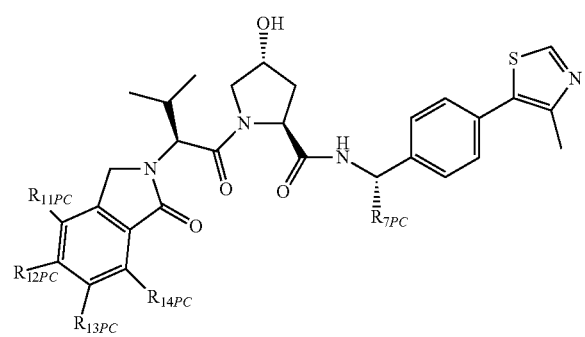

wherein $R_{11PC}$, $R_{12PC}$, $R_{13PC}$, and $R_{14PC}$ are each independently a

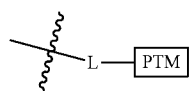

group, optionally substituted alkyl or H, or a pharmaceutically acceptable salt, solvate, or polymorph thereof.

13. A compound according to the chemical structure:

L-ULM, wherein:
L is absent or a chemical linker group, and
the ULM is selected from the group consisting of:

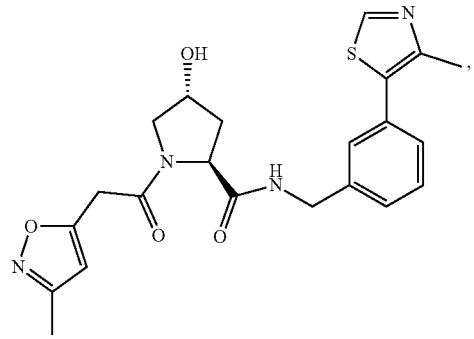

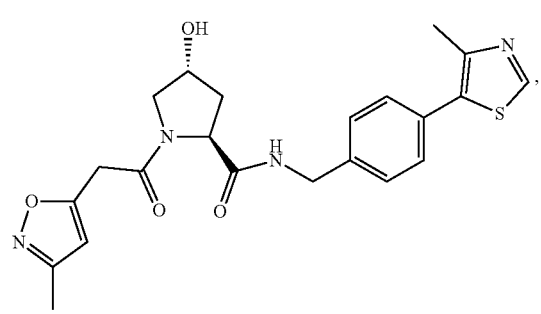

-continued

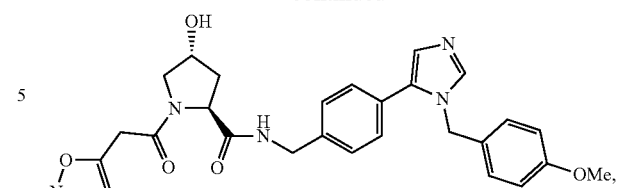

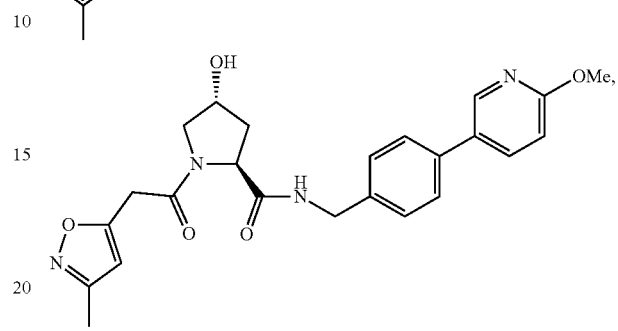

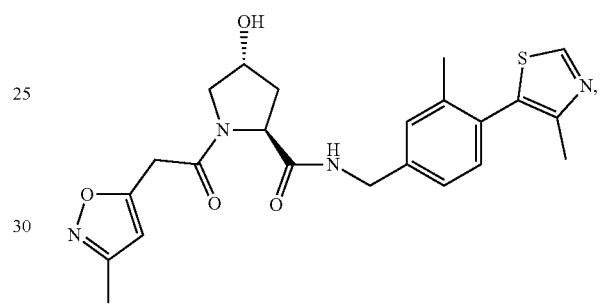

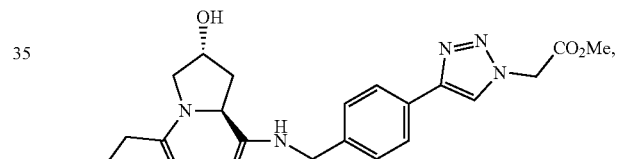

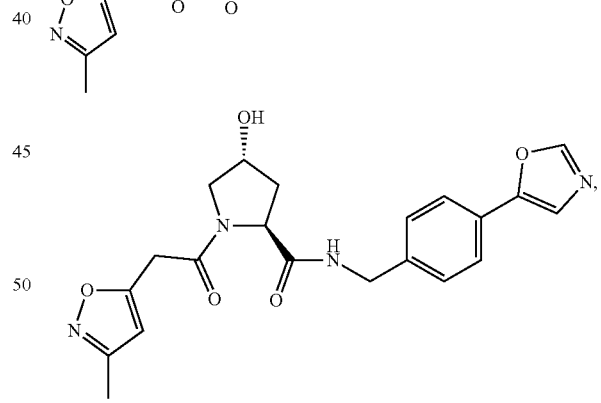

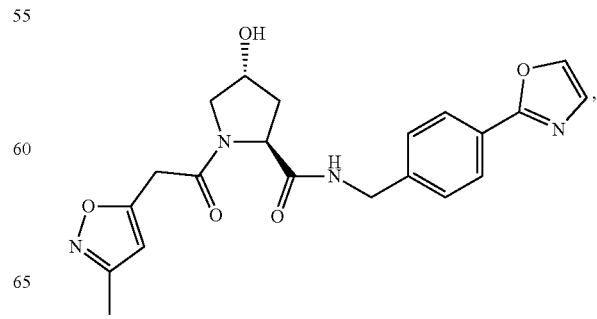

429
-continued
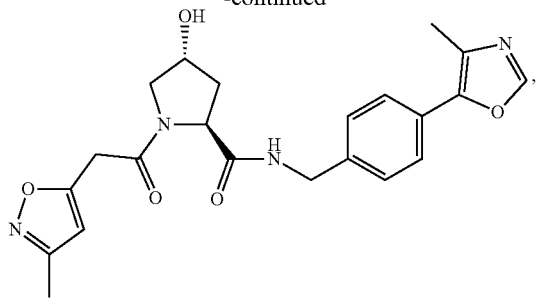
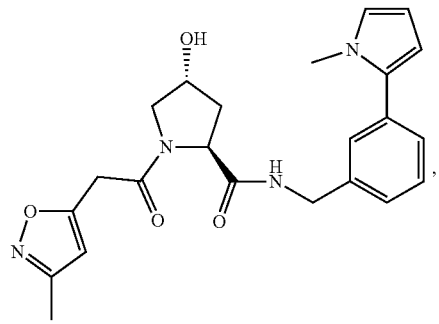
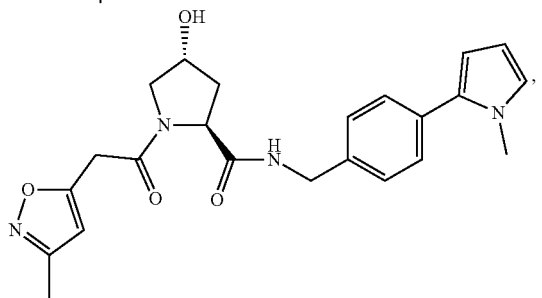
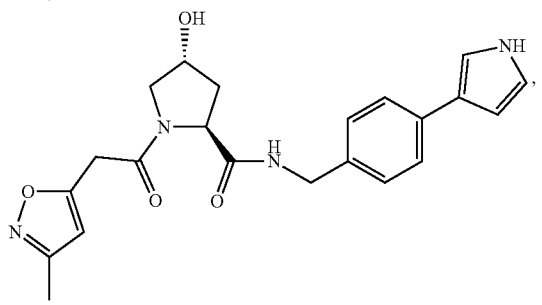
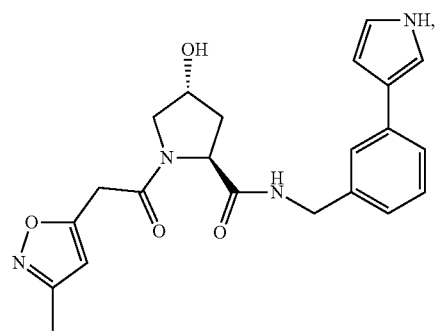
430
-continued
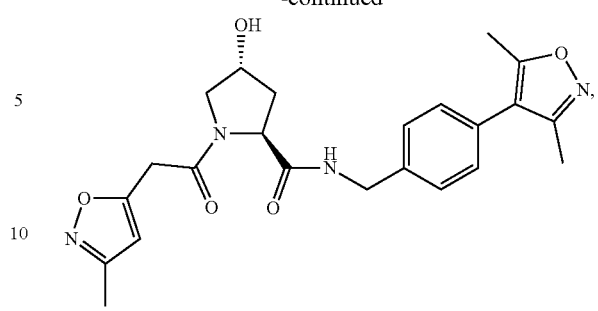
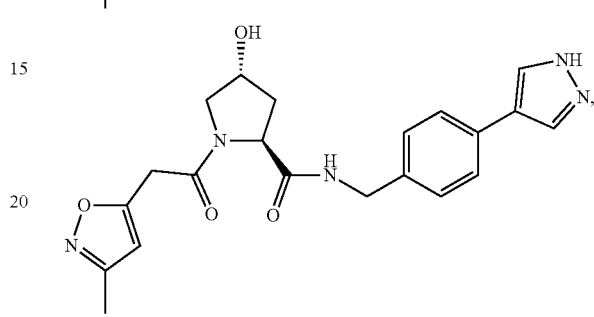
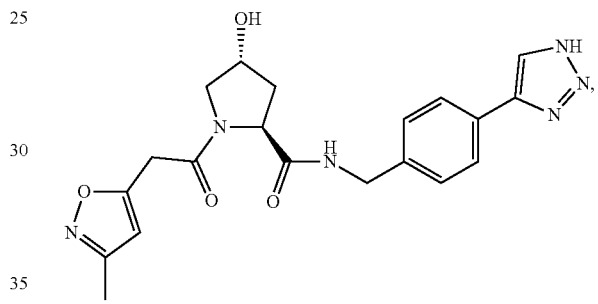
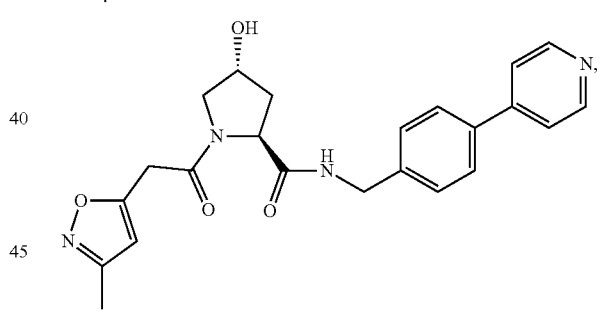
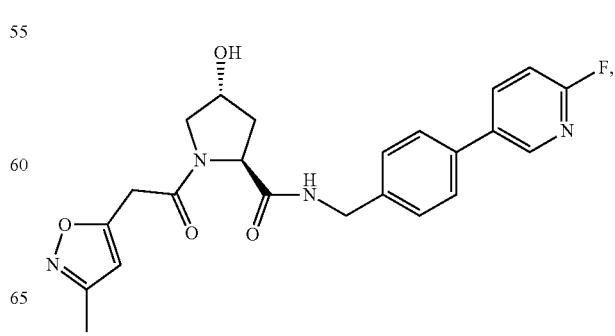

-continued
431
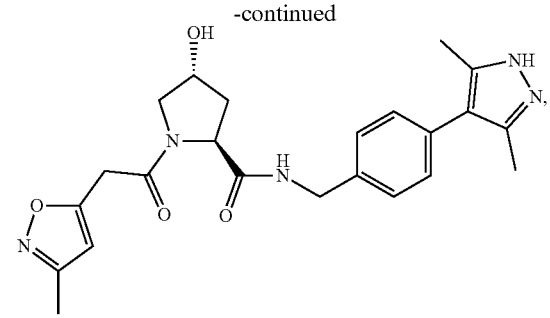
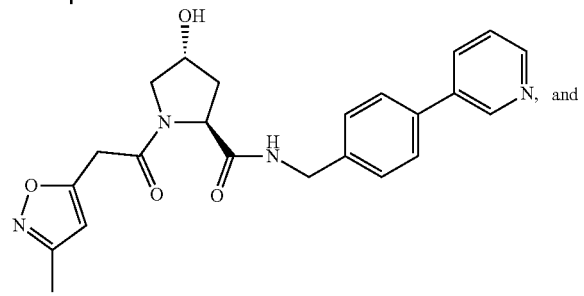
432
-continued
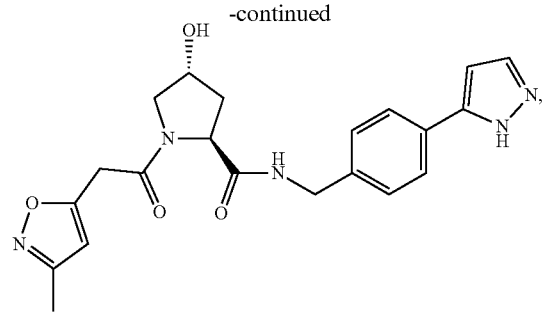
or a pharmaceutically acceptable salt, solvate, or polymorph thereof.
14. The compound of claim 1, wherein the L is further coupled to a PTM, wherein PTM is a moiety that binds to a target protein or polypeptide that is to be ubiquinated by VHL.
* * * * *

UNITED STATES PATENT AND TRADEMARK OFFICE
CERTIFICATE OF CORRECTION

PATENT NO. : 10,730,862 B2
APPLICATION NO. : 14/371956
DATED : August 4, 2020
INVENTOR(S) : Crews et al.

Page 1 of 1

It is certified that error appears in the above-identified patent and that said Letters Patent is hereby corrected as shown below:

On the Title Page

Item (60), "Provisional application No. 61/585,769, filed on Jan. 12, 2011" should be changed to
-- Provisional application No. 61/585,769, filed on Jan. 12, 2012 --

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*